US008501757B2

(12) United States Patent
Conn et al.

(10) Patent No.: US 8,501,757 B2
(45) Date of Patent: Aug. 6, 2013

(54) SUBSTITUTED PHENYLAMINE CARBOXAMIDE ANALOGS AS MGLUR5 NEGATIVE ALLOSTERIC MODULATORS AND METHODS OF MAKING AND USING THE SAME

(75) Inventors: P. Jeffrey Conn, Brentwood, TN (US); Craig W. Lindsley, Brentwood, TN (US); Kyle A. Emmitte, Spring Hill, TN (US); Charles David Weaver, Franklin, TN (US); Alice L. Rodriguez, Nashville, TN (US); Andrew S. Felts, Nashville, TN (US); Carrie K. Jones, Nashville, TN (US); Brittney S. Bates, Nashville, TN (US); Brian A. Chauder, Smyrna, TN (US)

(73) Assignee: Vanderbilt University, Nashville, TN (US)

( * ) Notice: Subject to any disclaimer, the term of this patent is extended or adjusted under 35 U.S.C. 154(b) by 285 days.

(21) Appl. No.: 12/885,420

(22) Filed: Sep. 17, 2010

(65) Prior Publication Data
US 2011/0166158 A1    Jul. 7, 2011

Related U.S. Application Data

(60) Provisional application No. 61/243,378, filed on Sep. 17, 2009.

(51) Int. Cl.
| A61K 31/505 | (2006.01) |
| A61K 31/44 | (2006.01) |
| C07D 239/02 | (2006.01) |
| C07D 403/12 | (2006.01) |
| C07D 401/12 | (2006.01) |
| C07D 213/62 | (2006.01) |
| A61K 31/4965 | (2006.01) |

(52) U.S. Cl.
USPC ....... 514/272; 514/255.05; 514/333; 514/335

(58) Field of Classification Search
USPC ............. 514/255.05, 335, 272, 333; 544/319, 544/295, 405; 546/261
See application file for complete search history.

(56) References Cited

U.S. PATENT DOCUMENTS

| 6,846,827 B1 | 1/2005 | Cumming |
| 2006/0199858 A1 | 9/2006 | Durst et al. |
| 2006/0235035 A1 | 10/2006 | Hogberg et al. |
| 2006/0235069 A1 | 10/2006 | Duggan et al. |
| 2007/0293457 A1 | 12/2007 | Baker et al. |
| 2009/0042855 A1 | 2/2009 | Conn et al. |
| 2009/0197883 A1 | 8/2009 | Armstrong et al. |
| 2010/0317643 A1* | 12/2010 | Goodacre et al. ........ 514/210.02 |
| 2011/0152299 A1 | 6/2011 | Conn et al. |
| 2011/0172247 A1 | 7/2011 | Conn et al. |
| 2011/0172248 A1 | 7/2011 | Conn et al. |

FOREIGN PATENT DOCUMENTS

| WO | WO-2009-047296 A2 | 4/2009 |
| WO | WO-2011-035214 A1 | 3/2011 |

OTHER PUBLICATIONS

Kulkarni et al., "Design and Synthesis of Novel Heterobiaryl Amides as Metabotrophic Glutamate Receptor Subtype 5 Antagonists," *Bioorg. Med. Chem. Lett.* vol. 17(7), pp. 2074-2079, 2007 (From NIH Public Access pp. 1-16).
International Preliminary Report on Patentability from International Application No. PCT/US10/049407, issued on Mar. 20, 2012 (6 pp).
International Search Report from International Application No. PCT/US10/049407, mailed Nov. 1, 2010 (1 page).
Written Opinion of the International Searching Authority from International Application No. PCT/US10/049400, mailed Nov. 1, 2010 (5 pp).

* cited by examiner

*Primary Examiner* — James O. Wilson
*Assistant Examiner* — Ebenezer O Sackey
(74) *Attorney, Agent, or Firm* — Clark & Elbing LLP

(57) ABSTRACT

Disclosed are negative allosteric modulators of the metabotropic glutamate receptor subtype 5 (mGluR5); synthetic methods for making the compounds; pharmaceutical compositions comprising the compounds; and methods of treating neurological and psychiatric disorders associated with glutamate dysfunction using the compounds and compositions. This abstract is intended as a scanning tool for purposes of searching in the particular art and is not intended to be limiting of the present invention.

11 Claims, 3 Drawing Sheets

SUBSTITUTED PHENYLAMINE CARBOXAMIDE ANALOGS AS MGLUR5 NEGATIVE ALLOSTERIC MODULATORS AND METHODS OF MAKING AND USING THE SAME

CROSS-REFERENCE TO RELATED APPLICATIONS

This application claims the benefit of U.S. Application No. 61/243,378, filed Sep. 17, 2009, which is hereby incorporated herein by reference in its entirety.

ACKNOWLEDGMENT

This invention was made with government support under Grant no. 1R01-DA023947-01 awarded by the National Institute on Drug Abuse (NIDA), under Grant no. 5R01-NS031373-15 awarded by the National Institute of Neurological Disorders and Stroke (NINDS), and under Grant no. 5R01-MH073676-04 awarded by the National Institute of Mental Health (NIMH). The United States government has certain rights in the invention.

BACKGROUND

Glutamate (L-glutamic acid) is the major excitatory transmitter in the mammalian central nervous system, exerting its effects through both ionotropic and metabotropic glutamate receptors. The metabotropic glutamater receptors (mGluRs) belong to family C (also known as family 3) of the G-protein-coupled receptors (GPCRs). They are characterized by a seven transmembrane (7™) α-helical domain connected via a cysteine rich-region to a large bi-lobed extracellular amino-terminal domain (FIG. 1). While the orthosteric binding site is contained in the amino-terminal domain, currently known allosteric binding sites reside in the 7™ domain. The mGluR family comprises eight known mGluRs receptor types (designated as mGluR1 through mGluR8). Several of the receptor types are expressed as specific splice variants, e.g. mGluR5a and mGluR5b or mGluR8a, mGluR8b and mGluR8c. The family has been classified into three groups based on their structure, preferred signal transduction mechanisms, and pharmacology. Group I receptors (mGluR1 and mGluR5) are coupled to Gαq, a process that results in stimulation of phospholipase C and an increase in intracellular calcium and inositol phosphate levels. Group II receptors (mGluR2 and mGluR3) and group III receptors (mGluR4, mGluR6, mGluR7, and mGluR8) are coupled to Gαi, which leads to decreases in cyclic adenosine monophosphate (cAMP) levels. While the Group I receptors are predominately located postsynaptically and typically enhance postsynaptic signaling, the group II and III receptors are located presynaptically and typically have inhibitory effects on neurotransmitter release. Without wishing to be bound by theory, increasing evidence indicates mGluRs play an important role in lasting changes in synaptic transmission, and studies of synaptic plasticity in the Fmr1 knockout mouse have identified a connection between the fragile X phenotype and mGluR signaling.

The identification of small molecule mGluR antagonists that bind at the orthosteric site has greatly increased the understanding of the roles played by these receptors and their corresponding relation to disease. Because the majority of these antagonists were designed as analogs of glutamate, they typically lack desired characteristics for drugs targeting mGluR such as oral bioavailability and/or distribution to the central nervous system (CNS). Moreover, because of the highly conserved nature of the glutamate binding site, most orthosteric antagonists lack selectivity among the various mGluRs.

A more recent strategy that has been able to successfully deal with the aforementioned issues has been the design of compounds that bind the mGluR at a site that is topographically distinct from the othosteric binding site, or an allosteric binding site. Selective negative allosteric modulators (NAMs) are compounds that do not directly deactivate receptors by themselves, but decrease the affinity of a glutamate-site agonist at its extracellular N-terminal binding site. Negative allosteric modulation is thus an attractive mechanism for inhibiting appropriate physiological receptor activation. Among the most studied and characterized small molecules are the mGluR5NAMs, 2-methyl-6-(phenylethynyl)pyridine (MPEP) and 3-[(2-methyl-1,3-thiazol-4-yl)ethynyl]pyridine (MTEP). Both MPEP and MTEP have proven efficacious in numerous rodent models of disease, including those for drug addiction and pain as well as anxiety. The compounds were also able to inhibit transient lower esophageal sphincter relaxation (TLESD), the major cause of gastroesophageal reflux disease (GERD), in dogs and ferrets. In addition, MPEP was efficacious in mouse models of fragile X syndrome (FXS) and Parkinson's disease (PD) as well as a baboon model of binge-eating disorder.

Although the utility of MPEP and MTEP as tool compounds has been clearly demonstrated, both molecules have issues that complicate or prevent their further development as therapeutic molecules. MPEP has been shown to directly inhibit the N-methyl-D-aspartate (NMDA) receptor activity at higher concentrations and is a positive allosteric modulator of mGluR4. While these selectivity issues are mitigated with MTEP, it is a potent inhibitor of cytochrome P450 1A2 and is efficiently cleared following intravenous administration to rhesus monkeys.

Potential adverse effects of known mGluR5NAMs, however, could reduce their ultimate therapeutic utility. Further, conventional mGluR5 receptor modulators which target the orthosteric binding site can lack satisfactory aqueous solubility, exhibit poor oral bioavailability, and/or exhibit adverse effects. Therefore, there remains a need for methods and compositions that overcome these deficiencies and that effectively provide selective negative allosteric modulators for the mGluR5 receptor.

SUMMARY

In accordance with the purpose(s) of the invention, as embodied and broadly described herein, the invention, in one aspect, relates to compounds useful as negative allosteric modulators of the metabotropic glutamate receptor subtype 5 (mGluR5), methods of making same, pharmaceutical compositions comprising same, and methods of treating disorders associated with glutamate dysfunction using same.

Disclosed are compounds, or pharmaceutically acceptable salts thereof, having a structure represented by a formula:

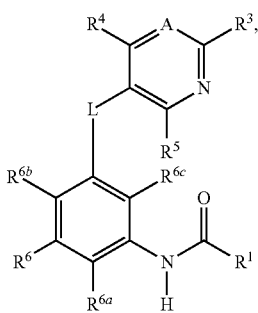

wherein A is CR² or N; wherein L is O or NR⁷, wherein R¹ has from 1 to 10 carbons and is selected from phenyl substituted with 1-3 of R⁹, wherein at least one R⁹ is meta substituted; 2-pyridinyl substituted with 0-3 of R⁹; and thiazole substituted with 0-2 of R⁹; wherein R² is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein R³ is selected from hydrogen, halogen, C1-C6 alkyl, C1-C6 haloalkyl, C1-C6 alkoxy, hydroxyl, CN, $SO_2R^8$, and $COR^8$; wherein R⁴ and R⁵ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein R⁶ is selected from hydrogen, halogen, CN, C1-C4 alkyl, C1-C4 haloalkyl, C3-C4 cycloalkyl, and C3-C4 halocycloalkyl; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein R⁷ is hydrogen, C1-C6 alkyl, or C1-C6 haloalkyl; wherein R⁸ is C1-C6 alkyl, C1-C6 cycloalkyl, amino, alkylamino, or dialkylamino; and wherein each R⁹, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$; wherein the compound exhibits partial or total inhibition of mGluR5 response to glutamate as a decrease in response to non-maximal concentrations of glutamate in human embryonic kidney cells transfected with rat mGluR5 in the presence of the compound, compared to the response to glutamate in the absence of the compound.

Also disclosed are pharmaceutical compositions comprising a therapeutically effective amount of a disclosed compound and a pharmaceutically acceptable carrier.

Also disclosed are methods of making a compound comprising the step of reacting a compound having a structure represented by a formula:

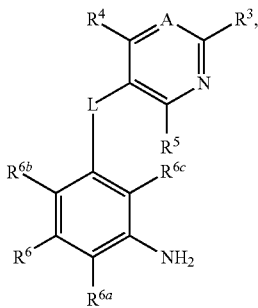

wherein A is CR² or N; wherein L is O or NR⁷, wherein R² is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein R³ is selected from hydrogen, halogen, C1-C6 alkyl, C1-C6 haloalkyl, C1-C6 alkoxy, hydroxyl, CN, $SO_2R^8$, and $COR^8$; wherein R⁴ and R⁵ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein R⁶ is selected from hydrogen, halogen, CN, C1-C4 alkyl, C1-C4 haloalkyl, C3-C4 cycloalkyl, and C3-C4 halocycloalkyl; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein R⁷ is hydrogen, C1-C6 alkyl, or C1-C6 haloalkyl; wherein R⁸ is C1-C6 alkyl, C1-C6 cycloalkyl, amino, alkylamino, or dialkylamino; and wherein each R⁹, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$; with an activated carbonyl compound, thereby forming an amide.

Also disclosed are methods of making a compound comprising the step of reacting a compound having a structure represented by a formula:

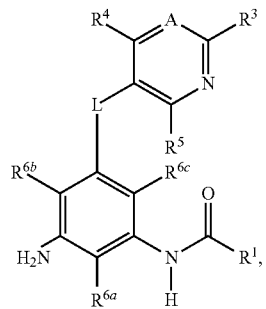

wherein A is CR² or N; wherein L is O or NR⁷, wherein R¹ has from 1 to 10 carbons and is selected from phenyl substituted with 1-3 of R⁹, wherein at least one R⁹ is meta substituted; 2-pyridinyl substituted with 0-3 of R⁹; and thiazole substituted with 0-2 of R⁹; wherein R² is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein R³ is selected from hydrogen, halogen, C1-C6 alkyl, C1-C6 haloalkyl, C1-C6 alkoxy, hydroxyl, CN, $SO_2R^8$, and $COR^8$; wherein R⁴ and R⁵ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein R⁷ is hydrogen, C1-C6 alkyl, or C1-C6 haloalkyl; wherein R⁸ is C1-C6 alkyl, C1-C6 cycloalkyl, amino, alkylamino, or dialkylamino; and wherein each R⁹, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$; under Sandmeyer reaction conditions, thereby producing a halogenated derivative.

Also disclosed are methods of making a compound comprising the step of reacting a compound having a structure represented by a formula:

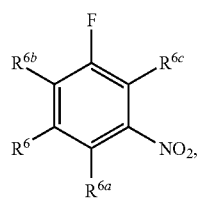

with a second compound having a structure represented by a formula:

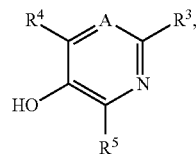

wherein A is $CR^2$ or N; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is selected from hydrogen, halogen, CN, C1-C4 alkyl, C1-C4 haloalkyl, C3-C4 cycloalkyl, and C3-C4 halocycloalkyl; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; and wherein $R^8$ is C1-C6 alkyl, C1-C6 cycloalkyl, amino, alkylamino, or dialkylamino; under basic conditions, thereby forming an ether.

Also disclosed are methods of making a compound comprising the steps of: (a) providing a compound having a structure represented by a formula:

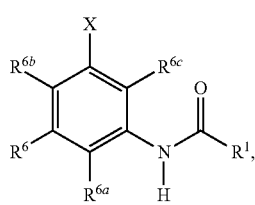

wherein X is halogen; wherein $R^1$ has from 1 to 10 carbons and is selected from phenyl substituted with 1-3 of $R^9$, wherein at least one $R^9$ is meta substituted; 2-pyridinyl substituted with 0-3 of $R^9$; and thiazole substituted with 0-2 of $R^9$; wherein $R^6$ is selected from hydrogen, halogen, CN, C1-C4 alkyl, C1-C4 haloalkyl, C3-C4 cycloalkyl, and C3-C4 halocycloalkyl; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$; (b) reacting with a second compound having a structure represented by a formula:

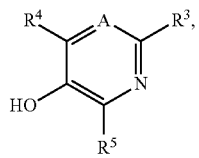

wherein A is $CR^2$ or N; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; and wherein $R^8$ is C1-C6 alkyl, C1-C6 cycloalkyl, amino, alkylamino, or dialkylamino; under basic conditions, thereby forming an ether.

Also disclosed are methods of making a compound comprising the step of reacting a compound having a structure represented by a formula:

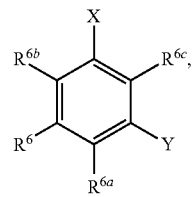

wherein X and Y are independently halogens; wherein $R^6$ is selected from hydrogen, halogen, CN, C1-C4 alkyl, C1-C4 haloalkyl, C3-C4 cycloalkyl, and C3-C4 halocycloalkyl; and wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; with a second compound having a structure represented by a formula:

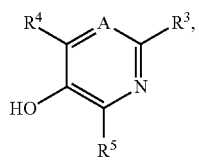

wherein A is $CR^2$ or N; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; and wherein $R^8$ is C1-C6 alkyl, C1-C6 cycloalkyl, amino, alkylamino, or dialkylamino; under basic conditions, thereby forming an ether.

Also disclosed are methods of making a compound comprising the step of reacting a compound having a structure represented by a formula:

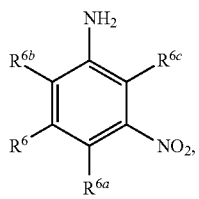

wherein $R^6$ is selected from hydrogen, halogen, CN, C1-C4 alkyl, C1-C4 haloalkyl, C3-C4 cycloalkyl, and C3-C4 halocycloalkyl; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; and wherein $R^8$ is C1-C6 alkyl, C1-C6 cycloalkyl, amino, alkylamino, or dialkylamino; with a second compound having a structure represented by a formula:

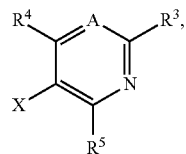

wherein X is halogen; wherein A is $CR^2$ or N; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; in the presence of a transition metal, thereby forming a diaryl amine moiety.

Also disclosed are products of the disclosed methods.

Also disclosed are pharmaceutical compositions comprising a therapeutically effective amount of a disclosed product and a pharmaceutically acceptable carrier.

Also disclosed are methods for manufacturing a medicament comprising combining at least one disclosed compound or at least one disclosed product with a pharmaceutically acceptable carrier or diluent.

Also disclosed are methods for the treatment of a disorder associated with mGluR5 activity in a mammal comprising the step of administering to the mammal at least one compound having a structure represented by a formula:

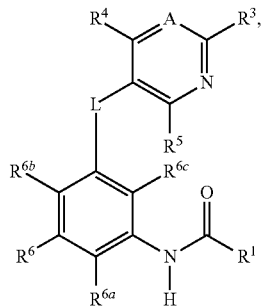

wherein A is $CR^2$ or N; wherein L is O or $NR^7$, wherein $R^1$ is aryl, heteroaryl, alkyl, cycloalkyl, heteroalkyl, or heterocycloalkyl, wherein $R^1$ is substituted with 0-3 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is hydrogen, halogen, C1-C6 alkyl, C1-C6 haloalkyl, C1-C6 alkoxy, cyano, hydroxyl, alkylamino, dialkylamino, $SO_2R^8$, or $COR^8$; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$, or a pharmaceutically acceptable salt thereof, in an effective amount to treat the disorder in the mammal.

Also disclosed are methods for decreasing mGluR5 activity in a mammal comprising the step of administering to the mammal at least one compound having a structure represented by a formula:

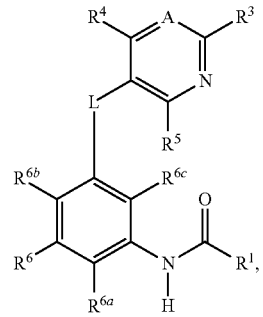

wherein A is $CR^2$ or N; wherein L is O or $NR^7$, wherein $R^1$ is aryl, heteroaryl, alkyl, cycloalkyl, heteroalkyl, or heterocycloalkyl, wherein $R^1$ is substituted with 0-3 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is hydrogen, halogen, C1-C6 alkyl, C1-C6 haloalkyl, C1-C6 alkoxy, cyano, hydroxyl, alkylamino, dialkylamino, $SO_2R^8$, or $COR^8$; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or COR⁸, or a pharmaceutically acceptable salt thereof, in an effective amount to decrease mGluR5 activity in the mammal.

Also disclosed are methods for inhibiting mGluR5 activity in at least one cell, comprising the step of contacting the at least one cell with at least one compound having a structure represented by a formula:

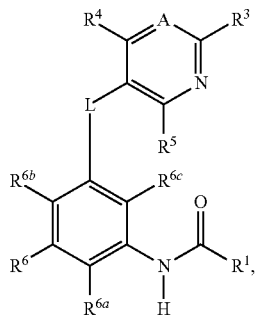

wherein A is $CR^2$ or N; wherein L is O or $NR^7$, wherein $R^1$ is aryl, heteroaryl, alkyl, cycloalkyl, heteroalkyl, or heterocycloalkyl, wherein $R^1$ is substituted with 0-3 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is hydrogen, halogen, C1-C6 alkyl, C1-C6 haloalkyl, C1-C6 alkoxy, cyano, hydroxyl, alkylamino, dialkylamino, $SO_2R^8$, or $COR^8$; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$, or a pharmaceutically acceptable salt thereof, in an effective amount to inhibit mGluR5 activity in the at least one cell.

Also disclosed are uses of a compound having a structure represented by a formula:

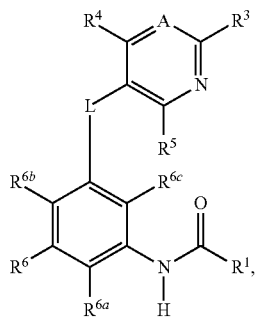

wherein A is $CR^2$ or N; wherein L is O or $NR^7$, wherein $R^1$ is aryl, heteroaryl, alkyl, cycloalkyl, heteroalkyl, or heterocycloalkyl, wherein $R^1$ is substituted with 0-3 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is hydrogen, halogen, C1-C6 alkyl, C1-C6 haloalkyl, C1-C6 alkoxy, cyano, hydroxyl, alkylamino, dialkylamino, $SO_2R^8$, or $COR^8$; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$, or a pharmaceutically acceptable salt thereof, in the manufacture of a medicament for the treatment of a disorder associated with glutamate dysfunction in a mammal.

Also disclosed are kits comprising at least one compound having a structure represented by a formula:

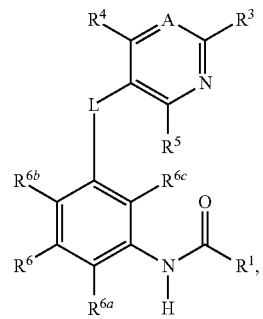

wherein A is $CR^2$ or N; wherein L is O or $NR^7$, wherein $R^1$ is aryl, heteroaryl, alkyl, cycloalkyl, heteroalkyl, or heterocycloalkyl, wherein $R^1$ is substituted with 0-3 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$, and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is hydrogen, halogen, C1-C6 alkyl, C1-C6 haloalkyl, C1-C6 alkoxy, cyano, hydroxyl, alkylamino, dialkylamino, $SO_2R^8$, or $COR^8$; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or COR[8], or a pharmaceutically acceptable salt thereof, in the manufacture of a medicament for the treatment of a disorder associated with glutamate dysfunction in a mammal and one or more of: at least one agent known to increase mGluR5 activity; at least one agent known to decrease mGluR5 activity; at least one agent known to treat a neurological and/or psychiatric disorder; at least one agent known to treat a disease of uncontrolled cellular proliferation; or instructions for treating a disorder associated with glutamate dysfunction.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
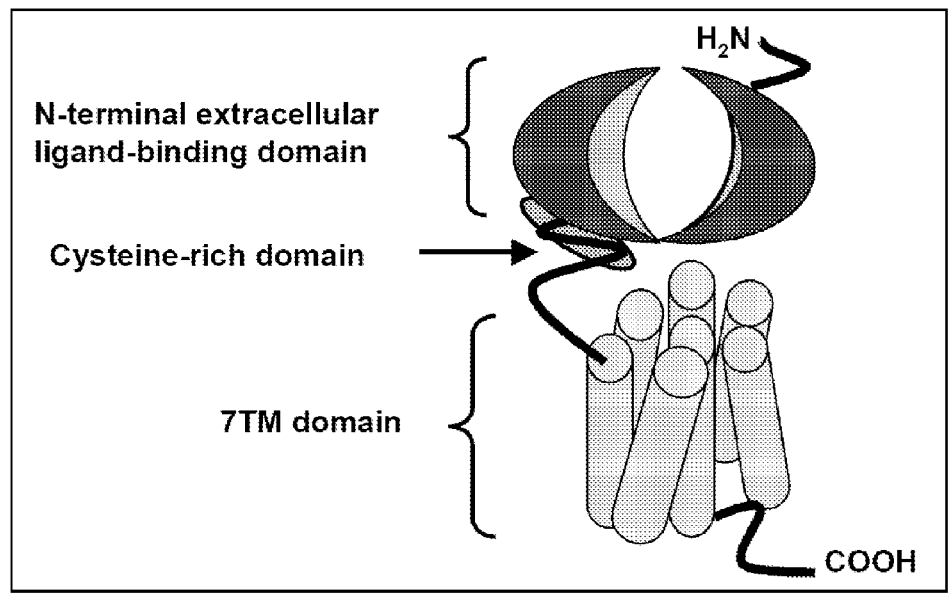
FIG. 1 is a schematic representation of an mGluR.
Figure 2:
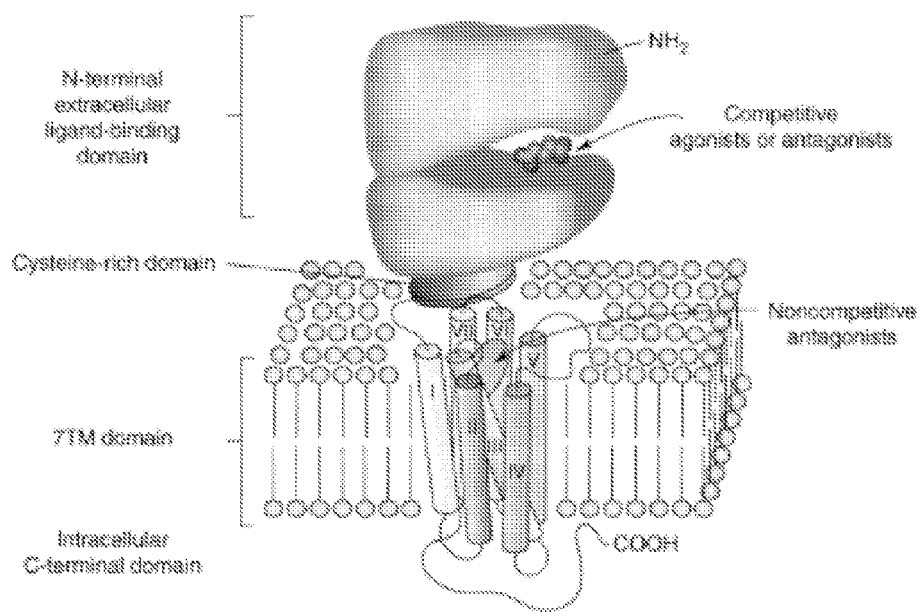
FIG. 2 illustrates allosteric modulation of mGluR5.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples and Figures included herein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound 1f given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "mGluR5 receptor negative allosteric modulator" refers to any exogenously administered compound or agent that directly or indirectly inhibits the activity of the mGluR5 receptor in the presence of the endogenous ligand (such as glutamate) in an animal, in particular a mammal, for example a human. The term is synonymous with the terms "mGluR5 receptor allosteric inhibitor," "mGluR5 receptor noncompetitive inhibitor," "mGluR5 receptor allosteric antagonist," and "mGluR5 receptor noncompetitive antagonist."

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more neurological and/or psychiatric disorder associated with glutamate dysfunction prior to the administering step. In some aspects of the disclosed method, the subject has been diagnosed with a need for negative allosteric modulation of metabotropic glutamate receptor activity prior to the administering step. In some aspects of the disclosed method, the subject has been diagnosed with a need for partial antagonism of metabotropic glutamate receptor activity prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by modulation of mGluR5" means having been subjected to a physical examination by a person of skill, for example, a physician, and found to have a condition that can be diagnosed or treated by a compound or composition that can modulate mGluR5. As a further example, "diagnosed with a need for modulation of mGluR5" refers to having been subjected to a physical examination by a person of skill, for example, a physician, and found to have a condition characterized by mGluR5 activity. Such a diagnosis can be in reference to a disorder, such as a neurodegenerative disease, and the like, as discussed herein. For example, the term "diagnosed with a need for negative allosteric modulation of metabotropic glutamate receptor activity" refers to having been subjected to a physical examination by a person of skill, for example, a physician, and found to have a condition that can be diagnosed or treated by negative allosteric modulation of metabotropic glutamate receptor activity. For example, "diagnosed with a need for partial antagonism of metabotropic glutamate receptor activity" means having been subjected to a physical examination by a person of skill, for example, a physician, and found to have a condition that can be diagnosed or treated by partial antagonism of metabotropic glutamate receptor activity. For example, "diagnosed with a need for treatment of one or more neurological and/or psychiatric disorder associated with glutamate dysfunction" means having been subjected to a physical examination by a person of skill, for example, a physician, and found to have one or more neurological and/or psychiatric disorder associated with glutamate dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to mGluR5 activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target metabotropic glutamate receptor, or other biological entity together in such a manner that the compound can affect the activity of the target (e.g., spliceosome, cell, etc.), either directly; i.e., by interacting with the target itself, or indirectly; i.e., by interacting with another molecule, co-factor, factor, or protein on which the activity of the target is dependent.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half maximal (50%) inhibitory concentration (IC) of a substance.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$—OA$^2$ or —OA$^1$—OA$^2$)$_a$—OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula C(O)OH.

The term "ester" as used herein is represented by the formula —OC(O)$A^1$ or C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula—$(A^1O(O)C-A^2-C(O)O)_a$— or —$(A^1O(O)C-A^2-OC(O))_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an interger from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula —$(A^1O-A^2O)_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$" where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$R$^\circ$; —O(CH$_2$)$_{0-4}$R$^\circ$, —O—(CH$_2$)$_{0-4}$C(O)OR$^\circ$; —(CH$_2$)$_{0-4}$—CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —SC(S)SR$^\circ$, —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —OP(O)R$^\circ$$_2$; —OP(O)(OR$^\circ$)$_2$; SiR$^\circ$$_3$; —(C$_{1-4}$ straight or branched)alkylene)O—N(R$^\circ$)$_2$; or —(C$_{1-4}$ straight or branched alkylene)C(O)O—N(R$^\circ$$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR•, —NH₂, —NHR•, —NR•₂, or —NO₂, wherein each R• is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or —N(R†)S(O)₂R†; wherein each R† is independently hydrogen, C₁₋₆ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of Rt, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH₂, —NHR•, —NR•₂, or —NO₂, wherein each R• is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

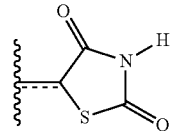

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z)

isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

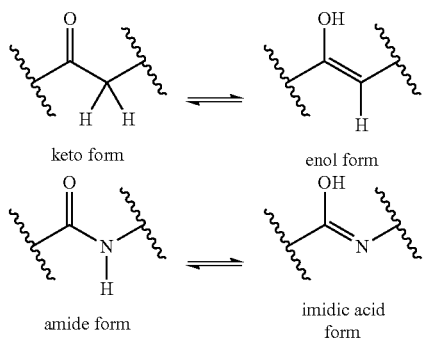

keto form     enol form amide form     imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

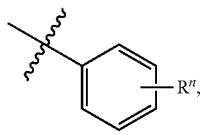

which is understood to be equivalent to a formula:

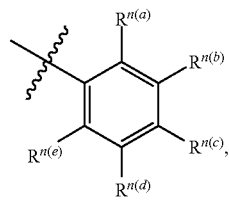

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. mGluR5 Negative Allosteric Modulators

In one aspect, the invention relates to compounds useful as negative allosteric modulators of the metabotropic glutamate receptor subtype 5 (mGluR5). Negative allosteric modulators are non-competitive antagonists and can include a range of maximal antagonist activity from partial antagonists to inverse agonists. In one aspect, the present invention relates to compounds that allosterically modulate mGluR5 receptor activity, affecting the sensitivity of mGluR5 receptors to agonists without acting as orthosteric agonists themselves. The compounds can, in one aspect, exhibit subtype selectivity. The compounds of the invention can be useful in the treatment neurological and psychiatric disorders associated with glutamate dysfunction and other diseases in which metabotropic glutamate receptors are involved, as further described herein. Generally, the disclosed compounds exhibit negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In further aspect, the human embryonic kidney cells are transfected with human mGluR5. In yet a further aspect, human embryonic kidney cells are transfected with mGluR5 of a mammal.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to compounds, or pharmaceutically acceptable salts thereof, having a structure represented by a formula:

Disclosed are compounds, or pharmaceutically acceptable salts thereof, having a structure rpresented by a formula:

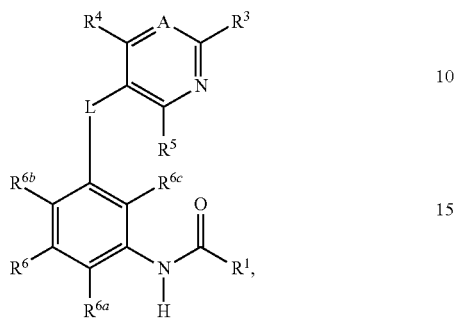

wherein A is $CR^2$ or N; wherein L is O or $NR^7$, wherein $R^1$ has from 1 to 10 carbons and is selected from phenyl substituted with 1-3 of $R^9$, wherein at least one $R^9$ is meta substituted; 2-pyridinyl substituted with 0-3 of $R^9$; and thiazole substituted with 0-2 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is selected from hydrogen, halogen, CN, C1-C4 alkyl, C1-C4 haloalkyl, C3-C4 cycloalkyl, and C3-C4 halocycloalkyl; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$; wherein the compound exhibits partial or total inhibition of mGluR5 response to glutamate as a decrease in response to non-maximal concentrations of glutamate in human embryonic kidney cells transfected with rat mGluR5 in the presence of the compound, compared to the response to glutamate in the absence of the compound.

In a further aspect, a compound has a structure selected from:

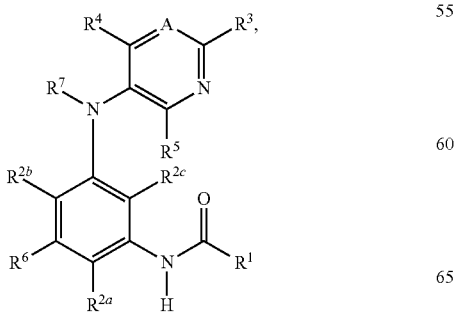

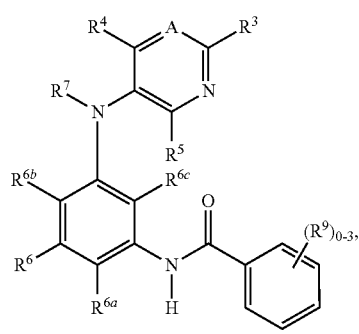

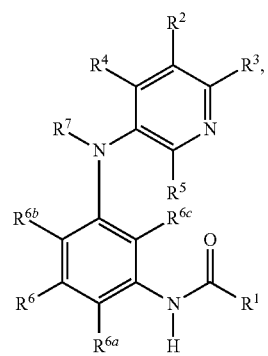

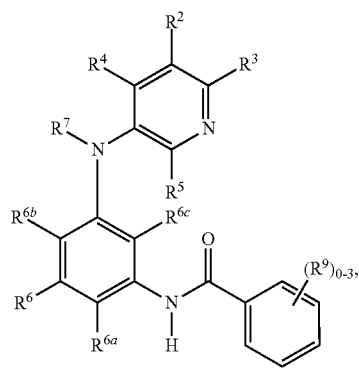

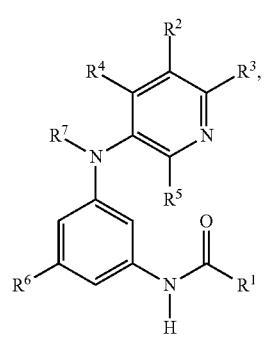

-continued
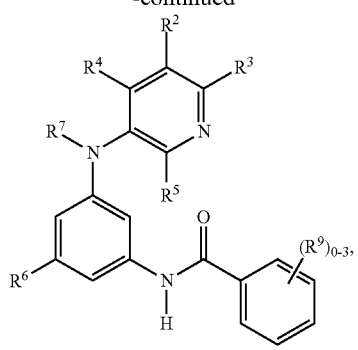
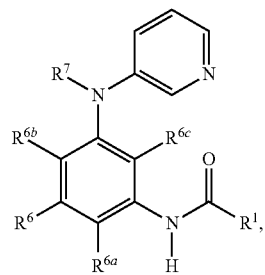
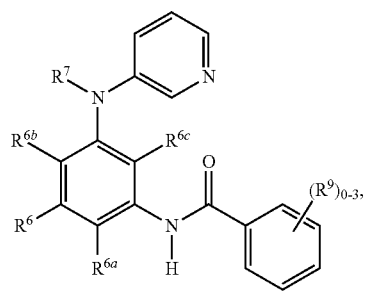
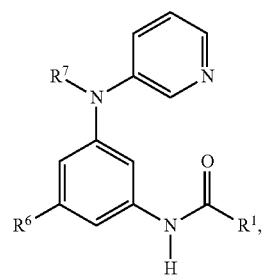
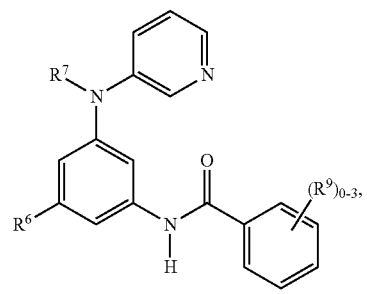
-continued
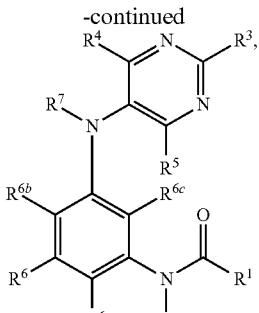
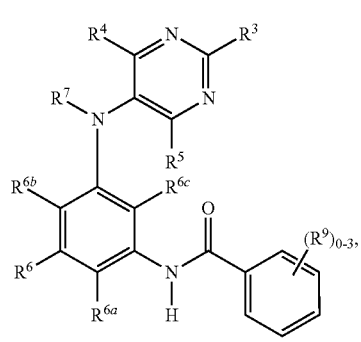
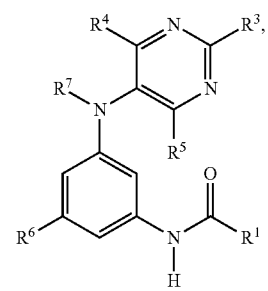
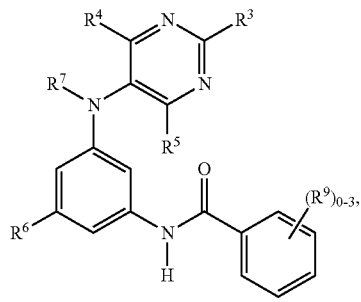

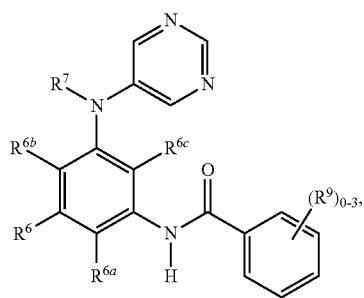
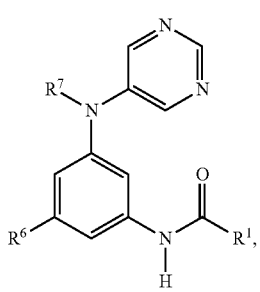
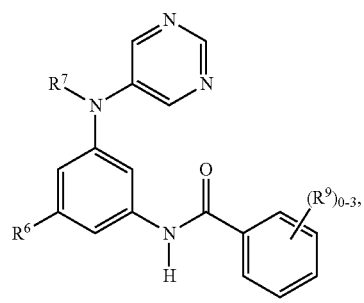
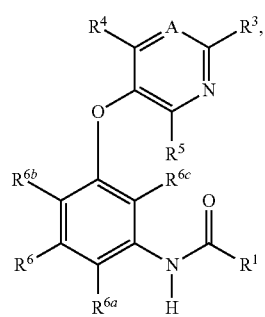
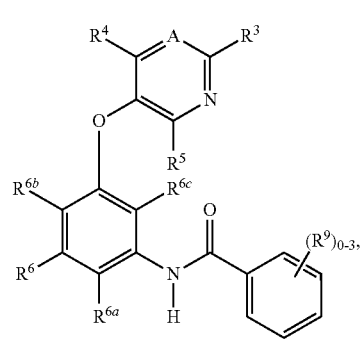
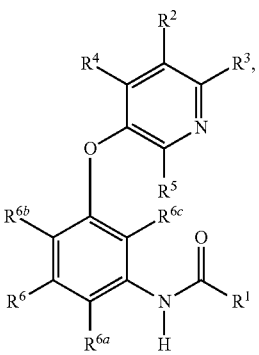
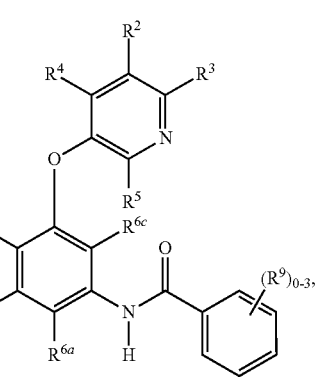
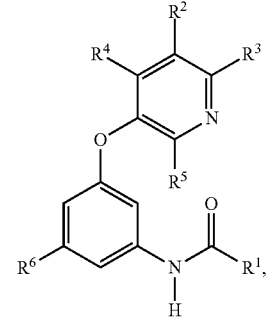
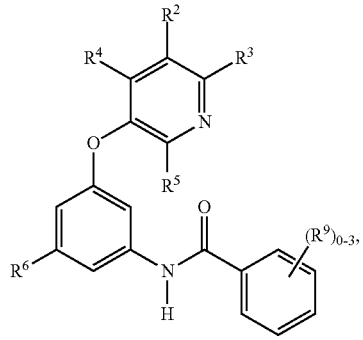
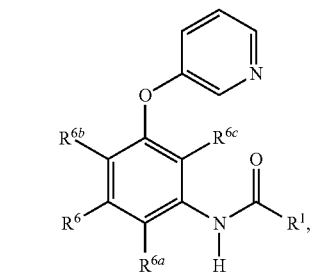

-continued
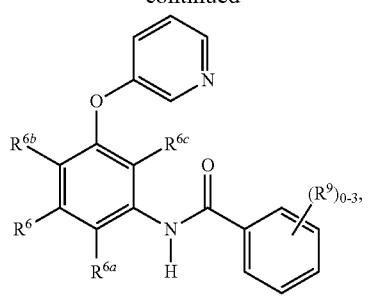
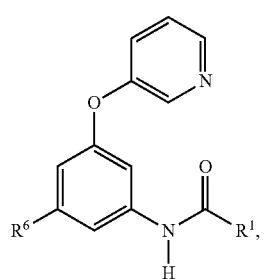
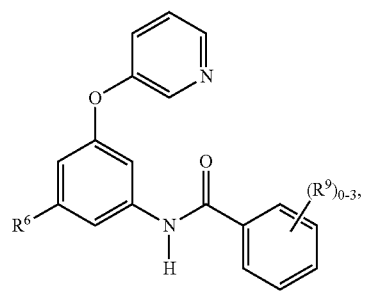
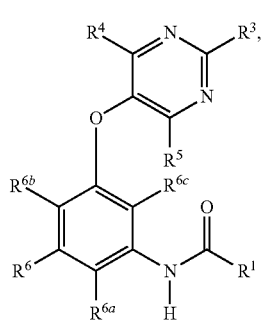
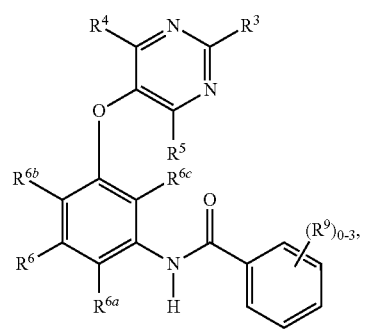
-continued
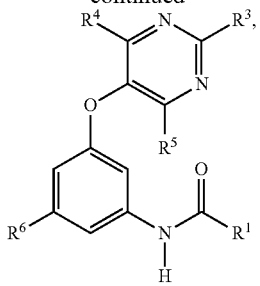
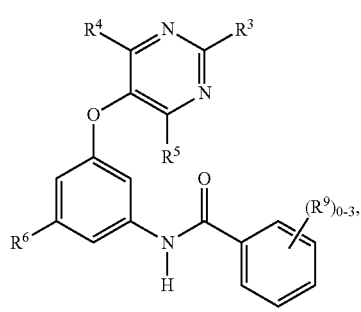
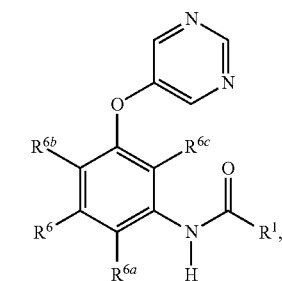
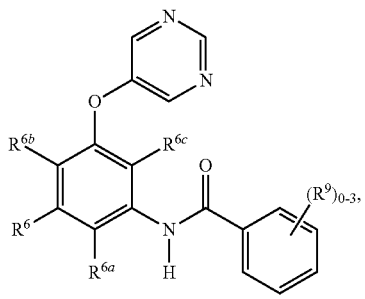
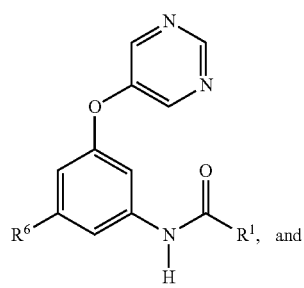 and

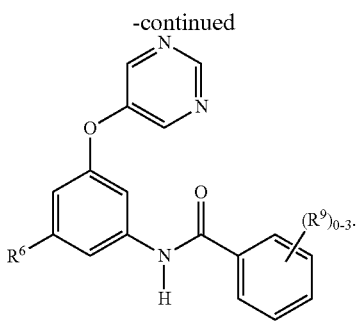

In a further aspect, a compound has a structure selected from:

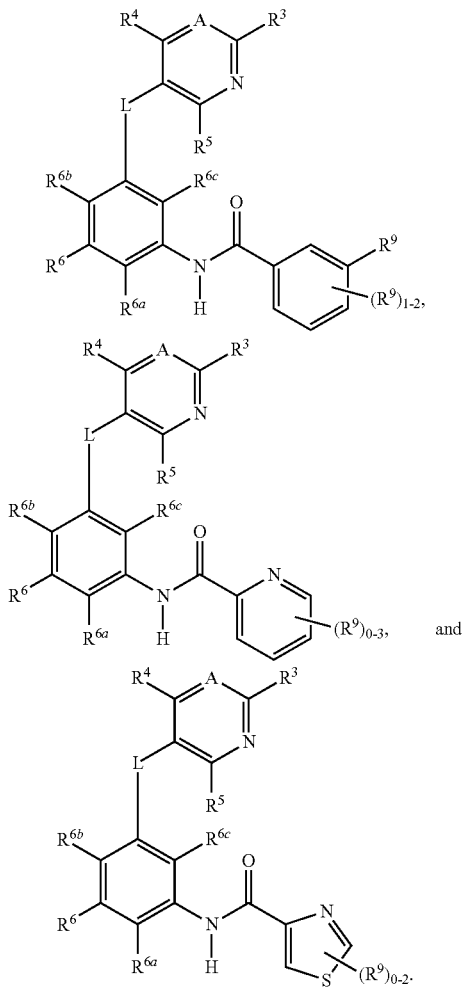

a. A Groups

In one aspect, A is $CR^2$ or N. In a further aspect, A is CH, and $R^3$, $R^4$, and $R^5$ are all H. In a yet further aspect, A is CH, $R^4$ and $R^5$ are H, and $R^3$ is $CH_3$. In a still further aspect, A is CH, $R^3$ and $R^4$ are H, and $R^5$ is $CH_3$. In an even further aspect, A is N and $R^3$, $R^4$, and $R^5$ are all H.

b. L Groups

In one aspect, L is O or $NR^7$. In a further aspect, L is O. In a yet further aspect, L is $NR^7$, wherein $R^7$ is alkyl or haloalkyl. In a still further aspect, L is $NR^7$, wherein $R^7$ is methyl or ethyl.

c. $R^1$ Groups

In one aspect, $R^1$ has from 1 to 10 carbons and is selected from phenyl substituted with 1-3 of $R^9$, wherein at least one $R^9$ is meta substituted; 2-pyridinyl substituted with 0-3 of $R^9$; and thiazole substituted with 0-2 of $R^9$. For example, $R^1$ can be phenyl substituted with 1-3 of $R^9$. That is, at least one $R^1$ group is present as a substituent on the phenyl group. As a further example, $R^1$ can be 2-pyridinyl substituted with 0-3 of $R^9$. As a yet further example, $R^1$ can be thiazole substituted with 0-2 of $R^9$. Various aspects of $R^1$ are shown below:

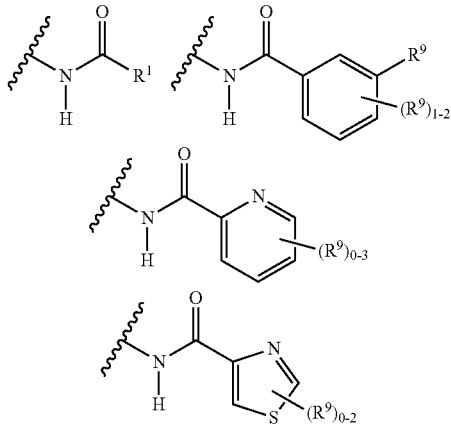

In one aspect, $R^1$ has from 1 to 10 carbons; wherein $R^1$ is selected from aryl, heteroaryl, cycloalkyl, and heterocycloalkyl; and wherein $R^1$ is substituted with 0-3 of $R^9$. In a further aspect, $R^1$ is phenyl substituted with 0-3 of $R^9$, and wherein $R^9$ is halogen, CN, alkyl, methyl. In a further aspect, $R^1$ is phenyl substituted with 0-3 of $R^9$. In a yet further aspect, $R^1$ is phenyl optionally substituted with 1-2 of $R^9$. In a still further aspect, $R^1$ is phenyl optionally substituted with 1 of $R^9$. $R^1$ is phenyl optionally substituted with 2 of $R^9$. In an even further aspect, $R^1$ is heterocyclic. In a further aspect, $R^1$ is selected from optionally substituted $C_3$-$C_8$ cycloalkyl, $C_3$-$C_8$ cycloalkenyl, $C_6$-$C_8$ cycloalkynyl, $C_3$-$C_8$ heterocycloalkyl, $C_3$-$C_8$ heterocycloalkenyl, and $C_6$-$C_8$ heterocycloalkynyl. In a yet further aspect, $R^1$ is selected from optionally substituted aryl, optionally substituted heteroaryl.

In a still further aspect, $R^1$ is selected from acridine, phenyl, benzyl, benzisoxazole, benzo[c]thiophene, benzofuran, benzothiazole, benzothiophene, benzoxazole, cinnoline, furan, imidazole, indazole, isobenzofuran, isoindole, isoquinoline, isoxazole, naphthalene, oxazole, purine, pyrazine, pyrazole, pyridazine, pyridine, pyrimidine, pyrrole, quinazoline, quinoline, quinoxaline, thiazole, and thiophene. In an even further aspect, $R^1$ is further substituted with 1-3 of $R^9$, for example, 1-2 of $R^9$, 2-3 of $R^9$, 1 of $R^9$, 2 of $R^9$, or 3 of $R^9$.

d. $R^2$ Groups

In one aspect, $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$. In a further aspect, $R^2$ is hydrogen, halogen, alkyl, haloalkyl, alkoxy. In a yet further aspect, $R^2$ is hydrogen. In a still further aspect, $R^2$ is halogen, alkyl, haloalkyl, alkoxy.

e. $R^3$ Groups

In one aspect, $R^3$ is selected from hydrogen, halogen, C1-C6 alkyl, C1-C6 haloalkyl, C1-C6 alkoxy, hydroxyl, CN, $SO_2R^8$, and $COR^8$. In a further aspect, $R^3$ is halogen, alkyl, haloalkyl, alkoxy, hydroxyl, CN, $SO_2R^8$, or $COR^8$. In a still further aspect. In an even further aspect, $R^3$ is alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

f. $R^4$ Groups

In one aspect, $R^4$ is hydrogen, halogen, C1-C6 alkyl, C1-C6 haloalkyl, C1-C6 alkoxy, and C1-C6 haloalkoxyNO$_2$, CN, SO$_2R^8$, or COR$^8$. In a further aspect, $R^4$ is hydrogen. In a yet further aspect, $R^4$ is halogen, alkyl, haloalkyl, alkoxy, amino, hydroxyl, alkylamino, dialkylamino, NO$_2$, CN, SO$_2R^8$, or COR$^8$. In a still further aspect, $R^4$ is alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

g. $R^5$ Groups

In one aspect, $R^5$ is hydrogen, halogen, C1-C6 alkyl, C1-C6 haloalkyl, C1-C6 alkoxy, and C1-C6 haloalkoxyNO$_2$, CN, SO$_2R^8$, or COR$^8$. In a further aspect, $R^5$ is hydrogen. In a yet further aspect, $R^5$ is halogen, alkyl, haloalkyl, alkoxy, amino, hydroxyl, alkylamino, dialkylamino, NO$_2$, CN, SO$_2R^8$, or COR$^8$. In a still further aspect, $R^5$ is alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

h. $R^6$ Groups

In one aspect, $R^6$ is hydrogen, halogen, CN, C1-C4 alkyl, and C1-C4 haloalkyl. In a further aspect, $R^6$ is hydrogen. In a yet further aspect, $R^6$ is selected from halogen, CN, C1-C4 alkyl, and C1-C4 haloalkyl. In a still further aspect, $R^6$ is selected from hydrogen, halogen, and CN. In an even further aspect, $R^6$ is selected from C1-C4 alkyl and C1-C4 haloalkyl.

i. $R^{6A}$ Groups

In one aspect, $R^{6a}$, $R^{6b}$, and $R^{6c}$ are independently hydrogen, halogen, C1-C6 alkyl, C1-C6 haloalkyl, C1-C6 alkoxy, amino, hydroxyl, alkylamino, dialkylamino, CN, SO$_2R^8$, and COR$^8$. In a yet further aspect, $R^{6a}$ is selected from halogen, CN, C1-C4 alkyl, and C1-C4 haloalkyl. In a still further aspect, $R^{6a}$ is selected from hydrogen, halogen, and CN. In an even further aspect, $R^{6a}$ is selected from C1-C4 alkyl and C1-C4 haloalkyl.

j. $R^{6B}$ Groups

In one aspect, $R^{6a}$, $R^{6b}$, and $R^{6c}$ are independently hydrogen, halogen, C1-C6 alkyl, C1-C6 haloalkyl, C1-C6 alkoxy, amino, hydroxyl, alkylamino, dialkylamino, CN, SO$_2R^8$, and COR$^8$. In a yet further aspect, $R^{6b}$ is selected from halogen, CN, C1-C4 alkyl, and C1-C4 haloalkyl. In a still further aspect, $R^{6b}$ is selected from hydrogen, halogen, and CN. In an even further aspect, $R^{6b}$ is selected from C1-C4 alkyl and C1-C4 haloalkyl.

k. $R^6$ Groups

In one aspect, $R^{6a}$, $R^{6b}$, and $R^{6c}$ are independently hydrogen, halogen, C1-C6 alkyl, C1-C6 haloalkyl, C1-C6 alkoxy, amino, hydroxyl, alkylamino, dialkylamino, CN, SO$_2R^8$, and COR$^8$. In a yet further aspect, $R^{6c}$ is selected from halogen, CN, C1-C4 alkyl, and C1-C4 haloalkyl. In a still further aspect, $R^{6c}$ is selected from hydrogen, halogen, and CN. In an even further aspect, $R^{6c}$ is selected from C1-C4 alkyl and C1-C4 haloalkyl.

l. $R^7$ Groups

In one aspect, $R^7$ is hydrogen, C1-C6 alkyl, or C1-C6 haloalkyl. In a further aspect, $R^7$ is hydrogen. In a yet further aspect, $R^7$ is alkyl or haloalkyl. In a still further aspect, $R^7$ is alkyl selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

m. $R^8$ Groups

In one aspect, $R^8$ is C1-C6 alkyl, C1-C6 cycloalkyl, amino, alkylamino, or dialkylamino. In a further aspect, $R^8$ is selected from alkyl, cycloalkyl, amino, alkylamino, and dialkylamino. In a yet further aspect, $R^8$ is selected from alkyl and cycloalkyl. In further aspects, $R^8$ can be selected from methyl, ethyl, n-propyl, i-propyl, cyclopropyl, n-butyl, i-butyl, s-butyl, cyclobutyl, n-pentyl, i-pentyl, s-pentyl, neopentyl, cyclopentyl, n-hexyl, i-hexyl, s-hexyl, dimethylbutyl, or cyclohexyl.

n. $R^9$ Groups

In one aspect, each $R^9$ when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, NO$_2$, CN, SO$_2R^8$, or COR$^8$. In a further aspect, at least one $R^9$ is present and each $R^9$ is independently selected from alkyl, halogen, haloalkyl, alkoxy, amino, hydroxyl, alkylamino, dialkylamino, NO$_2$, CN, SO$_2R^8$, and COR$^8$. In a yet further aspect, at least one $R^9$ is present and each $R^9$ is independently selected from alkyl, halogen, haloalkyl, alkoxy, amino, hydroxyl, alkylamino, dialkylamino, and CN. In a still further aspect, at least one $R^9$ is present and each $R^9$ is independently selected from alkyl, halogen, and haloalkyl.

In a further aspect, the compound is not N-(3-amino-5-(pyridin-3-yloxy)phenyl)-3-chlorobenzamide. In another example, the compound is not N-(3-(pyridin-3-yloxy)phenyl)-1H-benzo[d]imidazole-2-carboxamide.

It is contemplated that the disclosed compounds can be used in connection with the disclosed methods, compositions, products, uses, and kits.

2. Example Structures

In one aspect, a compound can be present as:

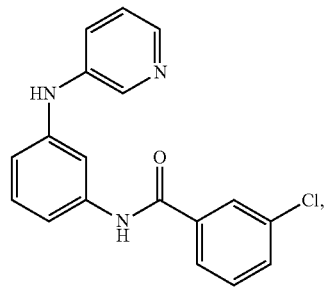

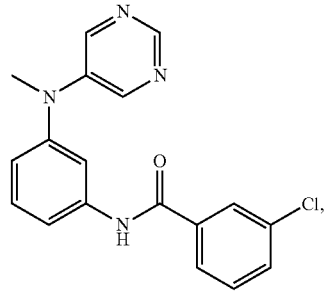

-continued
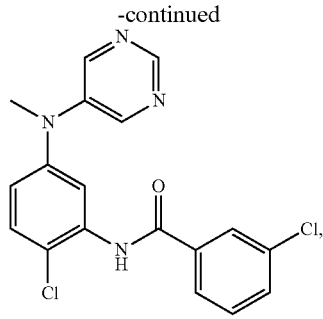
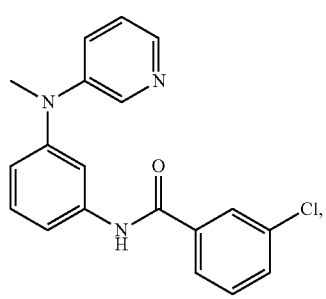
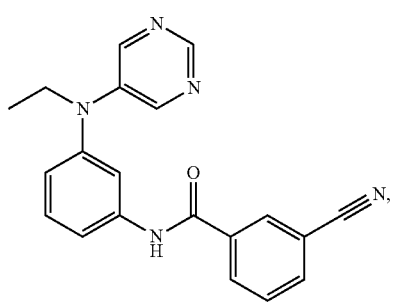
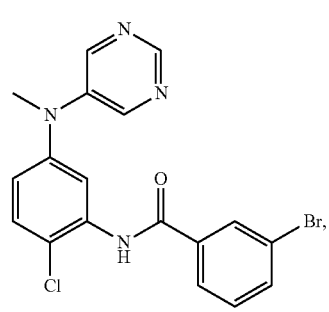
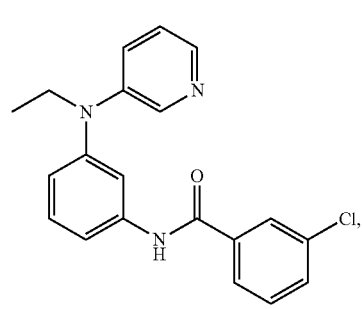
-continued
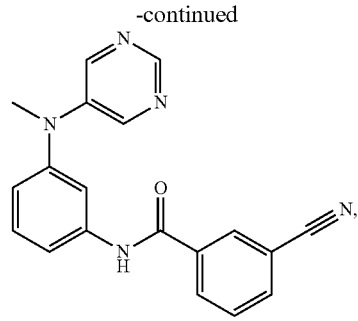
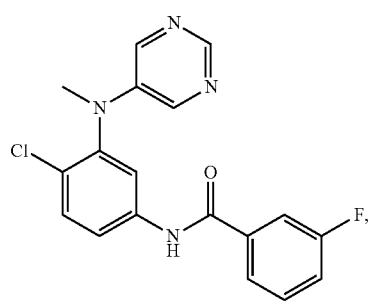
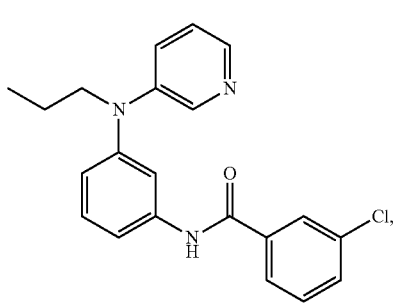
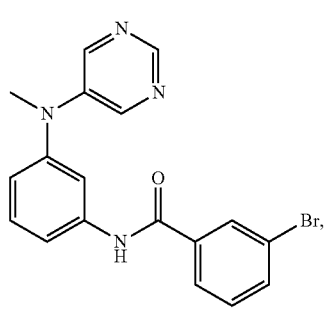
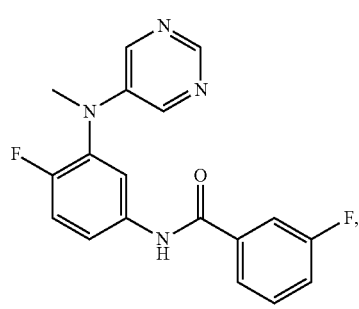

-continued

-continued
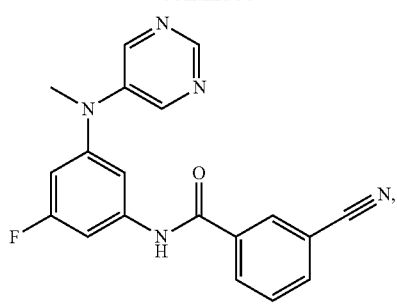
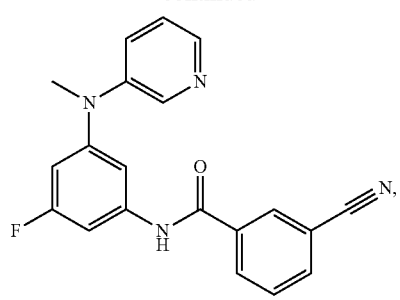
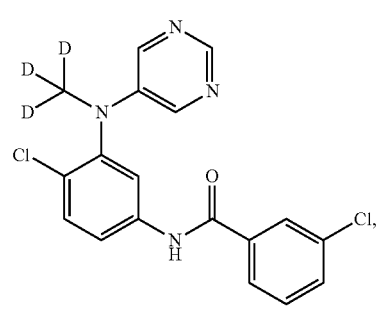
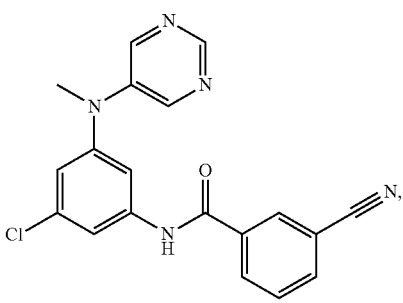
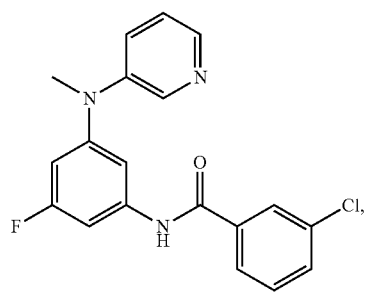
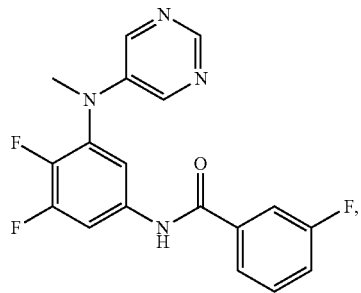
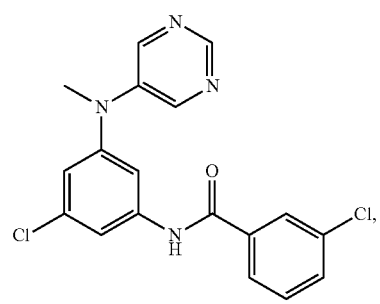
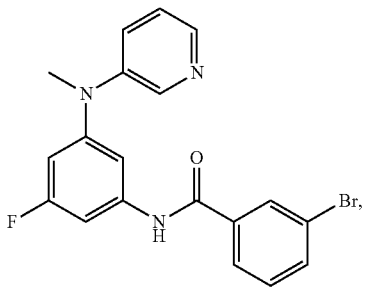
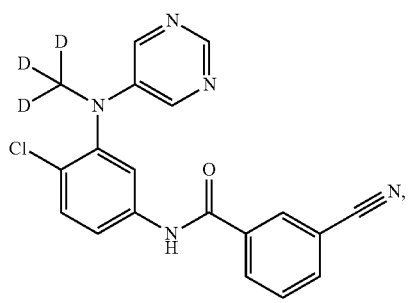
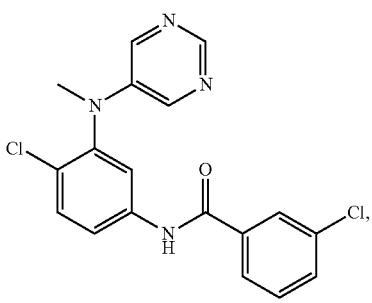

-continued
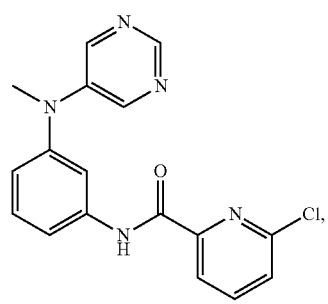
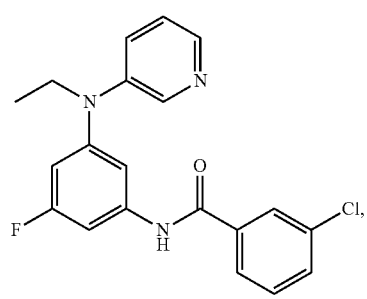
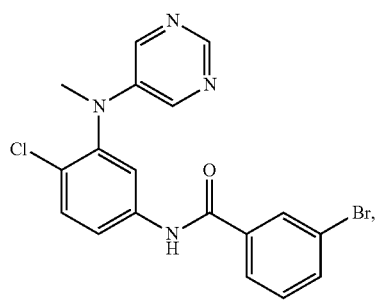
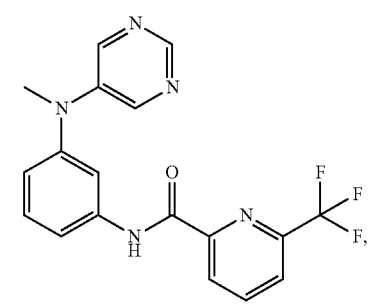
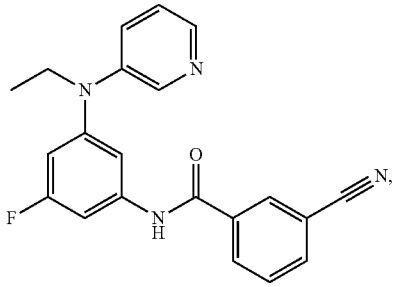
-continued
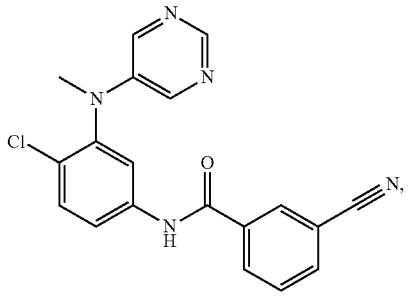
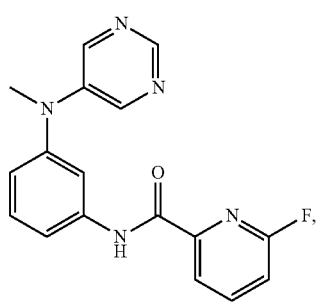
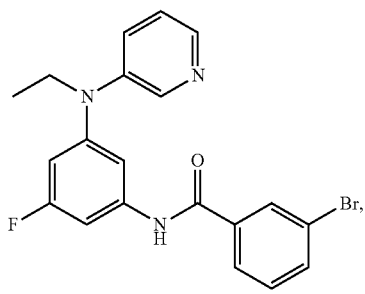
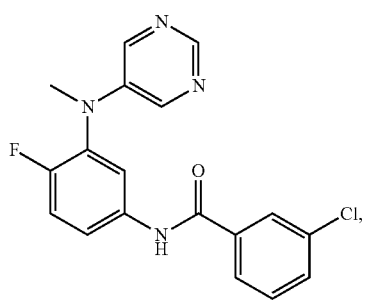
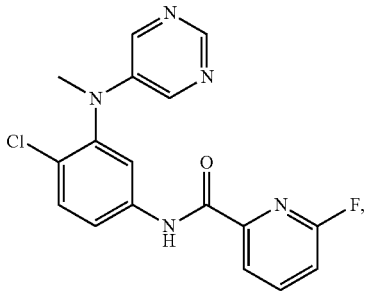

49
-continued
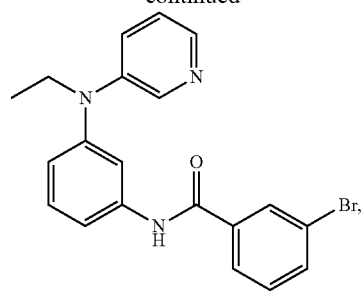
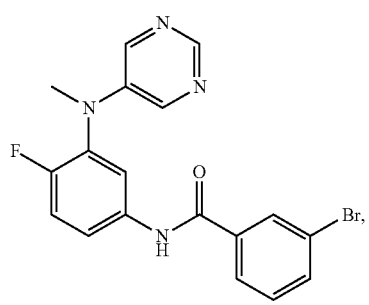
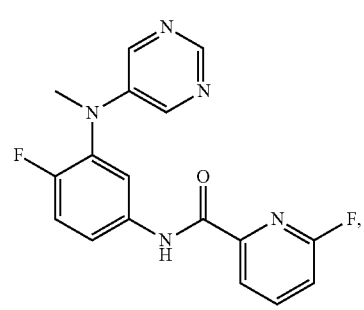
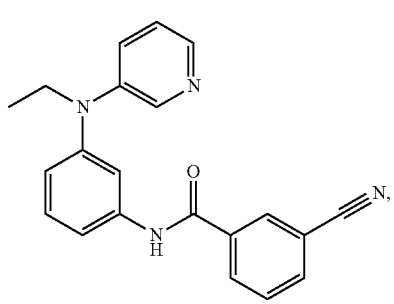
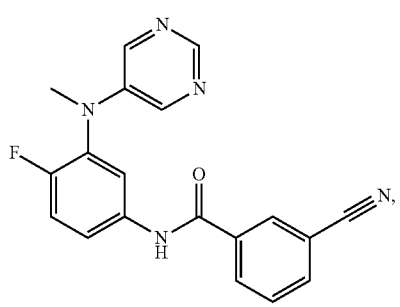
50
-continued
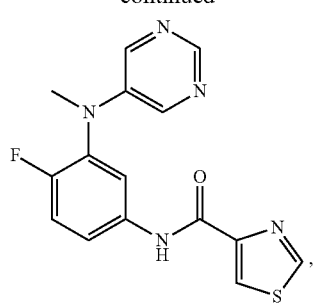
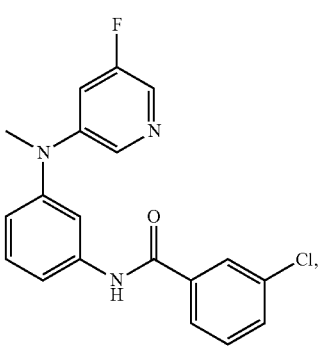
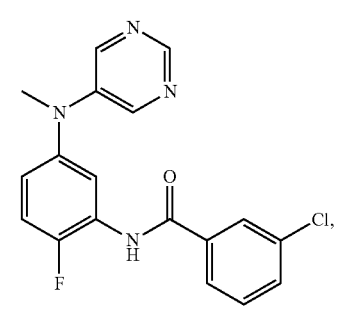
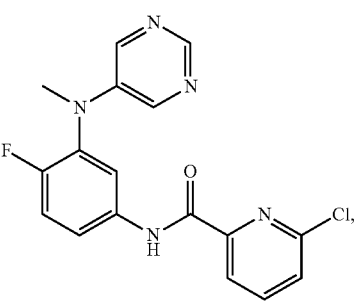
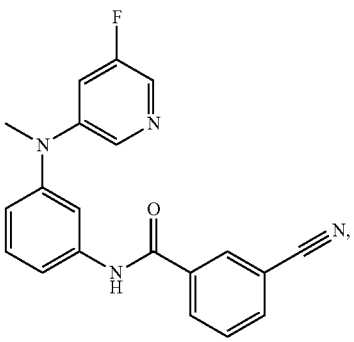

-continued
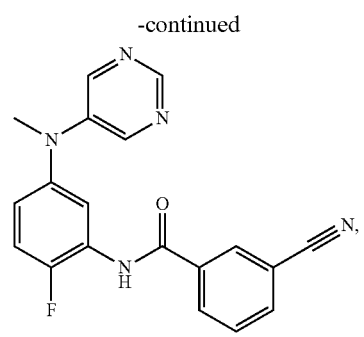
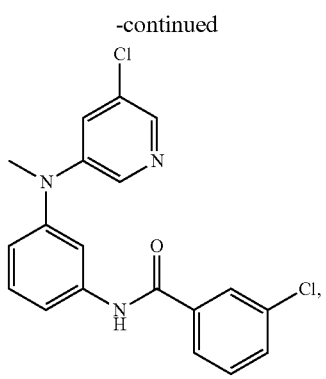
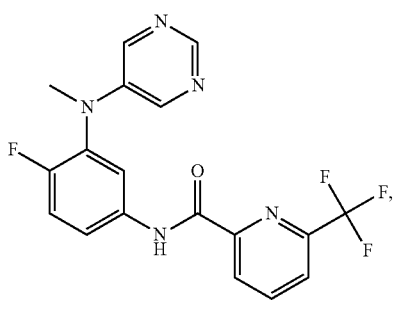
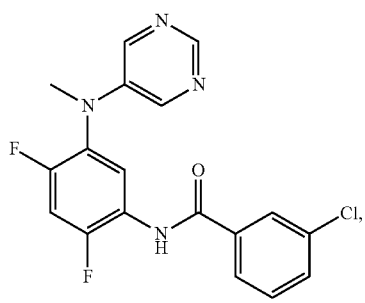
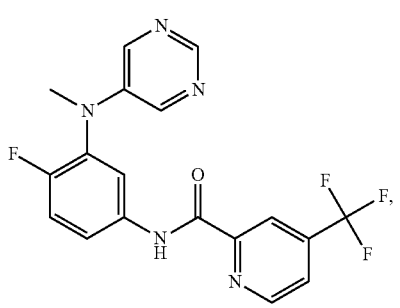
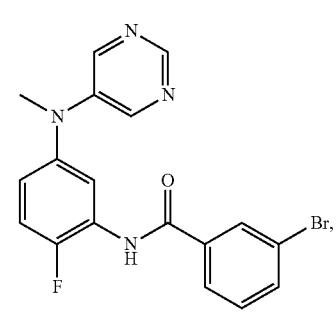
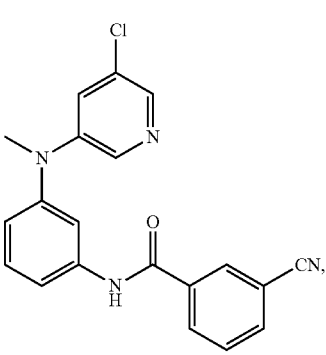
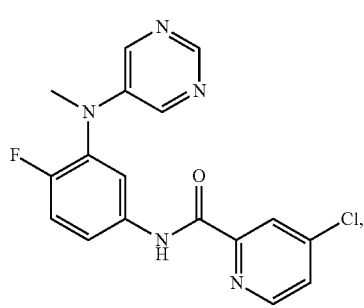
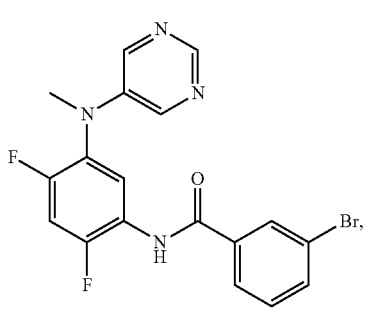

-continued
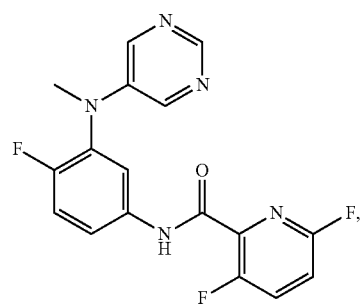
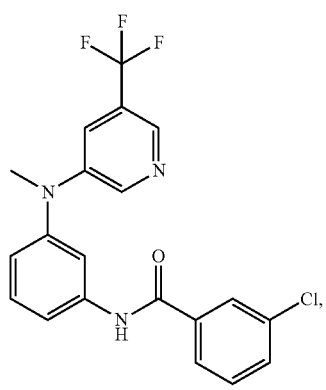
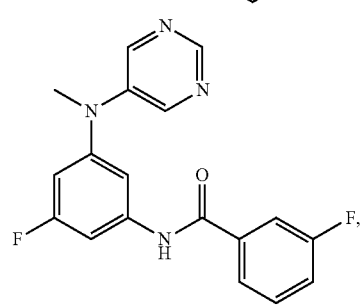
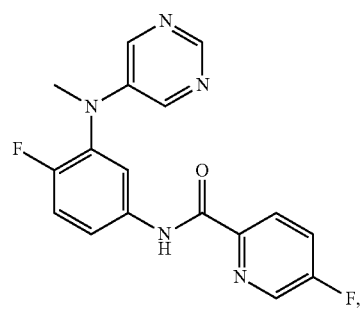
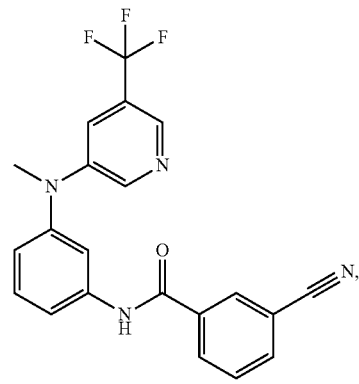
-continued
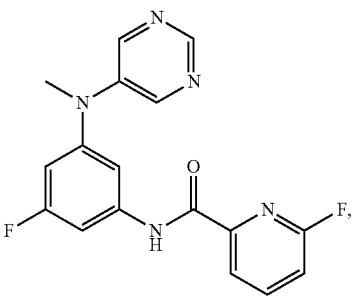
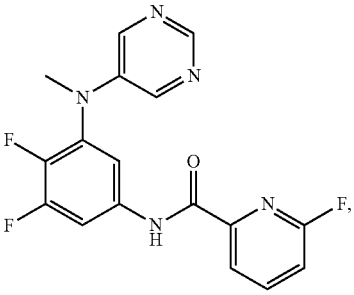
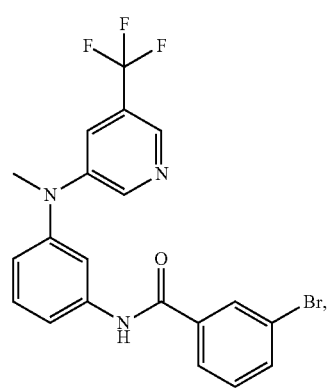
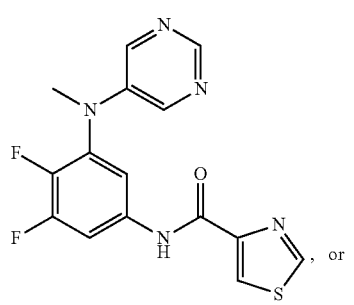, or
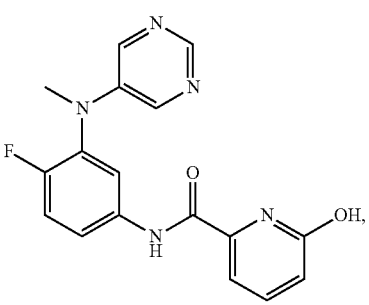

In a further aspect, a compound can be present as:
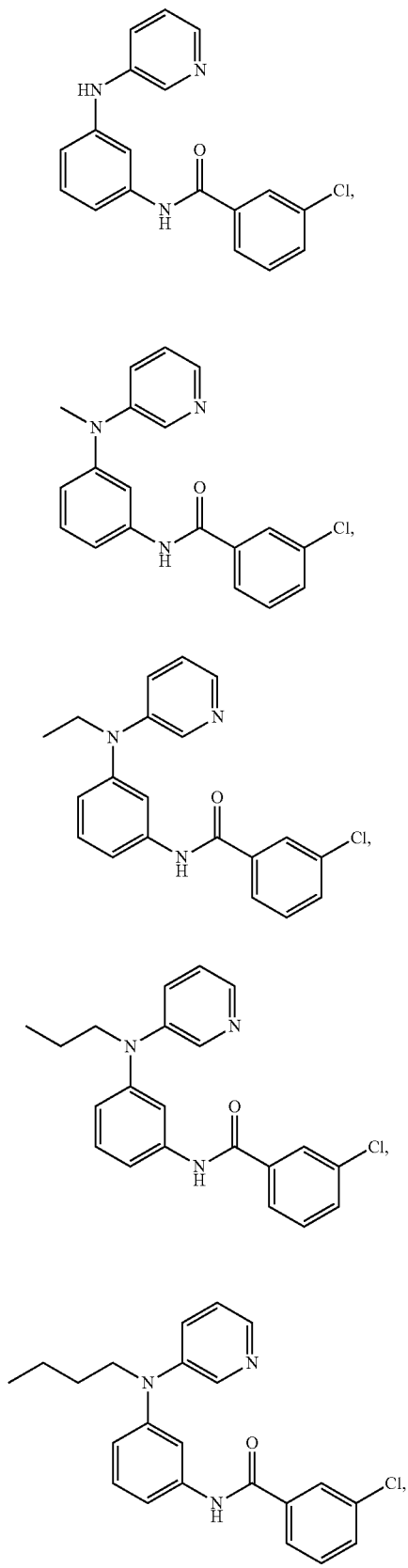

-continued
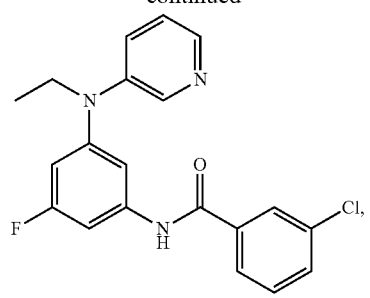
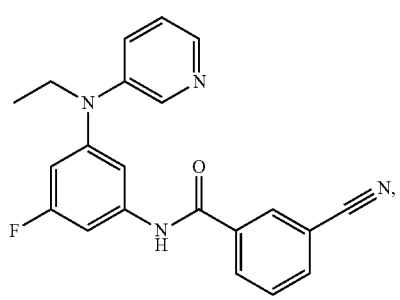

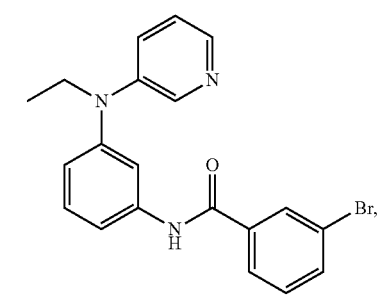
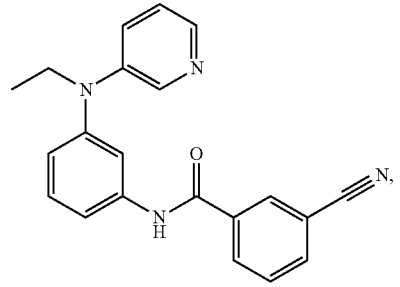
-continued
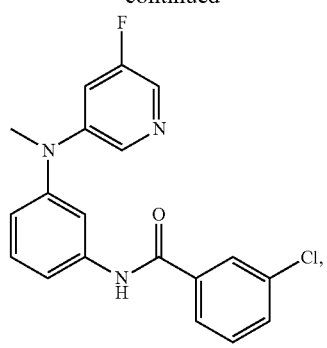
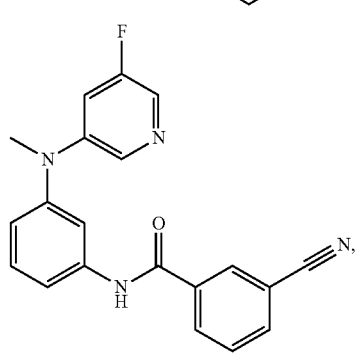
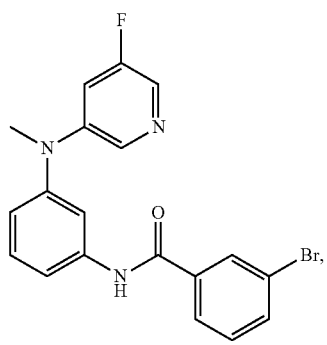
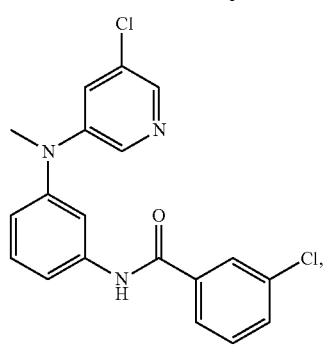
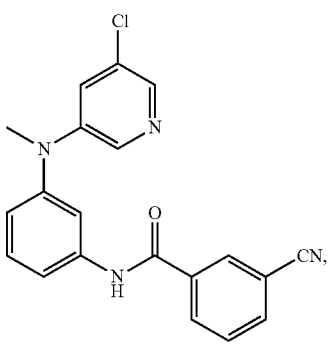

-continued
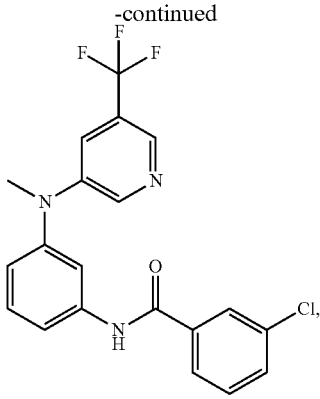
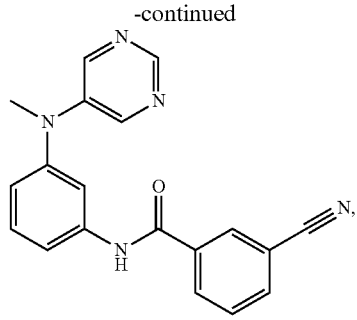
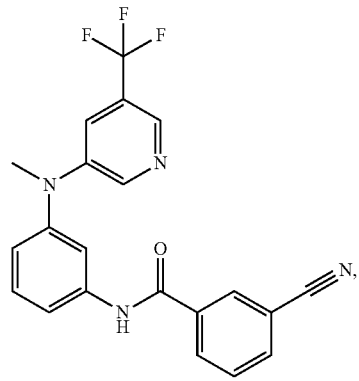
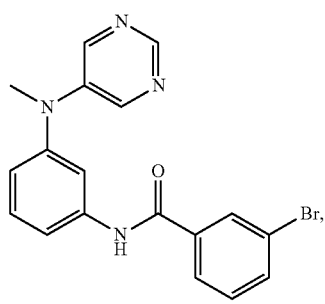
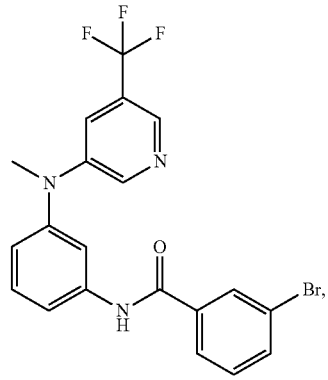
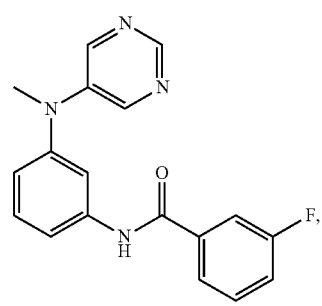
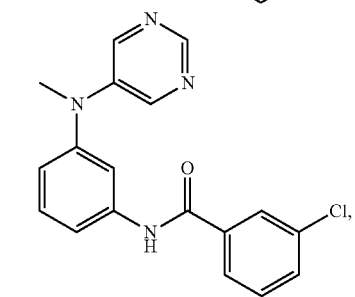
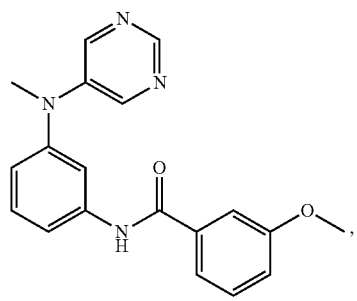
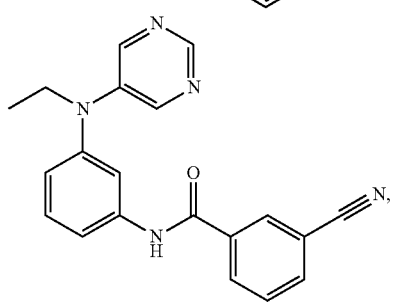

-continued
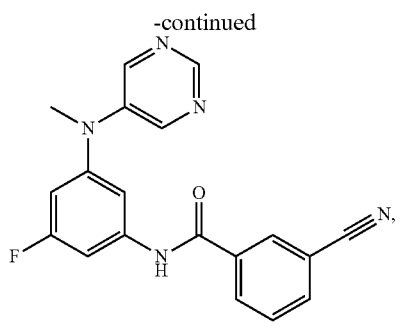
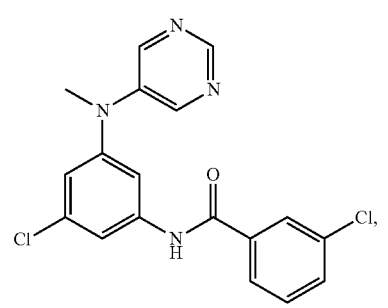
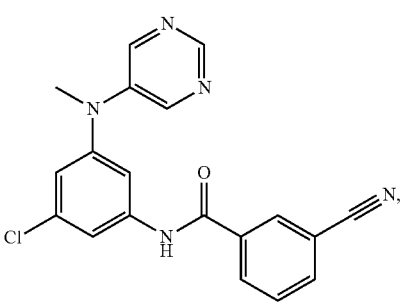
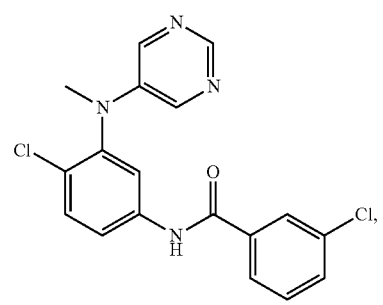
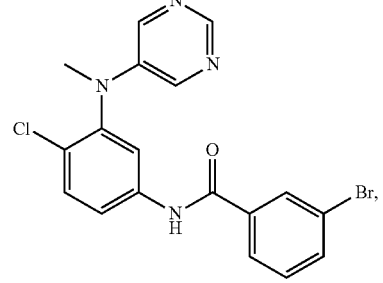
-continued
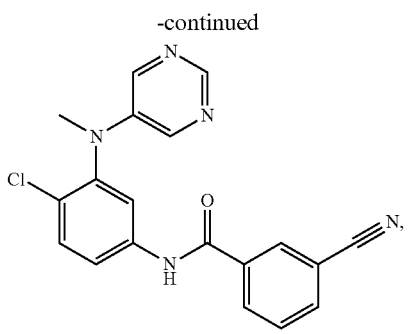
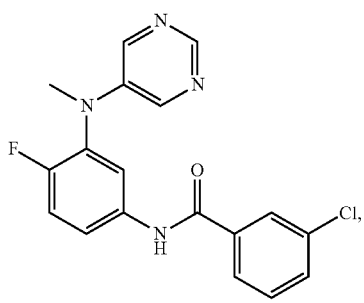
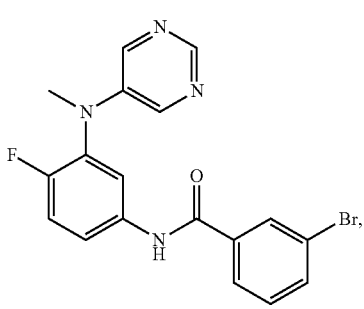
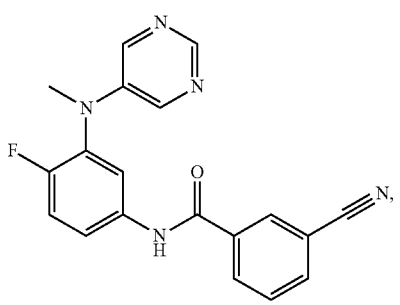
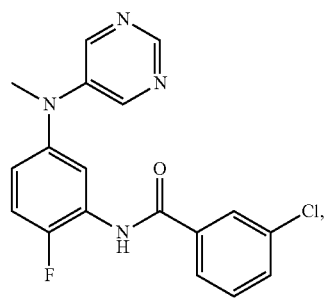

-continued
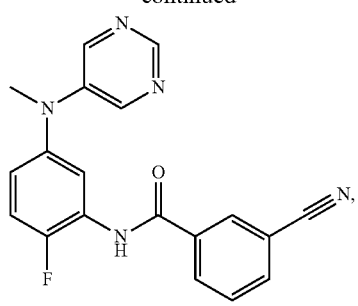
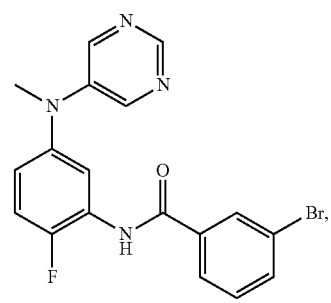
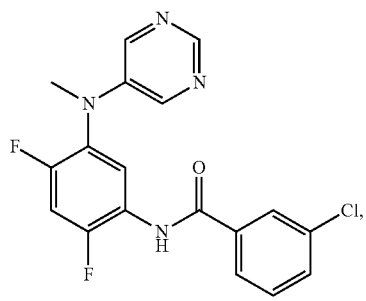
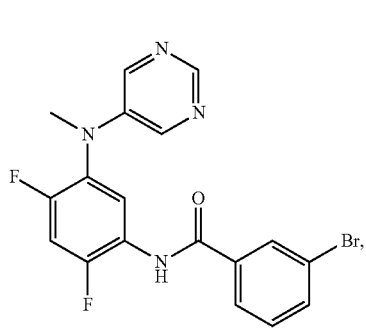
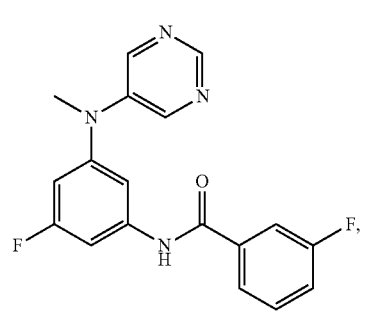
-continued
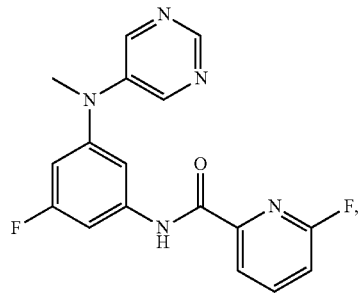
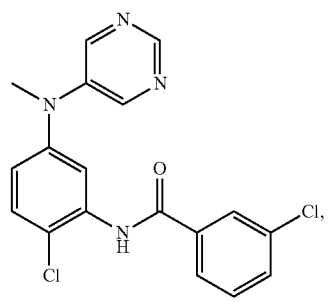
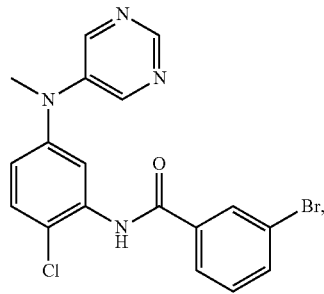
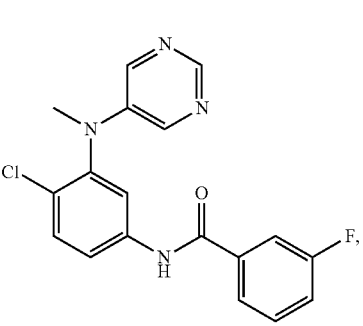
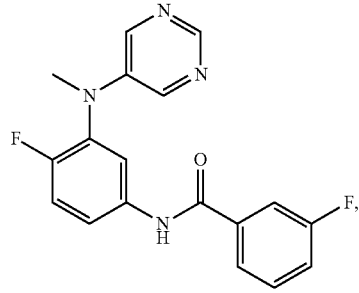

-continued
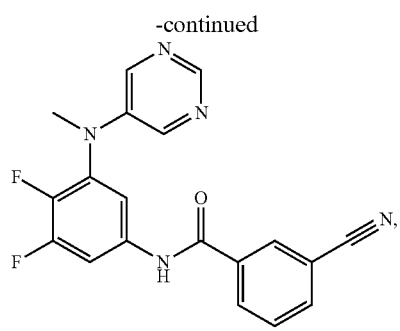
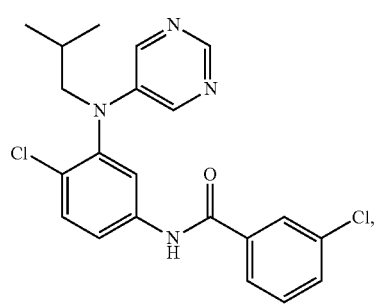
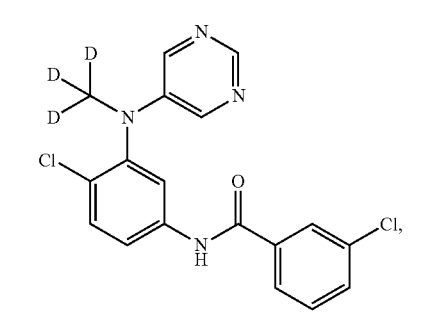
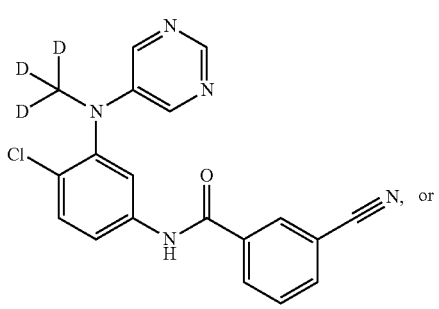
-continued
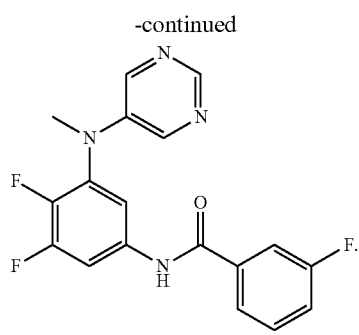
In a still further aspect, a compound can be present as:
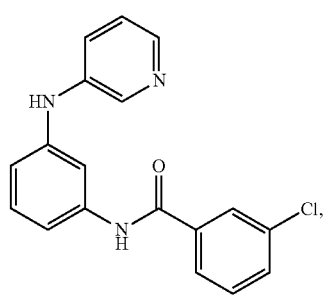
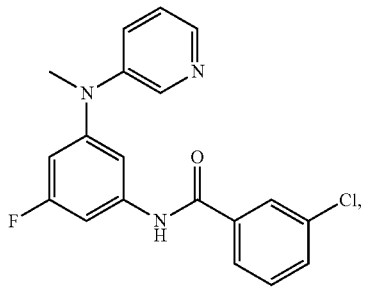
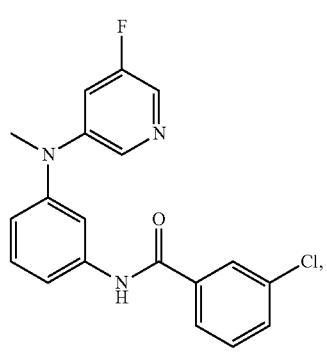
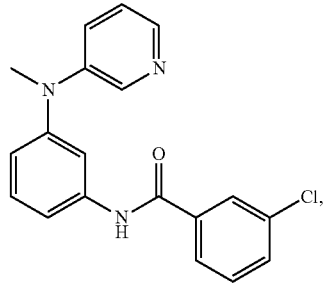

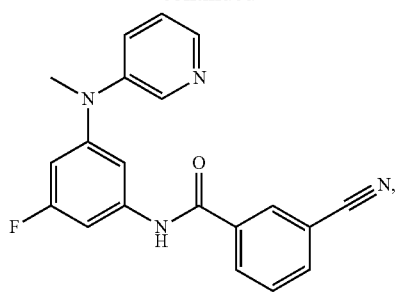
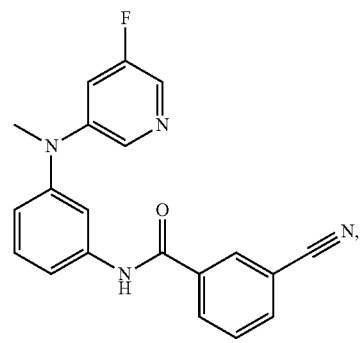
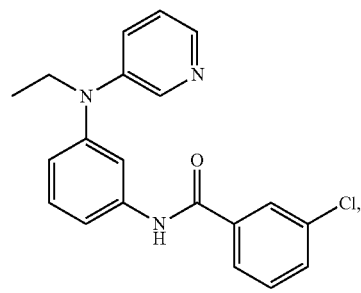
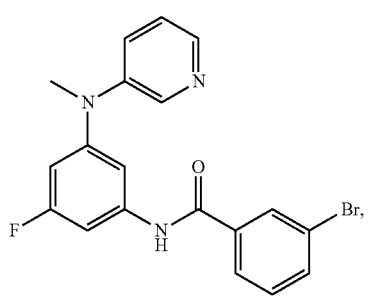
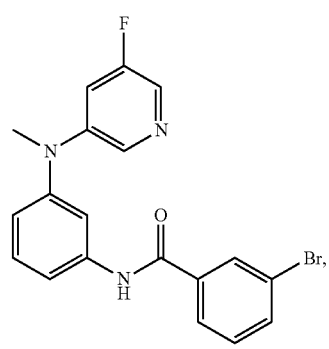
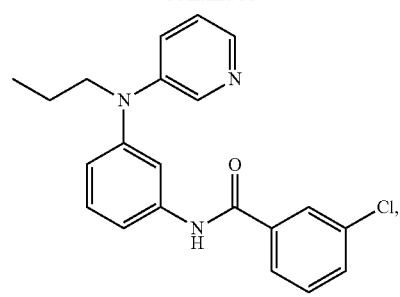
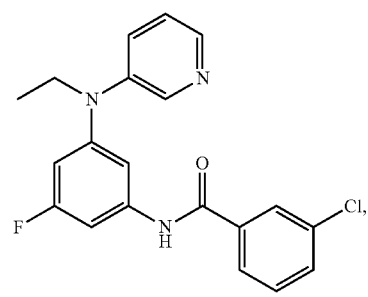
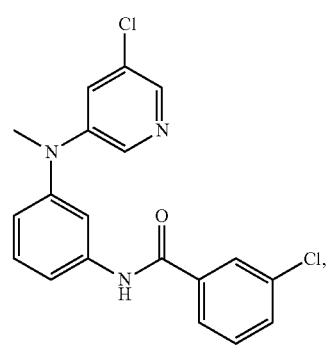
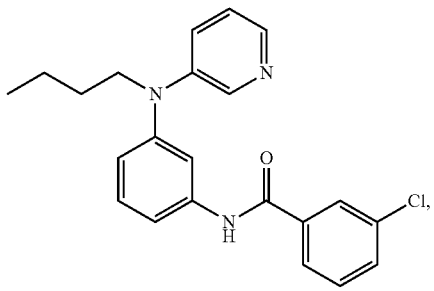
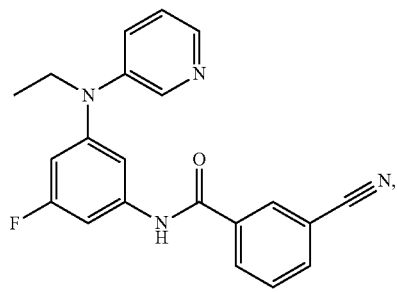

-continued
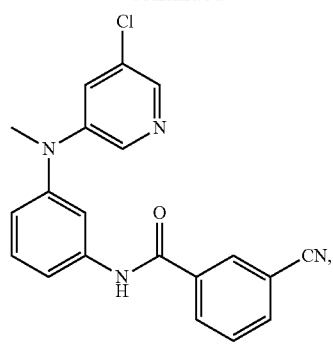
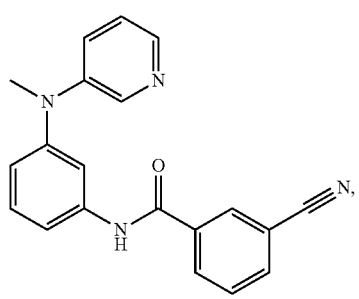
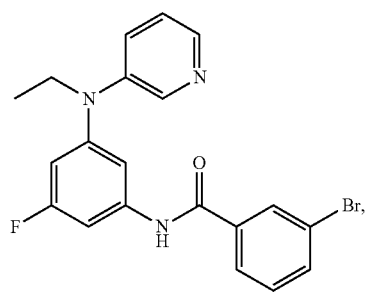
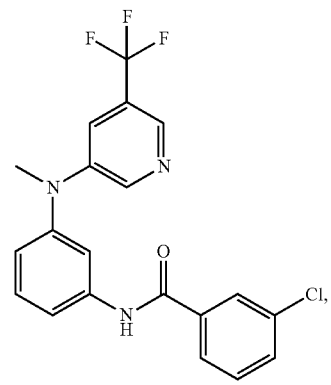
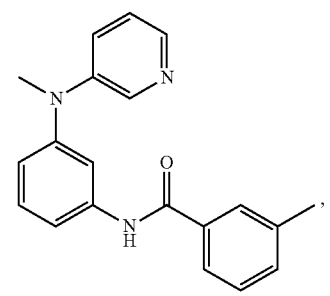
-continued
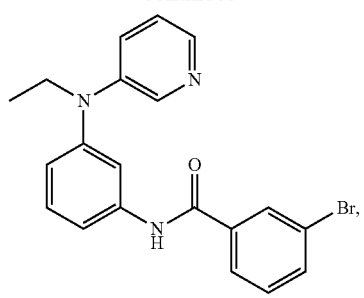
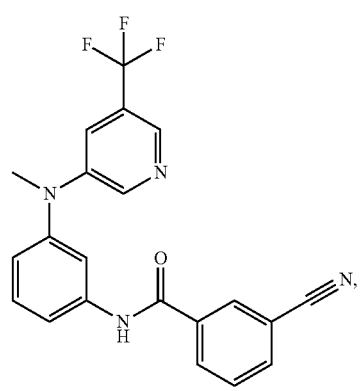
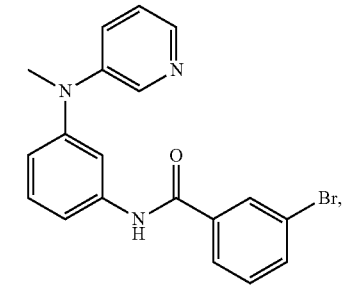
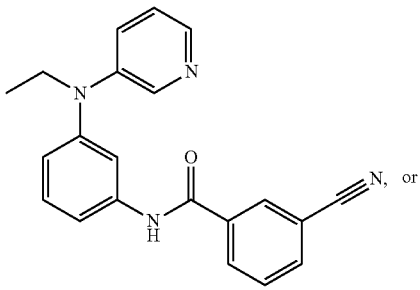, or
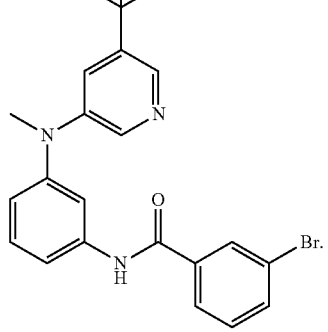

In a further aspect, a compound can be present as:
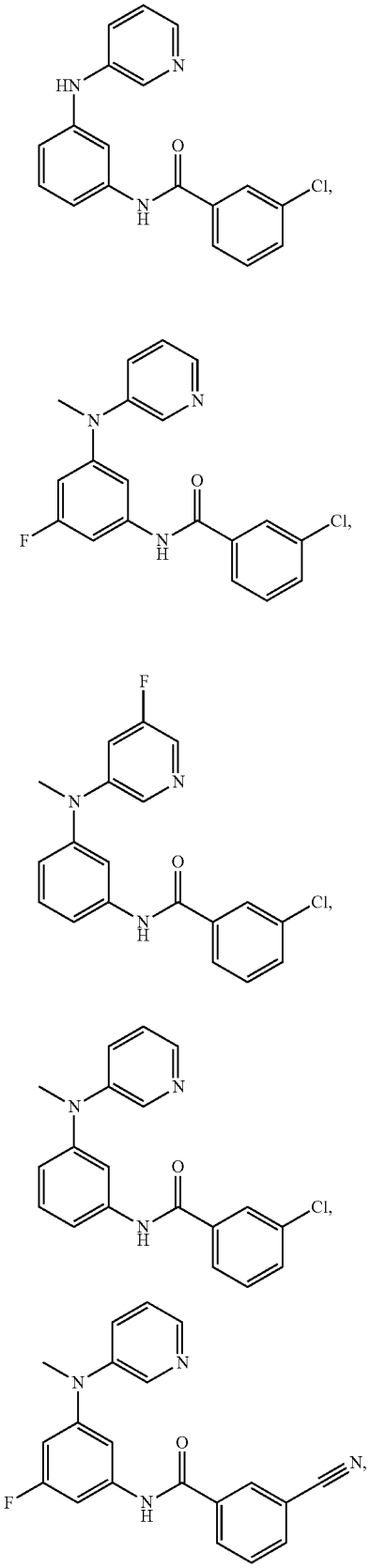
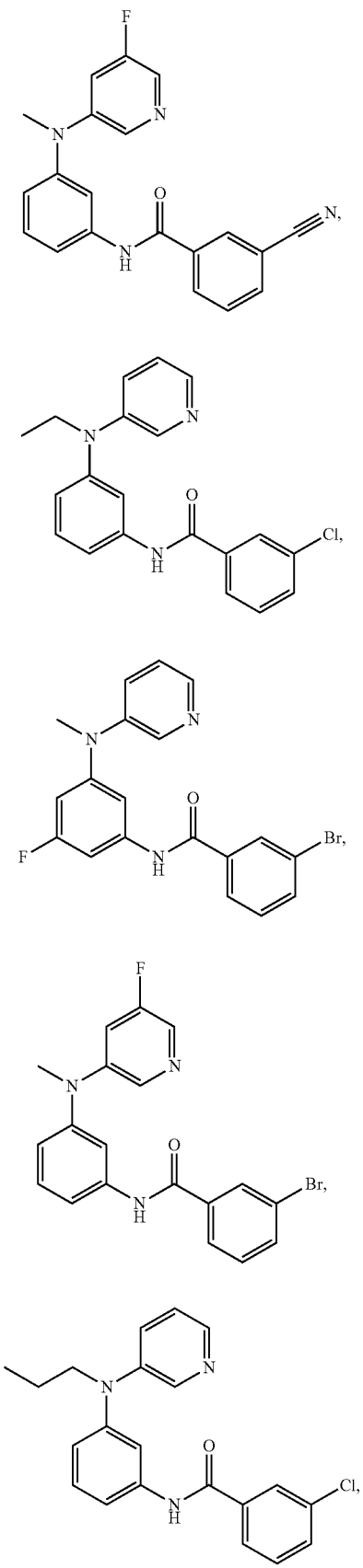

-continued
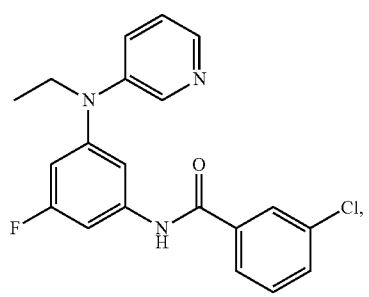
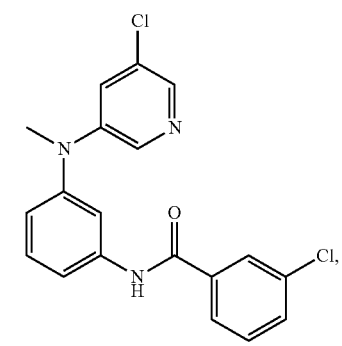
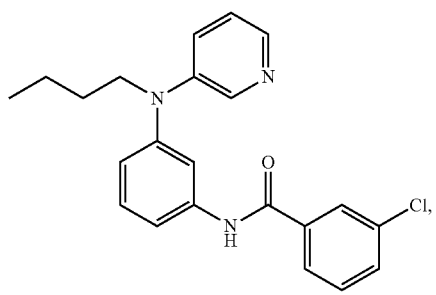
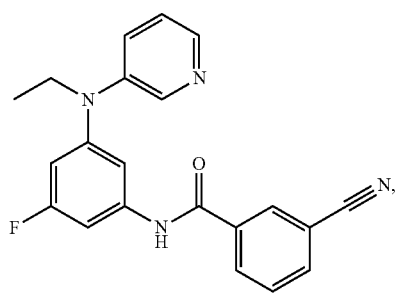
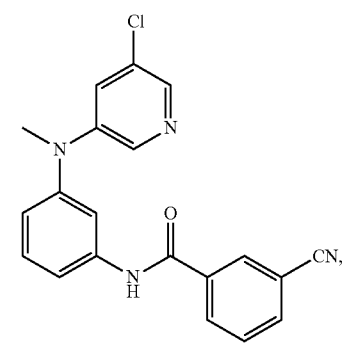
-continued
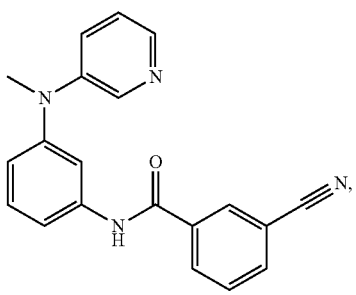
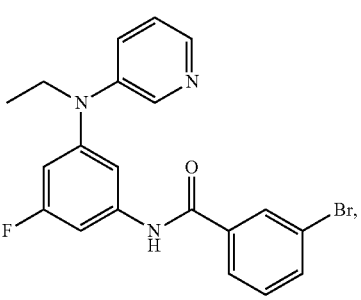
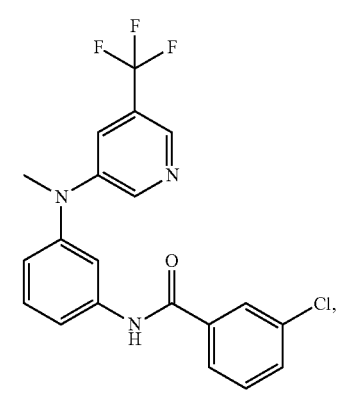
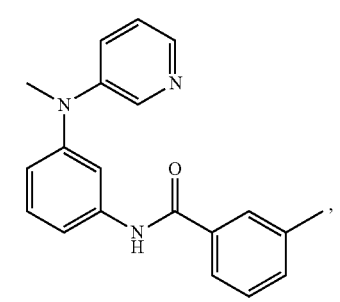
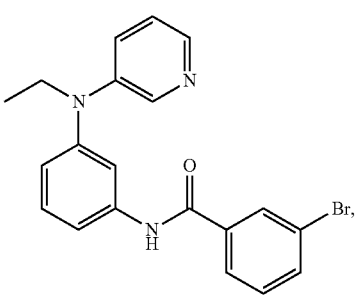

-continued
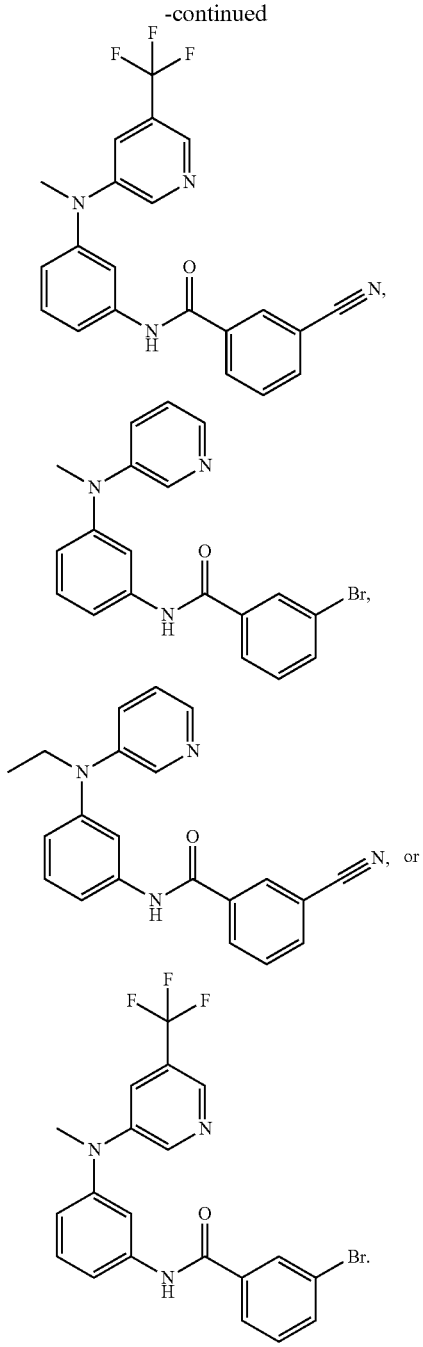
In a further aspect, a compound can be present as:
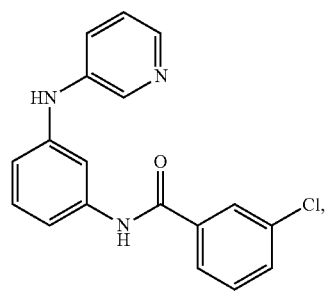
-continued
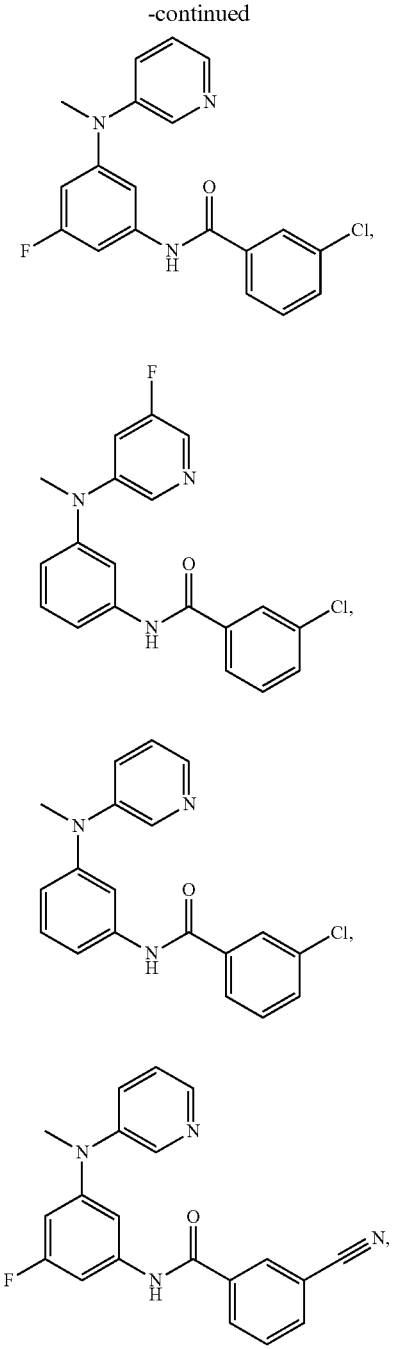
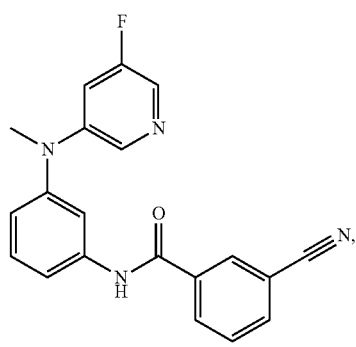

-continued
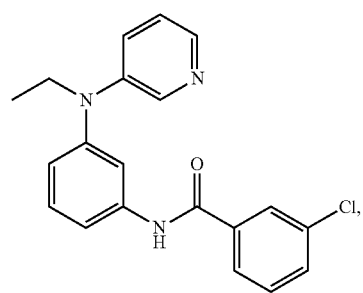
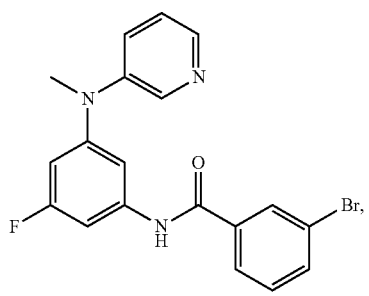
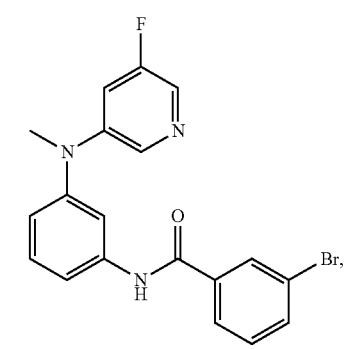
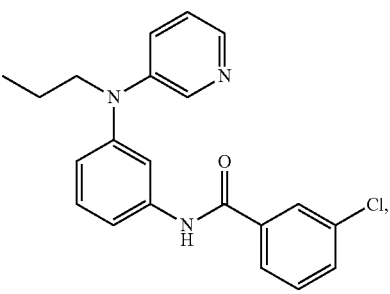
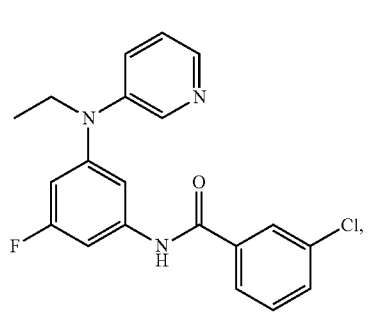
-continued
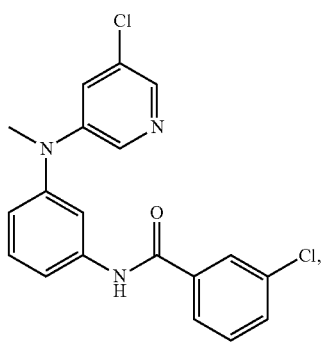
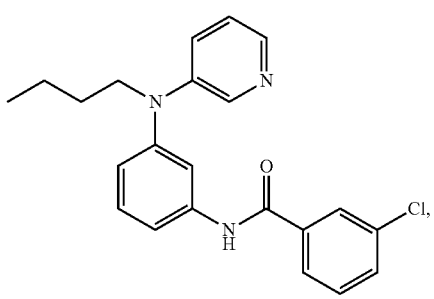
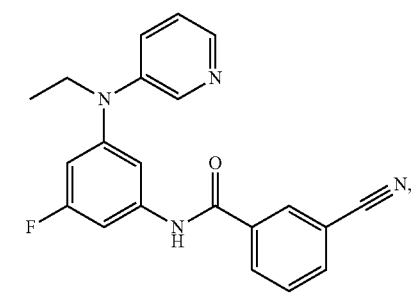
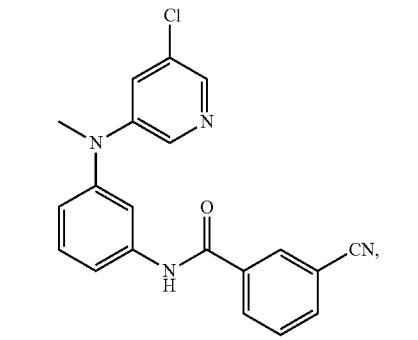
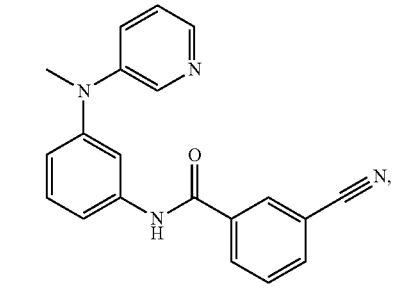

-continued
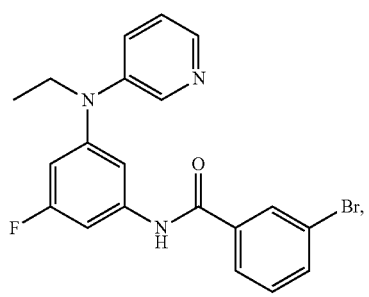
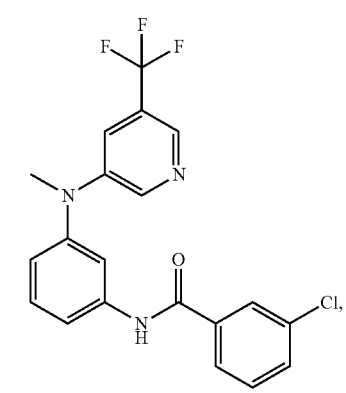
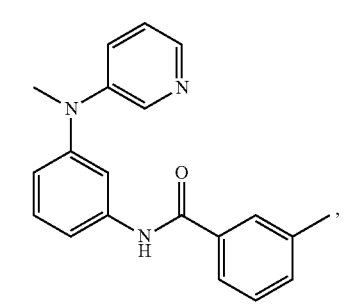
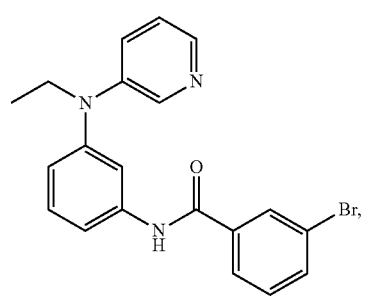
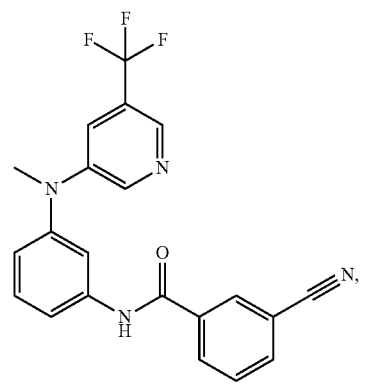
-continued
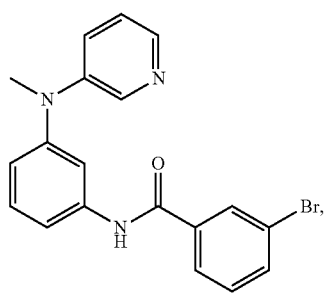
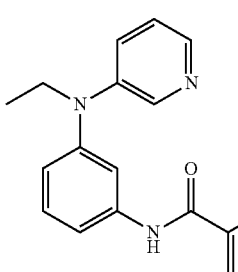
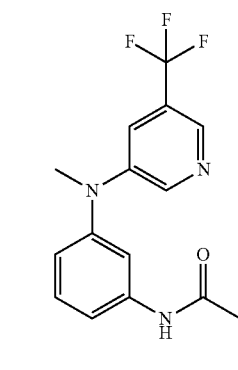
In a further aspect, a compound can be present as:
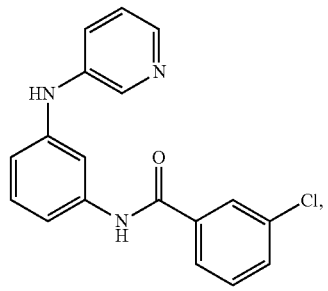
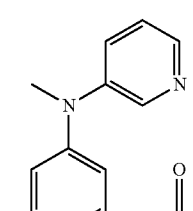

-continued
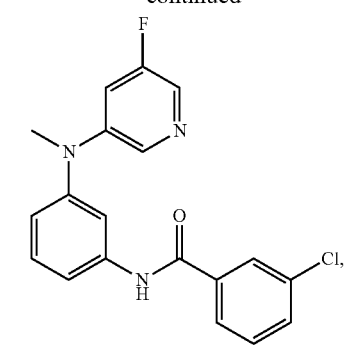
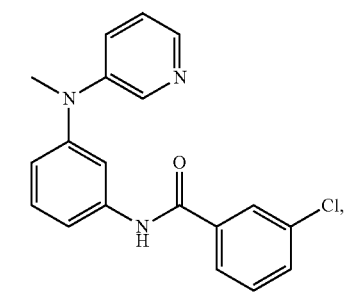
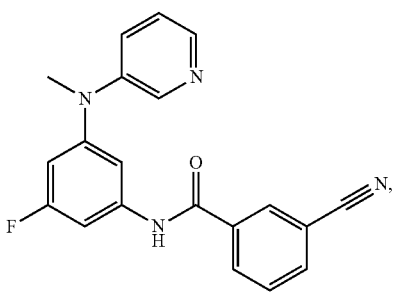
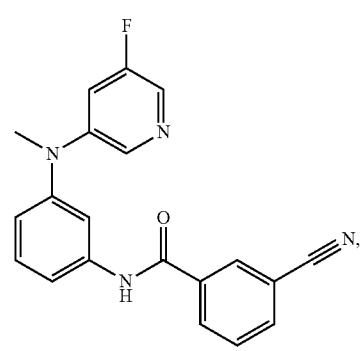
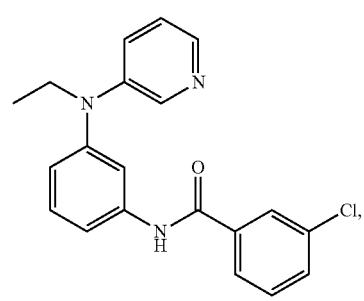
-continued
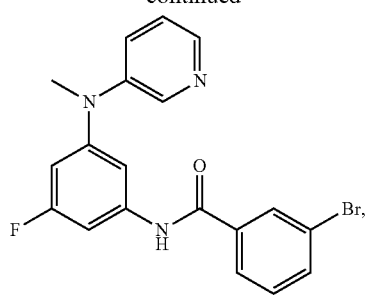
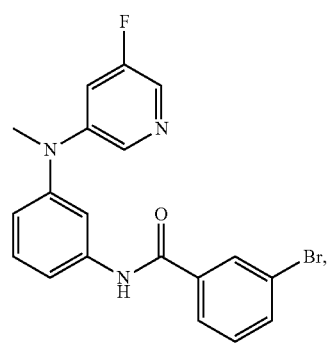
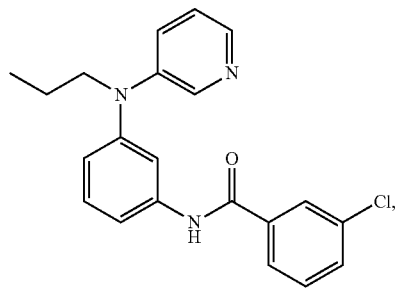
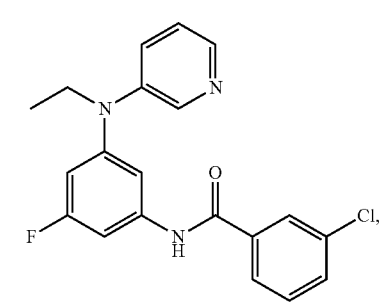
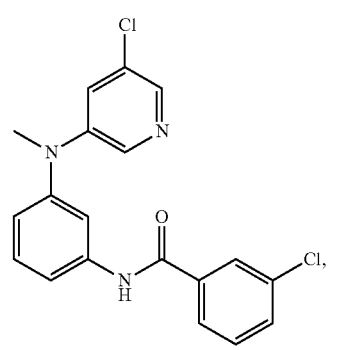

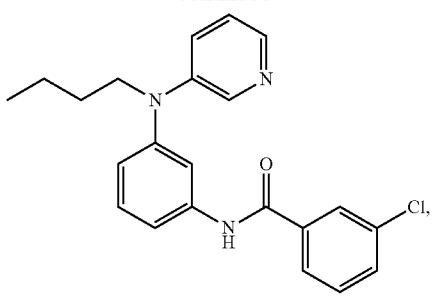
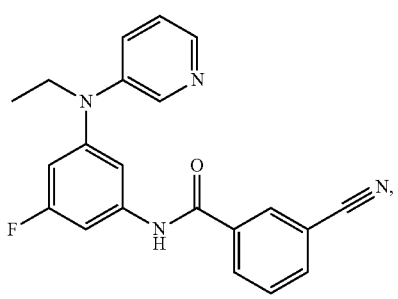
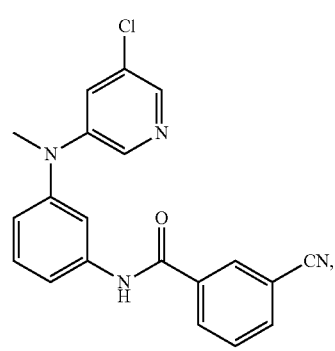
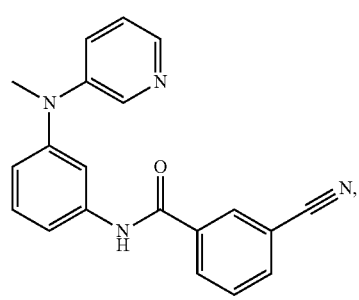
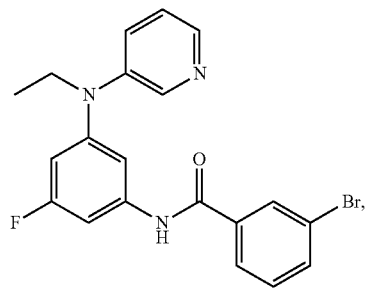
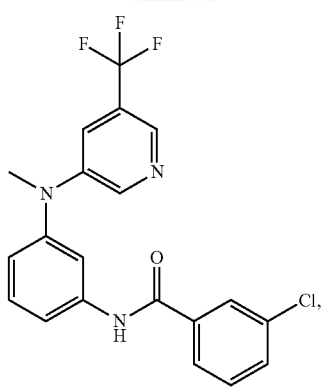
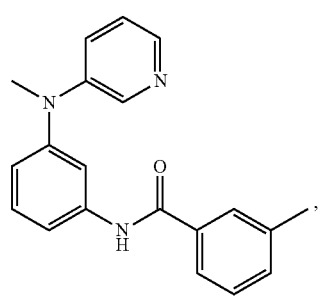
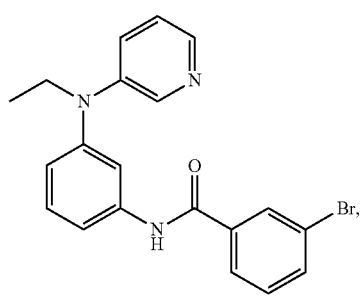
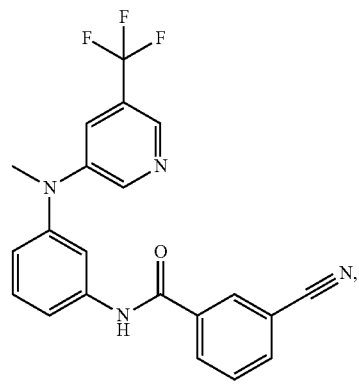
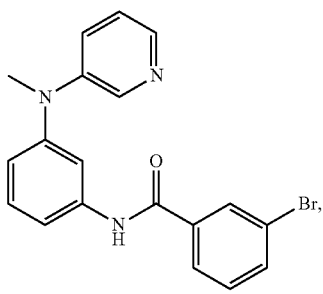

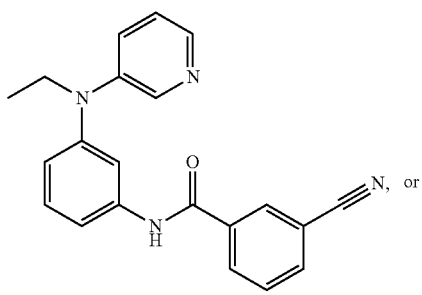
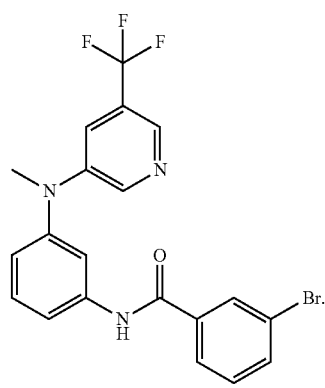
In a further aspect, a compound can be present as:
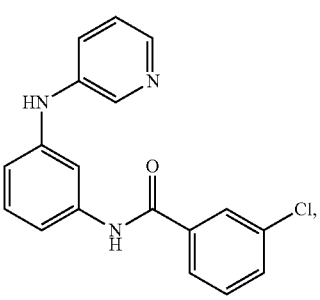
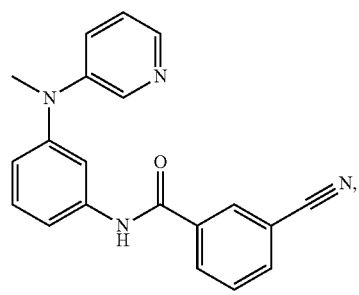
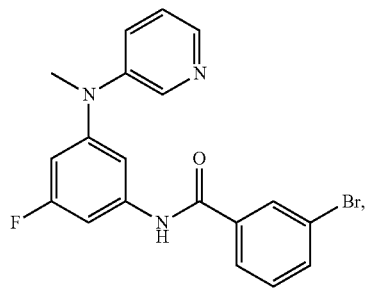
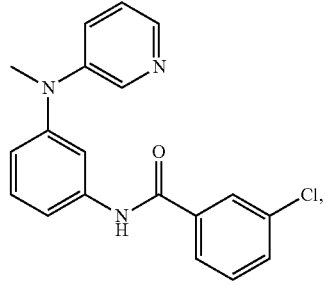
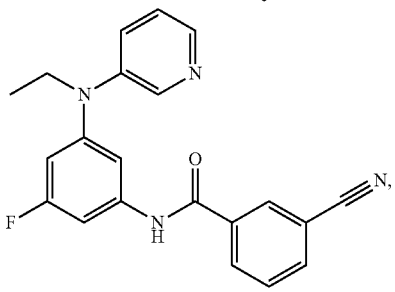

-continued
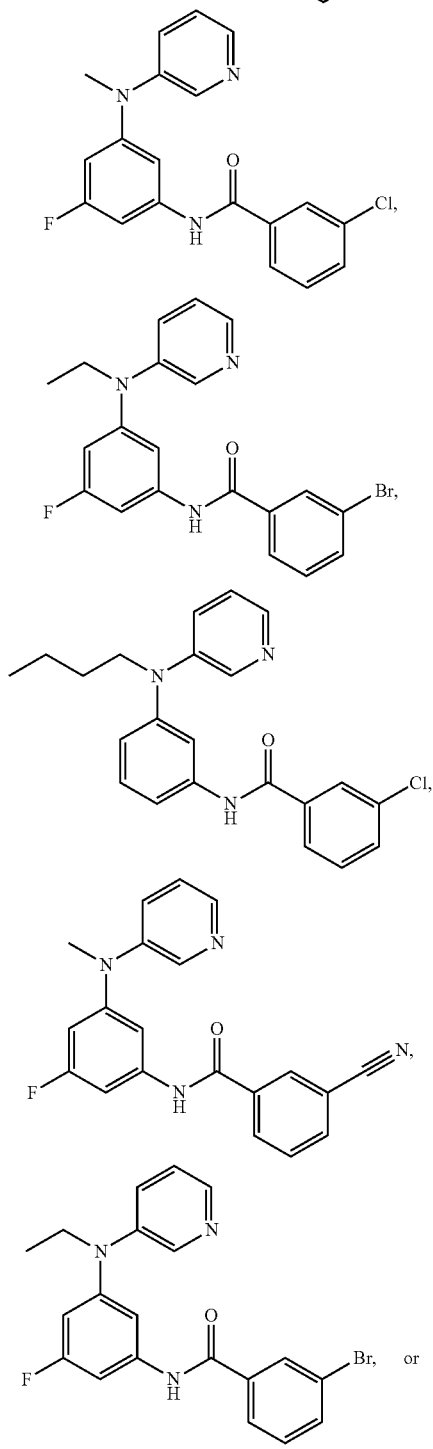
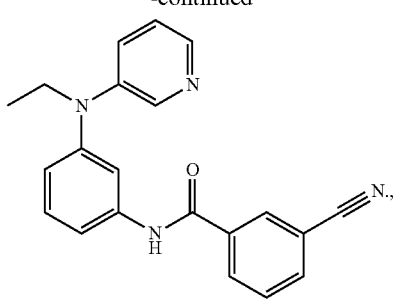
In a further aspect, a compound can be present as:
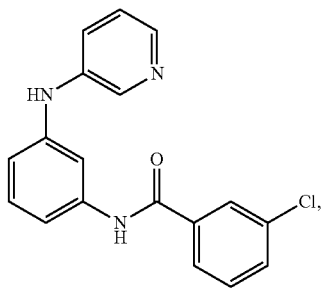
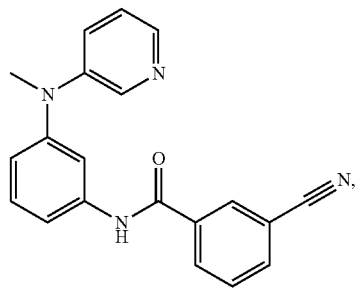
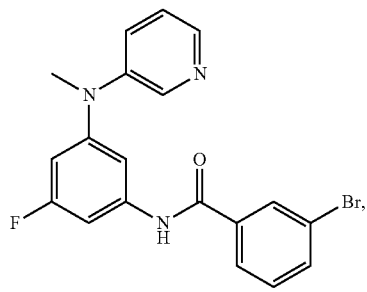
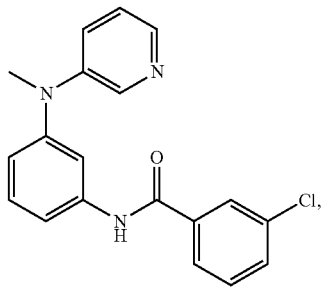

-continued
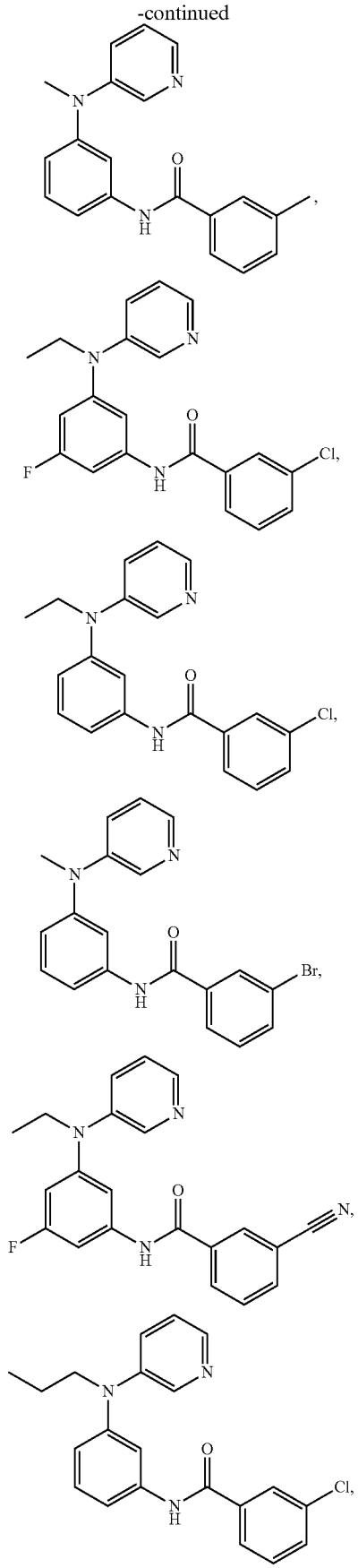
-continued
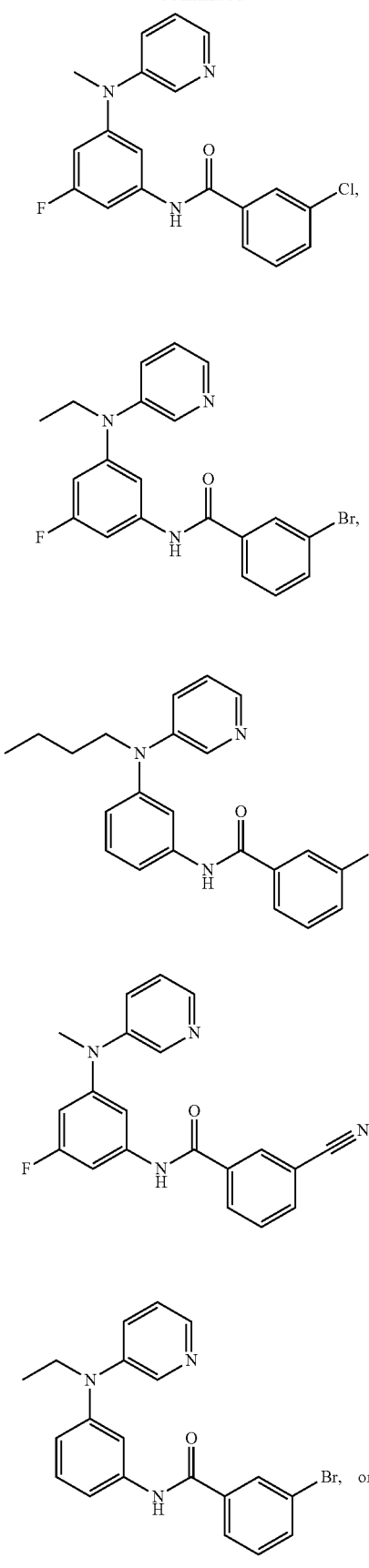

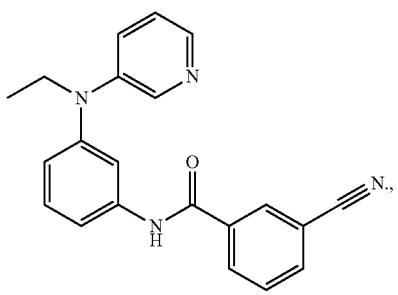
In a further aspect, a compound can be present as:
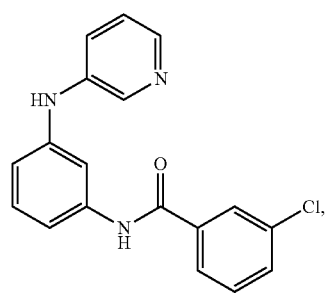
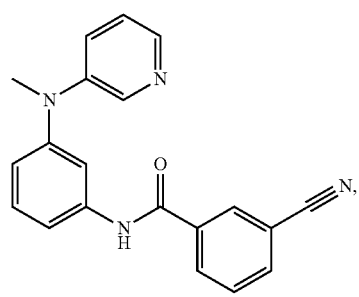
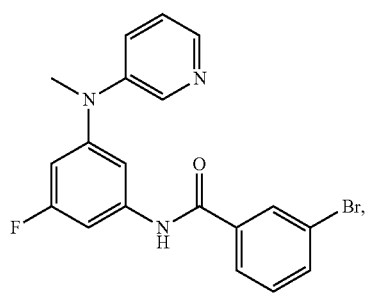
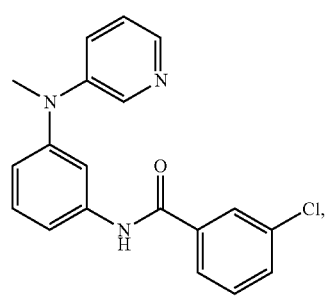
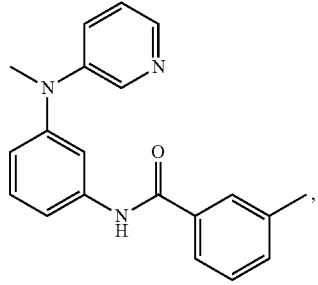
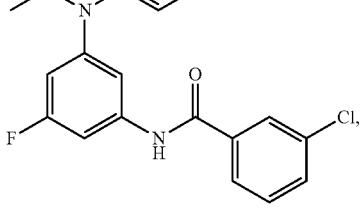
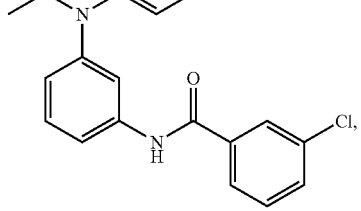
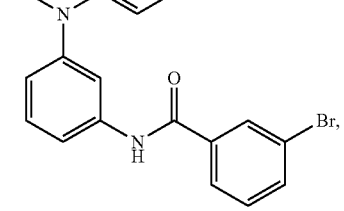
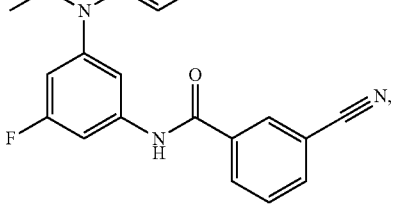
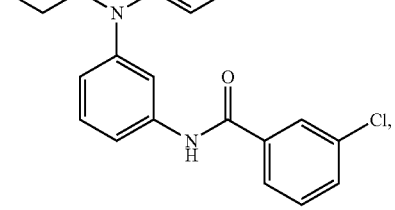

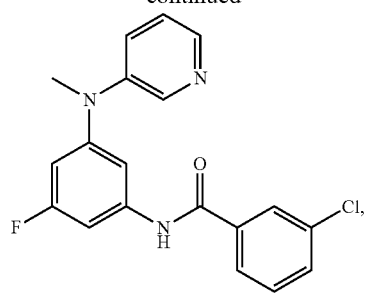
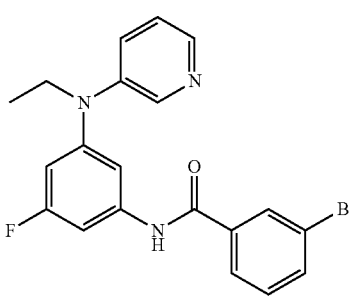
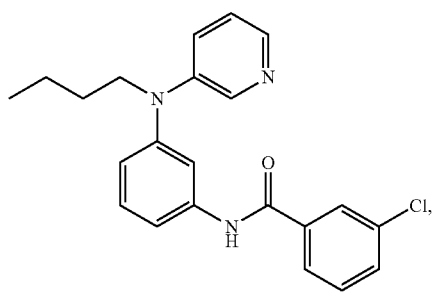
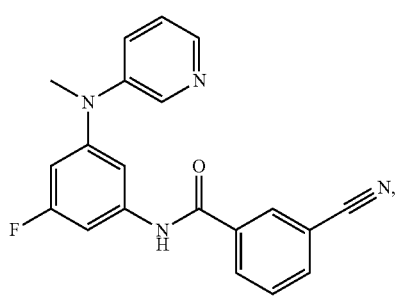
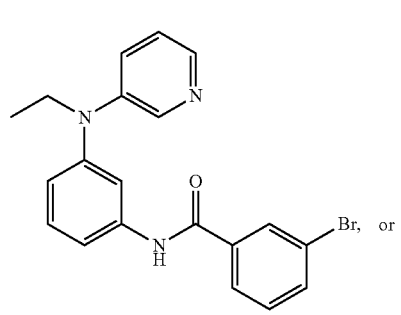
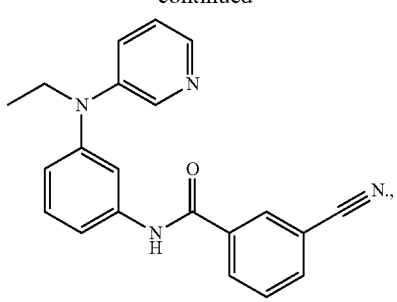
In a further aspect, a compound can be present as:
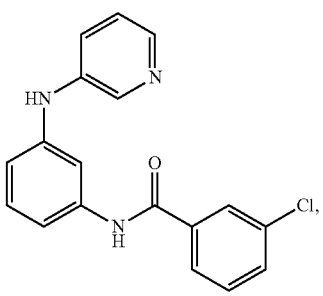
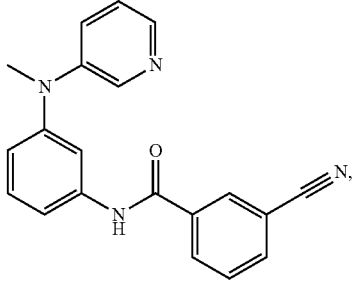
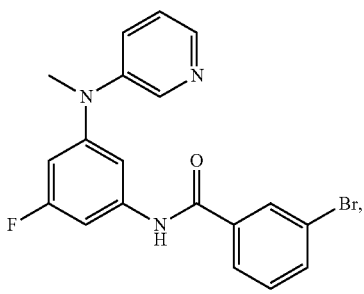

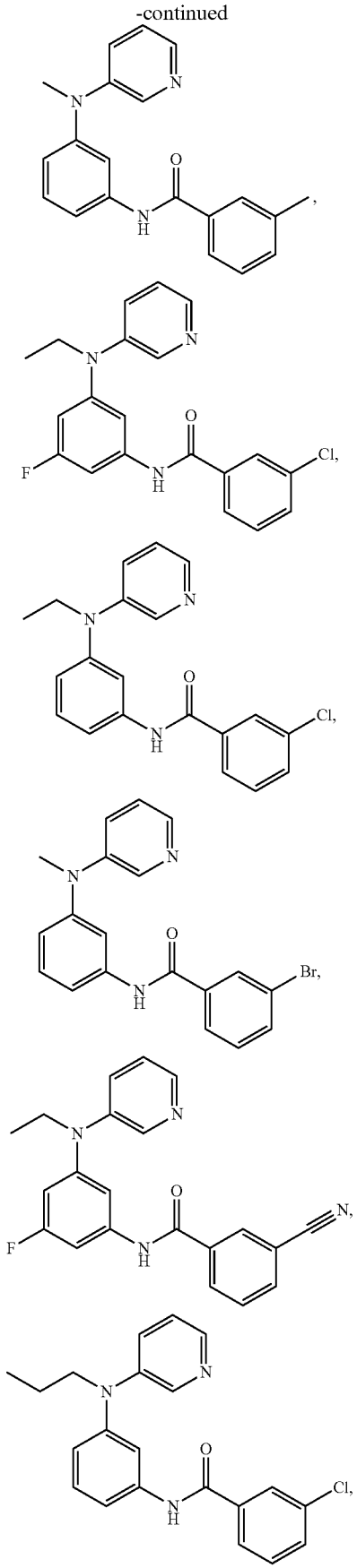
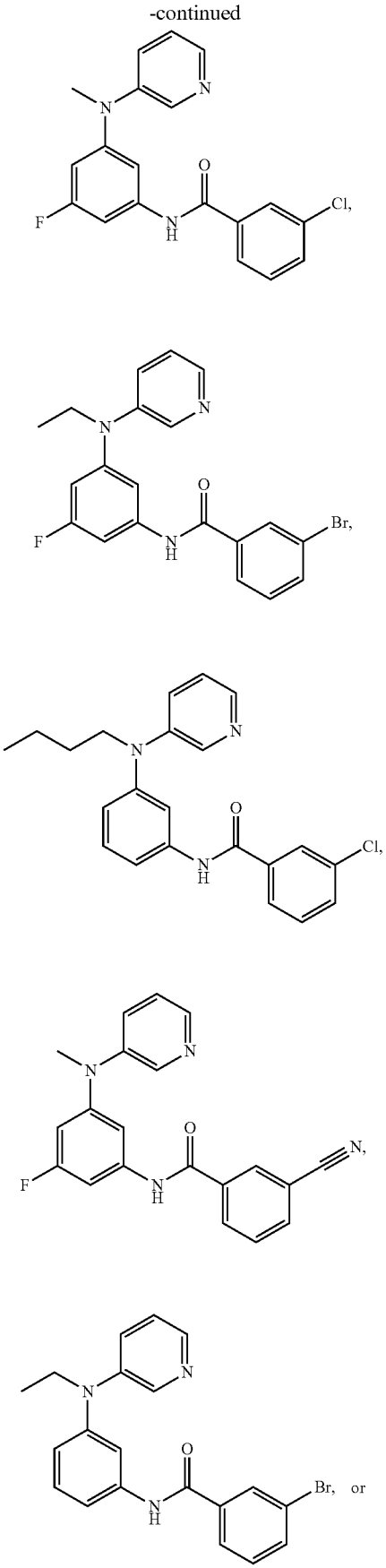

-continued

In a further aspect, a compound can be present as:

-continued
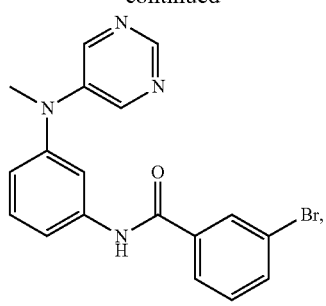
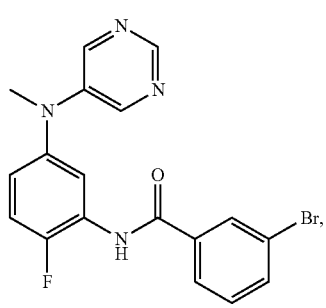
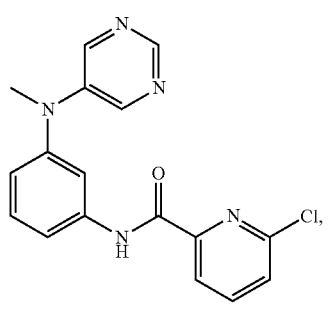
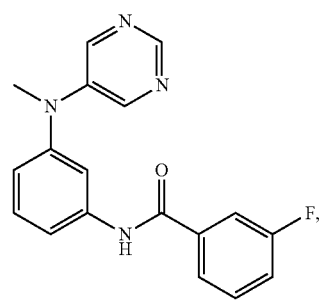
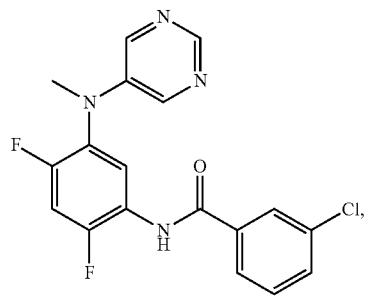
-continued
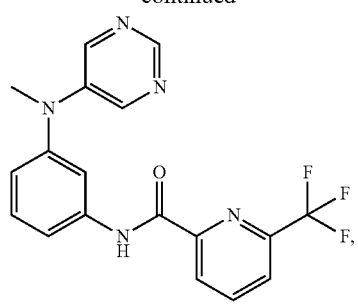
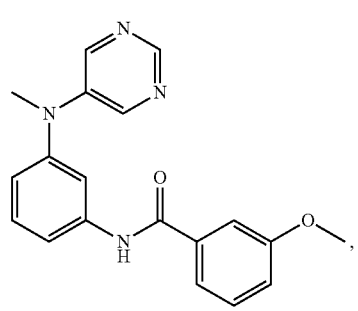
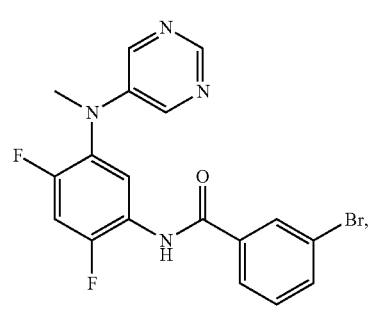
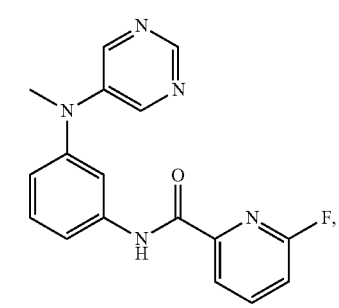
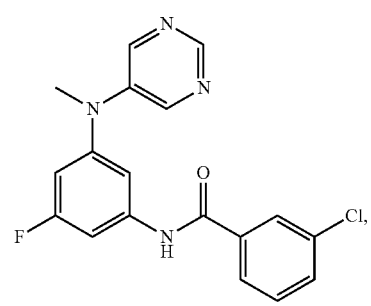

101
-continued
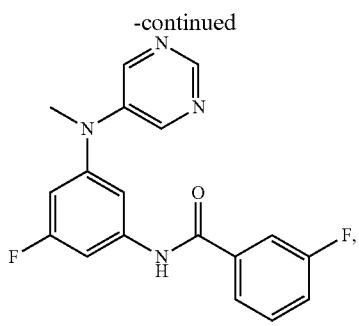
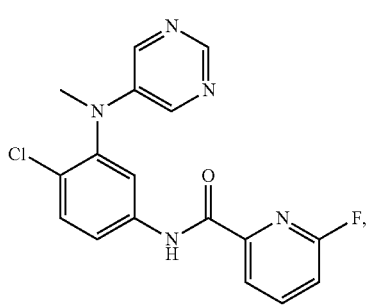
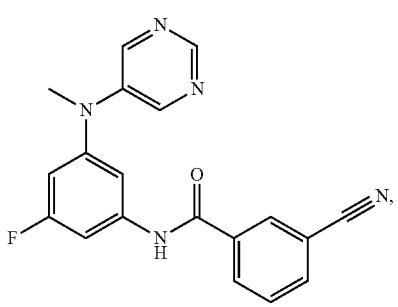
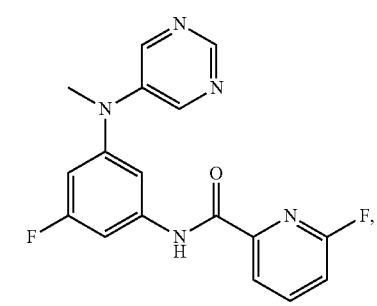
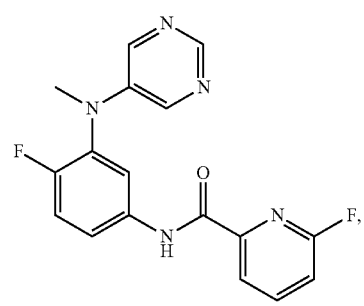
102
-continued
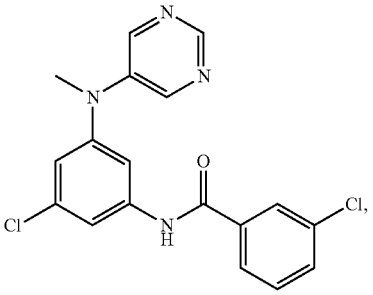
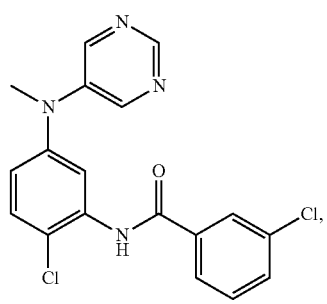
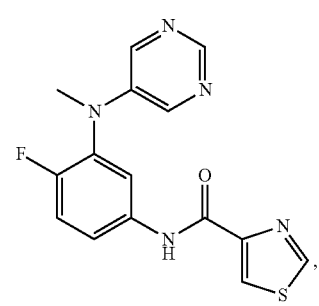
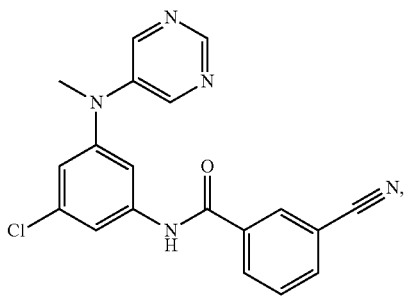
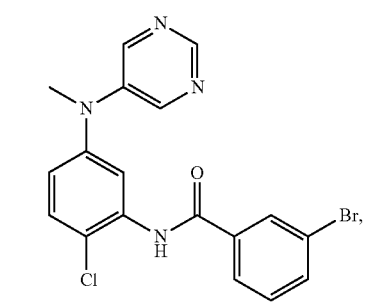

103
-continued
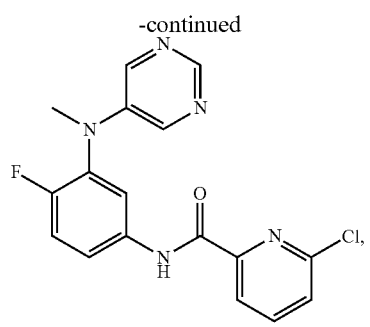
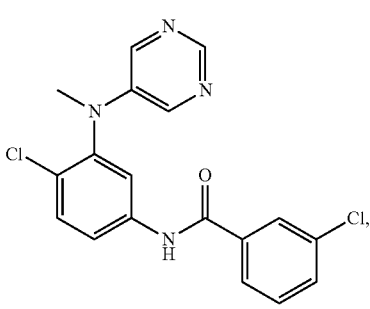
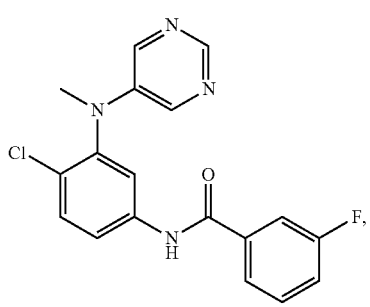
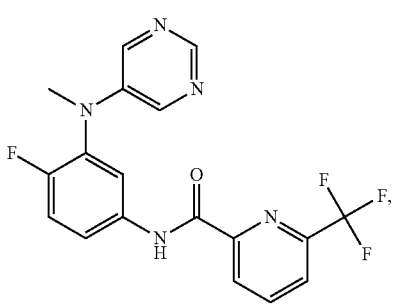
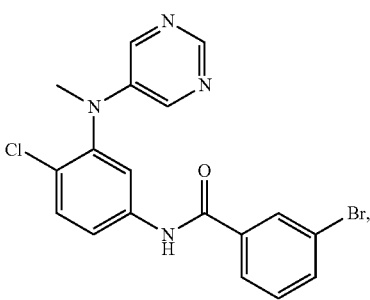
104
-continued
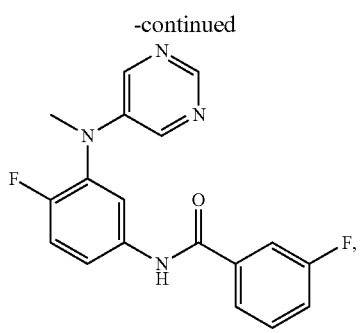
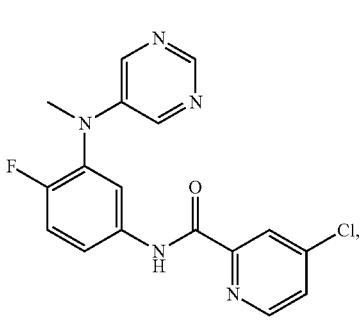
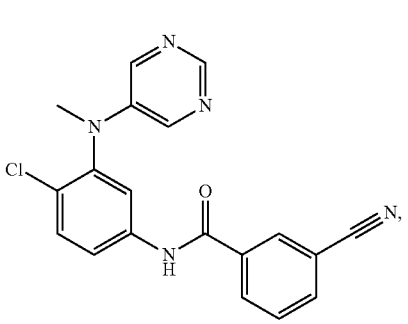
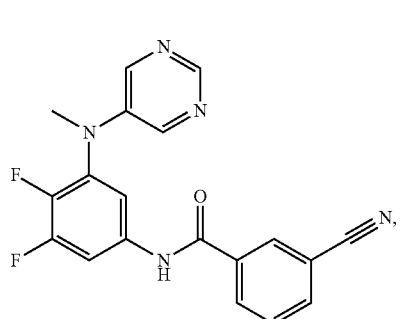

-continued
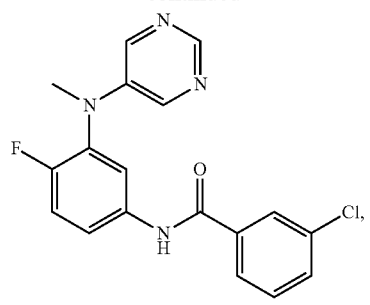
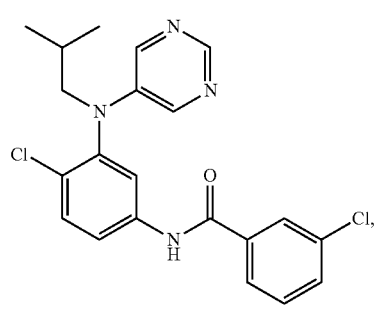
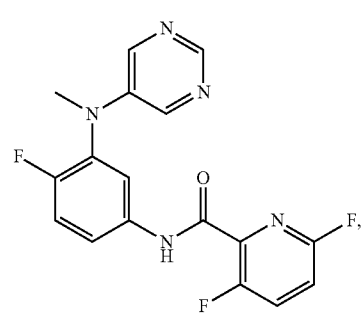
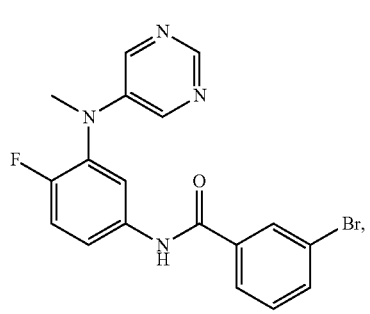
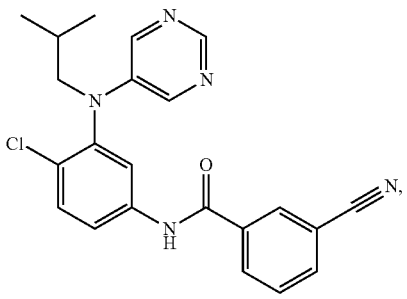
-continued
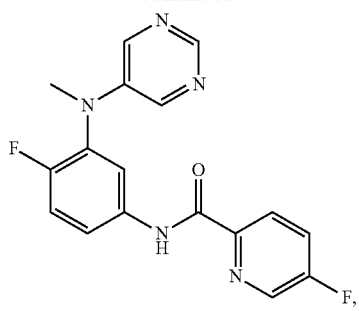
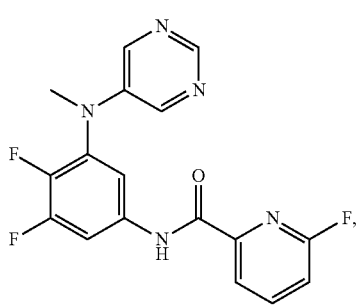
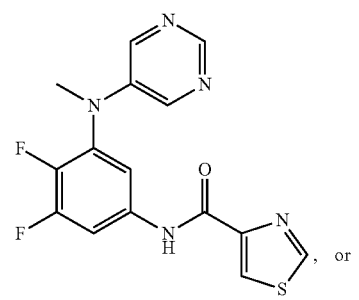, or
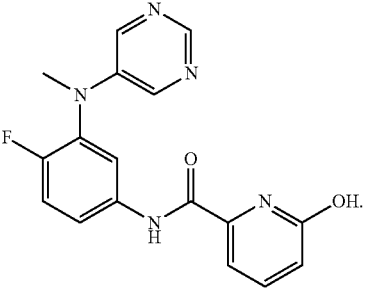
In a further aspect, a compound can be present as:
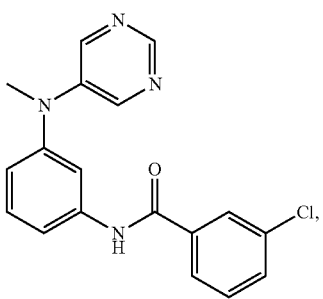

-continued
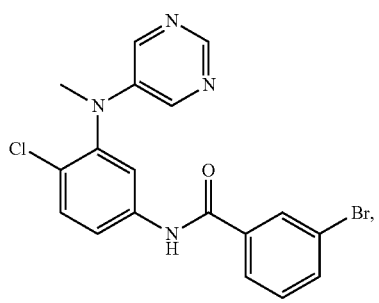
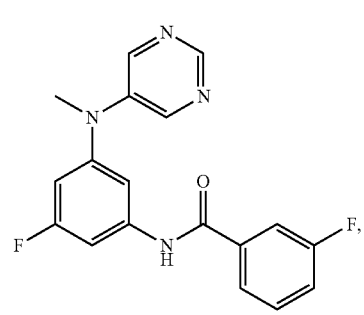
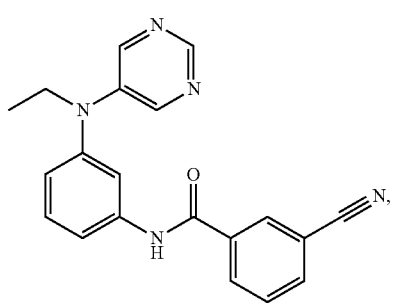
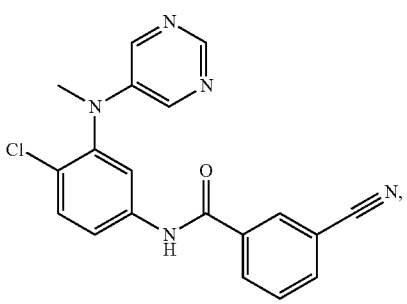
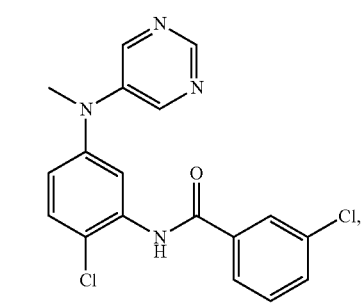
-continued
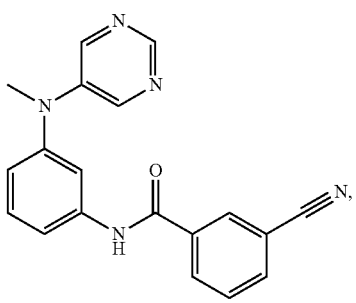
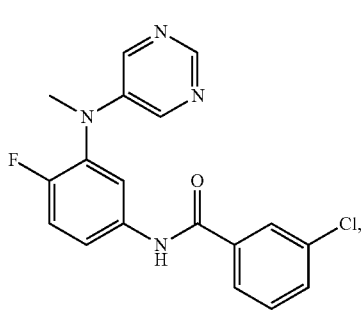
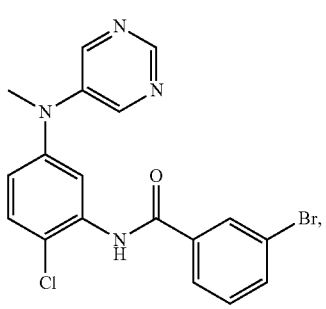
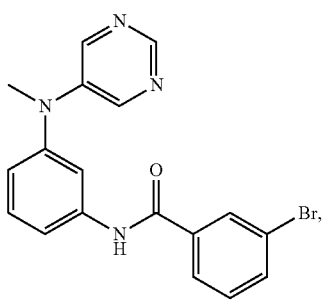
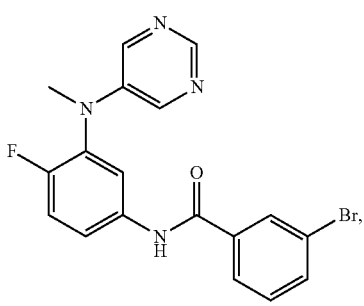

109
-continued
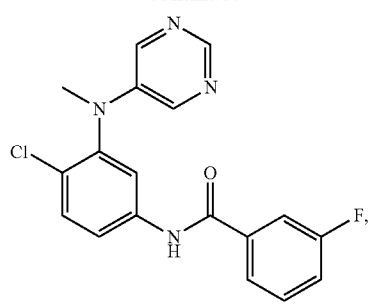
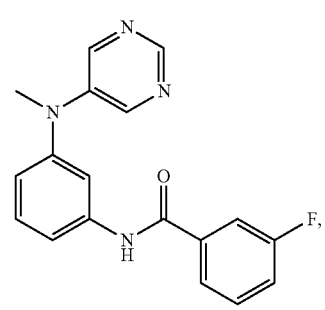
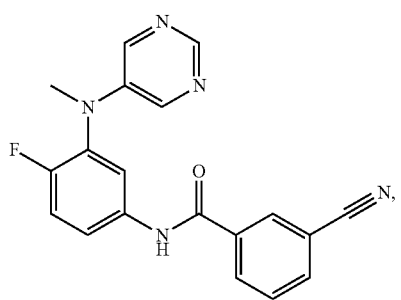
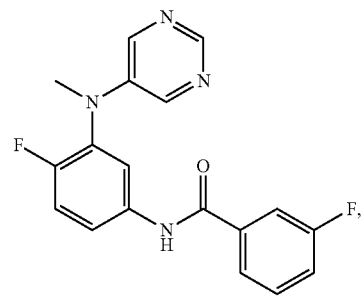
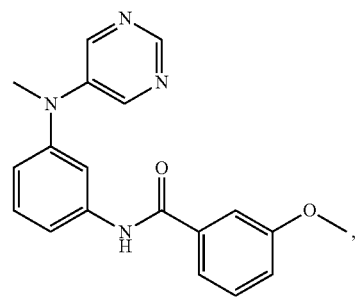
110
-continued
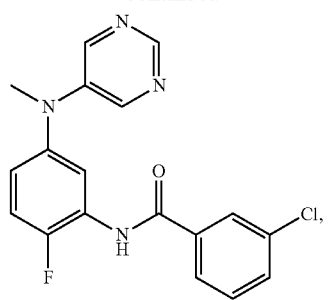
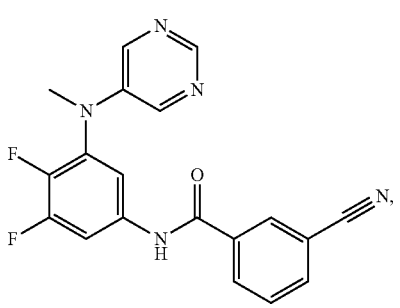
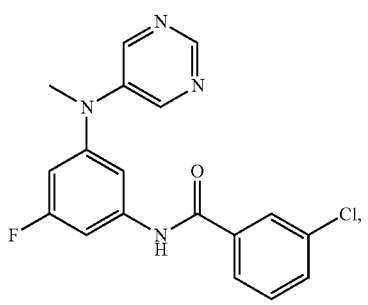
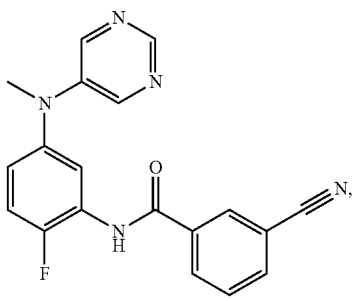
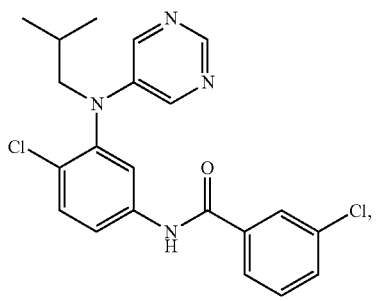

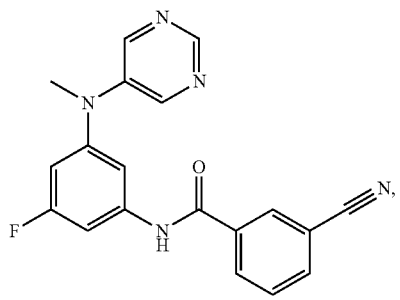
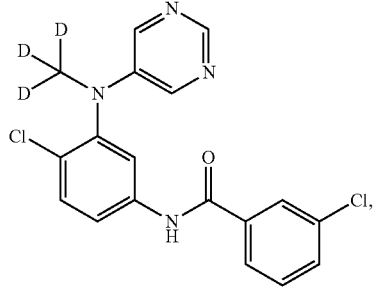
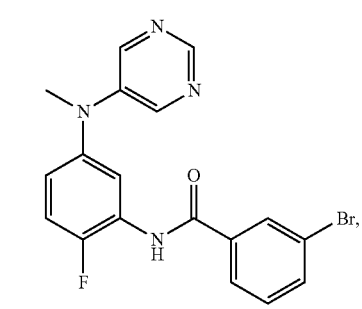
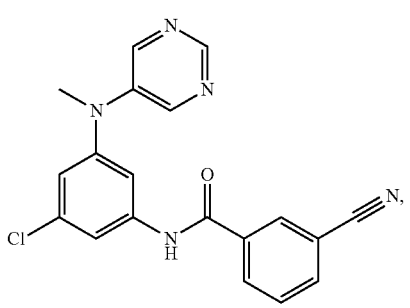
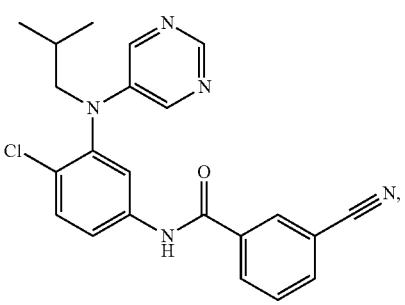
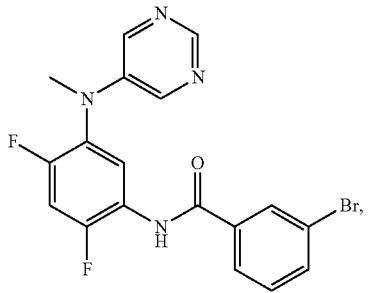
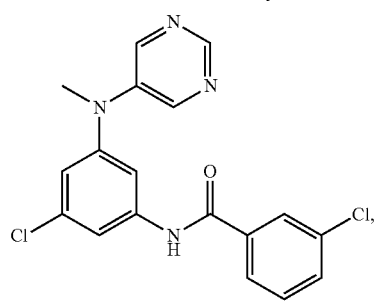
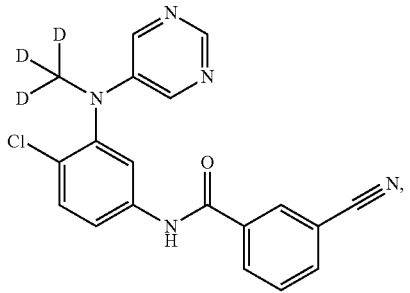
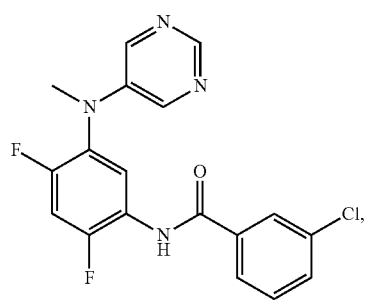
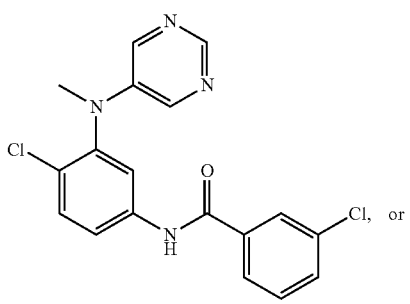

-continued
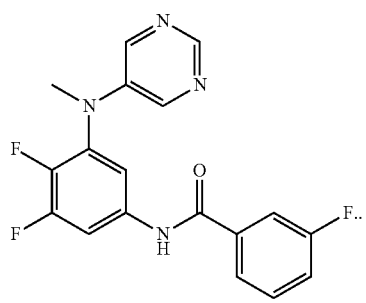
In a further aspect, a compound can be present as:
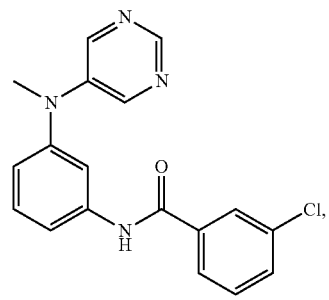
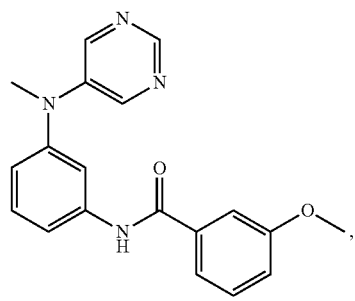
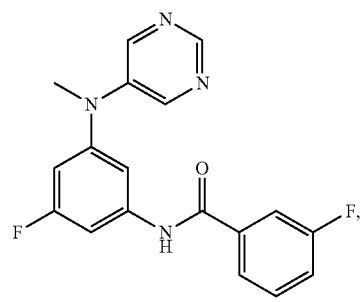
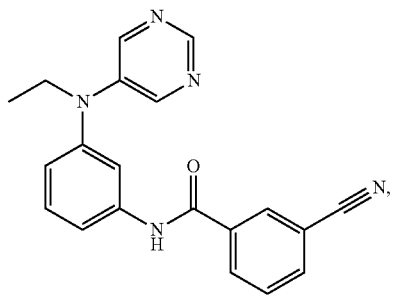
-continued
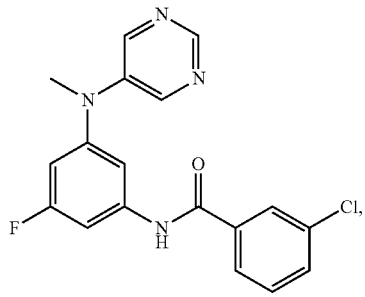
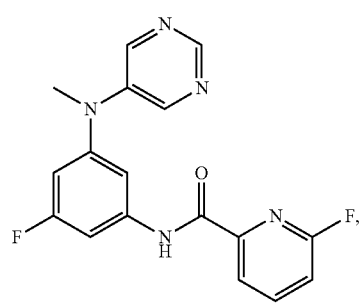
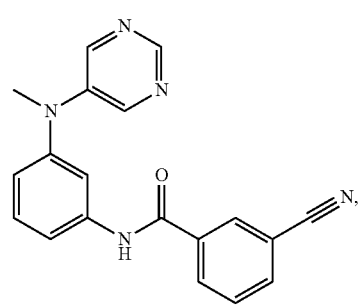
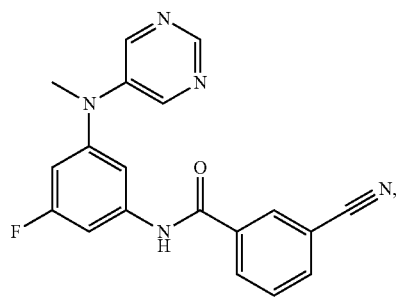

-continued
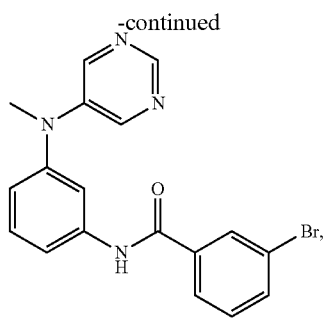
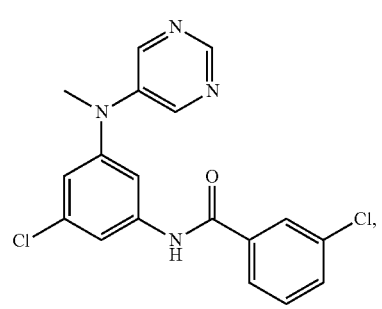
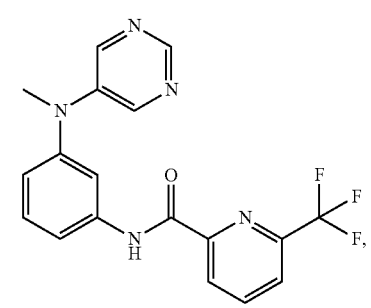
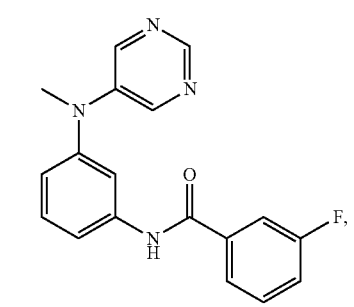
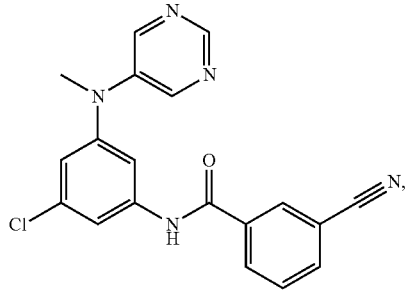
-continued
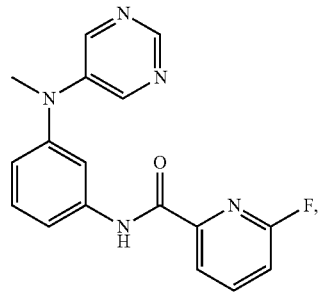
In a further aspect, a compound can be present as:
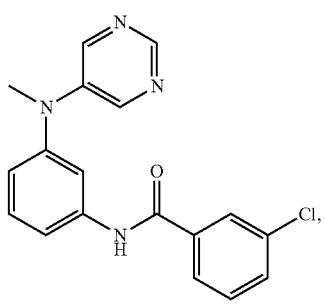
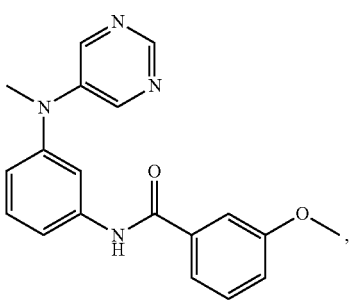
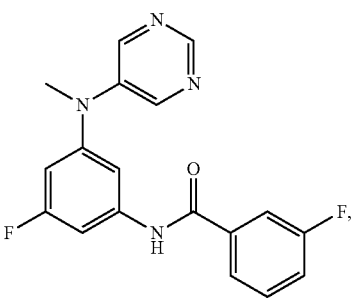
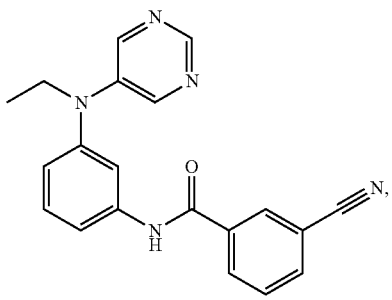

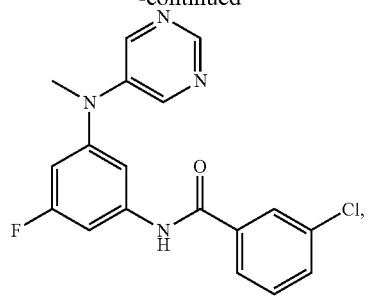
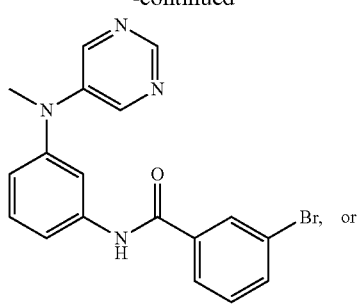
In a further aspect, a compound can be present as:

-continued

121
-continued
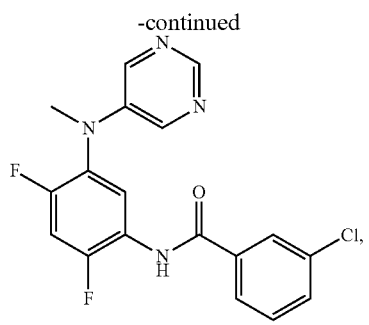
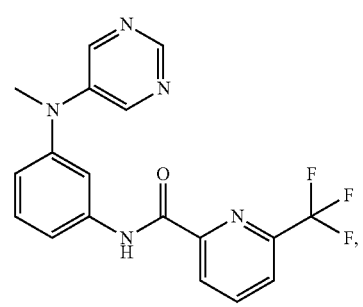
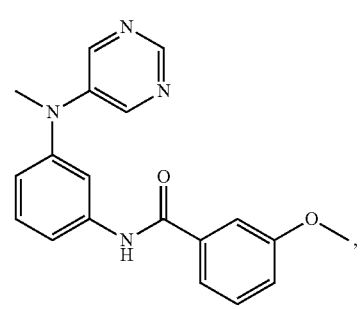
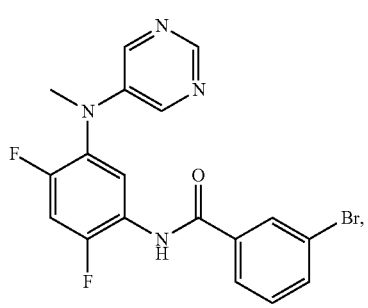
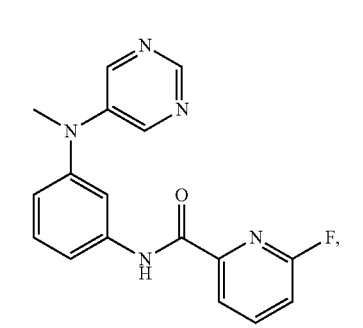
122
-continued
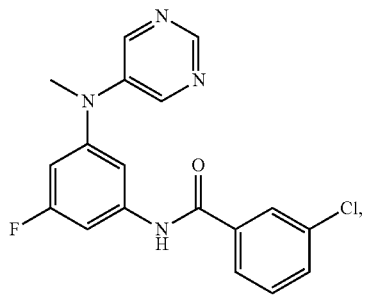
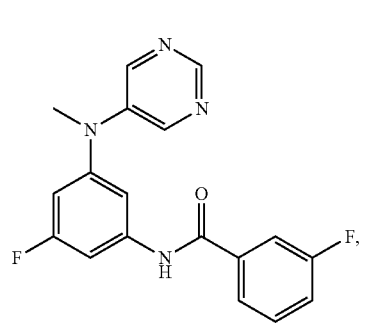
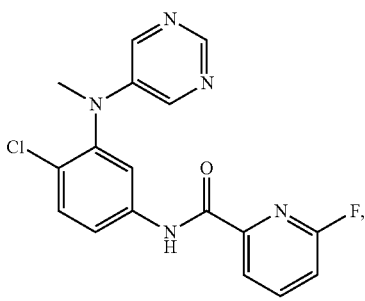
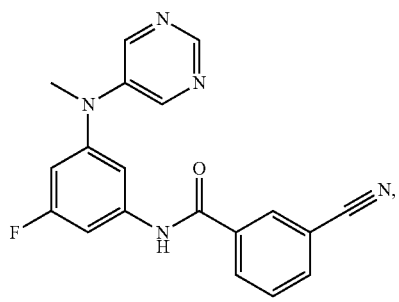

-continued
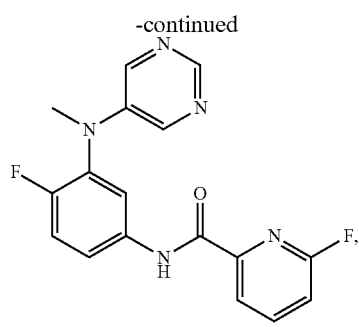
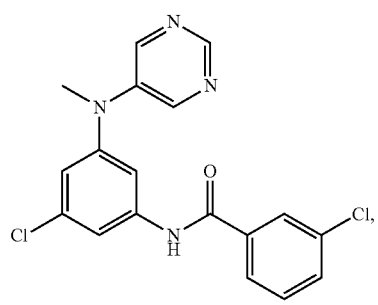
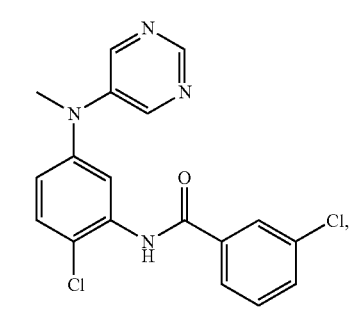
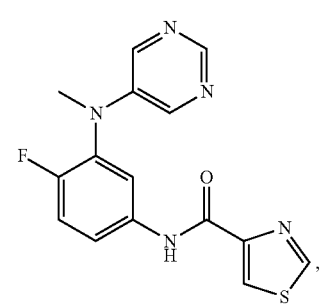
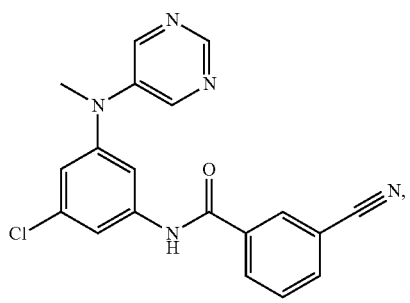
-continued
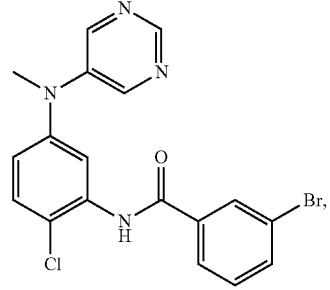
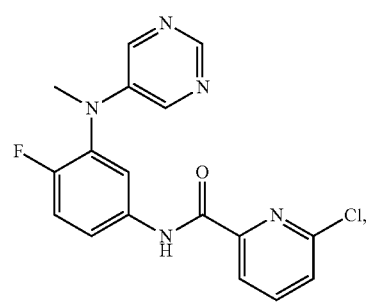
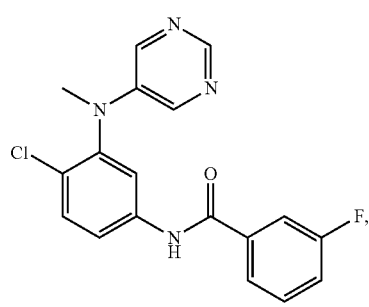
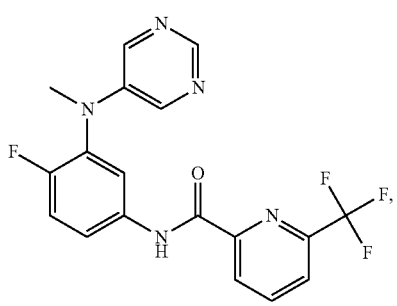

-continued
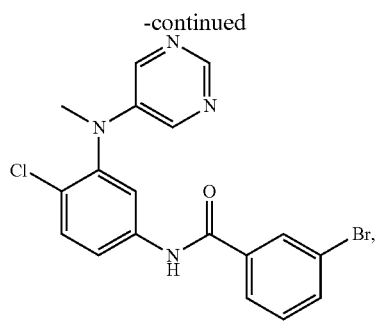
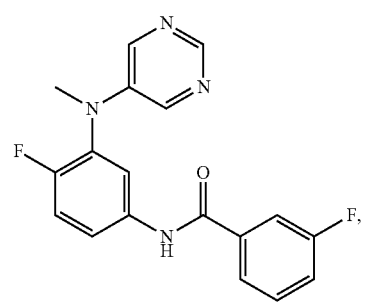
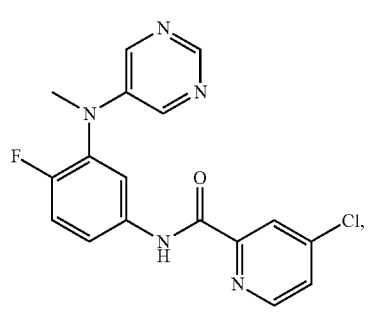
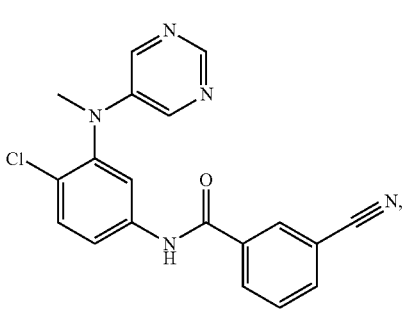
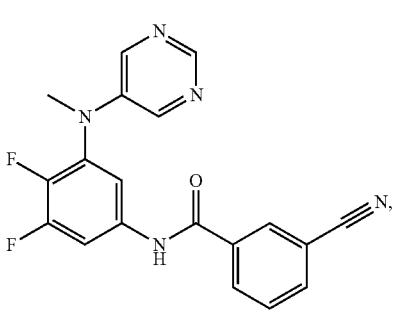
-continued
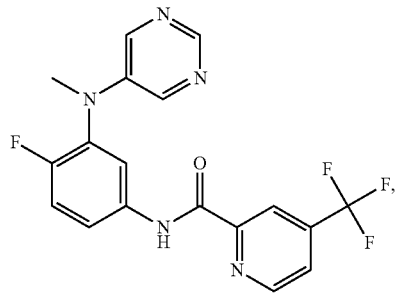
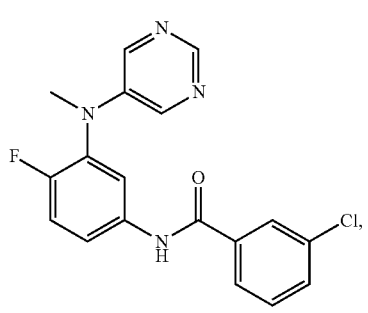
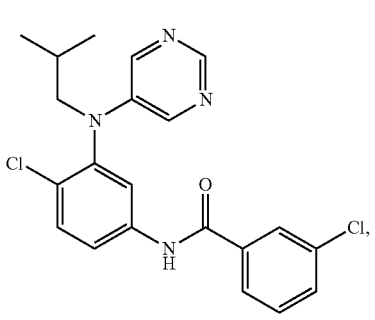
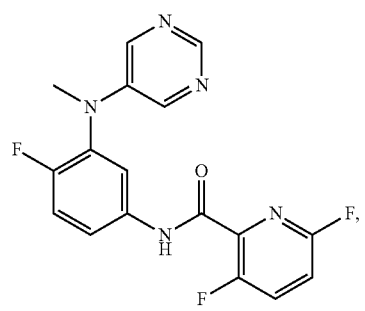
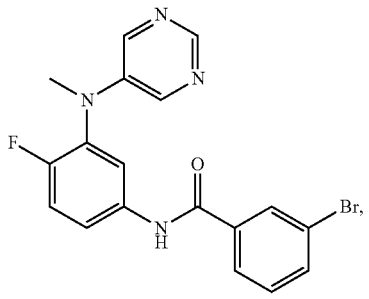

-continued
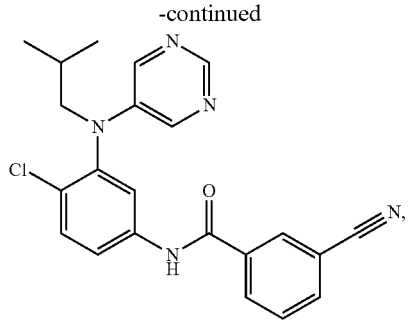
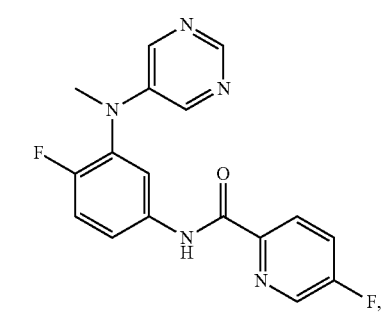
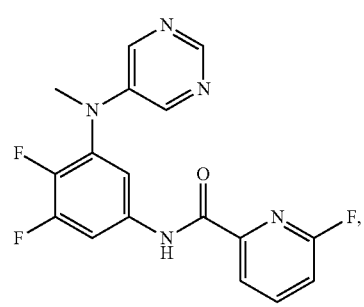
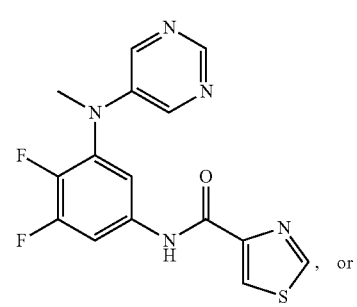, or
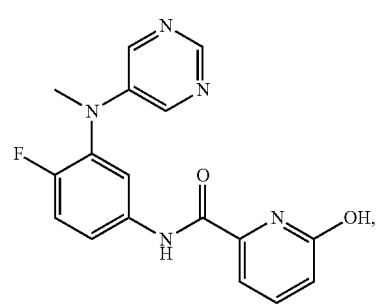
In a further aspect, a compound can be present as:
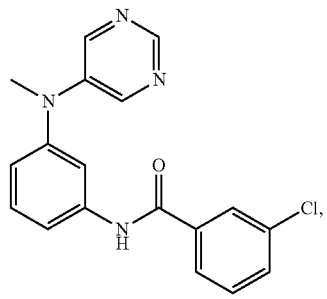
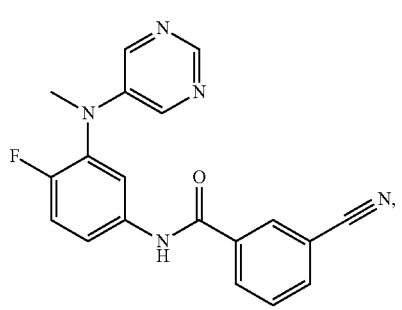
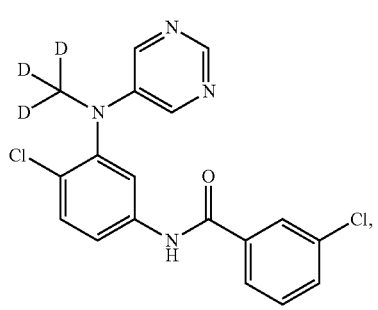
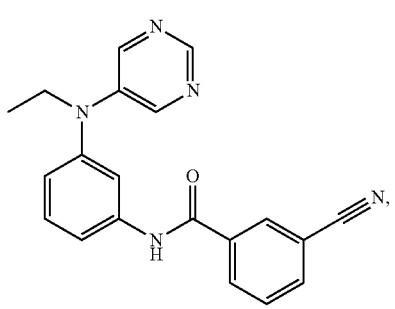
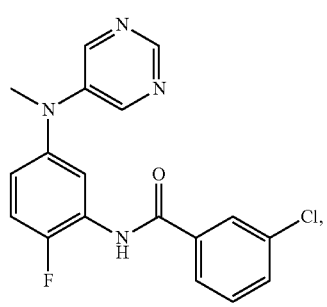

129
-continued
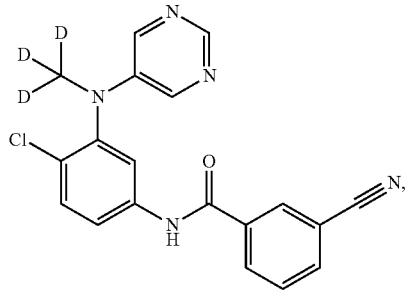
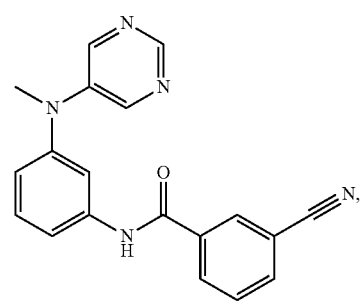
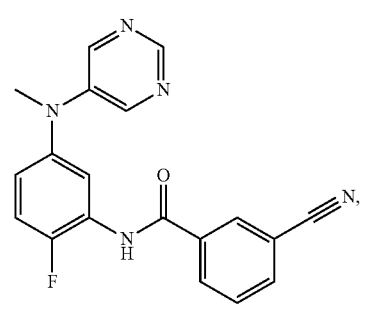
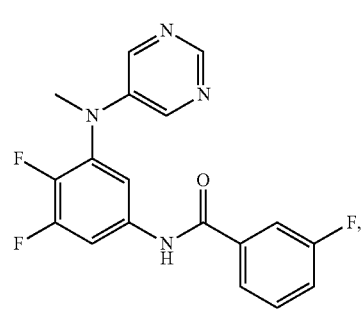
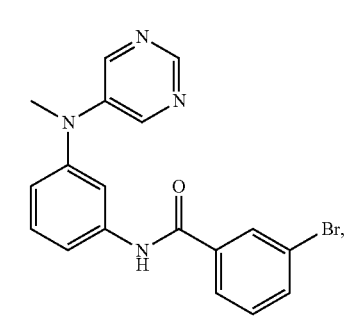
130
-continued
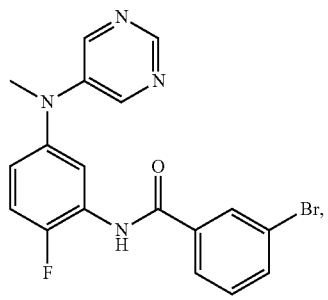
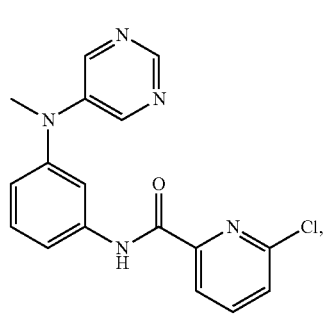
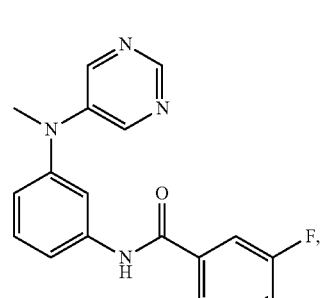
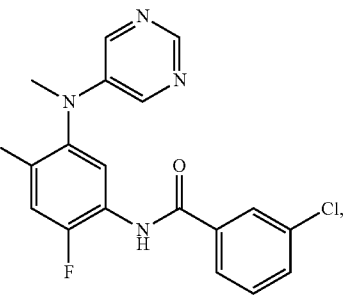
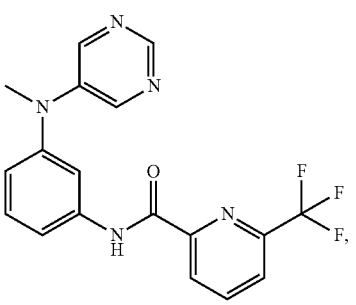

131
-continued
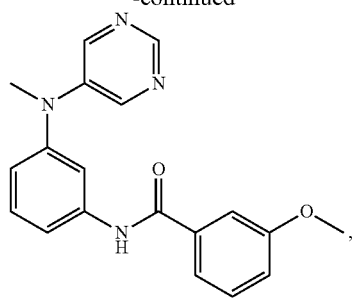
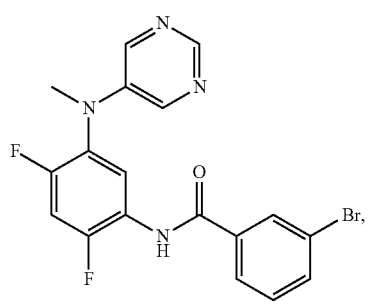
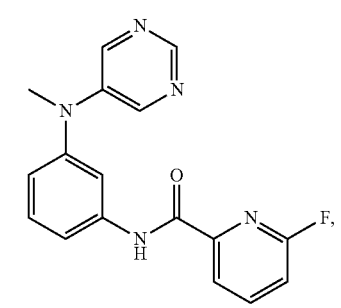
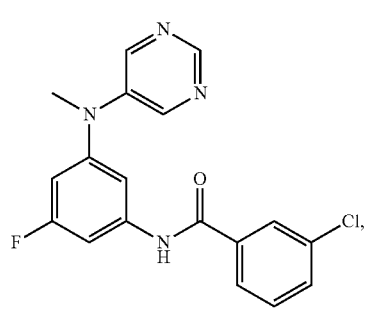
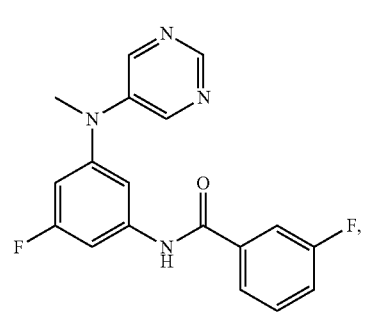
132
-continued
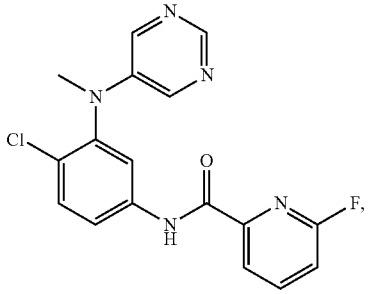
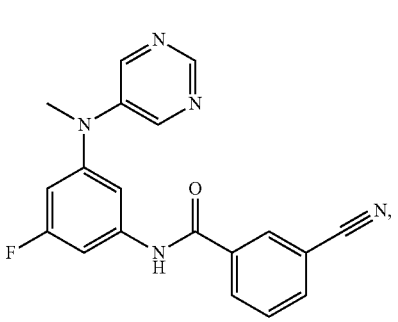
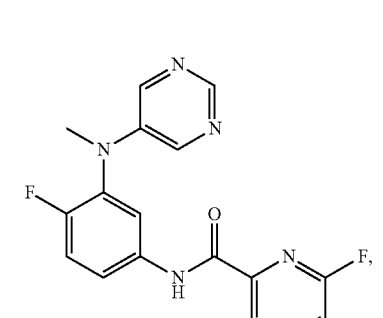
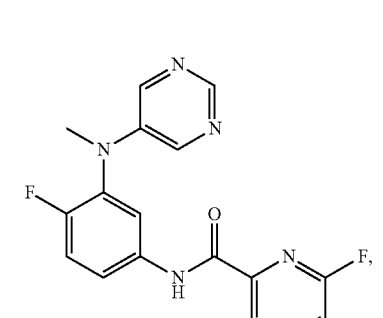
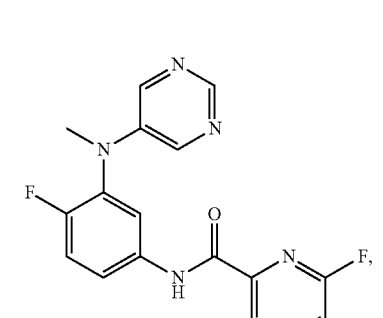

133
-continued
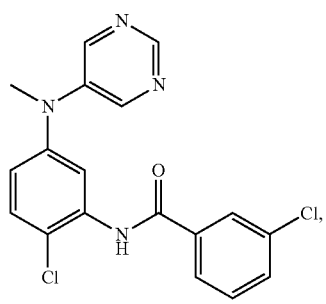
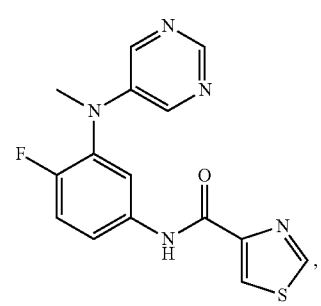
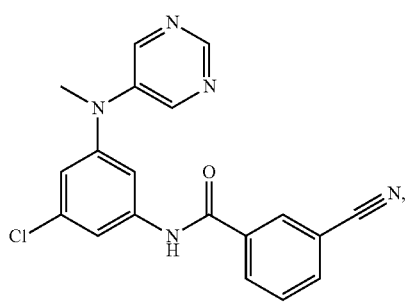
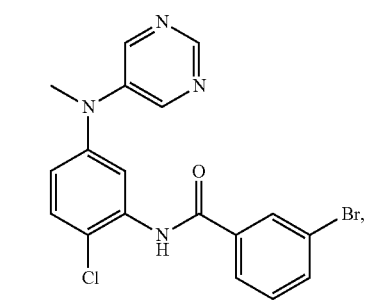
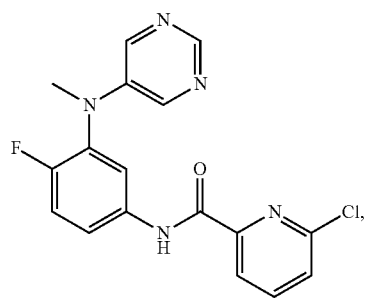
134
-continued
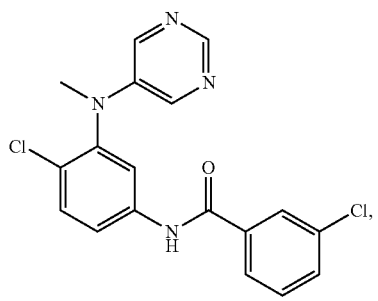
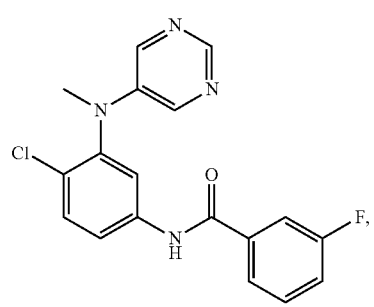
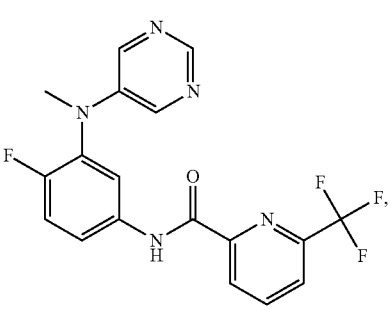
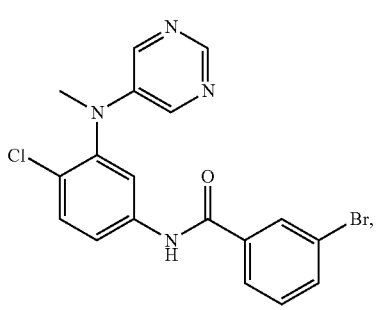
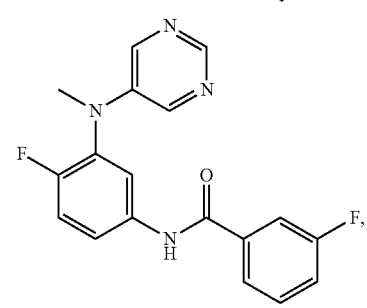

135
-continued
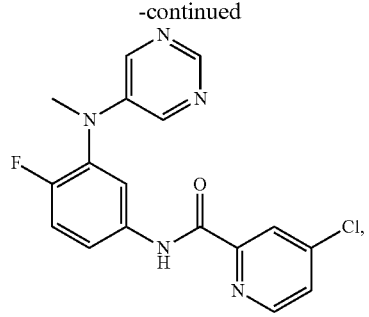
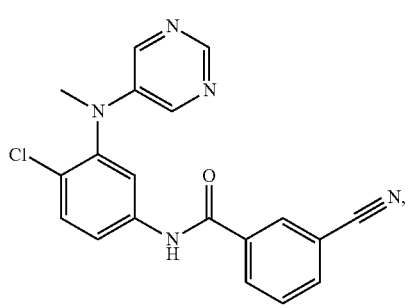
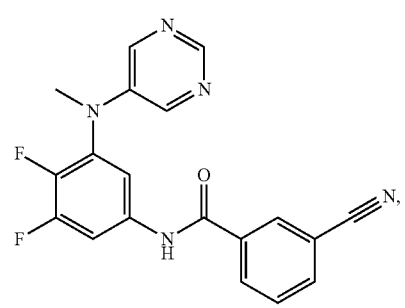
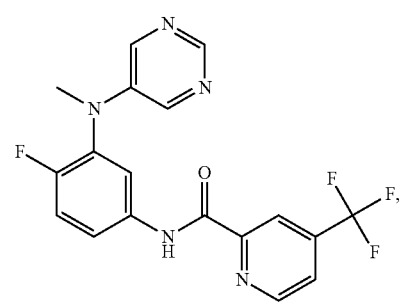
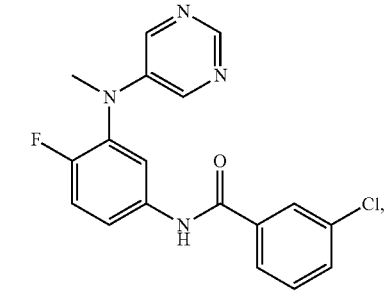
136
-continued
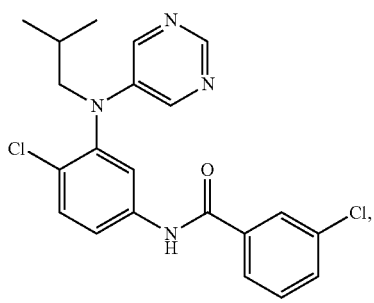
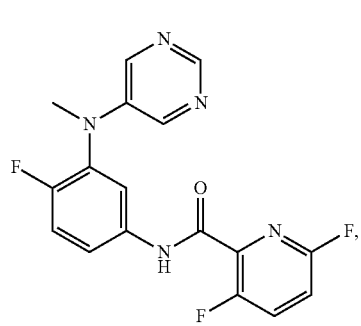
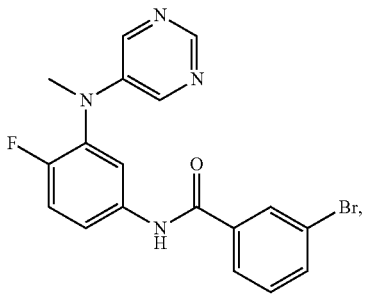
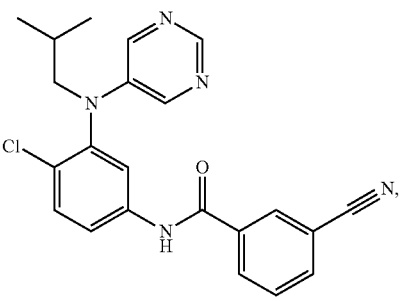
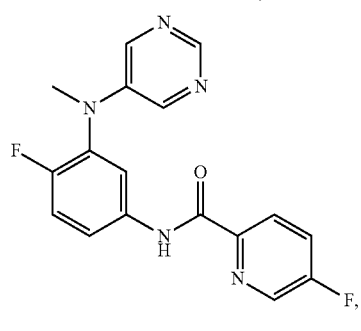

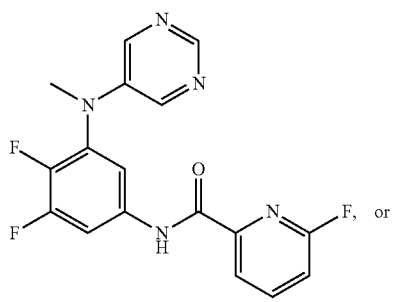
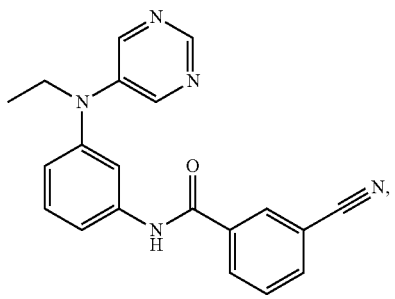
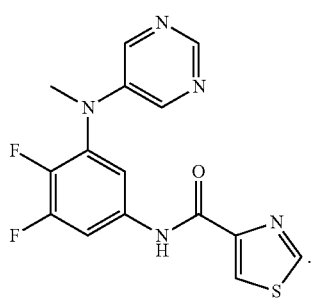
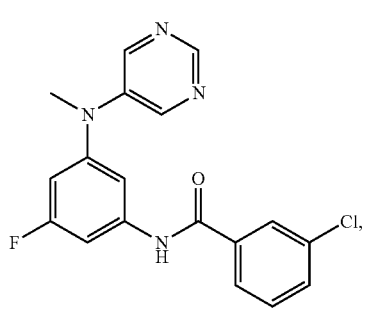
In a further aspect, a compound can be present as:
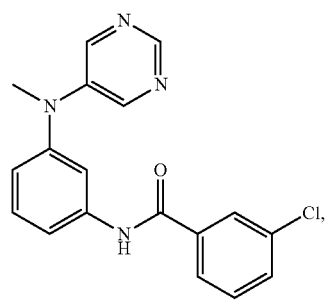 [SMILES: CN(c1cncnc1)c1cccc(NC(=O)c2cccc(F)c2)c1]
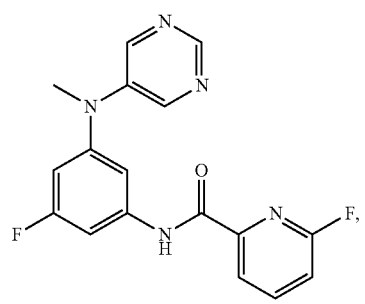
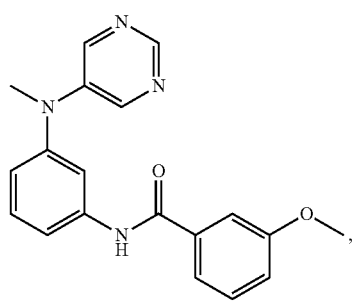
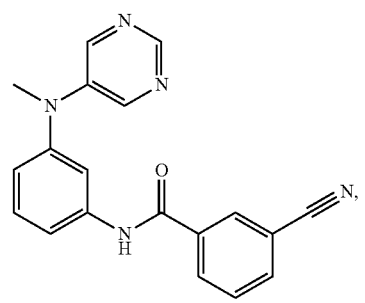
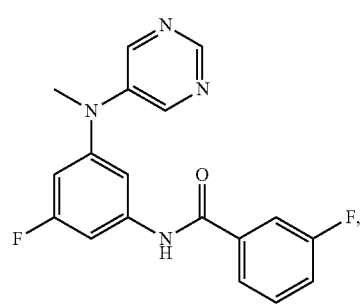
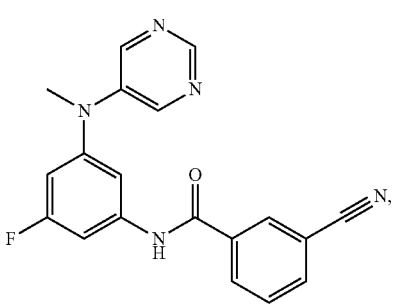

-continued
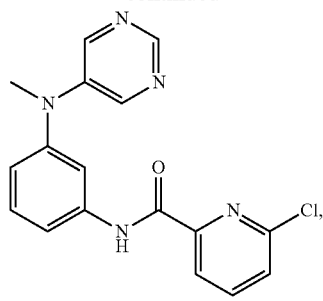
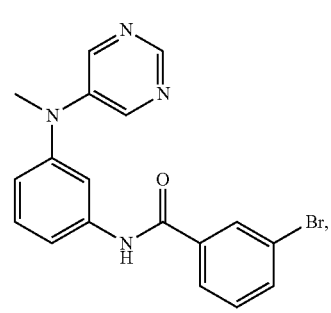
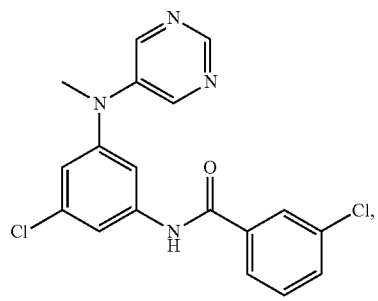
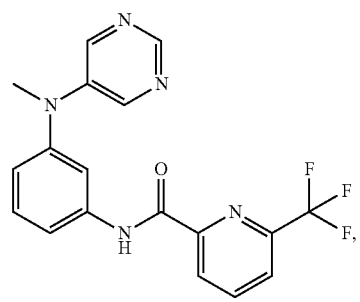
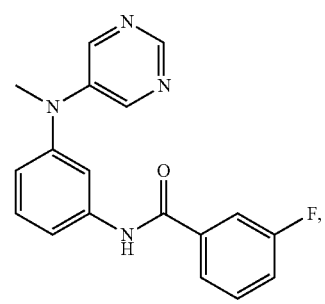
-continued
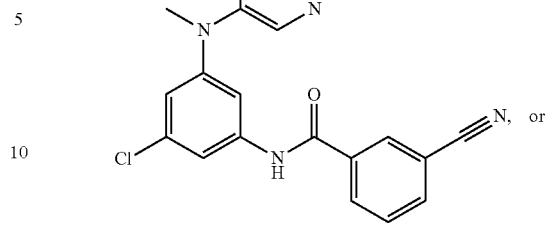
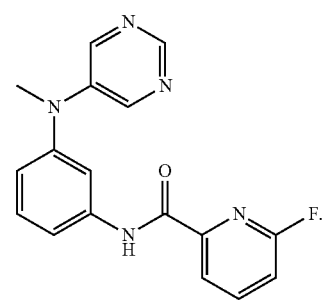
In a further aspect, a compound can be present as:
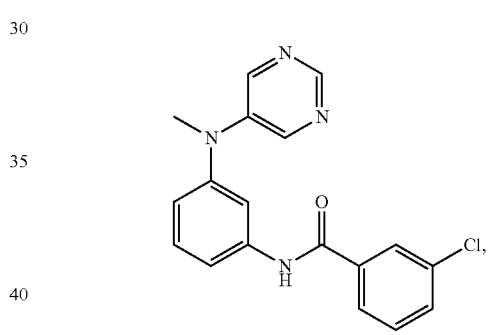
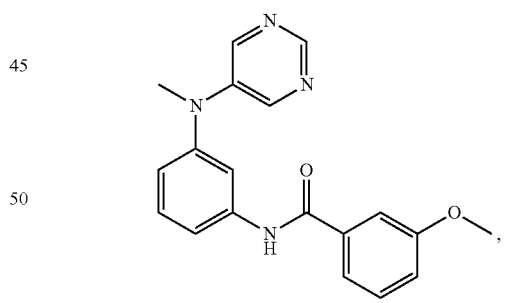
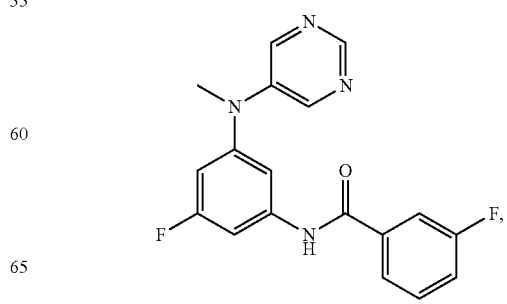

-continued
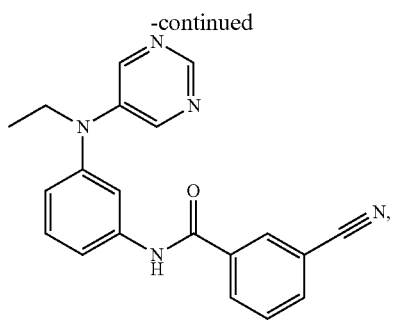
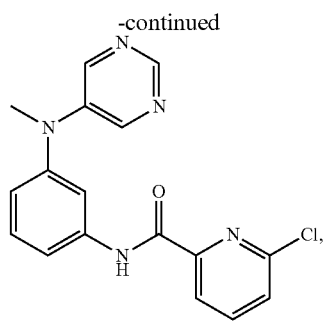

-continued
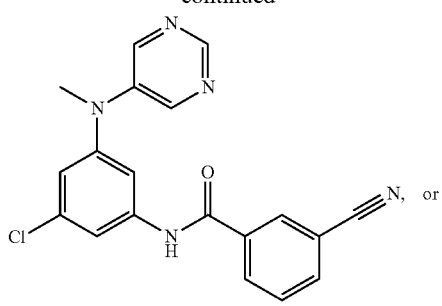
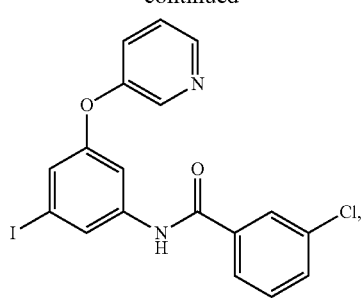
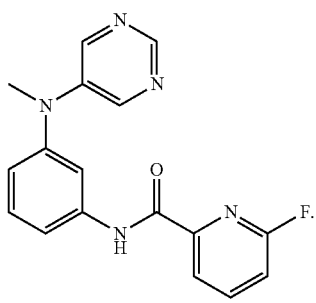
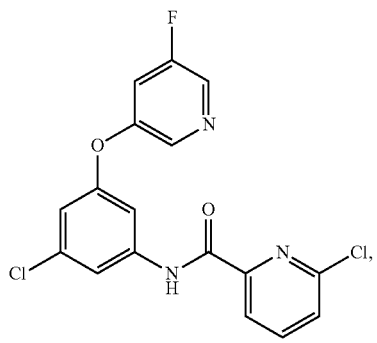
In a further aspect, a compound can be present as:
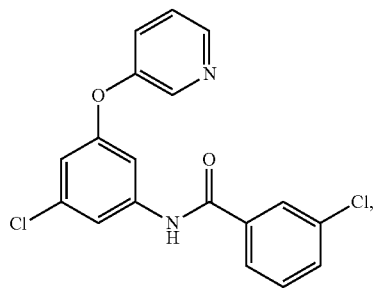
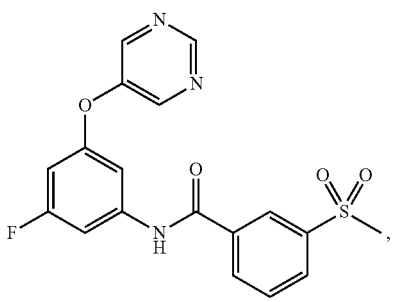
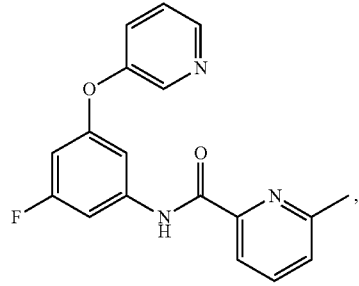
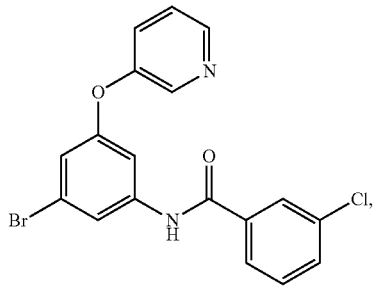
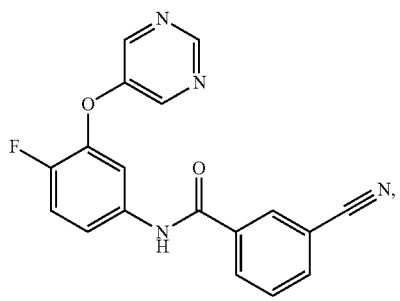
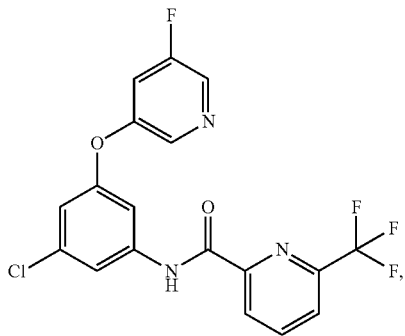

145
-continued
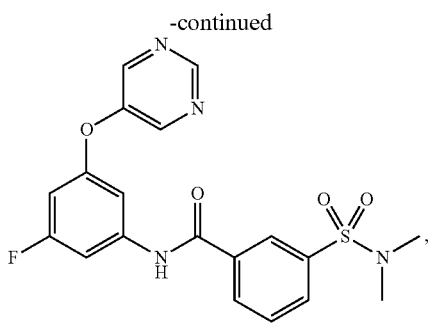
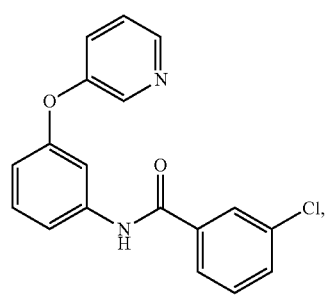
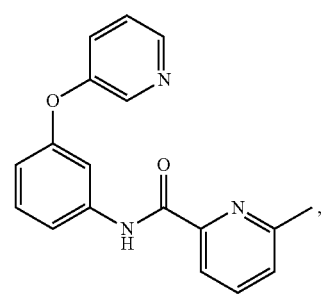
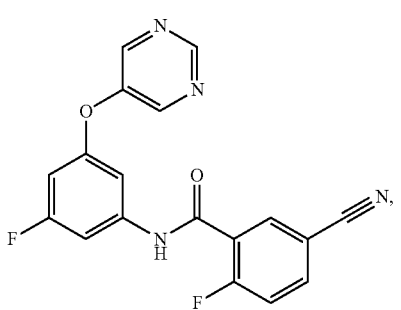
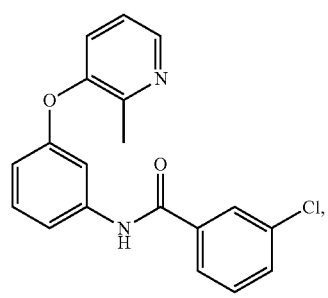
146
-continued
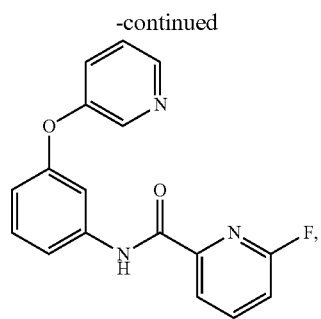
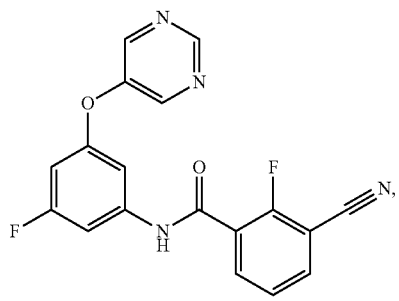
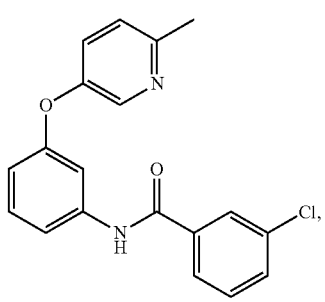
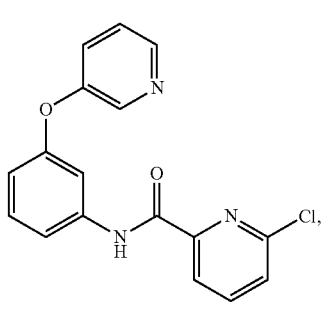
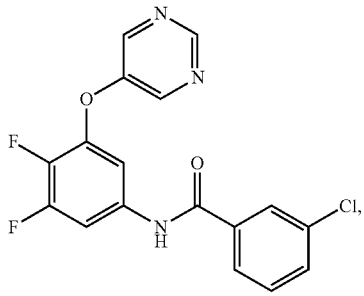

147
-continued
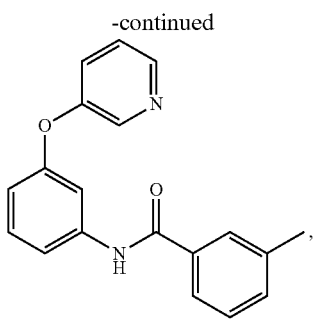
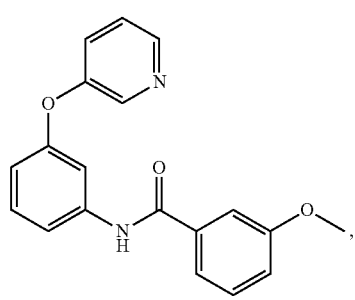
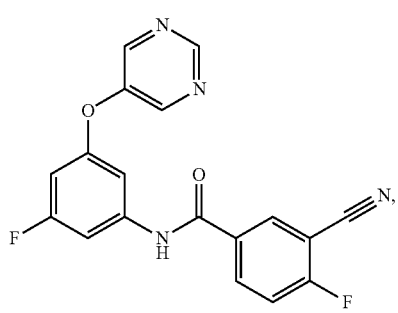
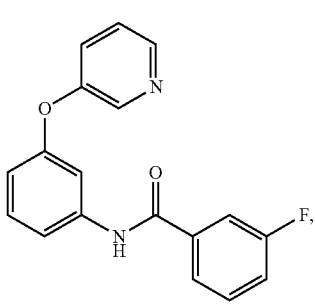
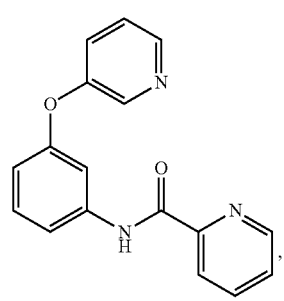
148
-continued
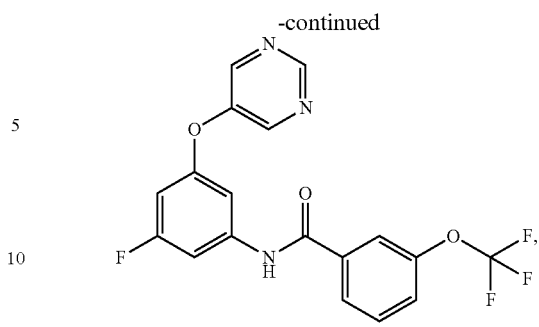
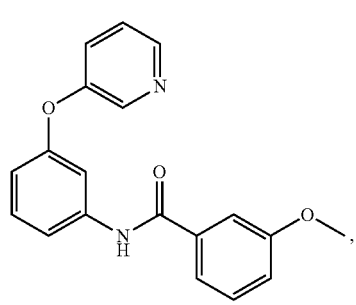
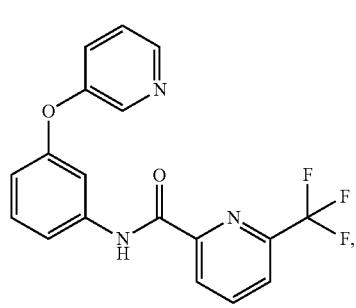
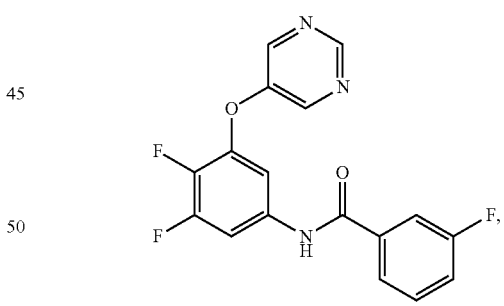
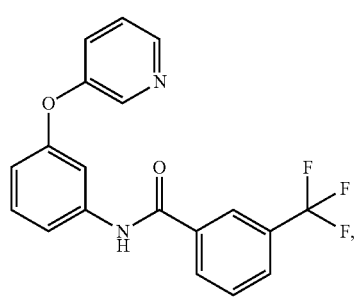

149
-continued
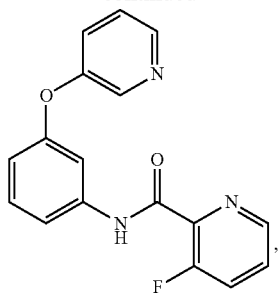
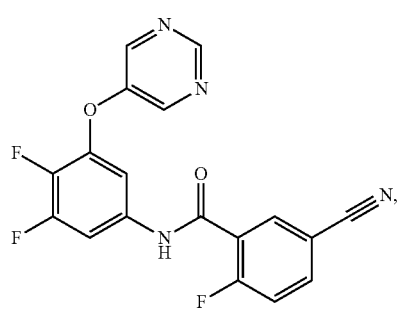
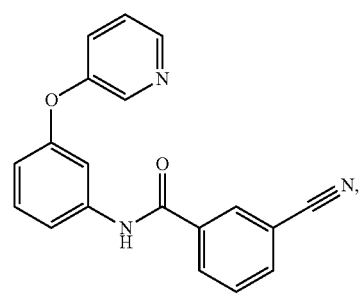
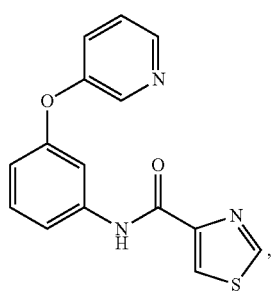
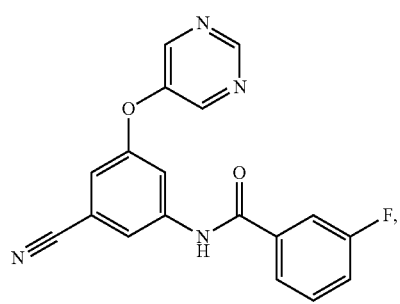
150
-continued
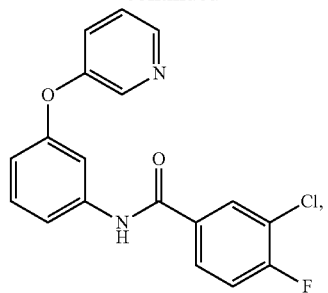
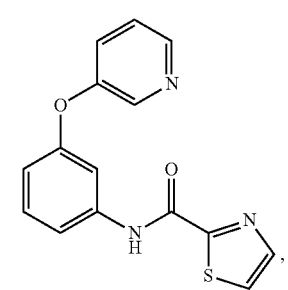
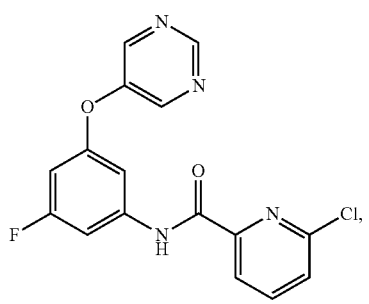
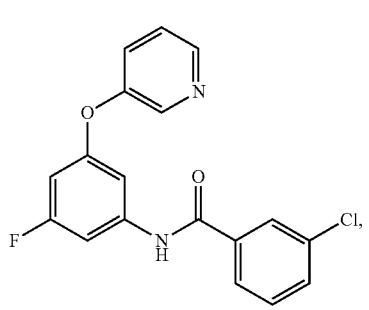
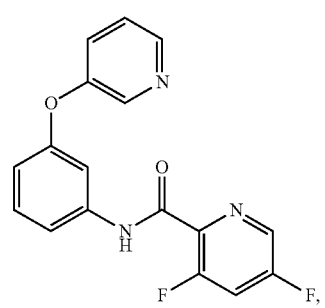

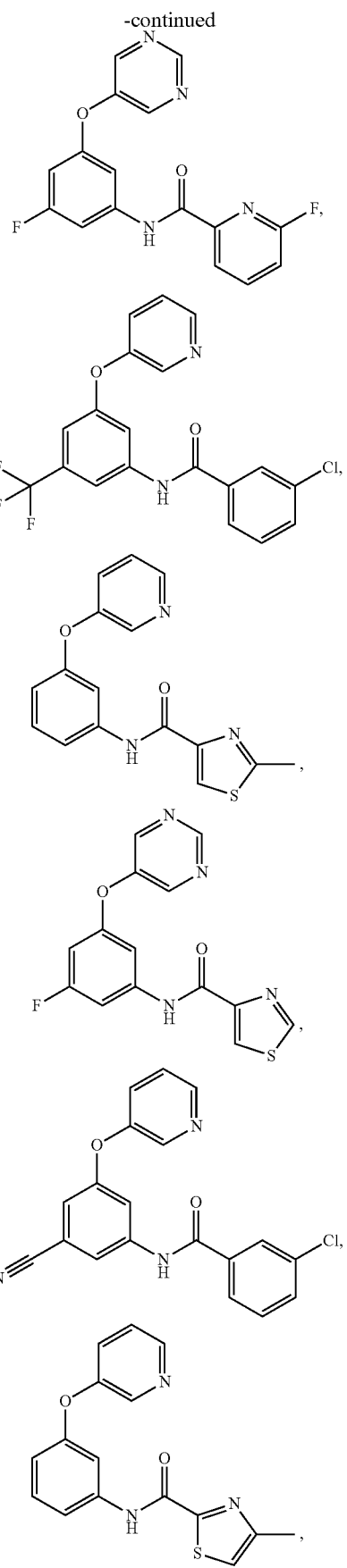
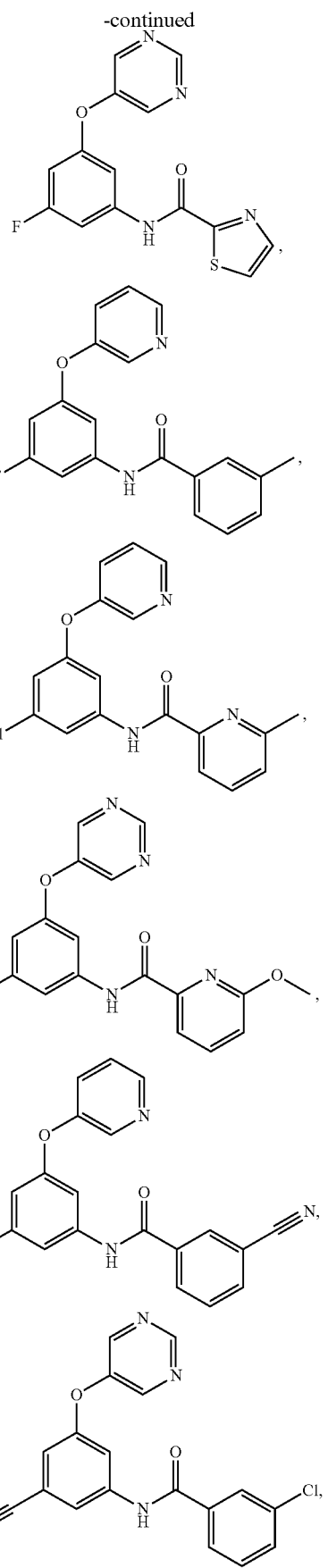

153
-continued
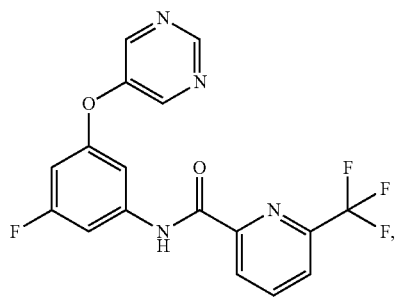
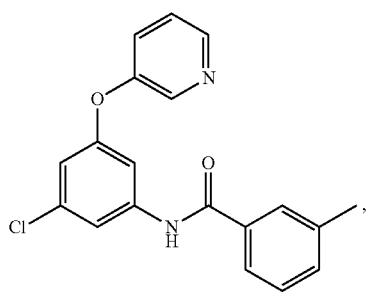
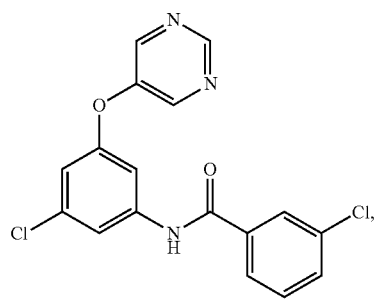
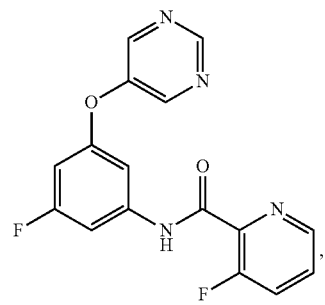
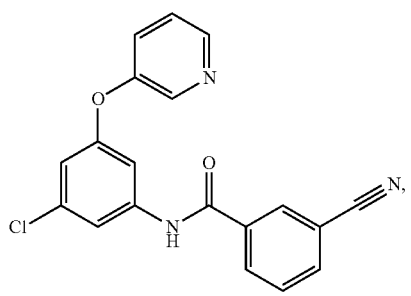
154
-continued
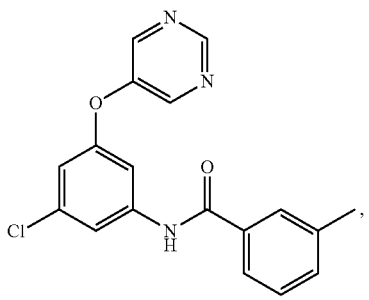
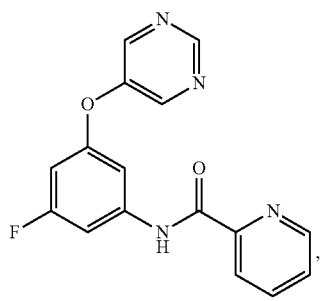
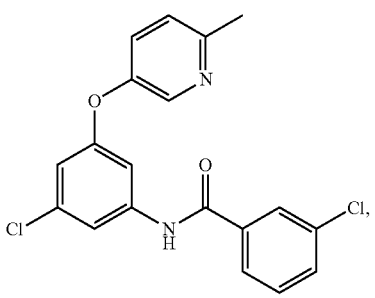
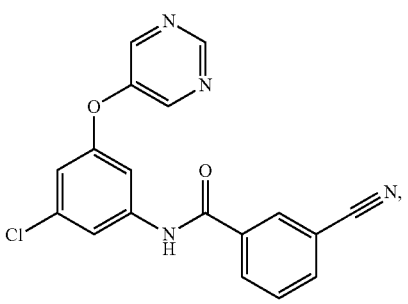
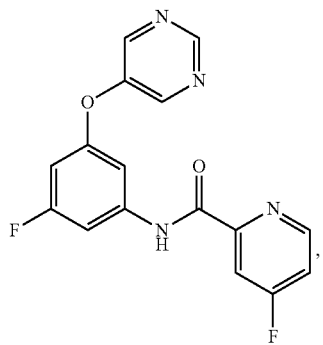

-continued
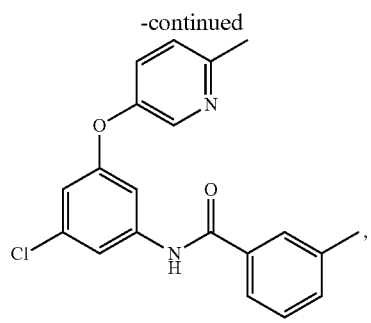
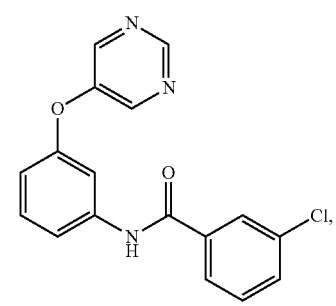
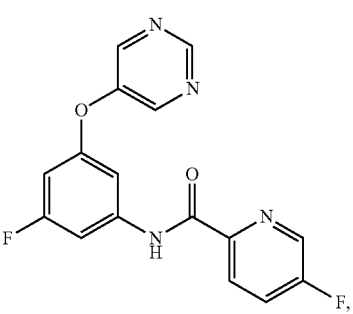
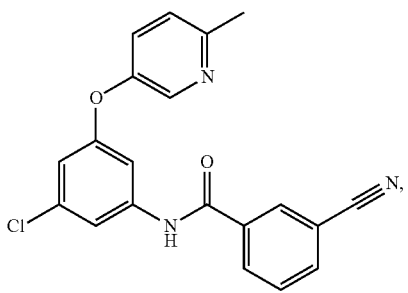
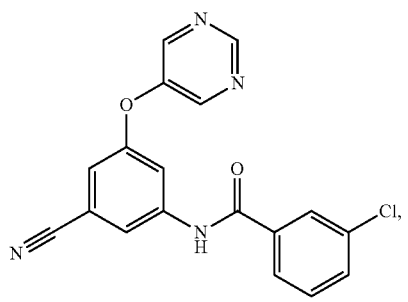
-continued
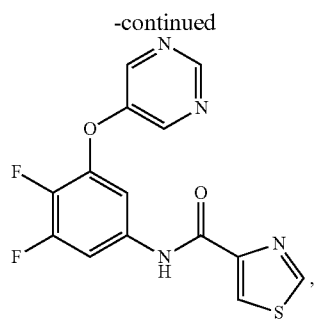
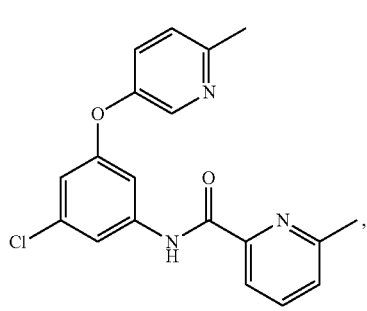
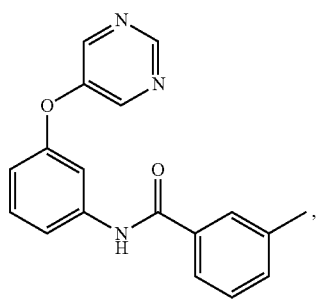
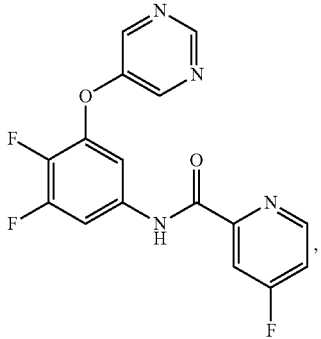
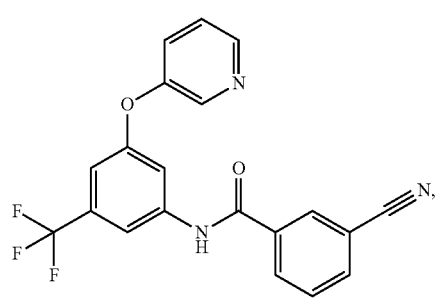

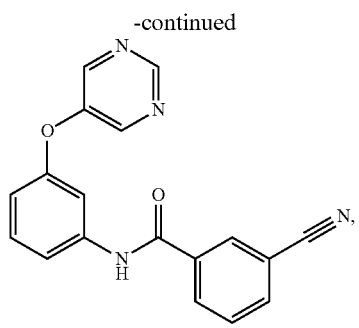
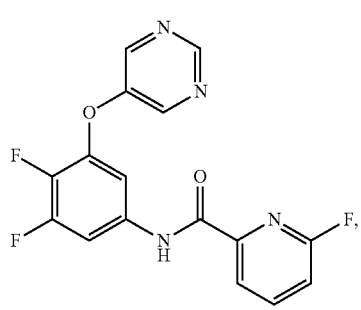
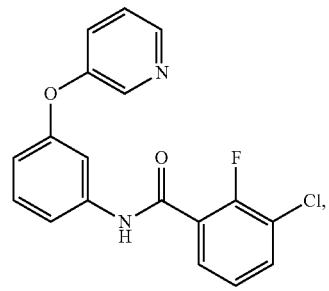
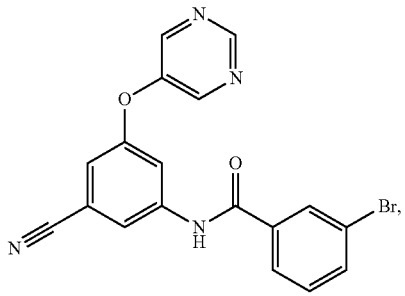
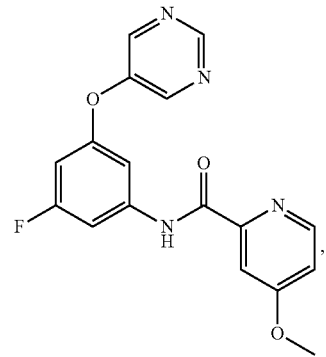
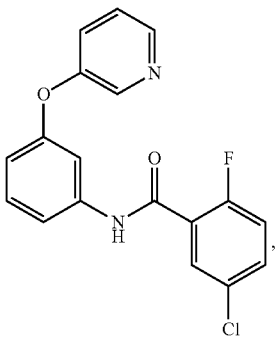
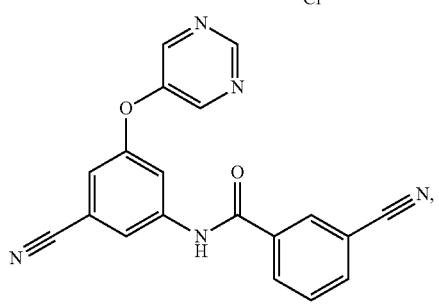
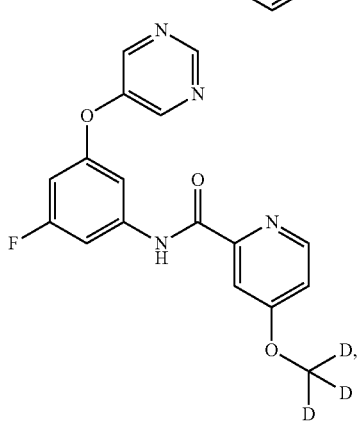
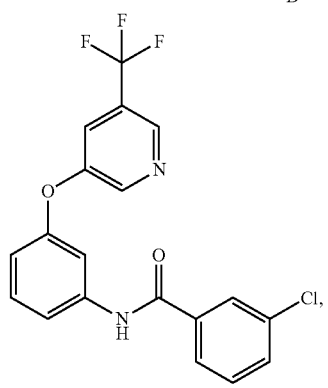
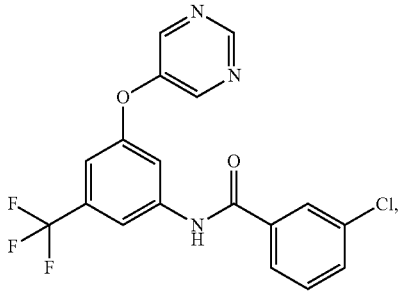

159
-continued
160
-continued
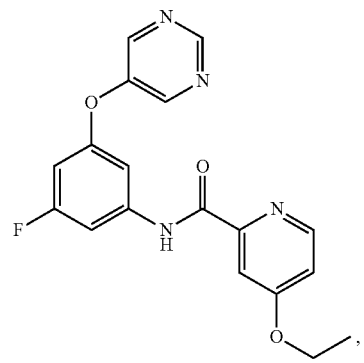
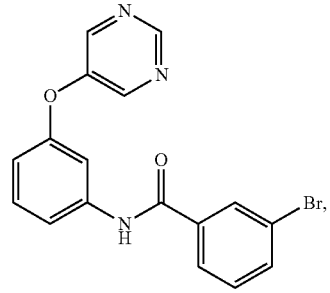

161
-continued
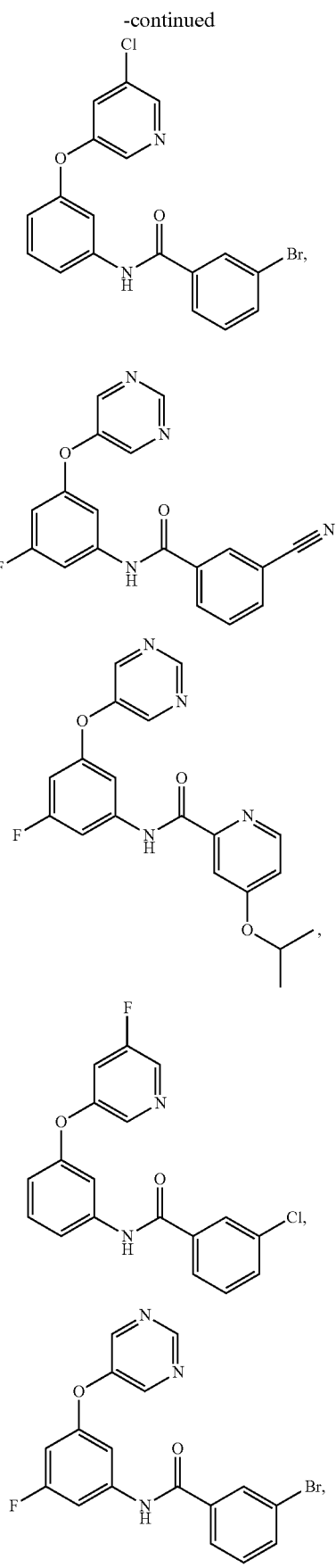
162
-continued
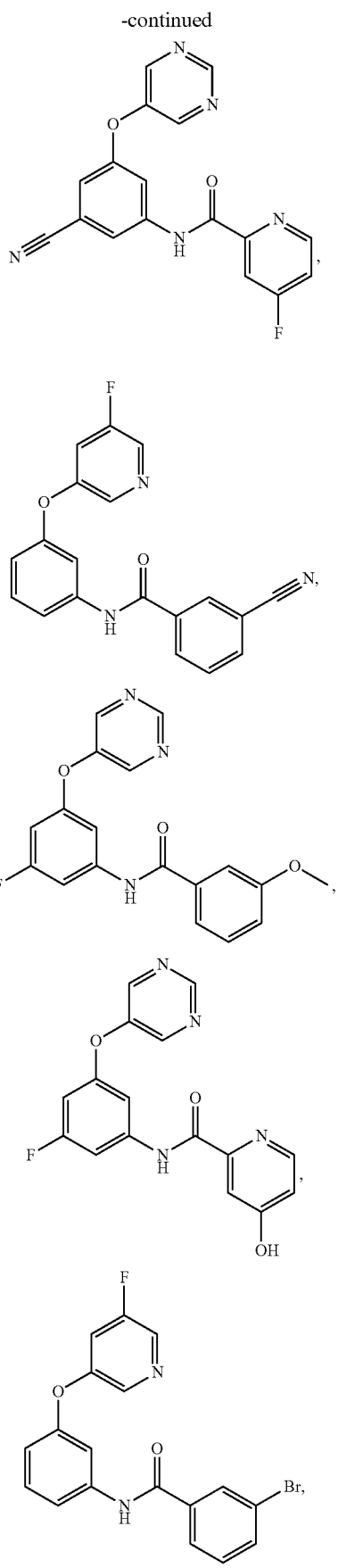

-continued
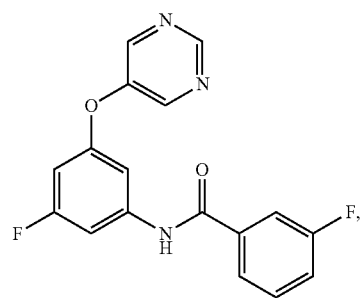
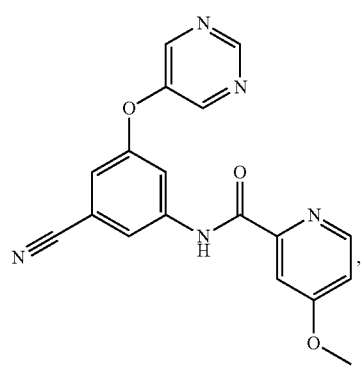
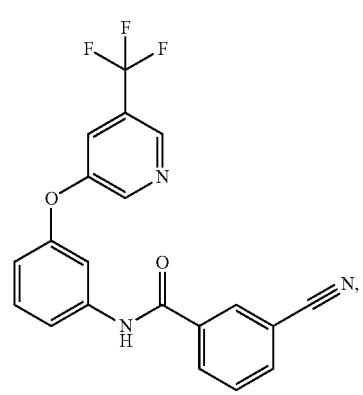
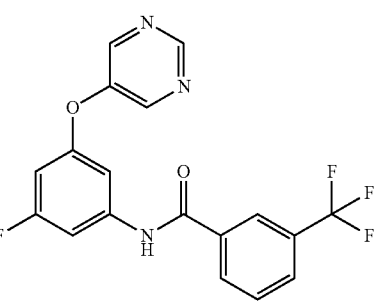
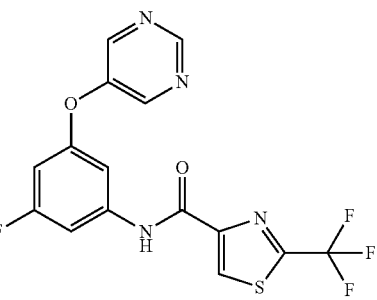
-continued
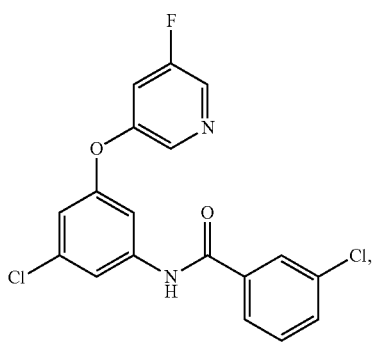
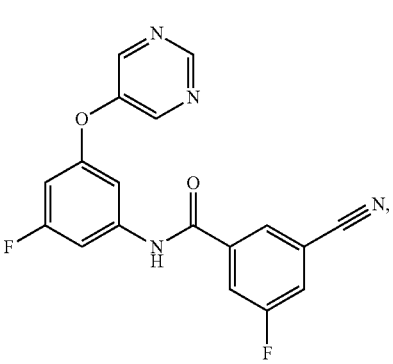
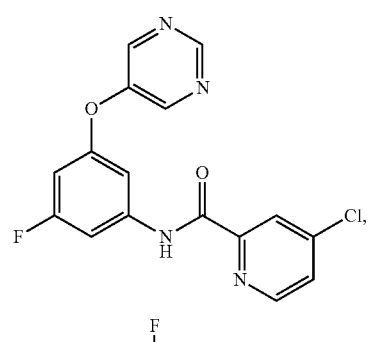
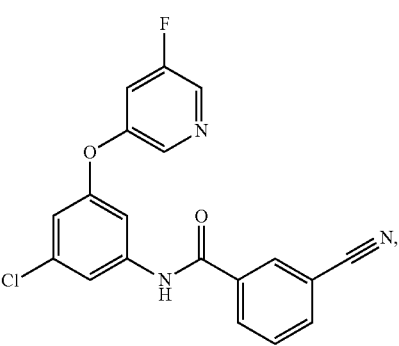 [SMILES: N#Cc1cccc(C(=O)Nc2cc(Cl)cc(Oc3cncc(F)c3)c2)c1]
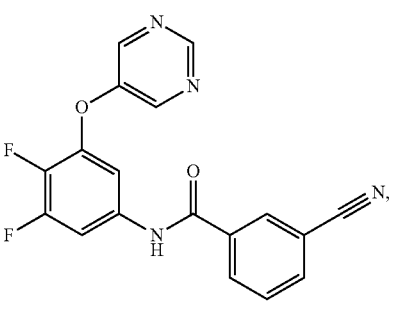

-continued
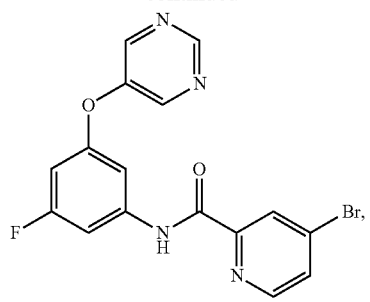
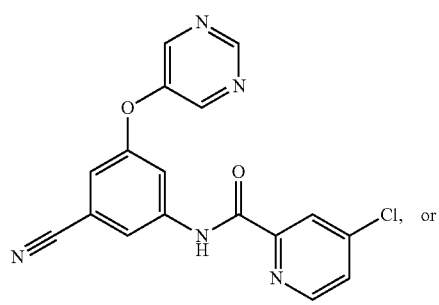
Cl, or
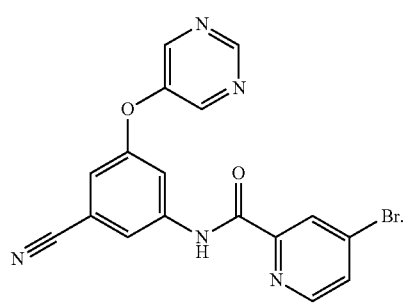
In a further aspect, a compound can be present as:
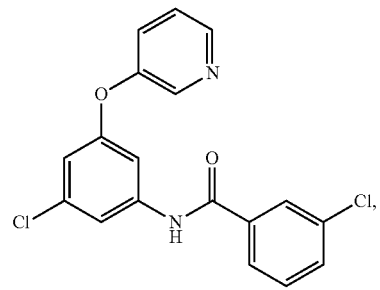
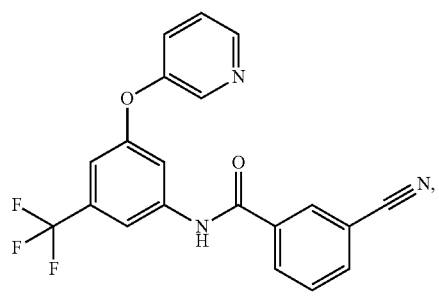
-continued
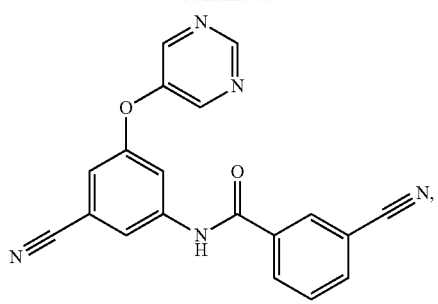
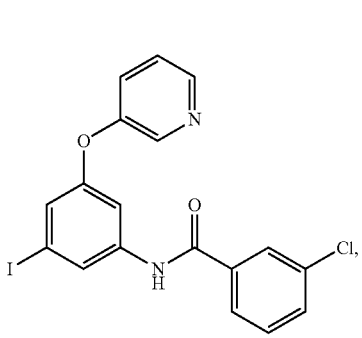
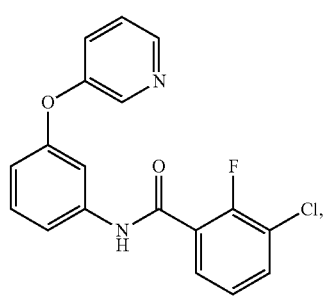
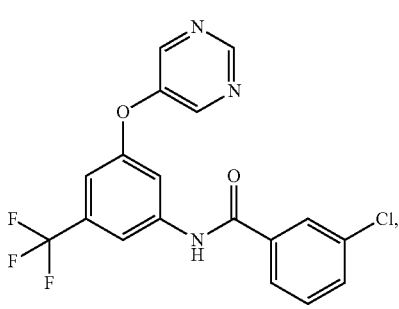
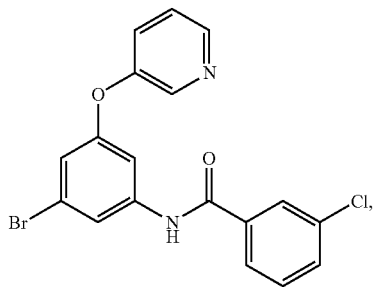

-continued
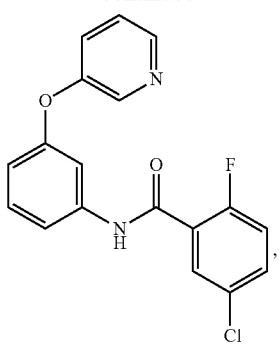
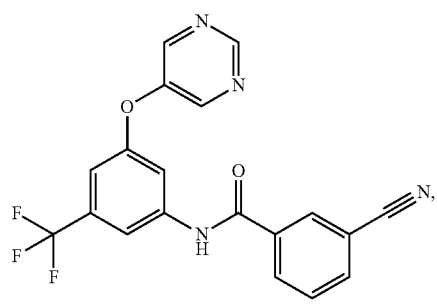
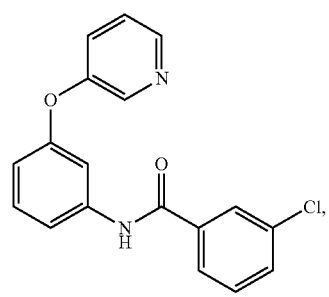
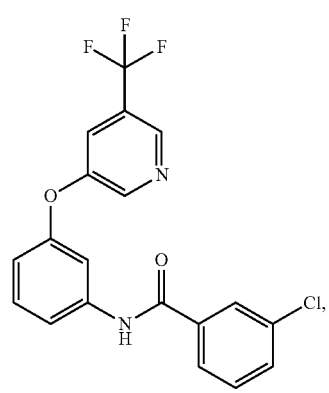
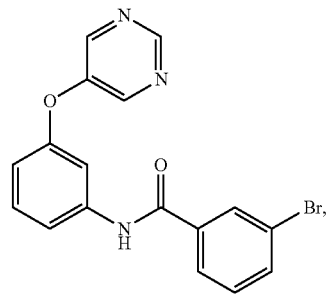
-continued
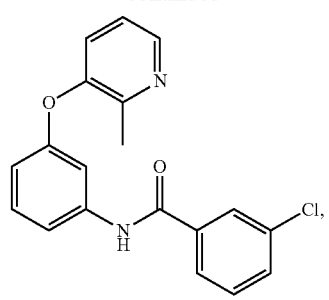
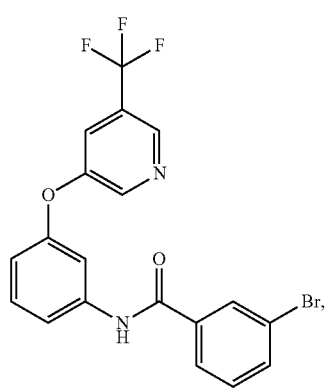
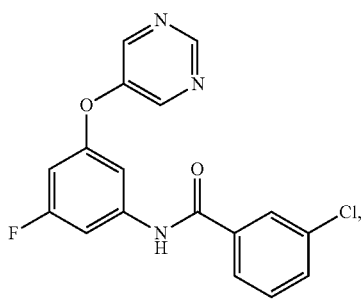
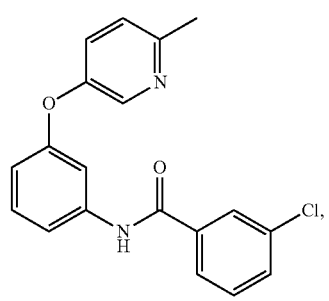
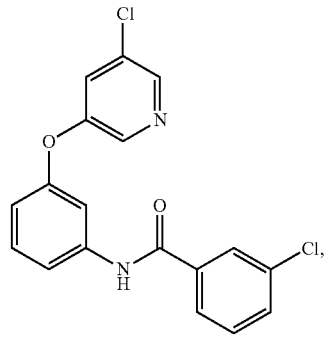

169
-continued

170
-continued

171
-continued
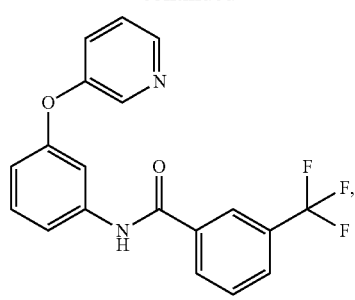
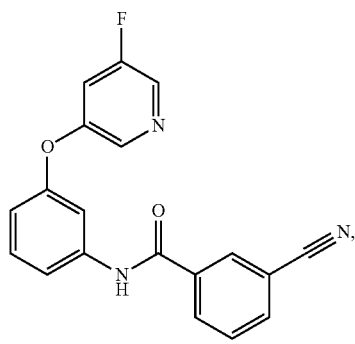
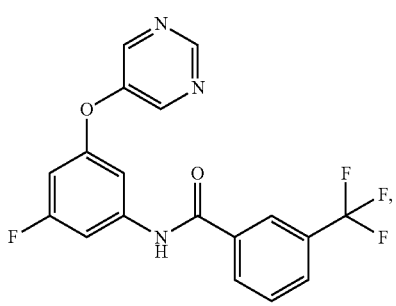
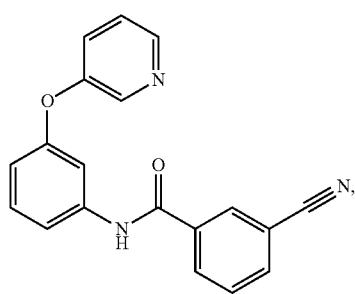
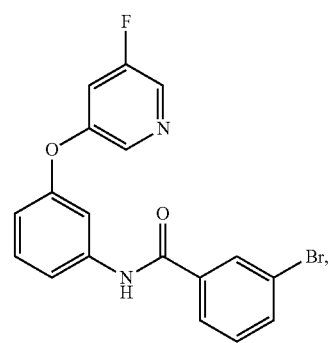
172
-continued
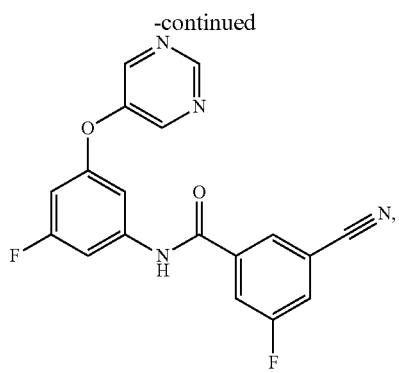
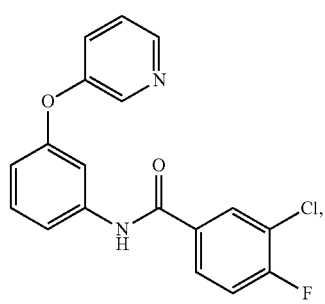
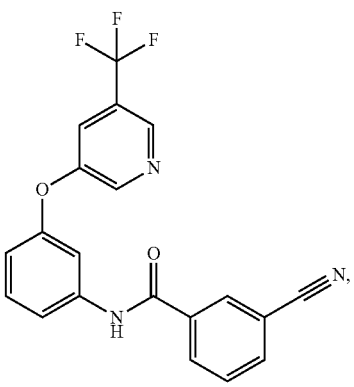
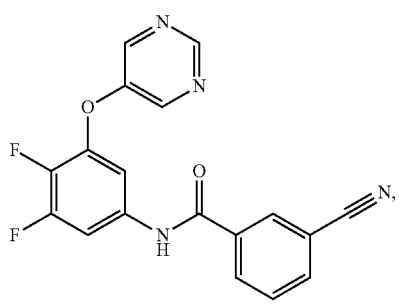
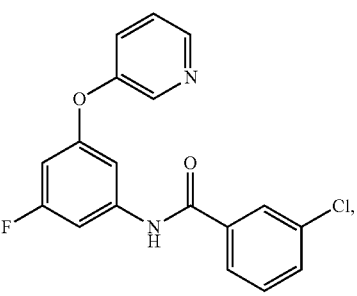

-continued
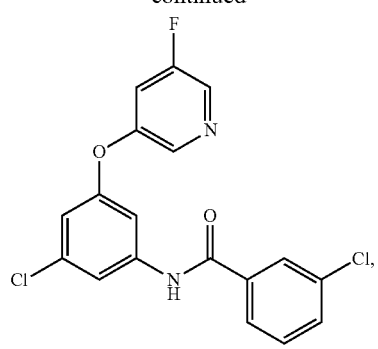
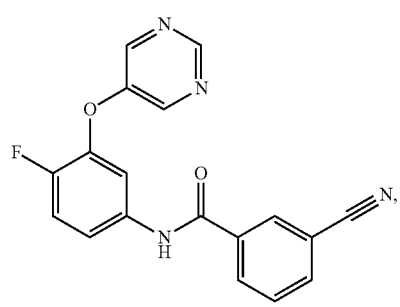
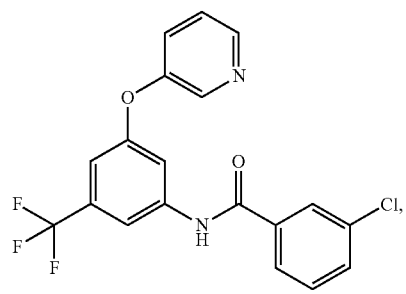
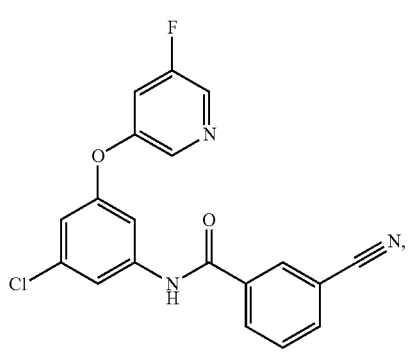 [SMILES: N#Cc1cccc(C(=O)Nc2cc(Cl)cc(Oc3cncc(F)c3)c2)c1]
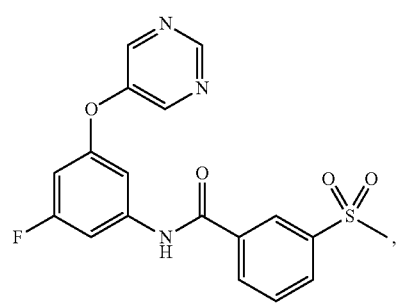
-continued
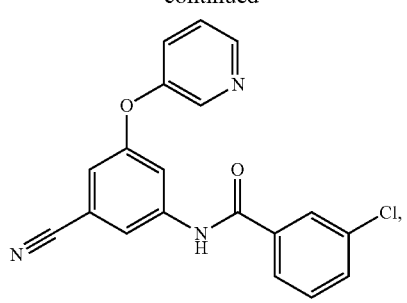
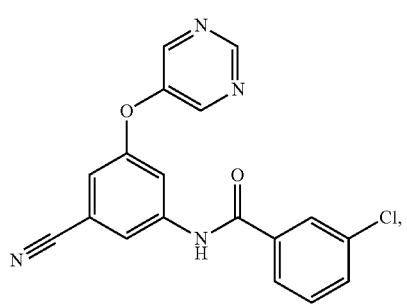
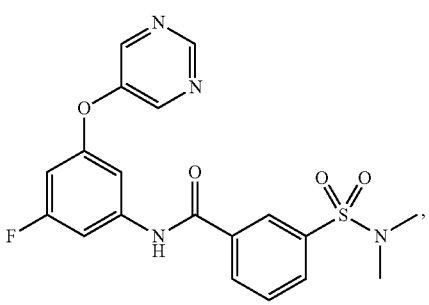
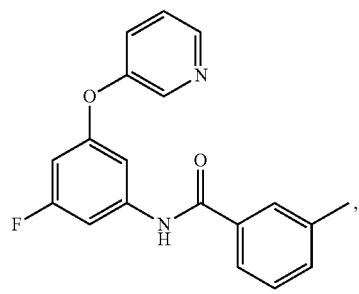
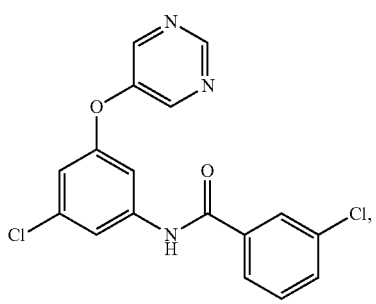

175
-continued
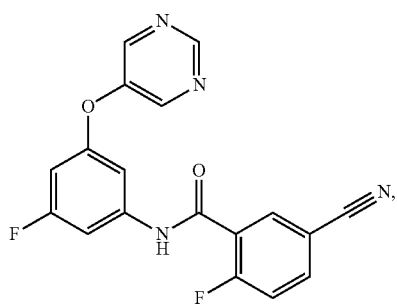
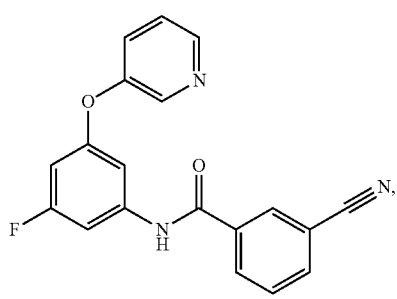
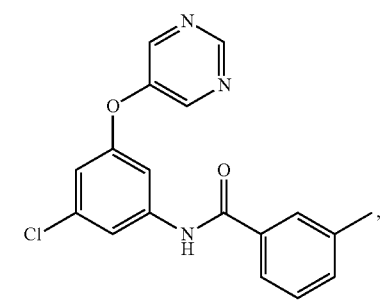
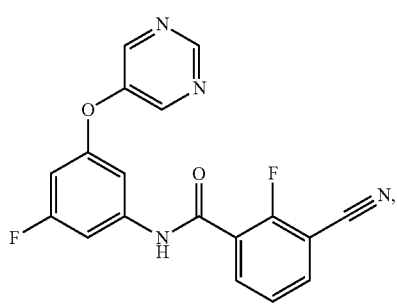
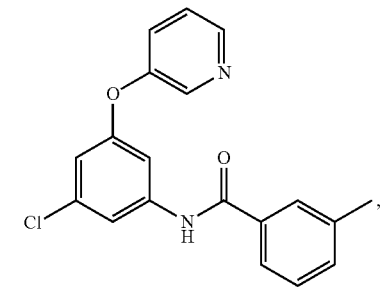
176
-continued
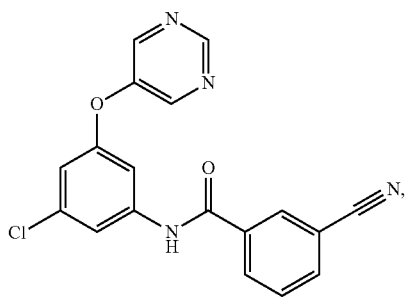
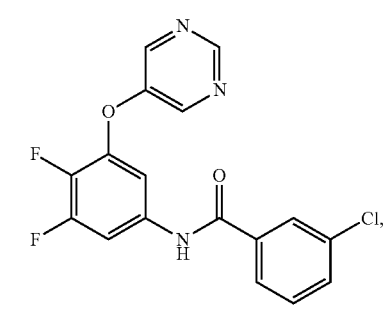
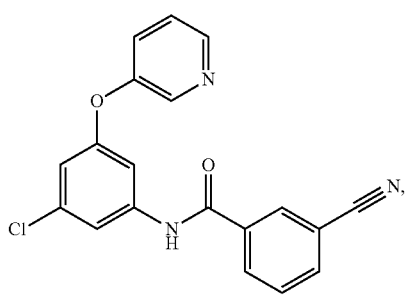
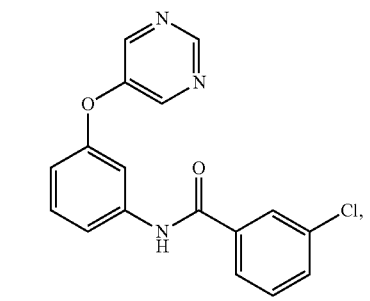
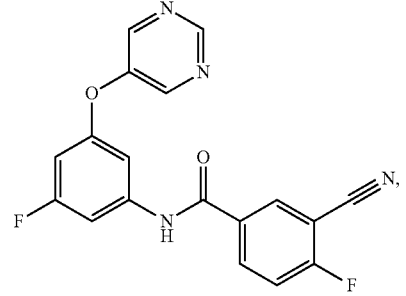

177
-continued
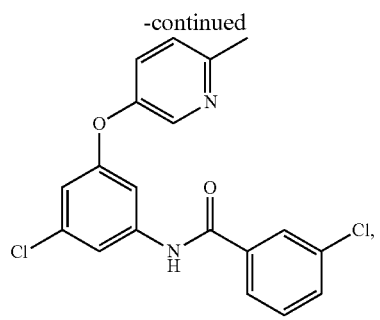
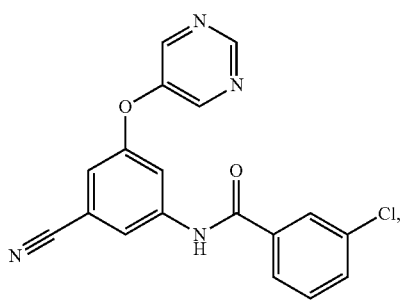
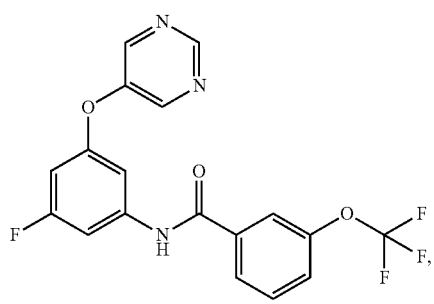
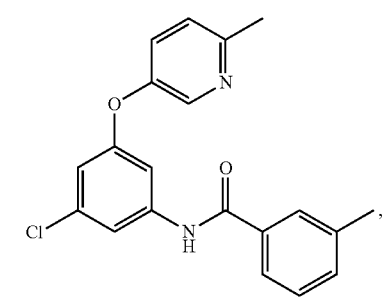
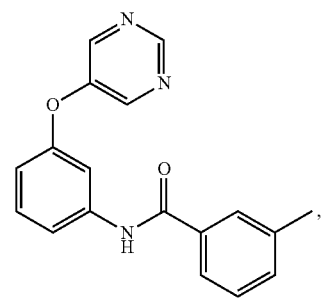
178
-continued
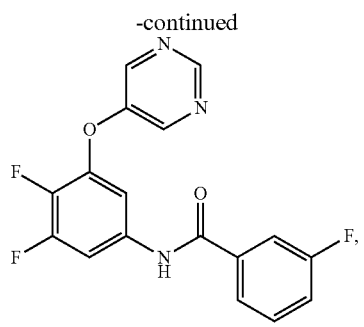
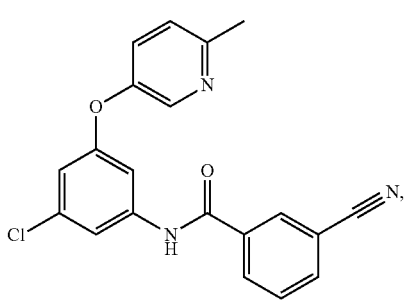
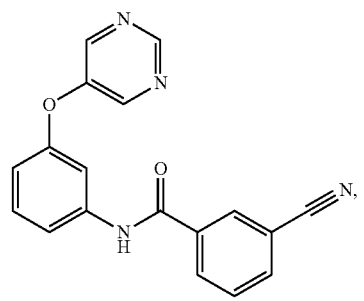
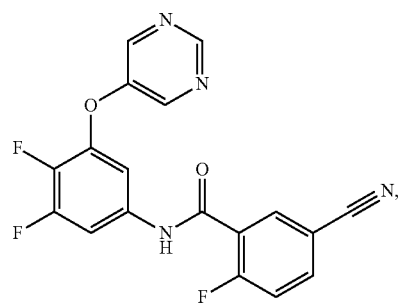
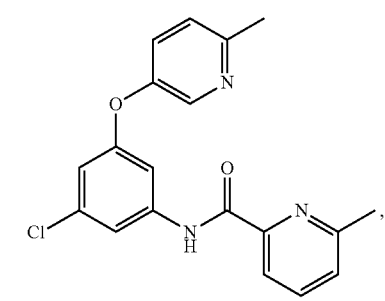

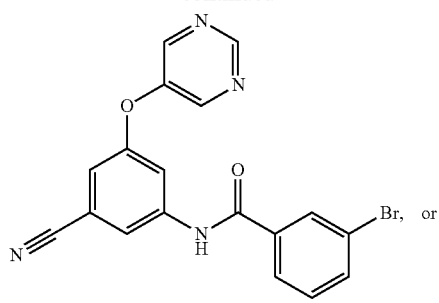
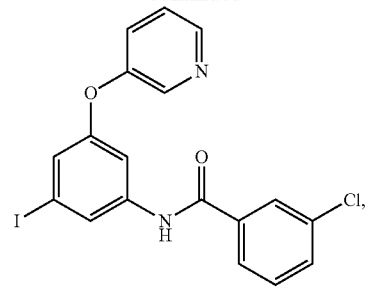
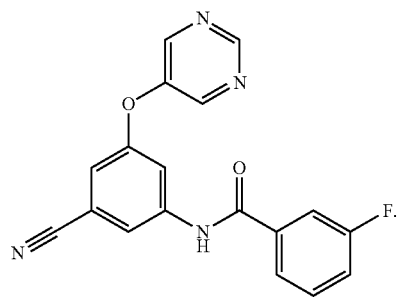
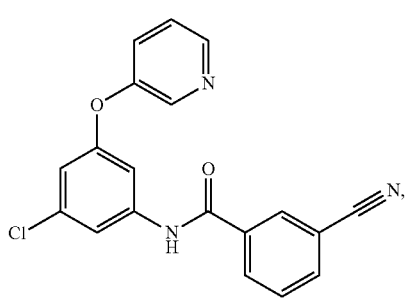
In a further aspect, a compound can be present as:
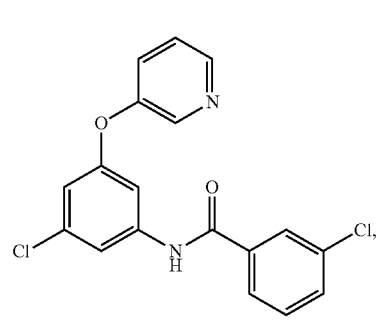
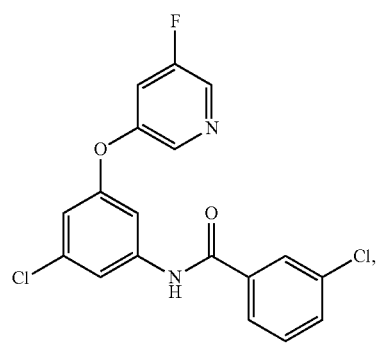
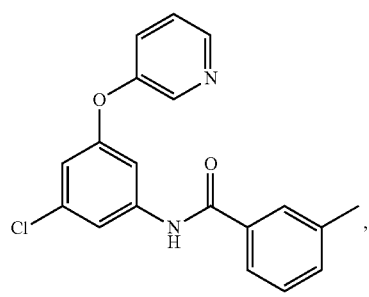
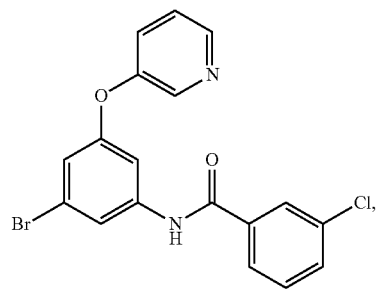
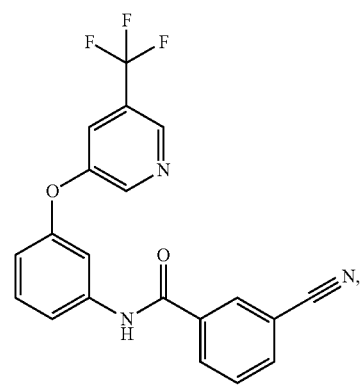
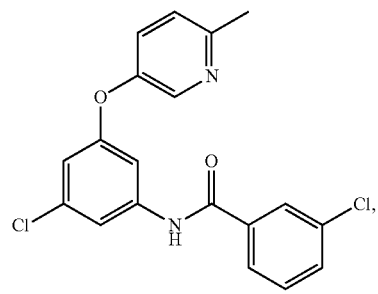

181
-continued
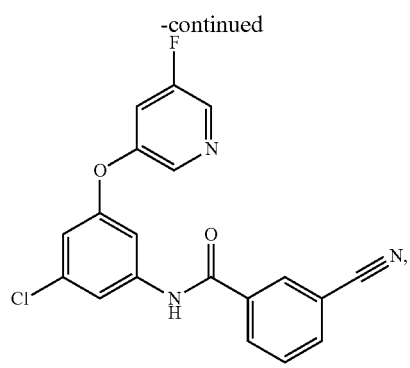
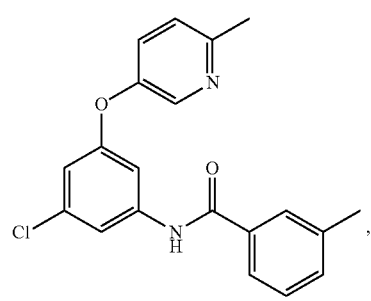
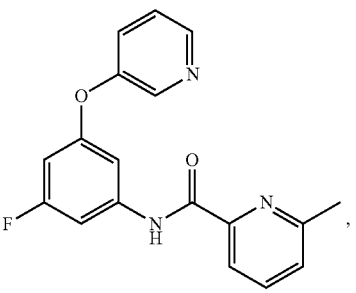
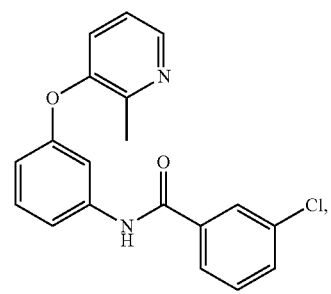
182
-continued
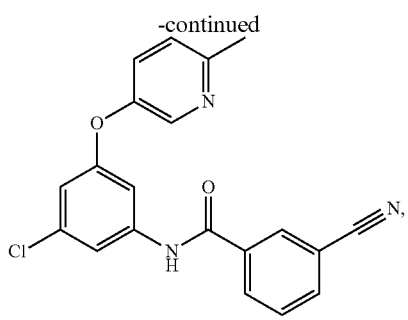
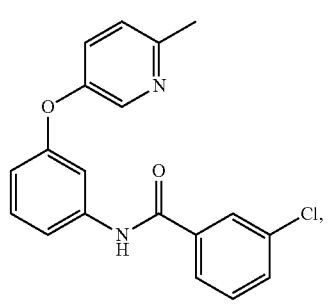
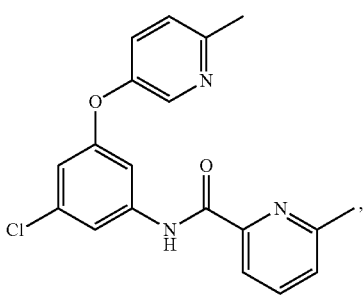
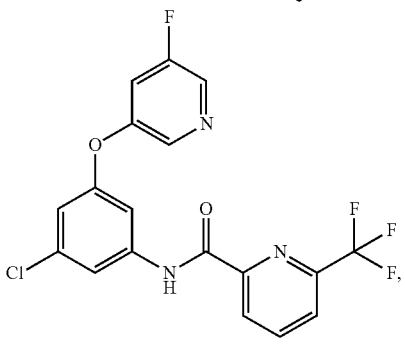

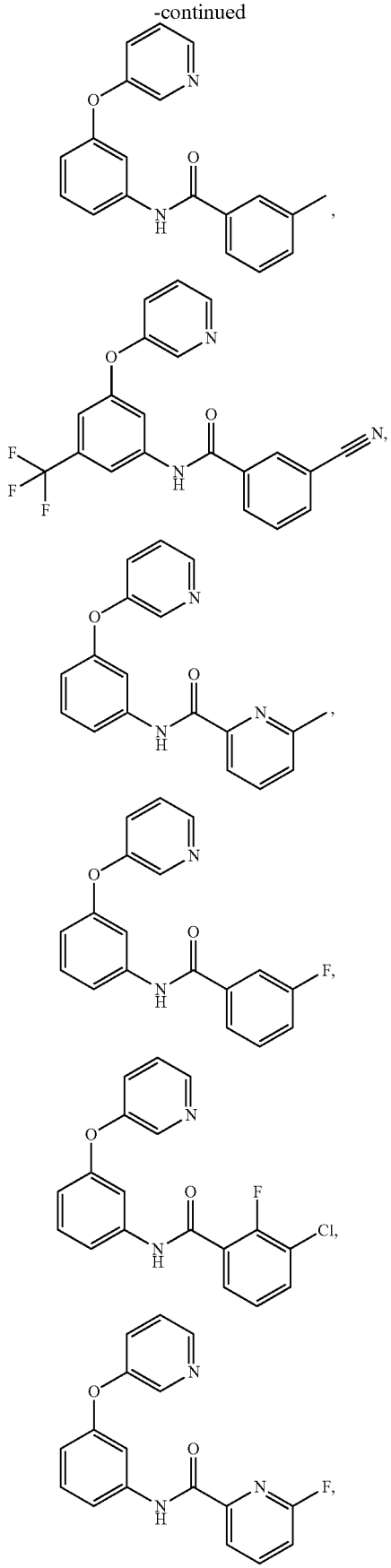
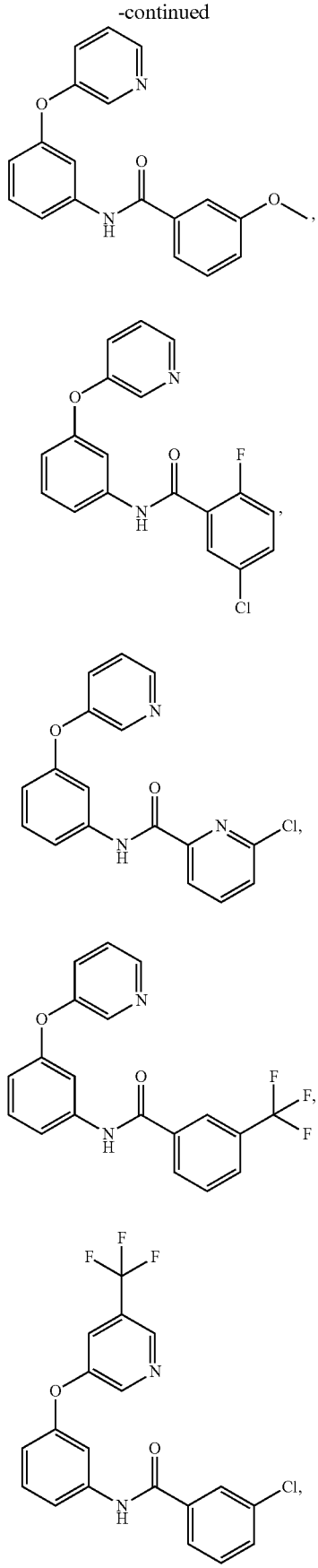

185
-continued
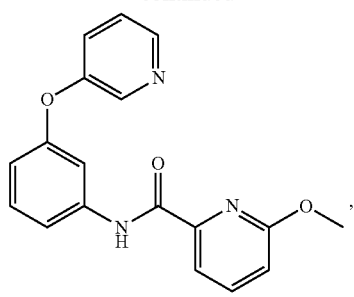
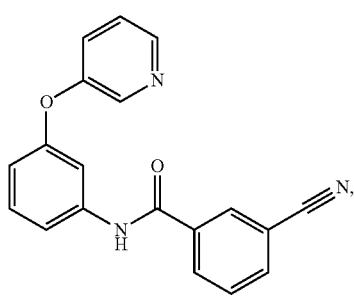
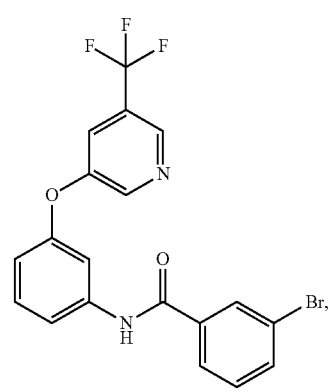
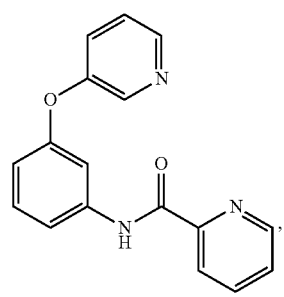
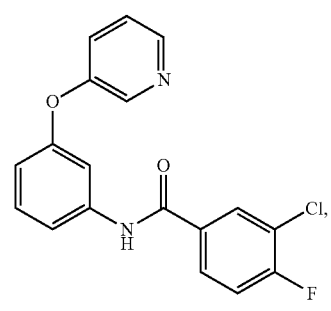
186
-continued
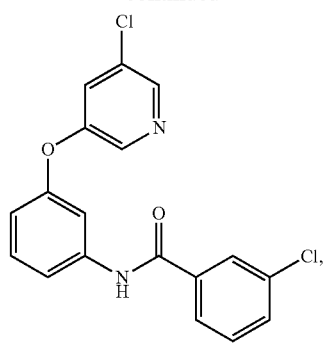
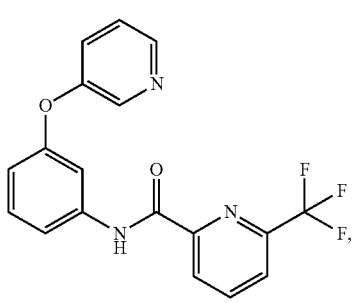
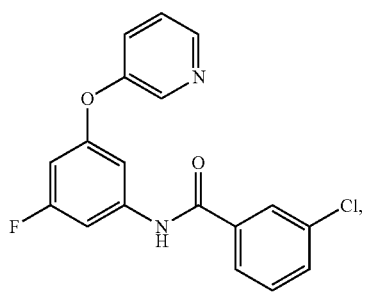
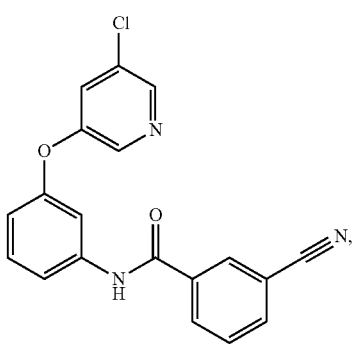
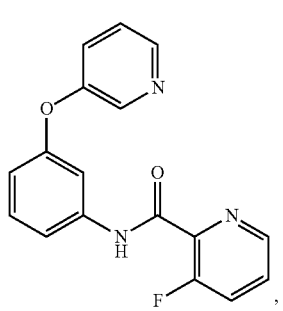

187
-continued

188
-continued

189
-continued
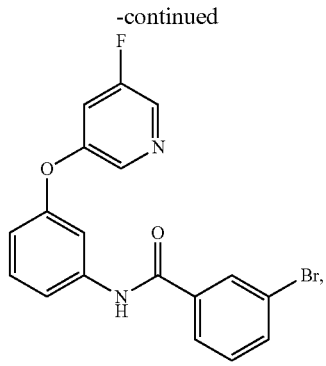
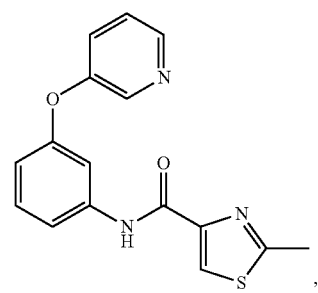
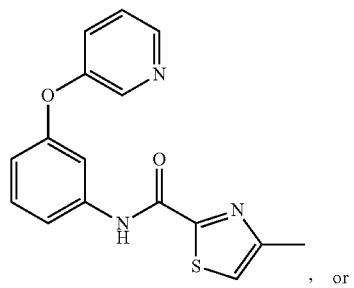
, or
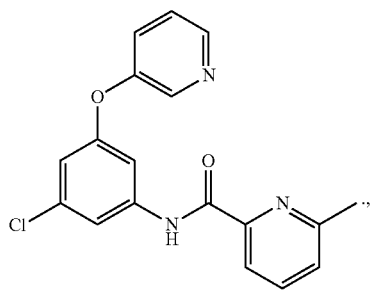
In a further aspect, a compound can be present as:
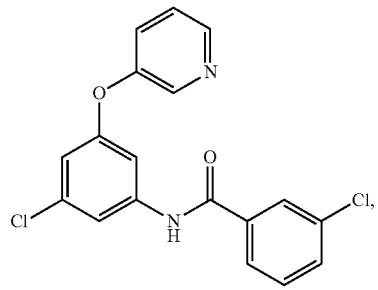
190
-continued
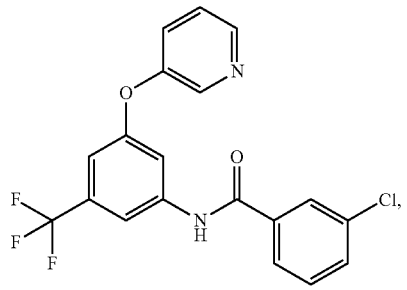
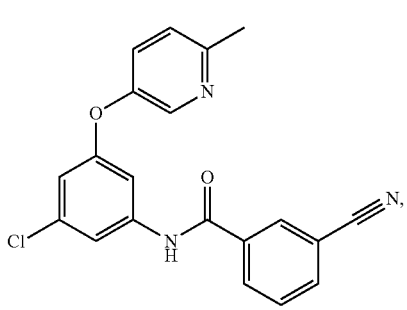
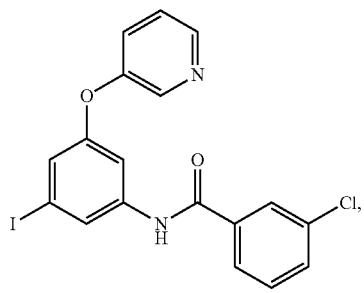
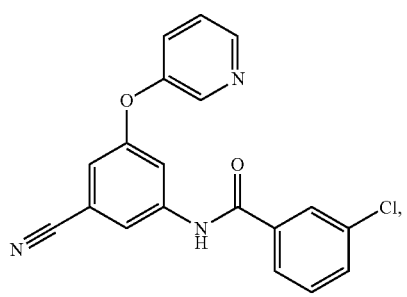
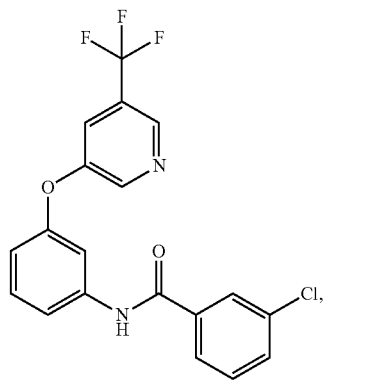

191
-continued
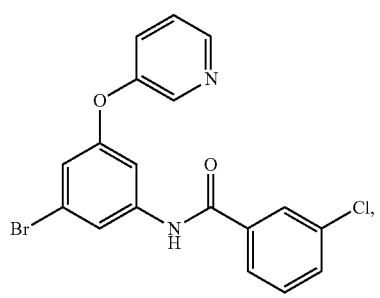
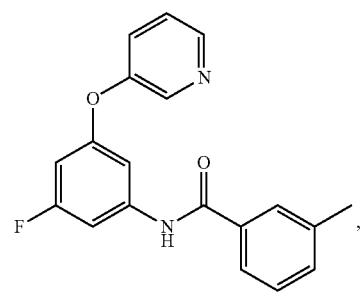
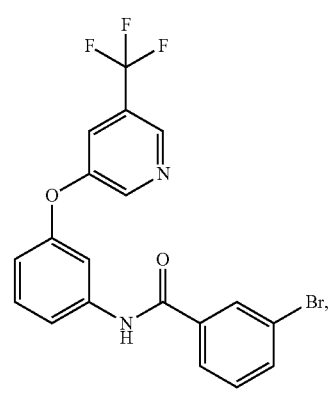
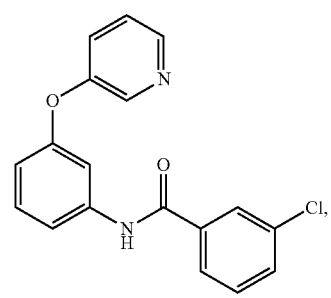
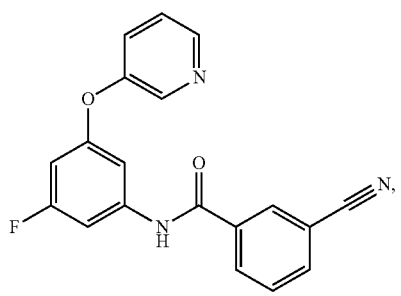
192
-continued
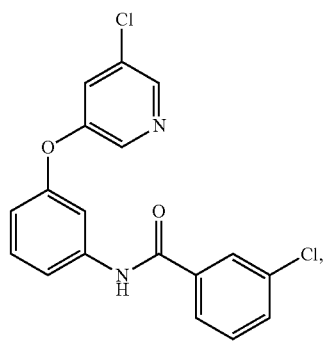
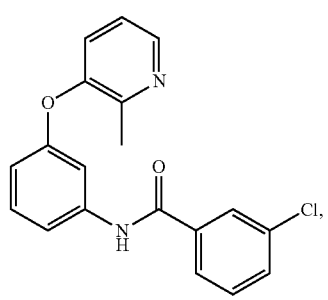
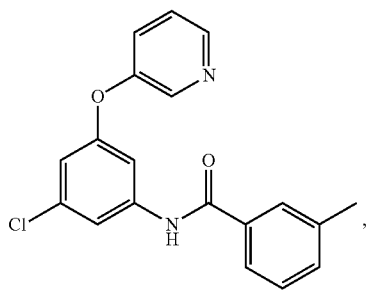
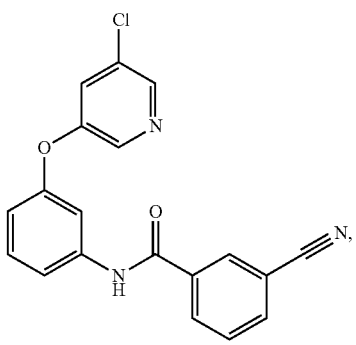
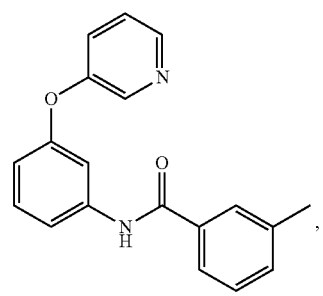

-continued
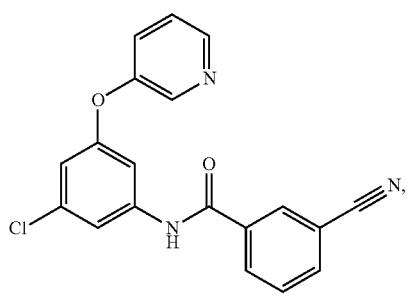
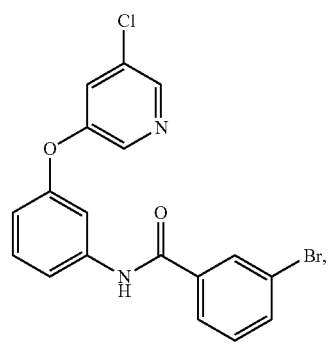
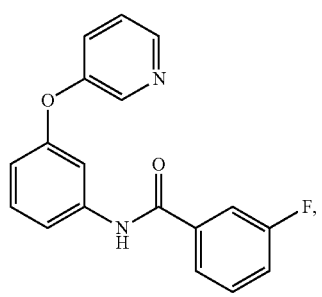
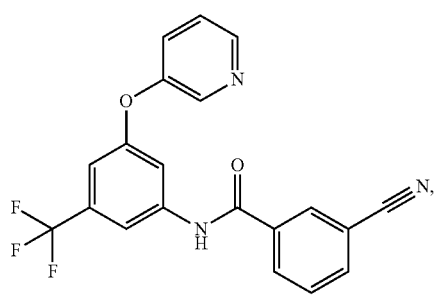
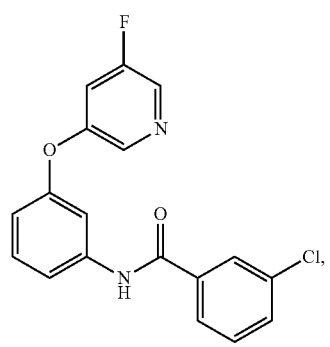
-continued
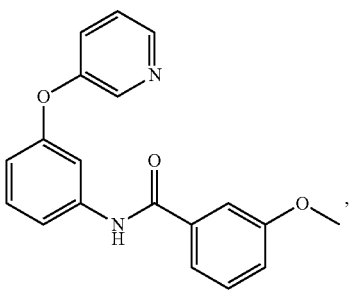
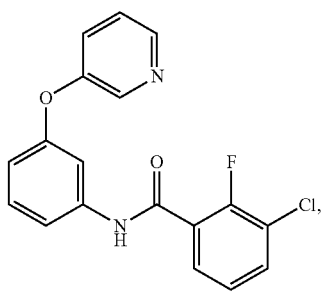
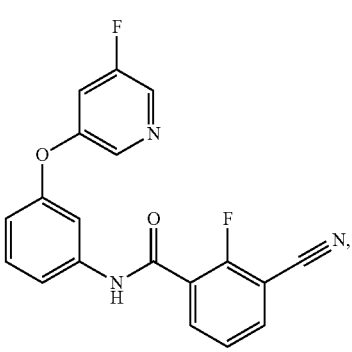
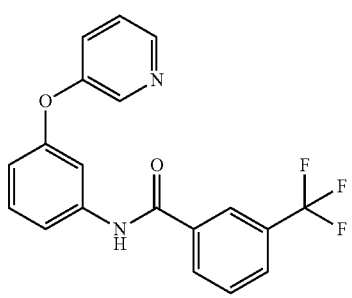
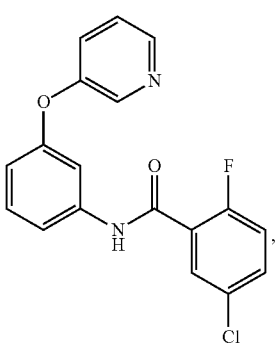 [SMILES: O=C(Nc1cccc(Oc2cccnc2)c1)c1cc(Cl)ccc1F]

195
-continued
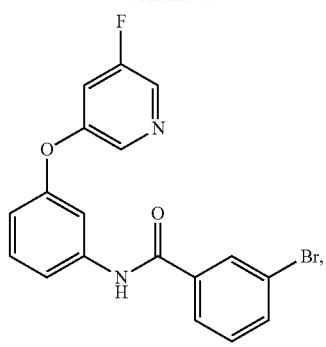
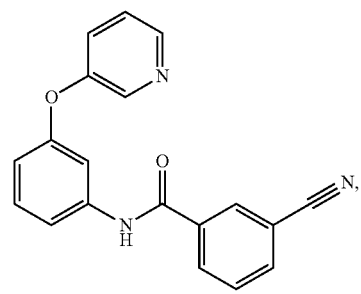
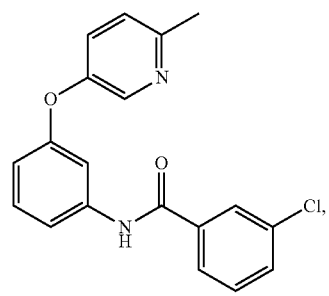
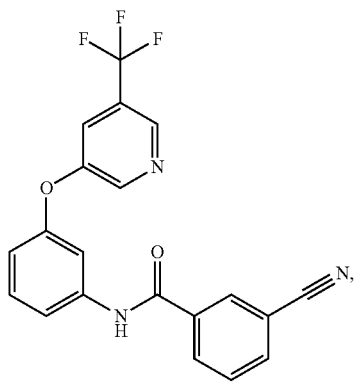
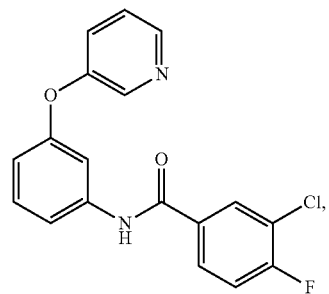
196
-continued
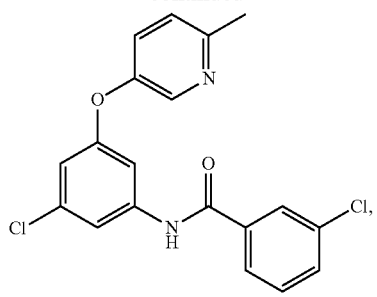
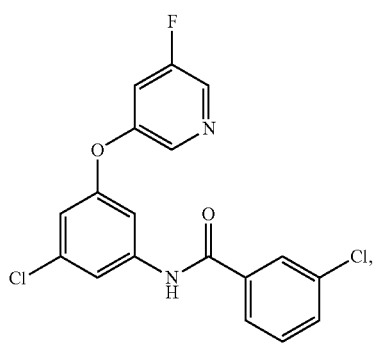
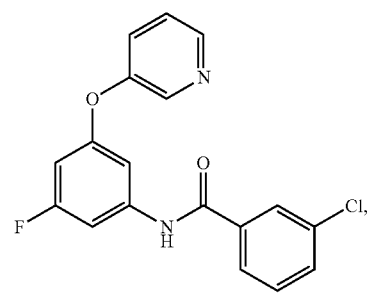
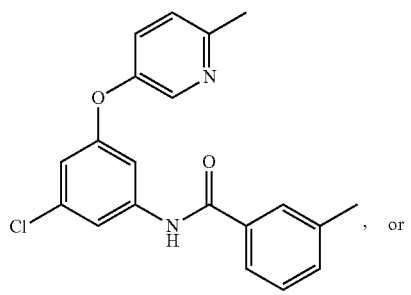, or

In a further aspect, a compound can be present as:
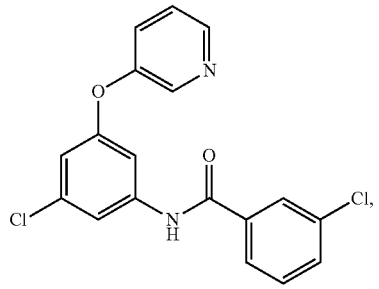
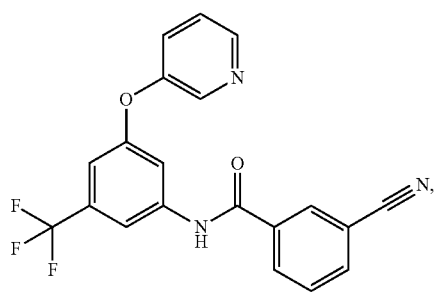
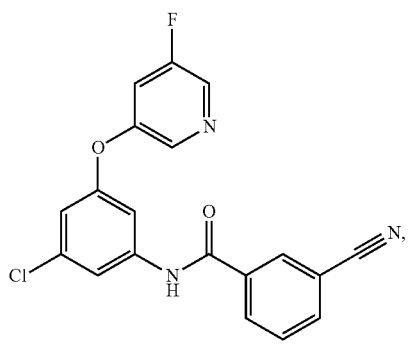
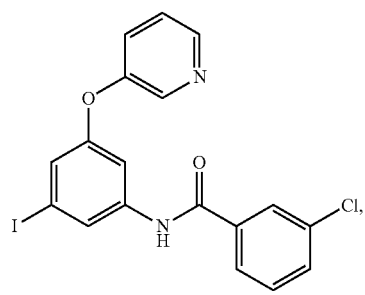
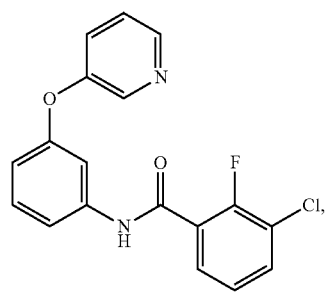
-continued
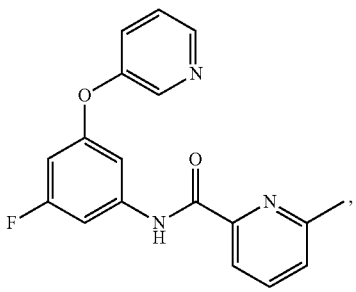
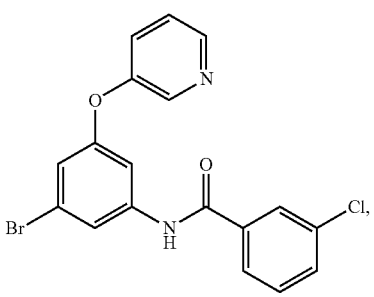
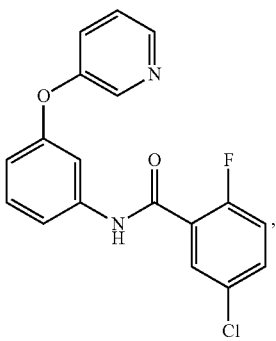
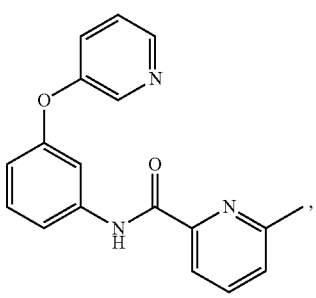
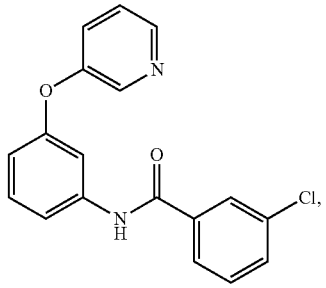

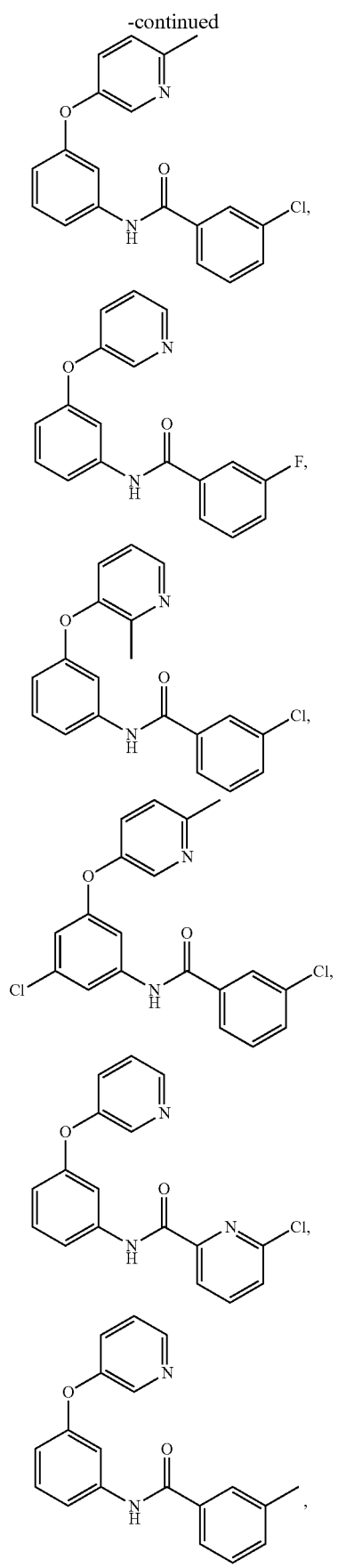
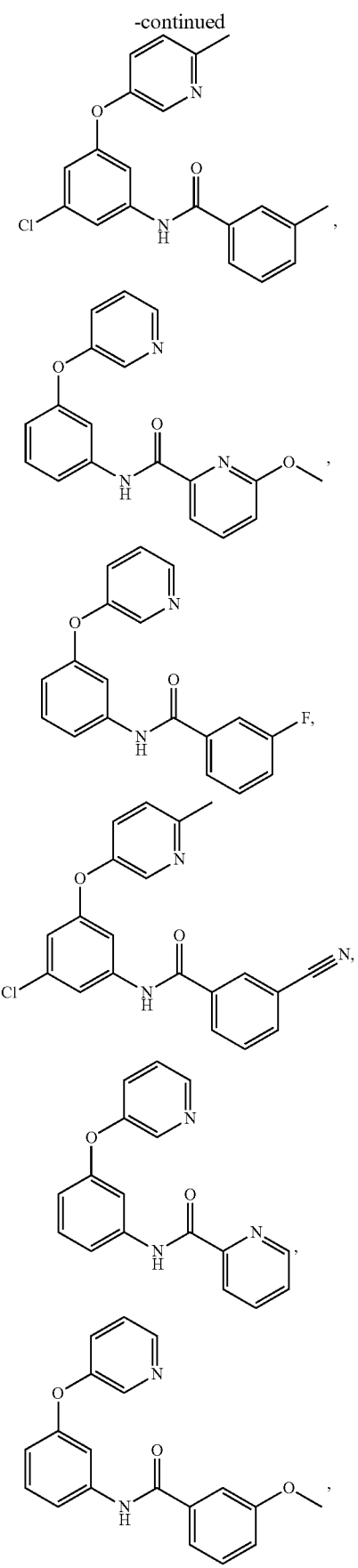

201
-continued
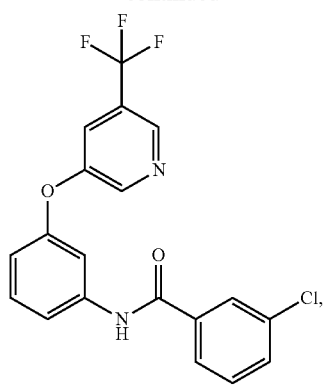
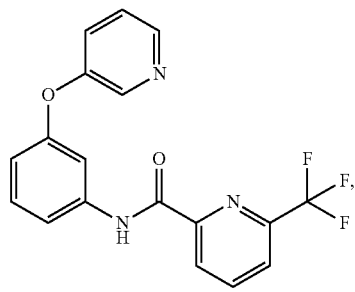
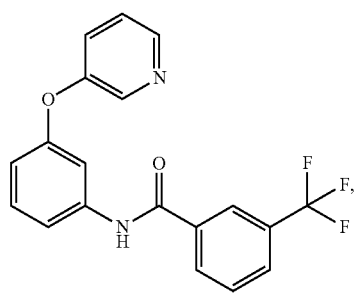
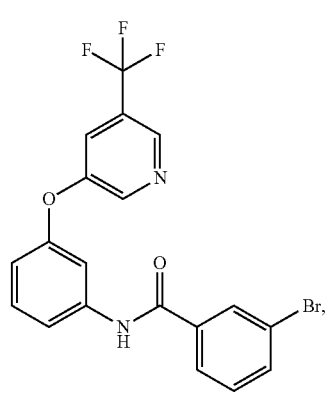
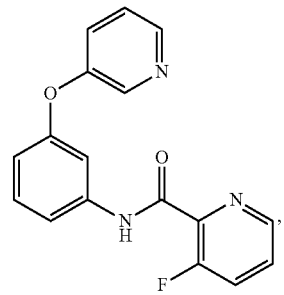
202
-continued
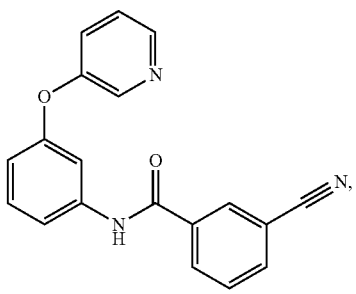
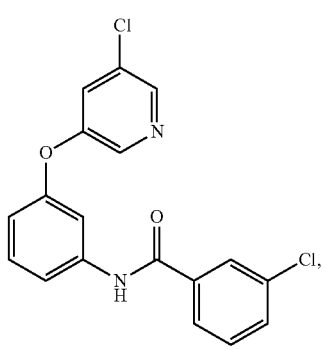
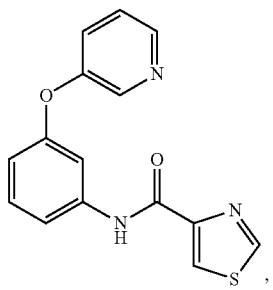
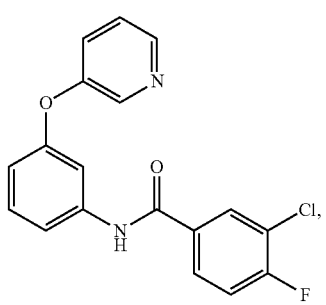
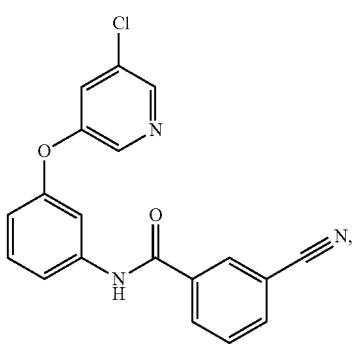

203
-continued
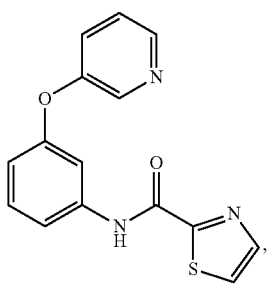
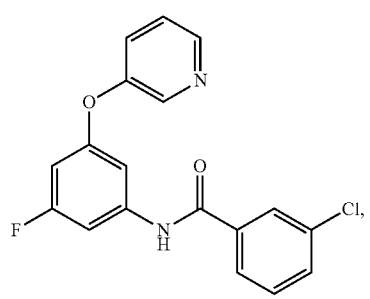
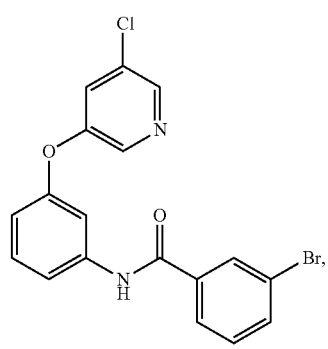
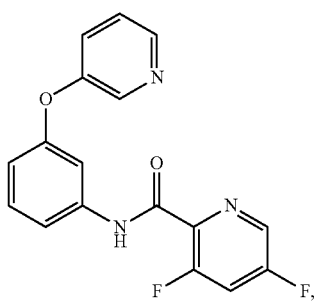
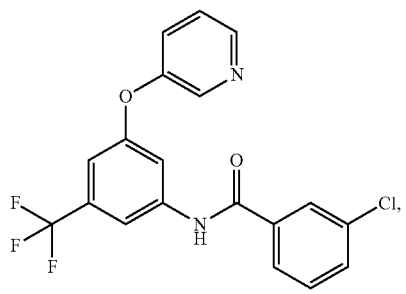
204
-continued
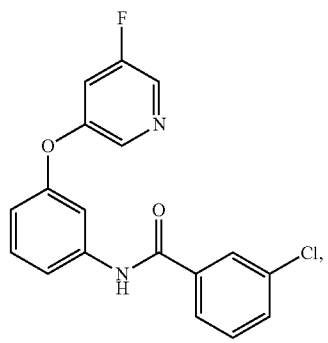
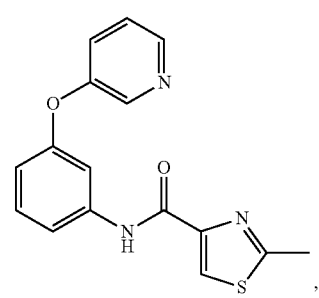
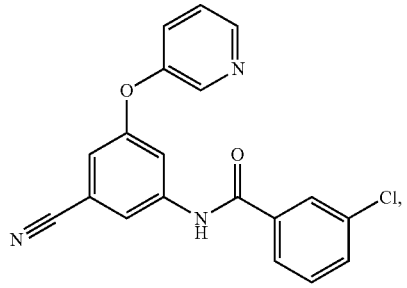
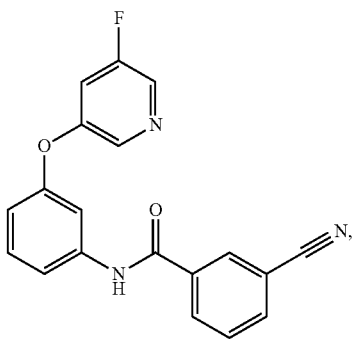
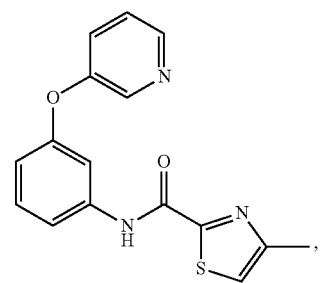

205
-continued
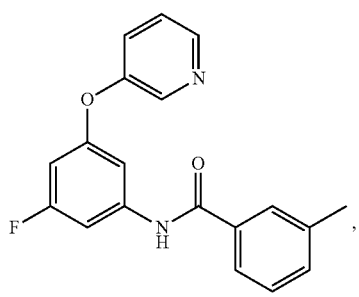
,
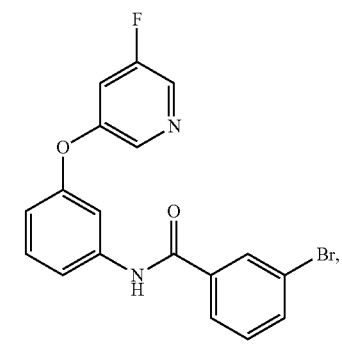
,
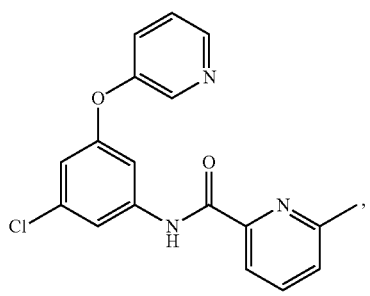
,
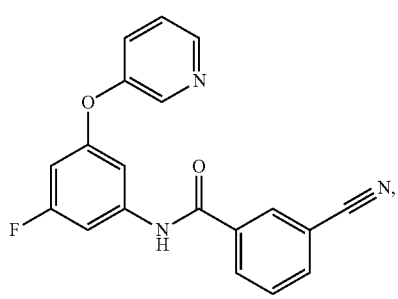
,
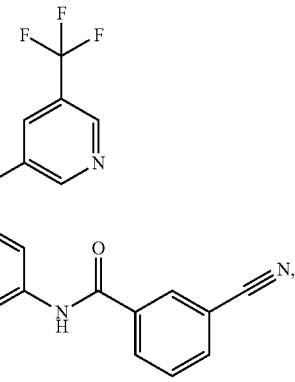
206
-continued
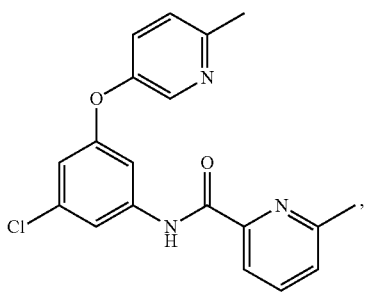
,
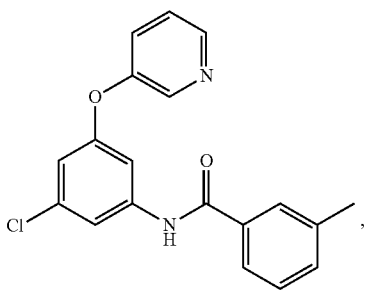
,
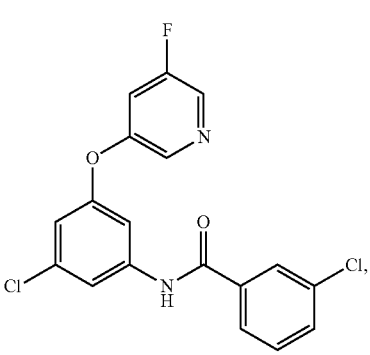
,
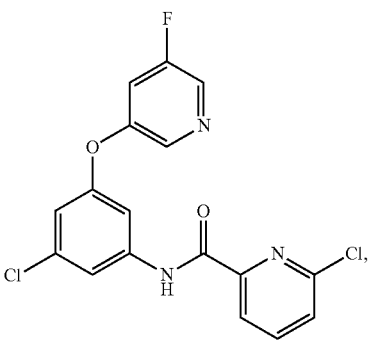
,
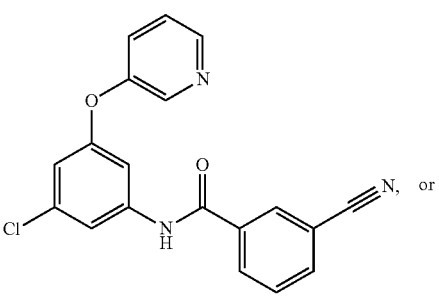 or

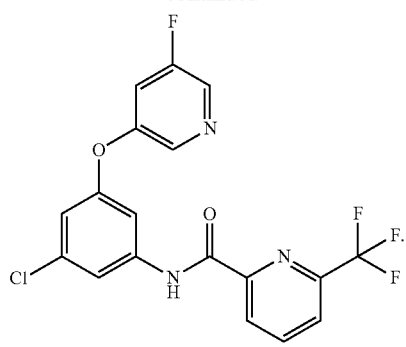
In a further aspect, a compound can be present as:
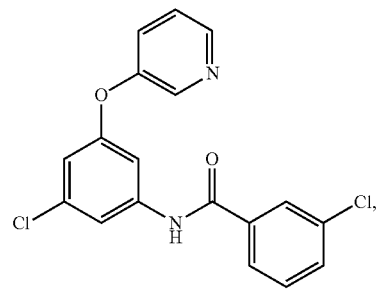
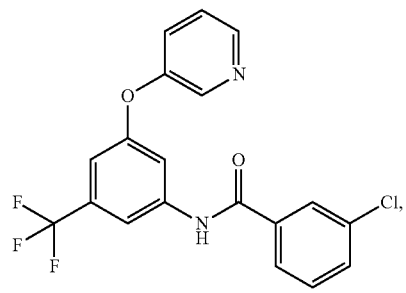
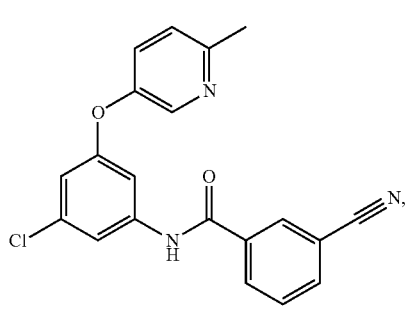
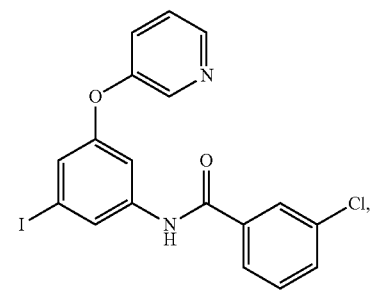
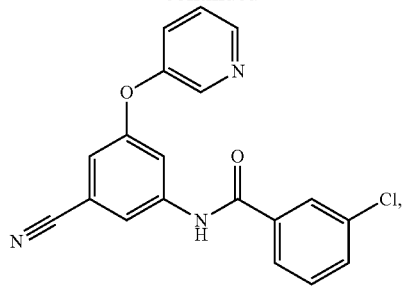
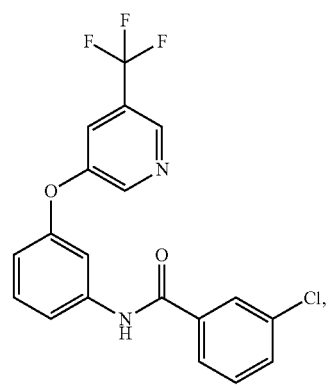
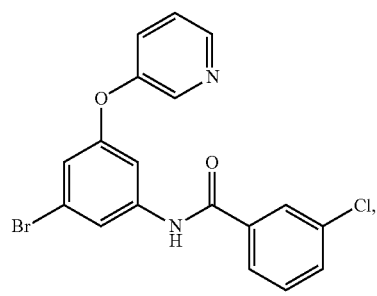
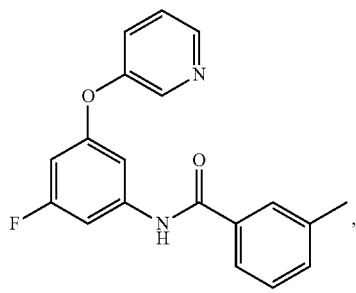
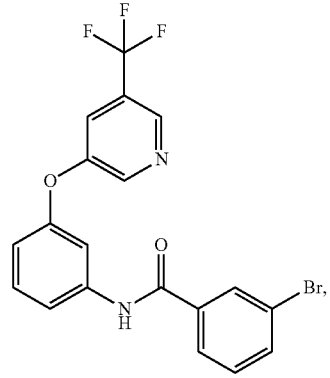

-continued
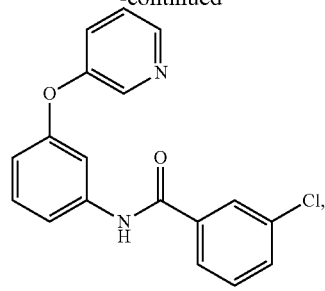
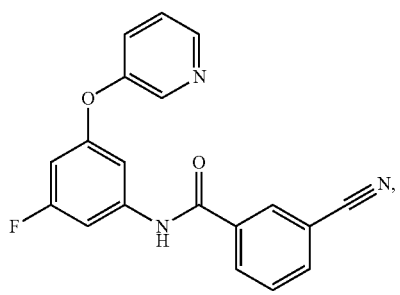
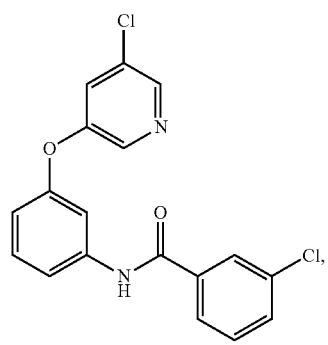
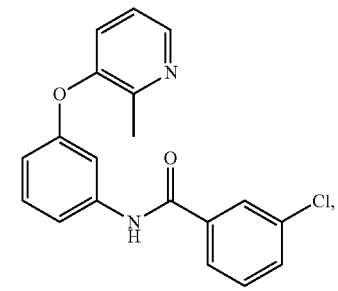
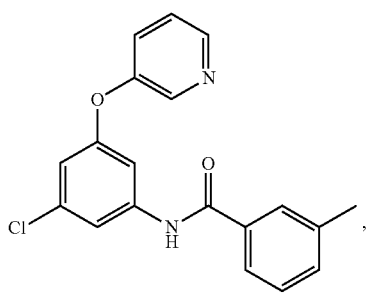
-continued
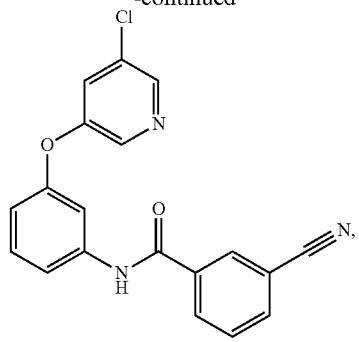
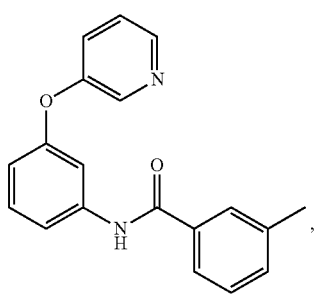
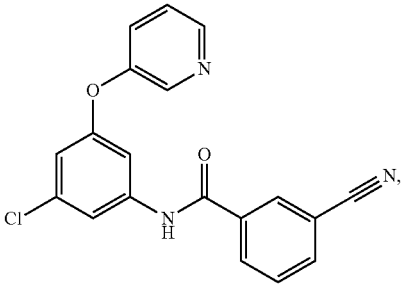
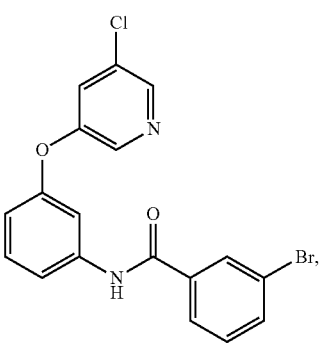
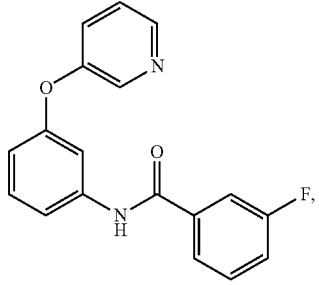

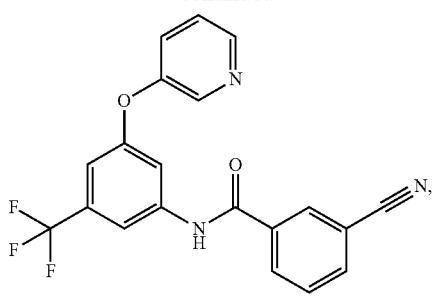
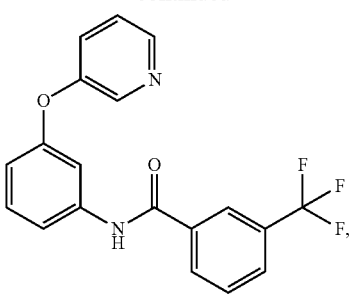

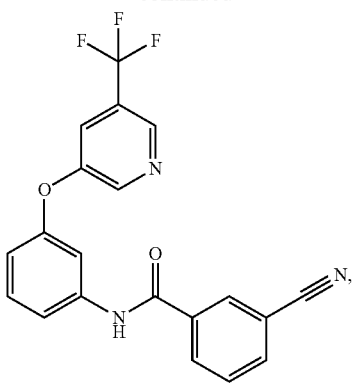
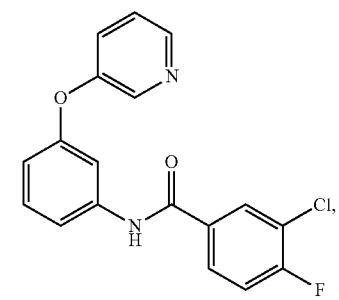
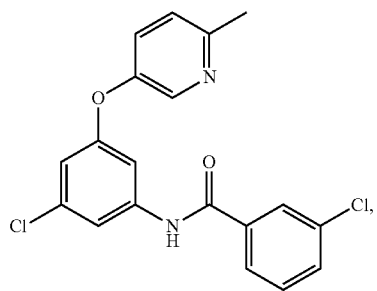
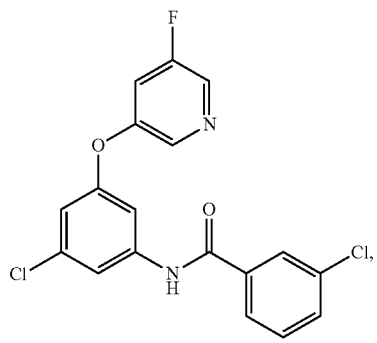
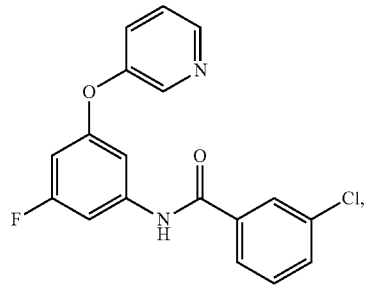
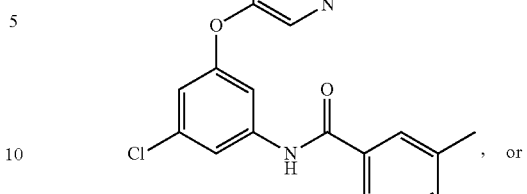
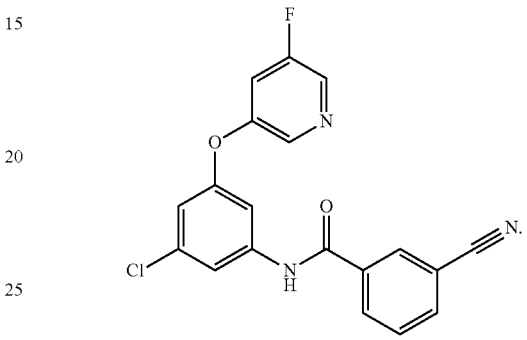
In a further aspect, a compound can be present as:
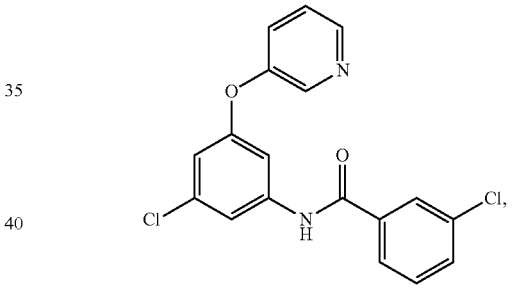
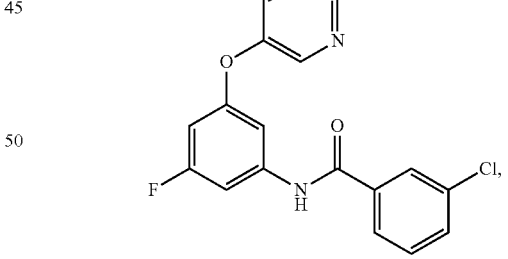
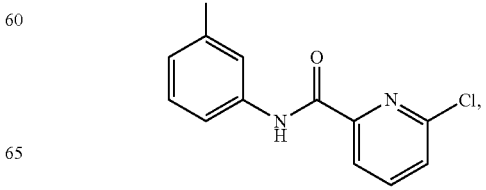

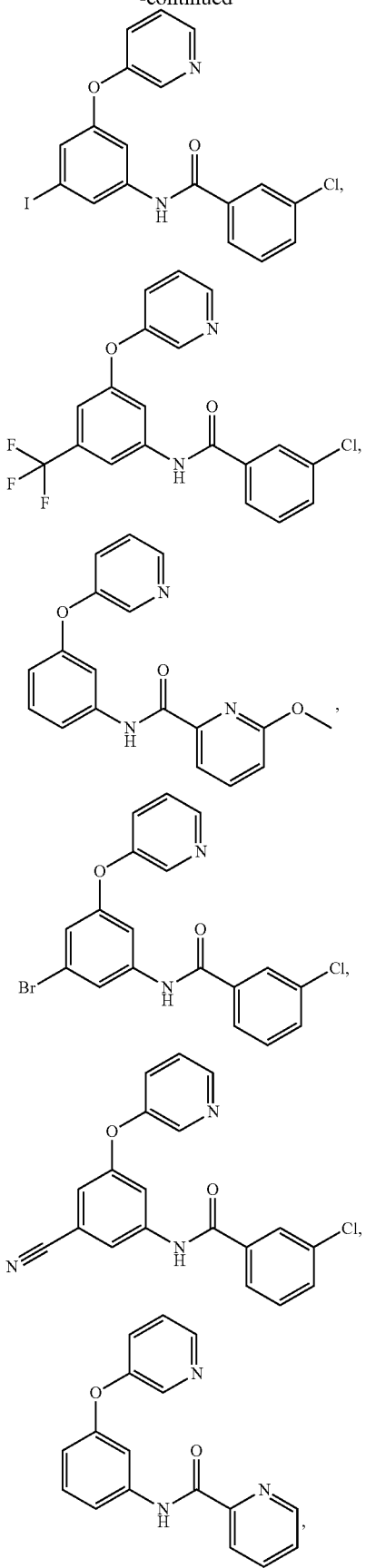
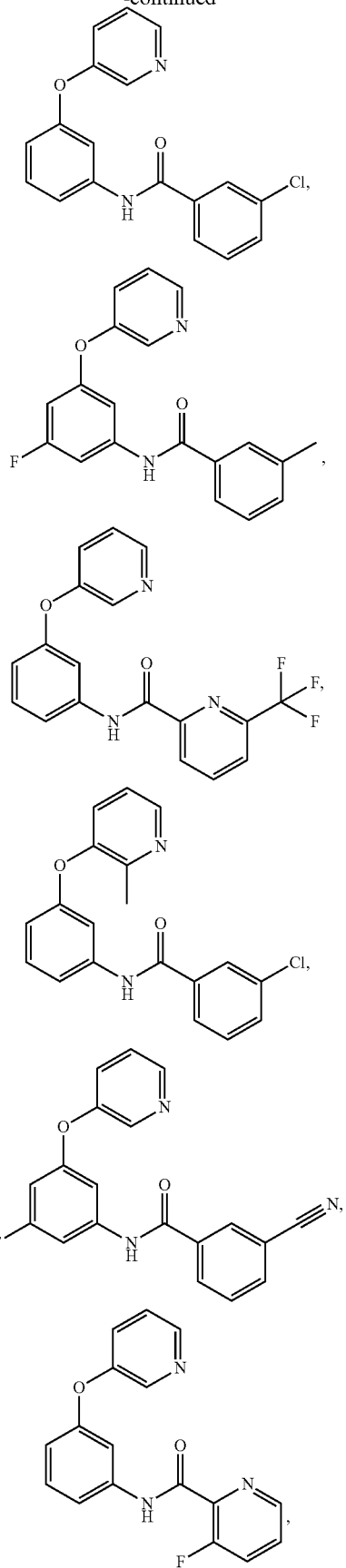

217
-continued
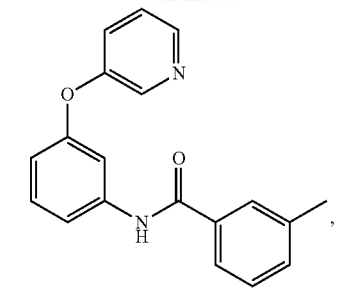
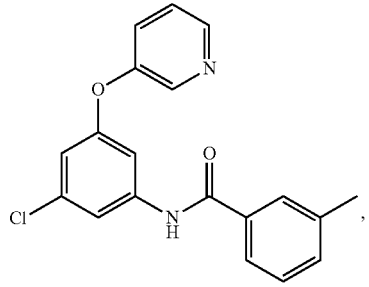
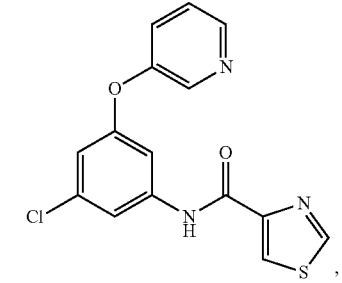
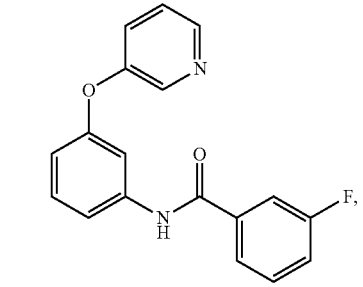
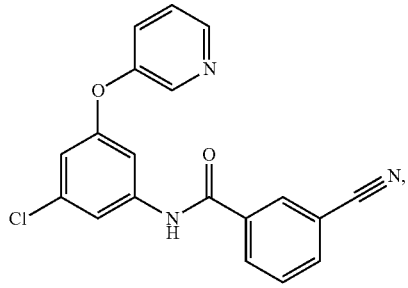
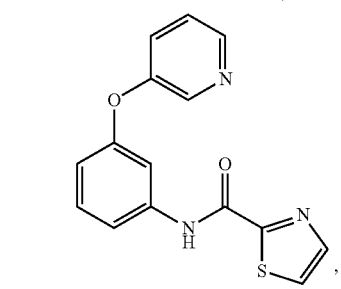
218
-continued
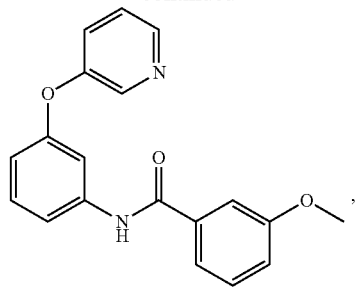
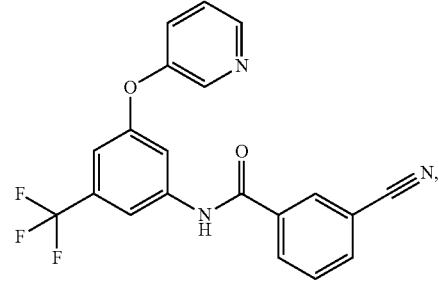
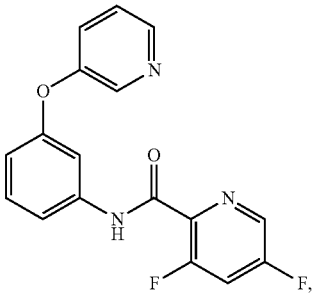
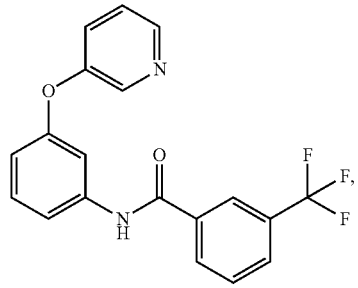
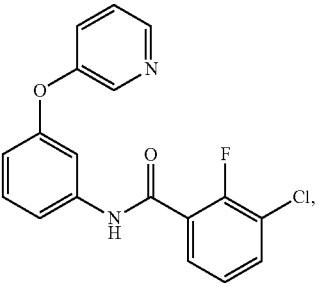
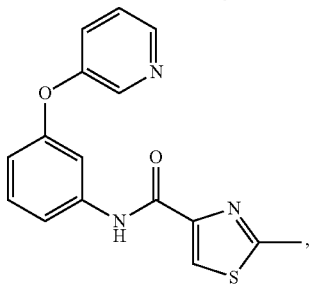

In a further aspect, a compound can be present as:

-continued
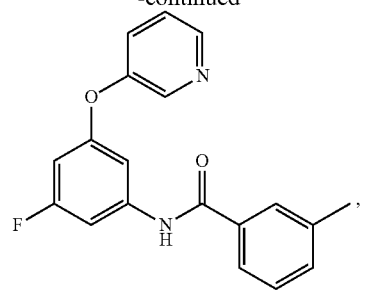
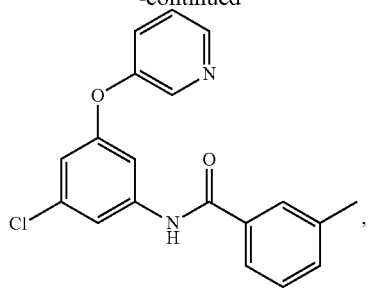

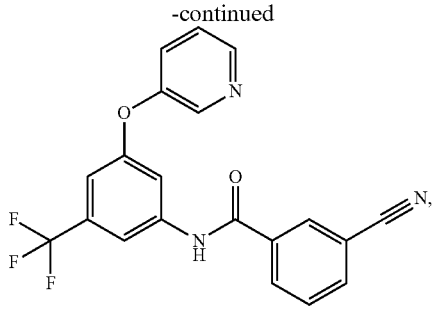
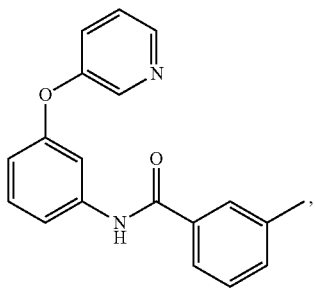
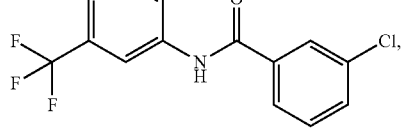
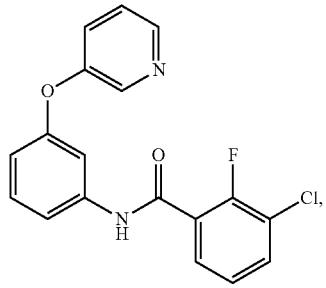
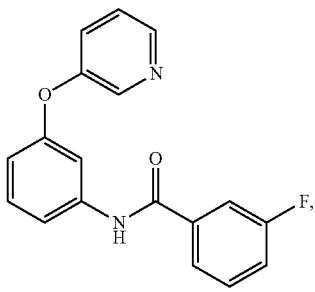
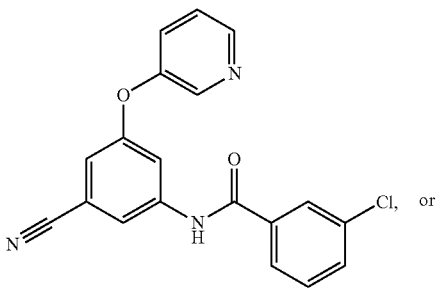 or
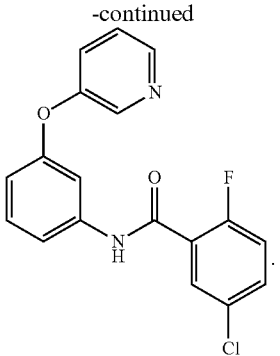
In a further aspect, a compound can be present as:
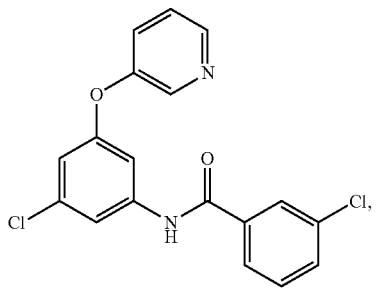
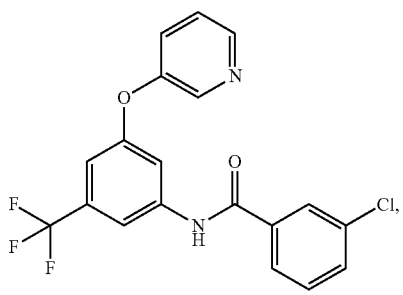
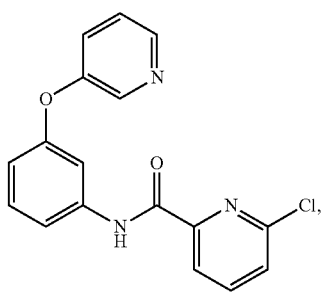
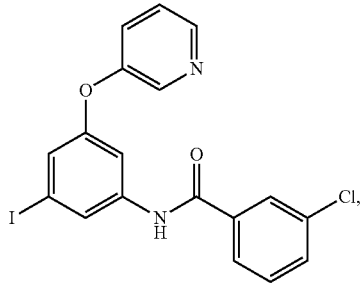

225
-continued
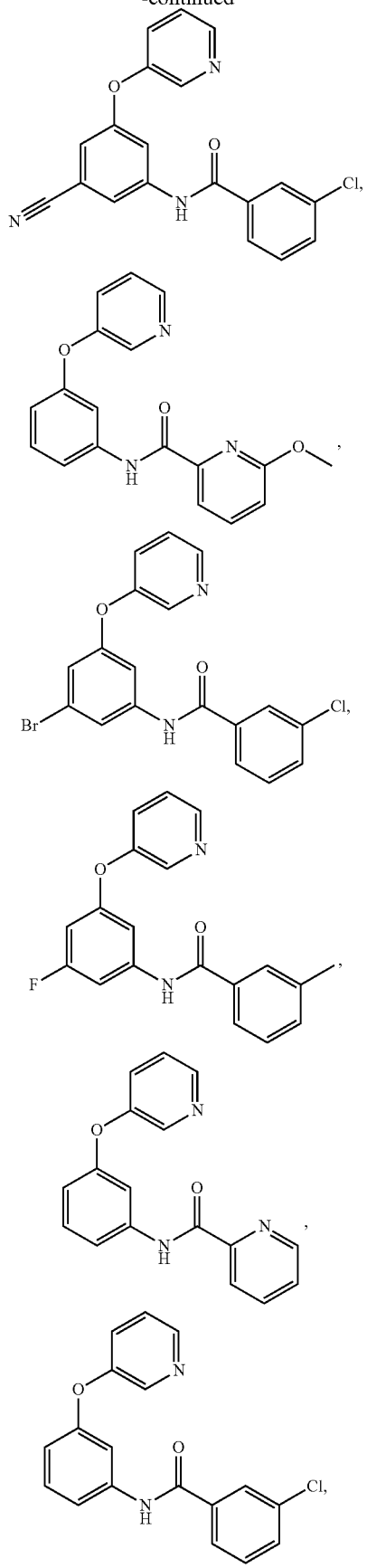
226
-continued
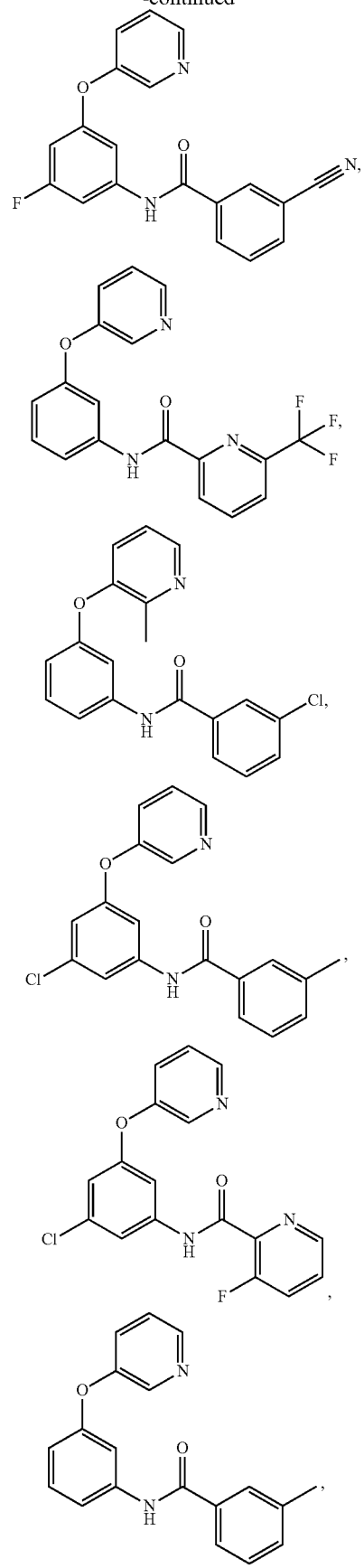

-continued
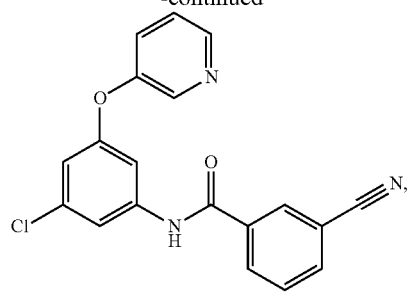
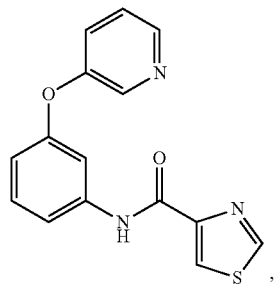
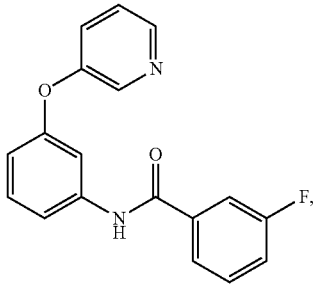
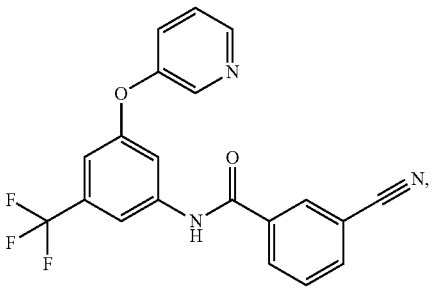
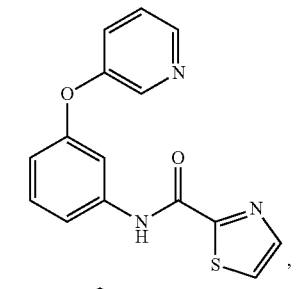
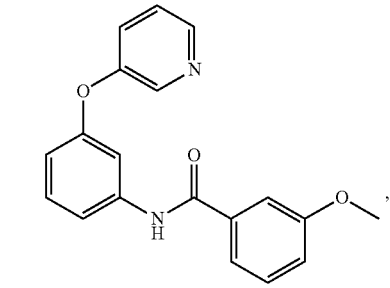
-continued
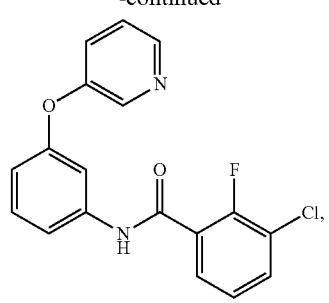
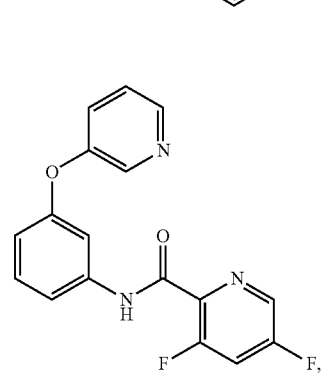
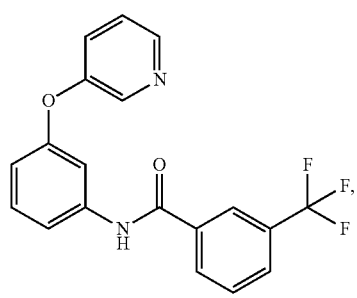
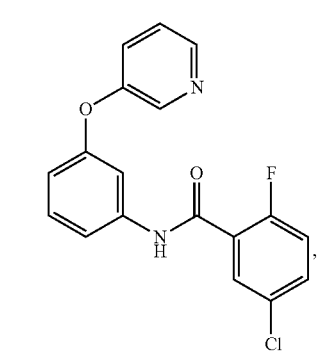 [SMILES: O=C(Nc1cccc(Oc2cccnc2)c1)c1cc(Cl)ccc1F]
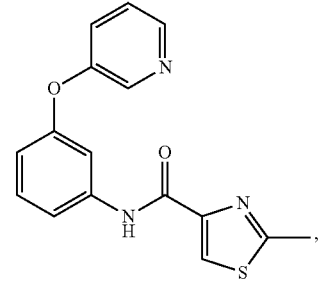

229
-continued
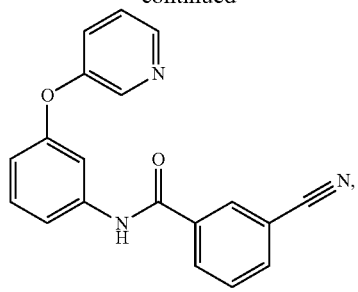
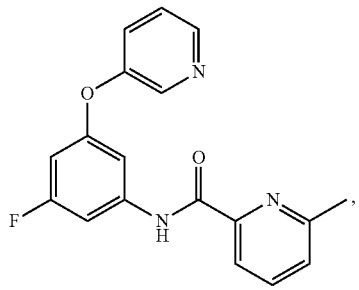
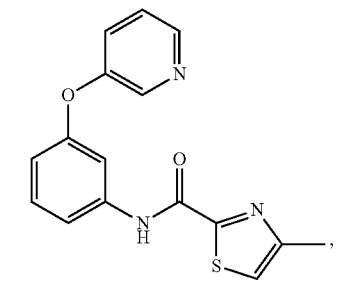
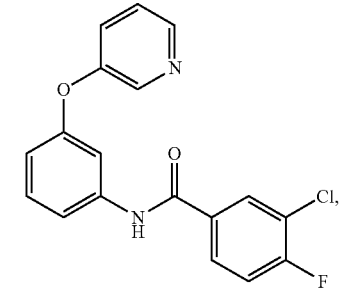
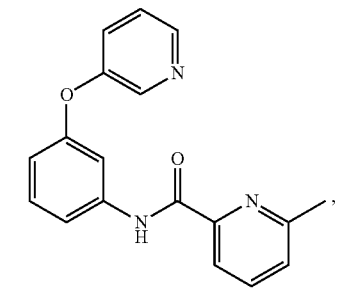
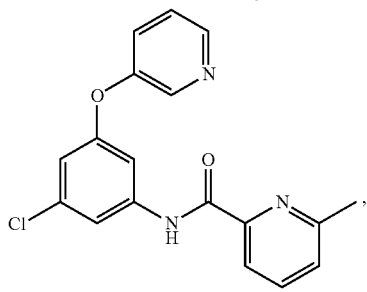
230
-continued
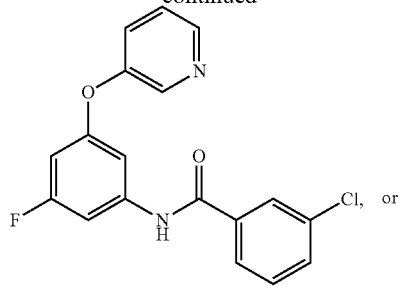
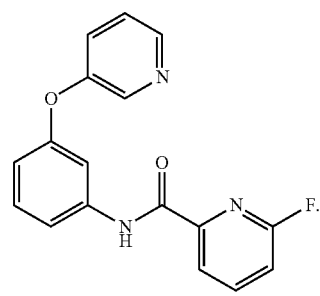
In a further aspect, a compound can be present as:
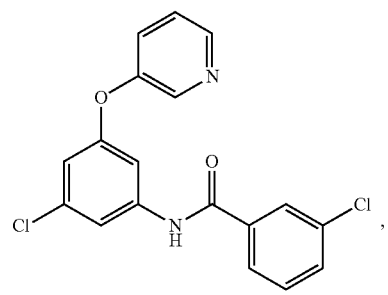
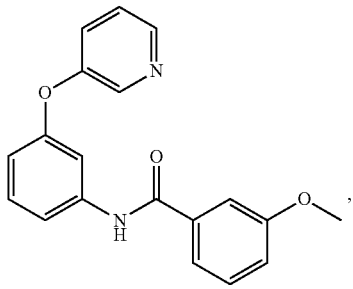
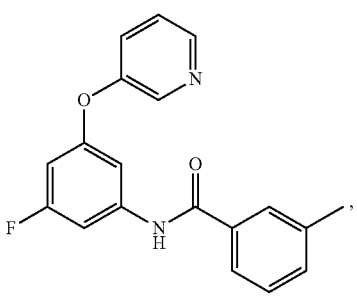

-continued
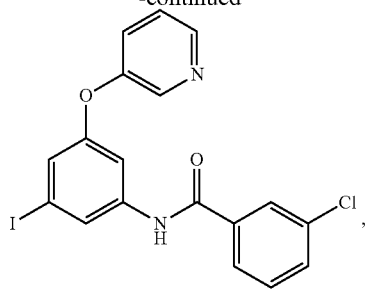
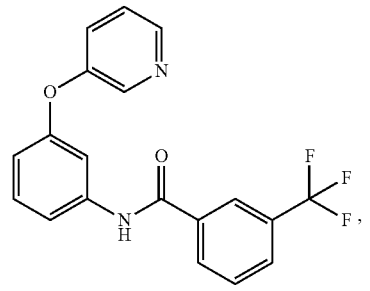
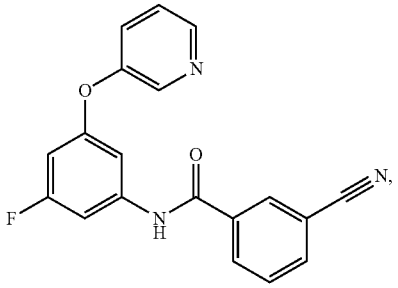
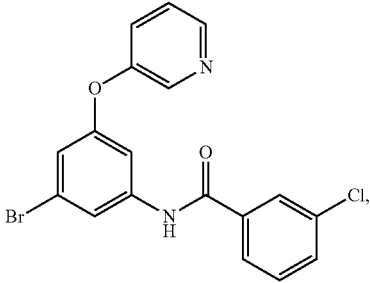
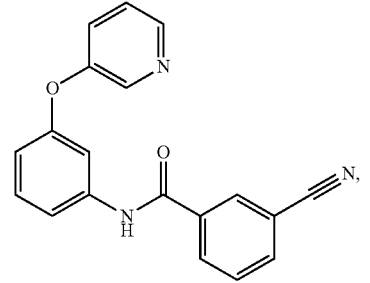
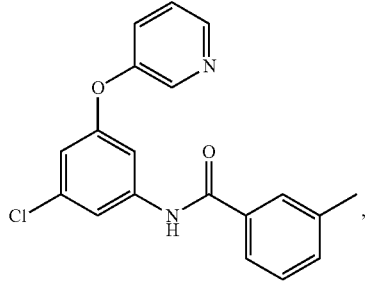
-continued
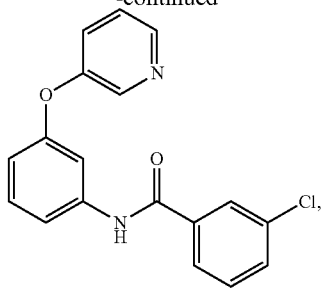
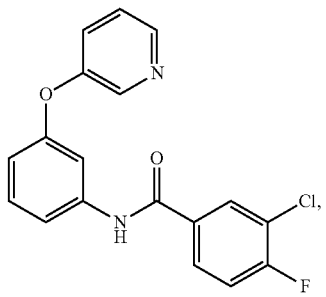
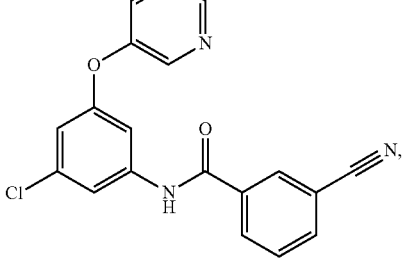
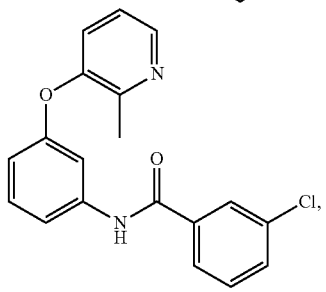
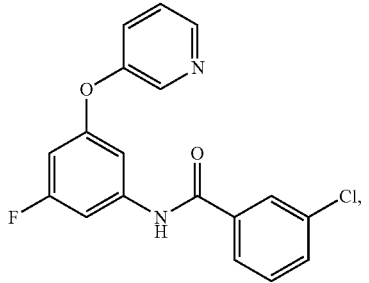
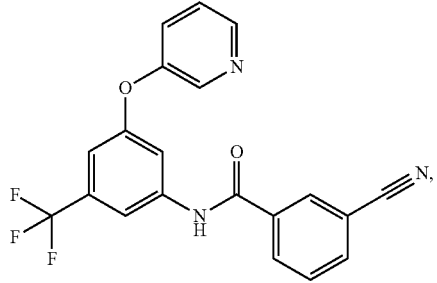

In a further aspect, a compound can be present as:

235
-continued
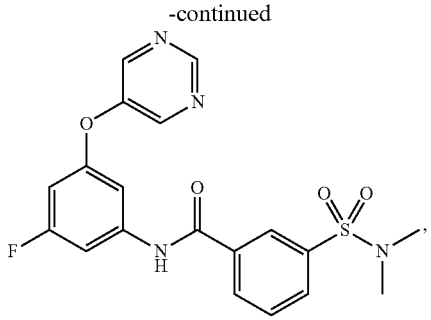
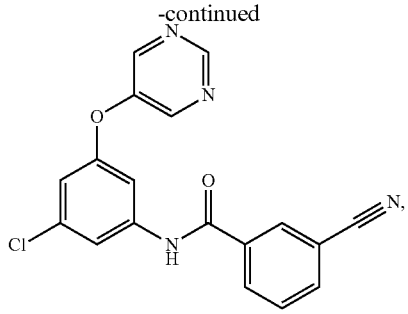
236
-continued
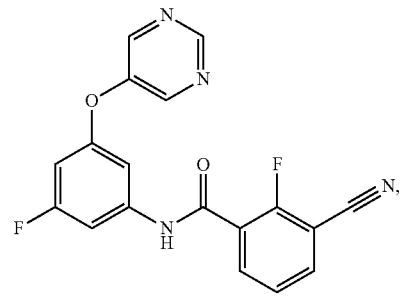
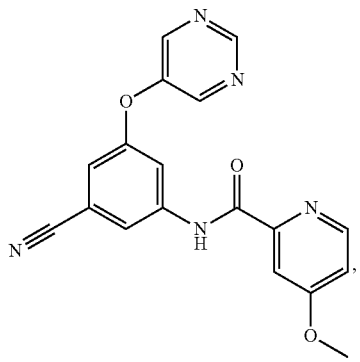
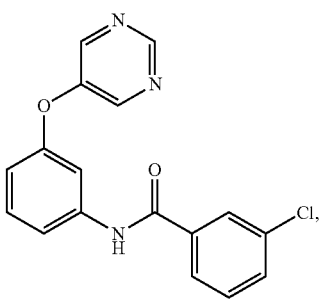
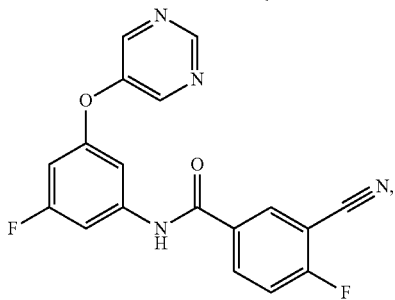

237
-continued
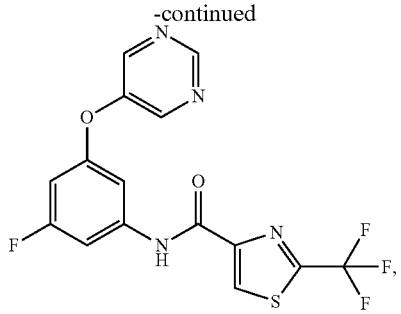
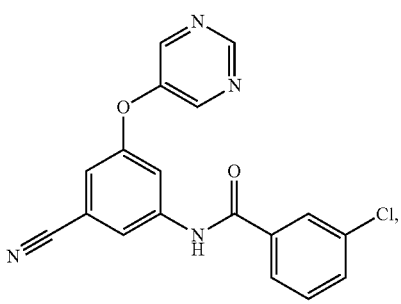
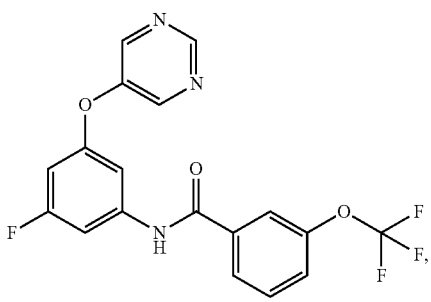
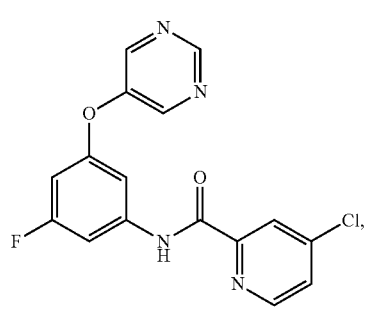
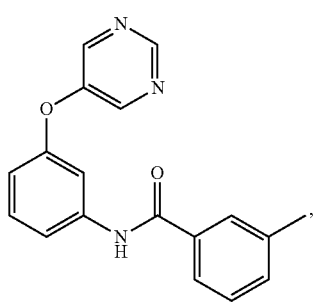
238
-continued
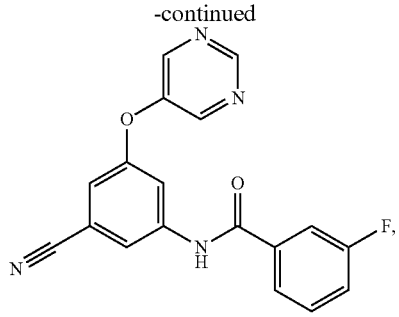
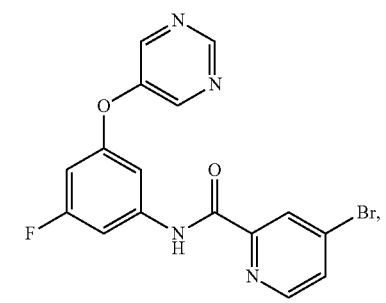
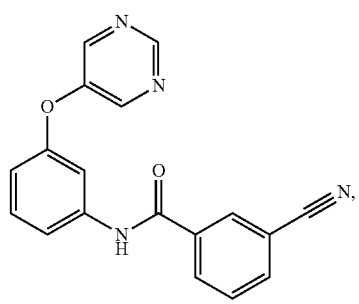
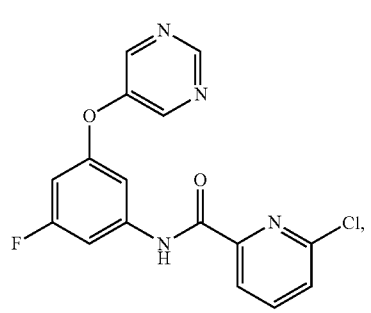
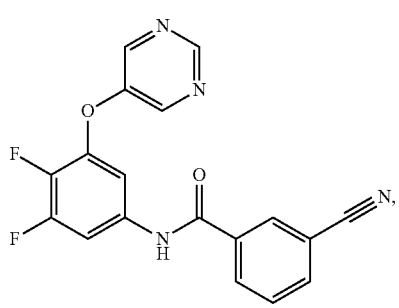

239
-continued
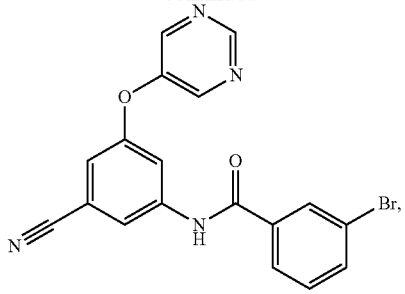
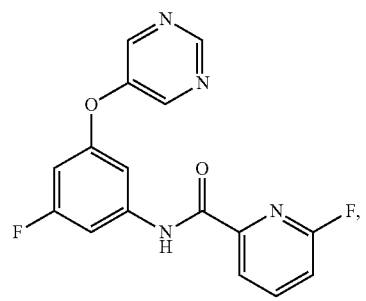
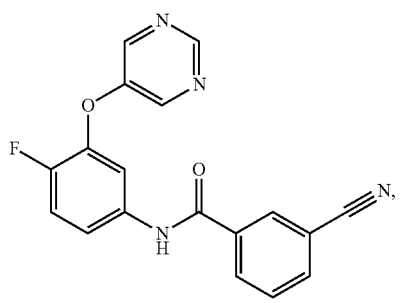
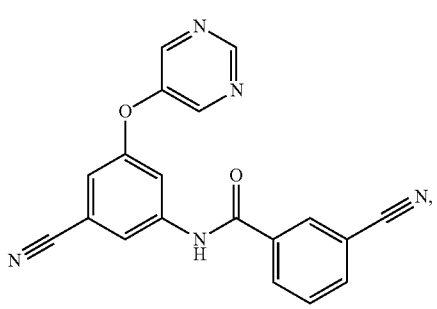
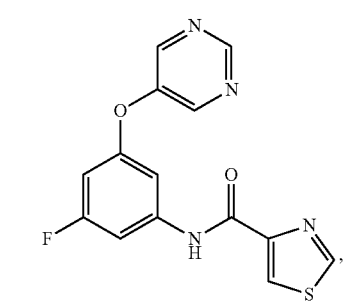
240
-continued
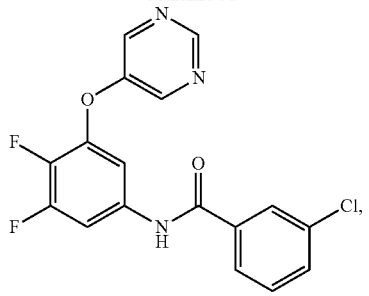
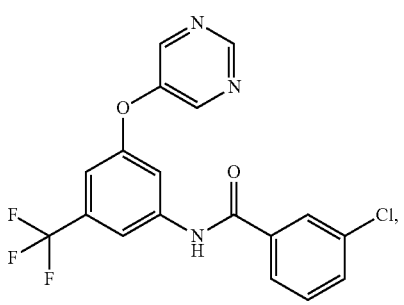
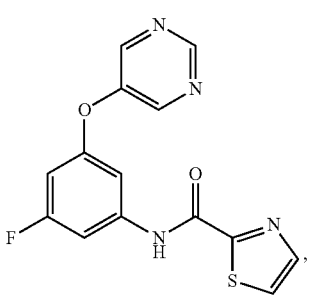
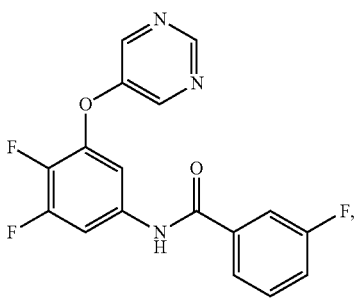
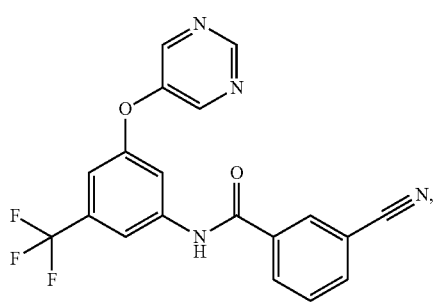

241
-continued
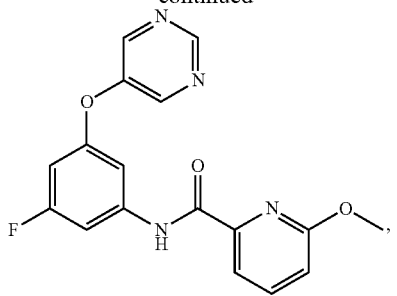
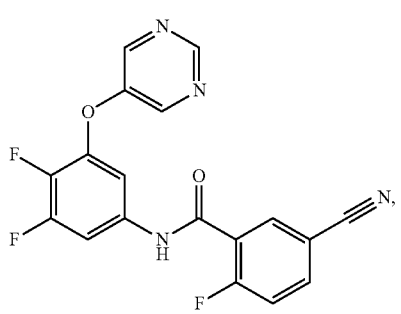
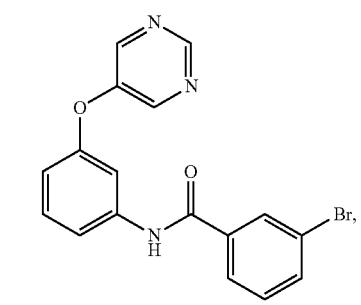
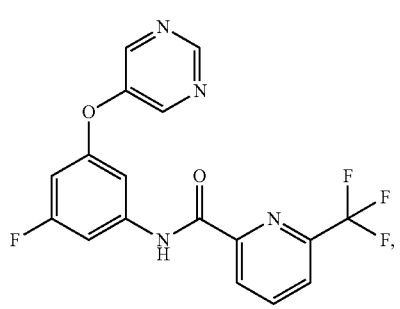
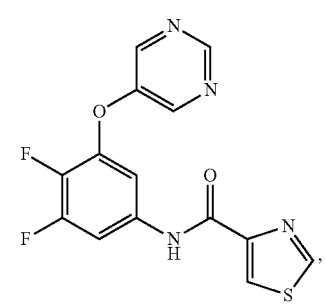
242
-continued
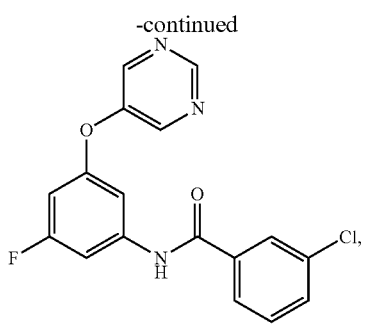
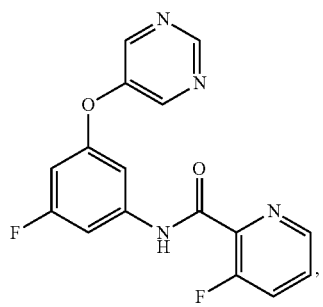
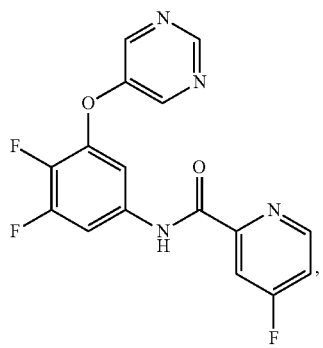
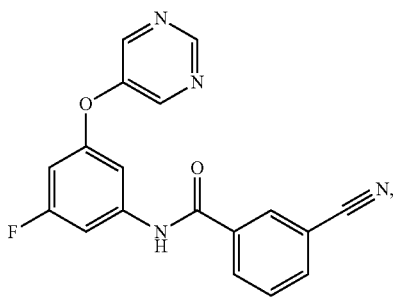
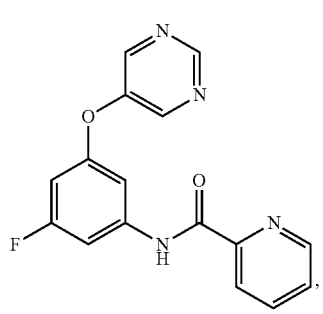

-continued
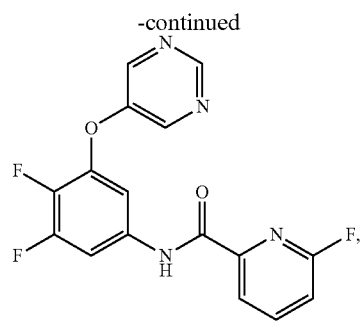
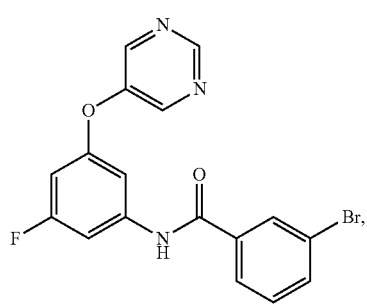
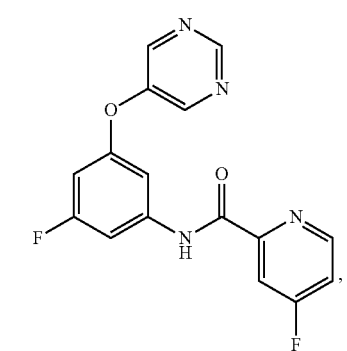
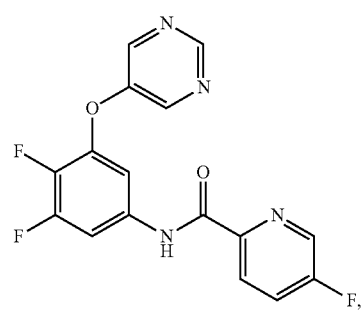
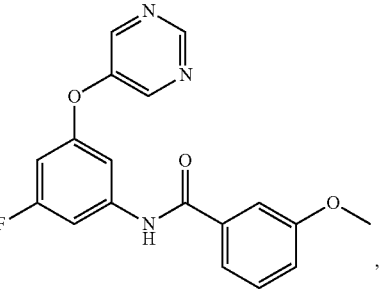
-continued
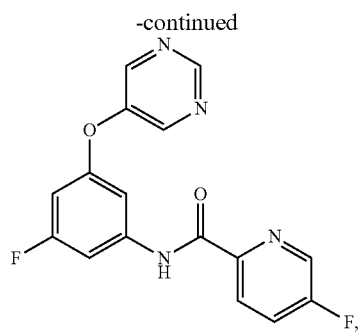
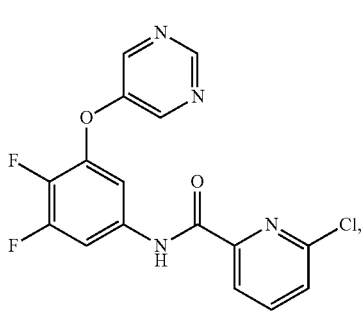
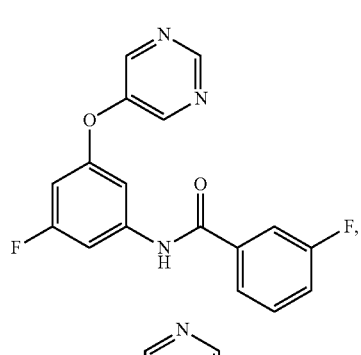
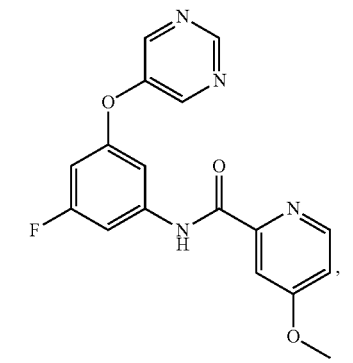
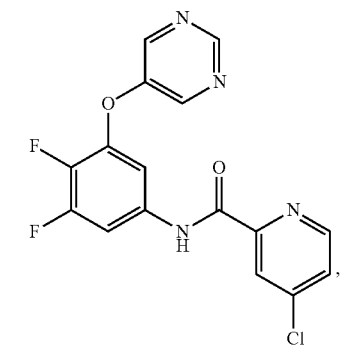

-continued
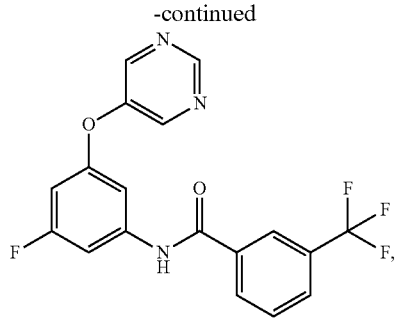
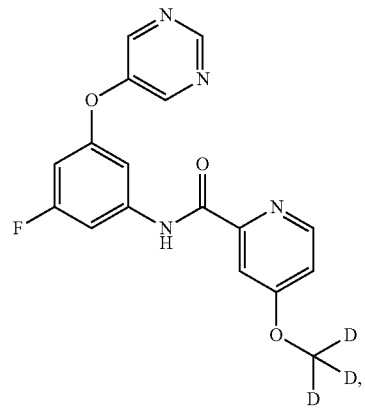
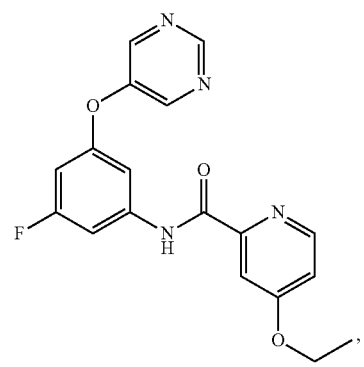
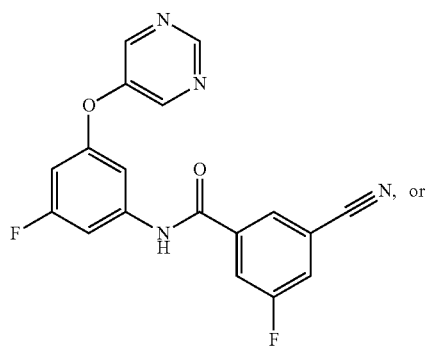, or
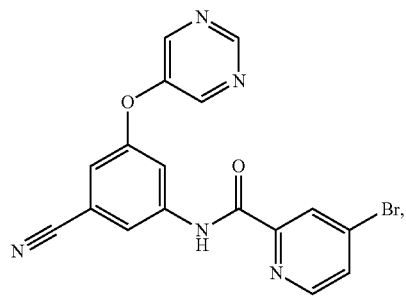
-continued
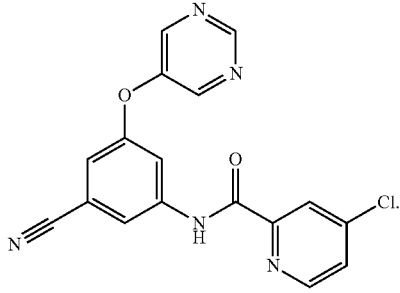
In a further aspect, a compound can be present as:
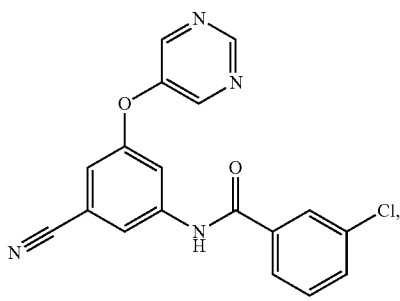
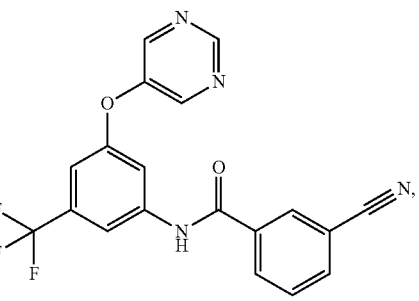
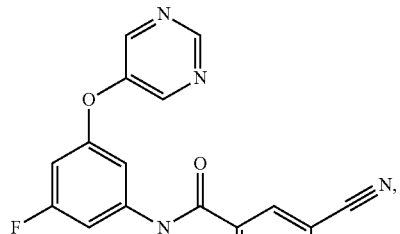
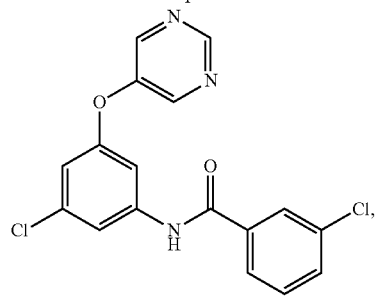

247
-continued
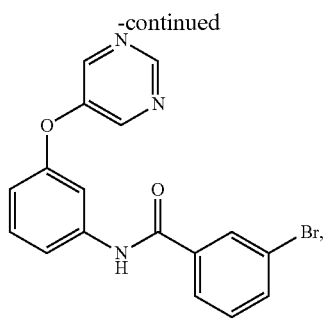
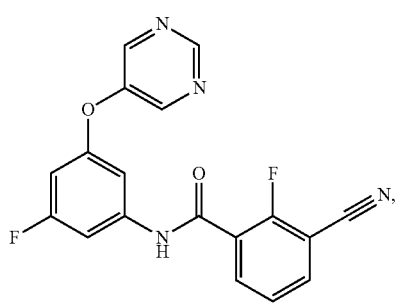
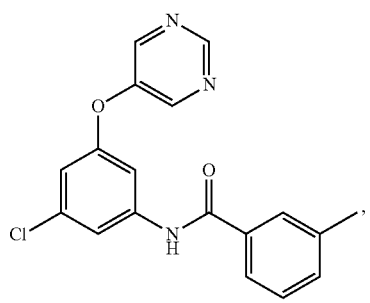
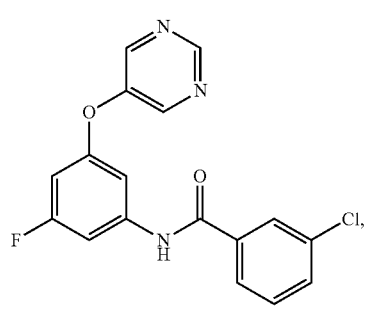
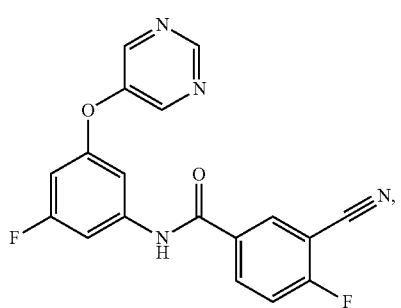
248
-continued
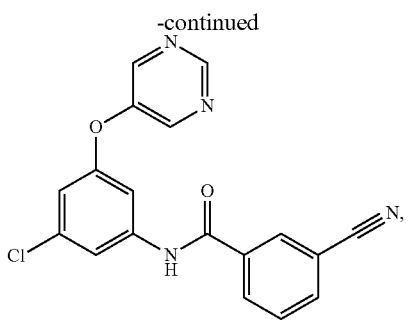
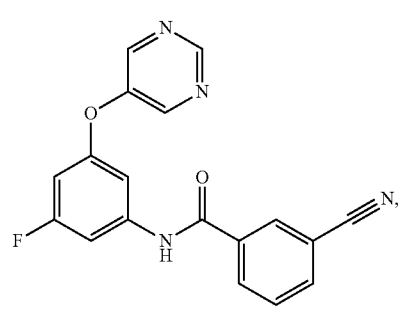
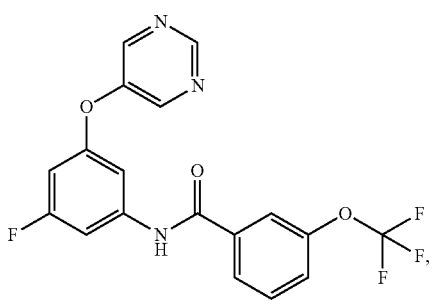
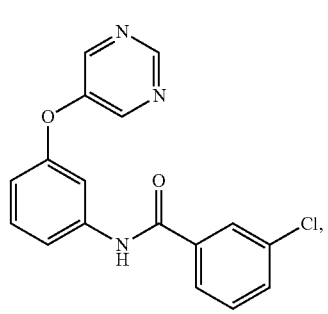
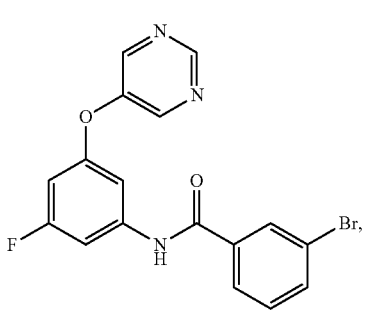

249
-continued
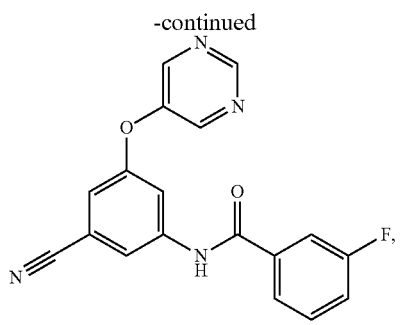
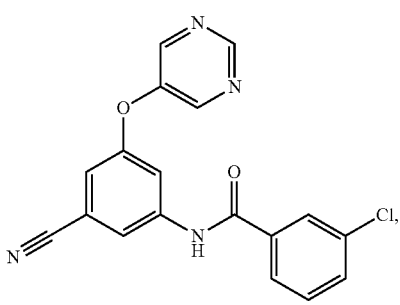
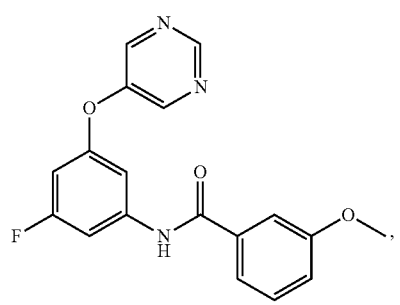
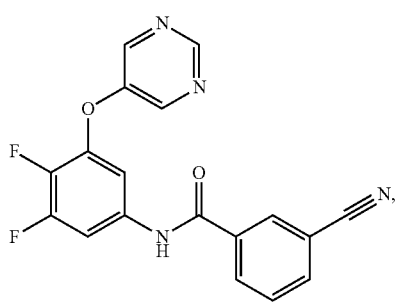
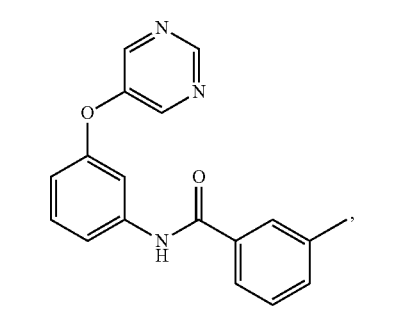
250
-continued
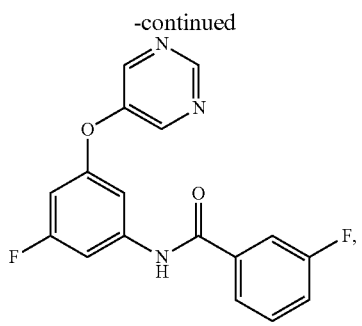
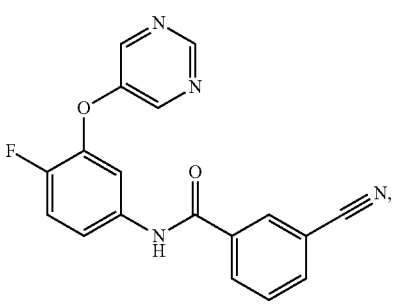
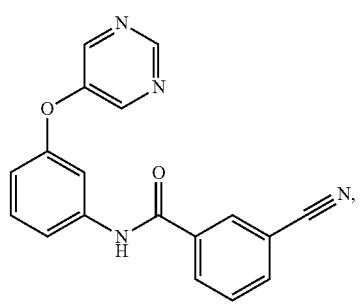
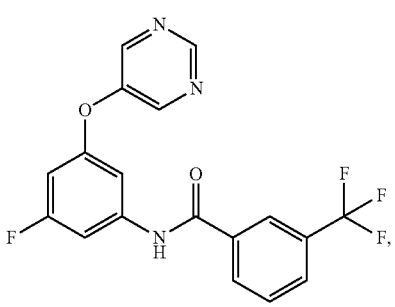
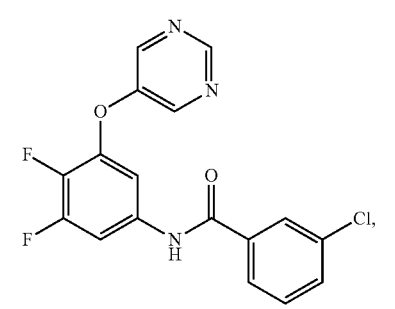

-continued
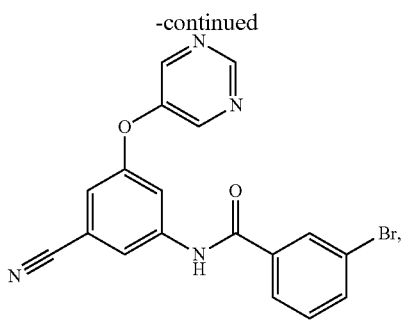
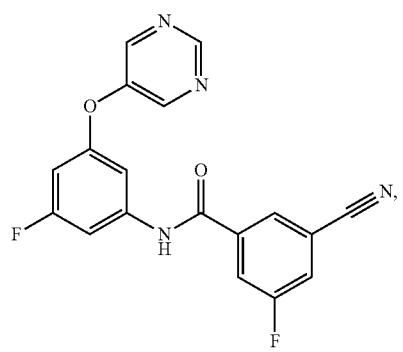
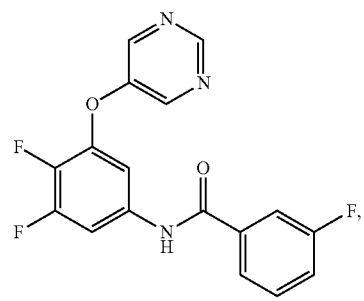
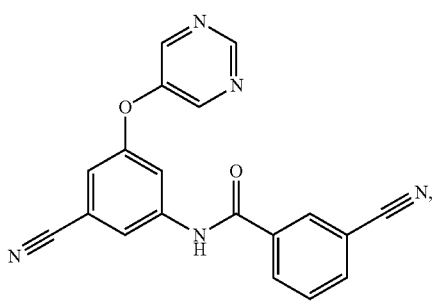
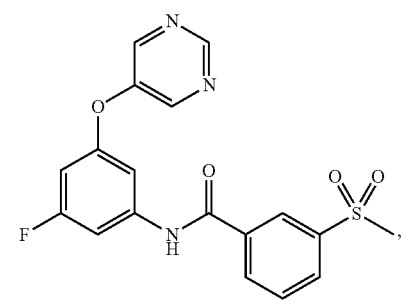
-continued
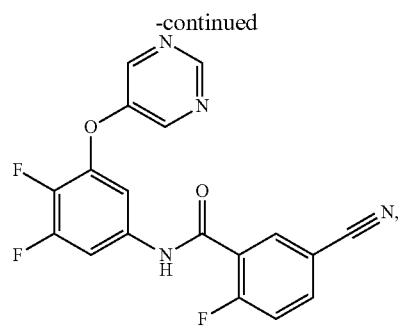
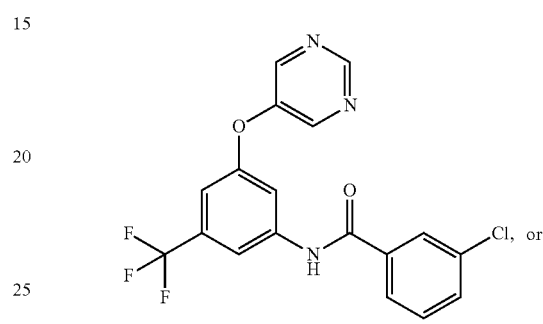
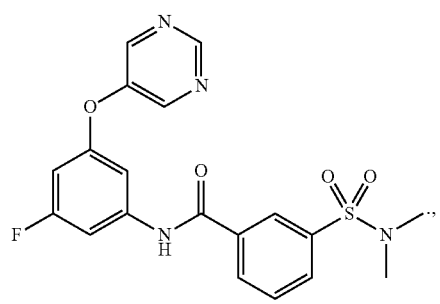
In a further aspect, a compound can be present as:
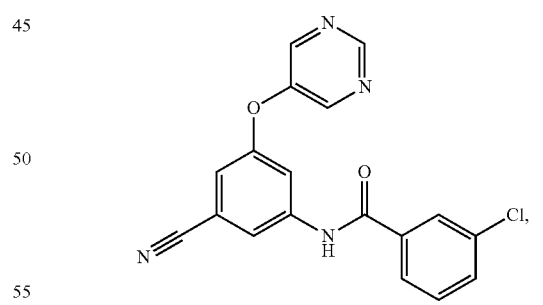
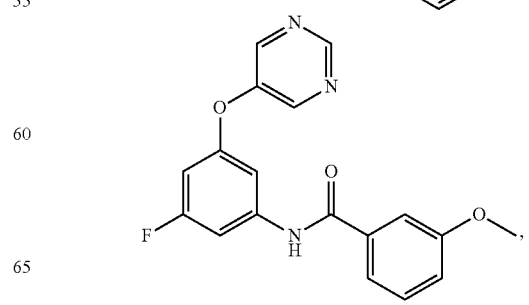

253
-continued
254
-continued
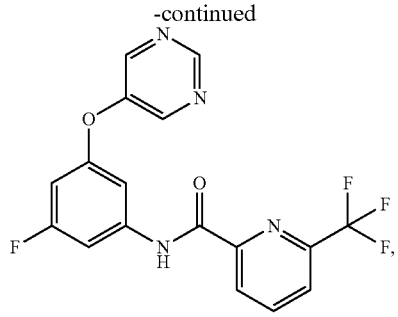
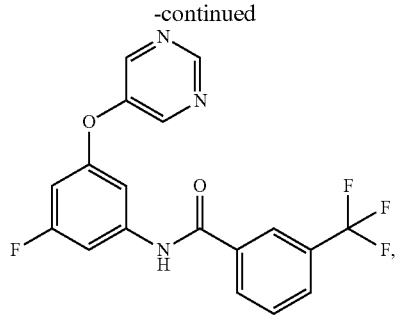

-continued
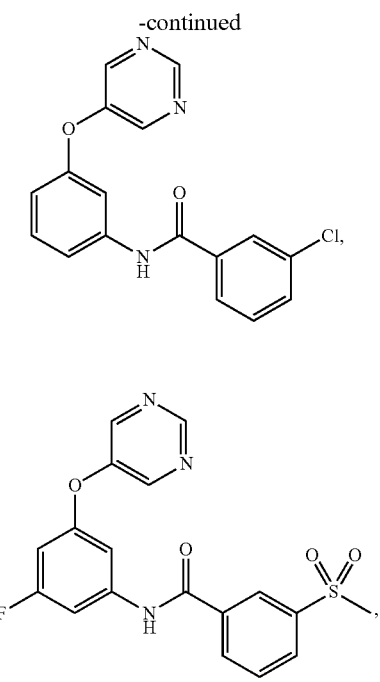
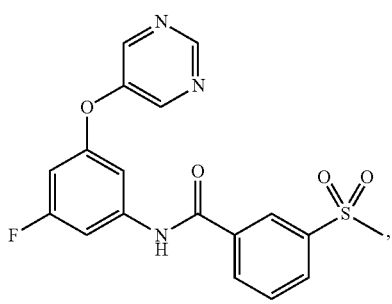
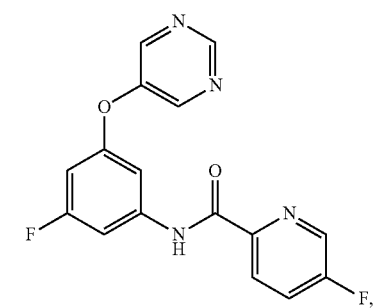
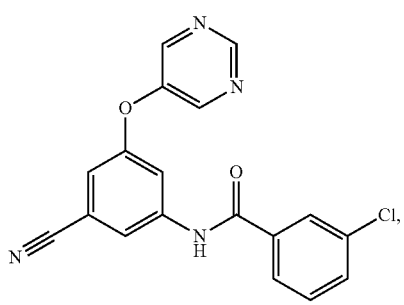
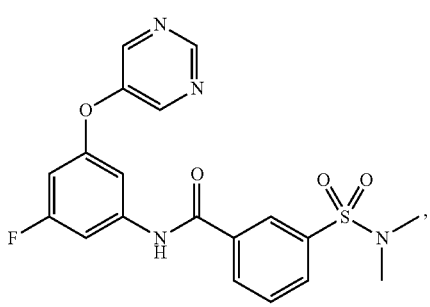
-continued
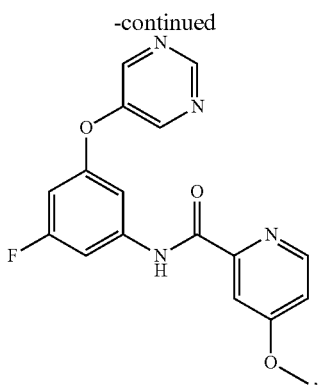
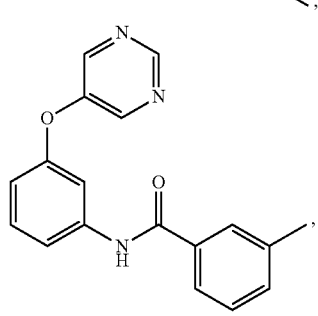
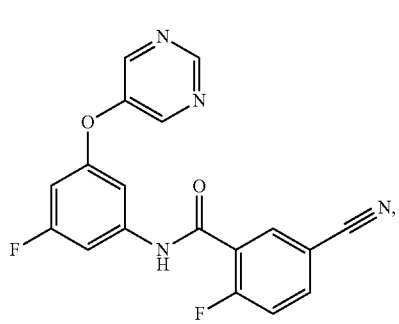
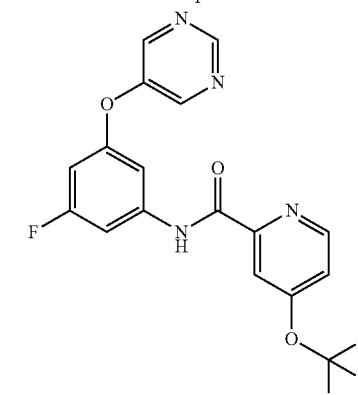
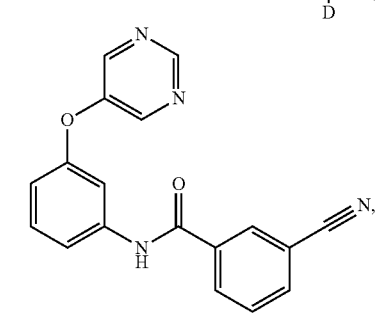

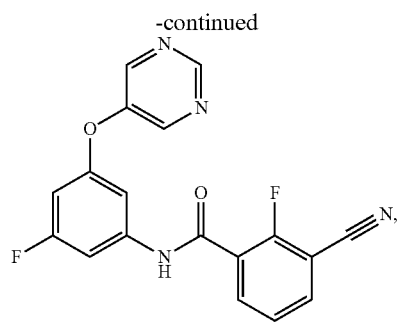
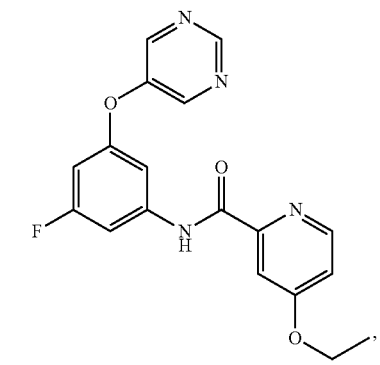
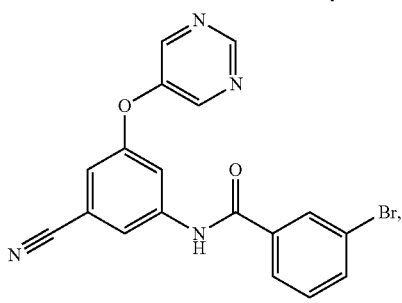
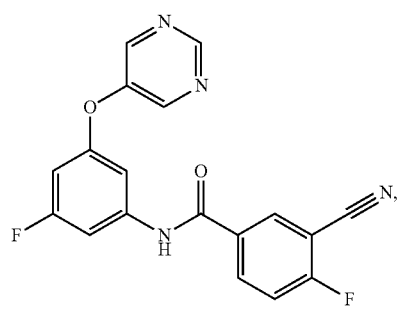
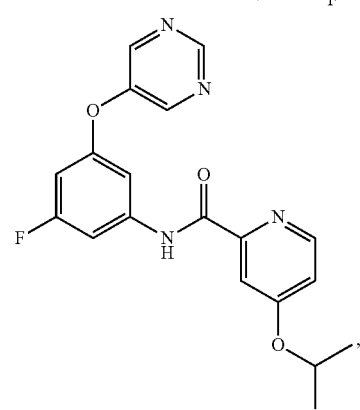
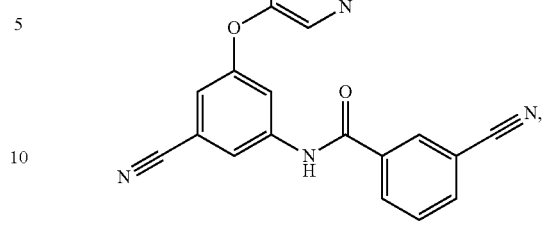
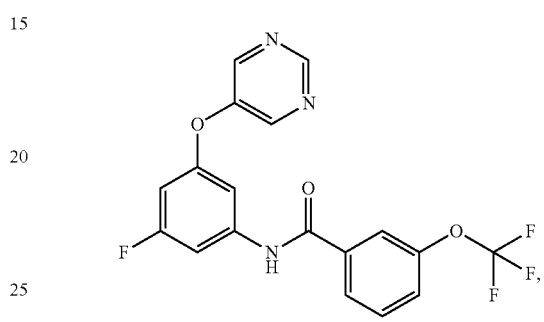
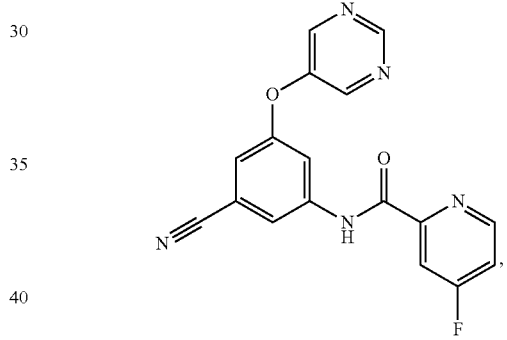
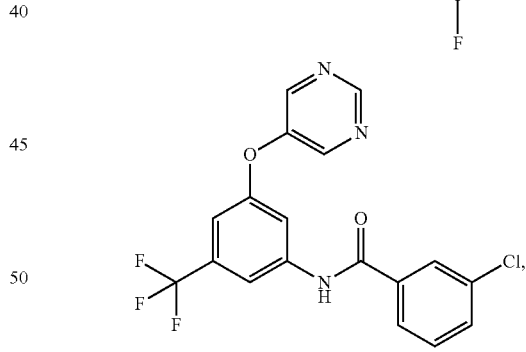
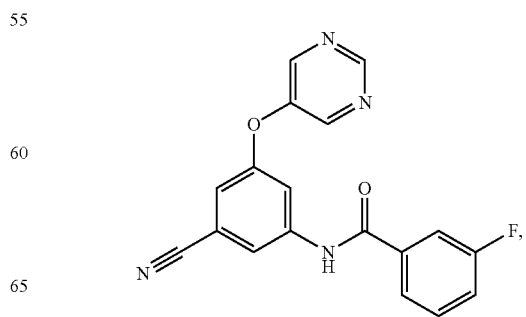

259
-continued
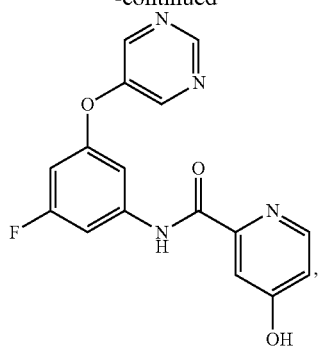
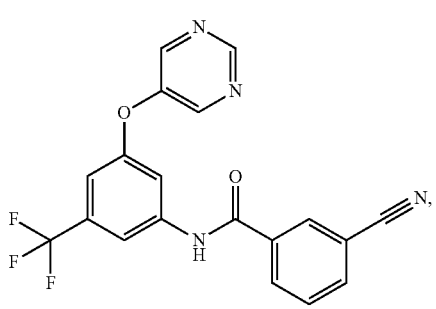
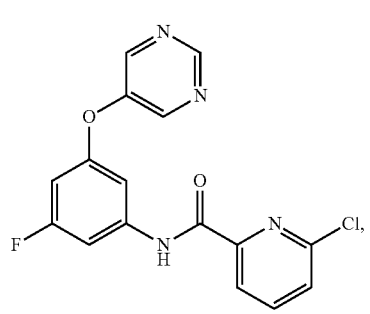
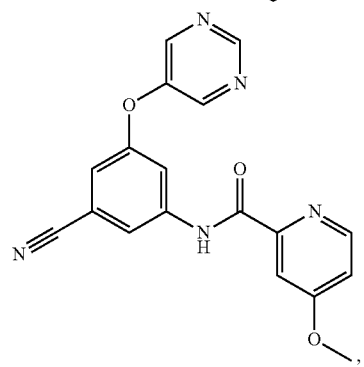
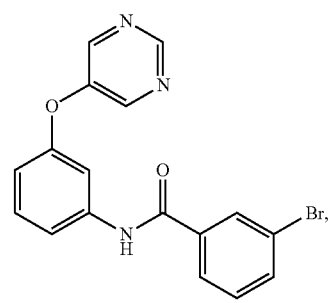
260
-continued
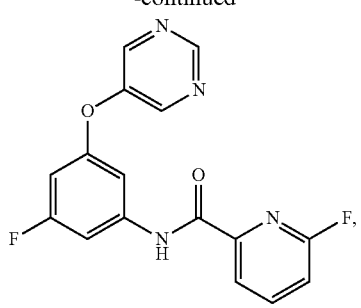
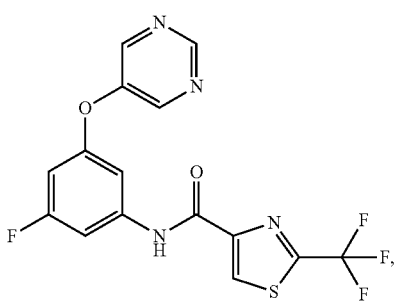
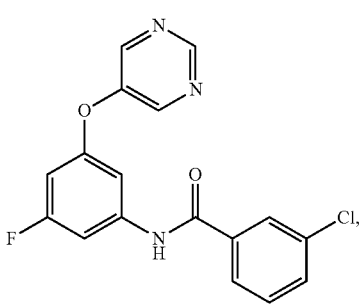
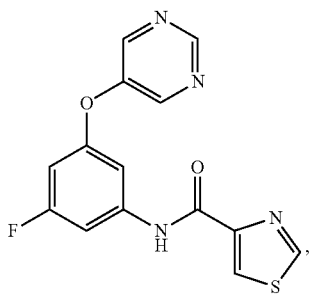
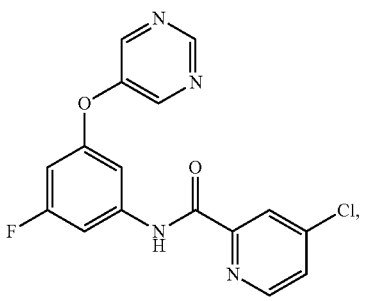

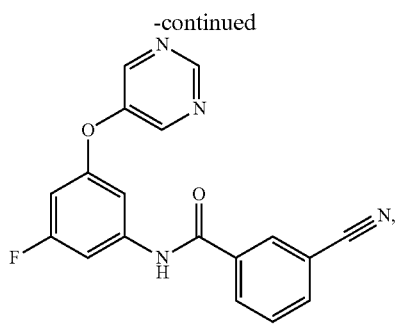
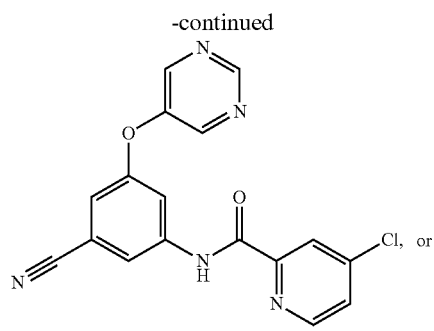
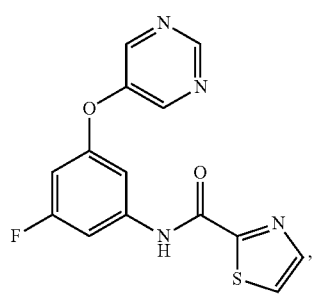
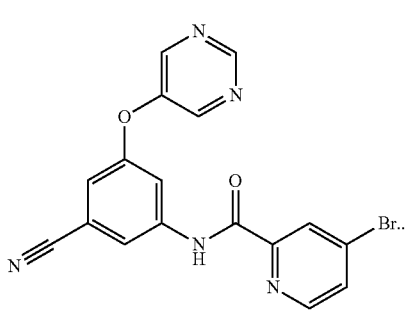 [SMILES: N#Cc1cc(NC(=O)c2cc(Br)ccn2)cc(Oc2cncnc2)c1]
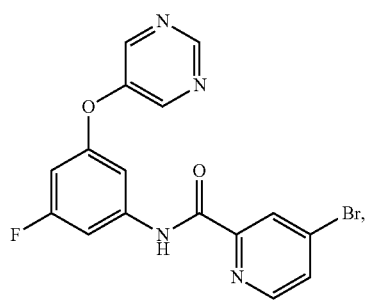
In a further aspect, a compound can be present as:
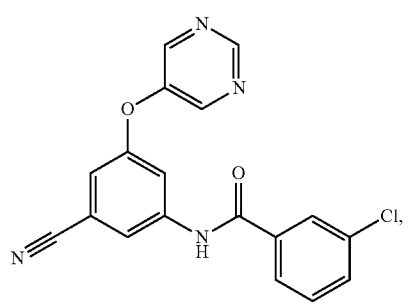
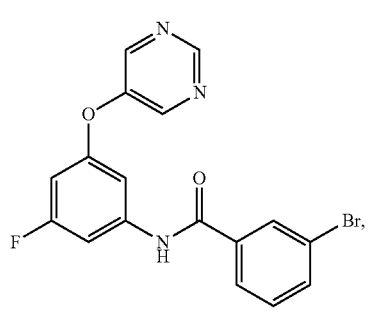
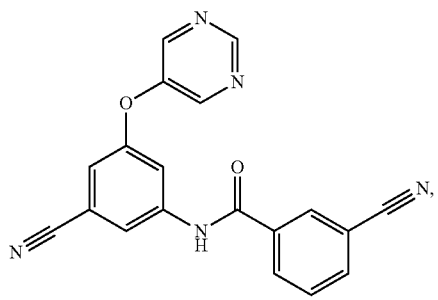
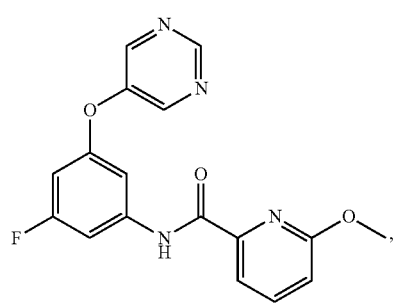

263
-continued
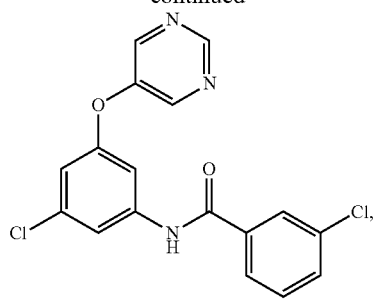
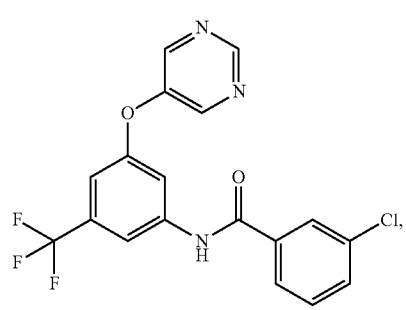
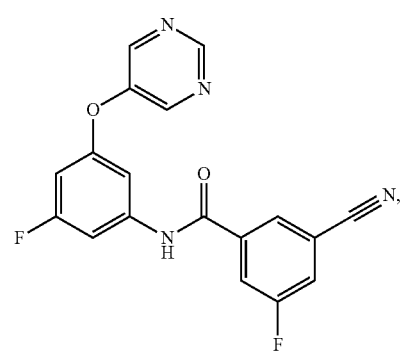
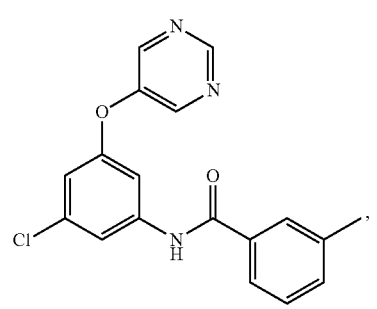
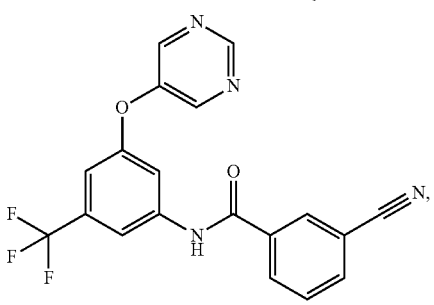
264
-continued
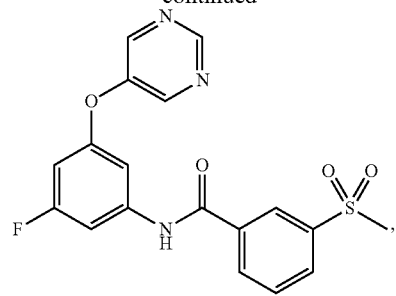
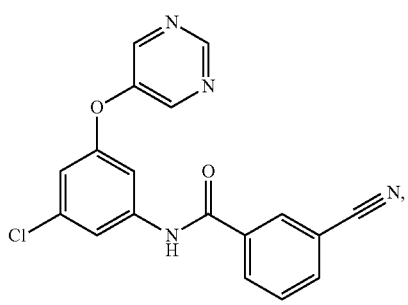
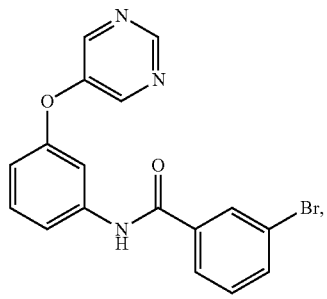
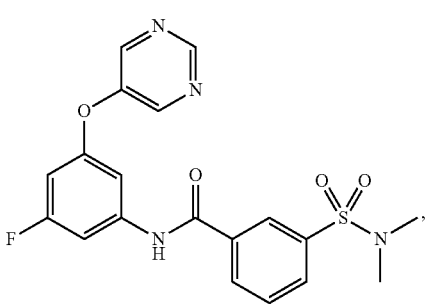
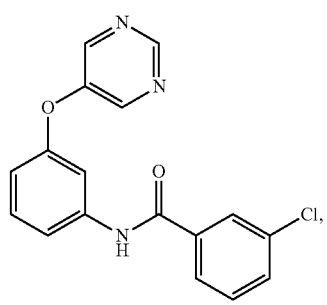

265
-continued
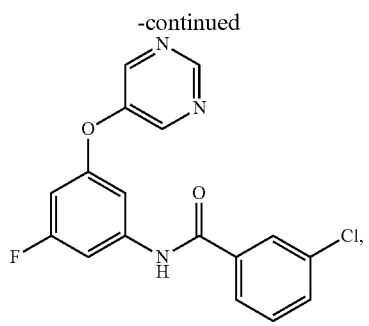
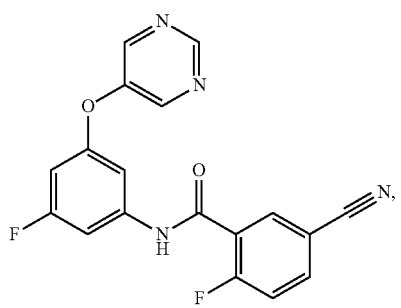
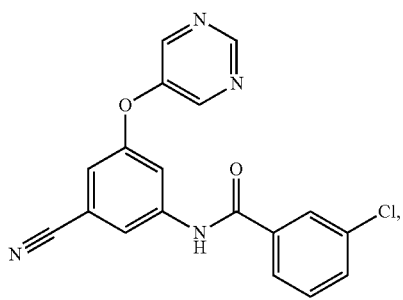
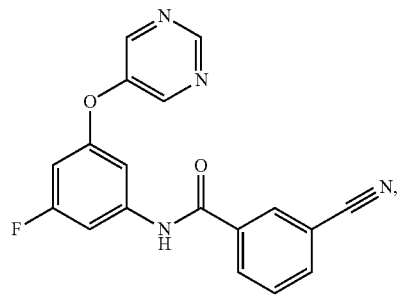
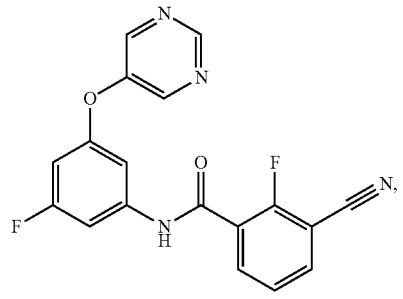
266
-continued
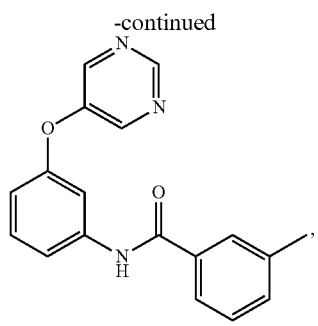
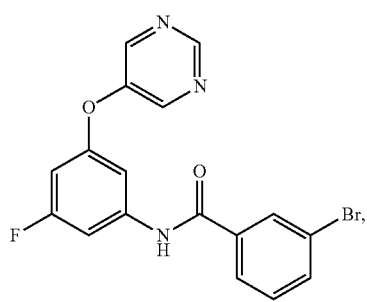
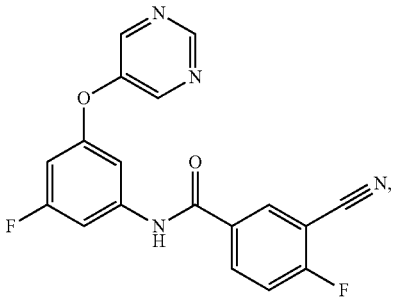
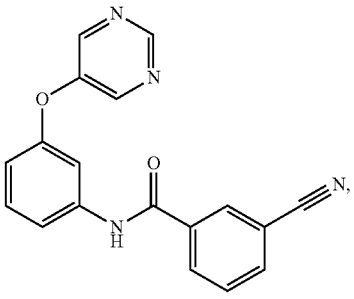
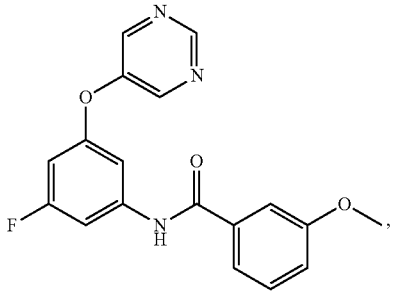

267
-continued
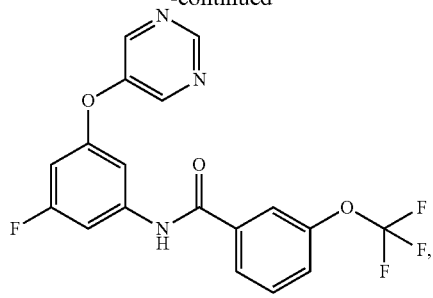
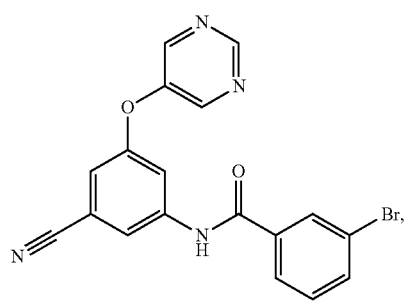
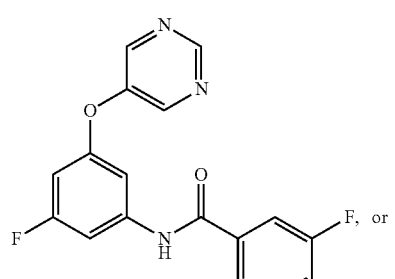, or
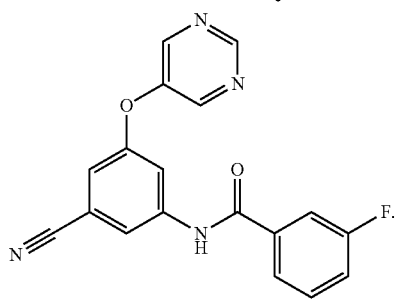
In a further aspect, a compound can be present as:
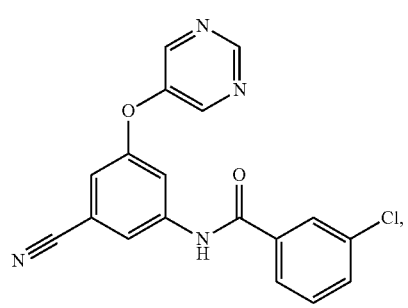
268
-continued
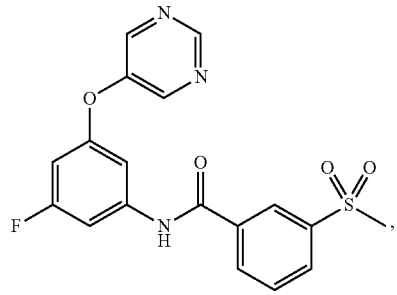
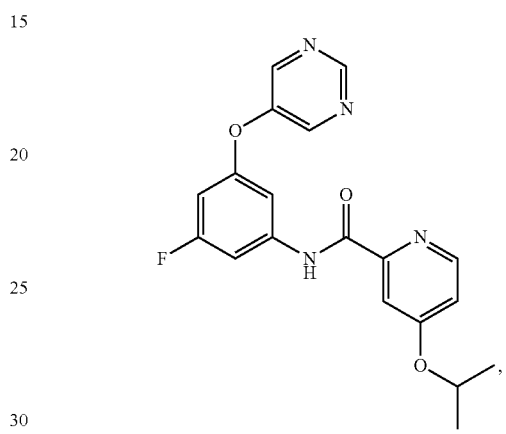
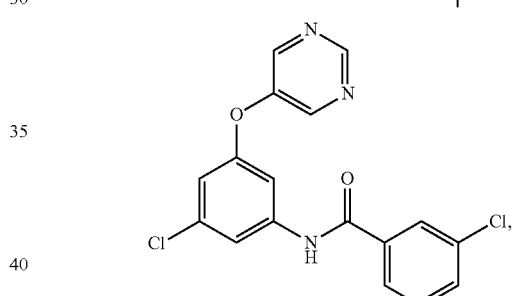
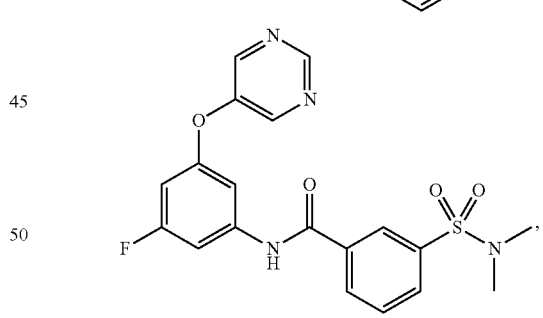
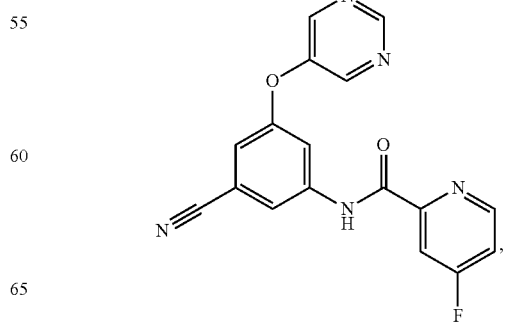

269
-continued
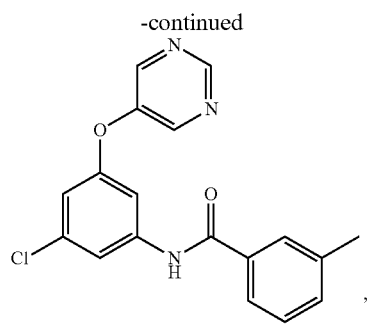
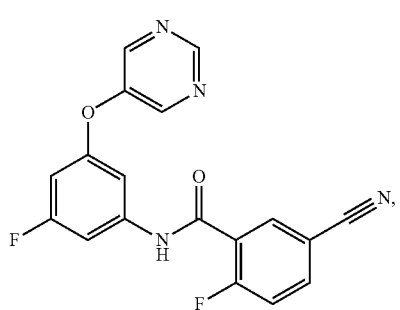
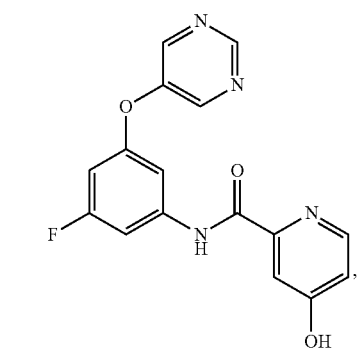
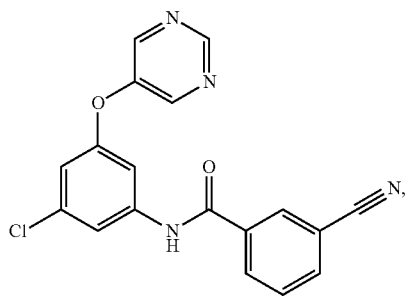
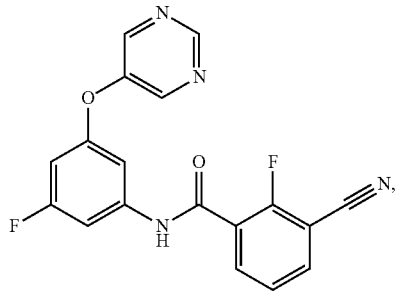
270
-continued
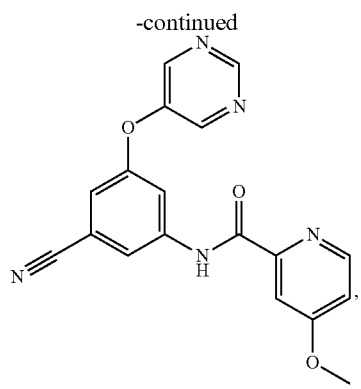
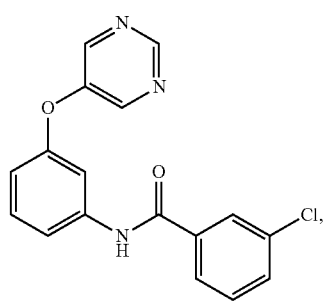
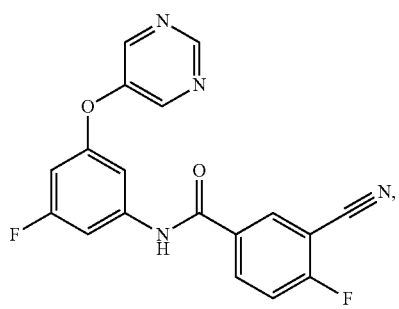
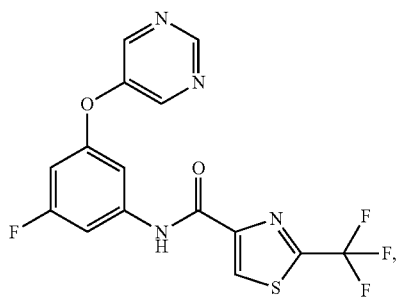
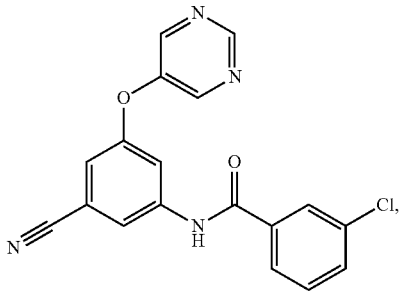

271
-continued
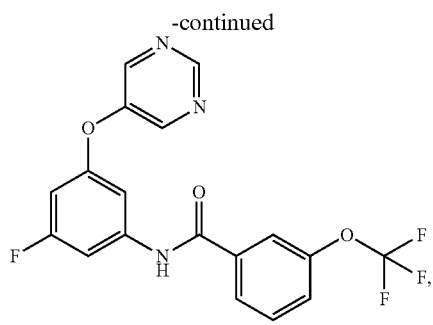
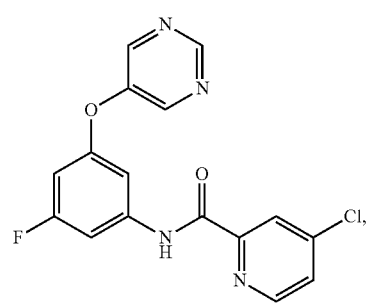
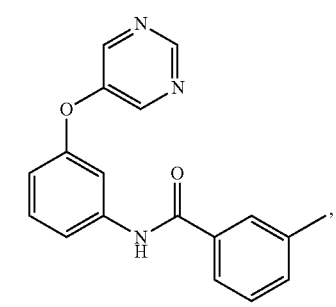
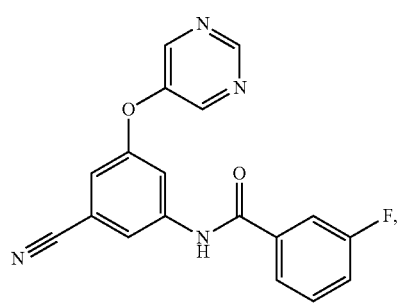
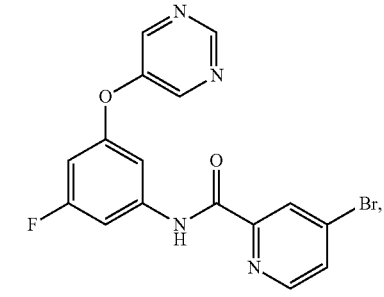
272
-continued
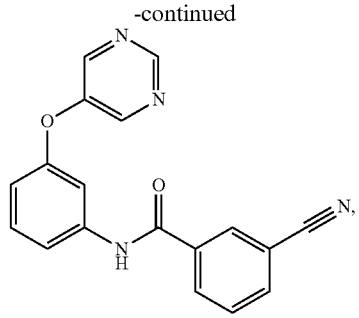
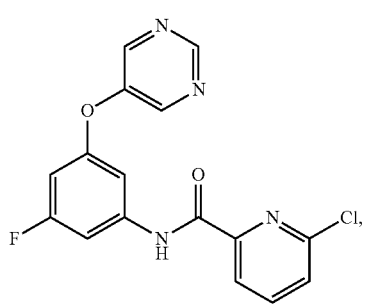
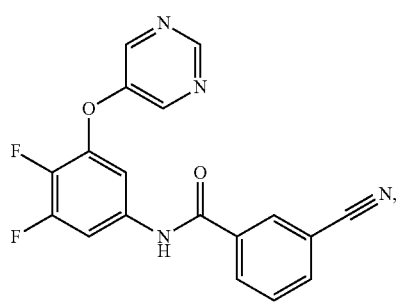
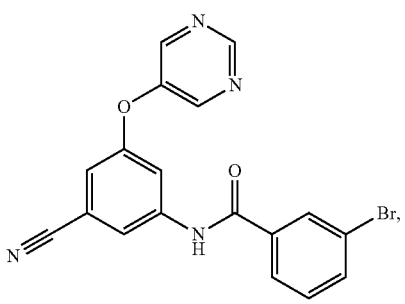
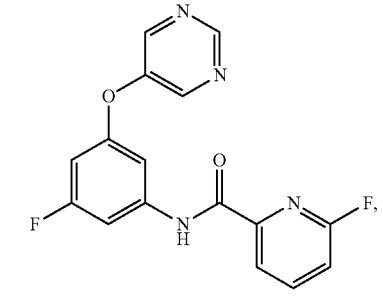

273
-continued
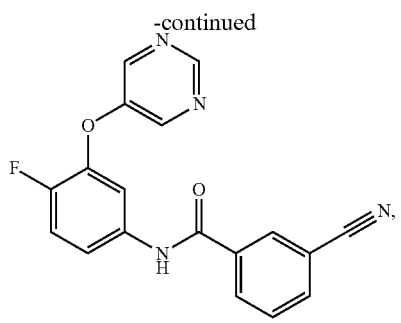
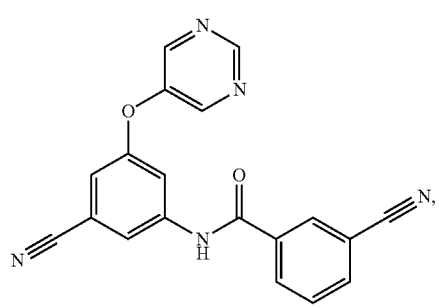
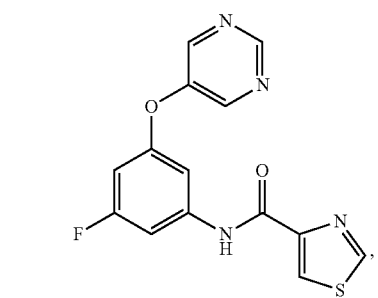
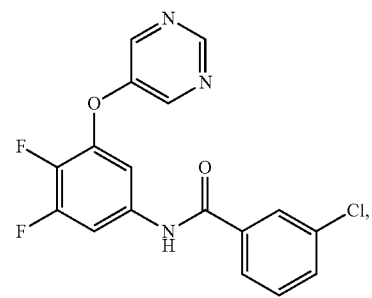
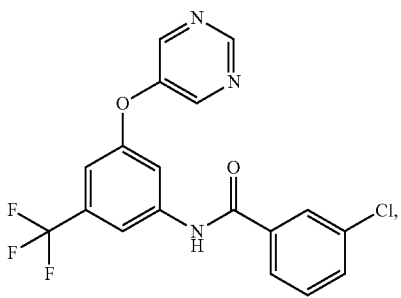
274
-continued
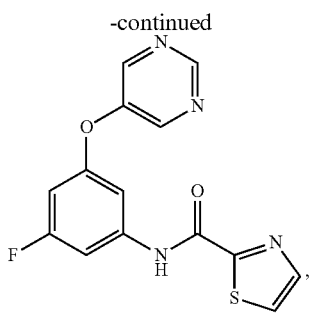
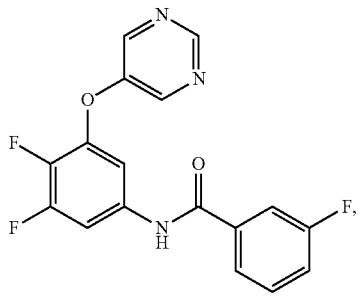
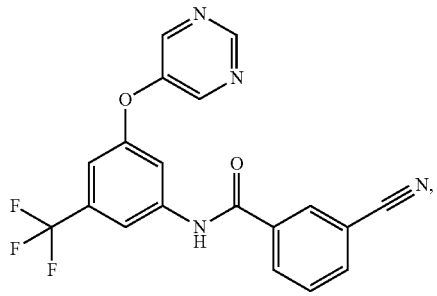
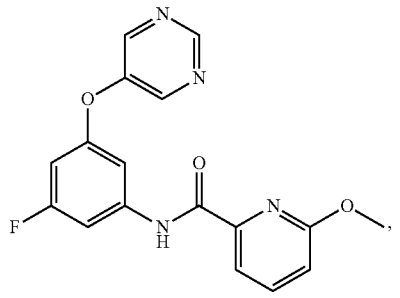
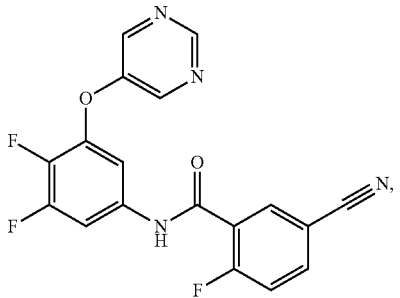

275
-continued
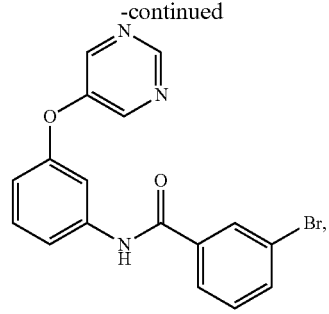
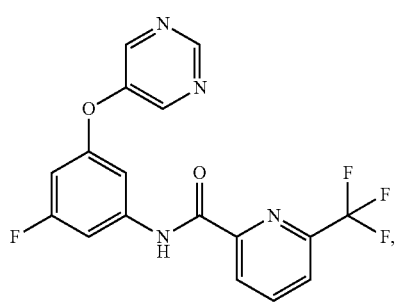
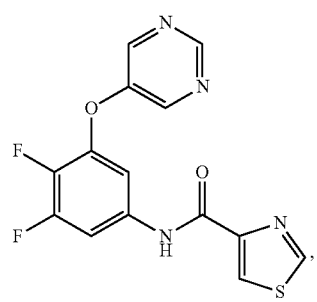
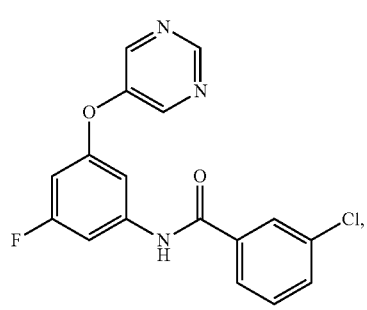
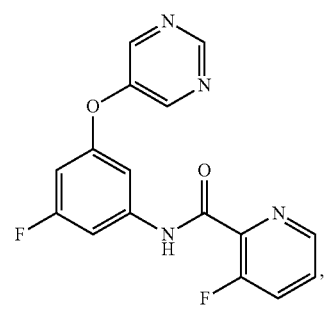
276
-continued
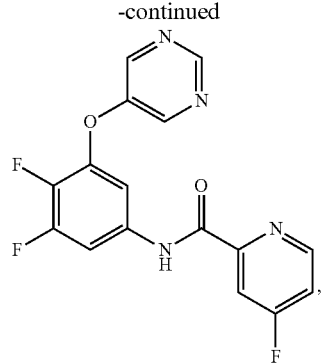
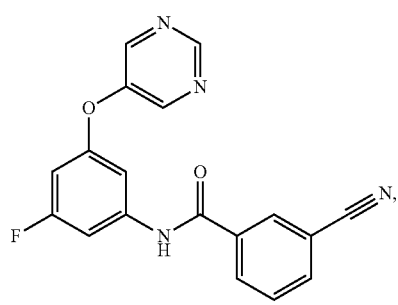
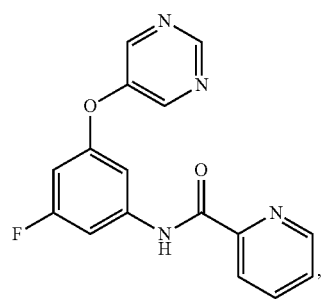
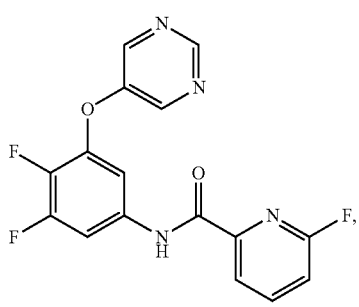
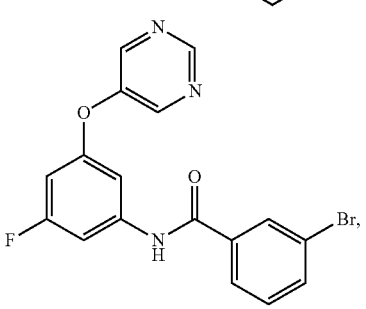

-continued
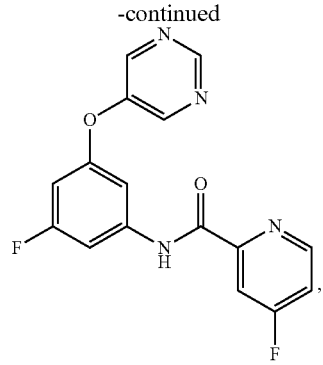
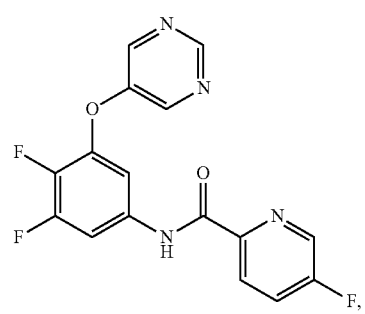
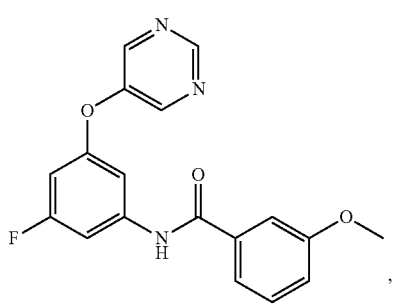
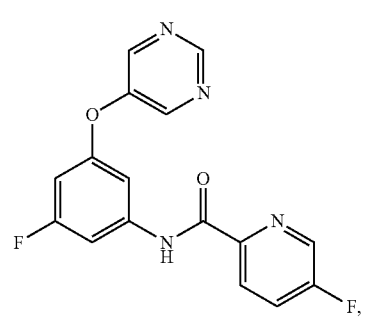
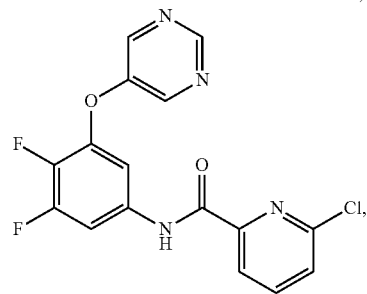
-continued
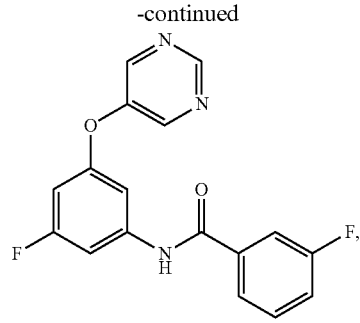
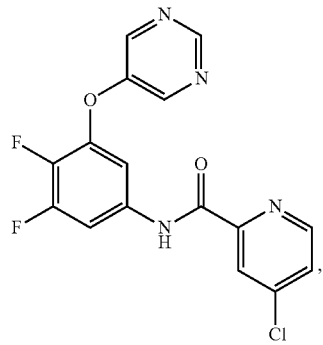
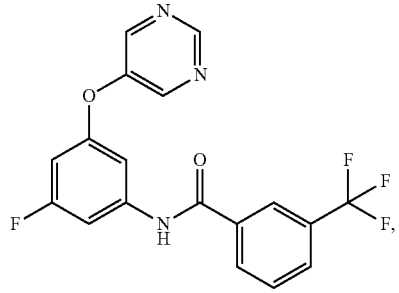
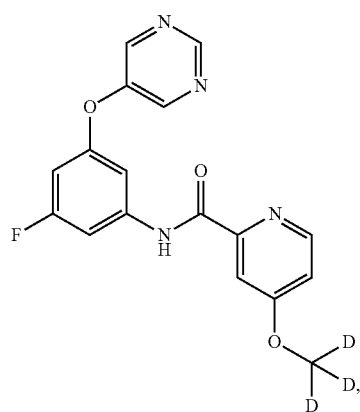

279
-continued
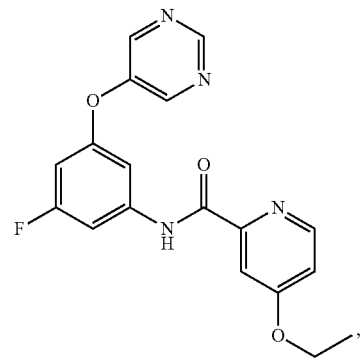
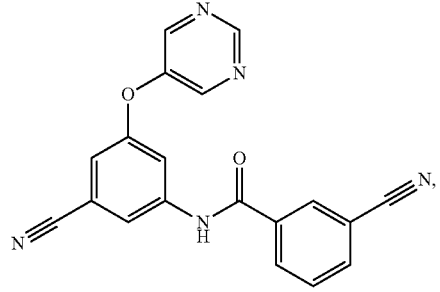
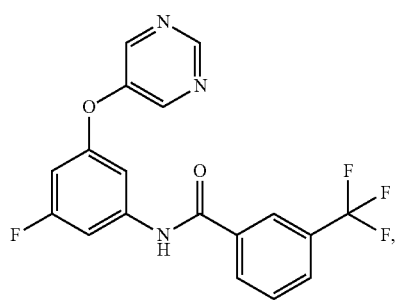
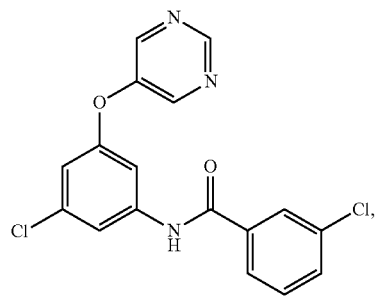
In a further aspect, a compound can be present as:
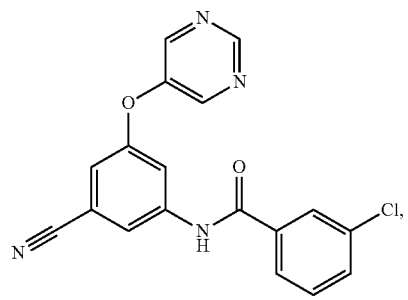
280
-continued 281
-continued
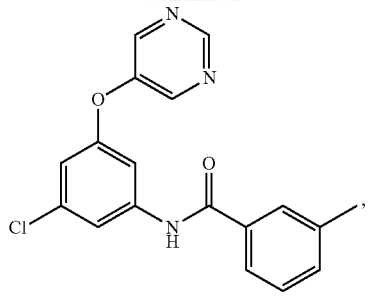
282
-continued
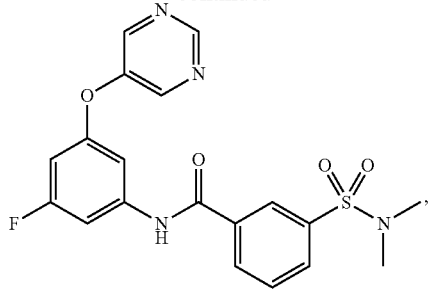
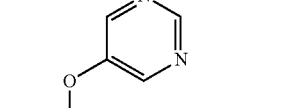

283
-continued
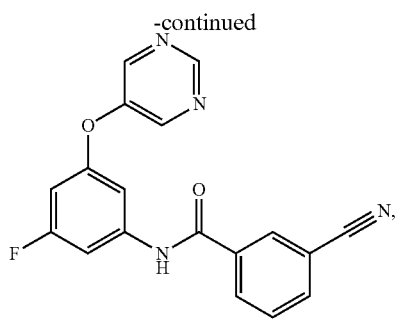
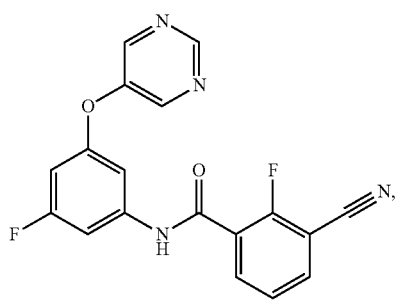
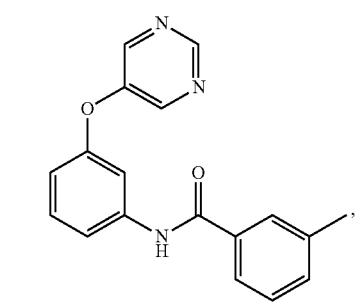
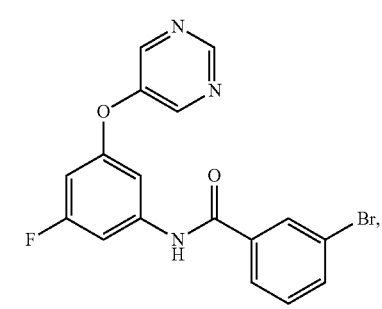
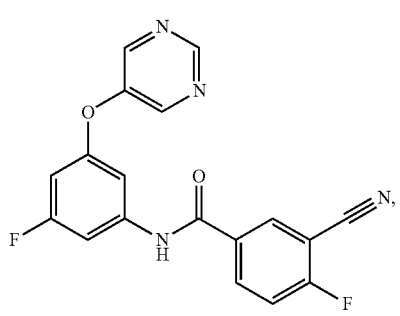
284
-continued
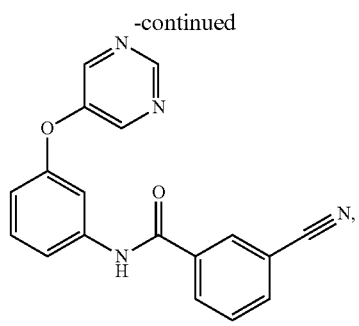
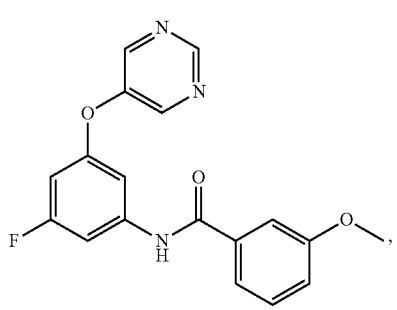
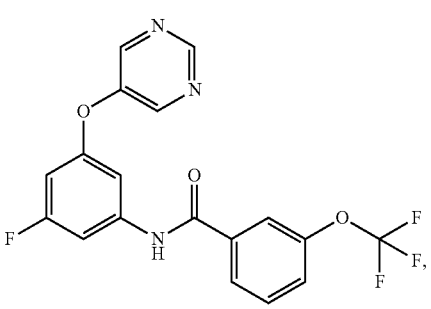
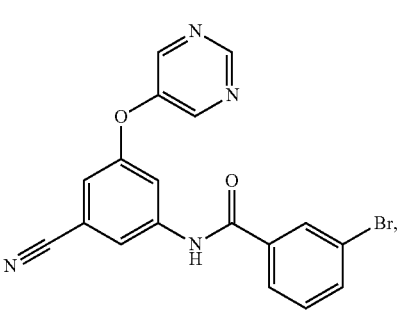
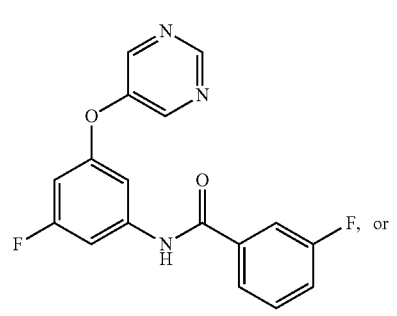

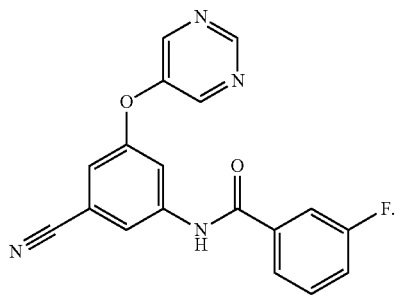
In a further aspect, a compound can be present as:
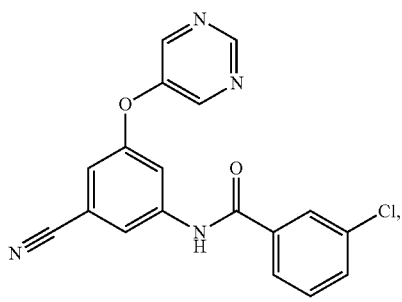
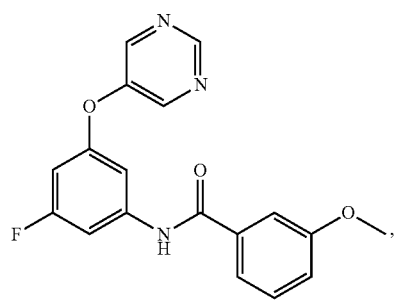
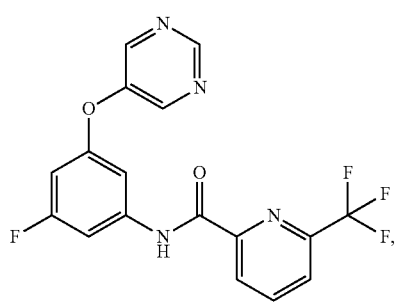
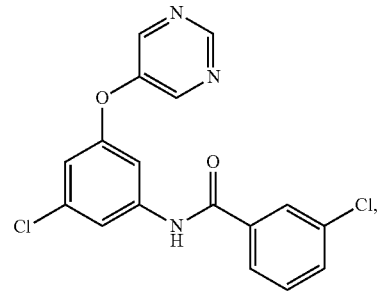
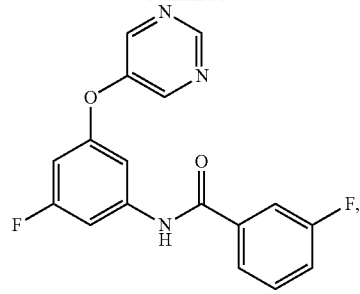
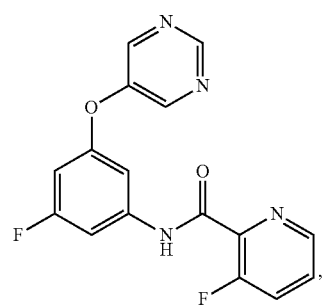
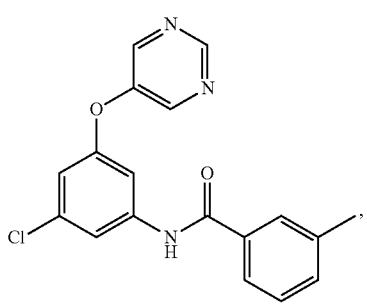
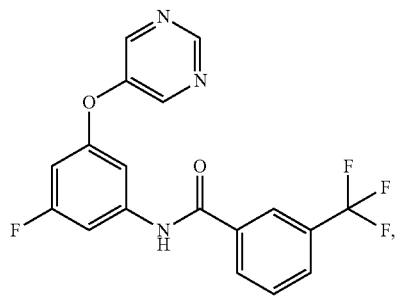
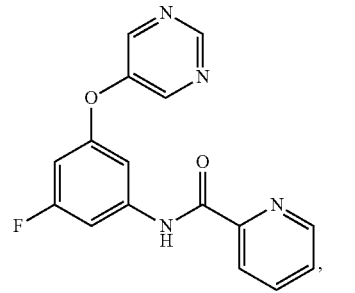

-continued
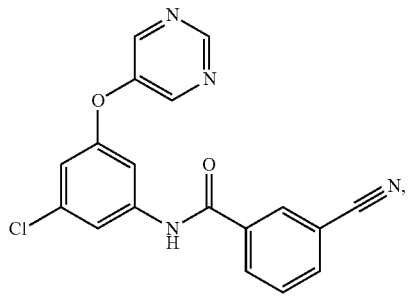
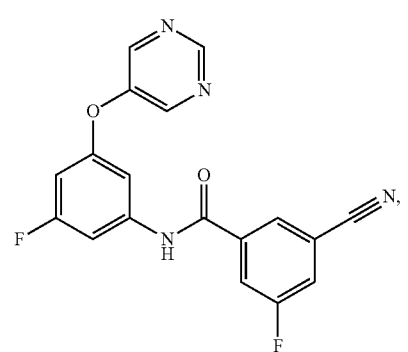
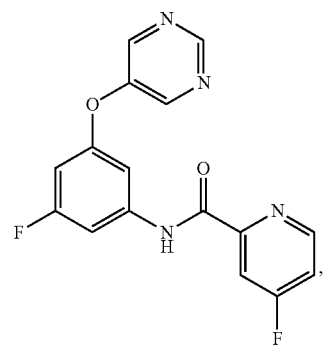
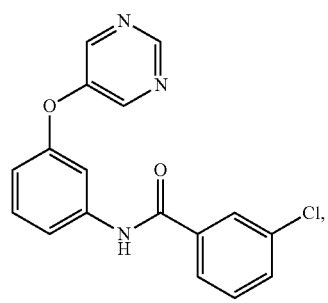
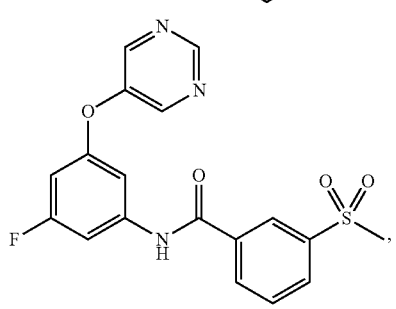
-continued
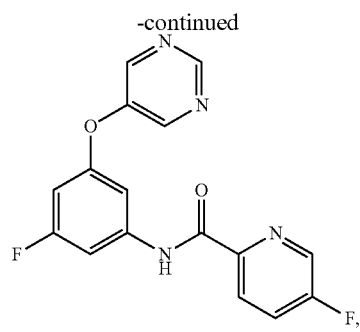
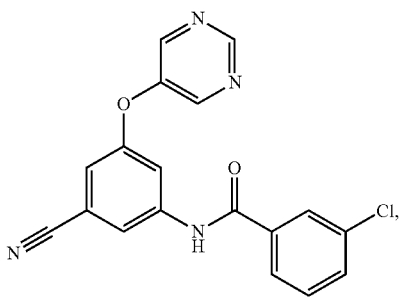
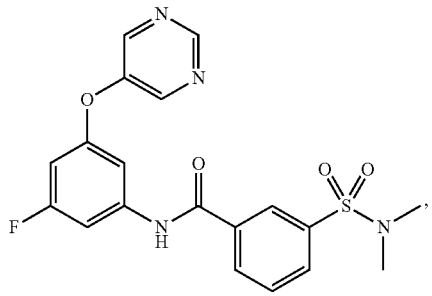
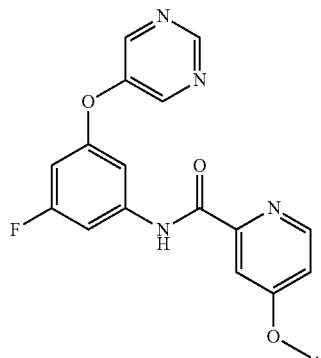
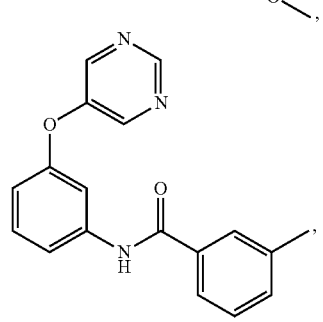

289
-continued
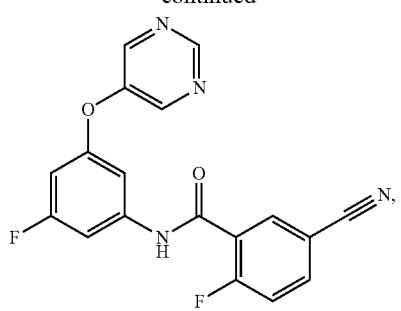
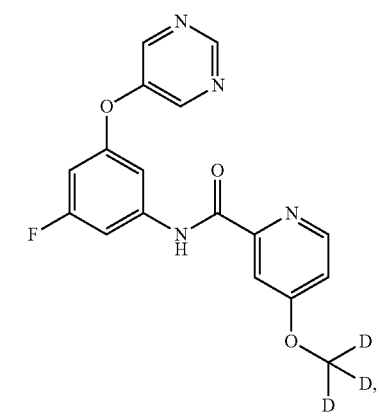
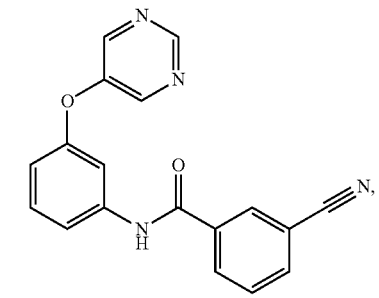
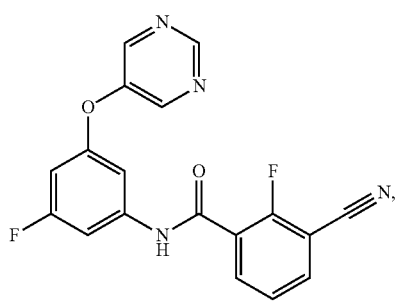
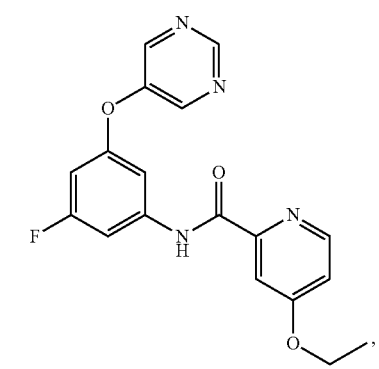
290
-continued
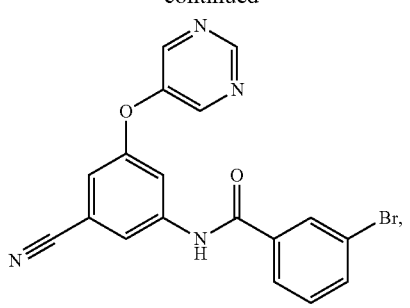
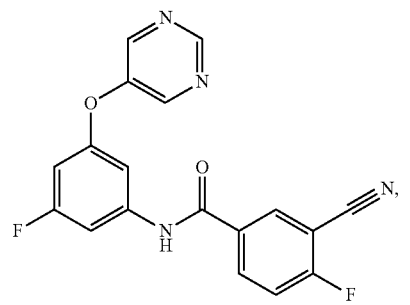
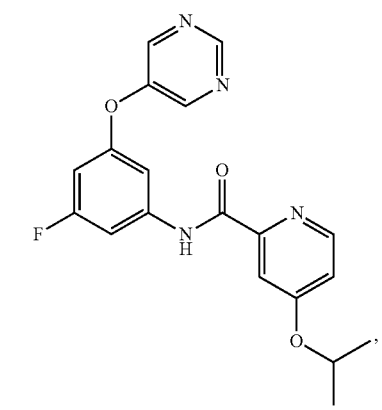
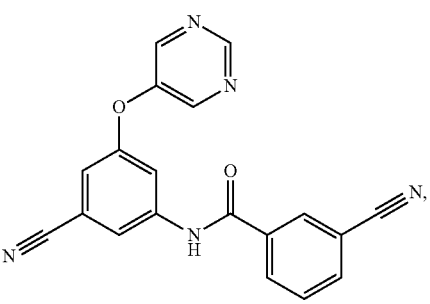
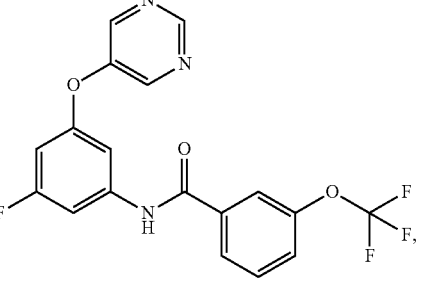

291
-continued
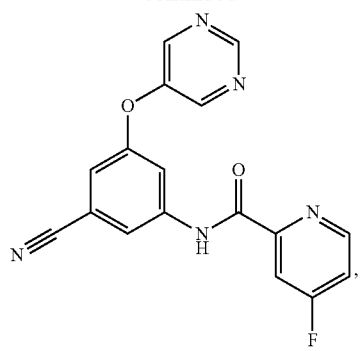
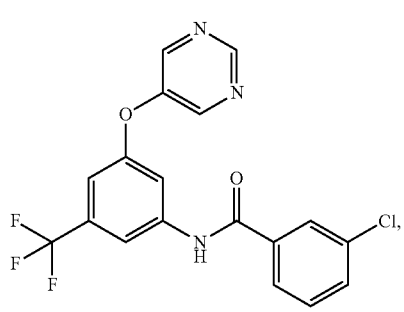
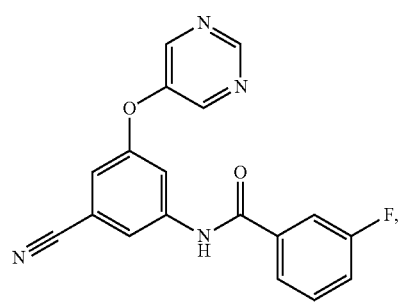
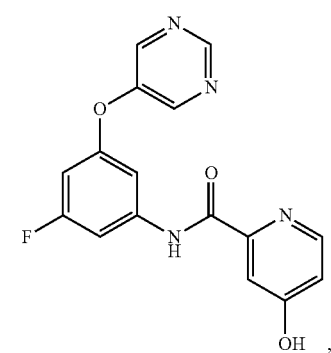
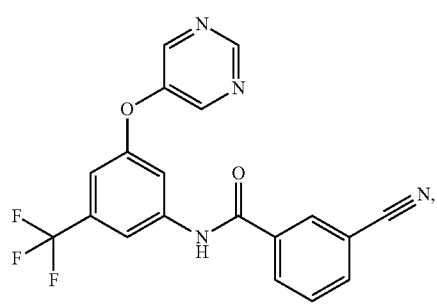
292
-continued
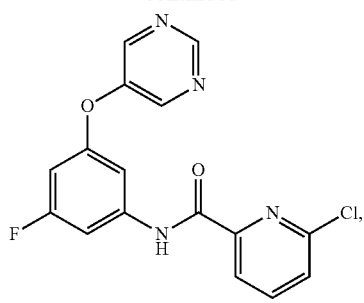
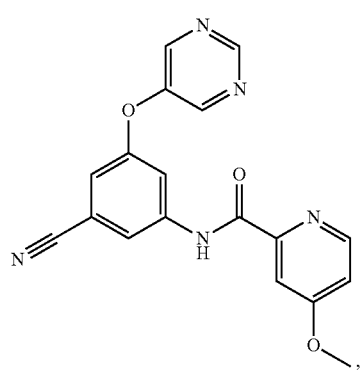
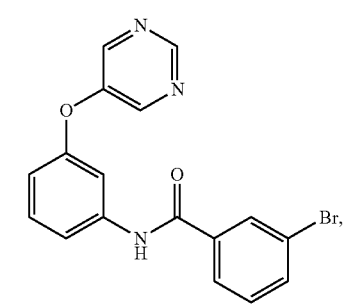
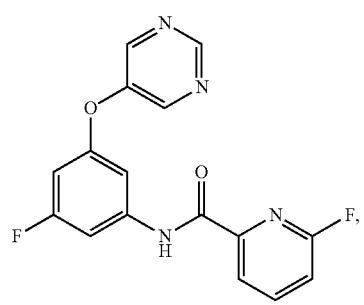
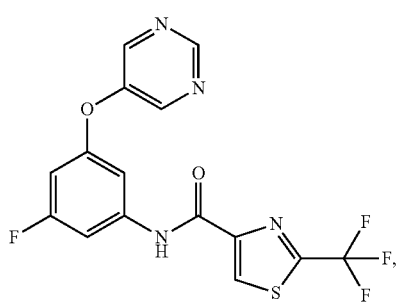

-continued
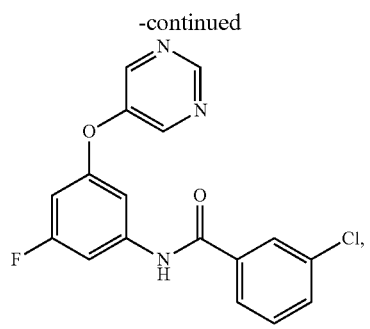
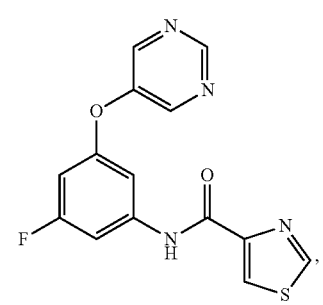
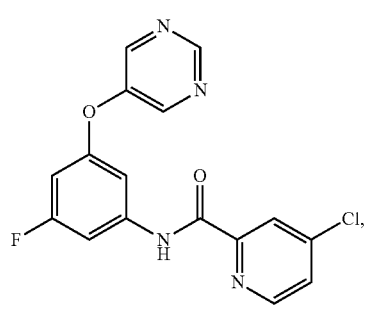
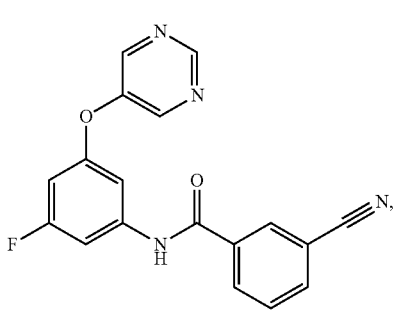
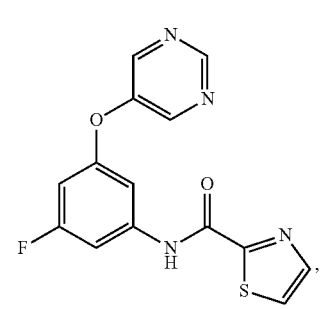
-continued
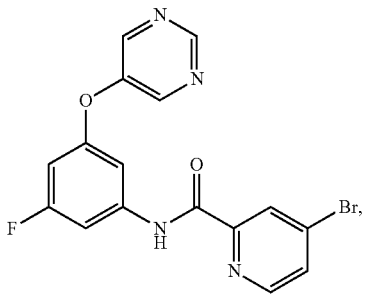
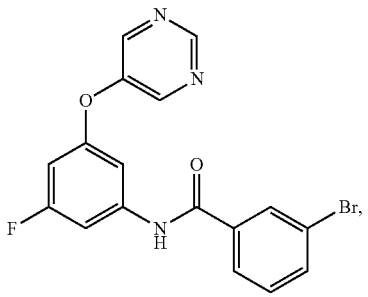
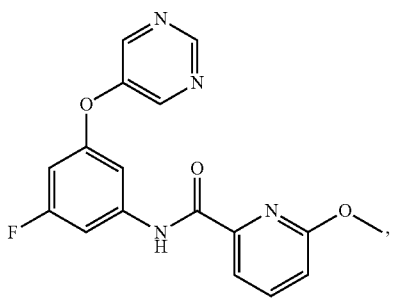
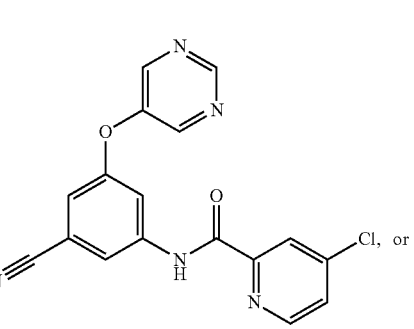
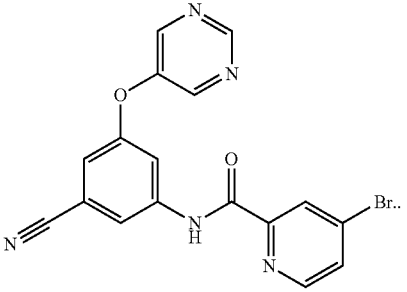

In a further aspect, a compound can be present as:
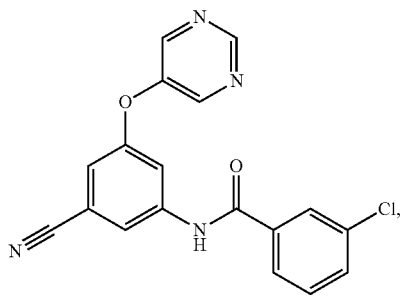
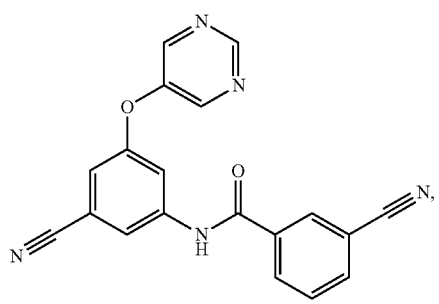
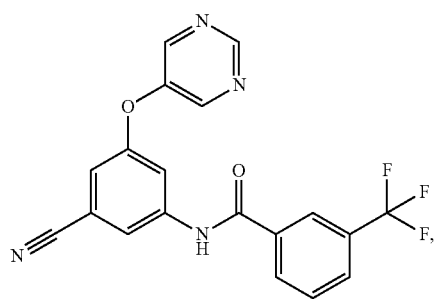
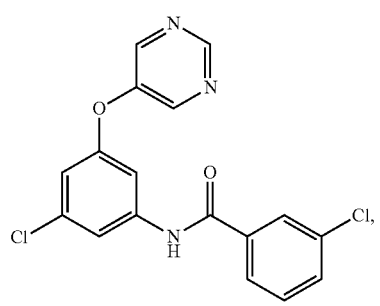
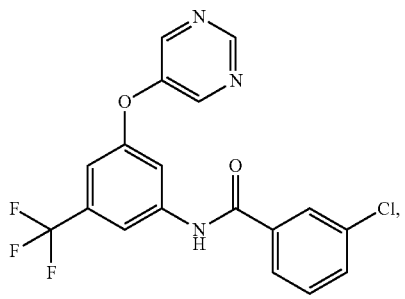
-continued
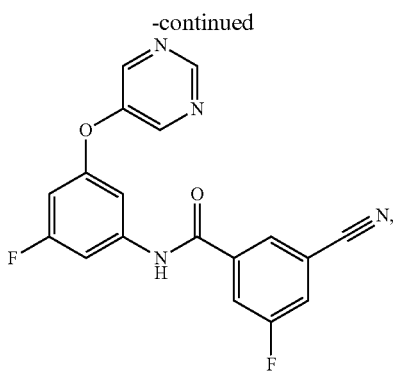
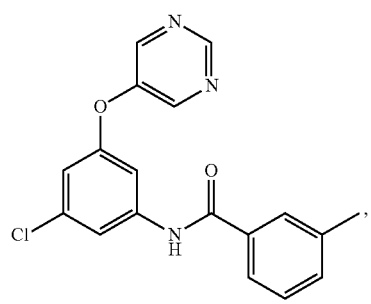
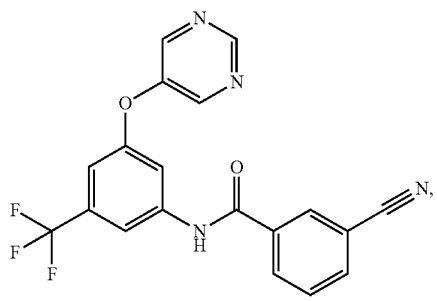
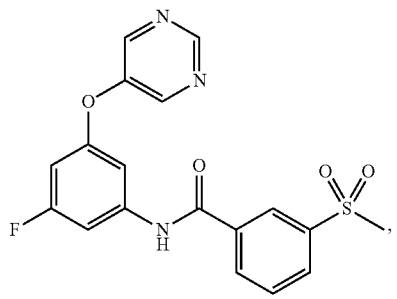
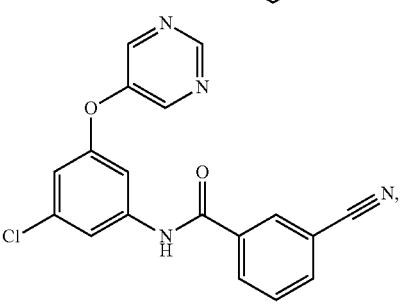

297
-continued
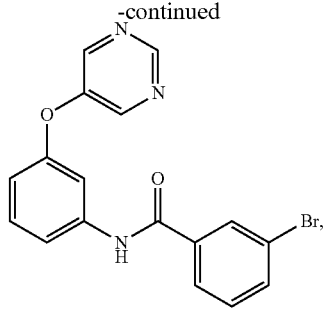
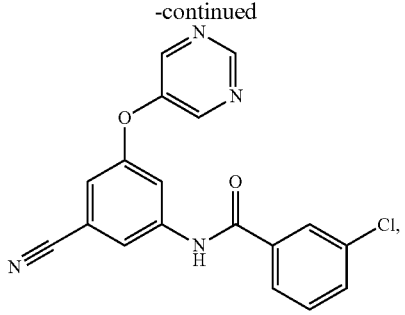
298
-continued
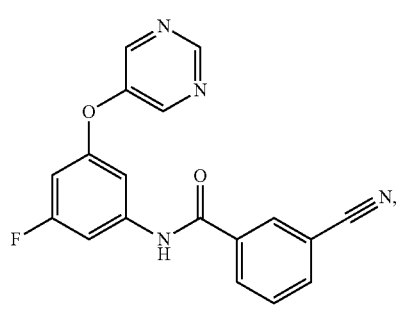
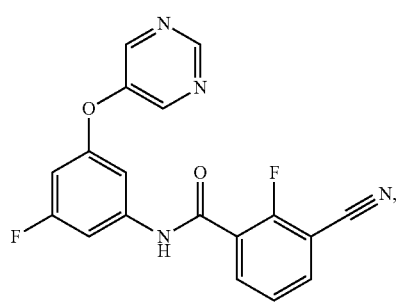
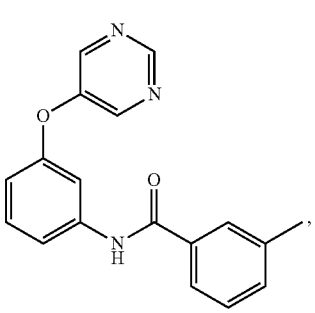
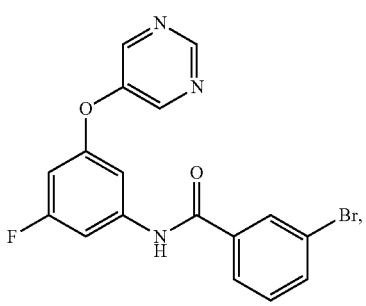

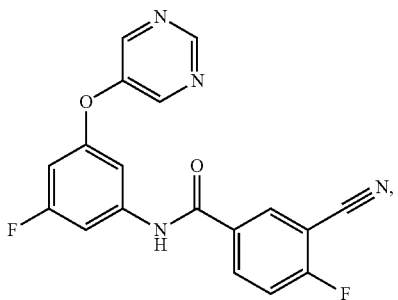
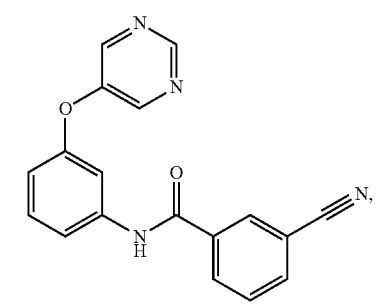
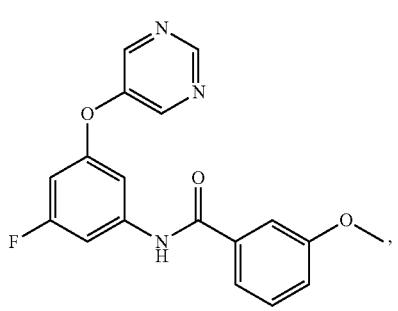
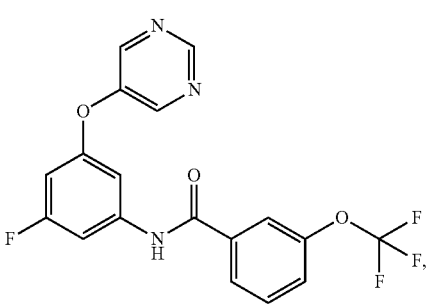
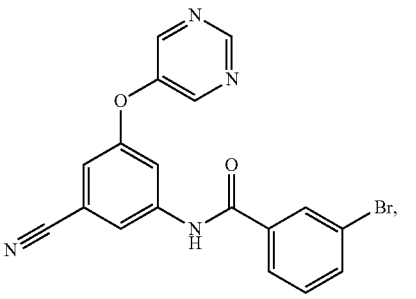
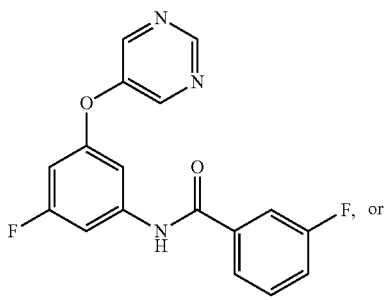
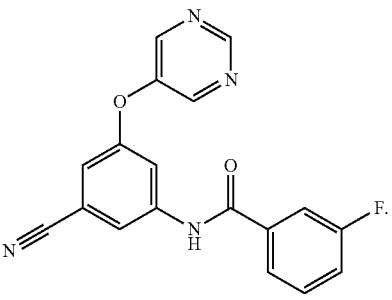
In a further aspect, a compound can be present as:
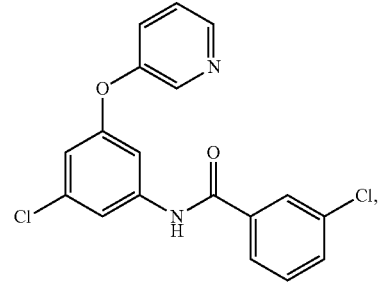
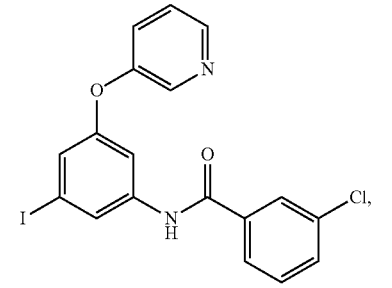
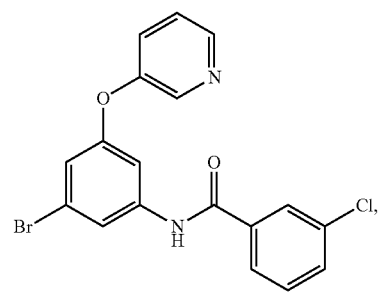

301
-continued
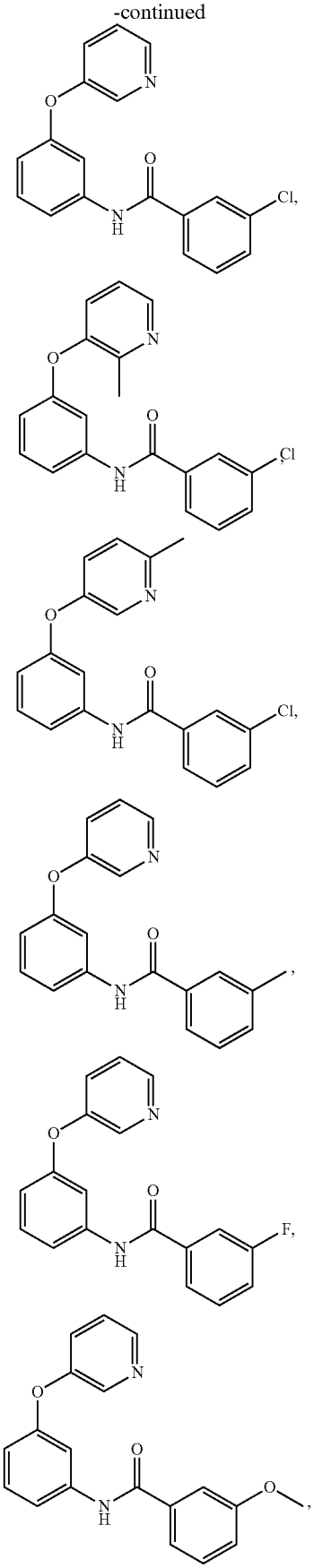
302
-continued
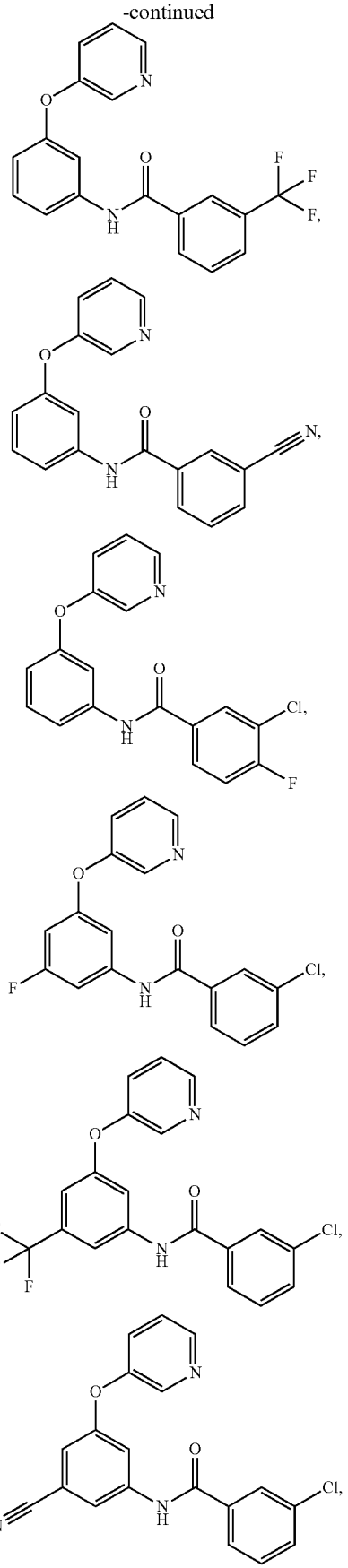

303
-continued
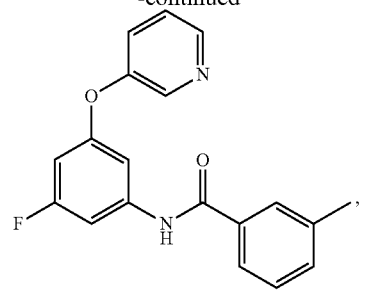
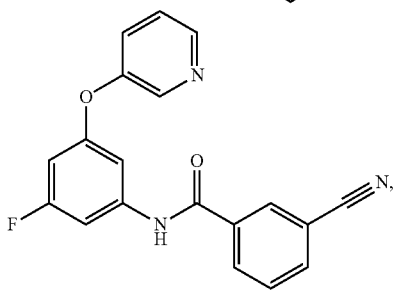
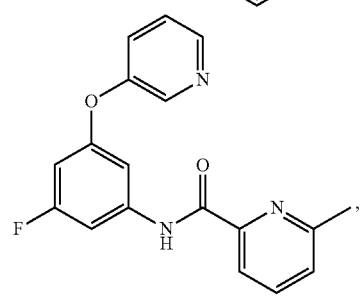
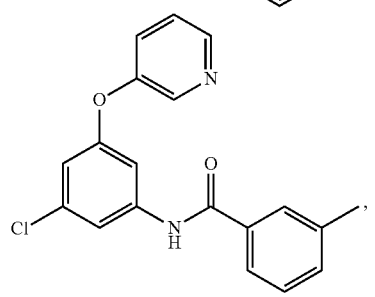
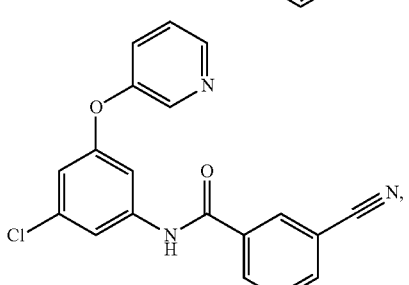
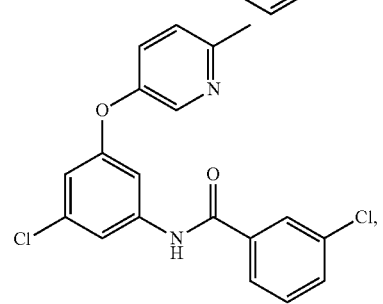
304
-continued
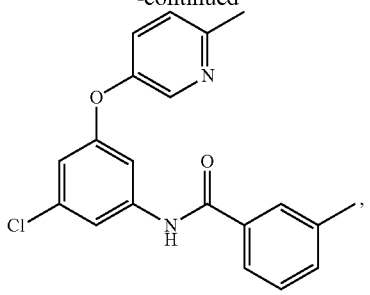
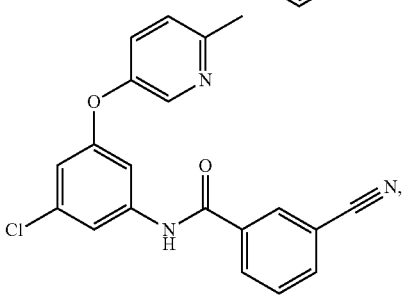
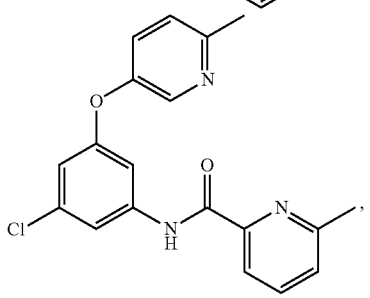
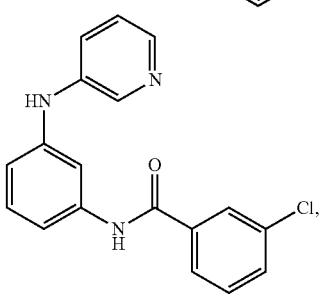
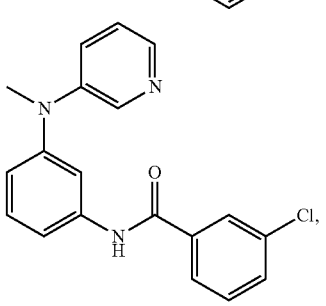
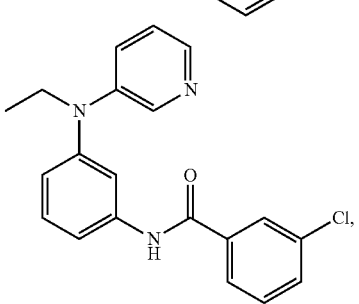

305
-continued
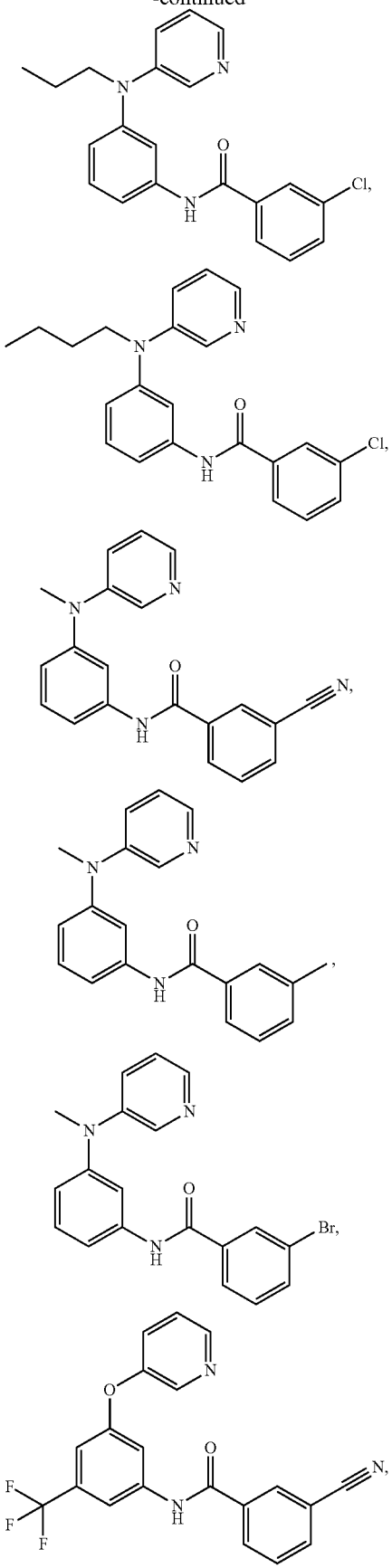
306
-continued
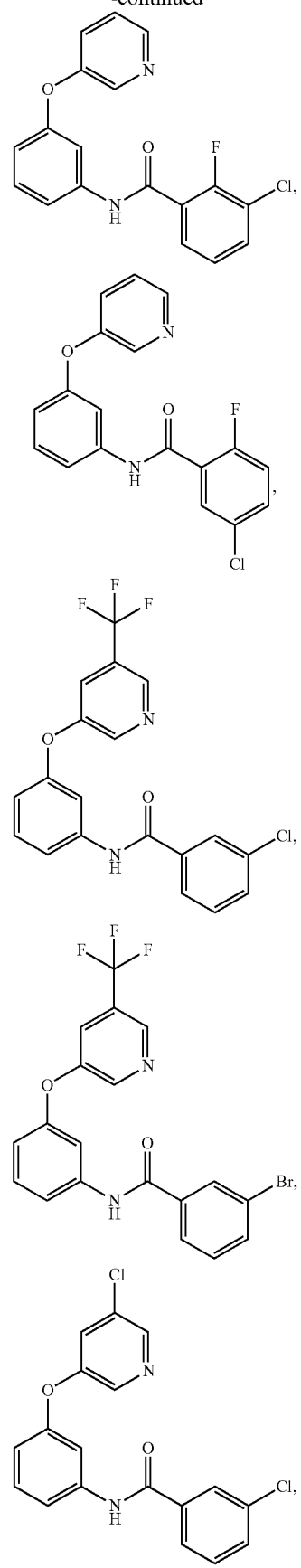

307
-continued
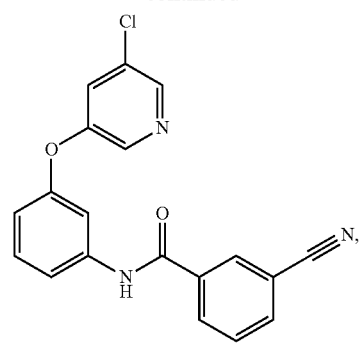
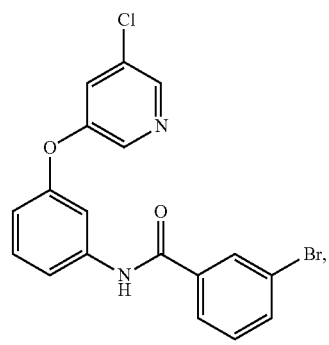
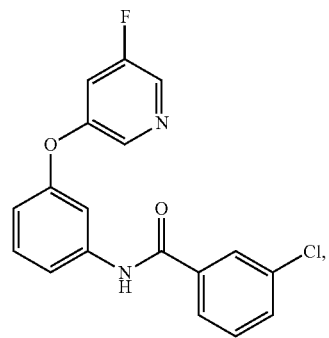
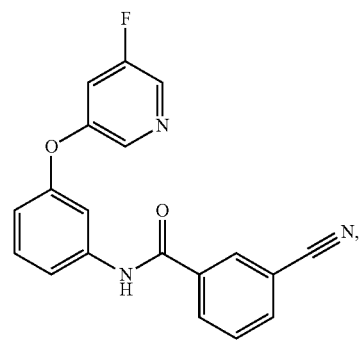
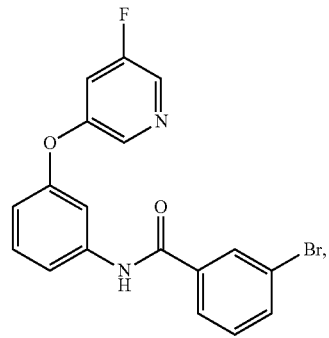
308
-continued
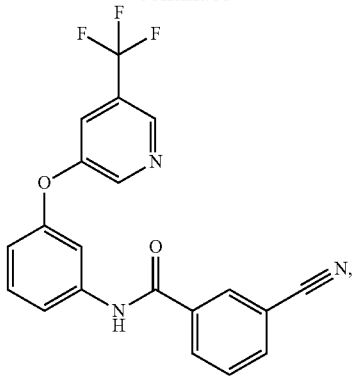
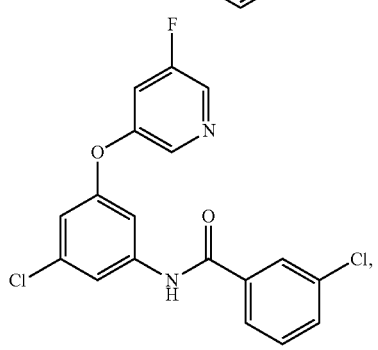
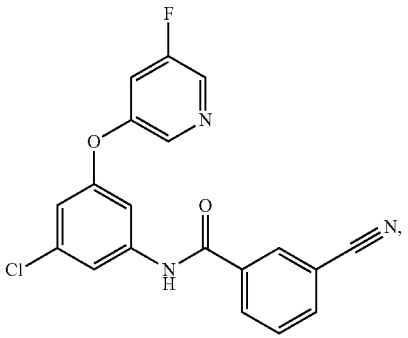
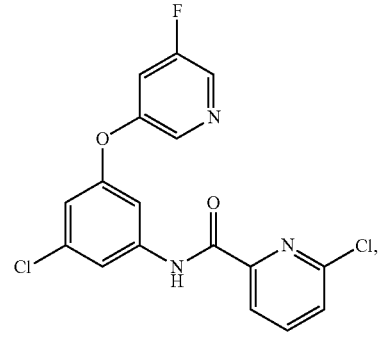
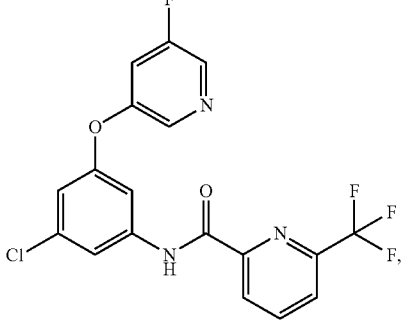

309
-continued
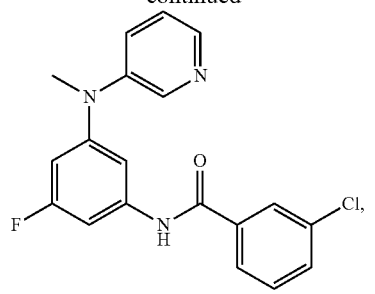
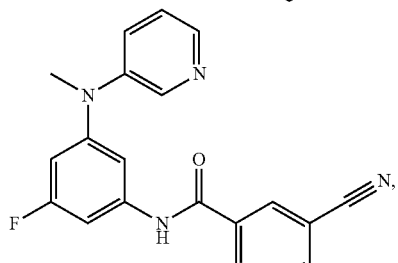
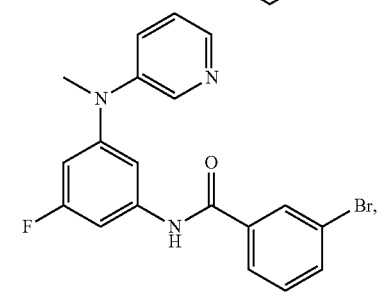
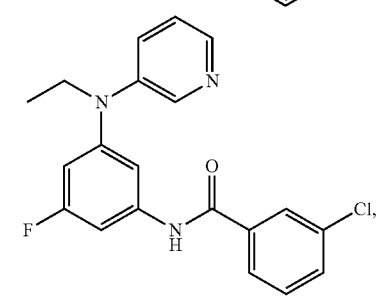
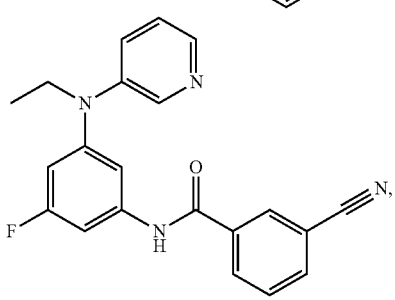
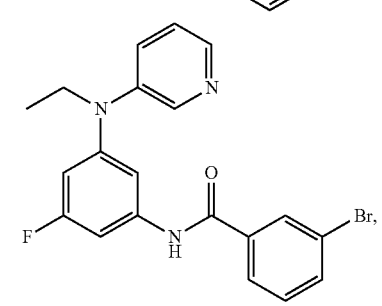
310
-continued
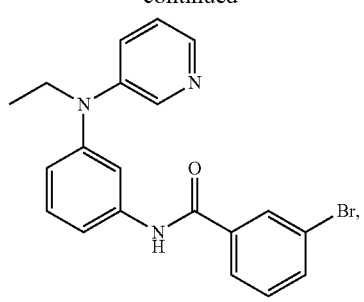
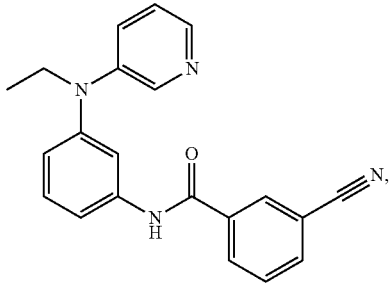
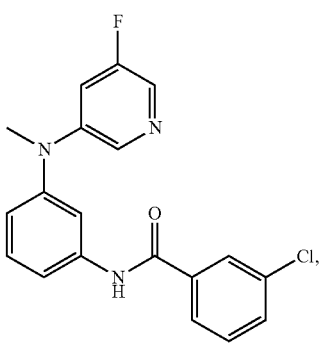
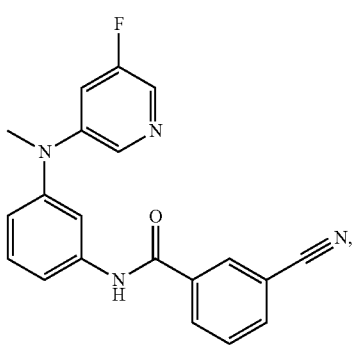
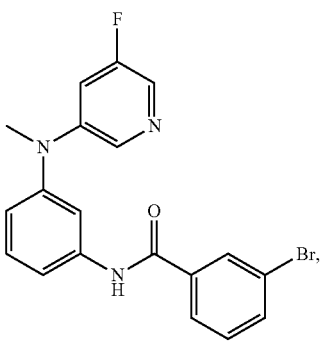

311
-continued
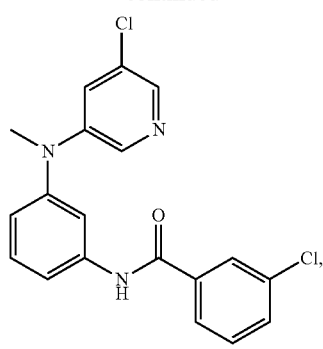
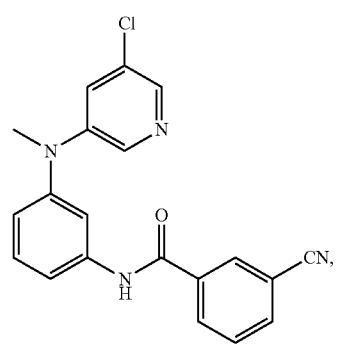
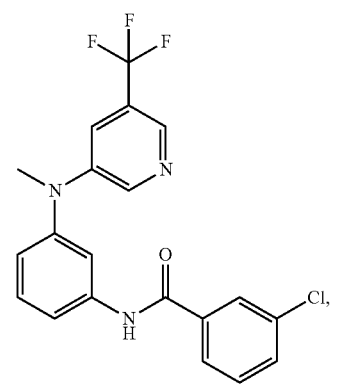
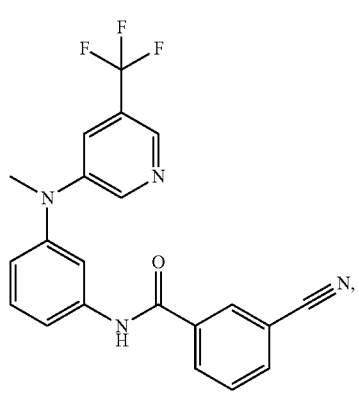
312
-continued
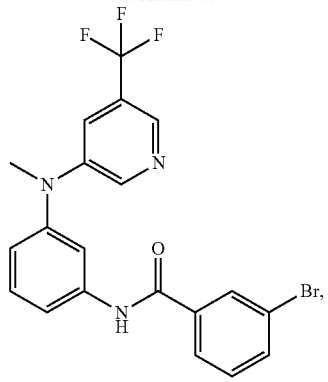
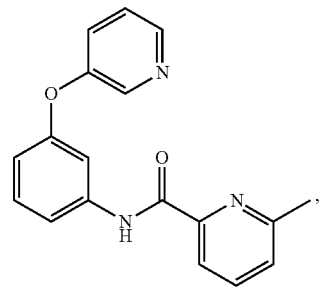 [SMILES: Cc1cccc(C(=O)Nc2cccc(Oc3cccnc3)c2)c1 ; ","]
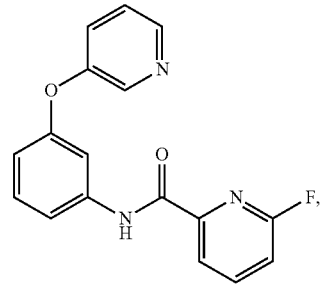
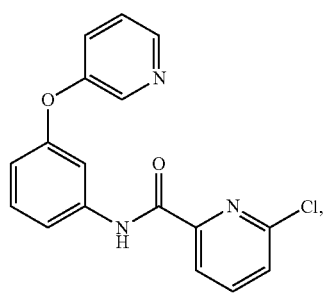
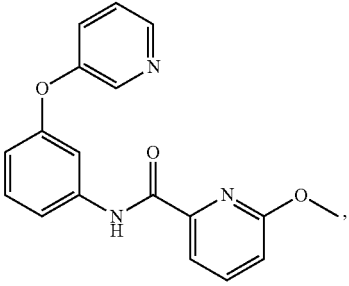

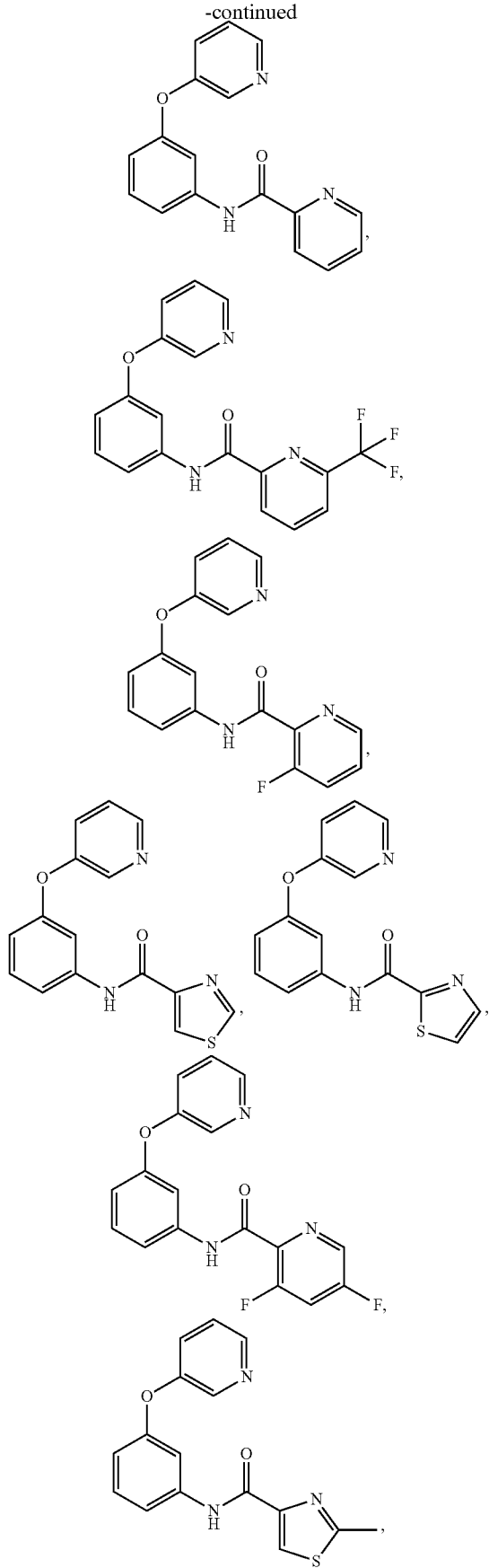
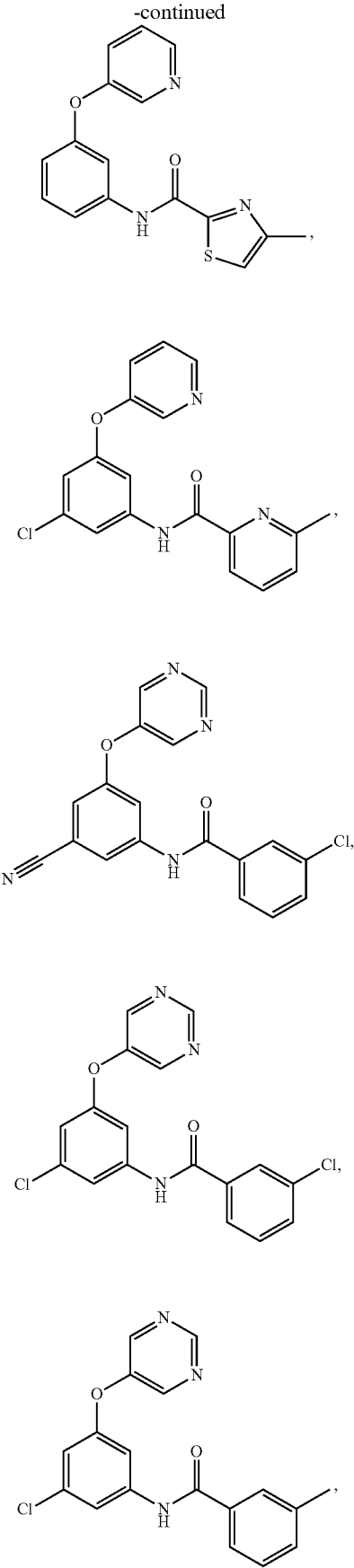

315
-continued
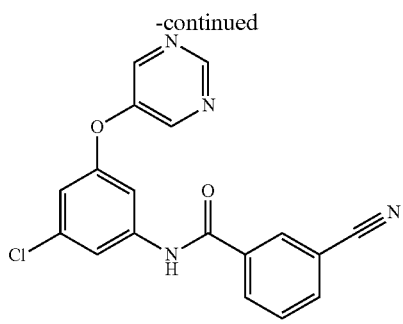
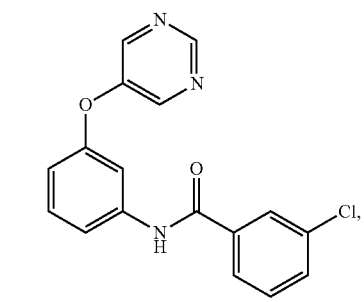
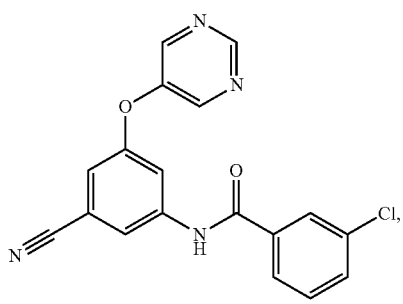
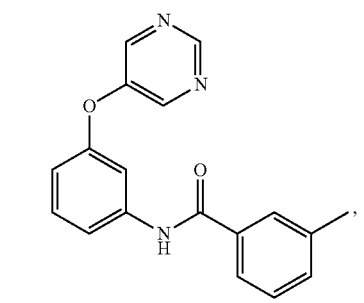
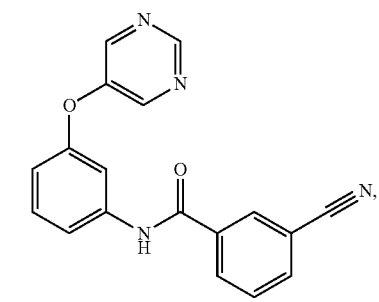
316
-continued
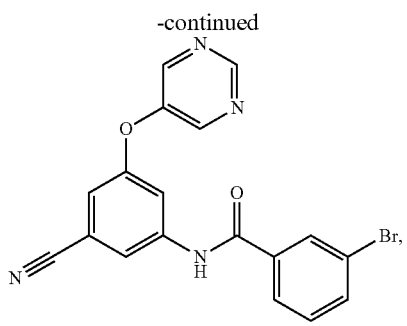
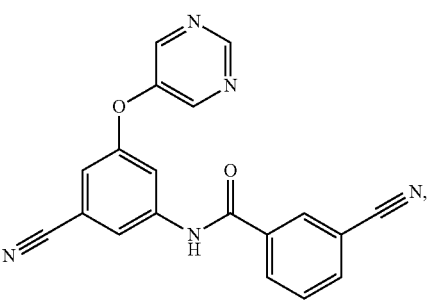
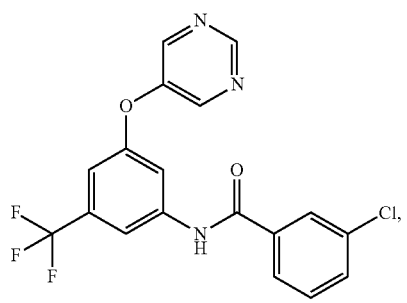
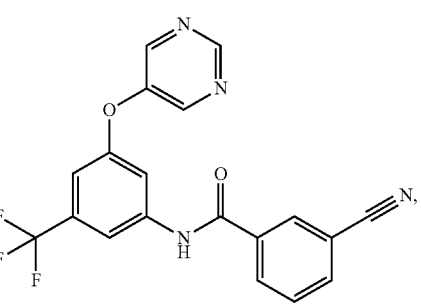
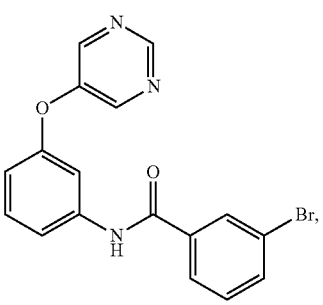

317
-continued
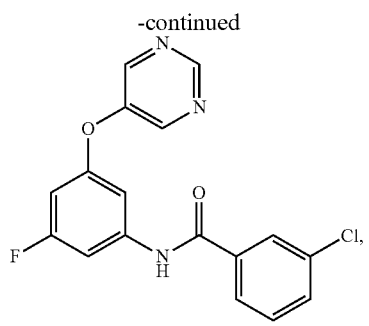
318
-continued
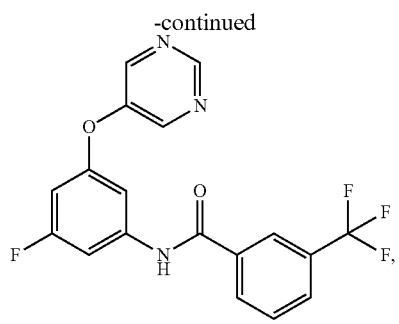
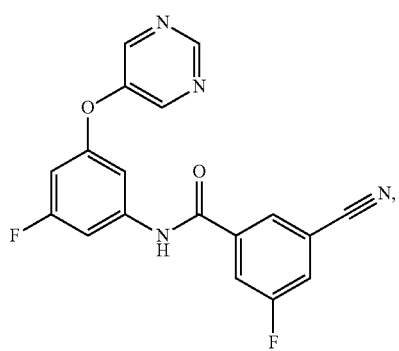
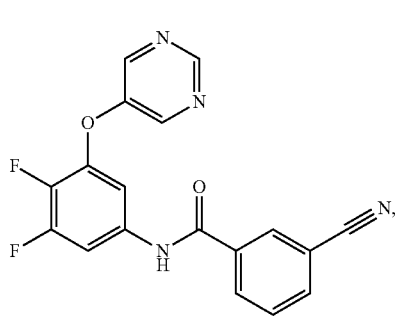
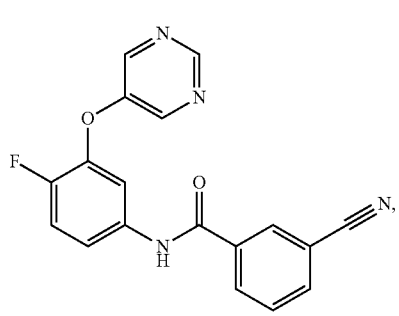
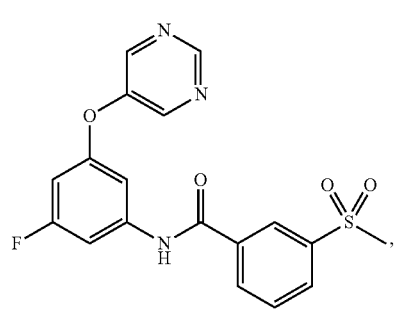

| 319 | 320 |
|---|---|
| -continued | -continued |
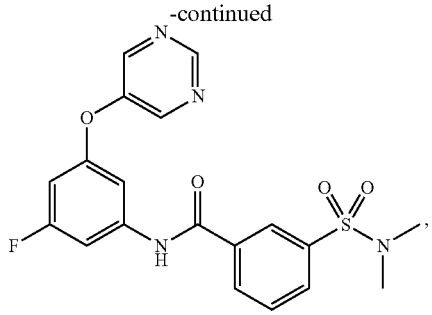
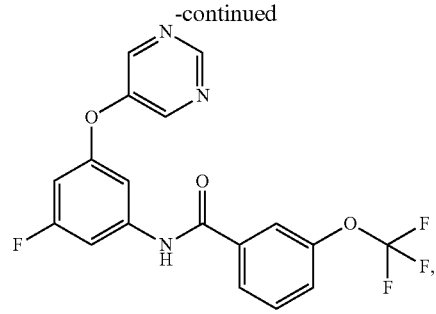
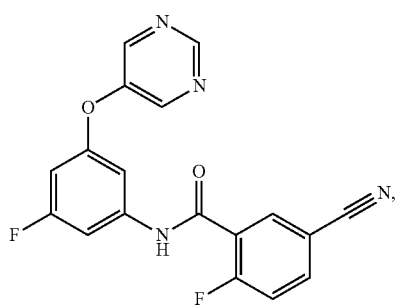
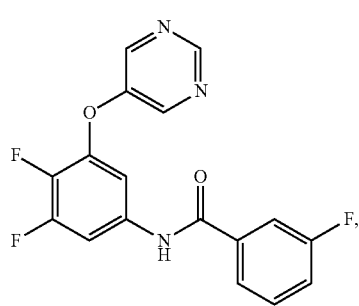
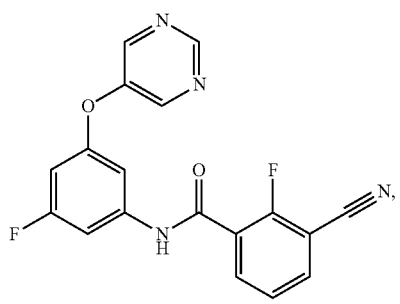
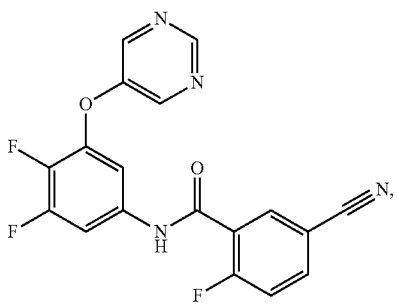
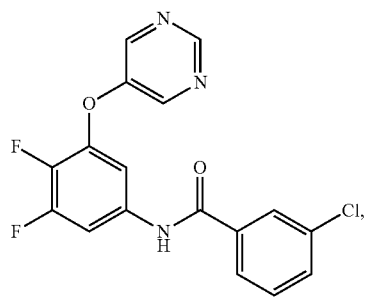
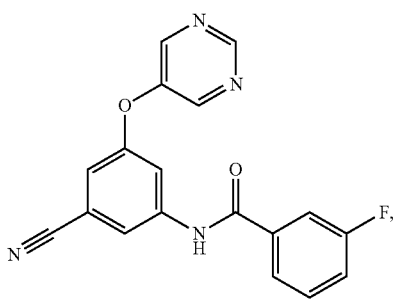
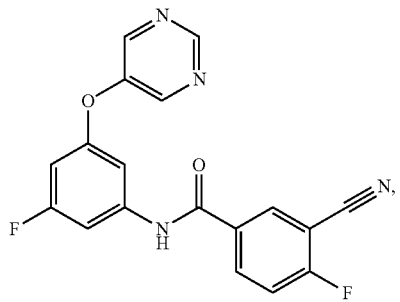
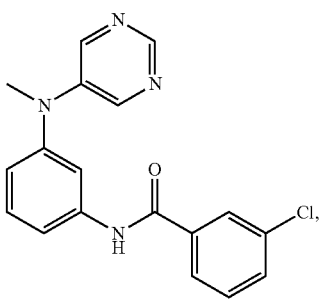

-continued
321
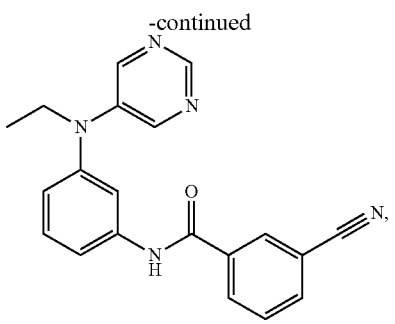
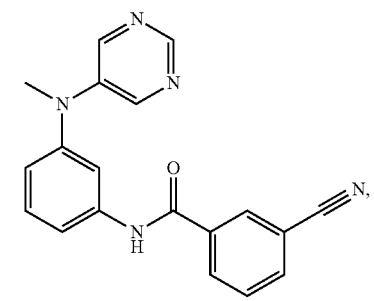
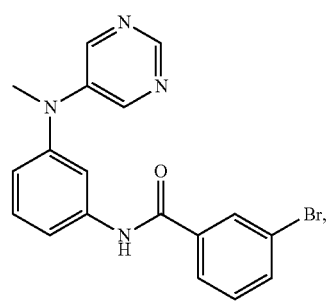
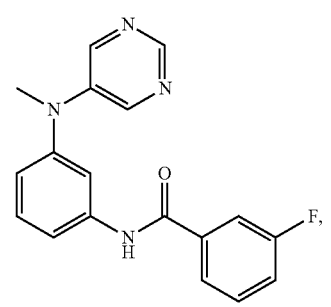
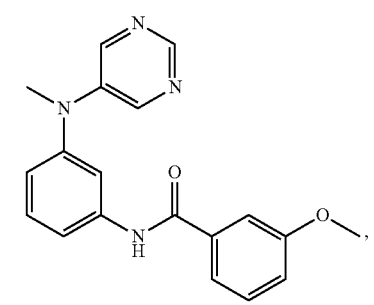
-continued
322
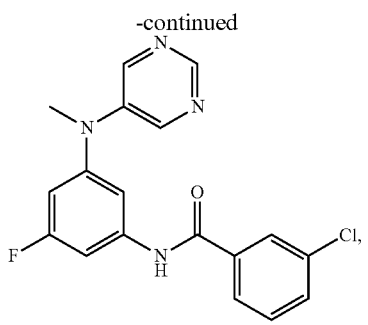
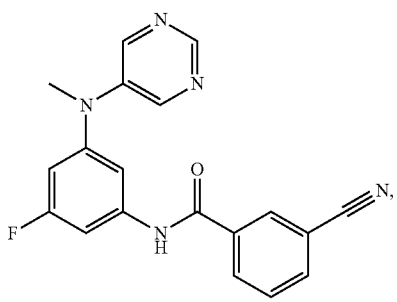
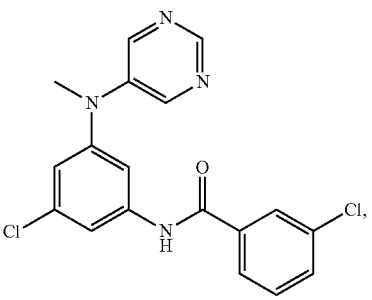
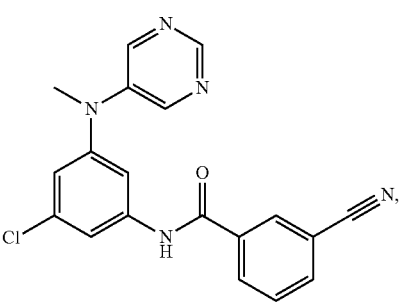
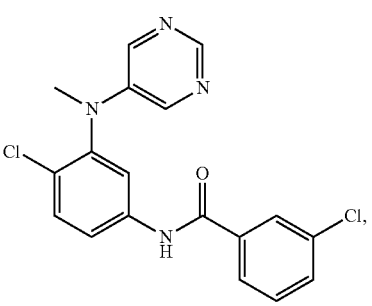

323
-continued
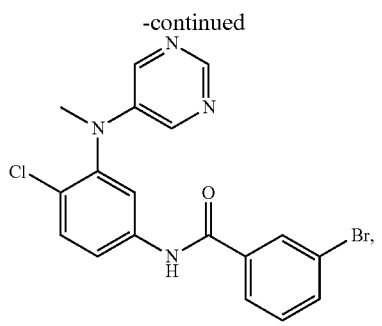
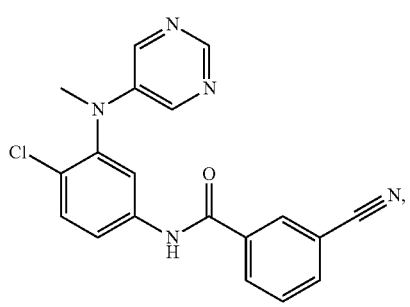
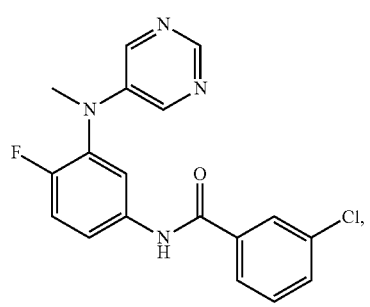
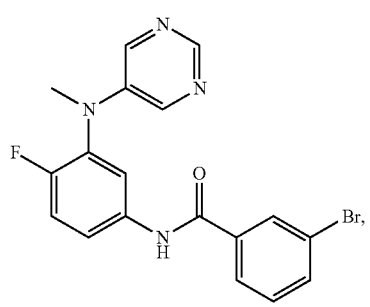
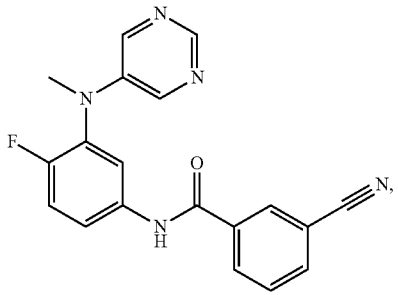
324
-continued
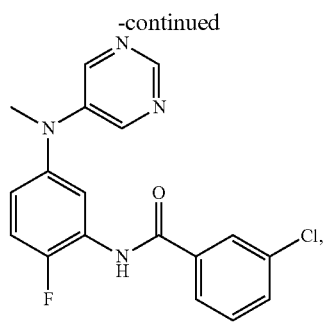
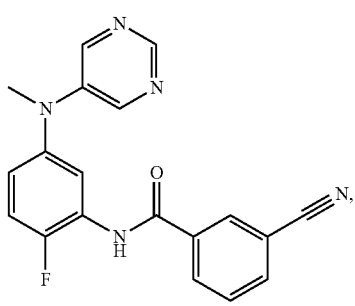
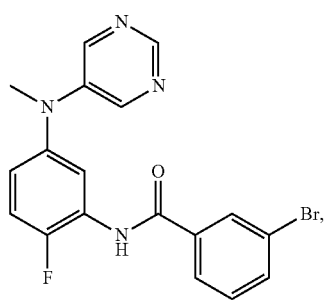
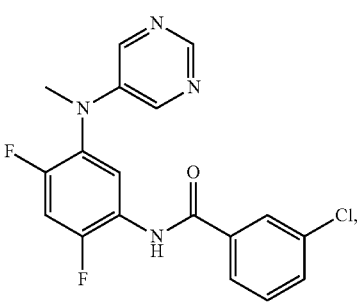
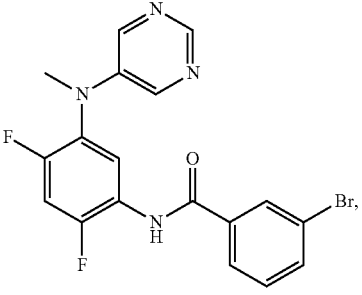

325
-continued
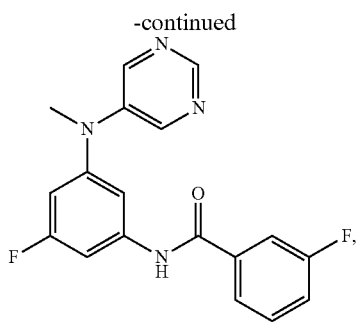
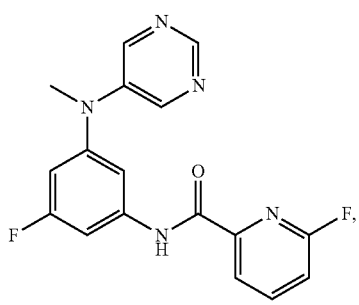
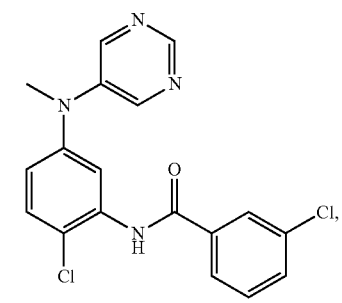
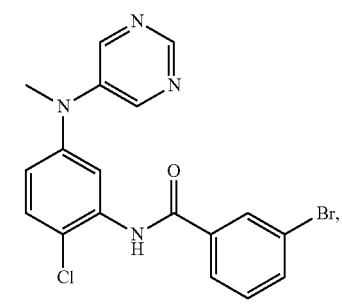
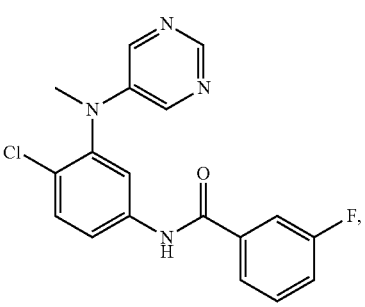
326
-continued
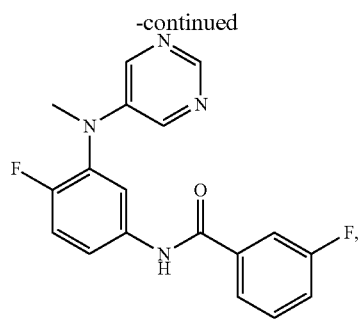
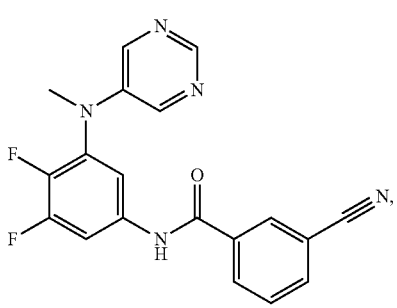
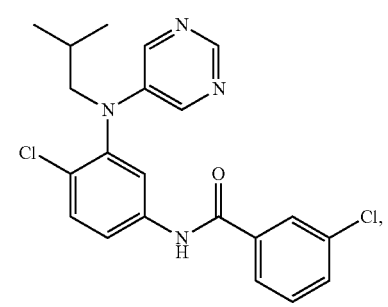
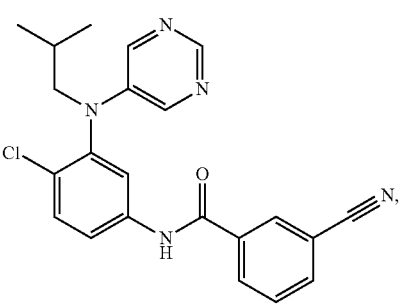
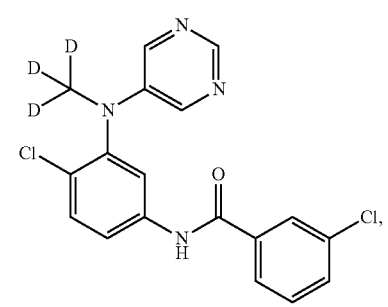

327
-continued
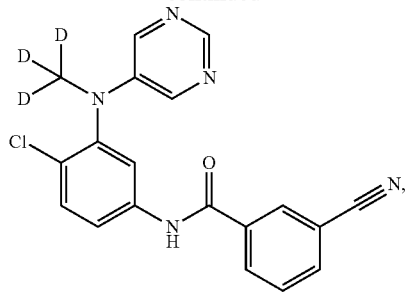
328
-continued
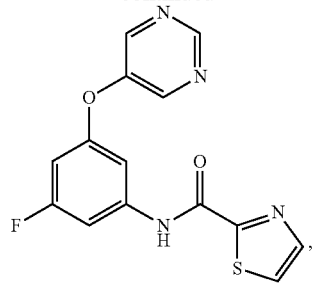
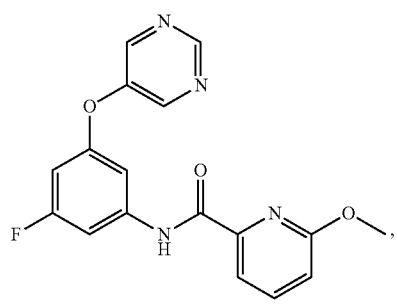
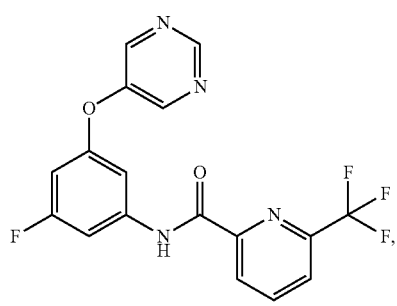
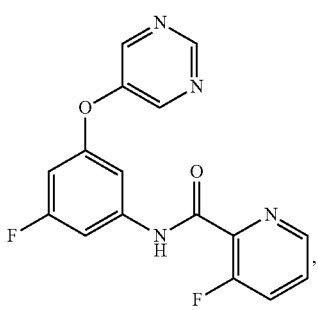
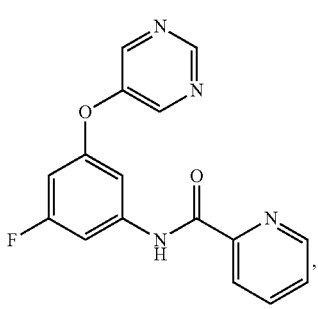

329
-continued
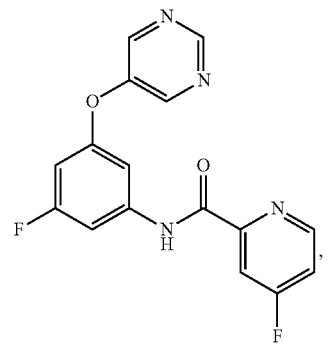
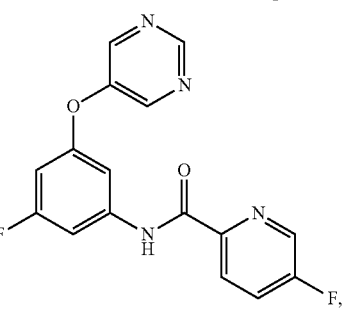
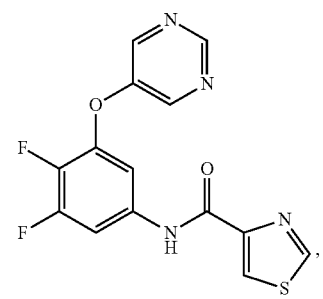
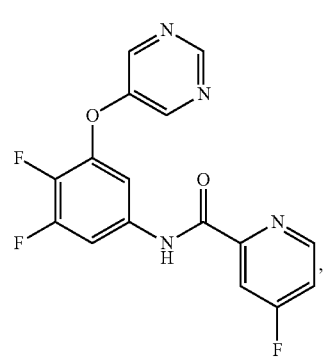
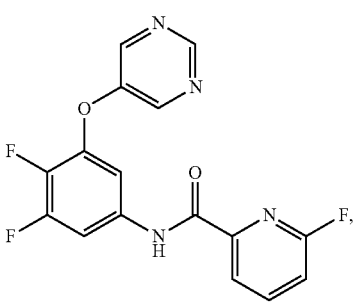
330
-continued
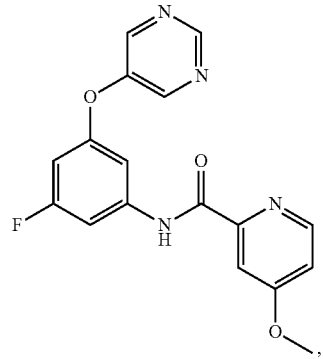
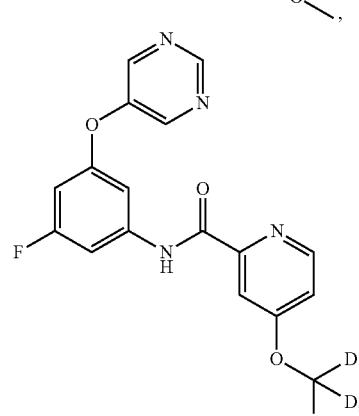
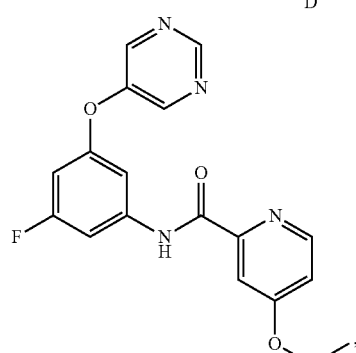
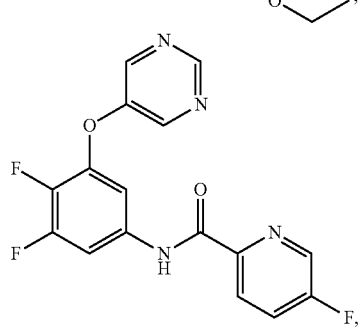
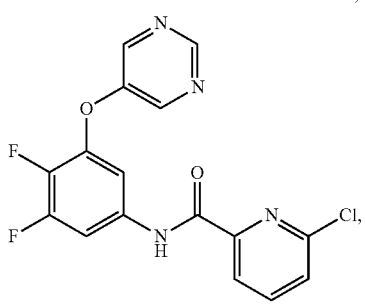

331
-continued
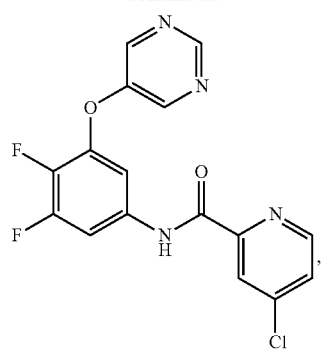
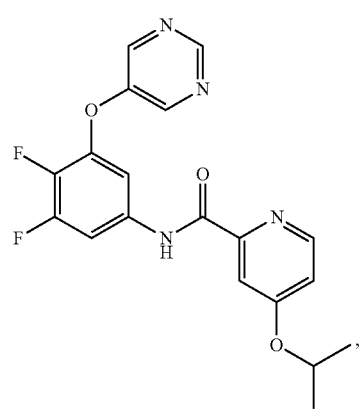
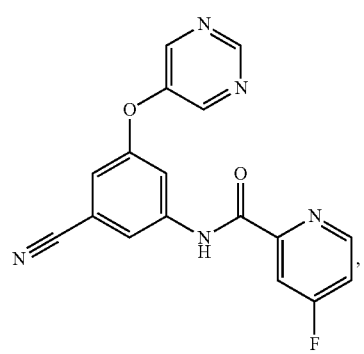
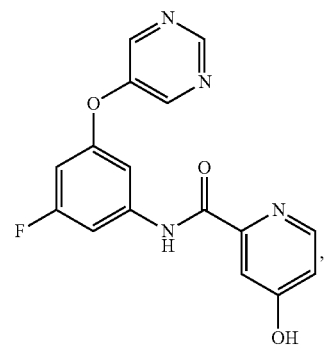
332
-continued
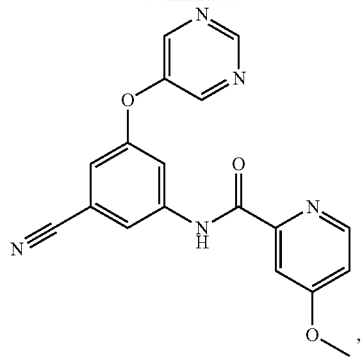
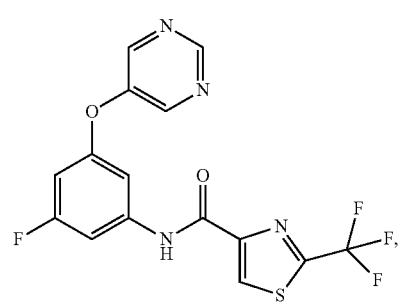
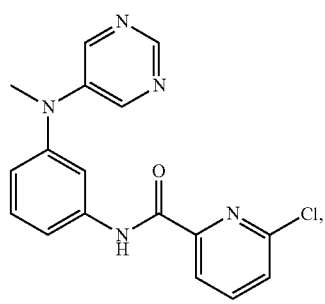
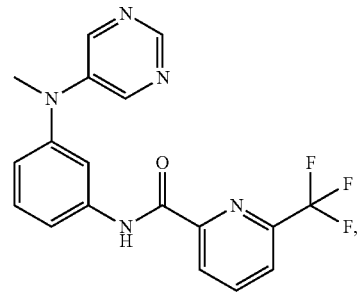
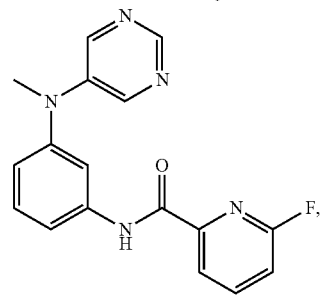

333
-continued
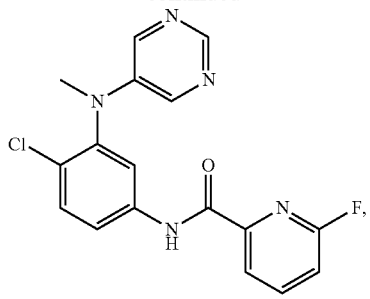
334
-continued
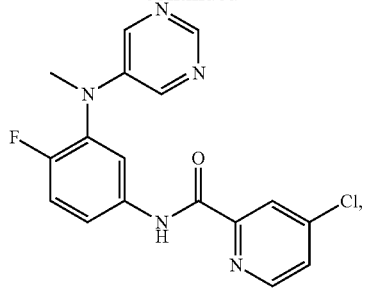
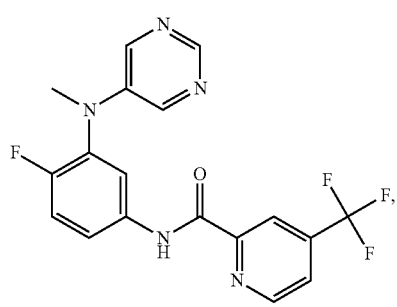
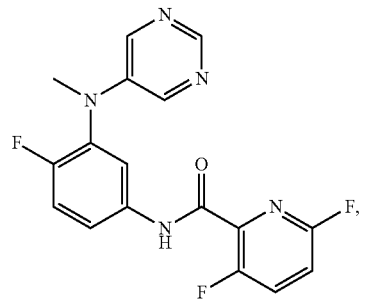
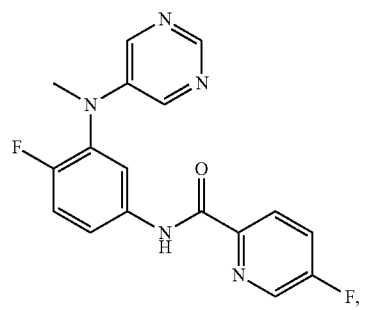
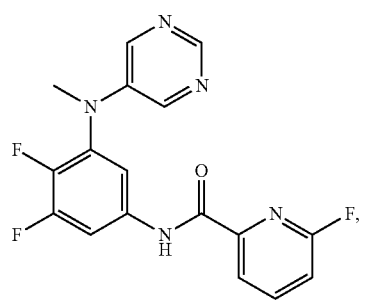

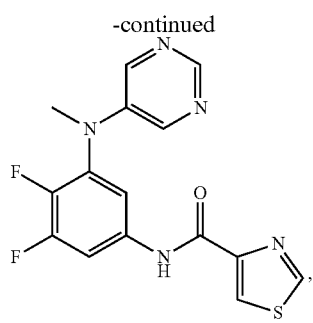
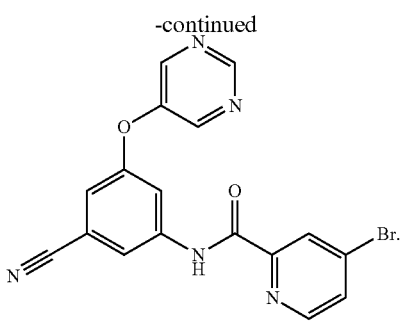
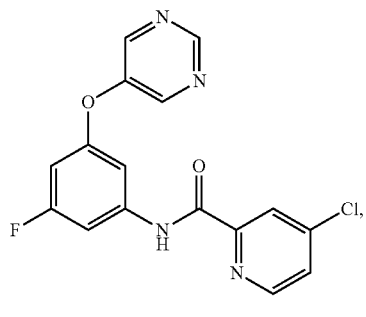
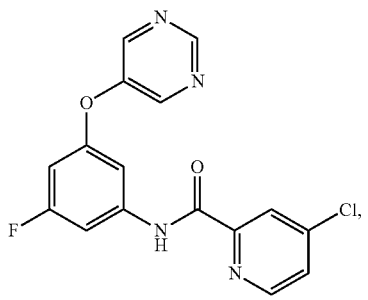
In a further aspect, a compound can be present as:
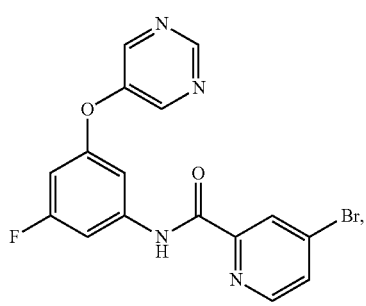
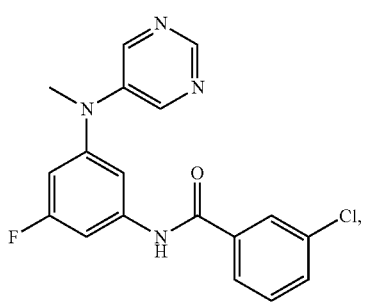
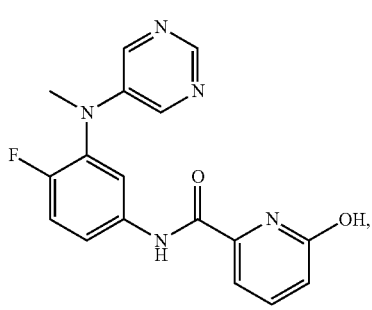
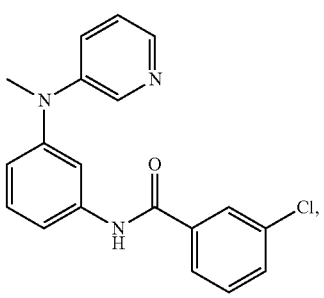
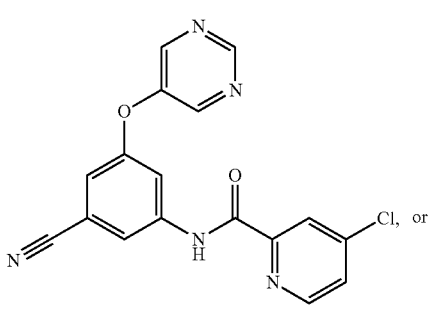
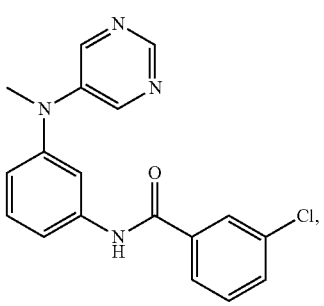

337
-continued
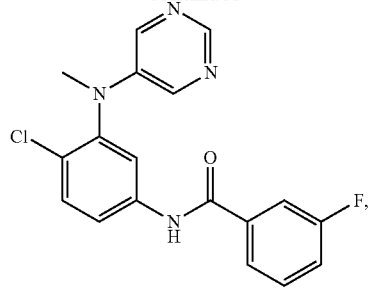
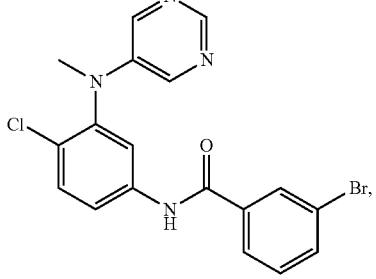
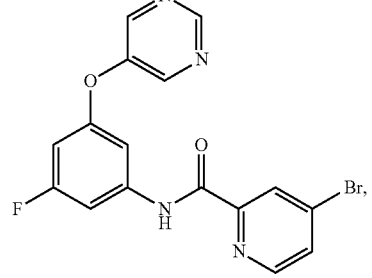
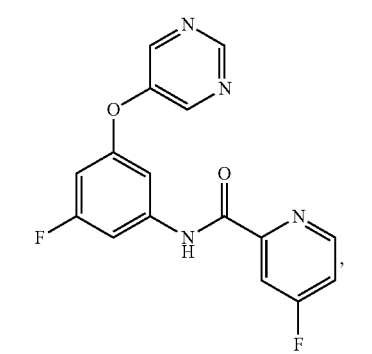
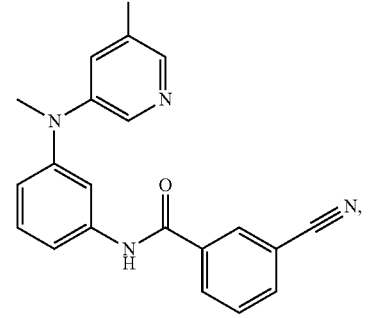
338
-continued
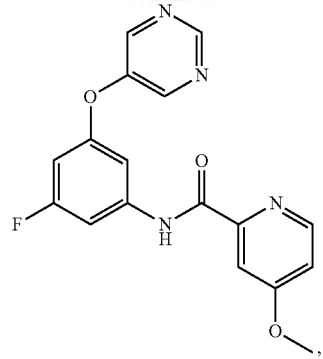
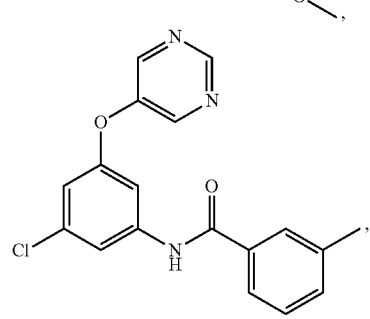
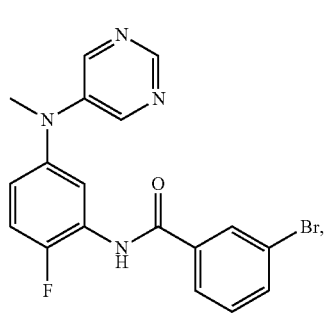
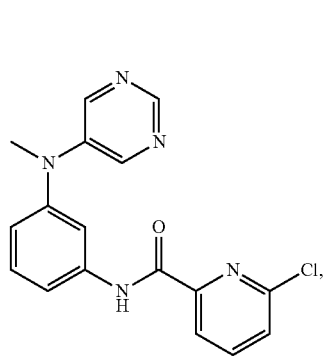
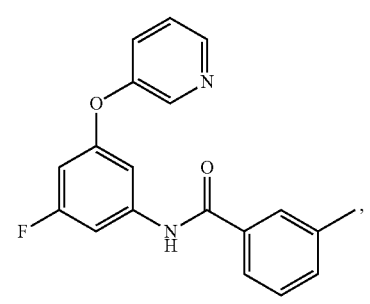

339
-continued
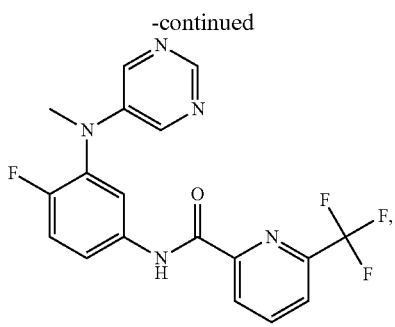
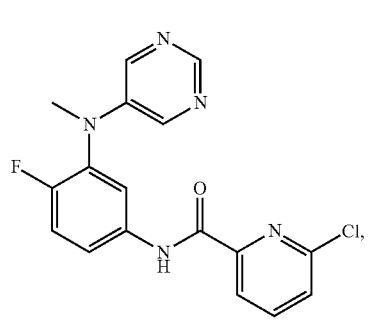
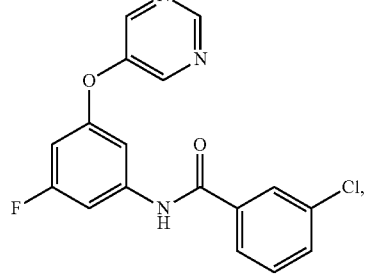
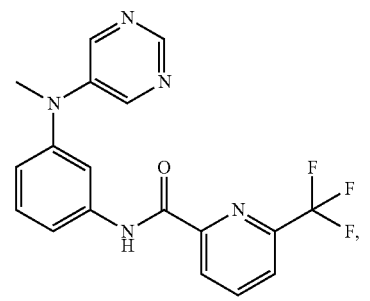
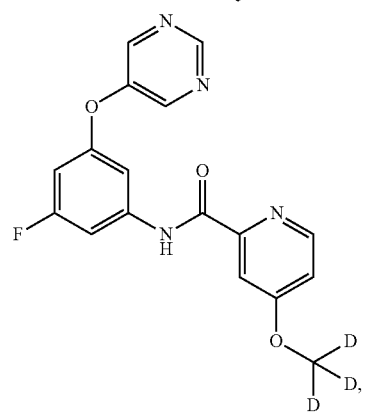
340
-continued
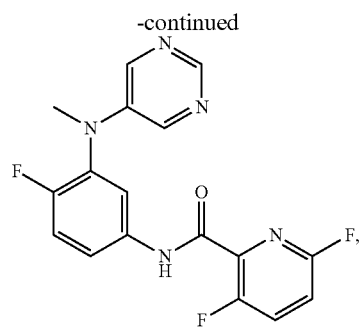
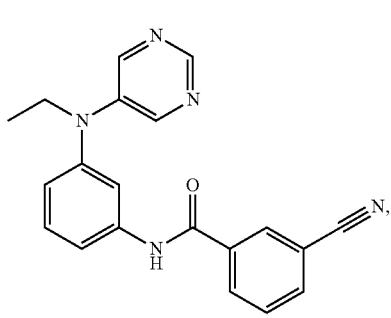
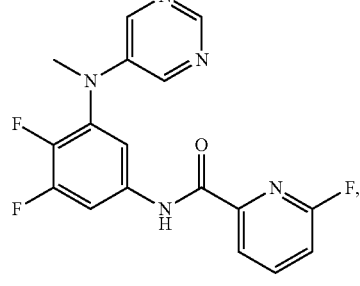
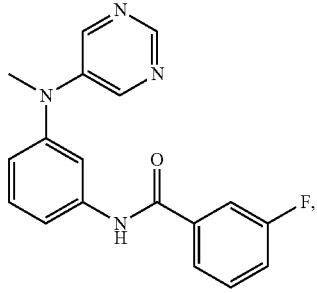
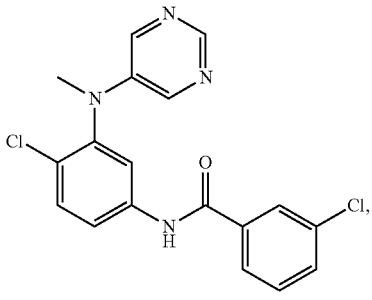

341
-continued
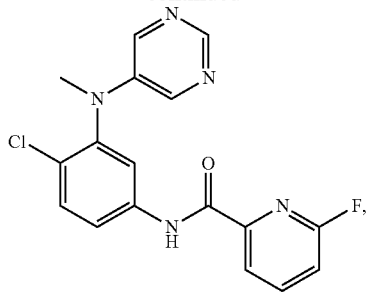
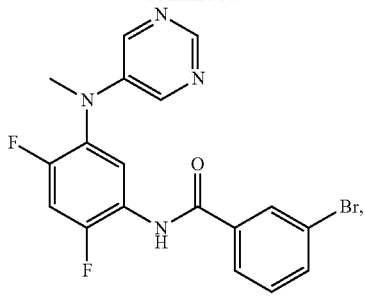
342
-continued
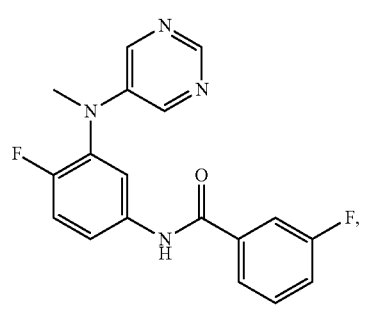
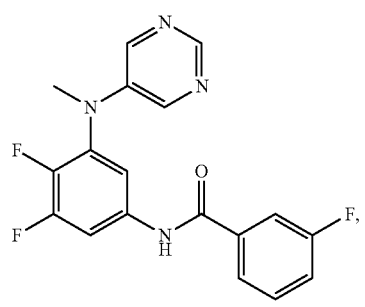
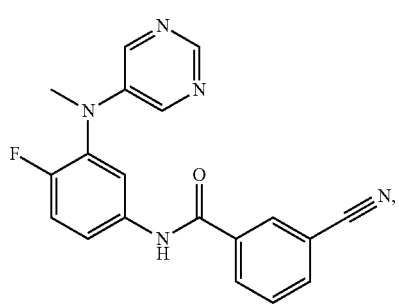
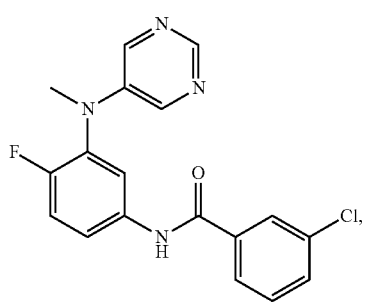

343
-continued
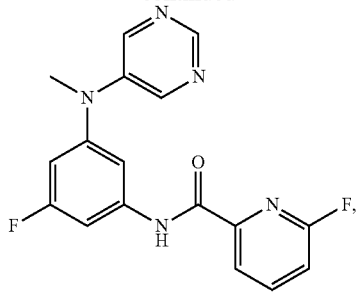
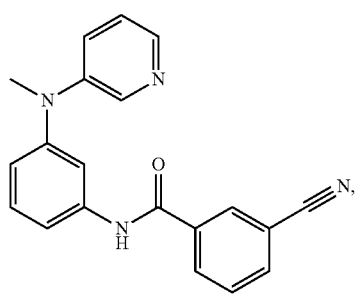
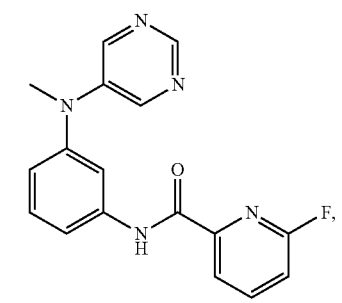
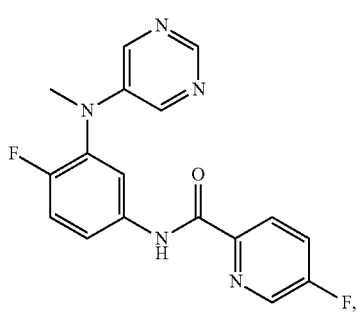
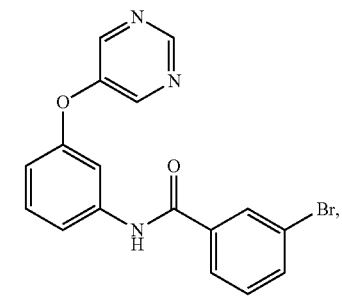
344
-continued
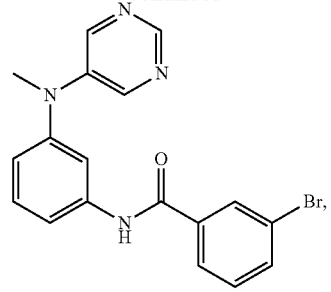
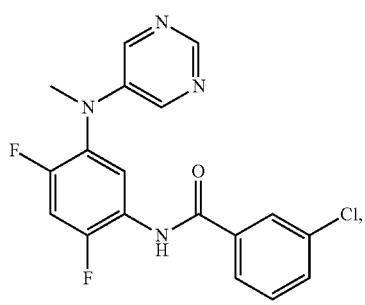
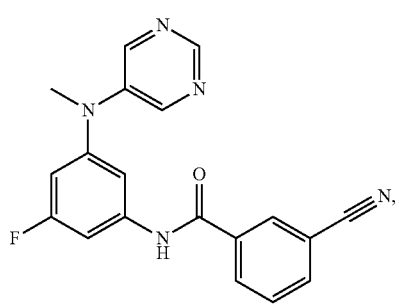
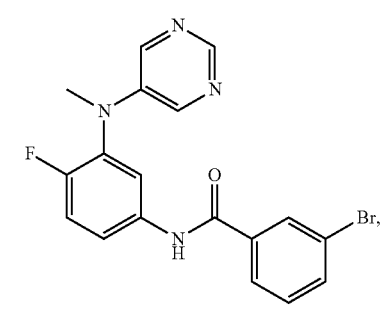
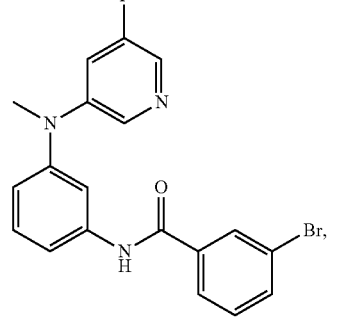

-continued
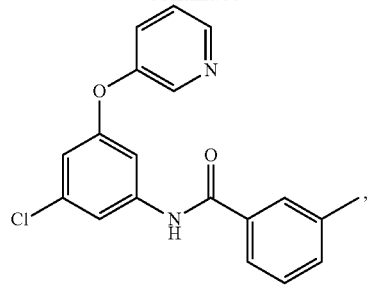
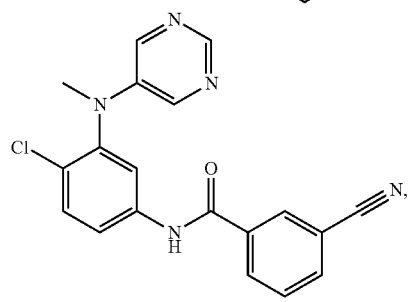
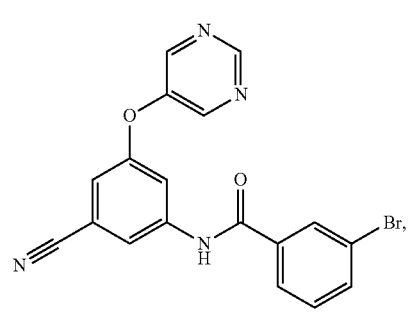
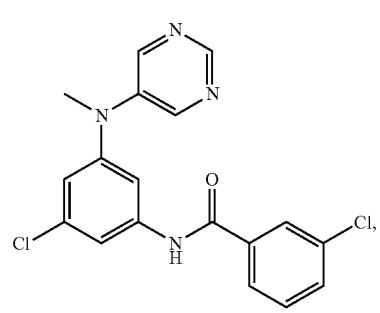
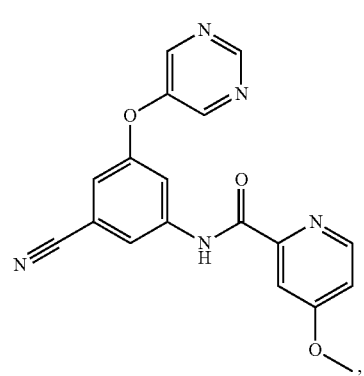
-continued
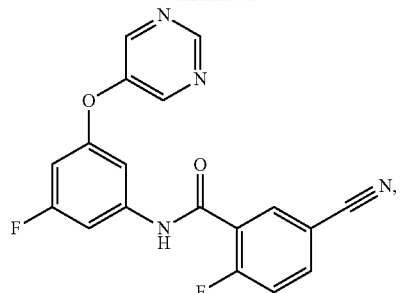
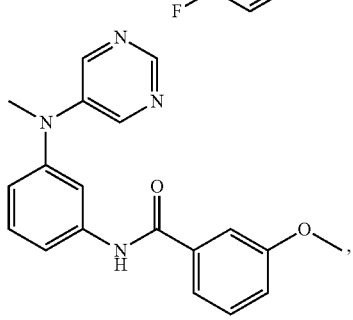
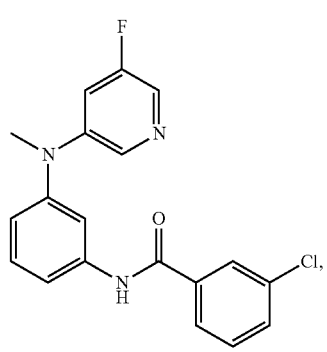
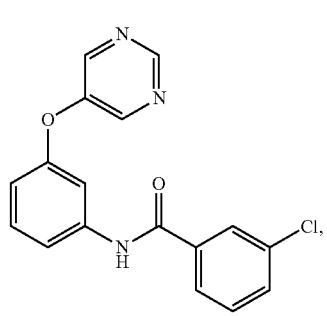
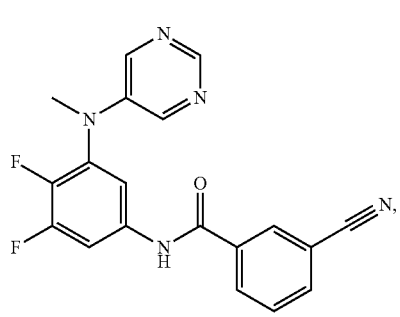

-continued
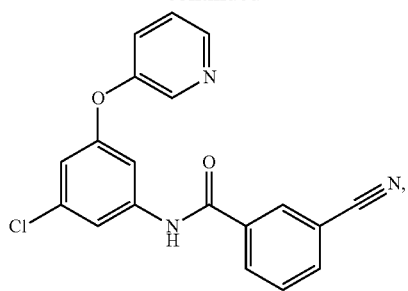
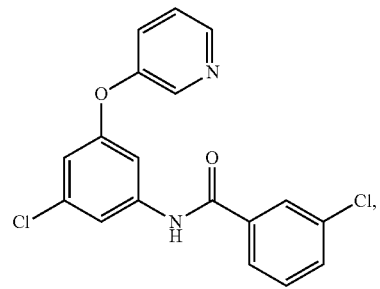
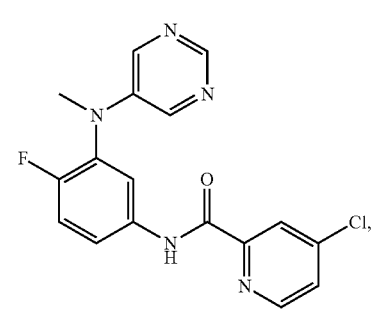
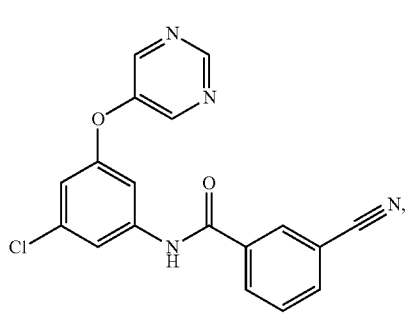
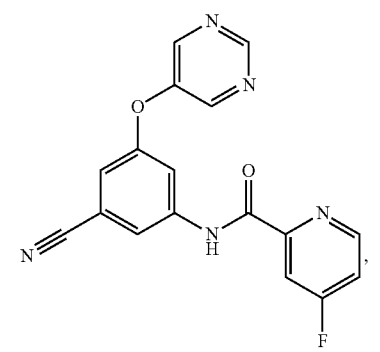
-continued
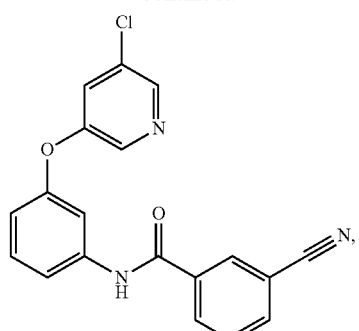
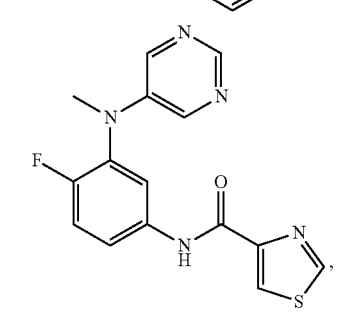
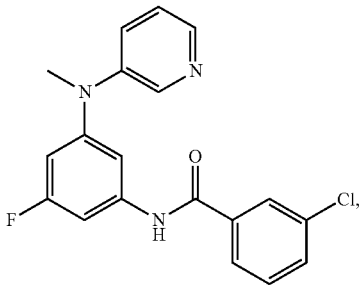
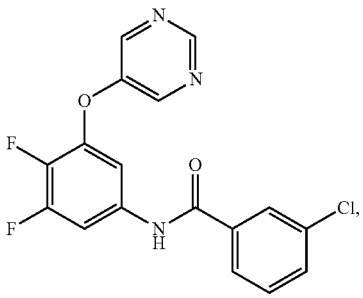
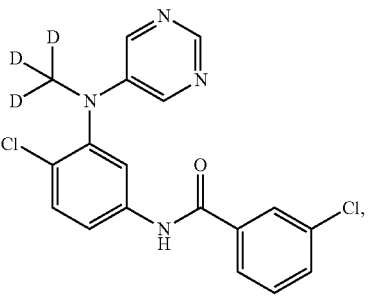

349
-continued
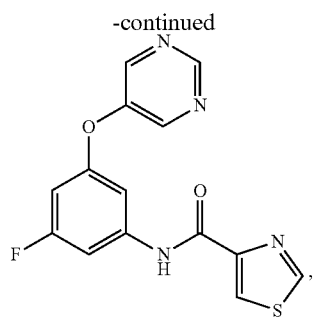
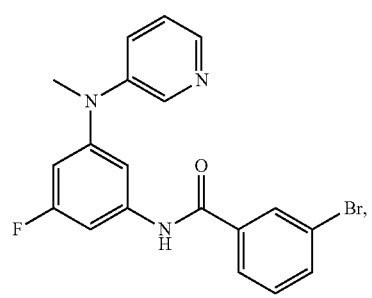
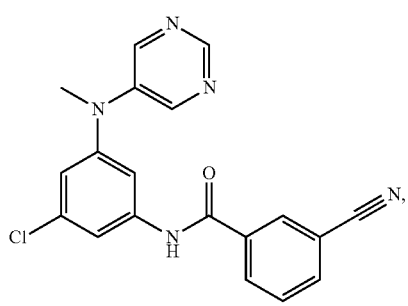
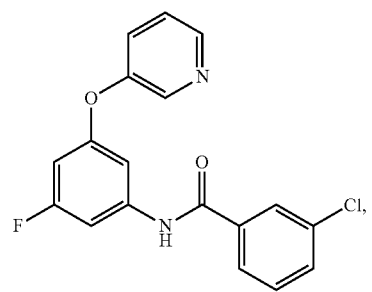
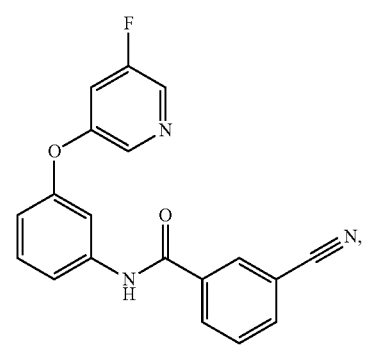
350
-continued
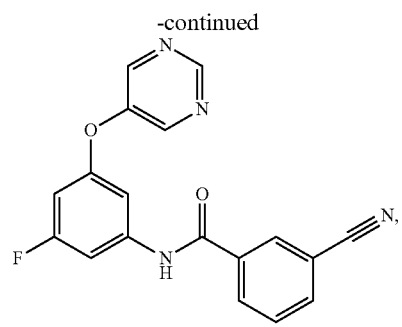
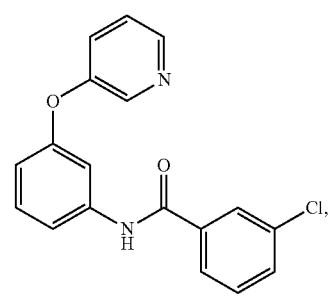
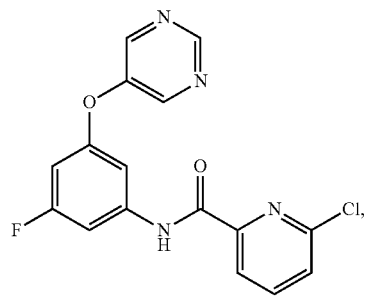
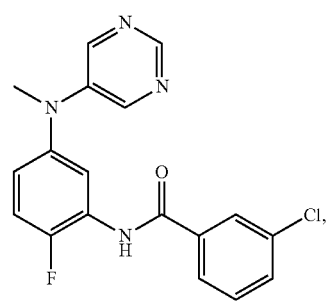
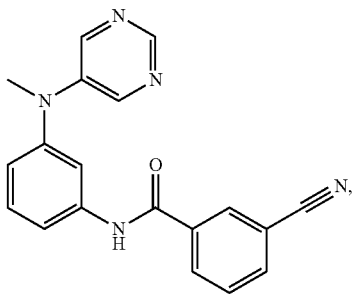

351
-continued
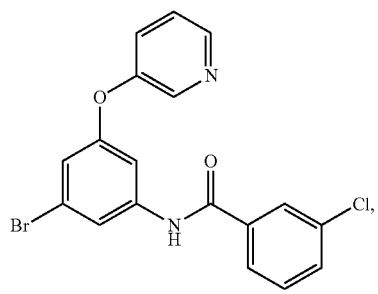
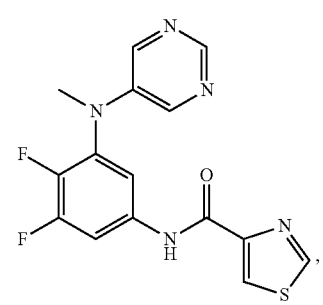
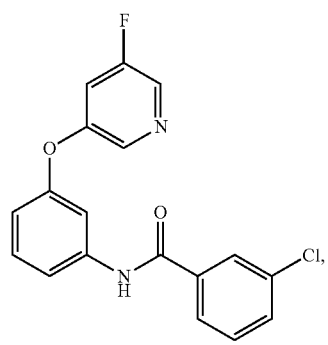
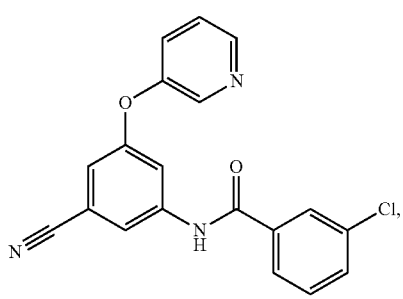
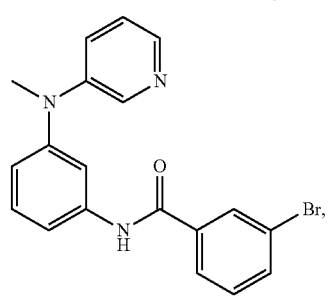
352
-continued
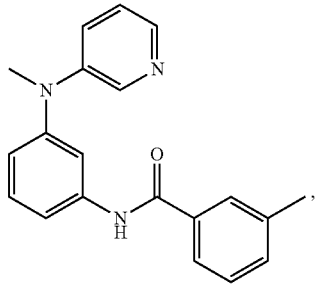
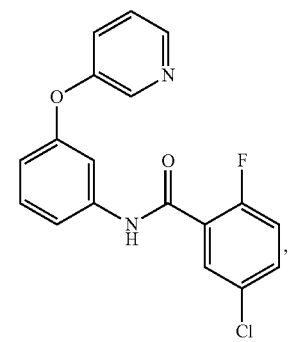
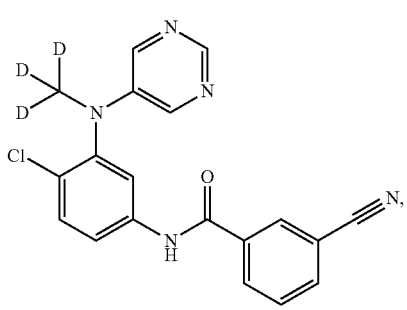
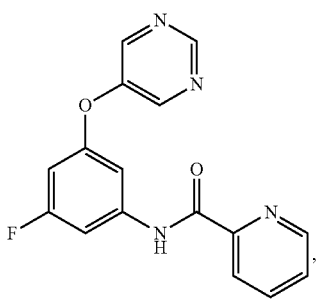
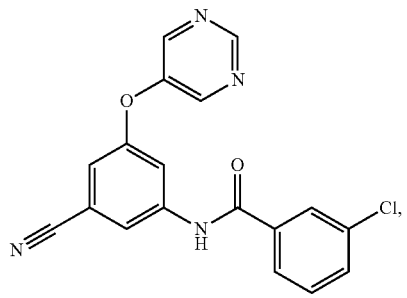

-continued
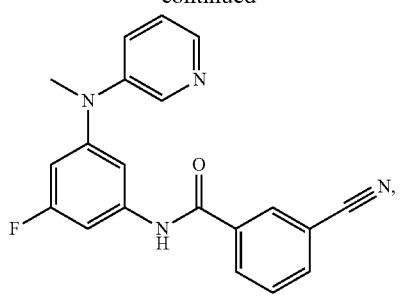
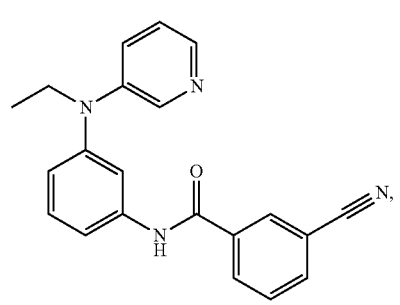
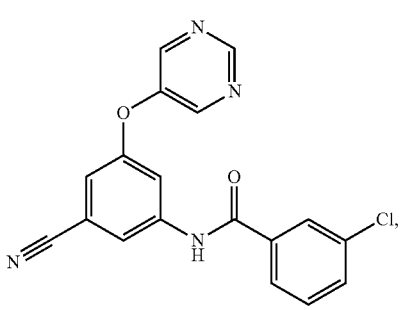
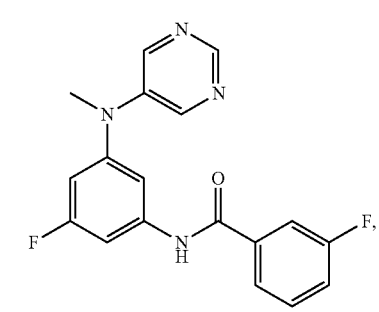
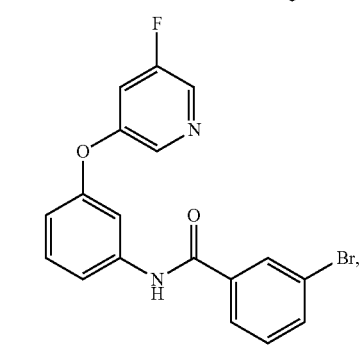
-continued
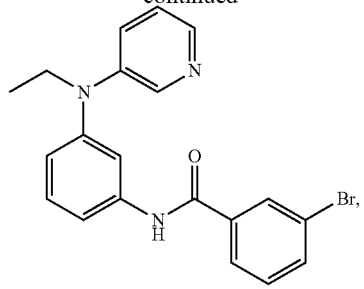
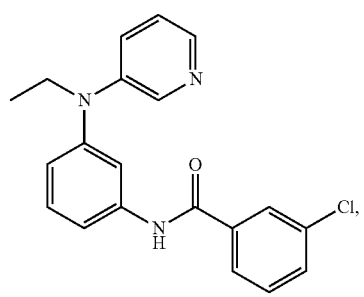
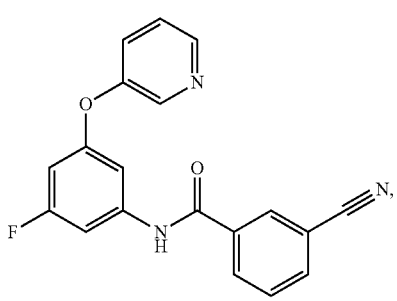
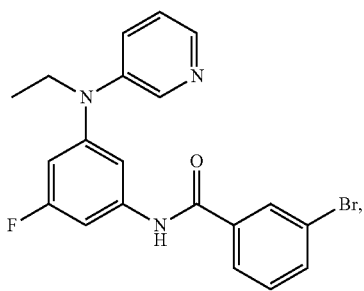
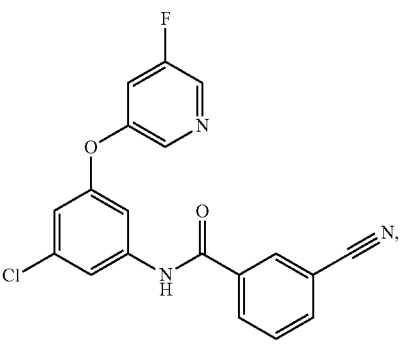

355
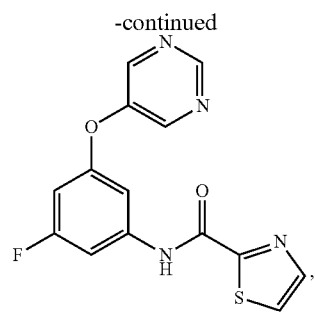
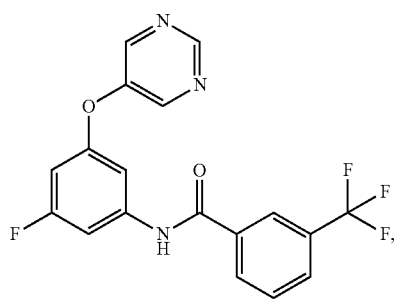
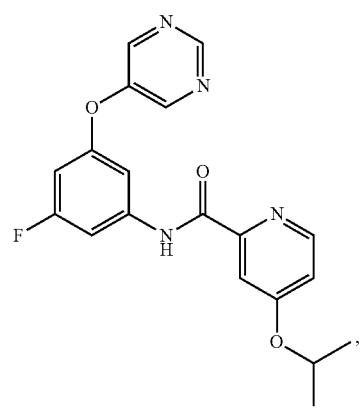
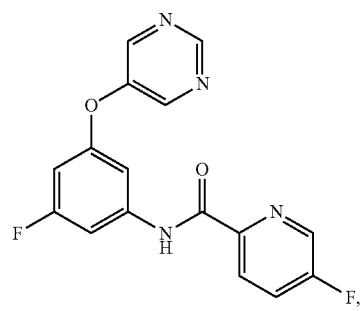
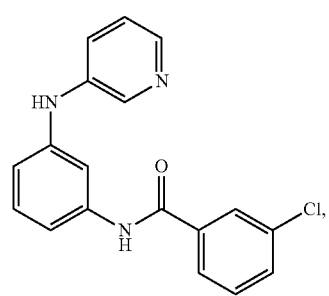
356
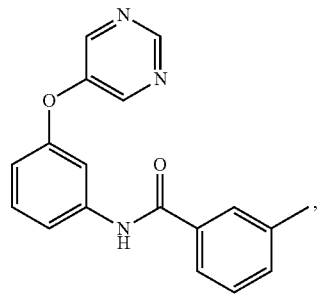
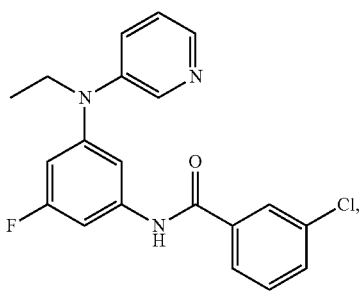
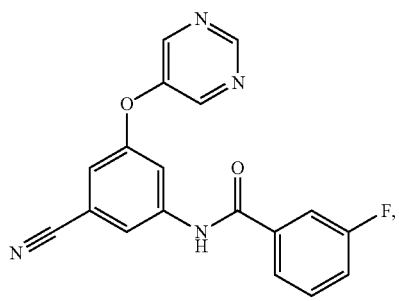
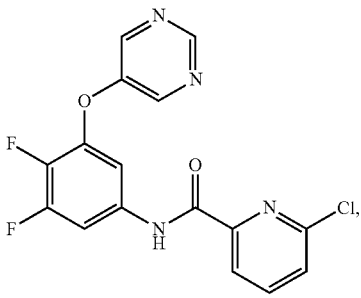
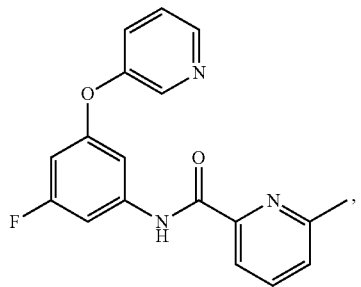

| 357 -continued | 358 -continued |
|---|---|
| 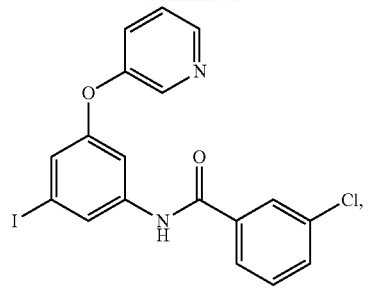 | 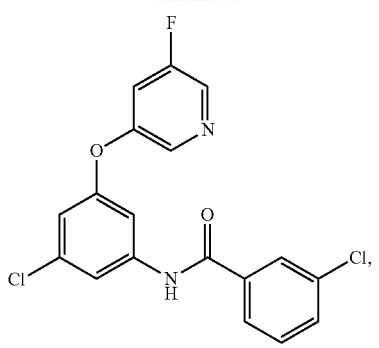 [SMILES: O=C(Nc1cc(Cl)cc(Oc2cncc(F)c2)c1)c1cccc(Cl)n1] |
| 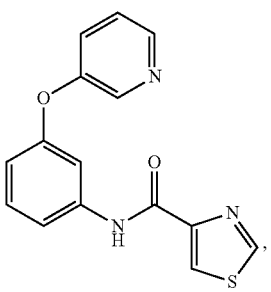 | 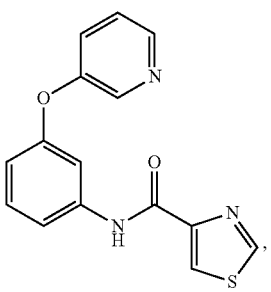 |

359
-continued
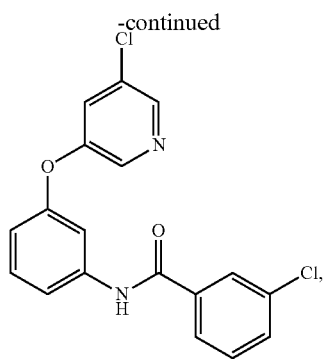
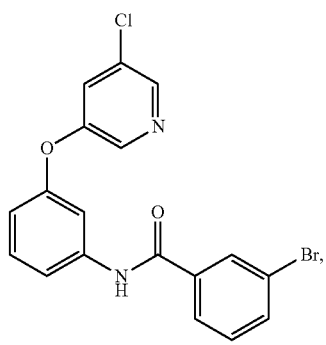
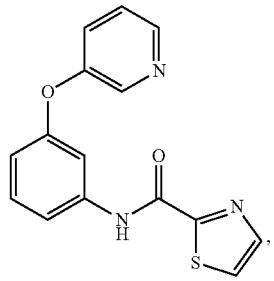
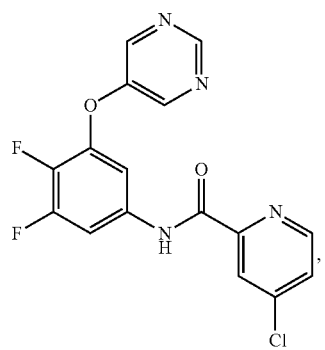
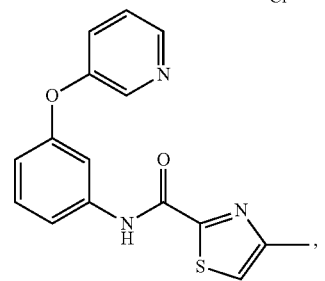
360
-continued
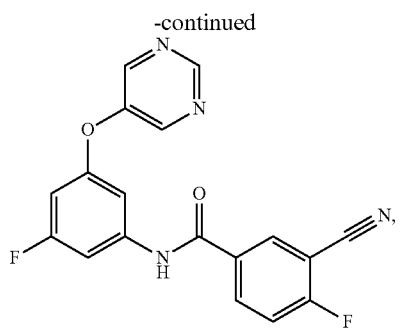
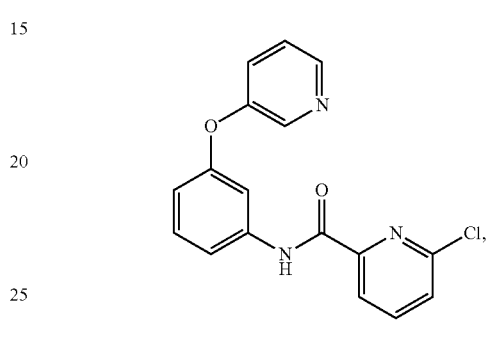
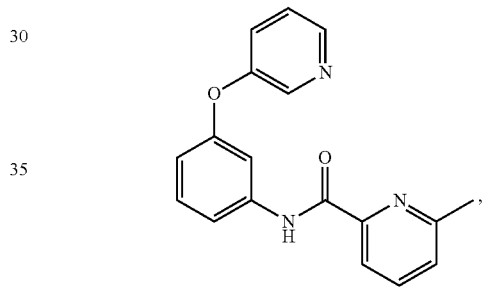
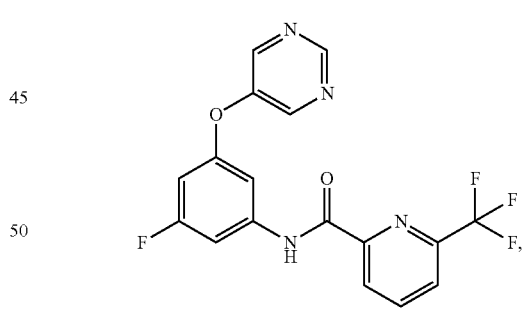
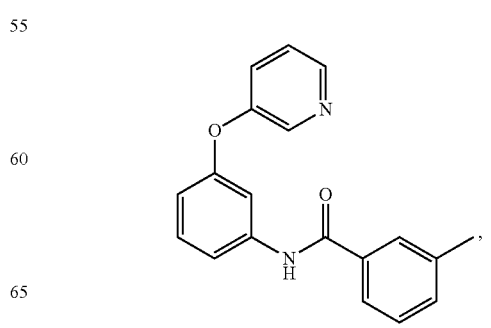

361
-continued
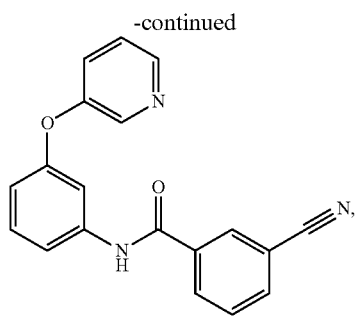
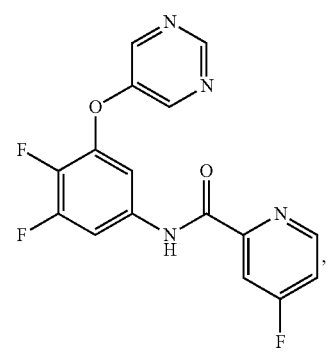
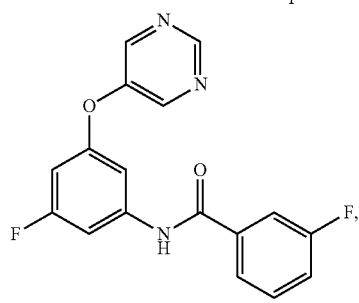
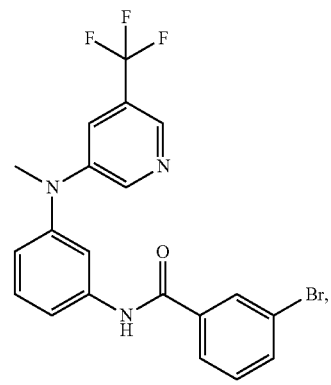
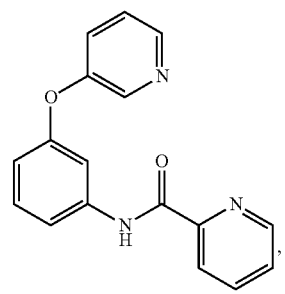
362
-continued
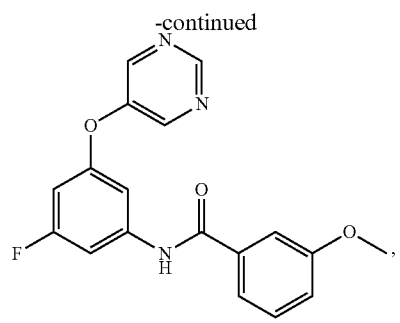
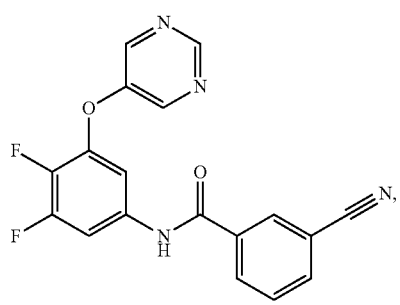
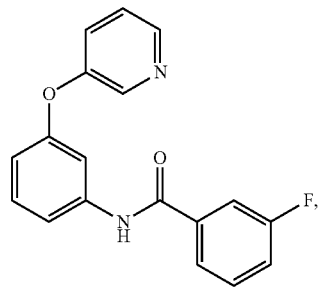
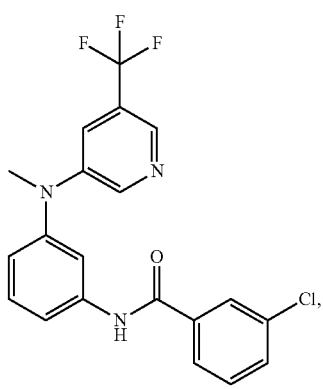
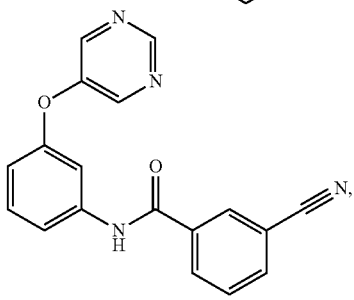

-continued
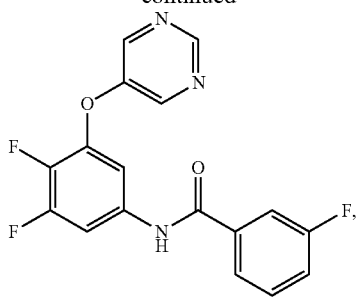
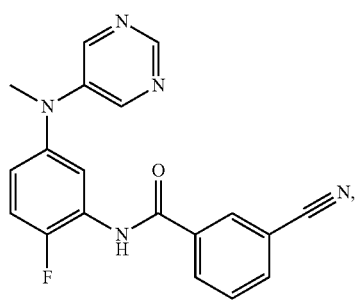
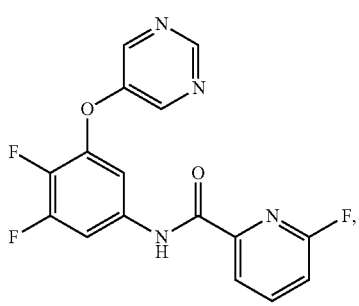
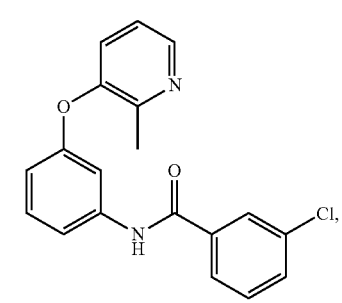
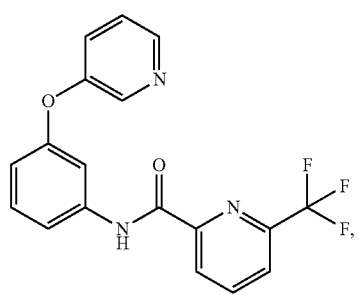
-continued
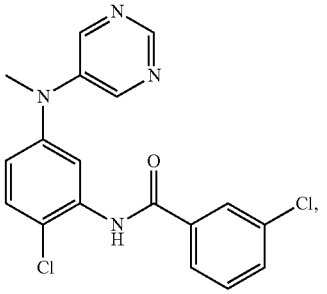
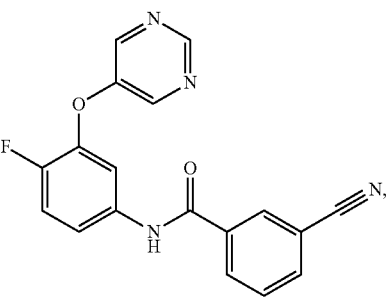
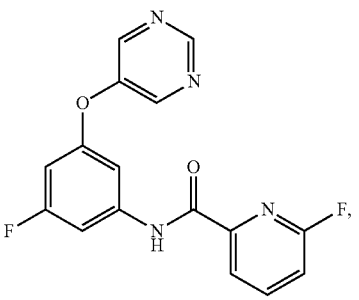
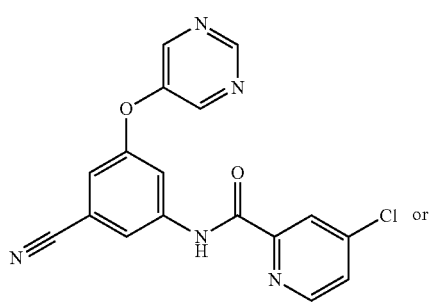 or
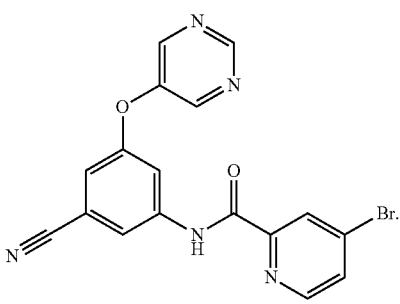 [SMILES: N#Cc1cc(NC(=O)c2cc(Br)ccn2)cc(Oc2cncnc2)c1]

In a further aspect, a compound can be present as:
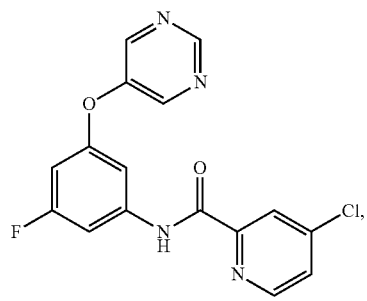
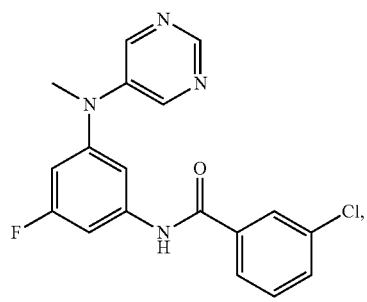
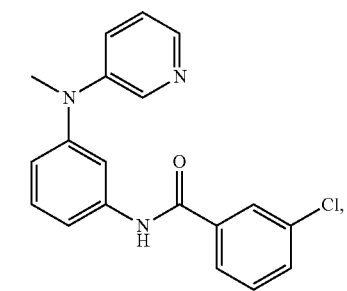
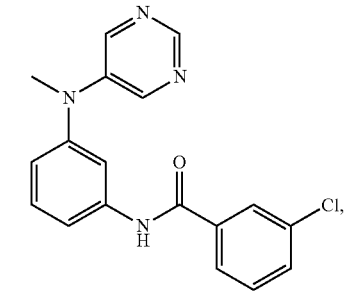
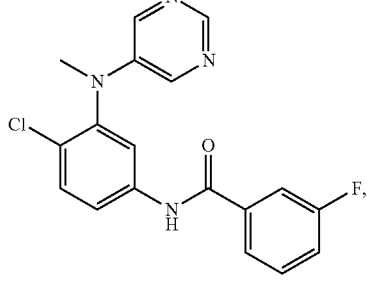
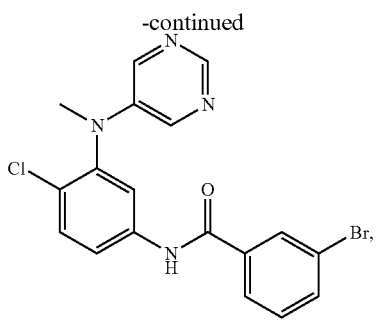
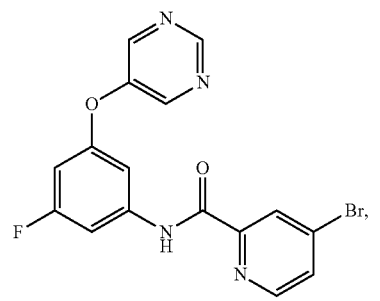
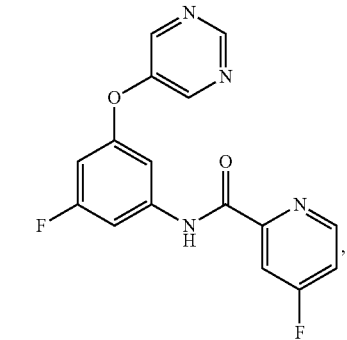
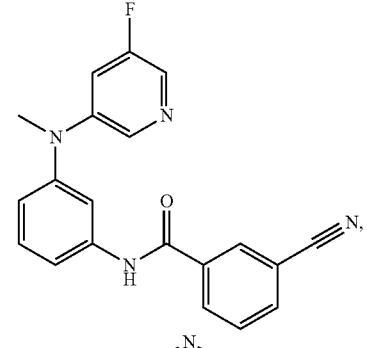
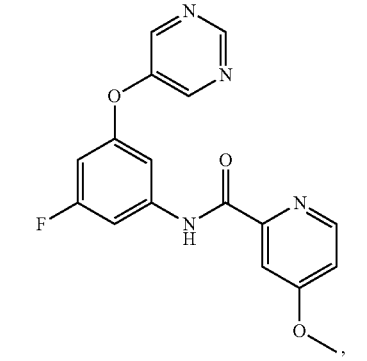

-continued
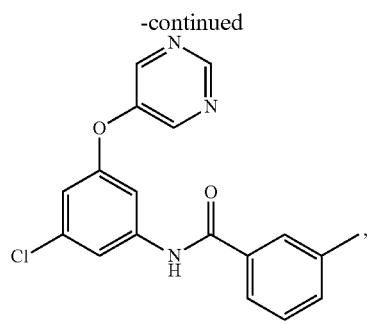
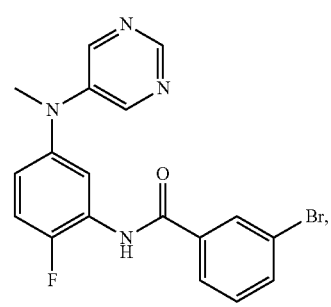
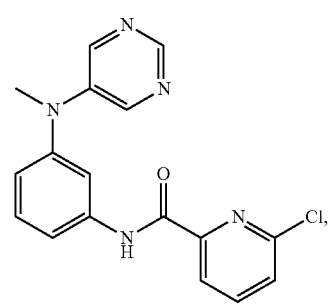
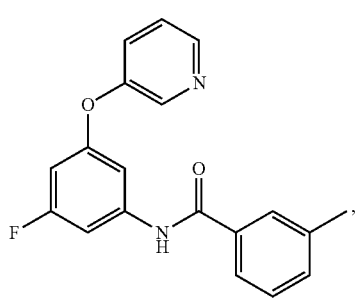
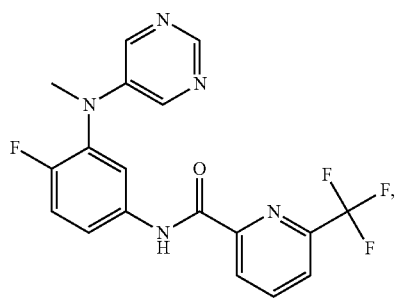
-continued
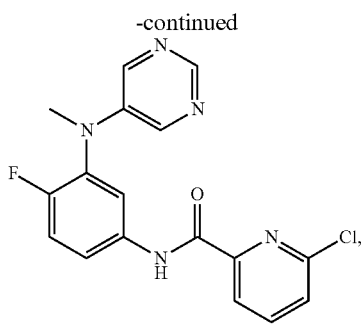
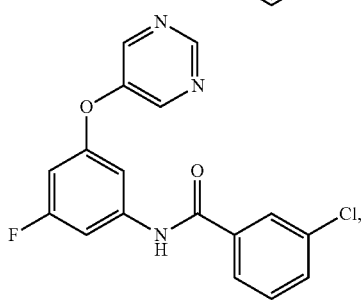
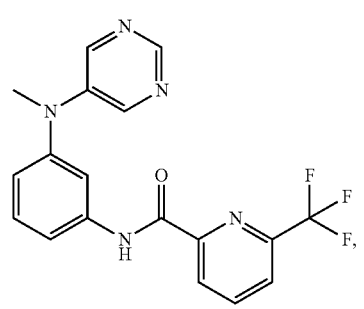
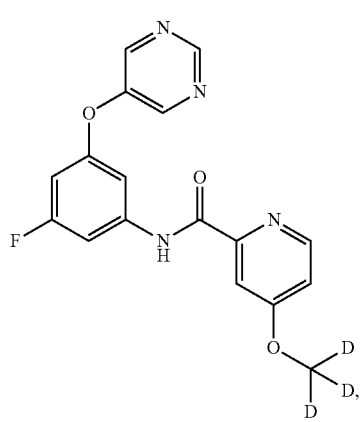
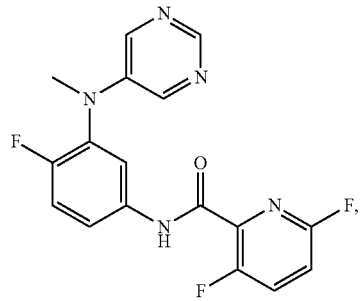

369
-continued
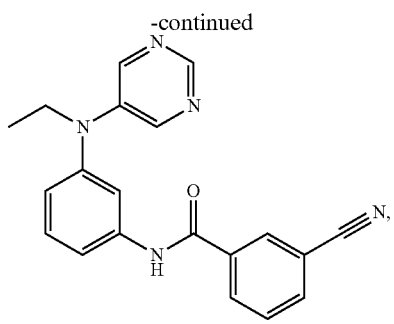
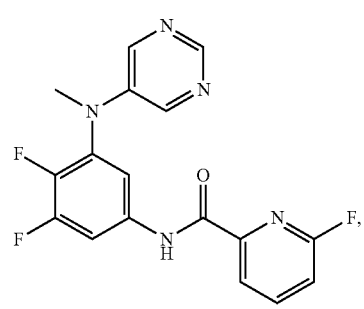
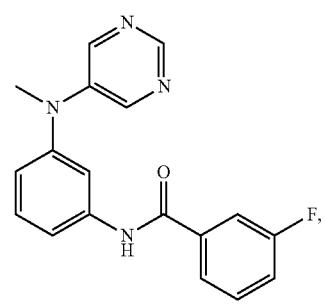
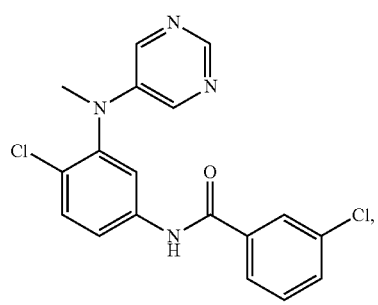
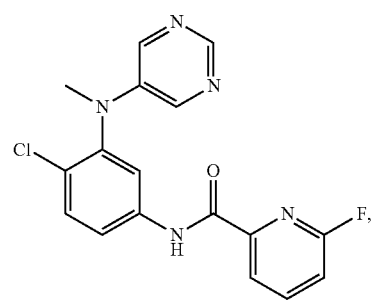
370
-continued
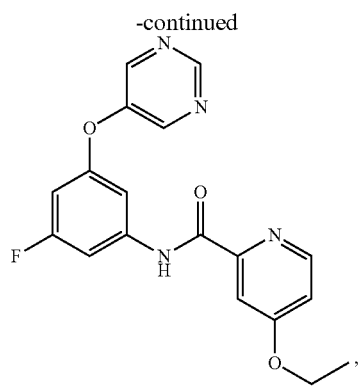
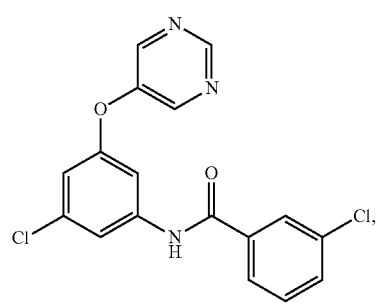
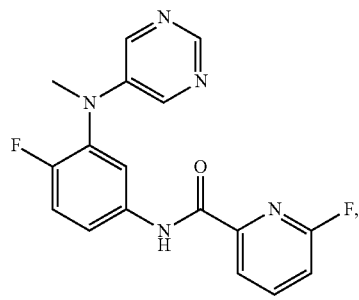
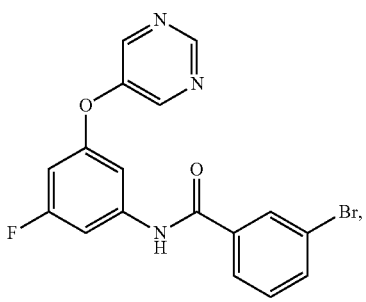
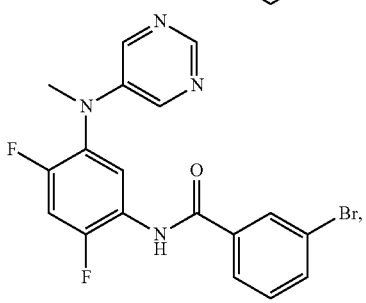

-continued
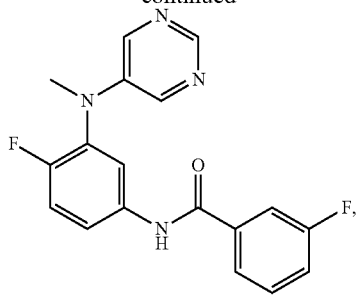
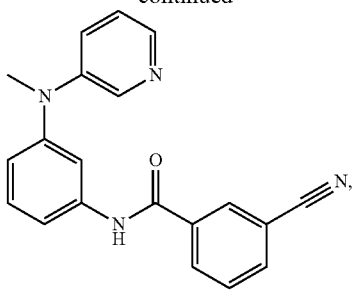

-continued
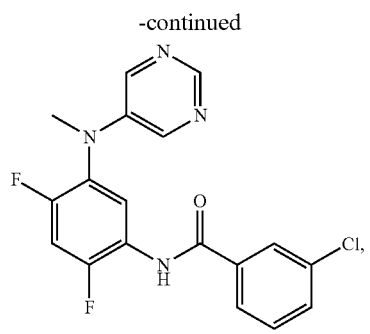
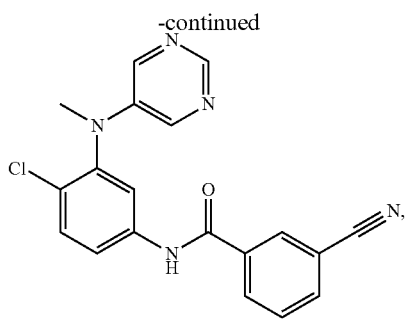
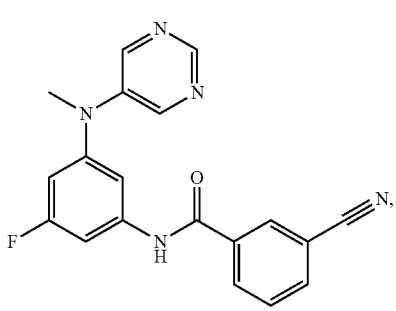
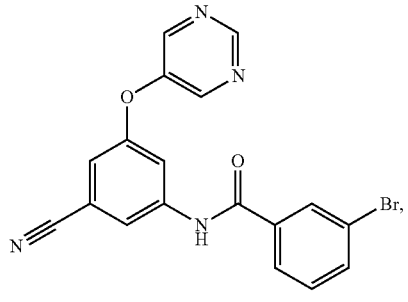
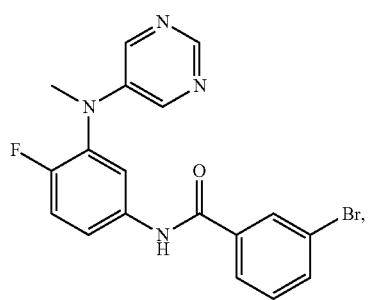
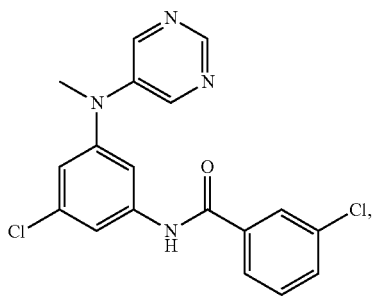
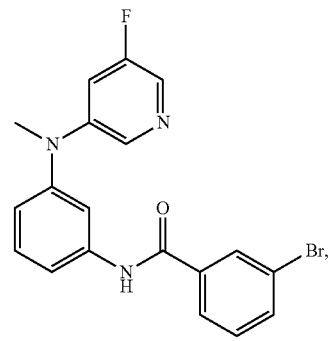
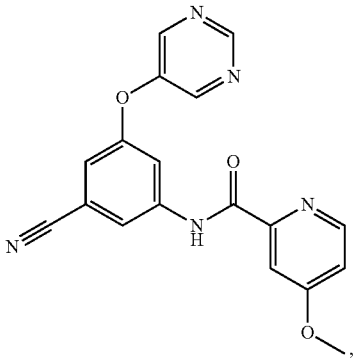
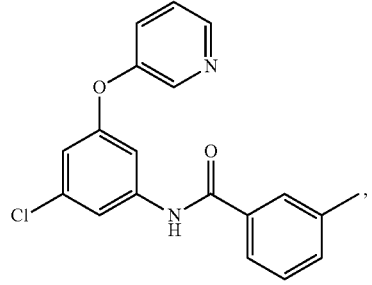
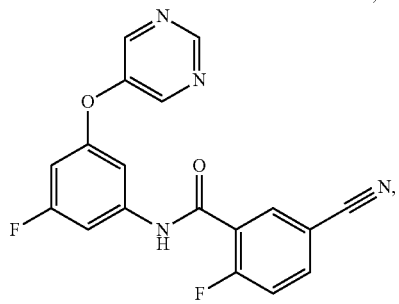

375
-continued
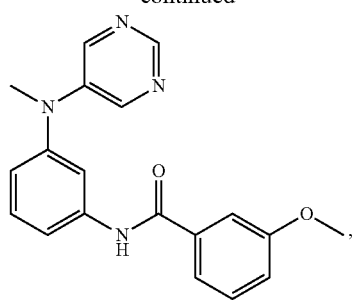
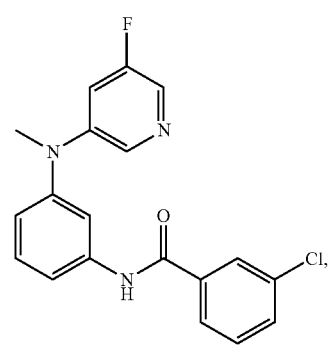
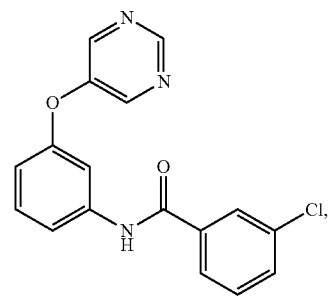
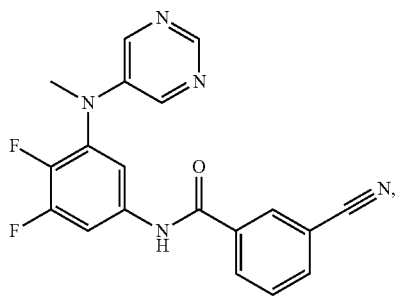
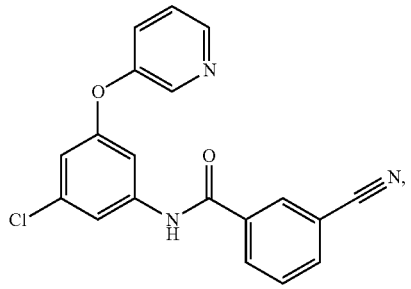
376
-continued
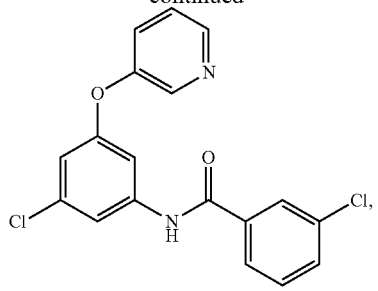
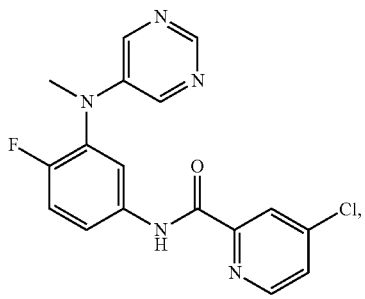
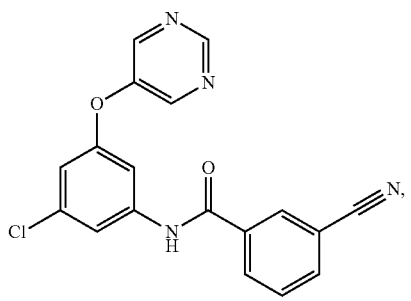
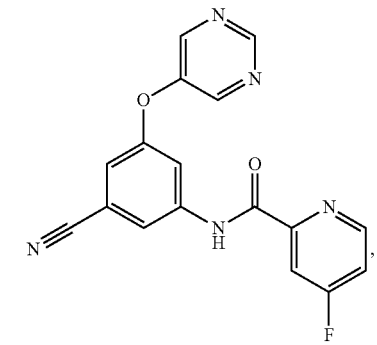
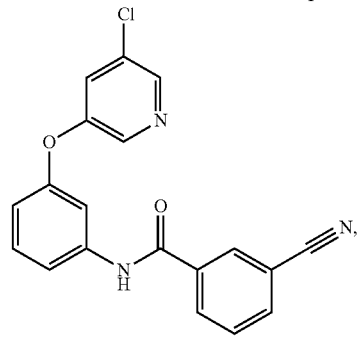

377
-continued

378
-continued

-continued
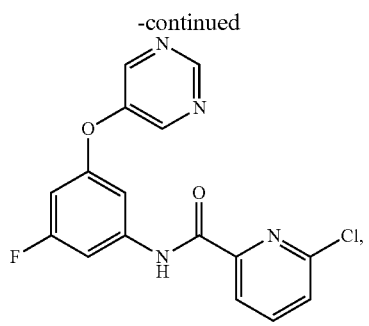
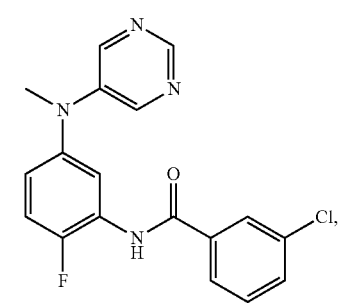
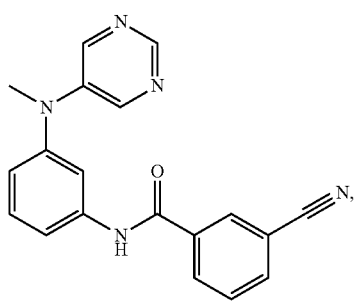
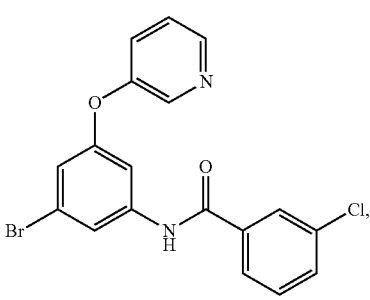
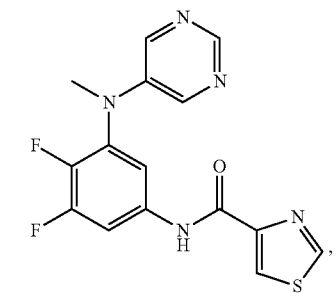
-continued
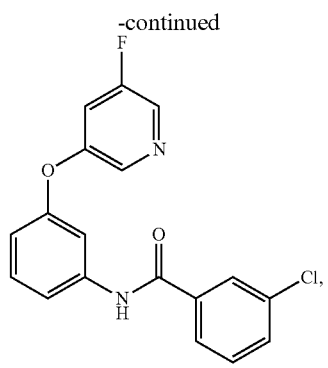
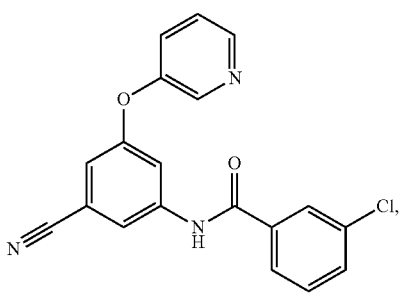
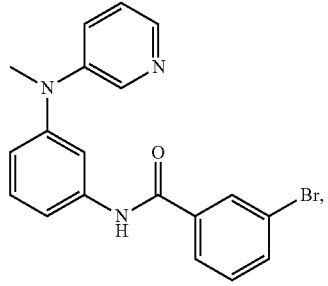
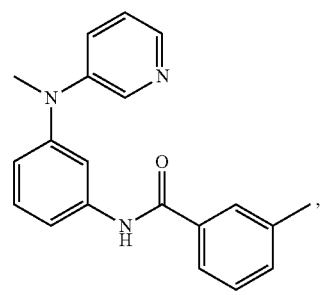
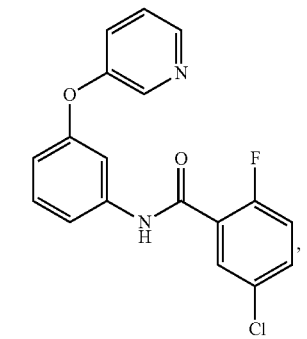

381
-continued
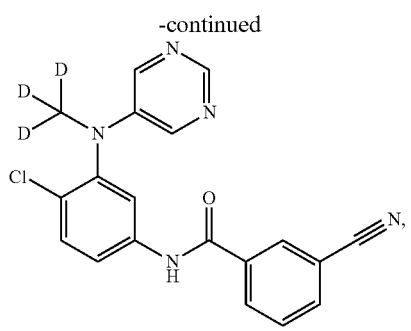
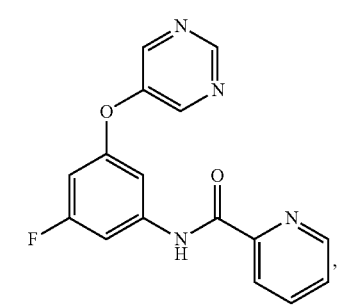
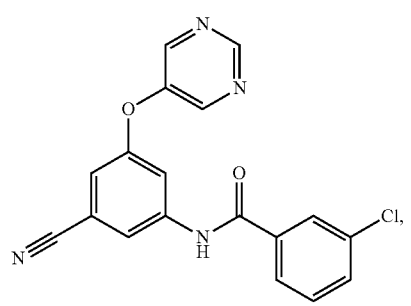
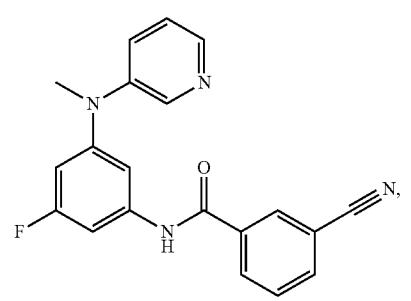
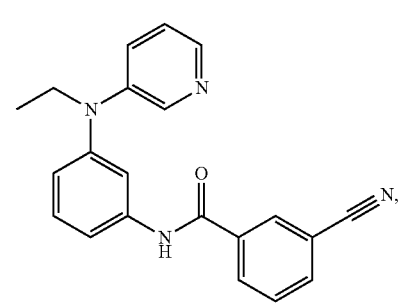
382
-continued
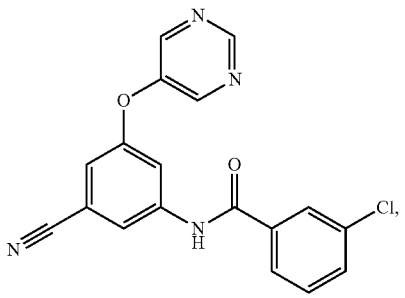
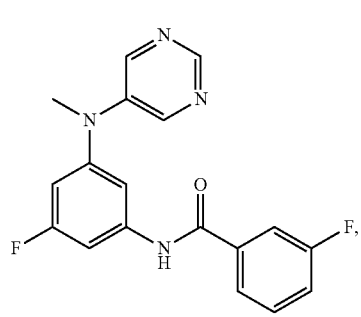
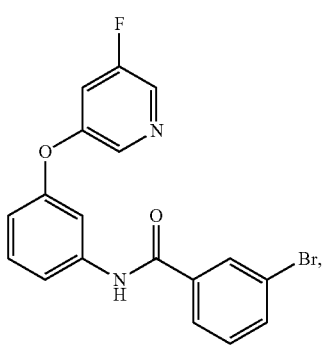
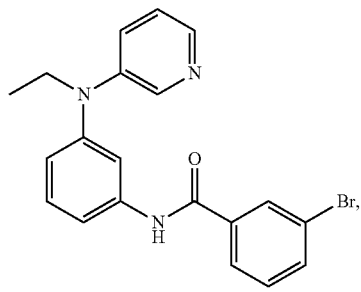

In a further aspect, a compound can be present as:

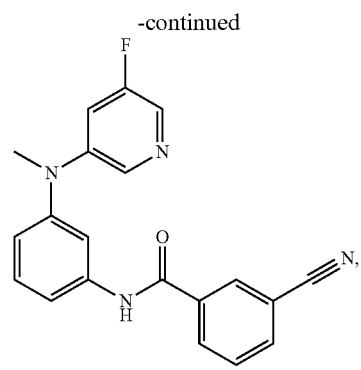
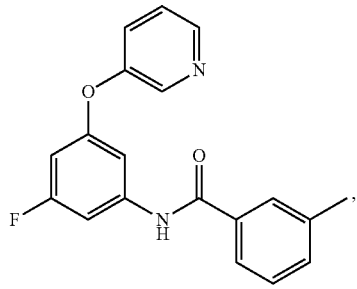

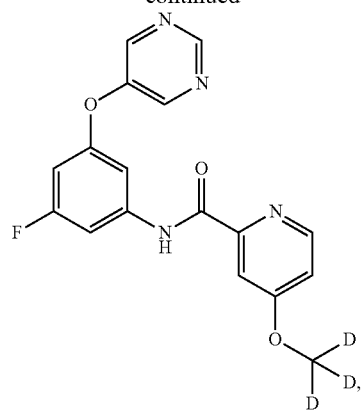
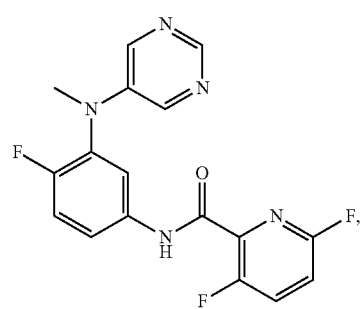
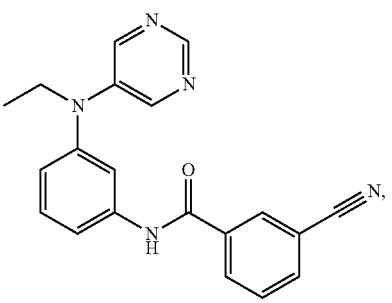
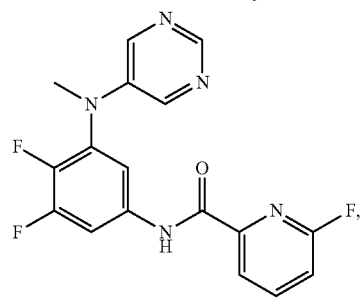
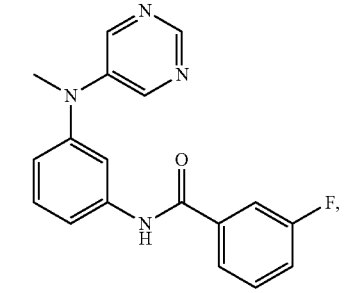
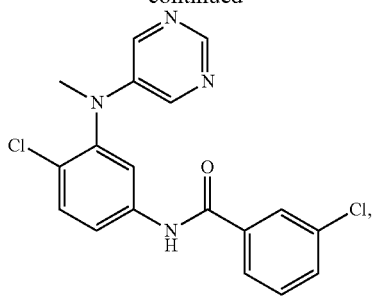
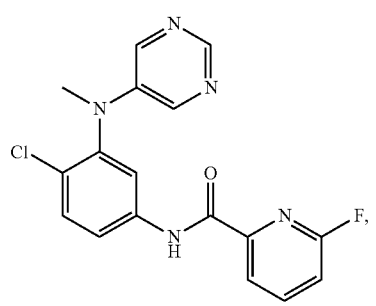
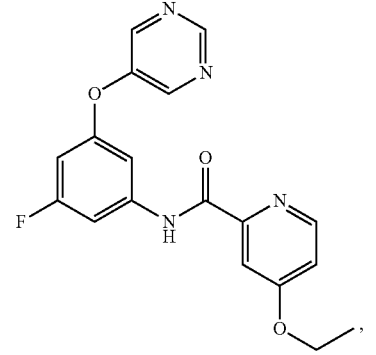
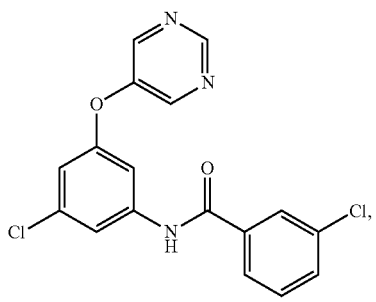
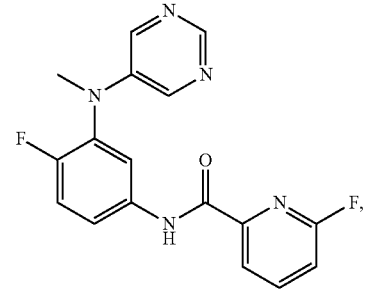

389
-continued
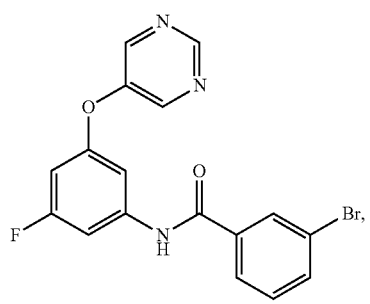
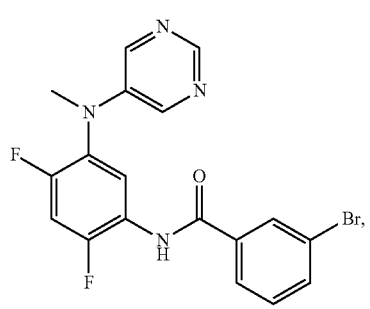
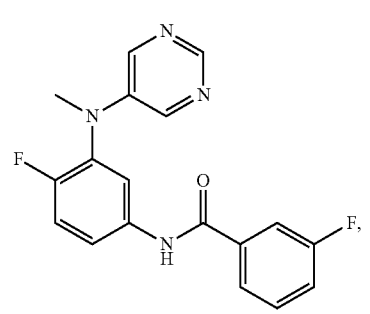
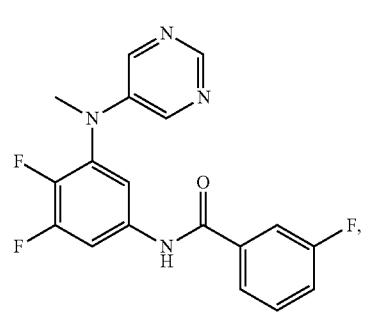
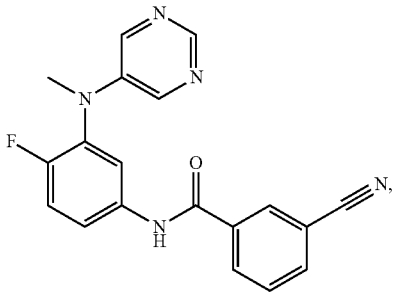
390
-continued
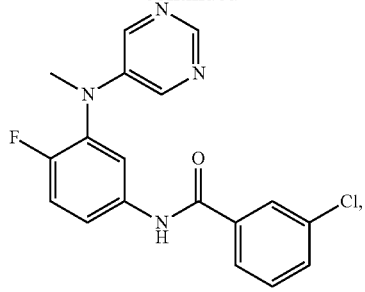
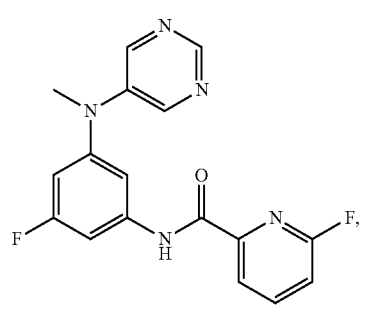
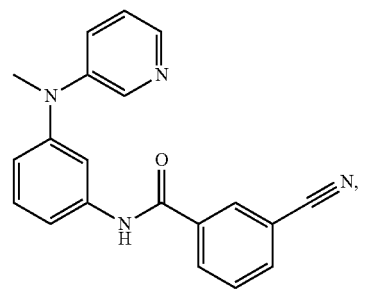
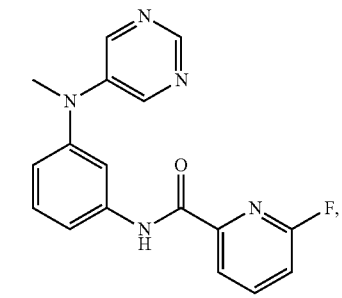
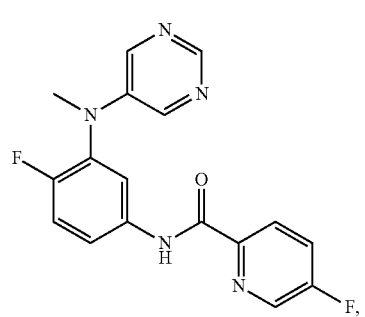

391
-continued
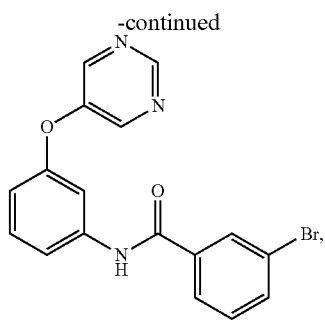
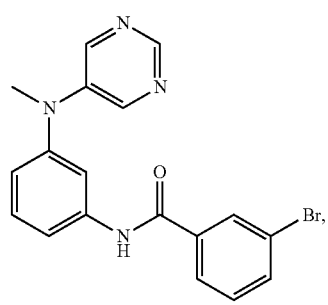
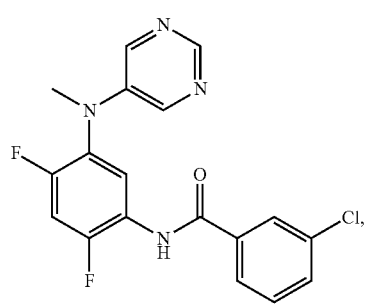
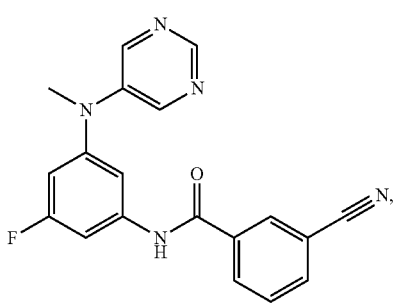
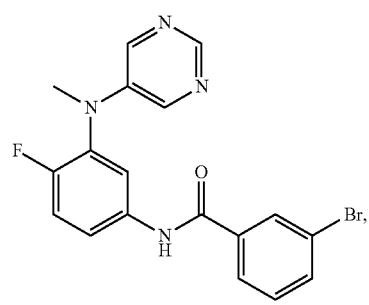
392
-continued
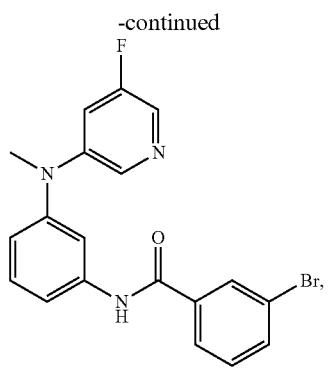
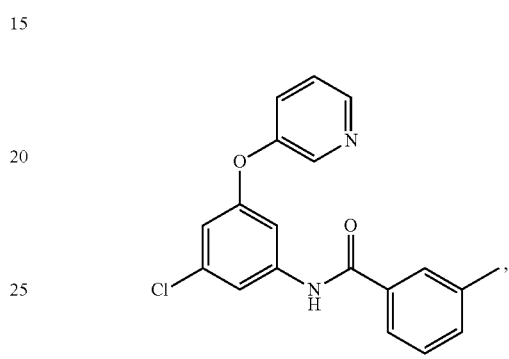
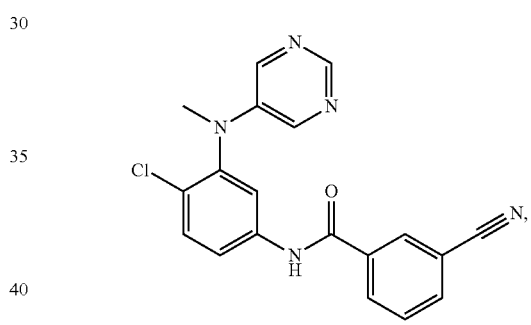
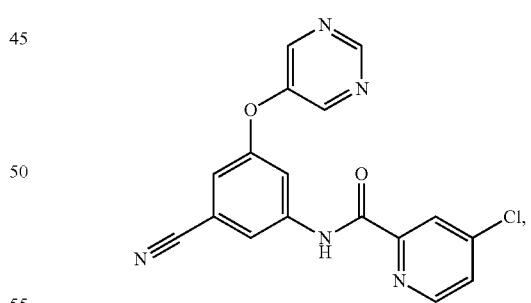
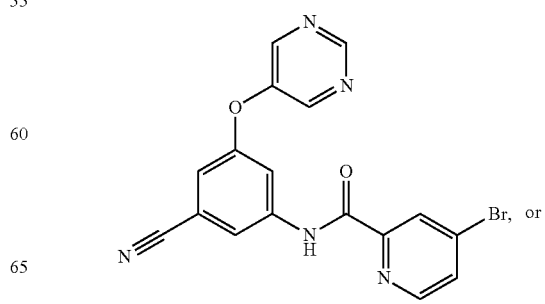

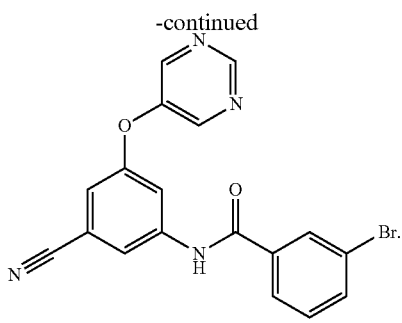

In yet a further aspect, the compound exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound exhibits negative allosteric modulation of mGluR5 after contacting a cell expressing mGluR5. In a further aspect, the compound produced exhibits partial or total inhibition of mGluR5 after contacting a cell expressing mGluR5.

It is contemplated that one or more example structures can be optionally omitted from the disclosed invention.

3. Atropisomeric Forms

Atropisomers are stereoisomers resulting from hindered rotation about single bonds where the steric strain barrier to rotation is high enough to allow for the isolation of the conformers. Atropisomers display axial chirality, but differ from other chiral compounds in that they can be equilibrated thermally, whereas in the other forms of chirality isomerization is usually only possible chemically. In certains aspects, the disclosed compounds can be provided as atropisomeric compounds. For example, disclosed compounds can be provided as single atropisomers or as a mixture of atropisomers.

It is contemplated that one atropisomer can exhibit greater negative allosteric modulation of mGluR5 response to glutamate than another, otherwise structurally identical, atropisomer. Thus, individual atropisomers of disclosed compounds can be isolated and used in disclosed methods. Separation of atropisomers can be achieved by chiral resolution methods such as selective crystallization.

In an atropo-enantioselective or atropselective synthesis, one atropisomer is formed at the expense of the other. Thus, it is also contemplated that a specific atropisomer can be preferentially prepared: atroposelective synthesis can be carried out by use of chiral auxiliaries or by approaches based on thermodynamic equilibration when an isomerization reaction favors one atropisomer over the other.

4. Negative Allosteric Modulation of mGluR5 Response

In one aspect, the compounds exhibit negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, the compound exhibits partial inhibition of mGluR5 response. In a further aspect, the compound exhibits total inhibition of mGluR5 response. In a further aspect, the compound exhibits negative allosteric modulation with an $IC_{50}$ of less than about $30 \times 10^{-6}$. In a further aspect, the compound exhibits negative allosteric modulation with an $IC_{50}$ of less than about $10 \times 10^{-6}$. In a further aspect, the compound exhibits partial or total inhibition with an $IC_{50}$ of less than about $1.0 \times 10^{-6}$, of less than about $1.0 \times 10^{-7}$, of less than about $1.0 \times 10^{-8}$ or of less than about $1.0 \times 10^{-9}$. In further aspect, the human embryonic kidney cells are transfected with human mGluR5. In yet a further aspect, human embryonic kidney cells are transfected with mGluR5 of a mammal.

C. Metabotropic Glutamate Receptor Activity

The utility of the compounds in accordance with the present invention as negative allosteric modulators of metabotropic glutamate receptor activity, in particular mGluR5 activity, can be demonstrated by methodology known in the art. Human embryonic kidney (HEK) cells transfected with rat mGluR5 were plated in clear bottom assay plates for assay in a Functional Drug Screening System (FDSS). The cells were loaded with a Ca2+-sensitive fluorescent dye (e.g., Fluo-4), and the plates were washed and placed in the FDSS instrument. Test compound was applied to cells 3 seconds after baseline readings were taken. Cells were incubated with the test compounds for 140 seconds and then stimulated with an EC20 concentration of an mGluR5 agonist (e.g., glutamate, 3,5-dihydroxyphenylglycine, or quisqualate); 60 seconds later an EC80 concentration of agonist was added and readings taken for an additional 40 seconds. Data were collected at 1 Hz. Negative allosteric modulation of the agonist response of mGluR5 by the compounds in the present invention was observed as a decrease in response to non-maximal concentrations of agonist (here, glutamate) in the presence of compound compared to the response to agonist in the absence of compound. Concentration response curves were generated using a four parameter logistical equation.

The above described assay was operated in two modes. In the first mode (utilizing a triple add protocol), a range of concentrations of the present compounds were added to cells, followed by two single fixed concentrations of agonist (EC20 followed by EC80). If a compound acted as a potentiator, an EC50 value for potentiation and a maximum extent of potentiation by the compound at this concentration of agonist was determined by non-linear curve fitting. If a compound acted as an antagonist, an $IC_{50}$ value for antagonism and a maximum extent of antagonism by the compound at this concentration of agonist was determined by non-linear curve fitting. In the second mode (utilizing a double add protocol), several fixed concentrations of the present compounds were added to various wells on a plate, followed by a range of concentrations of agonist for each concentration of present compound; the EC50 values for the agonist at each concentration of compound were determined by non-linear curve fitting. A decrease in the EC50 value of the agonist with increasing concentrations of the present compounds (a leftward shift of the agonist concentration-response curve) is an indication of the degree of mGluR5 positive allosteric modulation at a given concentration of the present compound. An increase in the EC50 value of the agonist with increasing concentrations of the present compounds (a rightward shift of the agonist concentration-response curve) is an indication of the degree of mGluR5 antagonism at a given concentration of the present compound. The second mode also indicates whether the present compounds also affect the maximum response to mGluR5 to agonists.

In particular, the disclosed compounds had activity in modulating the mGluR5 receptor in the aforementioned assays, generally with an $IC_{50}$ for modulation of less than about 30 µM. Preferred compounds within the present invention had activity in modulating the mGluR5 receptor with an $IC_{50}$ for negative allosteric modulation of less than about 500 nM. Preferred compounds reduced the response to an EC80 concentration of glutamate to less than 50% of the maximal response and also induced a rightward and downward shift of the glutamate concentration response curve. These compounds are negative allosteric modulators of human and rat mGluR5 and were selective for mGluR5 compared to the other six subtypes of metabotropic glutamate receptors.

D. Methods of Making the Compounds

In one aspect, the invention relates to methods of making compounds useful as negative allosteric modulators of the metabotropic glutamate receptor subtype 5 (mGluR5), which can be useful in the treatment neurological and psychiatric disorders associated with glutamate dysfunction and other diseases in which metabotropic glutamate receptors are involved.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

The disclosed compounds can be prepared by various routes. In certain specific examples, the disclosed compounds can be prepared by Routes I through VI, as described and exemplified below.

In a further aspect, a compound comprises the product of the disclosed methods. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

For example, in one aspect, a method of making a compound comprising the step of reacting a compound having a structure represented by a formula:

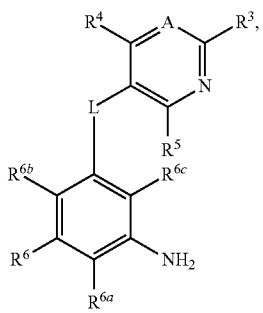

wherein A is $CR^2$ or N; wherein L is O or $NR^7$, wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is selected from hydrogen, halogen, CN, C1-C4 alkyl, C1-C4 haloalkyl, C3-C4 cycloalkyl, and C3-C4 halocycloalkyl; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$; with an activated carbonyl compound, thereby forming an amide.

In a further aspect, the compound has a structure represented by a formula:

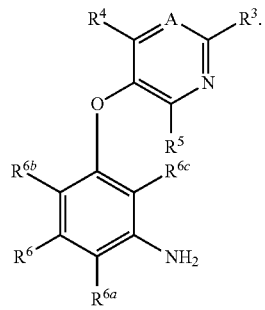

In a further aspect, the amide formed has a structure represented by a formula:

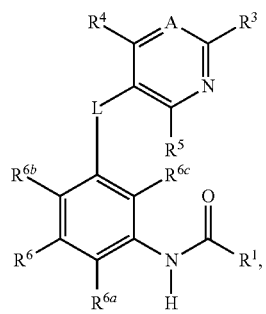

wherein $R^1$ has from 1 to 10 carbons and is selected from phenyl substituted with 1-3 of $R^9$, wherein at least one $R^9$ is meta substituted; 2-pyridinyl substituted with 0-3 of $R^9$; and thiazole substituted with 0-2 of $R^9$; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$.

In a further aspect, the amide formed exhibits partial or total inhibition of mGluR5 response to glutamate as a decrease in response to non-maximal concentrations of glutamate in human embryonic kidney cells transfected with rat mGluR5 in the presence of the compound, compared to the response to glutamate in the absence of the compound.

In one aspect, the invention relates to a method of making a compound comprising the step of reacting a compound having a structure represented by a formula:

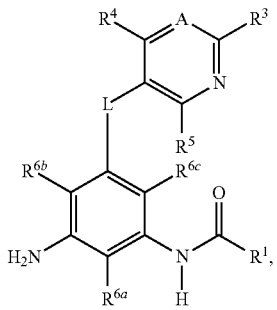

wherein A is $CR^2$ or N; wherein L is O or $NR^7$, wherein $R^1$ has from 1 to 10 carbons and is selected from phenyl substituted with 1-3 of $R^9$, wherein at least one $R^9$ is meta substituted; 2-pyridinyl substituted with 0-3 of $R^9$; and thiazole substituted with 0-2 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$; under Sandmeyer reaction conditions, thereby producing a halogenated derivative.

In a further aspect, the halogenated derivative produced has a structure represented by a formula:

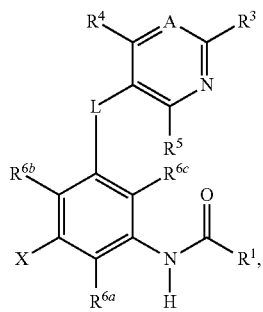

wherein X is Cl, Br, or I.

In a further aspect, the halogenated derivative produced has a structure represented by a formula:

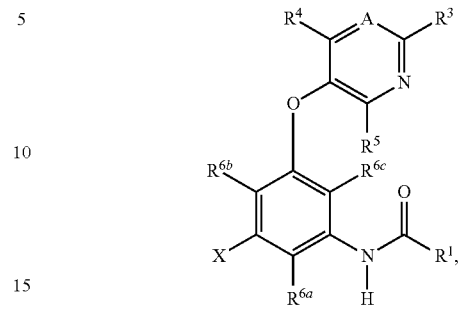

wherein X is Cl, Br, or I.

In a further aspect, the halogenated derivative produced exhibits partial or total inhibition of mGluR5 response to glutamate as a decrease in response to non-maximal concentrations of glutamate in human embryonic kidney cells transfected with rat mGluR5 in the presence of the compound, compared to the response to glutamate in the absence of the compound.

In one aspect, the invention relates a method of making a compound comprising the step of reacting a compound having a structure represented by a formula:

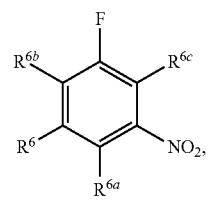

with a second compound having a structure represented by a formula:

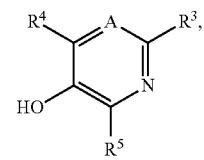

wherein A is $CR^2$ or N; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is selected from hydrogen, halogen, CN, C1-C4 alkyl, C1-C4 haloalkyl, C3-C4 cycloalkyl, and C3-C4 halocycloalkyl; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; and wherein $R^8$ is C1-C6 alkyl, C1-C6 cycloalkyl, amino, alkylamino, or dialkylamino; under basic conditions, thereby forming an ether.

In a further aspect, the ether produced has a structure represented by a formula:

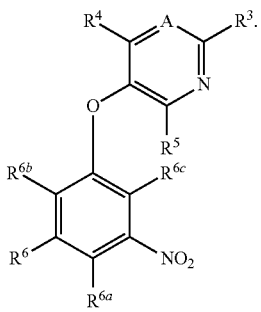

In a yet further aspect, the method comprises the step of reducing the nitro group, thereby forming an amine, having a structure represented by a formula:

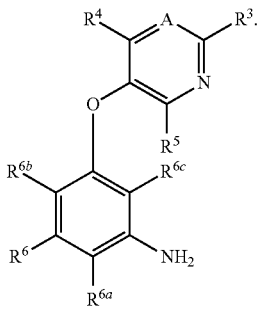

In a further aspect, the method further comprises the step of reacting the amine formed with an activated carbonyl compound, thereby forming an amide having a structure represented by a formula:

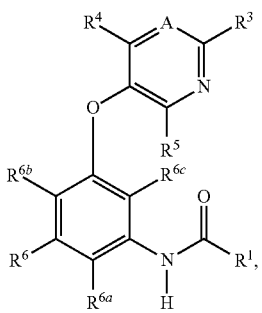

wherein $R^1$ has from 1 to 10 carbons and is selected from phenyl substituted with 1-3 of $R^9$, wherein at least one $R^9$ is meta substituted; 2-pyridinyl substituted with 0-3 of $R^9$; and thiazole substituted with 0-2 of $R^9$; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$.

In a further aspect, the compound produced exhibits partial or total inhibition of mGluR5 response to glutamate as a decrease in response to non-maximal concentrations of glutamate in human embryonic kidney cells transfected with rat mGluR5 in the presence of the compound, compared to the response to glutamate in the absence of the compound.

In one aspect, the invention relates to a method of making a compound comprising the steps of: (a) providing a compound having a structure represented by a formula:

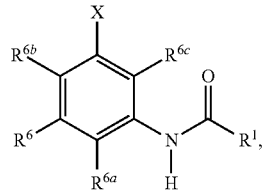

wherein X is halogen; wherein $R^1$ has from 1 to 10 carbons and is selected from phenyl substituted with 1-3 of $R^9$, wherein at least one $R^9$ is meta substituted; 2-pyridinyl substituted with 0-3 of $R^9$; and thiazole substituted with 0-2 of $R^9$; wherein $R^6$ is selected from hydrogen, halogen, CN, C1-C4 alkyl, C1-C4 haloalkyl, C3-C4 cycloalkyl, and C3-C4 halocycloalkyl; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$; (b) reacting with a second compound having a structure represented by a formula:

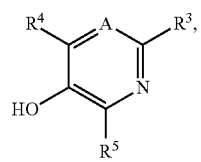

wherein A is $CR^2$ or N; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; and wherein $R^8$ is C1-C6 alkyl, C1-C6 cycloalkyl, amino, alkylamino, or dialkylamino; under basic conditions, thereby forming an ether.

In a further aspect, the method of making a compound wherein providing is reacting a compound having a structure represented by a formula:

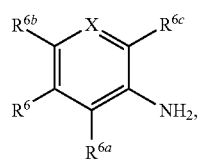

with an activated carboxylic compound, thereby forming an amide.

In a further aspect, the ether formed has a structure represented by a formula:

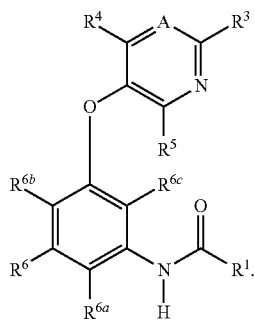

In a further aspect, the compound produced exhibits partial or total inhibition of mGluR5 response to glutamate as a decrease in response to non-maximal concentrations of glutamate in human embryonic kidney cells transfected with rat mGluR5 in the presence of the compound, compared to the response to glutamate in the absence of the compound.

In one aspect, the invention relates to a method of making a compound comprising the step of reacting a compound having a structure represented by a formula:

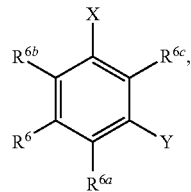

wherein X and Y are independently halogens; wherein $R^6$ is selected from hydrogen, halogen, CN, C1-C4 alkyl, C1-C4 haloalkyl, C3-C4 cycloalkyl, and C3-C4 halocycloalkyl; and wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; with a second compound having a structure represented by a formula:

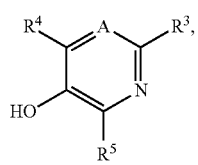

wherein A is $CR^2$ or N; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; and wherein $R^8$ is C1-C6 alkyl, C1-C6 cycloalkyl, amino, alkylamino, or dialkylamino; under basic conditions, thereby forming an ether.

In a further aspect, X is fluoro, and Y is chloro, bromo, or iodo.

In a further aspect, the ether formed has a structure represented by a formula:

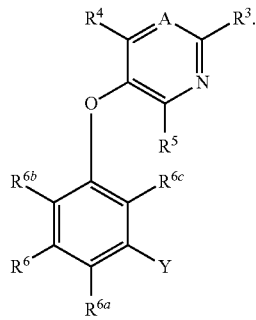

In a further aspect, the method further comprises the step of reacting with an amide anion in the presence of a transition metal, thereby forming an amide having a structure represented by a formula:

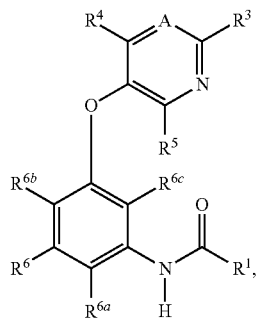

wherein $R^1$ has from 1 to 10 carbons and is selected from phenyl substituted with 1-3 of $R^9$, wherein at least one $R^9$ is meta substituted; 2-pyridinyl substituted with 0-3 of $R^9$; and thiazole substituted with 0-2 of $R^9$; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$.

In a further aspect, the compound produced exhibits partial or total inhibition of mGluR5 response to glutamate as a decrease in response to non-maximal concentrations of glutamate in human embryonic kidney cells transfected with rat mGluR5 in the presence of the compound, compared to the response to glutamate in the absence of the compound.

In one aspect, the invention relates to a method of making a compound comprising the step of reacting a compound having a structure represented by a formula:

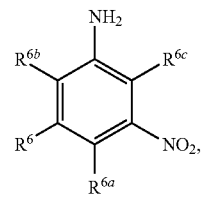

wherein $R^6$ is selected from hydrogen, halogen, CN, C1-C4 alkyl, C1-C4 haloalkyl, C3-C4 cycloalkyl, and C3-C4 halocycloalkyl; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; and wherein $R^8$ is C1-C6 alkyl, C1-C6 cycloalkyl, amino, alkylamino, or dialkylamino; with a second compound having a structure represented by a formula:

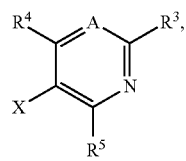

wherein X is halogen; wherein A is $CR^2$ or N; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; in the presence of a transition metal, thereby forming a diaryl amine moiety.

In a further aspect, diaryl amine produced has a structure represented by a formula:

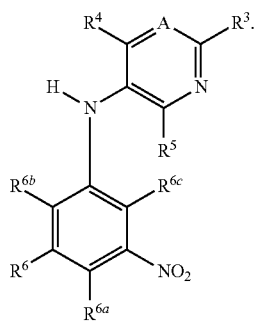

In a further aspect, the metho further comprises reaction with $R^7X$, wherein $R^7$ is alkyl or haloalkyl; and wherein X is a leaving group. In a yet further aspect, the transition metal is Pd.

1. Route I

In one aspect, amine-substituted analogs can be prepared as shown below.

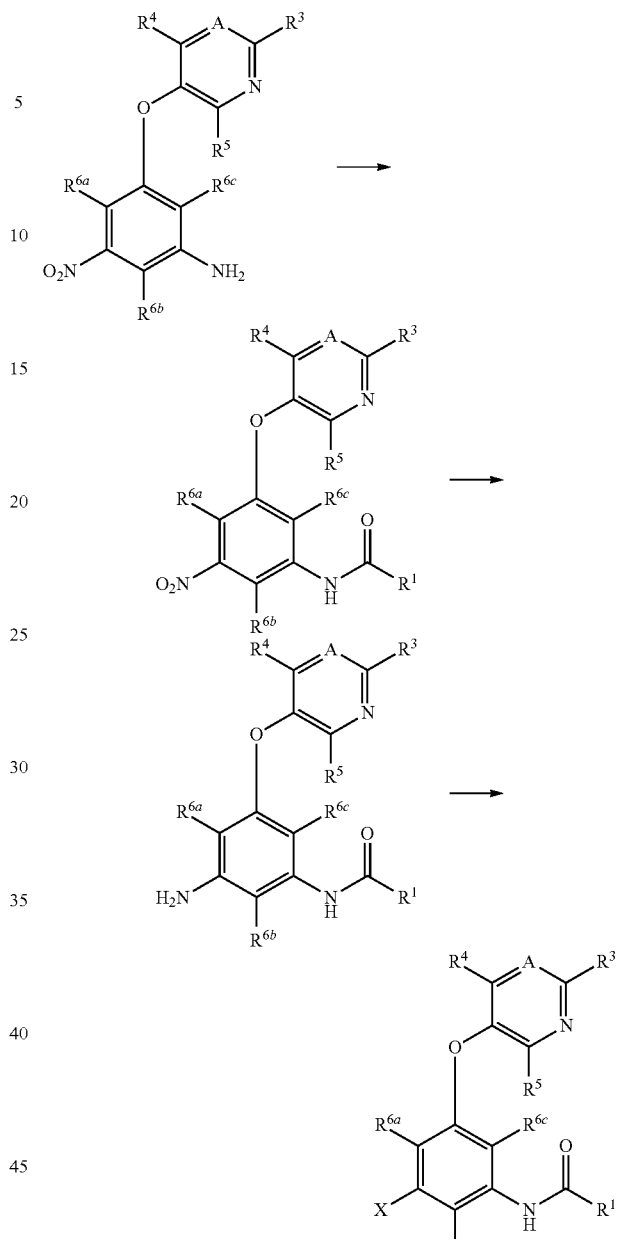

Compounds are represented in generic form, with substituents as noted in compound descriptions elsewhere herein. A more specific example is set forth below.

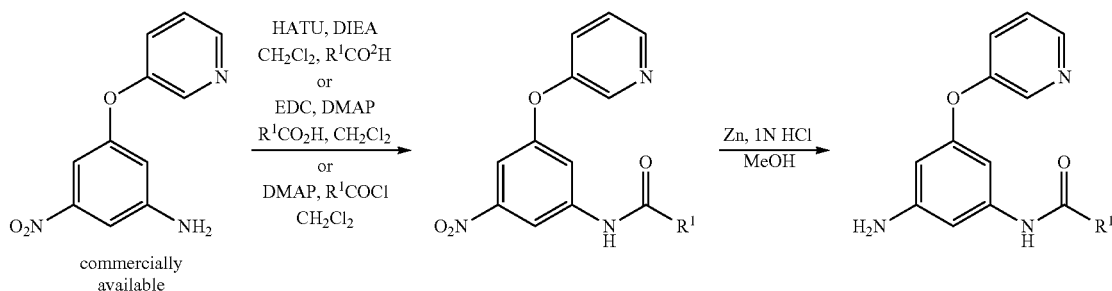

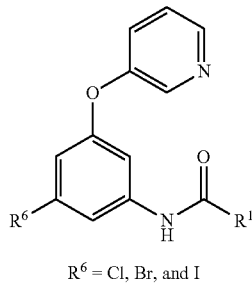

$R^6$ = Cl, Br, and I

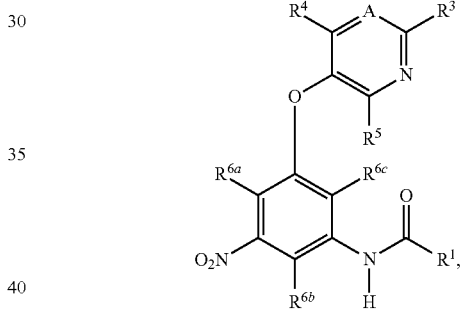

$R^6$ = Cl $^t$BuONO, CuCl$_2$, CH$_3$CN 50° C.
$R^6$ = Br NaNO$_2$, HBr, then CuBr, EtOH
$R^6$ = I NaNO$_2$, H$_2$O, HCl, then KI, HCl In one aspect, Route I begins with commercially available 3-nitro-5-(pyridin-3-yloxy)aniline. It then proceeds via a coupling reaction between the amine group and an activated carboxylic acid or acid halide. Such coupling reactions are generally well known. For example, carboxylic acids can be treated with activating reagents such as 1-ethyl-3-(3-dimethylaminopropyl) carbodiimide (EDC), dicyclohexylcarbodiimide (DCC), N,N'-diisopropyl-carbodiimide (DIP), 2-(1H-7-azabenzotriazol-1-yl)-1,1,3,3-tetramethyl uronium hexafluorophosphate methanaminium (HATU), benzotriazol-1-yl-oxy-tris-(dimethylamino)phosphonium hexa-fluorophosphate (BOP), hydroxybenzotriazole (HOBt), and N-methylmorpholine (NMM), including mixtures thereof, and then reacted with the amine. The next step involves a functional group transformation of the nitro group. Various methods for converting the nitro group to other functional groups are known. For example, the nitro group can be reduced to the amine, as shown in the scheme above. Further conversion of the amine group to a halide via the can be accomplished under Sandmeyer reaction conditions. That is, an aryl halide is prepared from an amine via an aryl diazonium salt intermediate. For example, an arylamine can react with a nitrite to form an aryl diazonium salt, which decomposes via radical-nucleophilic aromatic substitution reaction in the presence of a copper salt, thereby forming an aryl halide. It is appreciated that further copper salts (e.g., cuprous cyanide) can be used to form derivatives other than halide, if desired. Specific reactions conditions for various examples are provided in the schemes. Functional group transformation of the remaining substituents can yield further analogs.

Thus, in one aspect, the invention relates to a method of making a compound comprising the step of reacting a compound having a structure represented by a formula:

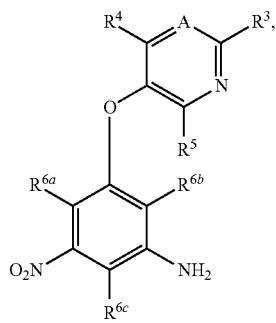

wherein A is $CR^2$ or N; wherein each of $R^{6a}$, $R^{6b}$, and $R^{6c}$ is independently selected from hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^4$, and $R^5$ are independently hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein the phenyl ring is optionally substituted with 0-3 $R^2$; wherein $R^3$ is hydrogen, halogen, C1-C6 alkyl, C1-C6 haloalkyl, C1-C6 alkoxy, hydroxyl, CN, $SO_2R^8$, or $COR^8$; wherein $R^8$ is C1-C6 alkyl, C1-C6 cycloalkyl, amino, alkylamino, or dialkylamino; with an activated carboxylic acid or acid halide, thereby forming an amide.

In a further aspect, the amide formed has a structure represented by a formula:

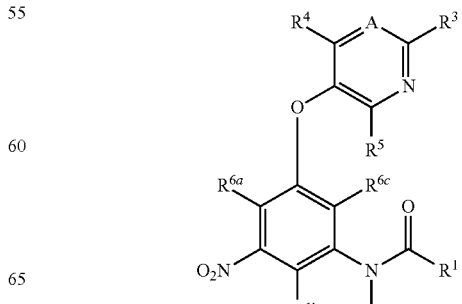

wherein $R^1$ is phenyl, pyridine, or thiazole; provided that where $R^1$ is phenyl, $R^1$ is substituted with 0-3 of $R^9$ and is meta-substituted relative to the amide carbonyl; provided that where $R^1$ is pyridine, the pyridine ring is considered a picolinamide (where the pyridine nitrogen is adjacent to the amide carbonyl) and is substituted with 0-3 of $R^9$; provided that where $R^1$ is thiazole, the thiazole ring is substituted with 0-2 of $R^9$.

In a further aspect, the methods further comprise the step of reducing the nitro group to an amine, having a structure represented by a formula:

In a further aspect, the compound produced has a structure represented by a formula:

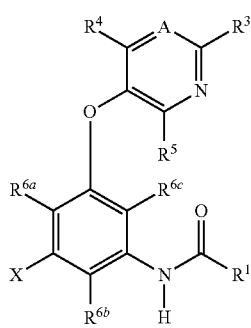

wherein X is Cl, Br, or I; wherein $R^1$ is phenyl, pyridine, or thiazole; provided that where $R^1$ is phenyl, $R^1$ is substituted with 0-3 of $R^9$ and is meta-substituted relative to the amide carbonyl; provided that where $R^1$ is pyridine, the pyridine ring is considered a picolinamide (where the pyridine nitrogen is adjacent to the amide carbonyl) and is substituted with 0-3 of $R^9$; provided that where $R^1$ is thiazole, the thiazole ring is substituted with 0-2 of $R^9$.

In yet a further aspect, the compound produced exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound produced exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound produced exhibits negative allosteric modulation of mGluR5 after contacting a cell expressing mGluR5. In a further aspect, the compound produced exhibits partial or total inhibition of mGluR5 after contacting a cell expressing mGluR5.

2. Route II

In one aspect, halo-substituted analogs can be prepared as shown below.

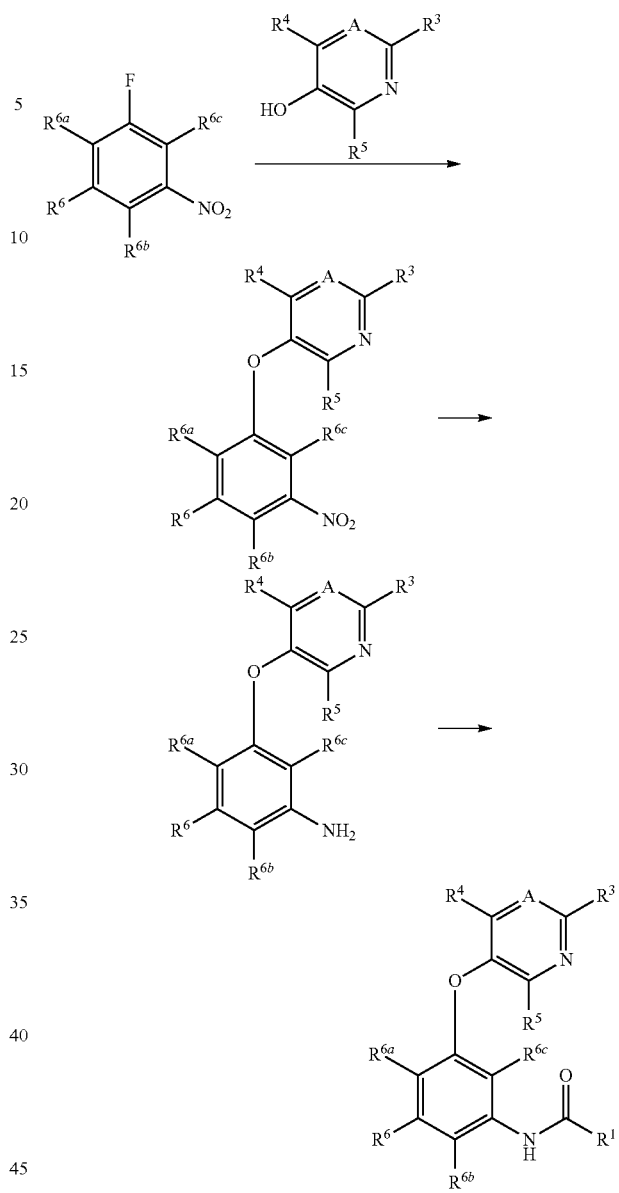

Compounds are represented in generic form, with substituents as noted in compound descriptions elsewhere herein. A more specific example is set forth below.

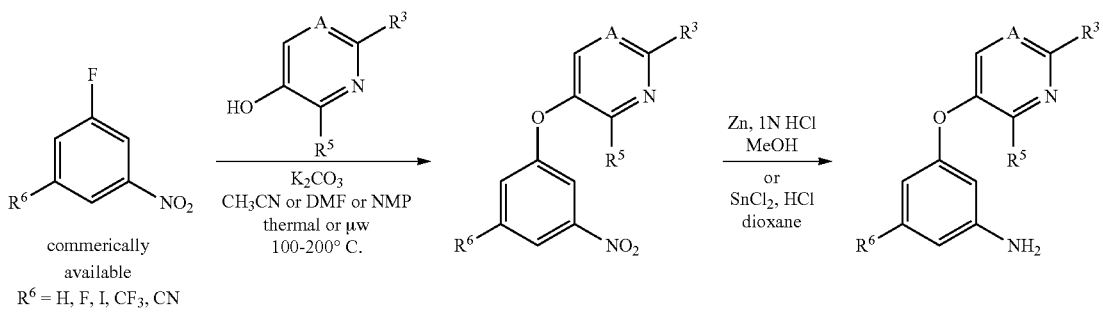

-continued

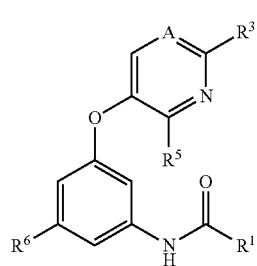

In one aspect, Route II begins with a commercially available substituted or unsubstituted 1-fluoro-3-$R^6$—5-nitrobenzene compound. The ether is formed via $S_NAr$ substitution of the fluorine under basic conditions, which is followed by a reduction of the nitro group. The resulting amine can then be coupled to an acid halide or activated carboxylic acid as described above in Route I. Functional group transformation of the remaining substituents can yield further analogs.

Thus, in one aspect, the invention relates to a method of making a compound comprising the step of reacting a compound having a structure represented by a formula:

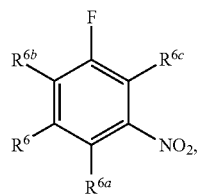

wherein each of $R^{6a}$, $R^{6b}$, and $R^{6c}$ is independently selected from hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^6$ is hydrogen, halogen, CN, C1-C4 alkyl, C3-C4 cycloalkyl, C1-C4 haloalkyl; wherein $R^8$ is C1-C6 alkyl, C1-C6 cycloalkyl, amino, alkylamino, or dialkylamino; with a second compound having a structure represented by a formula:

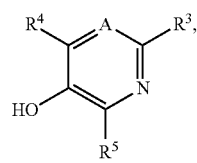

wherein A is $CR^2$ or N; wherein $R^4$ and $R^5$ are independently hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^3$ is hydrogen, halogen, C1-C6 alkyl, C1-C6 haloalkyl, C1-C6 alkoxy, hydroxyl, CN, $SO_2R^8$, or $COR^8$; wherein $R^8$ is C1-C6 alkyl, C1-C6 cycloalkyl, amino, alkylamino, or dialkylamino; under basic conditions, thereby forming an ether.

In a further aspect, the compound produced has a structure represented by a formula:

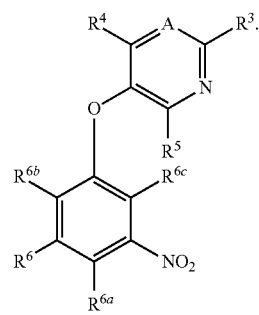

In a further aspect, the method further comprises the step of reducing the nitro group, thereby forming an amine, having a structure represented by a formula:

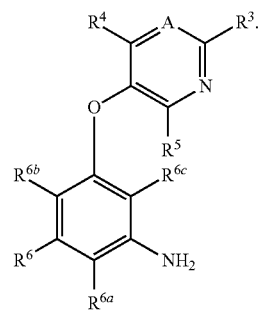

In a further aspect, the method further comprises the step of reacting with an activated carboxylic acid or acid halide, thereby forming an amide having a structure represented by a formula:

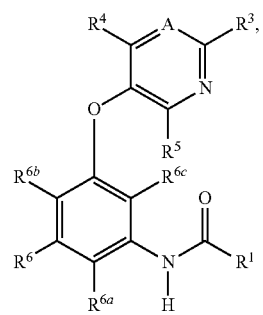

wherein R¹ is phenyl, pyridine, or thiazole; provided that where R¹ is phenyl, R¹ is substituted with 0-3 of R⁹ and is meta-substituted relative to the amide carbonyl; provided that where R¹ is pyridine, the pyridine ring is considered a picolinamide (where the pyridine nitrogen is adjacent to the amide carbonyl) and is substituted with 0-3 of R⁹; provided that where R¹ is thiazole, the thiazole ring is substituted with 0-2 of R⁹.

In yet a further aspect, the compound produced exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound produced exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound produced exhibits negative allosteric modulation of mGluR5 after contacting a cell expressing mGluR5. In a further aspect, the compound produced exhibits partial or total inhibition of mGluR5 after contacting a cell expressing mGluR5.

3. Route III

In one aspect, substituted analogs can be prepared as shown below.

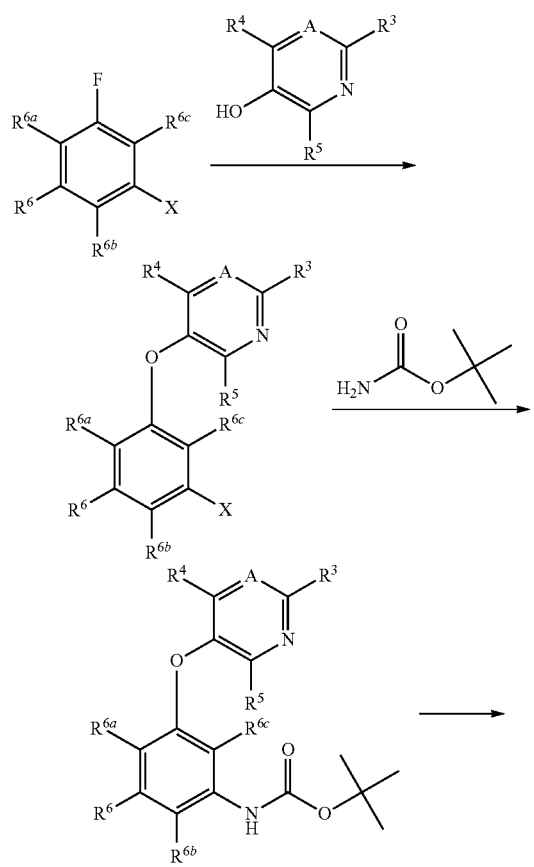

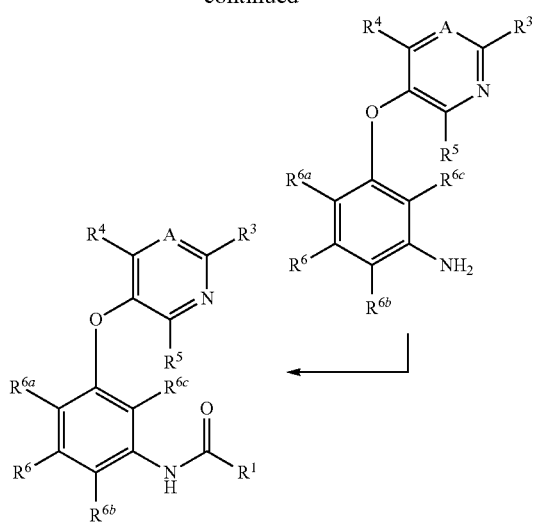

Compounds are represented in generic form, with substituents as noted in compound descriptions elsewhere herein. A more specific example is set forth below.

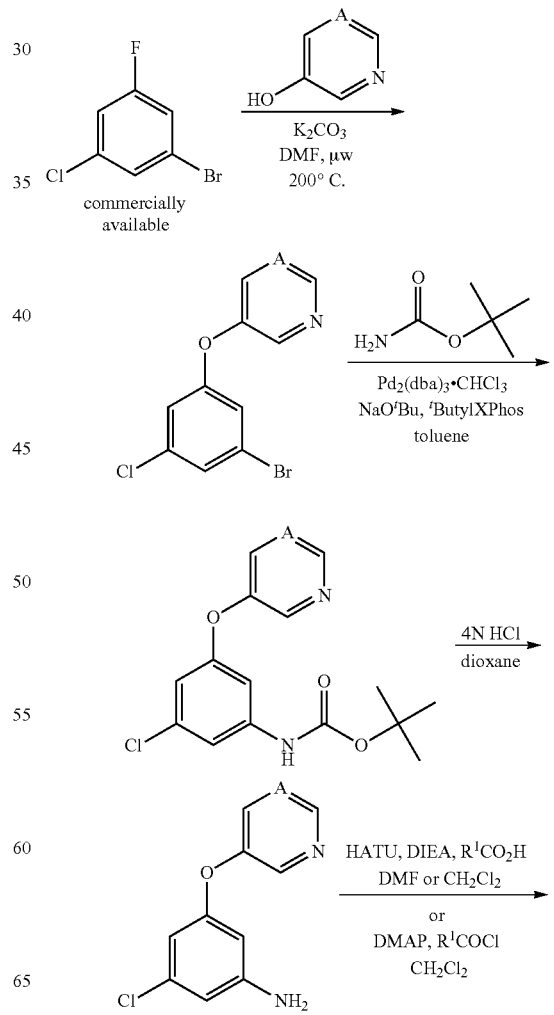

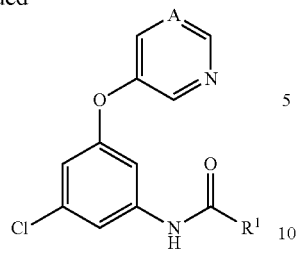

In one aspect, Route III begins with a commercially available substituted or unsubstituted 1-bromo-3-$R^6$-5-fluorobenzene or 1-fluoro-3-$R^6$-5-iodobenzene compound. The ether is formed via $S_NAr$ substituion of the fluorine under basic conditions, which is followed by a palladium catalyzed coupling with tert-butyl carbamate. It will be appreciated that a variety of palladium catalysts, phosphine ligands, and bases may be suitable for this coupling reaction (see *J. Org. Chem.* 2009, 74, 4634 and references therein). Examples of potentially useful palladium catalysts for this coupling include but are not limited to tris(dibenzylideneacetone)-dipalladium(0), palladium acetate, and tetrakis(triphenylphosphine)palladium. Examples of potentially useful phosphine ligands for this coupling include but are not limited to tert-butyl XPhos, XPhos, XANTPHOS, and BINAP. Examples of potentially useful bases for this coupling include but are not limited to sodium tert-butoxide, cesium carbonate, and tripotassium phosphate. The resulting carbamate can then be treated with acid to liberate the amine. The resultant amine can then be coupled to an acid halide or activated carboxylic acid as described above in Route I. Functional group transformation of the remaining substituents can yield further analogs.

Thus, in one aspect, the invention relates to a method of making a compound comprising the step of reacting a compound having a structure represented by a formula:

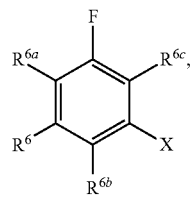

wherein each of $R^{6a}$, $R^{6b}$, and $R^{6c}$ is independently selected from hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^6$ is hydrogen, halogen, CN, C1-C4 alkyl, C3-C4 cycloalkyl, C1-C4 haloalkyl; wherein $R^8$ is C1-C6 alkyl, C1-C6 cycloalkyl, amino, alkylamino, or dialkylamino; wherein X is Br or I; with a second compound having a structure represented by a formula:

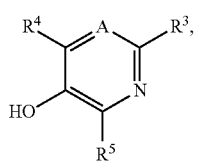

wherein A is $CR^2$ or N; wherein $R^4$ and $R^5$ are independently hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^3$ is hydrogen, halogen, C1-C6 alkyl, C1-C6 haloalkyl, C1-C6 alkoxy, hydroxyl, CN, $SO_2R^8$, or $COR^8$; wherein $R^8$ is C1-C6 alkyl, C1-C6 cycloalkyl, amino, alkylamino, or dialkylamino; under basic conditions, thereby forming an ether.

In a further aspect, the compound produced has a structure represented by a formula:

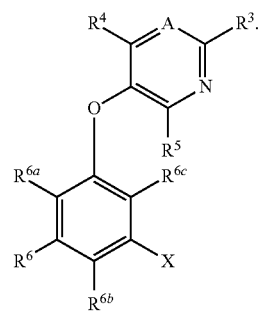

In a further aspect, the method further comprises the step of coupling with tert-butyl carbamate via a palladium catalyzed reaction thereby forming a carbamate, having a structure represented by a formula:

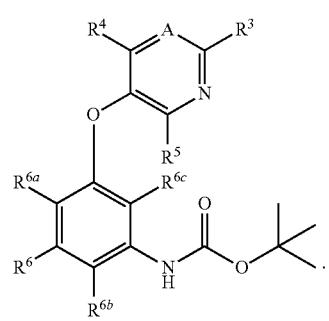

In a further aspect, the method further comprises the step of treating with acid thereby forming an amine, having a structure represented by a formula:

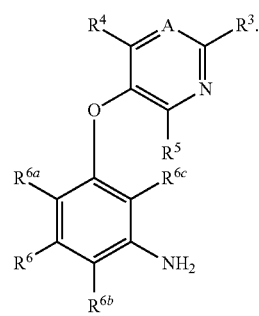

In a further aspect, the method further comprises the step of reacting with an activated carboxylic acid or acid halide compound, thereby forming an amide having a structure represented by a formula:

415

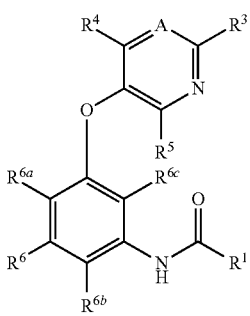

wherein R¹ is phenyl, pyridine, or thiazole; provided that where R¹ is phenyl, R¹ is substituted with 0-3 of R⁹ and is meta-substituted relative to the amide carbonyl; provided that where R¹ is pyridine, the pyridine ring is considered a picolinamide (where the pyridine nitrogen is adjacent to the amide carbonyl) and is substituted with 0-3 of R⁹; provided that where R¹ is thiazole, the thiazole ring is substituted with 0-2 of R⁹.

In yet a further aspect, the compound produced exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound produced exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound produced exhibits negative allosteric modulation of mGluR5 after contacting a cell expressing mGluR5. In a further aspect, the compound produced exhibits partial or total inhibition of mGluR5 after contacting a cell expressing mGluR5.

4. Route IV

In one aspect, substituted analogs can be prepared as shown below.

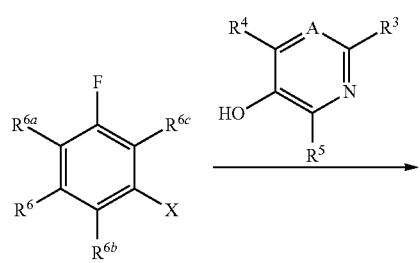

416

-continued

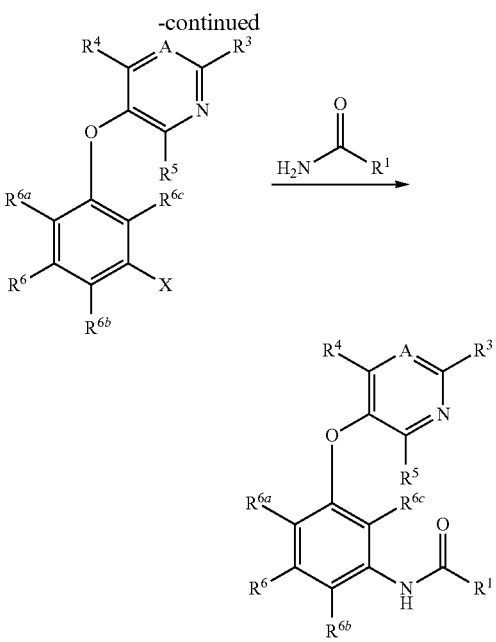

Compounds are represented in generic form, with substituents as noted in compound descriptions elsewhere herein. A more specific example is set forth below.

In one aspect, Route IV begins In one aspect, Route IV begins with a commercially available substituted or unsubstituted 1-bromo-3-R⁶-5-fluorobenzene or a commercially available substituted or unsubstituted 1-fluoro-3-R⁶-5-iodobenzene compound. The ether is formed via S$_N$Ar substituion of the fluorine under basic conditions, which is followed by a palladium catalyzed coupling with a primary amide. It will be appreciated that a variety of palladium catalysts, phosphine ligands, and bases may be suitable for this coupling reaction (see *J. Am. Chem. Soc.* 2007, 129, 13001 and references therein). Examples of potentially useful palladium catalysts for this coupling include but are not limited to tris(dibenzylideneacetone)dipalladium(0), palladium acetate, and tetrakis(triphenyl-phosphine)palladium. Examples of potentially useful phosphine ligands for this coupling include but are not limited to tert-butyl XPhos, XPhos, XANTPHOS, and BINAP. Examples of potentially useful bases for this coupling include but are not limited to sodium tert-butoxide, cesium carbonate, and tripotassium phosphate. Functional group transformation of the remaining substituents can yield further analogs.

Thus, in one aspect, the invention relates to a method of making a compound comprising the step of reacting a compound having a structure represented by a formula:

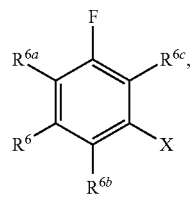

wherein each of $R^{6a}$, $R^{6b}$, and $R^{6c}$ is independently selected from hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^6$ is hydrogen, halogen, CN, C1-C4 alkyl, C3-C4 cycloalkyl, C1-C4 haloalkyl; wherein $R^8$ is C1-C6 alkyl, C1-C6 cycloalkyl, amino, alkylamino, or dialkylamino; wherein X is Br or I; with a second compound having a structure represented by a formula:

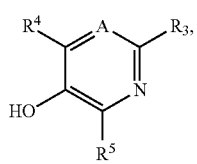

wherein A is $CR^2$ or N; wherein $R^4$ and $R^5$ are independently hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^3$ is hydrogen, halogen, C1-C6 alkyl, C1-C6 haloalkyl, C1-C6 alkoxy, hydroxyl, CN, $SO_2R^8$, or $COR^8$; wherein $R^8$ is C1-C6 alkyl, C1-C6 cycloalkyl, amino, alkylamino, or dialkylamino; under basic conditions, thereby forming an ether.

In a further aspect, the compound produced has a structure represented by a formula:

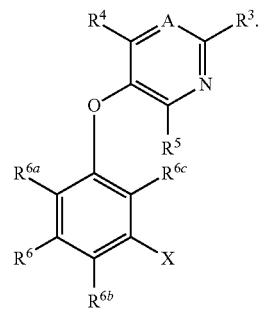

In a further aspect, the method further comprises the step of coupling with a primary amide via a palladium catalyzed reaction thereby forming an amide, having a structure represented by a formula:

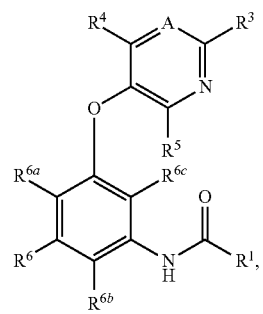

wherein $R^1$ is phenyl, pyridine, or thiazole; provided that where $R^1$ is phenyl, $R^1$ is substituted with 0-3 of $R^9$ and is meta-substituted relative to the amide carbonyl; provided that where $R^1$ is pyridine, the pyridine ring is considered a picolinamide (where the pyridine nitrogen is adjacent to the amide carbonyl) and is substituted with 0-3 of $R^9$; provided that where $R^1$ is thiazole, the thiazole ring is substituted with 0-2 of $R^9$.

In yet a further aspect, the compound produced exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound produced exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound produced exhibits negative allosteric modulation of mGluR5 after contacting a cell expressing mGluR5. In a further aspect, the compound produced exhibits partial or total inhibition of mGluR5 after contacting a cell expressing mGluR5.

5. Route V

In one aspect, substituted analogs can be prepared as shown below.

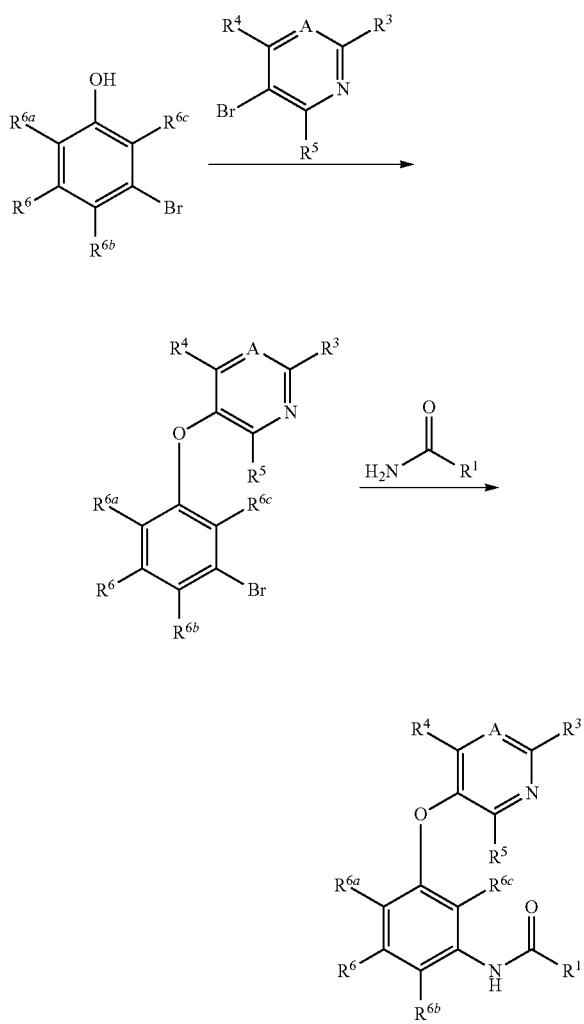

Compounds are represented in generic form, with substituents as noted in compound descriptions elsewhere herein. A more specific example is set forth below.

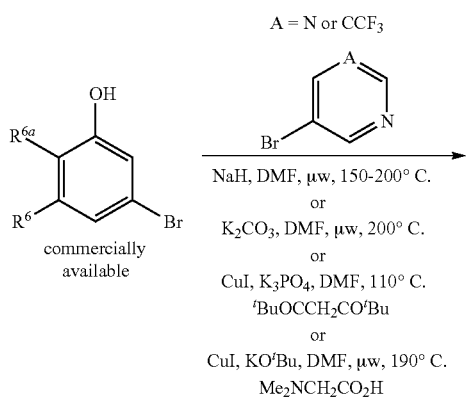

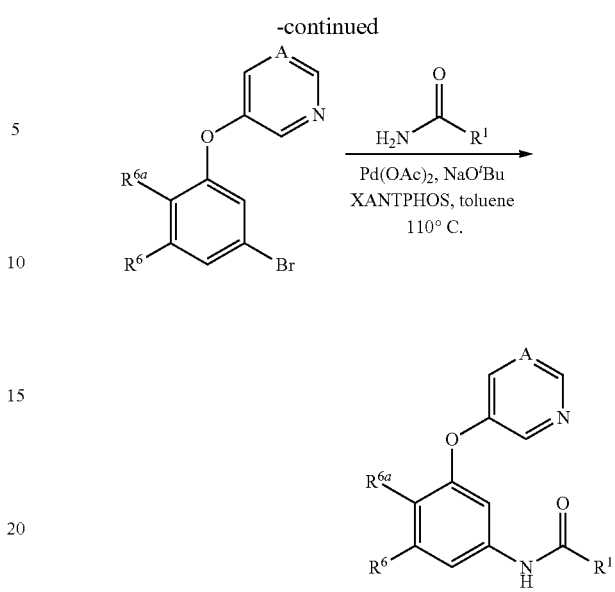

In one aspect, Route V begins with a substituted or unsubstituted commercially available 3-bromophenol compound. Formation of the phenoxide followed by $S_NAr$ substituion reaction with a haloarene yields a biaryl ether, which is followed by a palladium catalyzed coupling with a primary amide. It will be appreciated that the $S_NAr$ reaction may be carried out using with or without the aid of copper salts. Examples of potentially useful conditions without copper salts include but are not limited to sodium hydride in DMF with heating under microwave irradiation and potassium carbonate in DMF with heating under microwave irradiation. Examples of potentially useful conditions with copper salts include but are not limited to copper(I) iodide, tripotassium phosphate, and 2,2,6,6-tetramethylheptane-3,5-dione in DMF with heating (*Org. Lett.* 2002, 4, 1623) and copper(I) iodide, potassium tert-butoxide, and dimethylglycine in DMF with heating under microwave irradiation. The resulting intermediate can be coupled to a primary amide via a palladium catalyzed reaction as described in Route IV. Functional group transformation of the remaining substituents can yield further analogs.

Thus, in one aspect, the invention relates to a method of making a compound comprising the step of reacting a compound having a structure represented by a formula:

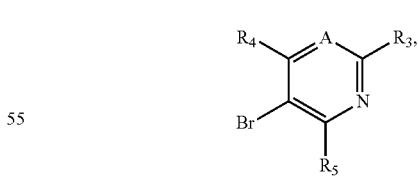

wherein A is $CR^2$ or N; wherein $R^4$ and $R^5$ are independently hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^3$ is hydrogen, halogen, C1-C6 alkyl, C1-C6 haloalkyl, C1-C6 alkoxy, hydroxyl, CN, $SO_2R^8$, or $COR^8$; wherein $R^8$ is C1-C6 alkyl, C1-C6 cycloalkyl, amino, alkylamino, or dialkylamino; with the anion of a compound having a structure represented by a formula:

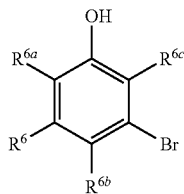

wherein $R^2$ is hydrogen, halogen, C1-C6 alkyl, C1-C6 haloalkyl, C1-C6 alkoxy, and C1-C6 haloalkoxy, CN, $SO_2R^8$, or $COR^8$; wherein $R^6$ is hydrogen, halogen, CN, C1-C4 alkyl, C3-C4 cycloalkyl, C1-C4 haloalkyl; wherein $R^8$ is C1-C6 alkyl, C1-C6 cycloalkyl, amino, alkylamino, or dialkylamino; thereby forming an ether.

In a further aspect, the compound produced has a structure represented by a formula:

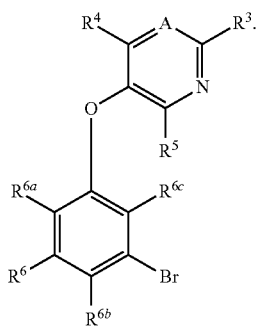

In a further aspect, the method further comprises the step of coupling with a primary amide via a palladium catalyzed reaction thereby forming an amide, having a structure represented by a formula:

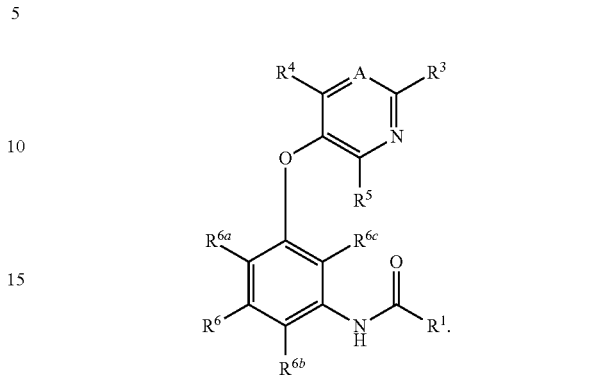

wherein $R^1$ is phenyl, pyridine, or thiazole; provided that where $R^1$ is phenyl, $R^1$ is substituted with 0-3 of $R^9$ and is meta-substituted relative to the amide carbonyl; provided that where $R^1$ is pyridine, the pyridine ring is considered a picolinamide (where the pyridine nitrogen is adjacent to the amide carbonyl) and is substituted with 0-3 of $R^9$; provided that where $R^1$ is thiazole, the thiazole ring is substituted with 0-2 of $R^9$.

In yet a further aspect, the compound produced exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound produced exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound produced exhibits negative allosteric modulation of mGluR5 after contacting a cell expressing mGluR5. In a further aspect, the compound produced exhibits partial or total inhibition of mGluR5 after contacting a cell expressing mGluR5.

6. Route VI

In one aspect, substituted analogs can be prepared as shown below.

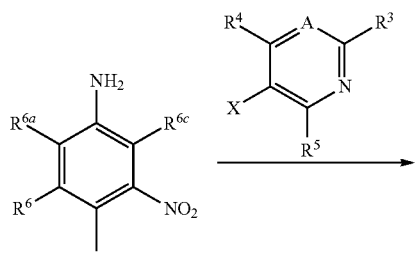

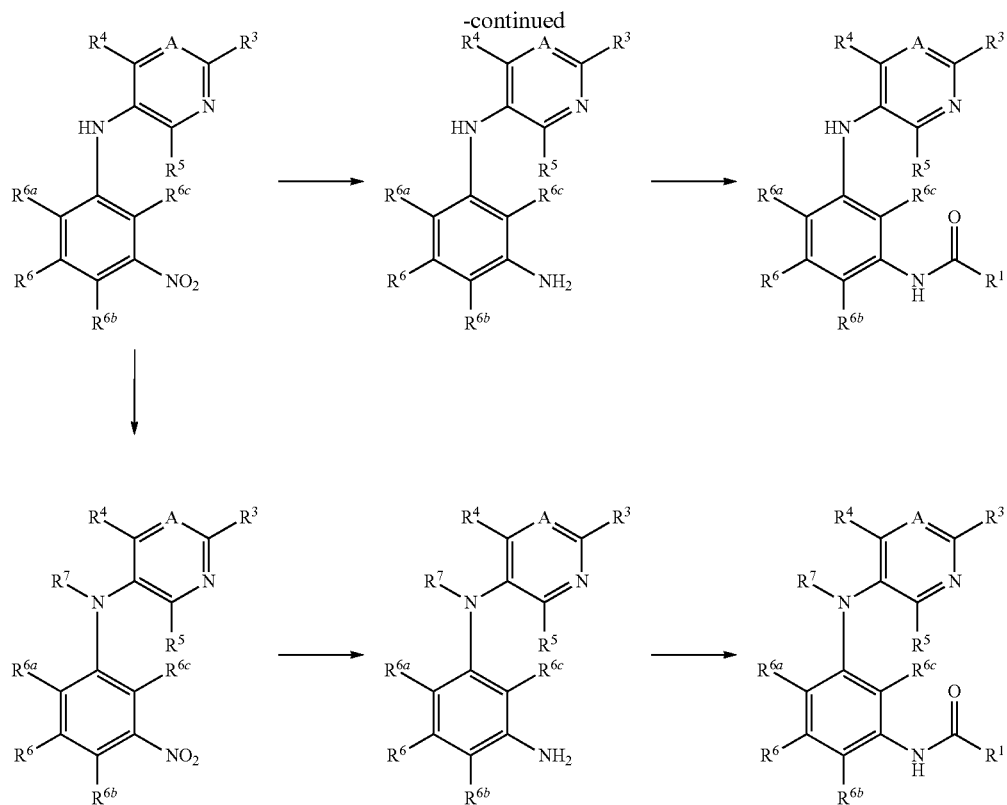
Compounds are represented in generic form, with substituents as noted in compound descriptions elsewhere herein. A more specific example is set forth below.
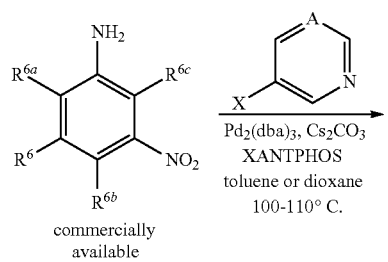
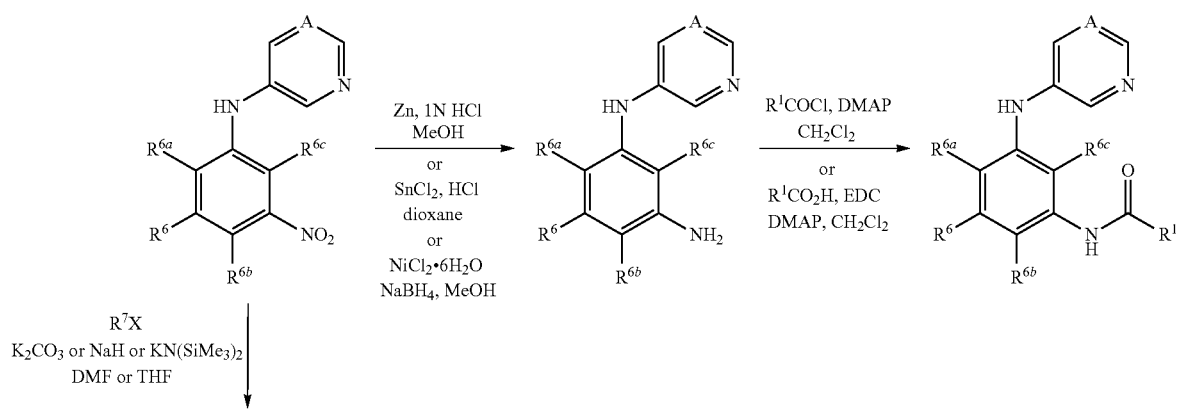

425

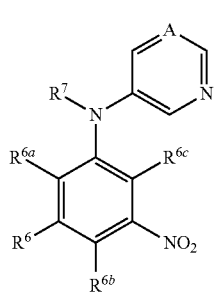

-continued

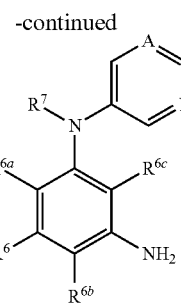

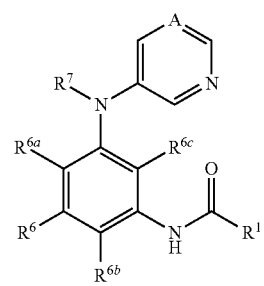

426

In one aspect, Route VI begins with a commercially available substituted or unsubstituted 3-nitroanaline and proceeds via a palladium coupling reaction with a substituted or unsubstituted 3-halopyridine or a substituted or unsubstituted 5-halopyrimidine in order to link that group to the amine of the aniline. It will be appreciated that a variety of palladium catalysts, phosphine ligands, and bases may be suitable for the palladium catalyzed coupling reaction (see *Nature Protocols* 2007, 2, 2881 and references therein). Examples of potentially useful palladium catalysts for this coupling include but are not limited to tris(dibenzylideneacetone)-dipalladium(0), palladium acetate, and tetrakis(triphenylphosphine)-palladium. Examples of potentially useful phosphine ligands for this coupling include but are not limited to tert-butyl XPhos, XPhos, XANTPHOS, and BINAP. Examples of potentially useful bases for this coupling include but are not limited to sodium tert-butoxide, cesium carbonate, and potassium phosphate. The nitro group can be reduced to the amine and coupled with an activated carboxylic acid or acid halide as described in Route I. Alternatively, following the palladium coupling, the secondary amine can be reacted with an alkyl halide under basic conditions to produce a tertiary amine. The resulting intermediate can be reduced and coupled to an activated carboxylic acid or acid halide as described in Route I.

Thus, in one aspect, the invention relates to a method of making a compound comprising the step of reacting a compound having a structure represented by a formula:

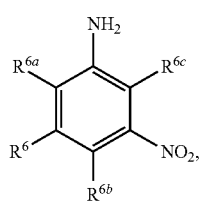

wherein each of $R^{6a}$, $R^{6b}$, and $R^{6c}$ is independently selected from hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^6$ is hydrogen, halogen, CN, C1-C4 alkyl, C3-C4 cycloalkyl, C1-C4 haloalkyl; wherein $R^8$ is C1-C6 alkyl, C1-C6 cycloalkyl, amino, alkylamino, or dialkylamino; with a second compound having a structure represented by a formula:

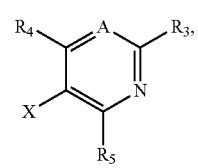

wherein A is $CR^2$ or N; wherein $R^4$ and $R^5$ are independently hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^3$ is hydrogen, halogen, C1-C6 alkyl, C1-C6 haloalkyl, C1-C6 alkoxy, hydroxyl, CN, $SO_2R^8$, or $COR^8$; wherein $R^8$ is C1-C6 alkyl, C1-C6 cycloalkyl, amino, alkylamino, or dialkylamino; wherein X is Cl, Br, I, or $OSO_2R^9$; wherein $R^9$ is alkyl, cycloalkyl, or aryl; in the presence of a palladium catalyst, thereby forming a diaryl amine moiety.

In a further aspect, the compound produced has a structure represented by a formula:

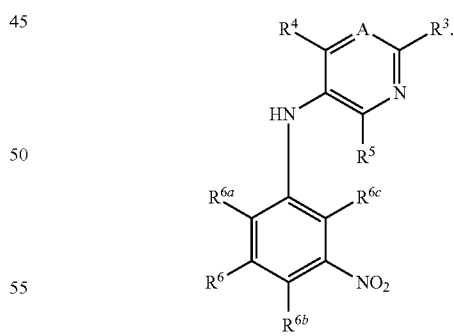

In a further aspect, the method further comprises reaction with $R^7X$, wherein $R^7$ is alkyl or haloalkyl; and wherein X is a leaving group.

In a further aspect, the compound produced has a structure represented by a formula:

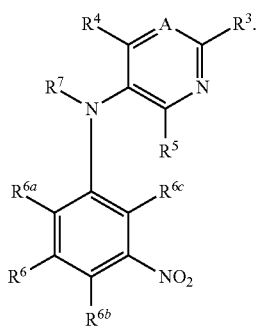

In a further aspect, the method further comprises the step of reducing the nitro group, thereby forming an amine, having a structure represented by a formula:

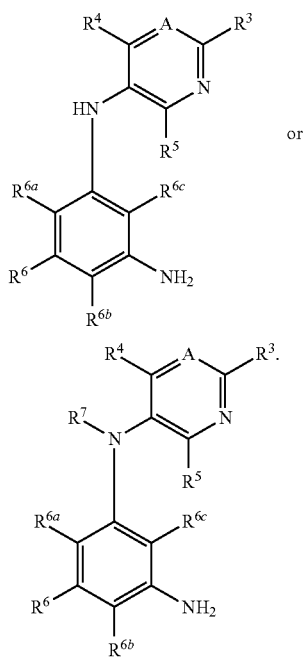

In a further aspect, the method further comprises the step of reacting with an activated carboxylic acid or acid halide compound, thereby forming an amide having a structure represented by a formula:

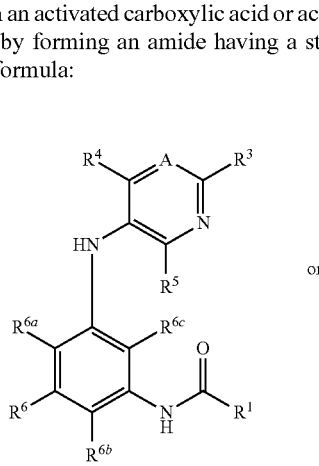

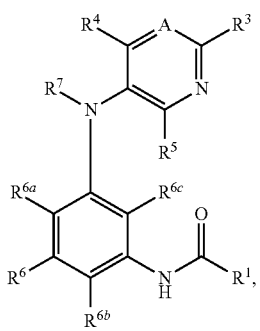

wherein $R^1$ is phenyl, pyridine, or thiazole; provided that where $R^1$ is phenyl, $R^1$ is substituted with 0-3 of $R^9$ and is meta-substituted relative to the amide carbonyl; provided that where $R^1$ is pyridine, the pyridine ring is considered a picolinamide (where the pyridine nitrogen is adjacent to the amide carbonyl) and is substituted with 0-3 of $R^9$; provided that where $R^1$ is thiazole, the thiazole ring is substituted with 0-2 of $R^9$.

In yet a further aspect, the compound produced exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound produced exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound produced exhibits negative allosteric modulation of mGluR5 after contacting a cell expressing mGluR5. In a further aspect, the compound produced exhibits partial or total inhibition of mGluR5 after contacting a cell expressing mGluR5.

7. Route VII

In one aspect, substituted analogs can be prepared as shown below.

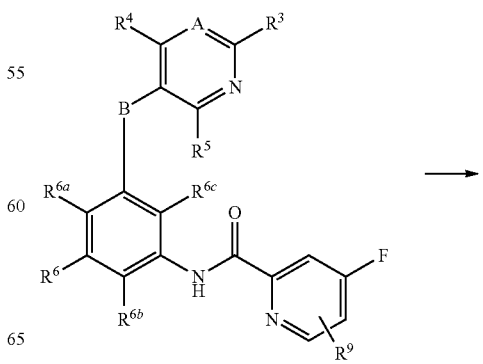

-continued

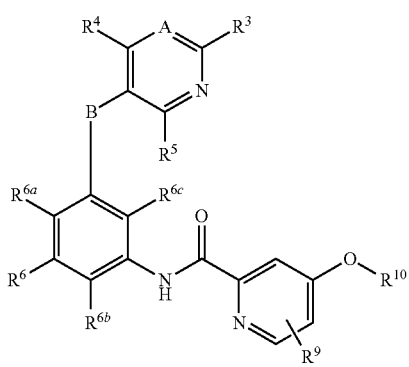

Compounds are represented in generic form, with substituents as noted in compound descriptions elsewhere herein. A more specific example is set forth below.

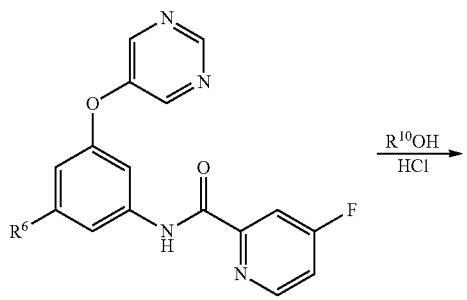

In one aspect, Route VII begins with a 4-fluoro-N-(substituted phenyl)picolinamide compound prepared according to methods described herein. The compound is treated with an alcohol in the presence of acid to produce an N-(substituted phenyl)-4-alkoxypicolinamide. Functional group transformation of the remaining substituents can yield further analogs.

In one aspect, Route VII relates to a method of making a compound comprising the step of reacting a compound having a structure represented by a formula:

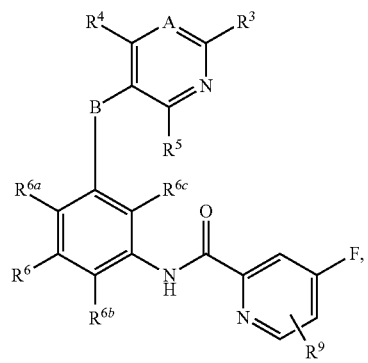

wherein A is $CR^2$ or N; wherein X is O or $NR^7$; wherein each of $R^{6a}$, $R^{6b}$, and $R^{6c}$ is independently selected from hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; $R^4$, and $R^5$ are independently hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^3$ is hydrogen, halogen, C1-C6 alkyl, C1-C6 haloalkyl, C1-C6 alkoxy, hydroxyl, CN, $SO_2R^8$, or $COR^8$; wherein $R^6$ is hydrogen, halogen, CN, C1-C4 alkyl, C3-C4 cycloalkyl, C1-C4 haloalkyl; wherein $R^7$ is optionally substituted alkyl or haloalkyl; wherein $R^8$ is C1-C6 alkyl, C1-C6 cycloalkyl, amino, alkylamino, or dialkylamino; wherein the picolinamide ring is substituted with 0-2 $R^9$; wherein the phenyl ring is substituted with 0-3 $R^9$; with an alcohol ($R^{10}OH$) in the presence of acid; wherein $R^{10}$ is hydrogen, alkyl, haloalkyl, cycloalkyl, or halocycloalkyl, thereby producing a N-(substituted phenyl)-4-alkoxypicolinamide.

In a further aspect, the compound produced has a structure represented by a formula:

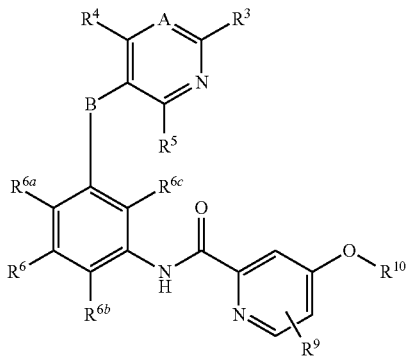

In yet a further aspect, the compound produced exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound produced exhibits partial or total inhibition of mGluR5 in response to glutamate as a decrease in response to non-maximal concentrations of glutamate in human embryonic kidney cells transfected with human, rat or mammalian mGluR5 in the pres-

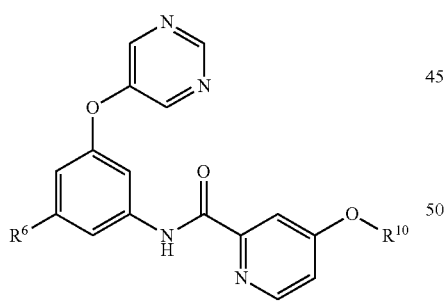

ence of the compound, compared to the response to glutamate in the absence of the compound. In yet a further aspect, the compound produced exhibits negative allosteric modulation of mGluR5 after contacting a cell expressing mGluR5. In a further aspect, the compound produced exhibits partial or total inhibition of mGluR5 after contacting a cell expressing mGluR5.

8. Route VIII

In one aspect, substituted analogs can be prepared as shown below.

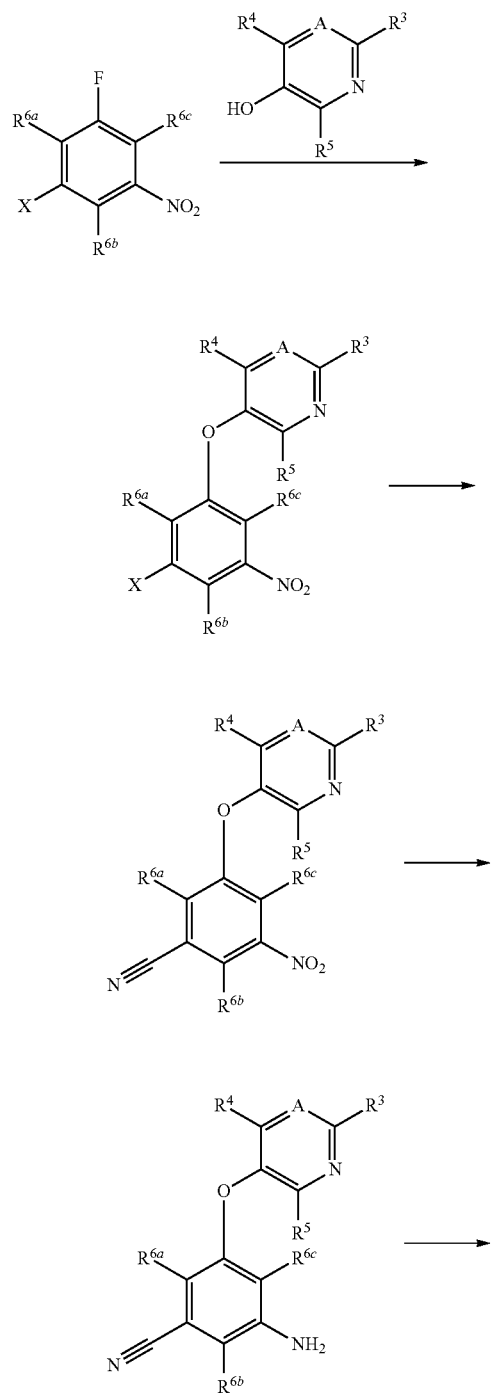

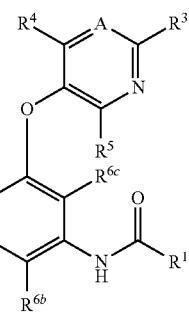

Compounds are represented in generic form, with substituents as noted in compound descriptions elsewhere herein. A more specific example is set forth below.

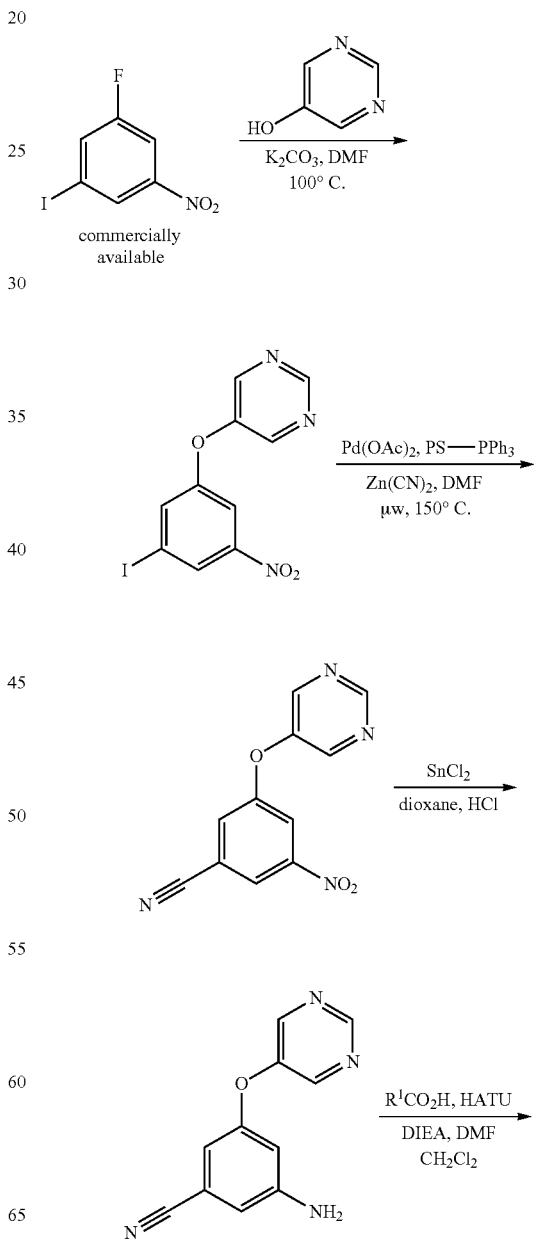

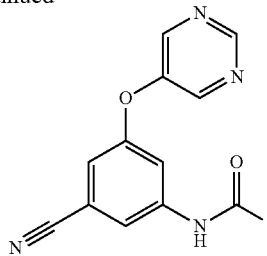

In one aspect, Route VIII involves begins with a commercially available substituted or unsubstituted 1-fluoro-3-halo-5-nitrobenzene compound. The ether is formed via $S_NAr$ substituion of the fluorine under basic conditions, which is followed by a palladium catalyzed cyanation reaction to generate the aryl nitrile compound. It will be appreciated that a variety of palladium catalysts, ligands, and cyanide sources may be suitable for this coupling reaction (see *Synthetic Comm.* 2007, 37, 431-438 and references therein). Examples of potentially useful palladium catalysts for this coupling include but are not limited to tris(dibenzylideneacetone)-dipalladium(0), palladium acetate, and tetrakis(triphenylphosphine)palladium. Examples of potentially useful phosphine ligands for this coupling include but are not limited to triphenylphosphine, 1,1'-bis(diphenylphosphino)ferrocene, and 1,4-bis(diphenylphosphino)butane. Examples of potentially useful cyanide sources for this coupling include but are not limited to zinc cyanide, potassium ferricyanide, trimethylsilyl cyanide, and potassium cyanide. It will be appreciated that other reagents may be used to introduce substituents other than cyano (e.g. dimethylzinc or sodium methanesulfinate). The nitro group can then be reduced to form the primary amine. The amine can then be coupled to an acid halide or activated carboxylic acid as described above in Route I. Functional group transformation of the remaining substituents can yield further analogs.

Thus, in one aspect, the invention relates to a method of making a compound comprising the step of reacting a compound having a structure represented by a formula:

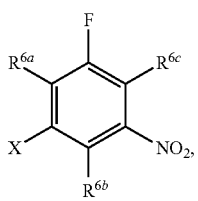

wherein each of $R^{6a}$, $R^{6b}$, and $R^{6c}$ is independently selected from hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^6$ is hydrogen, halogen, CN, C1-C4 alkyl, C3-C4 cycloalkyl, C1-C4 haloalkyl; wherein $R^8$ is C1-C6 alkyl, C1-C6 cycloalkyl, amino, alkylamino, or dialkylamino; wherein X is Cl, Br, or I; with a second compound having a structure represented by a formula:

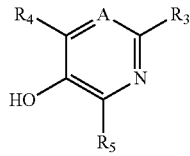

wherein A is $CR^2$ or N; wherein $R^4$ and $R^5$ are independently hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^3$ is hydrogen, halogen, C1-C6 alkyl, C1-C6 haloalkyl, C1-C6 alkoxy, hydroxyl, CN, $SO_2R^8$, or $COR^8$; wherein $R^8$ is C1-C6 alkyl, C1-C6 cycloalkyl, amino, alkylamino, or dialkylamino; under basic conditions, thereby forming an ether.

In a further aspect, the compound produced has a structure represented by a formula:

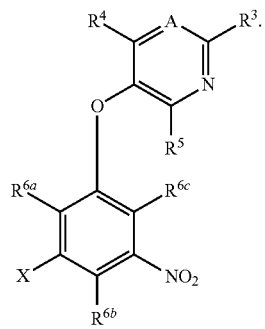

In a further aspect, the method further comprises the step of a palladium catalyzed cyanation reaction, thereby forming an aryl nitrile, having a structure represented by a formula:

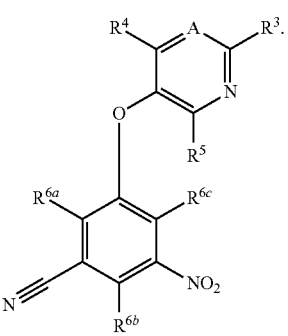

In a further aspect, the method further comprises the step of reducing the nitro group, thereby forming an amine, having a structure represented by a formula:

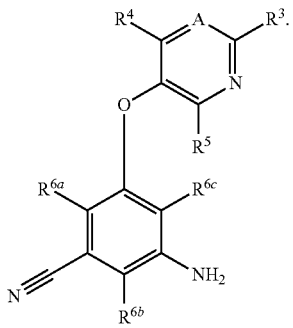

In a further aspect, the method further comprises the step of reacting with an activated carboxylic acid or acid halide compound, thereby forming an amide having a structure represented by a formula:

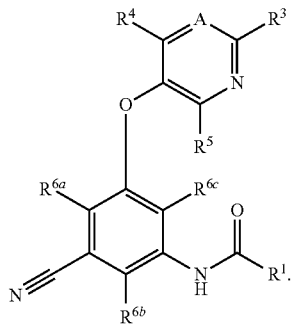

wherein R¹ is phenyl, pyridine, or thiazole; provided that where R¹ is phenyl, R¹ is substituted with 0-3 of R⁹ and is meta-substituted relative to the amide carbonyl; provided that where R¹ is pyridine, the pyridine ring is considered a picolinamide (where the pyridine nitrogen is adjacent to the amide carbonyl) and is substituted with 0-3 of R⁹; provided that where R¹ is thiazole, the thiazole ring is substituted with 0-2 of R⁹.

In yet a further aspect, the compound produced exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound produced exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound produced exhibits negative allosteric modulation of mGluR5 after contacting a cell expressing mGluR5. In a further aspect, the compound produced exhibits partial or total inhibition of mGluR5 after contacting a cell expressing mGluR5.

9. Route IX

In one aspect, substituted analogs can be prepared as shown below.

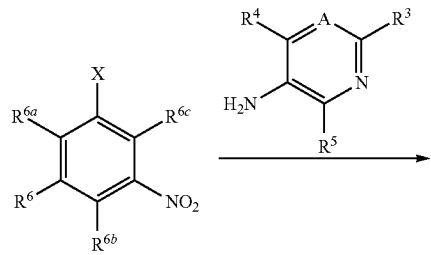

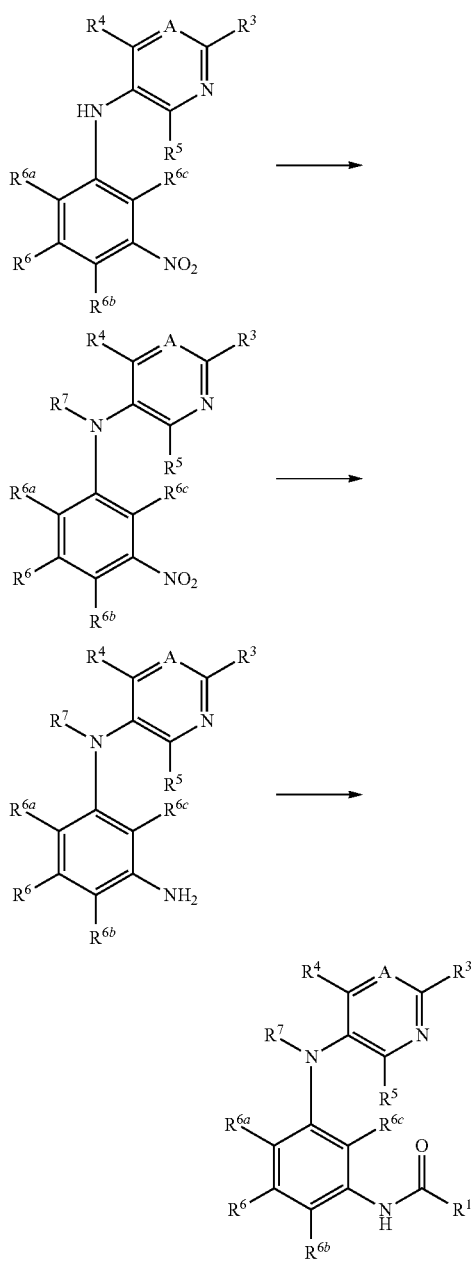

Compounds are represented in generic form, with substituents as noted in compound descriptions elsewhere herein. A more specific example is set forth below.

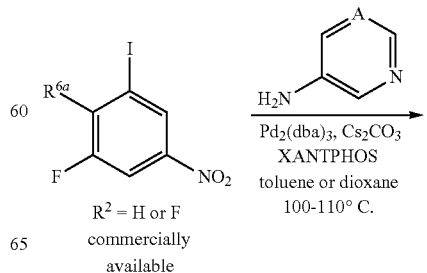

R² = H or F
commercially available

437

-continued

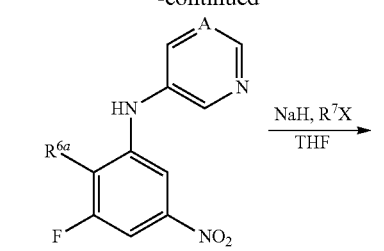

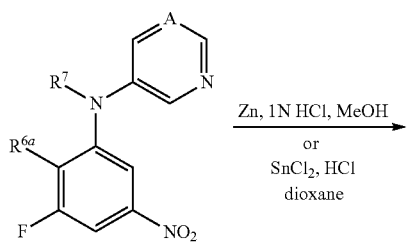

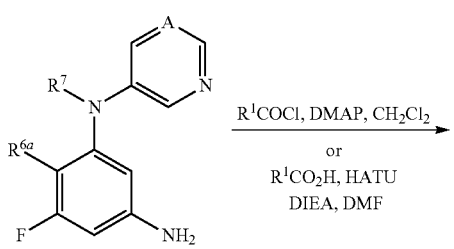

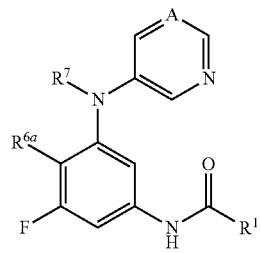

In one aspect, Route IX begins with a commercially available substituted or unsubstituted 3-halonitrobenzene compound. Alternatively, Route IX begins with a substituted or unsubstituted 3-nitrophenyl sulfonate. Such sulfonate compounds are either commercially available or readily prepared by one skilled in the art. Reaction proceeds with a substituted or unsubstituted 3-aminopyridine or a substituted or unsubstituted 5-aminopyrimidine using a palladium catalyzed coupling in order to link the two groups via a secondary amine as described in Route VI. Following the palladium coupling, the secondary amine can be reacted with an alkyl halide or alkyl group with another suitable leaving group under basic conditions to produce a tertiary amine. It will be appreciated that should the secondary rather than tertiary amine target be of interest that the aforementioned step would be skipped. The resulting intermediate can be reduced and coupled to an activated carboxylic acid or acid halide as described in Route I.

Thus, in one aspect, the invention relates to a method of making a compound comprising the step of reacting a compound having a structure represented by a formula:

438

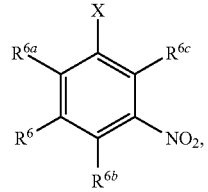

wherein $R^2$ is hydrogen, halogen, C1-C6 alkyl, C1-C6 haloalkyl, C1-C6 alkoxy, and C1-C6 haloalkoxy, CN, $SO_2R^8$, or $COR^8$; wherein the phenyl ring is optionally substituted with 0-3 $R^2$; wherein $R^6$ is hydrogen, halogen, CN, C1-C4 alkyl, C3-C4 cycloalkyl, C1-C4 haloalkyl; wherein $R^8$ is C1-C6 alkyl, C1-C6 cycloalkyl, amino, alkylamino, or dialkylamino; wherein X is Cl, Br, I, or $OSO_2R^9$; wherein $R^9$ is alkyl, haloalkyl, or aryl; with a second compound having a structure represented by a formula:

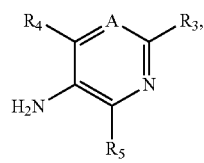

wherein A is $CR^2$ or N; wherein $R^4$ and $R^5$ are independently hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^3$ is hydrogen, halogen, C1-C6 alkyl, C1-C6 haloalkyl, C1-C6 alkoxy, hydroxyl, CN, $SO_2R^8$, or $COR^8$; wherein $R^8$ is C1-C6 alkyl, C1-C6 cycloalkyl, amino, alkylamino, or dialkylamino; in the presence of a palladium catalyst, thereby forming a diaryl amine moiety.

In a further aspect, the compound produced has a structure represented by a formula:

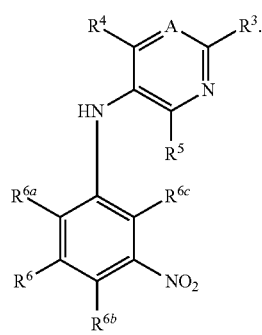

In a further aspect, the method further comprises reaction with $R^7X$, wherein $R^7$ is alkyl or haloalkyl; and wherein X is a leaving group.

In a further aspect, the compound produced has a structure represented by a formula:

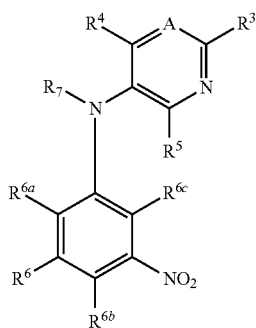

In a further aspect, the method further comprises the step of reducing the nitro group, thereby forming an amine, having a structure represented by a formula:

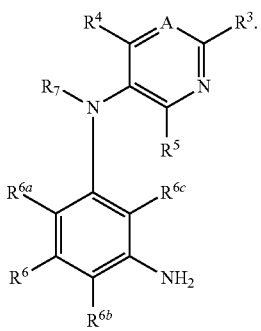

In a further aspect, the method further comprises the step of reacting with an activated carboxylic acid or acid halide compound, thereby forming an amide having a structure represented by a formula:

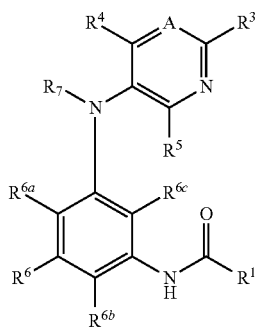

wherein $R^1$ is phenyl, pyridine, or thiazole; provided that where $R^1$ is phenyl, $R^1$ is substituted with 0-3 of $R^9$ and is meta-substituted relative to the amide carbonyl; provided that where $R^1$ is pyridine, the pyridine ring is considered a picolinamide (where the pyridine nitrogen is adjacent to the amide carbonyl) and is substituted with 0-3 of $R^9$; provided that where $R^1$ is thiazole, the thiazole ring is substituted with 0-2 of $R^9$.

In yet a further aspect, the compound produced exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound produced exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound produced exhibits negative allosteric modulation of mGluR5 after contacting a cell expressing mGluR5. In a further aspect, the compound produced exhibits partial or total inhibition of mGluR5 after contacting a cell expressing mGluR5.

10. Route X

In one aspect, optionally substituted diarylamine analogs can be prepared as shown below.

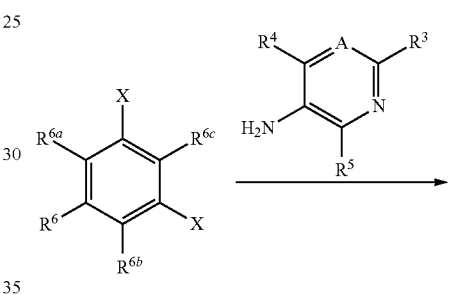

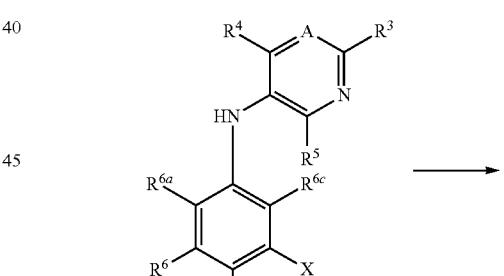

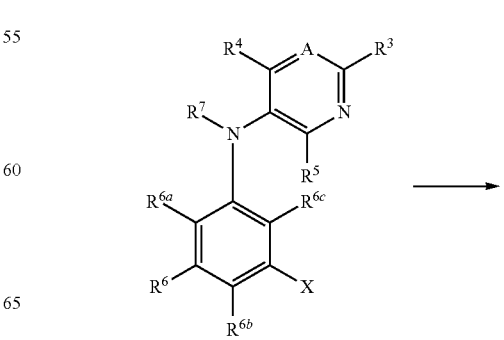

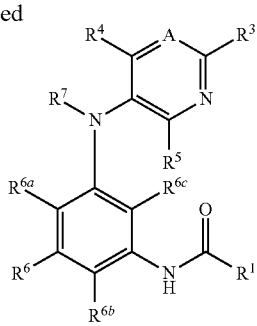

Compounds are represented in generic form, with substituents as noted in compound descriptions elsewhere herein. A more specific example is set forth below.

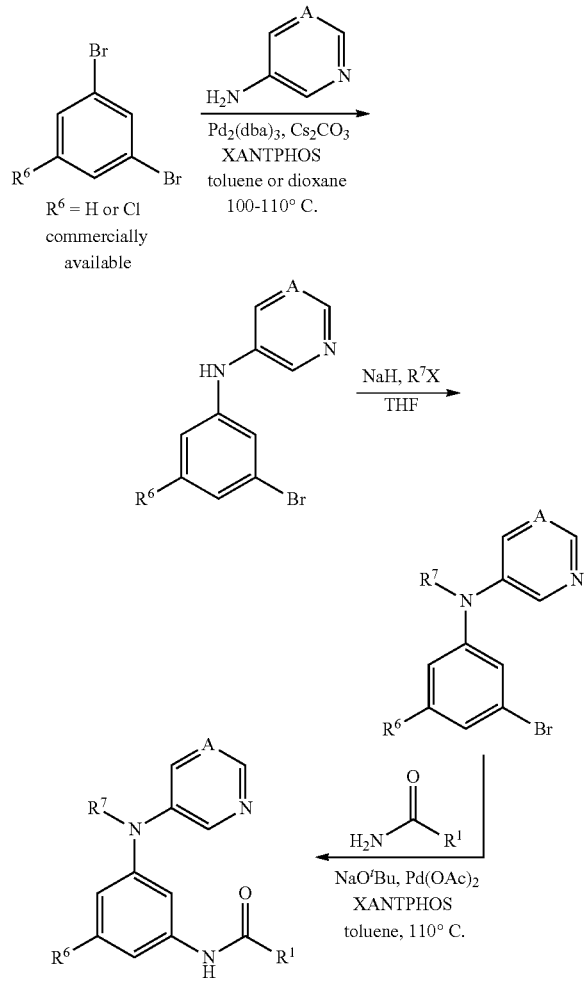

In one aspect, Route X begins with a commercially available substituted or unsubstituted 3-dihalobenzene compound. Alternatively, Route X begins with a substituted or unsubstituted 3-halophenyl sulfonate or 1,3-phenylene disulfonate. Such sulfonate compounds are either commercially available or readily prepared by one skilled in the art. Reaction proceeds with a substituted or unsubstituted 3-aminopyridine or a substituted or unsubstituted 5-aminopyrimidine using a palladium catalyzed coupling in order to link the two groups via a secondary amine as described in Route 6. Following the palladium coupling, the secondary amine can be reacted with an alkyl halide or alkyl group with another suitable leaving group under basic conditions to produce a tertiary amine. It will be appreciated that should the secondary rather than tertiary amine target be of interest that the aforementioned step would be skipped. The resulting intermediate can be coupled to a primary amide via a palladium catalyzed reaction as described in Route IV. Functional group transformation of the remaining substituents can yield further analogs.

Thus, in one aspect, the invention relates to a method of making a compound comprising the step of reacting a compound having a structure represented by a formula:

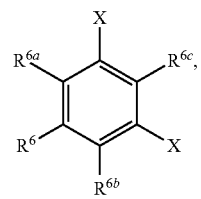

wherein each of $R^{6a}$, $R^{6b}$, and $R^{6c}$ is independently selected from hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^6$ is hydrogen, halogen, CN, C1-C4 alkyl, C3-C4 cycloalkyl, C1-C4 haloalkyl; wherein $R^8$ is C1-C6 alkyl, C1-C6 cycloalkyl, amino, alkylamino, or dialkylamino; wherein X is Cl, Br, I, or $OSO_2R^9$; wherein $R^9$ is alkyl, haloalkyl, or aryl; wherein each X is the same or different; with a second compound having a structure represented by a formula:

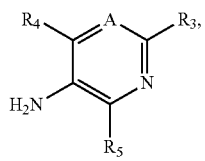

wherein A is $CR^2$ or N; wherein $R^4$ and $R^5$ are independently hydrogen, halogen, C1-C6 alkyl, C1-C6 haloalkyl, C1-C6 alkoxy, amino, hydroxyl, alkylamino, dialkylamino, CN, $SO_2R^8$, or $COR^8$; wherein $R^3$ is hydrogen, halogen, C1-C6 alkyl, C1-C6 haloalkyl, C1-C6 alkoxy, hydroxyl, CN, $SO_2R^8$, or $COR^8$; wherein $R^8$ is C1-C6 alkyl, C1-C6 cycloalkyl, amino, alkylamino, or dialkylamino; in the presence of a palladium catalyst, thereby forming a diaryl amine moiety.

In a further aspect, the compound produced has a structure represented by a formula:

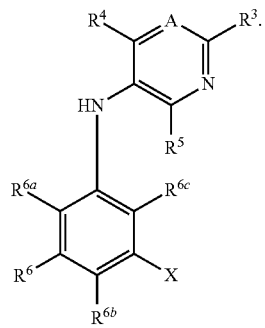

In a further aspect, the method further comprises reaction with R⁷X, wherein R⁷ is alkyl or haloalkyl; and wherein the X is bound to R⁷ is a leaving group.

In a further aspect, the compound produced has a structure represented by a formula:

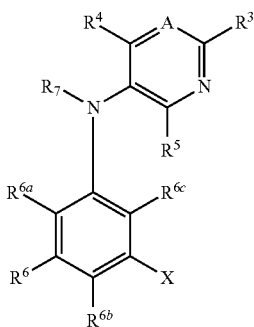

In a further aspect, the method further comprises the step of coupling with a primary amide via a palladium catalyzed reaction thereby forming an amide, having a structure represented by a formula:

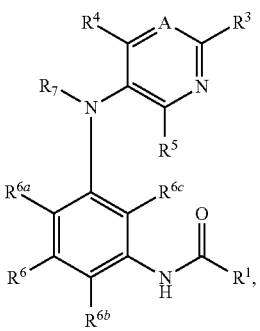

wherein $R^1$ is phenyl, pyridine, or thiazole; provided that where $R^1$ is phenyl, $R^1$ is substituted with 0-3 of $R^9$ and is meta-substituted relative to the amide carbonyl; provided that where $R^1$ is pyridine, the pyridine ring is considered a picolinamide (where the pyridine nitrogen is adjacent to the amide carbonyl) and is substituted with 0-3 of $R^9$; provided that where $R^1$ is thiazole, the thiazole ring is substituted with 0-2 of $R^9$.

In yet a further aspect, the compound produced exhibits negative allosteric modulation of mGluR5 response to glutamate as a decrease in response to non-maximal concentrations of glutamate in human embryonic kidney cells transfected with rat mGluR5 in the presence of the compound, compared to the response to glutamate in the absence of the compound. In a further aspect, human embryonic kidney cells are transfected with human mGluR5. In yet a further aspect, human embryonic kidney cells are transfected with mammalian mGluR5. In a further aspect, the compound produced exhibits partial or total inhibition of mGluR5 in response to glutamate as a decrease in response to non-maximal concentrations of glutamate in human embryonic kidney cells transfected with human, rat or mammalian mGluR5 in the presence of the compound, compared to the response to glutamate in the absence of the compound. In yet a further aspect, the compound produced exhibits negative allosteric modulation of mGluR5 after contacting a cell expressing mGluR5. In a further aspect, the compound produced exhibits partial or total inhibition of mGluR5 after contacting a cell expressing mGluR5.

It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

Table 1 below lists specific compounds as well as a preferred route for its synthesis, experimentally determined molecular mass, and mGluR5 activity determined in a cell-based assay. The mGluR5 activity was determined using the metabotropic glutamate receptor activity assays in human embryonic kidney cells as described herein, wherein the human embryonic kidney cells were transfected with rat mGluR5. The mGluR5 activity data for some compounds are shown as the average of at least three experiments with the standard error in these cases. If no error is indicated for the mGluR5 activity, the values given represent the results from a single experiment or the average of two experiments. The compounds in Table 1 were synthesized with methods identical or analogous to those shown herein. The requisite starting materials were commercially available, described in the literature, or readily synthesized by one skilled in the art of organic synthesis.

TABLE 1

| Structure | mGluR5 IC$_{50}$ (nM) | M + 1 | Synthetic Route Reference |
|---|---|---|---|
| 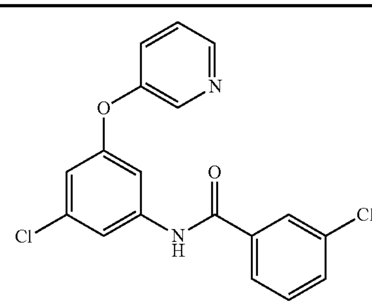 | 83 ± 9 | 359.0 | I and IV |

TABLE 1-continued

| Structure | mGluR5 IC$_{50}$ (nM) | M + 1 | Synthetic Route Reference |
|---|---|---|---|
| 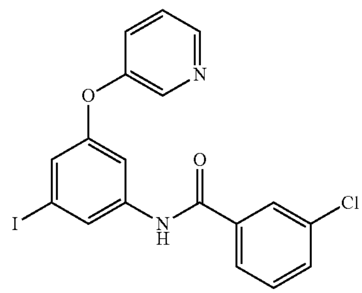 | 1030 | 451.0 | I |
| 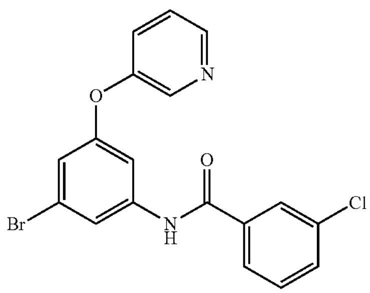 [SMILES: O=C(Nc1cc(Cl)cc(Oc2cccnc2)c1)c1cccc(Cl)c1] | 194 | 405.0 | I |
| 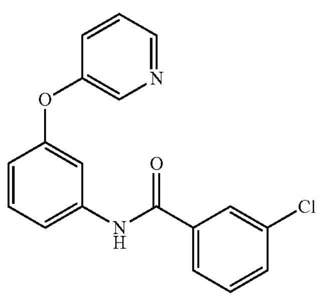 [SMILES: O=C(Nc1cccc(Oc2cccnc2)c1)c1cccc(Cl)c1] | 84 ± 14 | 325.1 | II |
| 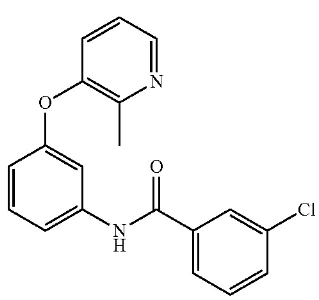 [SMILES: Cc1ncccc1Oc1cccc(NC(=O)c2cccc(Cl)c2)c1] | 2230 | 339.1 | II |
| 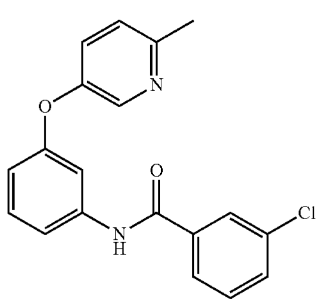 [SMILES: Cc1ccc(Oc2cccc(NC(=O)c3cccc(Cl)c3)c2)cn1] | 226 ± 40 | 339.1 | II |

TABLE 1-continued

| Structure | mGluR5 IC$_{50}$ (nM) | M + 1 | Synthetic Route Reference |
|---|---|---|---|
| 3-pyridyloxy-phenyl N-(3-methylbenzoyl)amide | 286 | 305.2 | II |
| 3-pyridyloxy-phenyl N-(3-fluorobenzoyl)amide | 2000 | 309.2 | II |
| 3-pyridyloxy-phenyl N-(3-methoxybenzoyl)amide | 3240 | 321.2 | II |
| 3-pyridyloxy-phenyl N-(3-trifluoromethylbenzoyl)amide | 5990 | 359.1 | II |
| 3-pyridyloxy-phenyl N-(3-cyanobenzoyl)amide | 536 | 316.2 | II |

TABLE 1-continued

| Structure | mGluR5 IC$_{50}$ (nM) | M + 1 | Synthetic Route Reference |
|---|---|---|---|
| 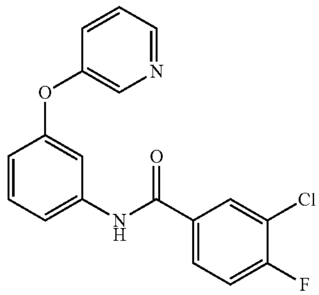 [SMILES: O=C(Nc1cccc(Oc2cccnc2)c1)c1ccc(F)c(Cl)c1] | 6250 | 343.0 | II |
| 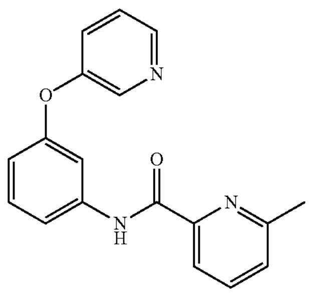 [SMILES: Cc1cccc(C(=O)Nc2cccc(Oc3cccnc3)c2)n1] | 532 | 306.2 | II |
| 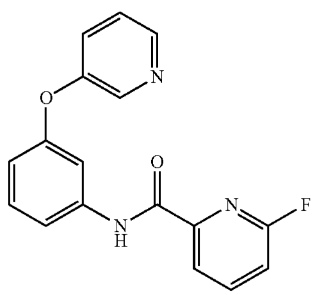 [SMILES: O=C(Nc1cccc(Oc2cccnc2)c1)c1cccc(F)n1] | 3530 | 310.1 | II |
| 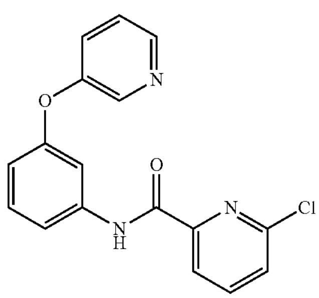 [SMILES: O=C(Nc1cccc(Oc2cccnc2)c1)c1cccc(Cl)n1] | 285 | 326.1 | II |
| 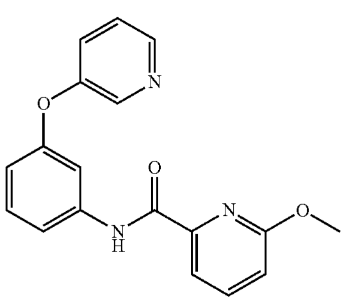 [SMILES: COc1cccc(C(=O)Nc2cccc(Oc3cccnc3)c2)n1] | 8340 | 322.2 | II |

TABLE 1-continued

| Structure | mGluR5 IC$_{50}$ (nM) | M + 1 | Synthetic Route Reference |
|---|---|---|---|
| 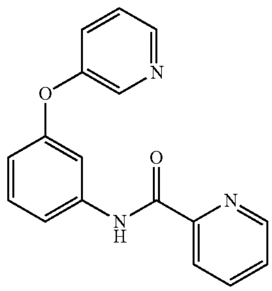 [SMILES: O=C(Nc1cccc(Oc2cccnc2)c1)c1ccccn1] | 1990 | 292.2 | II |
| 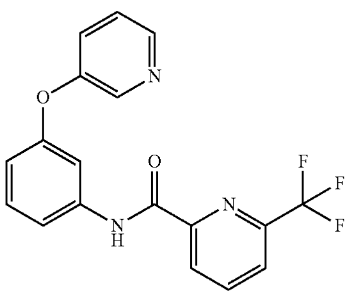 [SMILES: O=C(Nc1cccc(Oc2cccnc2)c1)c1cccc(C(F)(F)F)n1] | 2450 | 360.1 | II |
| 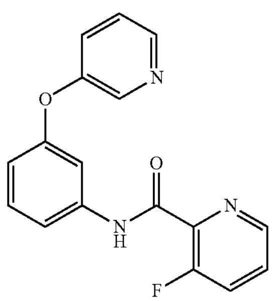 [SMILES: O=C(Nc1cccc(Oc2cccnc2)c1)c1ncccc1F] | >10,000 | 310.1 | II |
| 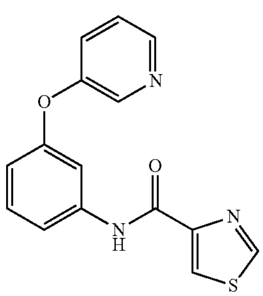 [SMILES: O=C(Nc1cccc(Oc2cccnc2)c1)c1cscn1] | 1270 | 298.1 | II |
| 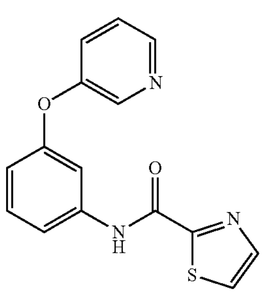 [SMILES: O=C(Nc1cccc(Oc2cccnc2)c1)c1nccs1] | 1600 | 298.1 | II |

TABLE 1-continued

| Structure | mGluR5 IC$_{50}$ (nM) | M + 1 | Synthetic Route Reference |
|---|---|---|---|
| 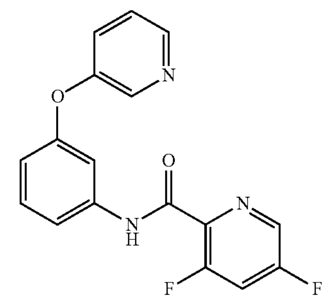 [SMILES: O=C(Nc1cccc(Oc2cccnc2)c1)c1ncc(F)cc1F] | >10,000 | 328.1 | II |
| 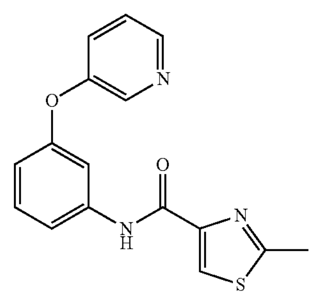 [SMILES: Cc1nc(C(=O)Nc2cccc(Oc3cccnc3)c2)cs1] | 4210 | 312.1 | II |
| 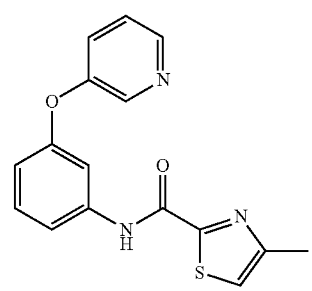 [SMILES: Cc1csc(C(=O)Nc2cccc(Oc3cccnc3)c2)n1] | 465 | 312.0 | II |
| 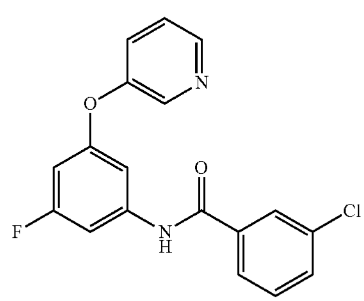 [SMILES: O=C(Nc1cc(F)cc(Oc2cccnc2)c1)c1cccc(Cl)c1] | 72 ± 25 | 343.0 | II |
| 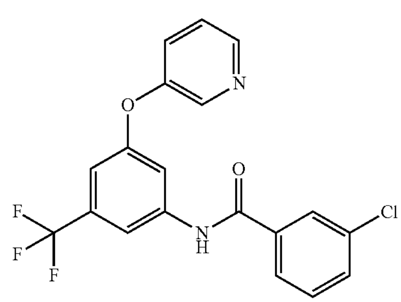 [SMILES: O=C(Nc1cc(Oc2cccnc2)cc(C(F)(F)F)c1)c1cccc(Cl)c1] | >30,000 | 393.0 | II |

TABLE 1-continued

| Structure | mGluR5 IC$_{50}$ (nM) | M + 1 | Synthetic Route Reference |
|---|---|---|---|
| 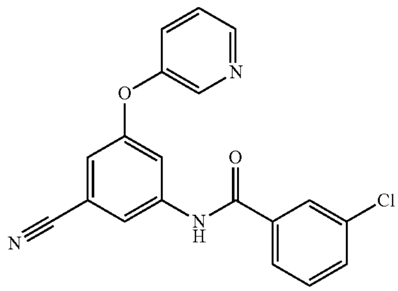 [SMILES: N#Cc1cc(NC(=O)c2cccc(Cl)c2)cc(Oc2cccnc2)c1] | 141 ± 57 | 350.1 | II |
| 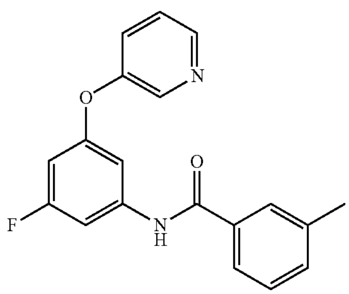 [SMILES: Cc1cccc(C(=O)Nc2cc(F)cc(Oc3cccnc3)c2)c1] | 19 | 323.1 | II |
| 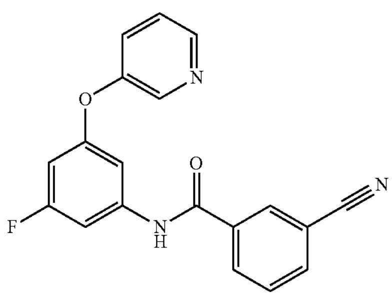 [SMILES: N#Cc1cccc(C(=O)Nc2cc(F)cc(Oc3cccnc3)c2)c1] | 36 ± 8 | 334.1 | II |
| 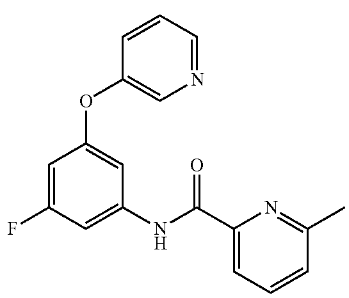 [SMILES: Cc1cccc(C(=O)Nc2cc(F)cc(Oc3cccnc3)c2)n1] | 414 | 324.1 | II |
| 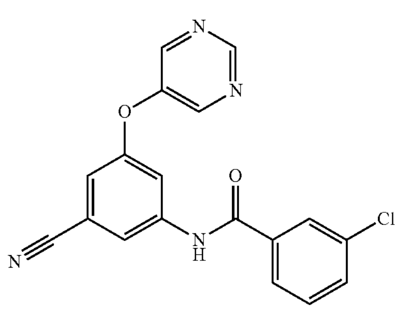 [SMILES: N#Cc1cc(NC(=O)c2cccc(Cl)c2)cc(Oc2cncnc2)c1] | 203 | 351.1 | II |

TABLE 1-continued

| Structure | mGluR5 IC$_{50}$ (nM) | M + 1 | Synthetic Route Reference |
|---|---|---|---|
| (3-chloro-5-(pyrimidin-5-yloxy)phenyl)-3-chlorobenzamide | 44 ± 5 | 360.0 | III and IV |
| (3-chloro-5-(pyrimidin-5-yloxy)phenyl)-3-methylbenzamide | 15 ± 3 | 340.1 | IV |
| (3-chloro-5-(pyrimidin-5-yloxy)phenyl)-3-cyanobenzamide | 63 ± 9 | 351.1 | IV |
| (3-chloro-5-(pyridin-3-yloxy)phenyl)-3-methylbenzamide | 56 | 339.1 | IV |
| (3-chloro-5-(pyridin-3-yloxy)phenyl)-3-cyanobenzamide | 68 | 350.1 | IV |

TABLE 1-continued

| Structure | mGluR5 IC$_{50}$ (nM) | M + 1 | Synthetic Route Reference |
|---|---|---|---|
| | >10,000 | 340.1 | IV |
| | >10,000 | 373.1 | IV |
| 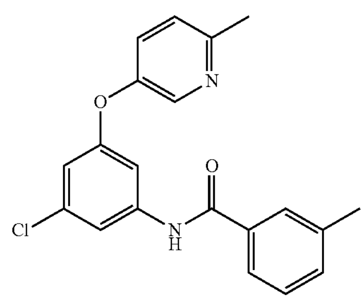 [SMILES: Cc1cccc(C(=O)Nc2cc(Cl)cc(Oc3ccc(C)nc3)c2)c1] | 6870 | 353.1 | IV |
| | >10,000 | 364.1 | IV |
| 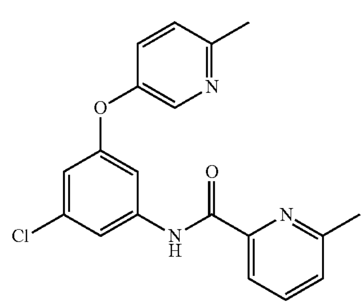 [SMILES: Cc1ccc(Oc2cc(Cl)cc(NC(=O)c3cccc(C)n3)c2)cn1] | 2980 | 354.1 | IV |

TABLE 1-continued

| Structure | mGluR5 IC$_{50}$ (nM) | M + 1 | Synthetic Route Reference |
|---|---|---|---|
| 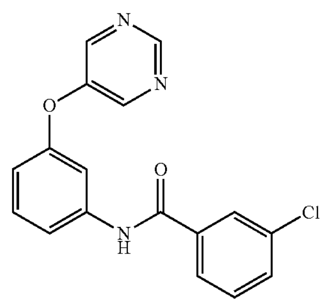 [SMILES: O=C(Nc1cccc(Oc2cncnc2)c1)c1cccc(Cl)c1] | 75 ± 13 | 326.1 | V |
| 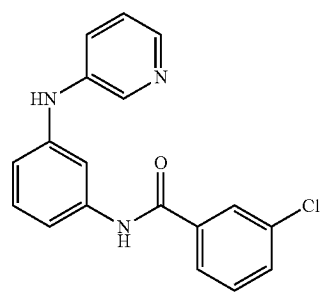 [SMILES: O=C(Nc1cccc(Nc2cccnc2)c1)c1cccc(Cl)c1] | 675 | 324.1 | VI |
| 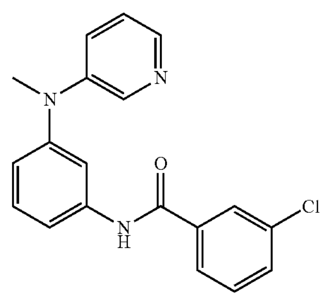 [SMILES: CN(c1cccnc1)c1cccc(NC(=O)c2cccc(Cl)c2)c1] | 31 ± 5 | 338.1 | VI |
| 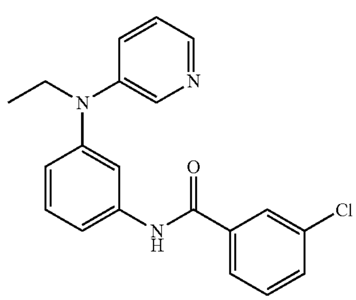 [SMILES: CCN(c1cccnc1)c1cccc(NC(=O)c2cccc(Cl)c2)c1] | 111 ± 21 | 352.0 | VI |
| 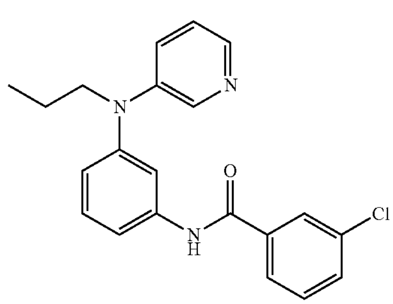 [SMILES: CCCN(c1cccnc1)c1cccc(NC(=O)c2cccc(Cl)c2)c1] | 5490 | 366.1 | VI |

TABLE 1-continued

| Structure | mGluR5 IC$_{50}$ (nM) | M + 1 | Synthetic Route Reference |
|---|---|---|---|
| 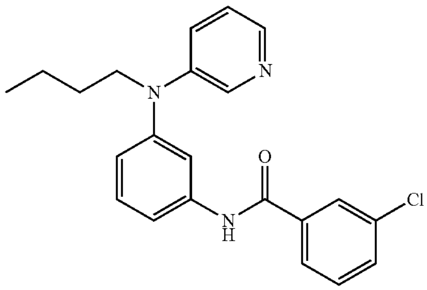 [SMILES: CCCCN(c1cccnc1)c1cccc(NC(=O)c2cccc(Cl)c2)c1] | >10,000 | 380.1 | VI |
| 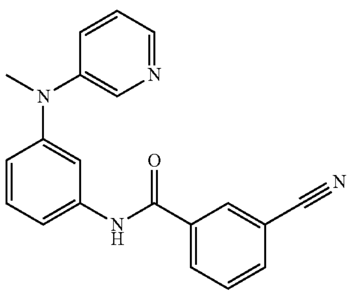 [SMILES: CN(c1cccnc1)c1cccc(NC(=O)c2cccc(C#N)c2)c1] | 50 ± 3 | 329.1 | VI |
| 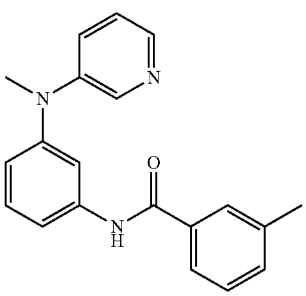 [SMILES: Cc1cccc(C(=O)Nc2cccc(N(C)c3cccnc3)c2)c1] | 107 | 318.2 | VI |
| 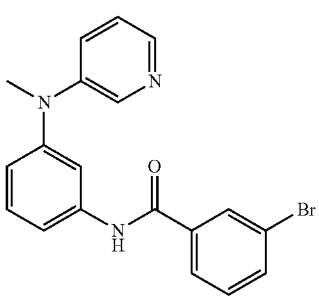 [SMILES: CN(c1cccnc1)c1cccc(NC(=O)c2cccc(Br)c2)c1] | 83 | 382.1 | VI |
| 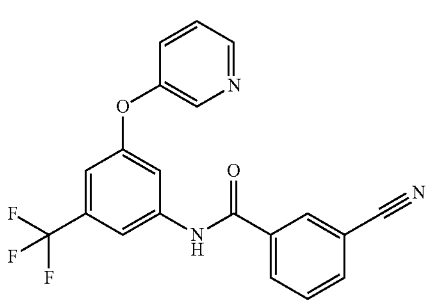 [SMILES: N#Cc1cccc(C(=O)Nc2cc(Oc3cccnc3)cc(C(F)(F)F)c2)c1] | >30,000 | 384.1 | II |

TABLE 1-continued

| Structure | mGluR5 IC$_{50}$ (nM) | M + 1 | Synthetic Route Reference |
|---|---|---|---|
| 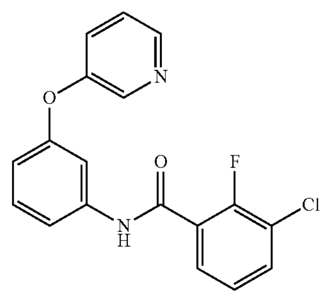 [SMILES: O=C(Nc1cccc(Oc2cccnc2)c1)c1cccc(Cl)c1F] | >10,000 | 343.8 | II |
| 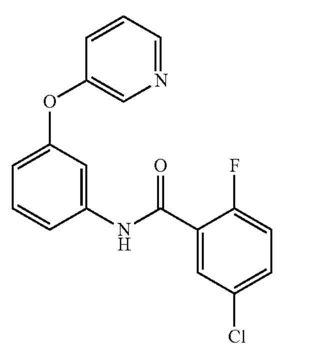 [SMILES: O=C(Nc1cccc(Oc2cccnc2)c1)c1cc(Cl)ccc1F] | 201 | 343.2 | II |
| 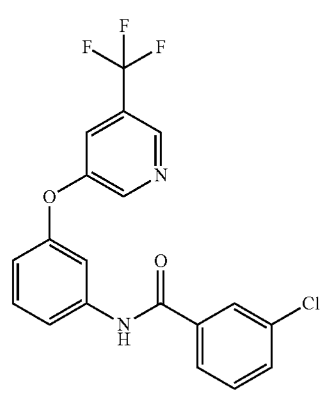 [SMILES: O=C(Nc1cccc(Oc2cncc(C(F)(F)F)c2)c1)c1cccc(Cl)c1] | 2750 | 393.0 | V |
| 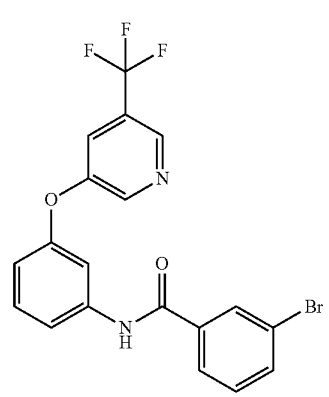 [SMILES: O=C(Nc1cccc(Oc2cncc(C(F)(F)F)c2)c1)c1cccc(Br)c1] | 4490 | 437.0 | V |

TABLE 1-continued

| Structure | mGluR5 IC$_{50}$ (nM) | M + 1 | Synthetic Route Reference |
|---|---|---|---|
| 5-chloropyridin-3-yl ether of N-(3-chlorobenzoyl)-3-aminophenol | 274 | 359.0 | II |
| 5-chloropyridin-3-yl ether of N-(3-cyanobenzoyl)-3-aminophenol | 155 | 350.0 | II |
| 5-chloropyridin-3-yl ether of N-(3-bromobenzoyl)-3-aminophenol | 445 | 405.0 | II |
| 5-fluoropyridin-3-yl ether of N-(3-chlorobenzoyl)-3-aminophenol | 93 ± 12 | 343.0 | II |

TABLE 1-continued

| Structure | mGluR5 IC$_{50}$ (nM) | M + 1 | Synthetic Route Reference |
|---|---|---|---|
| (5-fluoropyridin-3-yl)oxy-phenyl N-(3-cyanobenzamide) | 153 ± 23 | 334.1 | II |
| (5-fluoropyridin-3-yl)oxy-phenyl N-(3-bromobenzamide) | 124 | 387.0 | II |
| (5-trifluoromethylpyridin-3-yl)oxy-phenyl N-(3-cyanobenzamide) | 5800 | 384.1 | V |
| 3-chloro-5-[(5-fluoropyridin-3-yl)oxy]phenyl N-(3-chlorobenzamide) | 435 | 377.0 | III |

TABLE 1-continued

| Structure | mGluR5 IC$_{50}$ (nM) | M + 1 | Synthetic Route Reference |
|---|---|---|---|
| 3-chloro-5-(5-fluoropyridin-3-yloxy)phenyl 3-cyanobenzamide | 228 | 368.0 | III |
| 3-chloro-5-(5-fluoropyridin-3-yloxy)phenyl 6-chloropicolinamide | 5370 | 378.0 | III |
| 3-chloro-5-(5-fluoropyridin-3-yloxy)phenyl 6-(trifluoromethyl)picolinamide | >10,000 | 412.0 | III |
| 3-cyano-5-(pyrimidin-5-yloxy)phenyl 3-chlorobenzamide | 203 | 351.1 | II |

TABLE 1-continued

| Structure | mGluR5 IC$_{50}$ (nM) | M + 1 | Synthetic Route Reference |
|---|---|---|---|
| 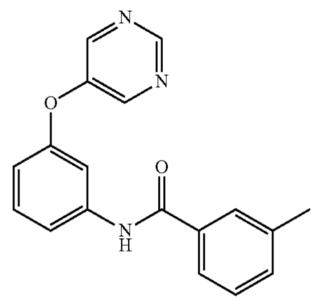 [SMILES: Cc1cccc(C(=O)Nc2cccc(Oc3cncnc3)c2)c1] | 236 | 306.1 | V |
| 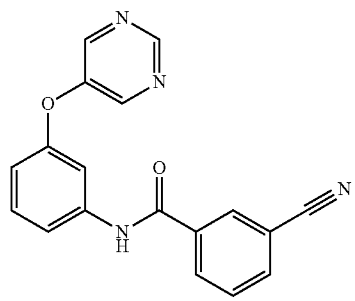 [SMILES: N#Cc1cccc(C(=O)Nc2cccc(Oc3cncnc3)c2)c1] | 580 | 317.1 | V |
| 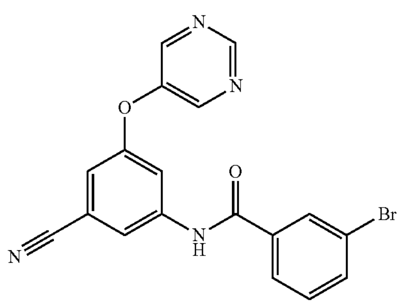 [SMILES: N#Cc1cc(NC(=O)c2cccc(Br)c2)cc(Oc2cncnc2)c1] | 57 ± 6 | 395.0 | II |
| 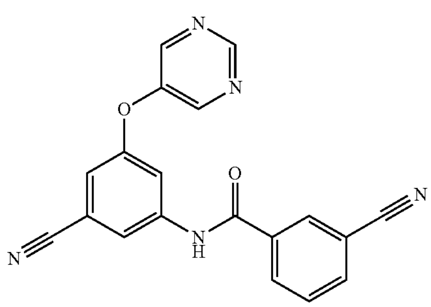 [SMILES: N#Cc1cc(NC(=O)c2cccc(C#N)c2)cc(Oc2cncnc2)c1] | 443 | 342.1 | II |
| 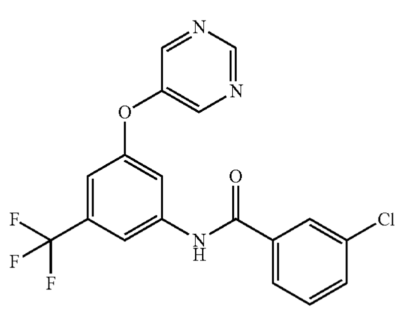 [SMILES: O=C(Nc1cc(Oc2cncnc2)cc(C(F)(F)F)c1)c1cccc(Cl)c1] | 3490 | 393.9 | II |

TABLE 1-continued

| Structure | mGluR5 IC$_{50}$ (nM) | M + 1 | Synthetic Route Reference |
|---|---|---|---|
| N-(3-(pyrimidin-5-yloxy)-5-(trifluoromethyl)phenyl)-3-cyanobenzamide | 5060 | 385.0 | II |
| 3-bromo-N-(3-(pyrimidin-5-yloxy)phenyl)benzamide | 53 | 370.0 | II |
| 3-chloro-N-(3-fluoro-5-(pyrimidin-5-yloxy)phenyl)benzamide | 17 ± 4 | 344.1 | II |
| N-(3-fluoro-5-(pyrimidin-5-yloxy)phenyl)-3-cyanobenzamide | 61 ± 15 | 335.1 | II |
| 3-bromo-N-(3-fluoro-5-(pyrimidin-5-yloxy)phenyl)benzamide | 24 ± 4 | 390.0 | II |

TABLE 1-continued
| Structure | mGluR5 IC$_{50}$ (nM) | M + 1 | Synthetic Route Reference |
|---|---|---|---|
| 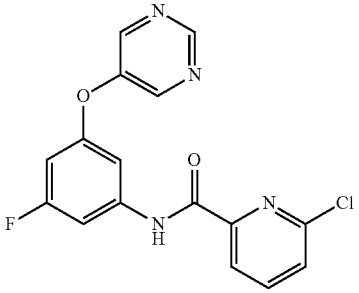 [SMILES: O=C(Nc1cc(F)cc(Oc2cncnc2)c1)c1cccc(Cl)n1] | 186 | 345.2 | II |
| 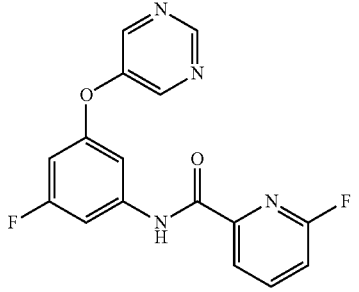 [SMILES: O=C(Nc1cc(F)cc(Oc2cncnc2)c1)c1cccc(F)n1] | 2560 | 329.2 | II |
| 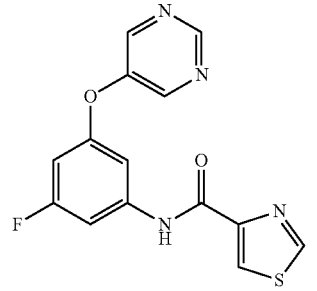 [SMILES: O=C(Nc1cc(F)cc(Oc2cncnc2)c1)c1cscn1] | 94 | 317.0 | II |
| 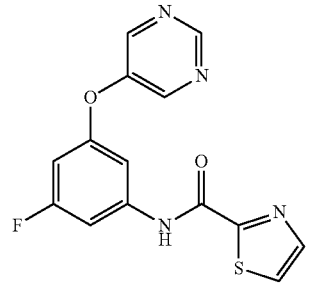 [SMILES: O=C(Nc1cc(F)cc(Oc2cncnc2)c1)c1nccs1] | 384 | 317.2 | II |
| 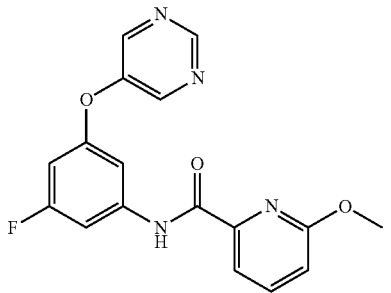 [SMILES: COc1cccc(C(=O)Nc2cc(F)cc(Oc3cncnc3)c2)n1] | 4000 | 341.1 | II |

TABLE 1-continued

| Structure | mGluR5 IC$_{50}$ (nM) | M + 1 | Synthetic Route Reference |
|---|---|---|---|
| 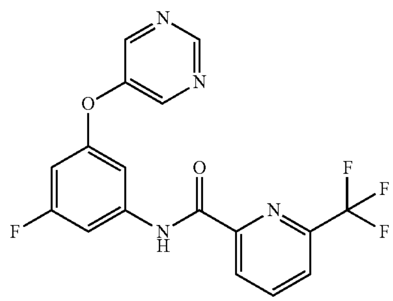 [SMILES: O=C(Nc1cc(F)cc(Oc2cncnc2)c1)c1cccc(C(F)(F)F)n1] | 1680 | 379.1 | II |
| 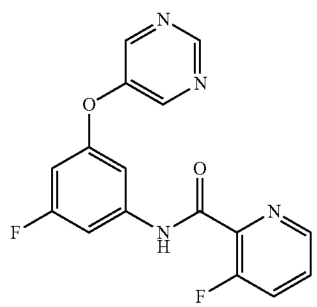 [SMILES: O=C(Nc1cc(F)cc(Oc2cncnc2)c1)c1ncccc1F] | >10,000 | 329.1 | II |
| 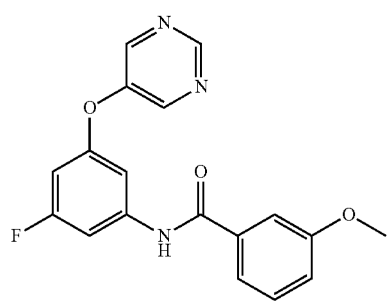 [SMILES: COc1cccc(C(=O)Nc2cc(F)cc(Oc3cncnc3)c2)c1] | 311 | 340.2 | II |
| 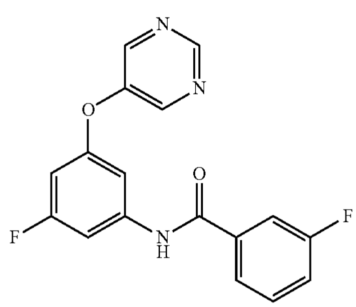 [SMILES: O=C(Nc1cc(F)cc(Oc2cncnc2)c1)c1cccc(F)c1] | 288 | 328.2 | II |
| 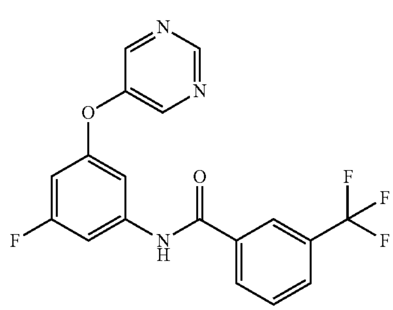 [SMILES: O=C(Nc1cc(F)cc(Oc2cncnc2)c1)c1cccc(C(F)(F)F)c1] | 663 | 378.2 | II |

TABLE 1-continued

| Structure | mGluR5 IC$_{50}$ (nM) | M + 1 | Synthetic Route Reference |
|---|---|---|---|
| 3-cyano-N-(3-fluoro-5-(pyrimidin-5-yloxy)phenyl)-5-fluorobenzamide | 6240 | 353.2 | II |
| N-(3-fluoro-5-(pyrimidin-5-yloxy)phenyl)picolinamide | 112 | 311.2 | II |
| 3-cyano-N-(3,4-difluoro-5-(pyrimidin-5-yloxy)phenyl)benzamide | 573 | 353.2 | V |
| 3-cyano-N-(4-fluoro-3-(pyrimidin-5-yloxy)phenyl)benzamide | 2420 | 335.2 | V |

TABLE 1-continued

| Structure | mGluR5 IC$_{50}$ (nM) | M + 1 | Synthetic Route Reference |
|---|---|---|---|
| 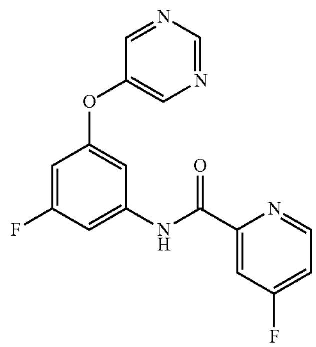 [SMILES: O=C(Nc1cc(F)cc(Oc2cncnc2)c1)c1cc(F)ccn1] | 15 (n = 2) | 329.2 | II |
| 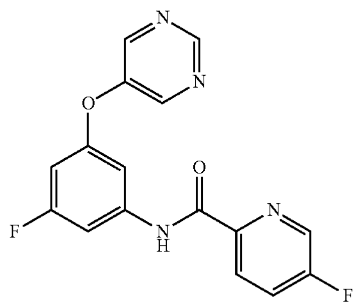 [SMILES: O=C(Nc1cc(F)cc(Oc2cncnc2)c1)c1ccc(F)cn1] | 384 | 329.2 | II |
| | >30,000 | 388.2 | II |
| | >30,000 | 417.2 | II |
| 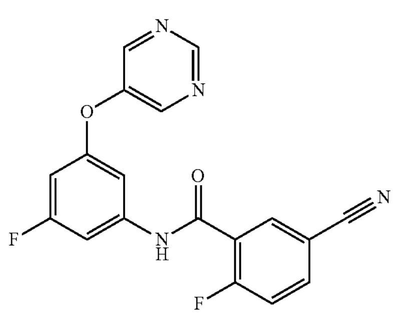 [SMILES: N#Cc1ccc(F)c(C(=O)Nc2cc(F)cc(Oc3cncnc3)c2)c1] | 87 | 353.2 | II |

TABLE 1-continued

| Structure | mGluR5 IC$_{50}$ (nM) | M + 1 | Synthetic Route Reference |
|---|---|---|---|
| 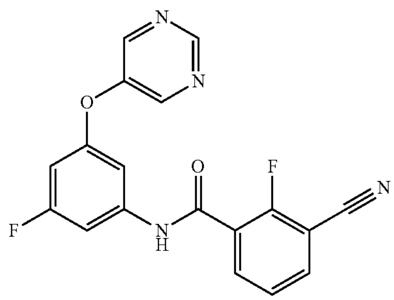 [SMILES: N#Cc1cccc(C(=O)Nc2cc(F)cc(Oc3cncnc3)c2)c1F] | 6110 | 353.2 | II |
| 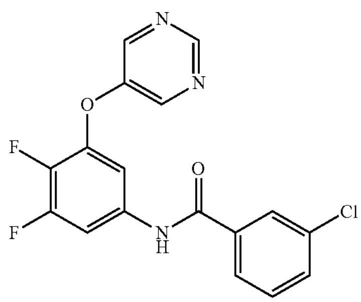 [SMILES: O=C(Nc1cc(F)c(F)c(Oc2cncnc2)c1)c1cccc(Cl)c1] | 166 | 362.0 | V |
| 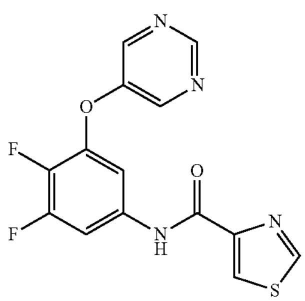 [SMILES: O=C(Nc1cc(F)c(F)c(Oc2cncnc2)c1)c1cscn1] | 5500 | 335.0 | V |
| 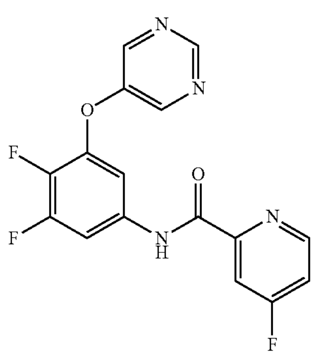 [SMILES: O=C(Nc1cc(F)c(F)c(Oc2cncnc2)c1)c1cc(F)ccn1] | 1690 | 347.1 | V |
| 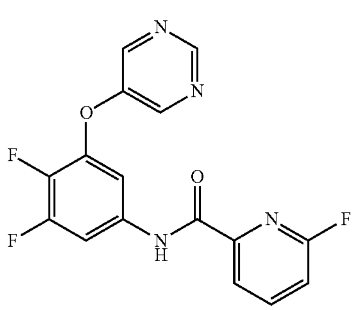 [SMILES: O=C(Nc1cc(F)c(F)c(Oc2cncnc2)c1)c1cccc(F)n1] | 630 | 347.1 | V |

TABLE 1-continued

| Structure | mGluR5 IC$_{50}$ (nM) | M + 1 | Synthetic Route Reference |
|---|---|---|---|
| 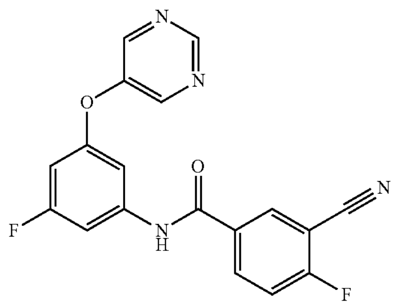 [SMILES: N#Cc1cc(C(=O)Nc2cc(F)cc(Oc3cncnc3)c2)ccc1F] | 1640 | 353.0 | II |
| 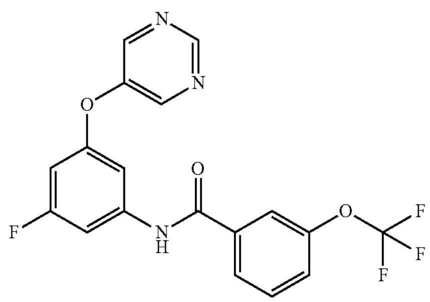 [SMILES: O=C(Nc1cc(F)cc(Oc2cncnc2)c1)c1cccc(OC(F)(F)F)c1] | 417 | 394.1 | II |
| 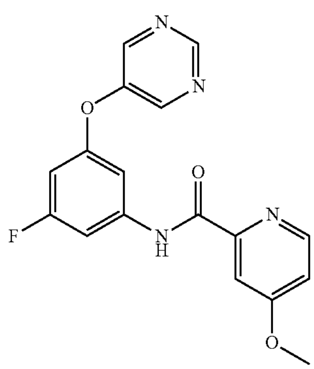 [SMILES: COc1ccnc(C(=O)Nc2cc(F)cc(Oc3cncnc3)c2)c1] | 5.4 | 341.1 | VII |
| 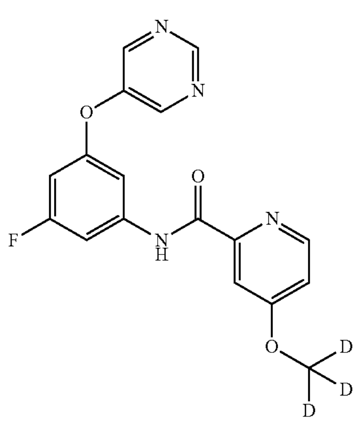 [SMILES: [2H]C([2H])([2H])Oc1ccnc(C(=O)Nc2cc(F)cc(Oc3cncnc3)c2)c1] | 7.1 | 344.2 | VII |

TABLE 1-continued

| Structure | mGluR5 IC$_{50}$ (nM) | M + 1 | Synthetic Route Reference |
|---|---|---|---|
| 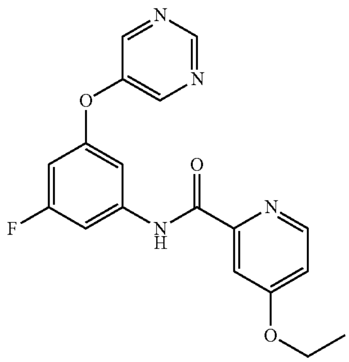 [SMILES: CCOc1ccnc(C(=O)Nc2cc(F)cc(Oc3cncnc3)c2)c1] | 27 | 355.1 | VII |
| 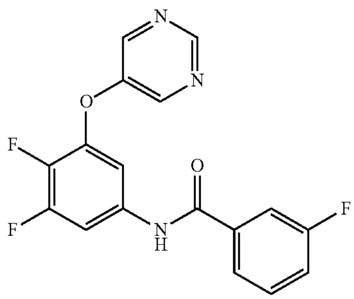 [SMILES: O=C(Nc1cc(F)c(F)c(Oc2cncnc2)c1)c1cccc(F)c1] | 2050 | 346.1 | V |
| 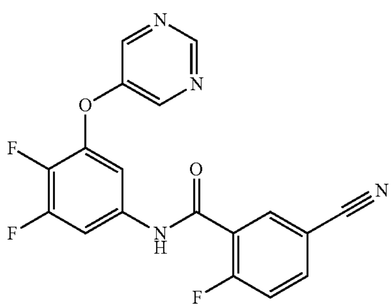 [SMILES: N#Cc1ccc(F)c(C(=O)Nc2cc(F)c(F)c(Oc3cncnc3)c2)c1] | 6580 | 371.1 | V |
| 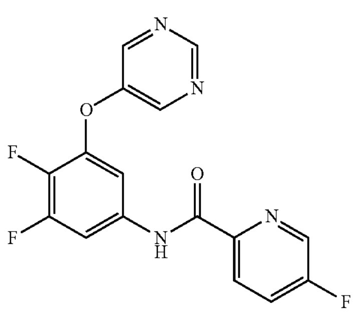 [SMILES: O=C(Nc1cc(F)c(F)c(Oc2cncnc2)c1)c1ccc(F)cn1] | 5420 | 347.0 | V |
| 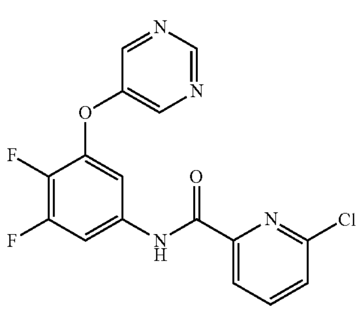 [SMILES: O=C(Nc1cc(F)c(F)c(Oc2cncnc2)c1)c1cccc(Cl)n1] | 246 | 363.0 | V |

TABLE 1-continued

| Structure | mGluR5 IC$_{50}$ (nM) | M + 1 | Synthetic Route Reference |
|---|---|---|---|
| 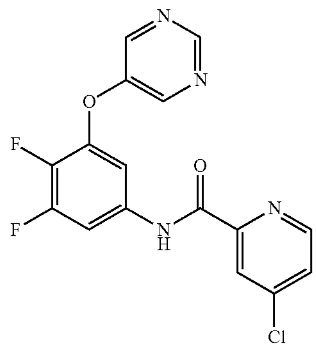 [SMILES: O=C(Nc1cc(F)c(F)c(Oc2cncnc2)c1)c1cc(Cl)ccn1] | 281 | 363.1 | V |
| 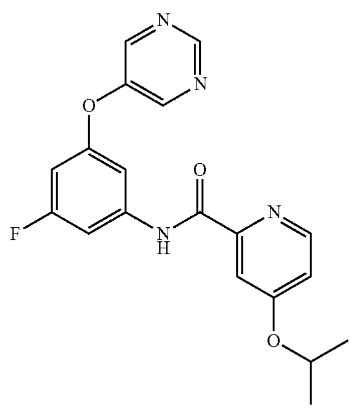 [SMILES: CC(C)Oc1ccnc(C(=O)Nc2cc(F)cc(Oc3cncnc3)c2)c1] | 230 | 369.2 | II |
| 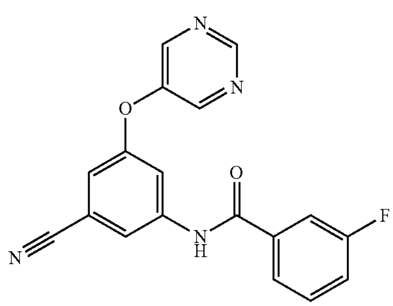 [SMILES: N#Cc1cc(NC(=O)c2cccc(F)c2)cc(Oc2cncnc2)c1] | 724 | 335.1 | VIII |
| 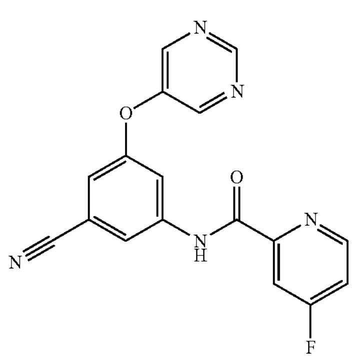 [SMILES: N#Cc1cc(NC(=O)c2cc(F)ccn2)cc(Oc2cncnc2)c1] | 92 | 336.1 | VIII |

TABLE 1-continued

| Structure | mGluR5 IC$_{50}$ (nM) | M + 1 | Synthetic Route Reference |
|---|---|---|---|
| (5-fluoro-3-(pyrimidin-5-yloxy)phenyl)-N-(4-hydroxypyridine-2-carboxamide) | 7670 | 327.2 | VII |
| (3-cyano-5-(pyrimidin-5-yloxy)phenyl)-N-(4-methoxypyridine-2-carboxamide) | 63 | 348.1 | VII |
| (3-fluoro-5-(pyrimidin-5-yloxy)phenyl)-N-(2-(trifluoromethyl)thiazole-4-carboxamide) | 1240 | 385.0 | II |
| 3-chloro-N-(3-fluoro-5-(methyl(pyridin-3-yl)amino)phenyl)benzamide | 79 ± 15 | 356.1 | IX |

TABLE 1-continued

| Structure | mGluR5 IC$_{50}$ (nM) | M + 1 | Synthetic Route Reference |
|---|---|---|---|
| 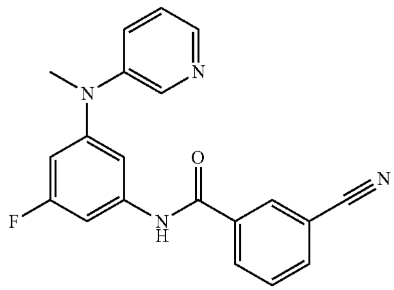 [SMILES: CN(c1cccnc1)c1cc(F)cc(NC(=O)c2cccc(C#N)c2)c1] | 71 ± 15 | 347.1 | IX |
| 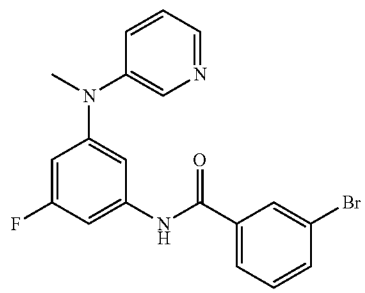 [SMILES: CN(c1cccnc1)c1cc(F)cc(NC(=O)c2cccc(Br)c2)c1] | 167 | 402.0 | IX |
| 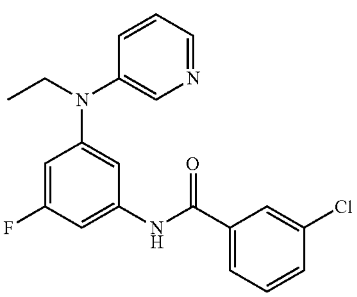 [SMILES: CCN(c1cccnc1)c1cc(F)cc(NC(=O)c2cccc(Cl)c2)c1] | 388 | 370.1 | IX |
| 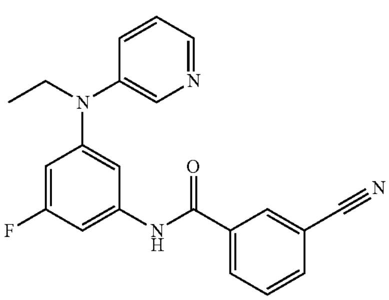 [SMILES: CCN(c1cccnc1)c1cc(F)cc(NC(=O)c2cccc(C#N)c2)c1] | 264 | 361.1 | IX |
| 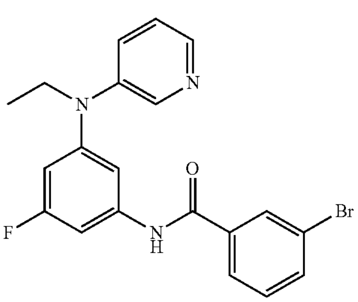 [SMILES: CCN(c1cccnc1)c1cc(F)cc(NC(=O)c2cccc(Br)c2)c1] | 656 | 416.1 | IX |

TABLE 1-continued
| Structure | mGluR5 IC$_{50}$ (nM) | M + 1 | Synthetic Route Reference |
|---|---|---|---|
| 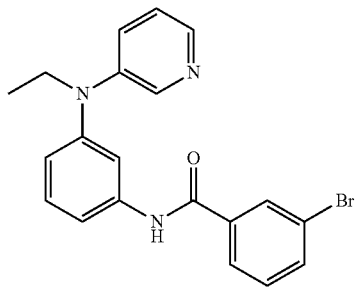 [SMILES: CCN(c1cccnc1)c1cccc(NC(=O)c2cccc(Br)c2)c1] | 208 | 396.1 | VI |
| 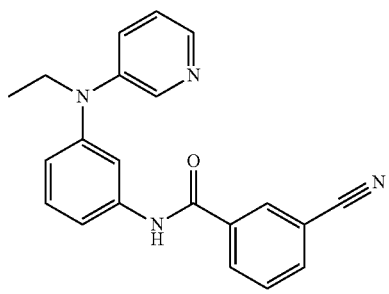 [SMILES: CCN(c1cccnc1)c1cccc(NC(=O)c2cccc(C#N)c2)c1] | 120 | 343.1 | VI |
| 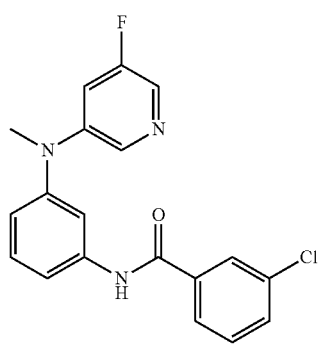 [SMILES: CN(c1cncc(F)c1)c1cccc(NC(=O)c2cccc(Cl)c2)c1] | 57 ± 9 | 356.1 | X |
| 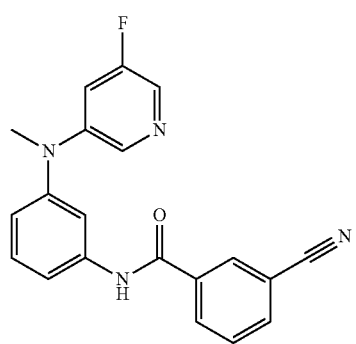 [SMILES: CN(c1cncc(F)c1)c1cccc(NC(=O)c2cccc(C#N)c2)c1] | 32 ± 5 | 347.1 | X |

TABLE 1-continued

| Structure | mGluR5 IC$_{50}$ (nM) | M + 1 | Synthetic Route Reference |
|---|---|---|---|
| 5-fluoropyridin-3-yl, N-methyl, 3-aminophenyl, N-H, 3-bromobenzamide | 32 | 400.0 | |
| 5-chloropyridin-3-yl, N-methyl, 3-aminophenyl, N-H, 3-chlorobenzamide | >10,000 | 372.0 | X |
| 5-chloropyridin-3-yl, N-methyl, 3-aminophenyl, N-H, 3-cyanobenzamide | >10,000 | 363.1 | X |
| 5-(trifluoromethyl)pyridin-3-yl, N-methyl, 3-aminophenyl, N-H, 3-chlorobenzamide | 311 | 406.1 | VI |

TABLE 1-continued

| Structure | mGluR5 IC$_{50}$ (nM) | M + 1 | Synthetic Route Reference |
|---|---|---|---|
| [3-cyano-N-(3-(N-methyl-N-(5-(trifluoromethyl)pyridin-3-yl)amino)phenyl)benzamide] | 261 | 397.1 | VI |
| [3-bromo-N-(3-(N-methyl-N-(5-(trifluoromethyl)pyridin-3-yl)amino)phenyl)benzamide] | 553 | 450.0 | VI |
| [3-chloro-N-(3-(N-methyl-N-(pyrimidin-5-yl)amino)phenyl)benzamide] | 4.6 | 339.1 | X |
| [3-cyano-N-(3-(N-ethyl-N-(pyrimidin-5-yl)amino)phenyl)benzamide] | 43 | 344.1 | X |

TABLE 1-continued

| Structure | mGluR5 IC$_{50}$ (nM) | M + 1 | Synthetic Route Reference |
|---|---|---|---|
| (3-cyano-N-(3-(methyl(pyrimidin-5-yl)amino)phenyl)benzamide) | 84 ± 14 | 330.1 | VI |
| (3-bromo-N-(3-(methyl(pyrimidin-5-yl)amino)phenyl)benzamide) | 10 ± 2 | 385.0 | VI |
| (3-fluoro-N-(3-(methyl(pyrimidin-5-yl)amino)phenyl)benzamide) | 21 ± 4 | 323.1 | VI |
| (3-methoxy-N-(3-(methyl(pyrimidin-5-yl)amino)phenyl)benzamide) | 108 ± 32 | 335.1 | VI |
| (6-chloro-N-(3-(methyl(pyrimidin-5-yl)amino)phenyl)picolinamide) | 5.4 ± 0.4 | 340.1 | VI |

TABLE 1-continued

| Structure | mGluR5 IC$_{50}$ (nM) | M + 1 | Synthetic Route Reference |
|---|---|---|---|
| 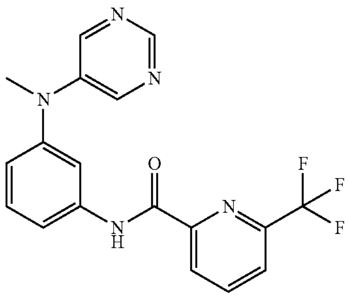 [SMILES: CN(c1cncnc1)c1cccc(NC(=O)c2cccc(C(F)(F)F)n2)c1] | 34 ± 7 | 374.1 | VI |
| 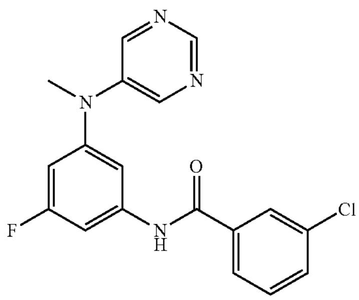 [SMILES: CN(c1cncnc1)c1cc(F)cc(NC(=O)c2cccc(Cl)c2)c1] | 16 | 357.1 | IX |
| 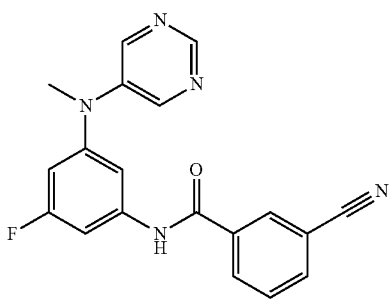 [SMILES: CN(c1cncnc1)c1cc(F)cc(NC(=O)c2cccc(C#N)c2)c1] | 54 | 348.1 | IX |
| 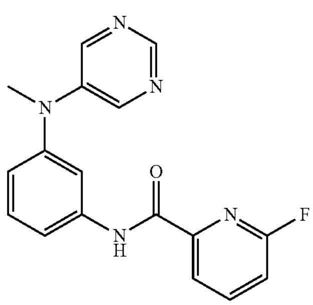 | 11 | 324.1 | VI |
| 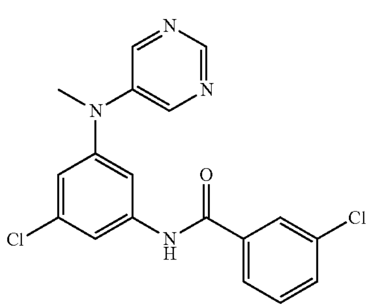 [SMILES: CN(c1cncnc1)c1cc(Cl)cc(NC(=O)c2cccc(Cl)c2)c1] | 138 | 373.0 | X |

TABLE 1-continued

| Structure | mGluR5 IC$_{50}$ (nM) | M + 1 | Synthetic Route Reference |
|---|---|---|---|
| 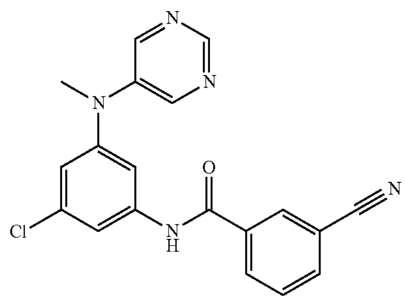 [SMILES: CN(c1cncnc1)c1cc(Cl)cc(NC(=O)c2cccc(C#N)c2)c1] | 75 | 364.1 | X |
| 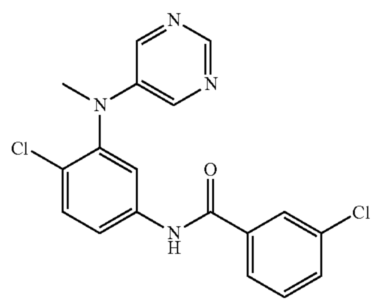 [SMILES: CN(c1cncnc1)c1cc(NC(=O)c2cccc(Cl)c2)ccc1Cl] | 43 | 373.1 | VI |
| 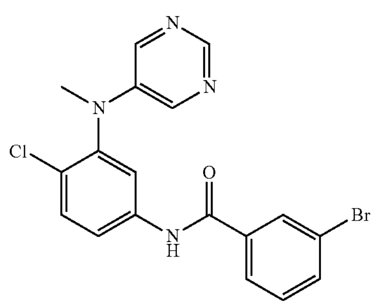 [SMILES: CN(c1cncnc1)c1cc(NC(=O)c2cccc(Br)c2)ccc1Cl] | 36 | 417.0 | VI |
| 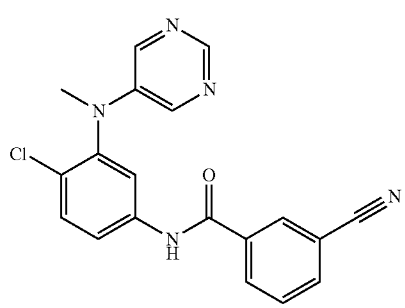 [SMILES: CN(c1cncnc1)c1cc(NC(=O)c2cccc(C#N)c2)ccc1Cl] | 59 | 364.1 | VI |
| 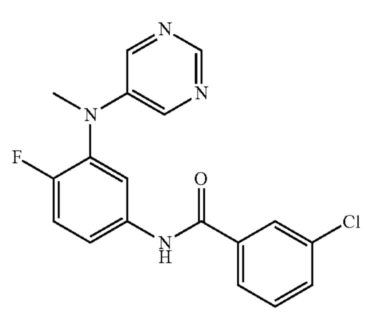 [SMILES: CN(c1cncnc1)c1cc(NC(=O)c2cccc(Cl)c2)ccc1F] | 10 | 357.1 | VI |

TABLE 1-continued

| Structure | mGluR5 IC$_{50}$ (nM) | M + 1 | Synthetic Route Reference |
|---|---|---|---|
| *N-(4-fluoro-3-(methyl(pyrimidin-5-yl)amino)phenyl)-3-bromobenzamide* | 14 | 401.0 | VI |
| *N-(4-fluoro-3-(methyl(pyrimidin-5-yl)amino)phenyl)-3-cyanobenzamide* | 51 | 348.1 | VI |
| *N-(2-fluoro-5-(methyl(pyrimidin-5-yl)amino)phenyl)-3-chlorobenzamide* | 80 | 357.1 | VI |
| *N-(2-fluoro-5-(methyl(pyrimidin-5-yl)amino)phenyl)-3-cyanobenzamide* | 334 | 348.1 | VI |
| *N-(2-fluoro-5-(methyl(pyrimidin-5-yl)amino)phenyl)-3-bromobenzamide* | 37 | 403.0 | VI |

TABLE 1-continued

| Structure | mGluR5 IC$_{50}$ (nM) | M + 1 | Synthetic Route Reference |
|---|---|---|---|
| 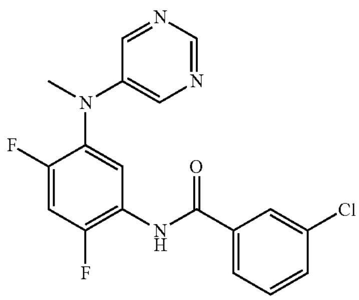 [SMILES: CN(c1cncnc1)c1cc(NC(=O)c2cccc(Cl)c2)c(F)cc1F] | 31 | 375.1 | VI |
| 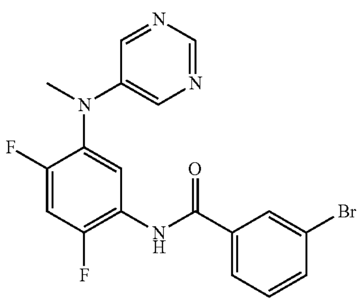 [SMILES: CN(c1cncnc1)c1cc(NC(=O)c2cccc(Br)c2)c(F)cc1F] | 50 | 419.0 | VI |
| 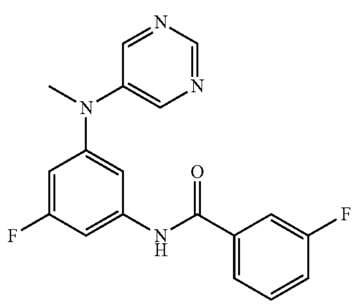 [SMILES: CN(c1cncnc1)c1cc(F)cc(NC(=O)c2cccc(F)c2)c1] | 127 | 341.1 | IX |
| 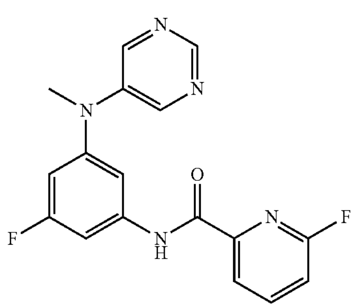 [SMILES: CN(c1cncnc1)c1cc(F)cc(NC(=O)c2cccc(F)n2)c1] | 29 | 342.1 | IX |
| 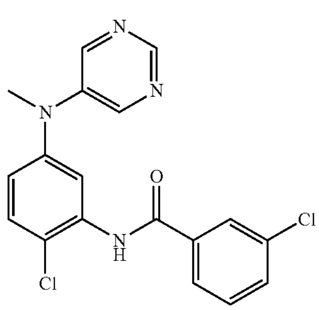 [SMILES: CN(c1cncnc1)c1ccc(Cl)c(NC(=O)c2cccc(Cl)c2)c1] | 2430 | 373.1 | VI |

TABLE 1-continued
| Structure | mGluR5 IC$_{50}$ (nM) | M + 1 | Synthetic Route Reference |
|---|---|---|---|
| 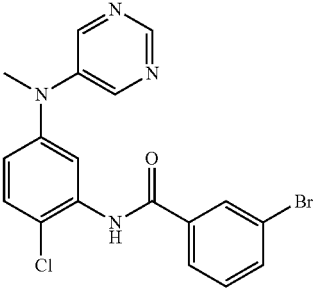 [SMILES: CN(c1cncnc1)c1ccc(Cl)c(NC(=O)c2cccc(Br)c2)c1] | 1400 | 417.0 | VI |
| 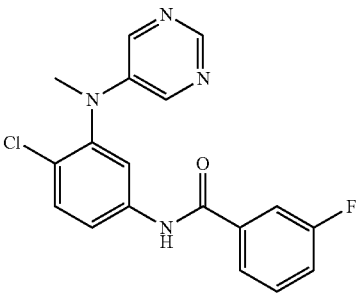 [SMILES: CN(c1cncnc1)c1cc(NC(=O)c2cccc(F)c2)ccc1Cl] | 16 | 357.1 | VI |
| 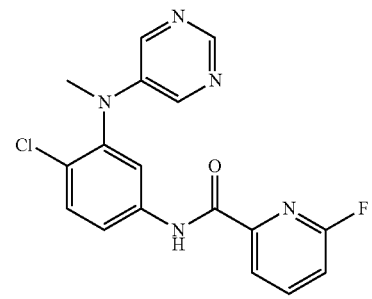 [SMILES: CN(c1cncnc1)c1cc(NC(=O)c2cccc(F)n2)ccc1Cl] | 7.5 | 358.1 | VI |
| 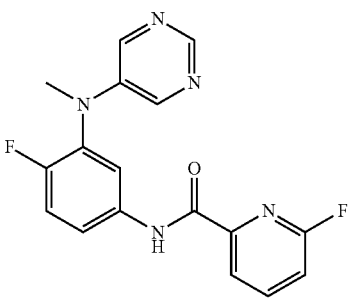 [SMILES: CN(c1cncnc1)c1cc(NC(=O)c2cccc(F)n2)ccc1F] | 8.6 | 342.1 | VI |
| 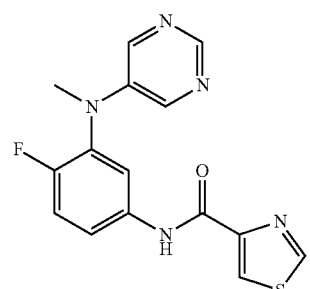 | 72 | 330.1 | VI |

TABLE 1-continued

| Structure | mGluR5 IC$_{50}$ (nM) | M + 1 | Synthetic Route Reference |
|---|---|---|---|
| 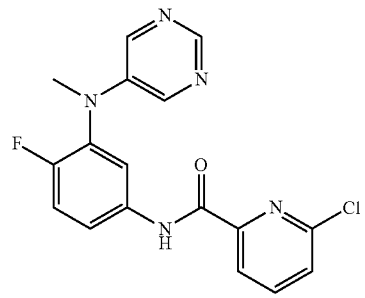 [SMILES: CN(c1cncnc1)c1cc(NC(=O)c2cccc(Cl)n2)ccc1F] | 6.5 | 358.1 | VI |
| 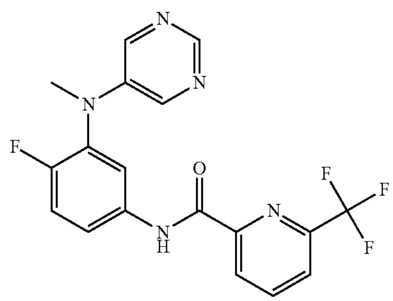 [SMILES: CN(c1cncnc1)c1cc(NC(=O)c2cccc(C(F)(F)F)n2)ccc1F] | 37 | 392.1 | VI |
| 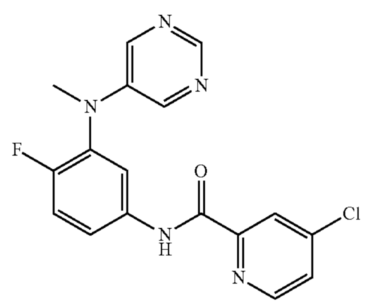 [SMILES: CN(c1cncnc1)c1cc(NC(=O)c2cc(Cl)ccn2)ccc1F] | 153 | 358.1 | VI |
| 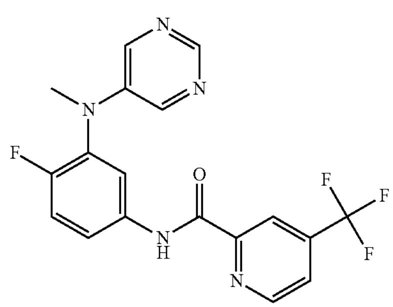 [SMILES: CN(c1cncnc1)c1cc(NC(=O)c2cc(C(F)(F)F)ccn2)ccc1F] | >10,000 | 392.1 | VI |
| 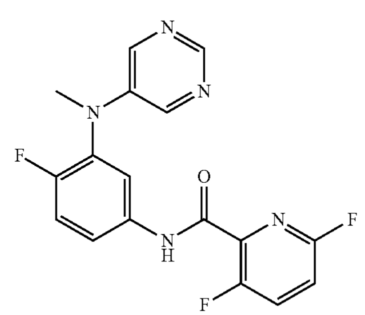 [SMILES: CN(c1cncnc1)c1cc(NC(=O)c2nc(F)ccc2F)ccc1F] | 22 | 360.1 | VI |

TABLE 1-continued

| Structure | mGluR5 IC$_{50}$ (nM) | M + 1 | Synthetic Route Reference |
|---|---|---|---|
| 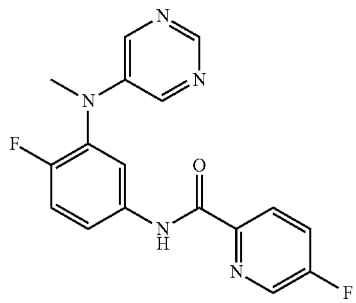 [SMILES: CN(c1cncnc1)c1cc(NC(=O)c2ccc(F)cn2)ccc1F] | 30 | 342.1 | VI |
| 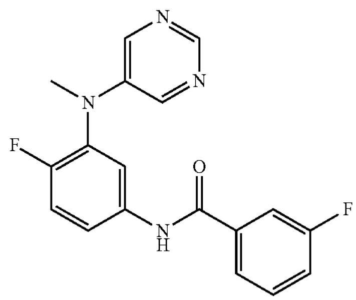 [SMILES: CN(c1cncnc1)c1cc(NC(=O)c2cccc(F)c2)ccc1F] | 9.8 | 341.1 | VI |
| 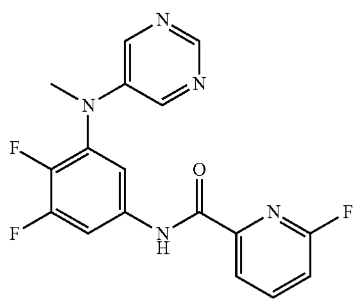 [SMILES: CN(c1cncnc1)c1cc(NC(=O)c2cccc(F)n2)cc(F)c1F] | 7.3 | 360.1 | IX |
| 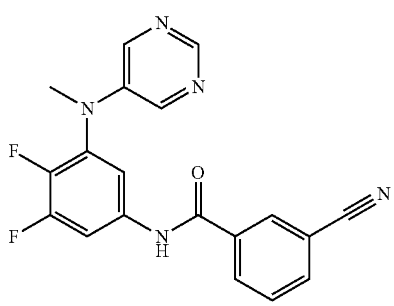 [SMILES: CN(c1cncnc1)c1cc(NC(=O)c2cccc(C#N)c2)cc(F)c1F] | 148 | 366.1 | IX |
| 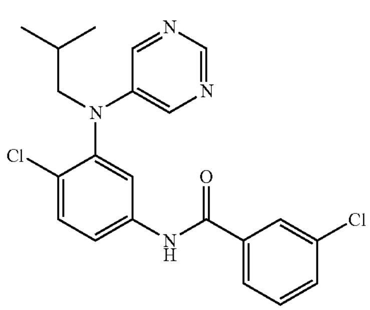 [SMILES: CC(C)CN(c1cncnc1)c1cc(NC(=O)c2cccc(Cl)c2)ccc1Cl] | >10,000 | 415.1 | VI |

TABLE 1-continued

| Structure | mGluR5 IC$_{50}$ (nM) | M + 1 | Synthetic Route Reference |
|---|---|---|---|
| 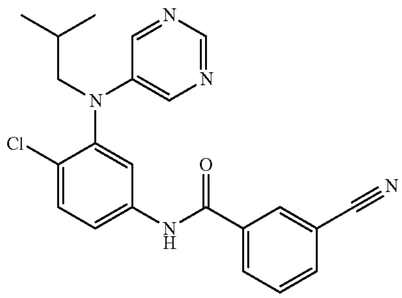 [SMILES: CC(C)CN(c1cncnc1)c1cc(NC(=O)c2cccc(C#N)c2)ccc1Cl] | >10,000 | 406.1 | VI |
| 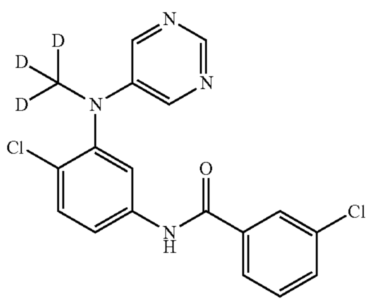 [SMILES: [2H]C([2H])([2H])N(c1cncnc1)c1cc(NC(=O)c2cccc(Cl)c2)ccc1Cl] | 72 | 376.1 | VI |
| 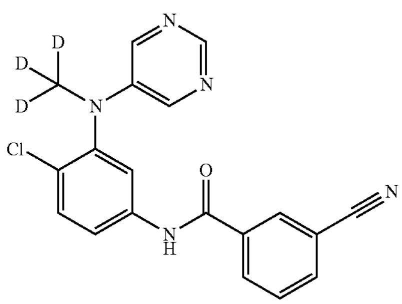 [SMILES: [2H]C([2H])([2H])N(c1cncnc1)c1cc(NC(=O)c2cccc(C#N)c2)ccc1Cl] | 84 | 367.1 | VI |
| 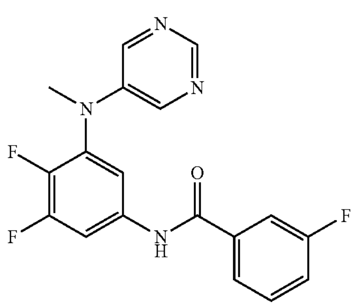 [SMILES: CN(c1cncnc1)c1cc(NC(=O)c2cccc(F)c2)cc(F)c1F] | 28 | 359.1 | IX |
| 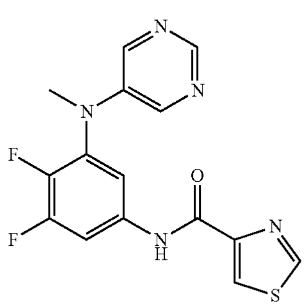 [SMILES: CN(c1cncnc1)c1cc(NC(=O)c2cscn2)cc(F)c1F] | 80 | 348.1 | IX |

TABLE 1-continued

| Structure | mGluR5 IC$_{50}$ (nM) | M + 1 | Synthetic Route Reference |
|---|---|---|---|
| (5-fluoro-3-(pyrimidin-5-yloxy)phenyl)-4-chloropyridine-2-carboxamide | 3.3 | 345.1 | II |
| (5-fluoro-3-(pyrimidin-5-yloxy)phenyl)-4-bromopyridine-2-carboxamide | 4.6 | 389.0 | II |
| N-(4-fluoro-3-(methyl(pyrimidin-5-yl)amino)phenyl)-6-hydroxypyridine-2-carboxamide | 2910 | 340.0 | VI |
| N-(3-cyano-5-(pyrimidin-5-yloxy)phenyl)-4-chloropyridine-2-carboxamide | 16 | 352.1 | VIII |
| N-(3-cyano-5-(pyrimidin-5-yloxy)phenyl)-4-bromopyridine-2-carboxamide | 17 | 396.0 | VIII |

Table 2 below lists representative compounds and the activity of each measured in human embryonic kidney cells expressing, as indicated, either the human mGluR5 or the rat mGluR5. The mGluR5 activity was determined using the metabotropic glutamate receptor activity assays in human embryonic kidney cells as described herein. The mGluR5 activity data for some compounds are shown as the average of at least three experiments with the standard error in these cases. If no error is indicated for the mGluR5 activity, the values given represent the results from a single experiment or the average of two experiments. The compounds in Table 2 were synthesized with methods identical or analogous to those shown herein. The requisite starting materials were commercially available, described in the literature, or readily synthesized by one skilled in the art of organic synthesis.

TABLE 2

| Structure | mGluR5, IC$_{50}$ (nM) | |
|---|---|---|
| | rat | human |
| (structure) | 83 ± 9 | 57 |
| (structure) | 44 ± 5 | 30 |
| (structure) | 36 ± 8 | 42 |

TABLE 2-continued

| Structure | mGluR5, IC$_{50}$ (nM) | |
|---|---|---|
| | rat | human |
| (structure) | 153 ± 23 | 24 |
| (structure) | 57 ± 6 | 94 |
| (structure) | 61 ± 15 | 0 |
| (structure) | 5.4 | 5.8 |

TABLE 2-continued

| Structure | mGluR5, IC$_{50}$ (nM) | |
|---|---|---|
| | rat | human |
| (structure) | 5.4 ± 0.4 | 4.2 |
| (structure) | 10 | 11 |
| (structure) | 7.5 | 10 |
| (structure) | 573 | 899 |
| (structure) | 663 | 586 |
| (structure) | 1680 | 1390 |
| (structure) | >30,000 | >30,000 |

E. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require negative allosteric modulation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 miligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating glutamate receptor activity (e.g., treatment of one or more neurological and/or psychiatric disorder associated with glutamate dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

F. Methods of Using the Compounds and Compositions

The amino acid L-glutamate (referred to herein simply as glutamate) is the principal excitatory neurotransmitter in the mammalian central nervous system (CNS). Within the CNS, glutamate plays a key role in synaptic plasticity (e.g., long term potentiation (the basis of learning and memory)), motor control and sensory perception. It is now well understood that a variety of neurological and psychiatric disorders are associated with dysfunctions in the glutamatergic system. Thus, modulation of the glutamatergic system is an important therapeutic goal. Glutamate acts through two distinct receptors: ionotropic and metabotropic glutamate receptors. The first class, the ionotropic glutamate receptors, is comprised of multi-subunit ligand-gated ion channels that mediate excitatory post-synaptic currents. Three subtypes of ionotropic glutamate receptors have been identified, and despite glutamate serving as agonist for all three receptor subtypes, selective ligands have been discovered that activate each subtype. The ionotropic glutamate receptors are named after their respective selective ligands: kainite receptors, AMPA receptors and NMDA receptors.

The second class of glutamate receptor, termed metabotropic glutamate receptors, (mGluRs), are G-protein coupled receptors (GPCRs) that modulate neurotransmitter release or the strength of synaptic transmission, based on their location (pre- or post-synaptic). The mGluRs are family C GPCR, characterized by a large (~560 amino acid) "venus fly trap" agonist binding domain in the amino-terminal domain of the receptor. This unique agonist binding domain distinguishes family C GPCRs from family A and B GPCRs wherein the agonist binding domains are located within the 7-strand transmembrane spanning (7TM) region or within the extracellular loops that connect the strands to this region. To date, eight distinct mGluRs have been identified, cloned and sequenced. Based on structural similarity, primary coupling to intracellular signaling pathways and pharmacology, the mGluRs have been assigned to three groups: Group I (mGluR1 and mGluR5), Group II (mGluR2 and mGluR3) and Group III (mGluR4, mGluR6, mGluR7 and mGluR8). Group I mGluRs are coupled through G$\alpha$q/11 to increase inositol phosphate and metabolism and resultant increases in intracellular calcium. Group I mGluRs are primarily located post-synaptically and have a modulatory effect on ion channel activity and neuronal excitability. Group II (mGluR2 and mGluR3) and Group III (mGluR4, mGluR6, mGluR7 and mGluR8) mGluRs are primarily located pre-synaptically where they regulate the release of neurotransmitters, such as glutamate. Group II and Group III mGluRs are coupled to G$\alpha$i and its associated effectors such as adenylate cyclase.

Post-synaptic mGluRs are known to functionally interact with post-synaptic ionotropic glutamate receptors, such as the NMDA receptor. For example, activation of mGluR5 by a selective agonist has been shown to increase post-synaptic NMDA currents (Mannaioni et al., *J. Neurosci.* 21:5925-5934 (2001)). Therefore, modulation of mGluRs is an approach to modulating glutamatergic transmission. Numerous reports indicate that mGluR5 plays a role in a number of disease states including anxiety (Spooren et al., *J. Pharmacol. Exp. Therapeut.* 295:1267-1275 (2000), Tatarczynska et al., *Br. J. Pharmaol.* 132:1423-1430 (2001)), addiction to cocaine (Chiamulera et al., *Nature Neurosci.* 4:873-874 (2001), Parkinson's disease (Awad et al., *J. Neurosci.* 20:7871-7879 (2000), Ossowska et al., *Neuropharmacol.* 41: 413-420 (2001), pain (Salt and Binns, *Neurosci.* 100:375-380 (2001)), and Fragile X syndrome (FXS) (see, e.g., de Vrij F M S, Levenga J, van der Linde H C, Koekkoek S K, De Zeeuw C I, Nelson D L, Oostra B A, Willemsen R: Rescue of behavioral phenotype and neuronal protrusion morphology in Fmr1 KO mice. *Neurobiol Disease* (2008) 31(1):127-132; Yan Q J, Rammal M, Tranfaglia M, Bauchwitz R P: Suppression of two major Fragile X Syndrome mouse model phenotypes by the mGluR5 antagonist MPEP. *Neuropharmacol* (2005) 49(7):1053-1066.).

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

In one aspect, the subject compounds can be coadministered with ant-Alzheimer's agents, beta-secretase inhibitors, gamma-secretase inhibitors, muscarinic agonists, muscarinic potentiators HMG-CoA reductase inhibitors, NSAIDs and anti-amyloid antibodies.

In a further aspect, the subject compounds can be administered in combination with sedatives, hypnotics, anxiolytics, antipsychotics, anti-epileptics, selective serotonin reuptake inhibitors ("SSRI") and/or selective serotonin and norepinephrine reuptake inhibitors ("SSNRI"), tricyclic antidepressant drugs, monoamine oxidase inhibitors (MAOIs), 5-HT2 agonists or antagonists, GlyT1 inhibitors and the like such as, but not limited to: risperidone, clozapine, olanzapine, haloperidol, fluoxetine, prazepam, xanomeline, lithium, phenobarbitol, and salts thereof and combinations thereof.

In a further aspect, the subject compound can be used in combination with levodopa (with or without a selective extracerebral decarboxylase inhibitor), anti-cholinergics such as biperiden, COMT inhibitors such as entacapone, A2a adenosine antagonists, cholinergic agonists, NMDA receptor agonists or antagonists and dopamine agonists.

In a further aspect, the subject compound can be administered in combination with opiate agonists or antagonists, calcium channel antagonists, sodium channel antagonists, COX-2 selective inhibitors, NK1 antagonists, non-steroidal anti-inflammatory drugs ("NSAID"), GABA-A receptor modulators, dopamine agonists or antagonists, norepinephrine modulators, nicotinic agonists or antagonists including nicotine, and muscarinic agonists or antagonists. In a yet further aspect, the subject compound can be administered in combination withheroin substituting drugs such as methadone, levo-alpha-acetylmethadol, buprenorphine and naltrexone, and disulfuram and acamprosate. In a further aspect, the subject compound can be administered in combination with L-DOPA, buspirone, valproate, and gabapentin.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of neurological and psychiatric disorders associated with glutamate dysfunction. Thus, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more neurological and/or psychiatric disorders associated with glutamate dysfunction in a subject comprising the step of administering to the subject at least one disclosed compound; at least one disclosed pharmaceutical composition; and/or at least one disclosed product in a dosage and amount effective to treat the disorder in the subject.

Examples of disorders associated with glutamate dysfunction include: acute and chronic neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, addictive behavior, including addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.), obesity, psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

Anxiety disorders that can be treated or prevented by the compositions disclosed herein include generalized anxiety disorder, panic disorder, and obsessive compulsive disorder. Addictive behaviors include addiction to substances (including opiates, nicotine, tobacco products, alcohol, benzodiazepines, cocaine, sedatives, hypnotics, etc.), withdrawal from such addictive substances (including substances such as opiates, nicotine, tobacco products, alcohol, benzodiazepines, cocaine, sedatives, hypnotics, etc.) and substance tolerance.

Also provided is a method for treating or prevention anxiety, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder, and anxiety disorder not otherwise specified.

Further disorders that can be treated or prevented by the compositions disclosed herein include autism spectrum disorders, which are neuropsychiatric conditions characterized by widespread abnormalities of social interactions and communication, as well as severely restricted interests and highly repetitive behavior. Autism spectrum disorders include autism, Asperger syndrome, Childhood Disintegrative Disorders, Pervasive Developmental Disorder Not Otherwise Specified (PDD-NOS), sometimes called atypical autism, and Rett Syndrome. Fragile X syndrome (FXS) is a single gene disorder almost universally associated with symptoms of autism spectrum disorder, the most common form of inherited mental retardation, and the most common known cause of autism, affecting 1 in 6,000 births. Therapeutic agents for treatment of patients with FXS are among the most critical of unmet medical needs, and there are very few proven effective treatment strategies for this patient population. Again, without wishing to be bound by theory, increasing evidence has identified a connection between the fragile X phenotype and mGluR signaling Compounds of the invention can be used, for example, for the treatment of fragile X syndrome and autism spectrum disorder in a manner that can improve symptoms (e.g., reduce anxiety and irritability; increase cognitive function, communication and/or social interaction). Thus, the methods of the invention can provide an effective manner to treat a subject having fragile X syndrome or autism spectrum disorder.

a. Treating a Disorder

In one aspect, the invention relates to a method for the treatment of a disorder associated with mGluR5 activity in a mammal comprising the step of administering to the mammal at least one disclosed compound or at least one disclosed product in a dosage and amount effective to treat the disorder in the mammal. In a further aspect, the mammal is a human. In a further aspect, the mammal has been diagnosed with a need for treatment of the disorder prior to the administering step. In a further aspect, the method further comprises the step of identifying a mammal in need of treatment of the disorder.

In one aspect, the invention relates to a method for the treatment of a disorder associated with mGluR5 activity in a mammal comprising the step of administering to the mammal at least one compound having a structure represented by a formula:

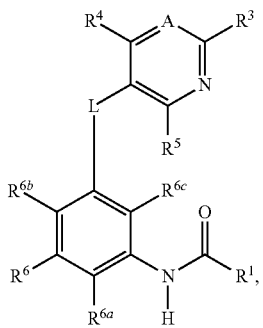

wherein A is $CR^2$ or N; wherein L is O or $NR^7$, wherein $R^1$ is aryl, heteroaryl, alkyl, cycloalkyl, heteroalkyl, or heterocycloalkyl, wherein $R^1$ is substituted with 0-3 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is hydrogen, halogen, C1-C6 alkyl, C1-C6 haloalkyl, C1-C6 alkoxy, cyano, hydroxyl, alkylamino, dialkylamino, $SO_2R^8$, or $COR^8$; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$, or a pharmaceutically acceptable salt thereof, in an effective amount to treat the disorder in the mammal. In a further aspect, L is O.

In a further aspect, the compound has a structure represented by a formula:

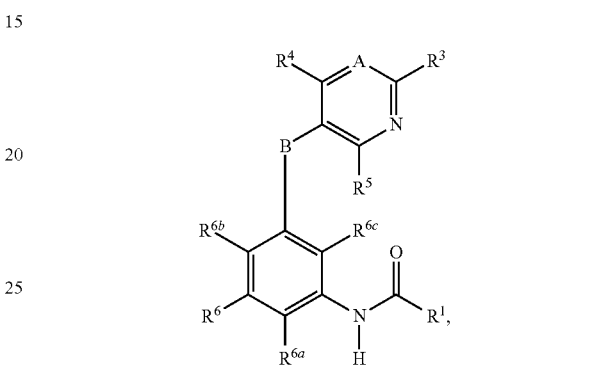

wherein A is $CR^2$ or N; wherein L is O or $NR^7$, wherein $R^1$ has from 1 to 10 carbons and is selected from phenyl substituted with 1-3 of R9, wherein at least one R9 is meta substituted; 2-pyridinyl substituted with 0-3 of R9; and thiazole substituted with 0-2 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is selected from hydrogen, halogen, CN, C1-C4 alkyl, C1-C4 haloalkyl, C3-C4 cycloalkyl, and C3-C4 halocycloalkyl; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$, or a pharmaceutically acceptable salt thereof.

In a further aspect, the compound administered is any disclosed compound or a product of a disclosed method.

In a further aspect, the mammal is human. In a yet further aspect, the mammal has been diagnosed with a need for treatment of the disorder prior to the administering step. In a still further aspect, the treatment of the disorder further comprises the step of identifying a mammal in need of treatment of the disorder. In an even further aspect, the disorder is a neurological and/or psychiatric disorder associated with glutamate dysfunction. In a further aspect, the disorder is selected from autism spectrum disorders, addiction, anxiety, fragile x syndrome, gastroesophageal reflux disease (GERD), Parkinson's disease, and pain.

In a further aspect, the disorder is a disease of uncontrolled cellular proliferation. In yet further aspect, the uncontrolled cellular proliferation is cancer. In a still further aspect, the cancer is selected from breast cancer, renal cancer, gastric cancer, and colorectal cancer. In yet further aspect, the cancer is selected from lymphoma, cancers of the brain, genitourinary tract cancer, lymphatic system cancer, stomach cancer, larynx cancer, lung, pancreatic cancer, breast cancer, and malignant melanoma.

In a further aspect, mGluR5 activity is partially inhibited. In a still further aspect, mGluR5 activity is totally inhibited. In a yet further aspect, the compound or product exhibits negative allosteric modulation with an $IC_{50}$ of less than about $30 \times 10^{-6}$.

In one aspect, the disorder is a neurological and/or psychiatric disorder associated with glutamate dysfunction. In a further aspect, the disorder is selected from addiction, affective disorder, age-related cognitive decline, Alzheimer's disease, amnestic disorders, amyotrophic lateral sclerosis, anxiety disorders, Angelmans's syndrome, Asperger's syndrome, attention deficit hyperactivity disorder, autism spectrum disorders, bipolar disorder, brain edema, chronic pain, delirium, dementia, depression, diabetes, Down Syndrome, dystonia, eating disorders, epilepsy, fibromyalgia, fragile-X syndrome, Huntington's-related chorea, levadopa-induced dyskinesia, manic-depressive illness, migraine, movement disorders, multiple sclerosis, narcolepsy, neurofibromatosis type 1, neuropathic pain, obesity, pain, paranoia, Parkinson's disease, post-herpatic neuropathic pain, psychotic disorders, PTEN harmartoma syndrome, Rett syndrome, senile dementia, sleep disorder, substance-related disorder, or unipolar depression.

In one aspect, the disorder is a disease of uncontrolled cellular proliferation. In a further aspect, the disorder is cancer. In a further aspect, the disorder is glioblastoma, other astrocytomas, or another other form of cancer. In a further aspect, the disorder is selected from breast cancer, renal cancer, gastric cancer, and colorectal cancer. In a further aspect, the disorder is selected from lymphoma, cancers of the brain, genitourinary tract cancer, lymphatic system cancer, stomach cancer, larynx cancer, lung, pancreatic cancer, breast cancer, and malignant melanoma.

In a further aspect, mGluR5 activity is partially inhibited. In a further aspect, mGluR5 activity is totally inhibited. In a further aspect, the compound or product exhibits negative allosteric modulation with an $IC_{50}$ of less than about $30 \times 10^{-6}$.

b. Decreasing mGluR5 Activity

In one aspect, the invention relates to a method for decreasing mGluR5 activity in a mammal comprising the step of administering to the mammal at least one disclosed compound or at least one disclosed product in a dosage and amount effective to decrease mGluR5 activity in the mammal. In a further aspect, the mammal is a human. In a further aspect, the mammal has been diagnosed with a need for decreasing mGluR5 activity prior to the administering step. In a further aspect, the mammal has been diagnosed with a need for treatment of a disorder related to mGluR5 activity prior to the administering step. In a further aspect, the method further comprises the step of identifying a mammal in need of decreasing mGluR5 activity.

In one aspect, the invention relates to a method for decreasing mGluR5 activity in a mammal comprising the step of administering to the mammal at least one compound having a structure represented by a formula:

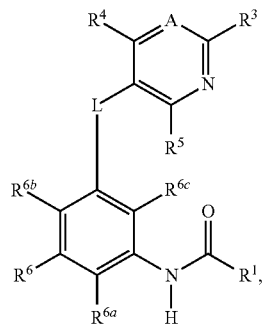

wherein A is $CR^2$ or N; wherein L is O or $NR^7$, wherein $R^1$ is aryl, heteroaryl, alkyl, cycloalkyl, heteroalkyl, or heterocycloalkyl, wherein $R^1$ is substituted with 0-3 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is hydrogen, halogen, C1-C6 alkyl, C1-C6 haloalkyl, C1-C6 alkoxy, cyano, hydroxyl, alkylamino, dialkylamino, $SO_2R^8$, or $COR^8$; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$, or a pharmaceutically acceptable salt thereof, in an effective amount to decrease mGluR5 activity in the mammal. In a further aspect, L is O.

In a further aspect, the compound has a structure represented by a formula:

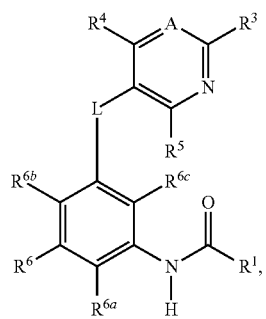

wherein A is $CR^2$ or N; wherein L is O or $NR^7$, wherein $R^1$ has from 1 to 10 carbons and is selected from phenyl substituted with 1-3 of R9, wherein at least one R9 is meta substituted; 2-pyridinyl substituted with 0-3 of R9; and thiazole substituted with 0-2 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is selected from hydrogen, halogen, CN, C1-C4 alkyl, C1-C4 haloalkyl, C3-C4 cycloalkyl, and C3-C4 halocycloalkyl; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$, or a pharmaceutically acceptable salt thereof.

In a further aspect, the compound administered is a disclosed compound or a product of a disclosed method of making a compound.

In a further aspect, the mammal is a human. In a still further aspect, the mammal has been diagnosed with a need for decreasing mGluR5 activity prior to the administering step. In an even further aspect, the mammal has been diagnosed with a need for treatment of a disorder related to mGluR5 activity prior to the administering step. In a further aspect, the treatment further comprises the step of identifying a mammal in need of decreasing mGluR5 activity. In a yet further aspect, the decrease in mGluR5 activity treats a disorder associated with mGluR5 activity in the mammal. In a still further aspect, the mammal has been diagnosed with a need for treatment of the disorder prior to the administering step. In an even further aspect, treatment further comprises the step of identifying a mammal in need of treatment of the disorder.

In a further aspect, the disorder is a neurological and/or psychiatric disorder associated with glutamate dysfunction. In a still further aspect, the disorder is selected from autism, addiction, anxiety, fragile x syndrome, gastroesophageal reflux disease (GERD), Parkinson's disease, and pain.

In a further aspect, the disorder is a disease of uncontrolled cellular proliferation. In a yet further aspect, the uncontrolled cellular proliferation is cancer. In a still further aspect, cancer is selected from breast cancer, renal cancer, gastric cancer, and colorectal cancer. In an even further aspect, the cancer is selected from lymphoma, cancers of the brain, genitourinary tract cancer, lymphatic system cancer, stomach cancer, larynx cancer, lung, pancreatic cancer, breast cancer, and malignant melanoma.

In a further aspect, mGluR5 activity is partially inhibited. In a still further aspect, mGluR5 activity is totally inhibited. In a yet further aspect, the compound or product exhibits negative allosteric modulation with an $IC_{50}$ of less than about $30\times10^{-6}$.

c. Inhibiting mGluR5 Activity in Cells

In one aspect, the invention relates to a method for inhibiting mGluR5 activity in at least one cell, comprising the step of contacting the at least one cell with at least one disclosed compound or at least one disclosed product in an amount effective to inhibit mGluR5 activity in the at least one cell.

In one aspect, the invention relates to a method for inhibiting mGluR5 activity in at least one cell, comprising the step of contacting the at least one cell with at least one compound having a structure represented by a formula:

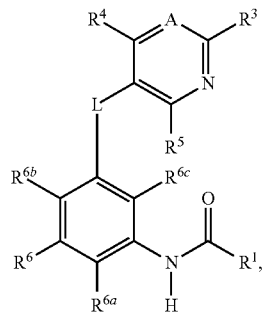

wherein A is $CR^2$ or N; wherein L is O or $NR^7$, wherein $R^1$ is aryl, heteroaryl, alkyl, cycloalkyl, heteroalkyl, or heterocycloalkyl, wherein $R^1$ is substituted with 0-3 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is hydrogen, halogen, C1-C6 alkyl, C1-C6 haloalkyl, C1-C6 alkoxy, cyano, hydroxyl, alkylamino, dialkylamino, $SO_2R^8$, or $COR^8$; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$, or a pharmaceutically acceptable salt thereof, in an effective amount to inhibit mGluR5 activity in the at least one cell. In a further aspect, L is O.

In a further aspect, the compound has a structure represented by a formula:

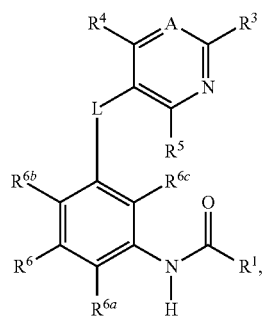

wherein A is $CR^2$ or N; wherein L is O or $NR^7$, wherein $R^1$ has from 1 to 10 carbons and is selected from phenyl substituted with 1-3 of R9, wherein at least one R9 is meta substituted; 2-pyridinyl substituted with 0-3 of R9; and thiazole substituted with 0-2 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, SO$_2$R$^8$, and COR$^8$; wherein R$^4$ and R$^5$ are independently hydrogen, halogen, C1-C6 alkyl, C1-C6 haloalkyl, C1-C6 alkoxy, amino, hydroxyl, alkylamino, dialkylamino, NO$_2$, CN, SO$_2$R$^8$, or COR$^8$; wherein R$^6$ is selected from hydrogen, halogen, CN, C1-C4 alkyl, C1-C4 haloalkyl, C3-C4 cycloalkyl, and C3-C4 halocycloalkyl; wherein each of R$^{6a}$, R$^{6b}$, and R$^{6c}$ is independently selected from hydrogen, halogen, C1-C6 alkyl, C1-C6 haloalkyl, C1-C6 alkoxy, and C1-C6 haloalkoxy, CN, SO$_2$R$^8$, and COR$^8$; wherein R$^7$ is hydrogen, C1-C6 alkyl, or C1-C6 haloalkyl; wherein R$^8$ is C1-C6 alkyl, C1-C6 cycloalkyl, amino, alkylamino, or dialkylamino; and wherein each R$^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, NO$_2$, CN, SO$_2$R$^8$, or COR$^8$, or a pharmaceutically acceptable salt thereof.

In a further aspect, the compound administered is a disclosed compound or a product of a disclosed method of making a compound.

In a further aspect, the cell is mammalian. In a yet further aspect, the cell is human. In a still further aspect, the cell has been isolated from a mammal prior to the contacting step. In an even further aspect, contacting the cell is via administration to a mammal. In a further aspect, inhibiting mGluR5 activity in the at least one cell decreases mGluR5 activity in the mammal. In a yet further aspect, the decrease in mGluR5 activity in the mammal treats a disorder associated with mGluR5 activity in the mammal.

In a further aspect, the disorder is a neurological and/or psychiatric disorder associated with glutamate dysfunction. In a still further aspect, the disorder is selected from autism, addiction, anxiety, fragile x syndrome, gastroesophageal reflux disease (GERD), Parkinson's disease, and pain.

In a further aspect, the disorder is a disease of uncontrolled cellular proliferation. In a still further aspect, the uncontrolled cellular proliferation is cancer. In a yet further aspect, the cancer is selected from breast cancer, renal cancer, gastric cancer, and colorectal cancer. In an even further aspect, the cancer is selected from lymphoma, cancers of the brain, genitourinary tract cancer, lymphatic system cancer, stomach cancer, larynx cancer, lung, pancreatic cancer, breast cancer, and malignant melanoma.

In a further aspect, mGluR5 activity is partially inhibited. In a still further aspect, mGluR5 activity is totally inhibited. In a yet further aspect, the compound or product exhibits negative allosteric modulation with an IC$_{50}$ of less than about 30×10$^{-6}$.

In a further aspect, the cell is mammalian, for example, human. In a further aspect, the cell has been isolated from a mammal prior to the contacting step. In a further aspect, contacting is via administration to a mammal.

2. Use of Compounds

Also provided are the uses of the disclosed compounds and products. In one aspect, the use relates to a treatment of a disorder in a mammal. In one aspect, the use is characterized in that the mammal is a human. In one aspect, the use is characterized in that the disorder is a neurological and/or psychiatric disorder associated with glutamate dysfunction. In one aspect, the use relates to negative allosteric modulation of metabotropic glutamate receptor activity in a mammal.

In one aspect, the invention relates to a use of a compound having a structure represented by a formula:

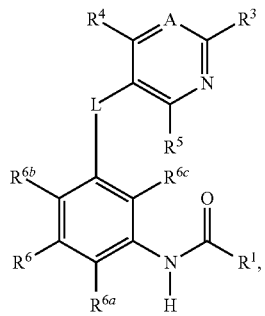

wherein A is CR$^2$ or N; wherein L is O or NR$^7$, wherein R$^1$ is aryl, heteroaryl, alkyl, cycloalkyl, heteroalkyl, or heterocycloalkyl, wherein R$^1$ is substituted with 0-3 of R$^9$; wherein R$^2$ is hydrogen, halogen, C1-C6 alkyl, C1-C6 haloalkyl, C1-C6 alkoxy, C1-C6 haloalkoxy, amino, hydroxyl, alkylamino, dialkylamino, NO$_2$, CN, SO$_2$R$^8$, or COR$^8$; wherein R$^3$ is selected from hydrogen, halogen, C1-C6 alkyl, C1-C6 haloalkyl, C1-C6 alkoxy, hydroxyl, CN, SO$_2$R$^8$, and COR$^8$; wherein R$^4$ and R$^5$ are independently hydrogen, halogen, C1-C6 alkyl, C1-C6 haloalkyl, C1-C6 alkoxy, amino, hydroxyl, alkylamino, dialkylamino, NO$_2$, CN, SO$_2$R$^8$, or COR$^8$; wherein R$^6$ is hydrogen, halogen, C1-C6 alkyl, C1-C6 haloalkyl, C1-C6 alkoxy, cyano, hydroxyl, alkylamino, dialkylamino, SO$_2$R$^8$, or COR$^8$; wherein each of R$^{6a}$, R$^{6b}$, and R$^{6c}$ is independently selected from hydrogen, halogen, C1-C6 alkyl, C1-C6 haloalkyl, C1-C6 alkoxy, and C1-C6 haloalkoxy, CN, SO$_2$R$^8$, and COR$^8$; wherein R$^7$ is hydrogen, C1-C6 alkyl, or C1-C6 haloalkyl; wherein R$^8$ is C1-C6 alkyl, C1-C6 cycloalkyl, amino, alkylamino, or dialkylamino; and wherein each R$^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, NO$_2$, CN, SO$_2$R$^8$, or COR$^8$, or a pharmaceutically acceptable salt thereof, in the manufacture of a medicament for the treatment of a disorder associated with glutamate dysfunction in a mammal. In a further aspect, L is O.

In a further aspect, the compound has a structure represented by a formula:

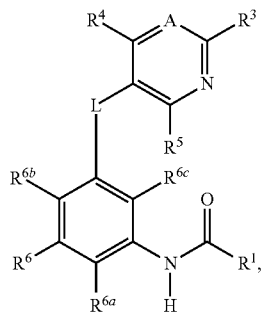

wherein A is CR$^2$ or N; wherein L is O or NR$^7$, wherein R$^1$ has from 1 to 10 carbons and is selected from phenyl substituted with 1-3 of R9, wherein at least one R9 is meta substituted; 2-pyridinyl substituted with 0-3 of R9; and thiazole substituted with 0-2 of R$^9$; wherein R$^2$ is hydrogen, halogen, C1-C6 alkyl, C1-C6 haloalkyl, C1-C6 alkoxy, C1-C6 haloalkoxy, amino, hydroxyl, alkylamino, dialkylamino, NO$_2$, CN, SO$_2$R$^8$, or COR$^8$; wherein R$^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is selected from hydrogen, halogen, CN, C1-C4 alkyl, C1-C4 haloalkyl, C3-C4 cycloalkyl, and C3-C4 halocycloalkyl; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$, or a pharmaceutically acceptable salt thereof.

In a further aspect, the compound exhibits partial or total inhibition of mGluR5 response to glutamate as a decrease in response to non-maximal concentrations of glutamate in human embryonic kidney cells transfected with rat mGluR5 in the presence of the compound, compared to the response to glutamate in the absence of the compound. In yet further aspect, the compound is any disclosed compound or product of a disclosed method.

In a further aspect, the disorder is a neurological and/or psychiatric disorder. In a still further aspect, the disorder is selected from autism, addiction, anxiety, fragile x syndrome, gastroesophageal reflux disease (GERD), Parkinson's disease, and pain.

In a further aspect, the disorder is a disease of uncontrolled cellular proliferation. In a still further aspect, the uncontrolled cellular proliferation is cancer. In a yet further aspect, the cancer is selected from breast cancer, renal cancer, gastric cancer, and colorectal cancer. In an even further aspect, the cancer is selected from lymphoma, cancers of the brain, genitourinary tract cancer, lymphatic system cancer, stomach cancer, larynx cancer, lung, pancreatic cancer, breast cancer, and malignant melanoma.

In a further aspect, mGluR5 activity is partially inhibited. In a still further aspect, mGluR5 activity is totally inhibited. In a yet further aspect, the compound or product exhibits negative allosteric modulation with an $IC_{50}$ of less than about $30 \times 10^{-6}$.

In one aspect, the invention relates to the use of a disclosed compound or a disclosed product in the manufacture of a medicament for the treatment of a disorder associated with glutamate dysfunction in a mammal. In a further aspect, the disorder is a neurological and/or psychiatric disorder. In a further aspect, the disorder is a disease of uncontrolled cellular proliferation.

3. Kits

In one aspect, the invention relates to a kit comprising at least one disclosed compound or at least one disclosed product and one or more of at least one agent known to increase mGluR5 activity; at least one agent known to decrease mGluR5 activity; at least one agent known to treat a neurological and/or psychiatric disorder; at least one agent known to treat a disease of uncontrolled cellular proliferation; or instructions for treating a disorder associated with glutamate dysfunction. In a further aspect, the at least one compound or the at least one product and the at least one agent are co-formulated. In a further aspect, the at least one compound or the at least one product and the at least one agent are co-packaged.

In one aspect, the invention relates to a kit comprising at least one compound having a structure represented by a formula:

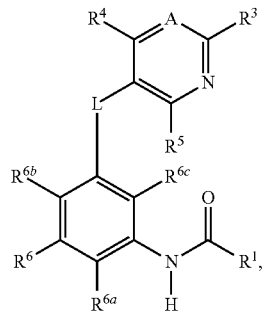

wherein A is $CR^2$ or N; wherein L is O or $NR^7$, wherein $R^1$ is aryl, heteroaryl, alkyl, cycloalkyl, heteroalkyl, or heterocycloalkyl, wherein $R^1$ is substituted with 0-3 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$, and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is hydrogen, halogen, C1-C6 alkyl, C1-C6 haloalkyl, C1-C6 alkoxy, cyano, hydroxyl, alkylamino, dialkylamino, $SO_2R^8$, or $COR^8$; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$, or a pharmaceutically acceptable salt thereof, in the manufacture of a medicament for the treatment of a disorder associated with glutamate dysfunction in a mammal and one or more of: at least one agent known to increase mGluR5 activity; at least one agent known to decrease mGluR5 activity; at least one agent known to treat a neurological and/or psychiatric disorder; at least one agent known to treat a disease of uncontrolled cellular proliferation; or instructions for treating a disorder associated with glutamate dysfunction. In a further aspect, L is O.

In a further aspect, the compound has a structure represented by a formula:

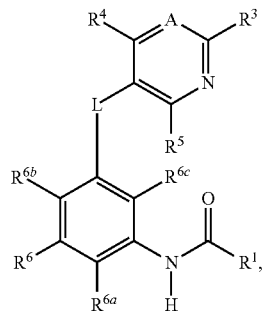

wherein A is $CR^2$ or N; wherein L is O or $NR^7$, wherein $R^1$ has from 1 to 10 carbons and is selected from phenyl substituted with 1-3 of $R^9$, wherein at least one $R^9$ is meta substituted; 2-pyridinyl substituted with 0-3 of $R^9$; and thiazole substituted with 0-2 of $R^9$; wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$; wherein $R^3$ is selected from hydrogen, halogen, C1-C6 alkyl, C1-C6 haloalkyl, C1-C6 alkoxy, hydroxyl, CN, $SO_2R^8$, and $COR^8$; wherein $R^4$ and $R^5$ are independently hydrogen, halogen, C1-C6 alkyl, C1-C6 haloalkyl, C1-C6 alkoxy, amino, hydroxyl, alkylamino, dialkylamino, $NO_2$, CN, $SO_2R^8$, or $COR^8$; wherein $R^6$ is selected from hydrogen, halogen, CN, C1-C4 alkyl, C1-C4 haloalkyl, C3-C4 cycloalkyl, and C3-C4 halocycloalkyl; wherein each of $R^{6a}$, $R^{6b}$, and $R^{6c}$ is independently selected from hydrogen, halogen, C1-C6 alkyl, C1-C6 haloalkyl, C1-C6 alkoxy, and C1-C6 haloalkoxy, CN, $SO_2R^8$, and $COR^8$; wherein $R^7$ is hydrogen, C1-C6 alkyl, or C1-C6 haloalkyl; wherein $R^8$ is C1-C6 alkyl, C1-C6 cycloalkyl, amino, alkylamino, or dialkylamino; and wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, or $COR^8$, or a pharmaceutically acceptable salt thereof.

In a further aspect, the kit comprises a disclosed compound or a product of a disclosed method.

In a further aspect, the at least one compound and the at least one agent are co-formulated. In a still further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

4. Non-Medical Uses

Also provided are the uses of the disclosed compounds and products as pharmacological tools in the development and standardization of in vitro and in vivo test systems for the evaluation of the effects of potentiators of mGluR related activity in laboratory animals such as cats, dogs, rabbits, monkeys, rats and mice, as part of the search for new therapeutic agents of mGluR. In a further aspect, the invention relates to the use of a disclosed compound or a disclosed product as pharmacological tools in the development and standardization of in vitro and in vivo test systems for the evaluation of the effects of potentiators of mGluR5 related activity in laboratory animals such as cats, dogs, rabbits, monkeys, rats and mice, as part of the search for new therapeutic agents of mGluR5.

G. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. All $^1$H NMR spectra were obtained on instrumentation at a field strength of 300 to 500 MHz.

1. Route 1

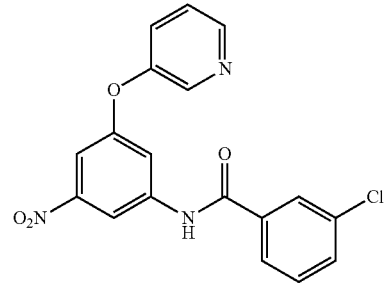 [SMILES: O=C(Nc1cc(Oc2cccnc2)cc([N+](=O)[O-])c1)c1cccc(Cl)c1]

a. 3-chloro-N-(3-nitro-5-(pyridin-3-yloxy)phenyl) benzamide (1)

3-Chlorobenzoyl chloride (79 mg, 0.45 mmol, 1.05 eq), 4-dimethylaminopyridine (55 mg, 0.45 mmol, 1.05 eq) and 3-nitro-5-(pyridin-3-yloxy)aniline (0.1 g, 0.43 mmol, 1 eq) were dissolved in $CH_2Cl_2$ (5 mL) and stirred at rt for 18 h. Water was added and the organic layer separated, dried ($MgSO_4$), filtered, and concentrated in vacuo to afford 140 mg (88%) of the title compound as a yellow solid: $^1$H NMR (400 MHz, DMSO-$d_6$) δ 10.78 (s, 1H), 8.58 (t, J=1.9 Hz, 1H), 8.53 (d, J=2.8 Hz, 1H), 8.50 (dd, J=4.6, 1.0 Hz, 1H), 8.01 (t, J=1.8 Hz, 1H), 7.91-7.87 (m, 2H), 7.70-7.65 (m, 2H), 7.60-7.56 (m, 2H), 7.53 (dd, J=8.4, 4.7 Hz, 1H); ES-MS [M+1]$^+$: 370.1.

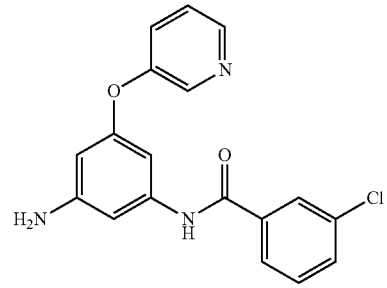

b. N-(3-Amino-5-(pyridin-3-yloxy)phenyl)-3-chlorobenzamide (2)

Compound 1 (710 mg, 1.92 mmol, 1.00 eq) was dissolved in 1N HCl in MeOH (22 mL) and zinc (377 mg, 5.77 mmol, 3.00 eq) was added. The reaction was stirred for 1 hour and additional zinc (251 mg, 3.84 mmol, 2.00 eq) was added to drive the reaction to completion as determined by TLC. The reaction was neutralized with 1N NaOH, filtered and extracted with $CH_2Cl_2$ (3×). The combined organics were dried ($MgSO_4$), filtered and concentrated in vacuo. Purification by flash chromatography on silica gel afforded 555 mg (85%) of the title compound as a brown solid: $^1$H NMR (400 MHz, DMSO-$d_6$) δ 10.09 (s, 1H), 8.37 (dd, J=2.7, 0.8 Hz, 1H), 8.34 (dd, J=4.3, 1.7 Hz, 1H), 7.93 (t, J=1.8 Hz, 1H), 7.84

(dt, J=7.9, 1.2 Hz, 1H), 7.63 (ddd, J=8.1, 2.1, 1.0 1H), 7.52 (t, J=7.8 Hz, 1H), 7.43 (m, 2H), 6.94 (t, J=1.8 Hz, 1H), 6.62 (t, J=2.0 Hz, 1H), 6.00 (t, J=2.1 Hz, 1H), 5.37 (s, 2H); ES-MS [M+1]$^+$: 340.1.

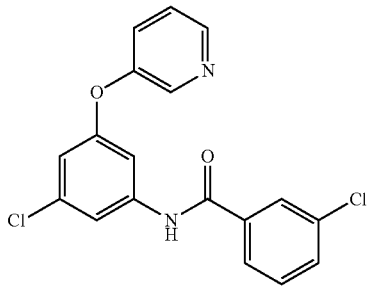 [SMILES: O=C(Nc1cc(Cl)cc(Oc2cccnc2)c1)c1cccc(Cl)c1]

c. 3-Chloro-N-(3-chloro-5-(pyridin-3-yloxy)phenyl)benzamide (3)

CuCl$_2$ (47.5 mg, 0.353 mmol, 1.20 eq) was dissolved in acetonitrile (2 mL) in a flame-dried 3-neck flask flushed with argon and equipped with a condenser. t-Butyl nitrite (45.5 mg, 0.441 mmol, 1.50 eq) was added and the reaction heated at 55° C. Compound 2 (100 mg, 0.294 mmol, 1.00 eq) was dissolved in acetonitrile (0.1 mL) and added dropwise to the reaction. After 10 minutes the reaction was cooled to rt, poured into 20% HCl and extracted with CH$_2$Cl$_2$ (3×). The combined organics were dried (MgSO$_4$), filtered and concentrated in vacuo. Purification by flash chromatography on silica gel afforded 67 mg (63%) f the title compound as a pale yellow solid: $^1$H NMR (400 MHz, DMSO-d$_6$) 10.50 (s, 1H), 8.47 (d, J=2.8 Hz, 1H), 8.45 (dd, J=4.6, 1.3 Hz, 1H), 7.96 (t, J=1.8 Hz, 1H), 7.86 (dt, J=7.9, 1.2 Hz, 1H), 7.77 (t, J=1.8 Hz, 1H), 7.68-7.66 (m, 1H), 7.58 (ddd, J=8.4, 3.0, 1.5 Hz, 1H), 7.56 (t, J=7.9 Hz, 1H), 7.48 (dd, J=8.4, 4.6 Hz, 1H), 7.40 (t, J=2.0 Hz, 1H), 6.94 (t, J=2.0 Hz, 1H); ES-MS [M+1]$^+$: 359.0.

2. Route 2

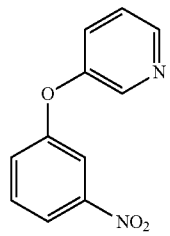

a. 3-(3-Nitrophenoxy)pyridine (4)

1-fluoro-3-nitrobenzene (1 g, 7 mmol, 1 eq), 3-hydroxypyridine (674 mg, 7.09 mmol, 1.00 eq), K$_2$CO$_3$ (1.18 g, 8.54 mmol, 1.20 eq) and DMF (10 mL) were added to a microwave vial and microwaved at 200° C. for 30 minutes. The reaction was filtered and concentrated on silica gel (5 g). The silica gel was loaded on top a fresh bed of silica gel and washed with 50% ethyl acetate/hexane. The solvents were removed in vacuo and the crude mixture was purified by flash chromatography on silica gel afforded 1.1 g (72%) of the title compound as a brown oil: $^1$H NMR (400 MHz, DMSO-d$_6$) 8.49 (d, J=2.8 Hz, 1H), 8.46 (d, J=4.6 Hz, 1H), 8.02 (dd, J=8.2, 2.0 Hz, 1H), 7.78 (t, J=2.3 Hz, 1H), 7.70 (t, J=8.2 Hz, 1H), 7.60 (m, 1H), 7.54 (dd, J=8.3, 2.4 Hz, 1H), 7.49 (dd, J=8.4, 4.6 Hz, 1H); ES-MS [M+1]$^+$: 217.2

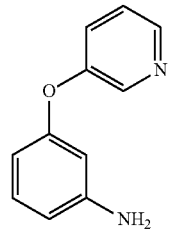 [SMILES: Nc1cccc(Oc2cccnc2)c1]

b. 3-(Pyridin-3-yloxy)aniline (5)

Compound 4 (1.613 g, 7.461 mmol, 1.000 eq) was dissolved in 1N HCl in MeOH (75 mL) and zinc (1.46 g, 22.3 mmol, 3.00 eq) was added. The reaction was stirred for 1 hour and additional zinc (975 mg, 14.9 mmol, 2 eq) was added to drive the reaction to completion as determined by TLC. The reaction was neutralized with 1N NaOH (75 mL), filtered and extracted (3×) with CH$_2$Cl$_2$. The combined organics were dried (MgSO$_4$), filtered and concentrated in vacuo. Purification by flash chromatography on silica gel afforded 555 mg (85%) of the title compound as a brown oil: $^1$H NMR (400 MHz, DMSO-d$_6$) δ 8.33-8.31 (m, 2H), 7.39-7.38 (m, 2H), 7.01 (t, J=8.0 Hz, 1H), 6.35 (dd, J=8.0, 1.6 Hz, 1H), 6.19 (t, J=2.2 Hz, 1H), 6.14 (dd, J=7.9, 2.0 Hz, 1H), 5.27 (s, 2H); ES-MS [M+1]$^+$: 87.2.

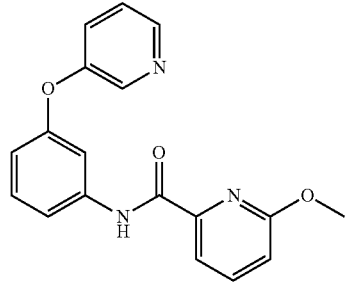 [SMILES: COc1cccc(C(=O)Nc2cccc(Oc3cccnc3)c2)n1]

c. 6-Methoxy-N-(3-(pyridin-3-yloxy)phenyl)picolinamide (6)

Compound 5 (25 mg, 0.13 mmol, 1.0 eq), 6-methoxypicolinic acid (23 mg, 0.15 mmol, 1.1 eq), 2-(1H-7-Azabenzotriazol-1-yl)-1,1,3,3-tetramethyluronium hexafluorophosphate (56 mg, 0.15 mmol, 1.1 eq) and DIEA (25.7 µL, 0.148 mmol, 1.10 eq) were dissolved in CH$_2$Cl$_2$ (1.5 mL) and stirred at rt overnight. Water was added and the layers separated. The organic layer was dried (MgSO$_4$), filtered and concentrated in vacuo. Purification by flash chromatography on silica gel afforded 39 mg (90%) of the title compound as a yellow solid: $^1$H NMR (400 MHz, DMSO-d$_6$) δ 10.26 (s, 1H), 8.41 (d, J=2.5 Hz, 1H), 8.38 (dd, J=4.4, 1.5 Hz, 1H), 7.92 (t, J=7.8 Hz, 1H), 7.70-7.69 (m, 2H), 7.65 (d, J=8.6 Hz, 1H), 7.48 (ddd, J=8.4, 2.7, 1.6 Hz, 1H), 7.45-7.39 (m, 2H), 7.08 (d, J=8.0 Hz, 1H), 6.84 (dd, J=8.1, 1.9 Hz, 1H), 4.04 (s, 3H); ES-MS [M+1]$^+$: 322.2.

3. Route 3

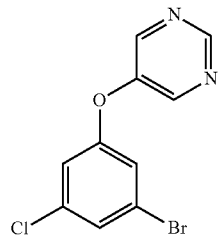 [SMILES: Clc1cc(Br)cc(Oc2cncnc2)c1]

a. 5-(3-bromo-5-chlorophenoxy)pyrimidine (7)

1-Bromo-3-chloro-5-fluorobenzene (1.0 g, 4.8 mmol, 1.0 eq), 5-hydroxypyrimidine (454 mg, 5.02 mmol, 1.05 eq), $K_2CO_3$ (792 mg, 5.73 mmol, 1.20 eq) and DMF (15 mL) were added to a microwave vial and microwaved at 200° C. for 30 minutes. The reaction was filtered and concentrated on silica gel (5 g). The silica gel was loaded on top a fresh bed of silica gel and washed with 50% ethyl acetate/hexane. The solvents were removed in vacuo and the crude mixture was purified by flash chromatography on silica gel afforded 735 mg (43%) of the title compound as a golden oil: $^1$H NMR (400 MHz, DMSO-$d_6$) δ 9.07 (s, 1H), 8.73 (s, 2H), 7.58 (t, J=1.7 Hz, 1H), 7.43 (t, J=1.9 Hz, 1H), 7.35 (t, J=2.0 Hz, 1H); ES-MS [M+1]$^+$: 285.0.

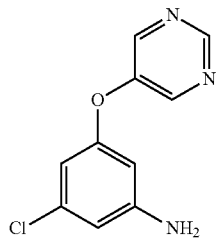 [SMILES: Nc1cc(Cl)cc(Oc2cncnc2)c1]

b. tert-Butyl 3-chloro-5-(pyrimidin-5-yloxy)phenylcarbamate (8)

Compound 7 (50 mg, 0.17 mmol, 1.0 eq), tert-butyl carbamate (25 mg, 0.21 mmol, 1.2 eq), sodium tert-butoxide (24 mg, 0.25 mmol, 1.4 eq), Tris(dibenzylideneacetone)dipalladium(0) chloroform adduct (5.4 mg, 0.0052 mmol, 0.030 eq), 2-di-tert-butylphosphino-2',4',6'-triisopropylbiphenyl (8 mg, 0.02 mmol, 0.09 eq) and toluene (0.65 mL) were added to a round-bottom flask, purged with argon and stirred at room temperature overnight. The reaction was filtered over a plug of celite and the plug was washed with 5% MeOH/$CH_2Cl_2$. The solvents were removed in vacuo and the crude mixture was purified by flash chromatography on silica gel afforded 41 mg (73%) of the title compound as a yellow oil: $^1$H NMR (400 MHz, CDCl$_3$) δ 9.05 (s, 1H), 8.55 (s, 2H), 7.26 (s, 1H), 7.18 (s, 1H), 6.90 (s, 1H), 6.73 (t, J=1.9 Hz, 1H), 1.54 (s, 9H); ES-MS [M+1]$^+$: 322.1.

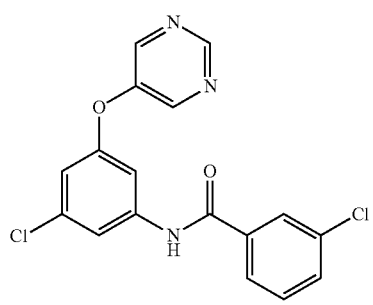 [SMILES: O=C(Nc1cc(Cl)cc(Oc2cncnc2)c1)c1cccc(Cl)c1]

c. 3-chloro-5-(pyrimidin-5-yloxy)aniline (9)

Compound 8 (48 mg, 0.15 mmol, 1.0 eq) was dissolved in 4N HCl in dioxane (0.75 mL) and stirred at room temperature until determination of completion by TLC. The reaction was neutralized with 1N NaOH and extracted with EtOAc (3×). The combined organics were dried (MgSO$_4$), filtered and concentrated in vacuo to give 29 mg (88%) of an orange solid: $^1$H NMR (400 MHz, DMSO-$d_6$) δ 9.03 (s, 1H), 8.67 (s, 2H), 6.55 (s, 1H), 6.42 (s, 1H), 6.30 (s, 1H); ES-MS [M+1]$^+$: 222.0.

d. 3-chloro-N-(3-chloro-5-(pyrimidin-5-yloxy)phenyl)benzamide (10)

Compound 9 (29 mg, 0.13 mmol, 1.0 eq) was dissolved in $CH_2Cl_2$ (1.2 mL) and DMAP (32 mg, 0.26 mmol, 2.0 eq) was added and the reaction stirred for 5 min. 3-Chlorobenzoyl chloride (23 mg, 0.13 mmol, 1.0 eq) was added and the reaction was stirred until determination of completion by LCMS. The reaction was diluted with $CH_2Cl_2$, washed with water (1×), dried (MgSO$_4$), filtered and concentrated in vacuo. Purification by flash chromatography on silica gel afforded 2.9 mg (6%) of the title compound as a white solid: $^1$H NMR (400 MHz, DMSO-$d_6$) δ 10.54 (s, 1H), 9.07 (s, 1H), 8.75 (s, 2H), 7.96 (t, J=1.7 Hz, 1H), 7.87 (d, J=7.8 Hz, 1H), 7.81 (t, J=1.7 Hz, 1H), 7.68-7.66 (m, 1H), 7.56 (t, J=7.9 Hz, 1H), 7.46 (t, J=2.0 Hz, 1H), 7.05 (t, J=2.0 Hz, 1H); ES-MS [M+1]$^+$: 360.1.

4. Route 4

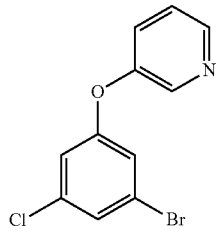 [SMILES: Clc1cc(Br)cc(Oc2cccnc2)c1]

a. 3-(3-Bromo-5-chlorophenoxy)pyridine (11)

1-Bromo-3-chloro-5-fluorobenzene (1.0 g, 4.8 mmol, 1.0 eq), 3-hydroxypyridine (454 mg, 4.77 mmol, 1.00 eq), $K_2CO_3$ (792 mg, 5.73 mmol, 1.20 eq) and DMF (15 mL) were added to a microwave vial and microwaved at 200° C. for 30 minutes. The reaction was filtered and concentrated on silica gel (5 g). The silica gel was loaded on top a fresh bed of silica gel and washed with 50% ethyl acetate/hexane. The solvents were removed in vacuo and the crude mixture was purified by flash chromatography on silica gel afforded 950 mg (55%) of the title compound as a golden oil: $^1$H NMR (400 MHz, $CDCl_3$) δ 8.45-8.44 (m, 2H), 7.58 (dd, J=8.4, 1.5 Hz, 1H), 7.52 (t, J=1.7 Hz, 1H), 7.47 (dd, J=8.5, 4.6 Hz, 1H), 7.25 (t, J=2.1 Hz, 1H), 7.18 (t, J=2.0 Hz, 1H); [M+1]$^+$: 284.0.

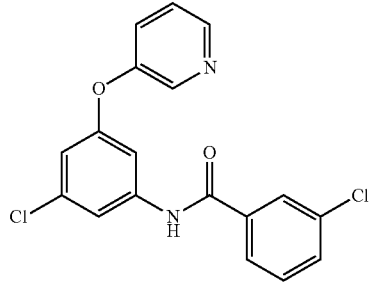 [SMILES: O=C(Nc1cc(Cl)cc(Oc2cccnc2)c1)c1cccc(Cl)c1]

b. 3-Chloro-N-(3-chloro-5-(pyridin-3-yloxy)phenyl)benzamide (12)

Compound 11 (1.0 g, 3.5 mmol, 1.0 eq), 3-chlorobenzamide (820 mg, 5.27 mmol, 1.50 eq), NaOt-Bu (473 mg, 4.92 mmol, 1.40 eq), $Pd(OAc)_2$ (40 mg, 0.18 mmol, 0.050 eq) and Xantphos (203 mg, 0.351 mmol, 0.100 eq) were dissolved in toluene (15 mL) in a microwave vial. The vial was purged with argon, capped, and heated at 110° C. for 18 h. After cooling the reaction was filtered over a plug of celite and the plug was washed with 5% $MeOH/CH_2Cl_2$. The solvents were removed in vacuo and the crude mixture was purified by flash chromatography on silica gel afforded 921 mg (73%) of the title compound as a white solid: $^1$H NMR (400 MHz, $CDCl_3$) δ 10.5 (s, 1H), 8.47 (d, J=2.8 Hz, 1H), 8.45 (dd, J=4.6, 1.3 Hz, 1H), 7.95 (t, J=1.8 Hz, 1H), 7.86 (dt, J=7.8, 1.3 Hz, 1H), 7.77 (t, J=1.8 Hz, 1H), 7.67 (dq, J=8.1, 1.2 Hz, 1H), 7.58 (ddd, J=8.4, 2.9, 1.4 Hz, 1H), 7.56 (t, J=7.9 Hz, 1H), 7.49 (dd, J=8.4, 4.7, 1H), 7.40 (t, J=2.1 Hz, 1H), 6.94 (t, J=2.1 Hz, 1H); [M+1]$^+$: 359.2.

5. Route 5

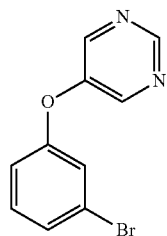 [SMILES: Brc1cccc(Oc2cncnc2)c1]

a. 5(3-Bromophenoxy)pyrimidine (13)

NaH (166 mg, 6.92 mmol, 1.10 eq) in DMF (15 mL) in a flame-dried microwave vial was cooled to 0° C. and 3-bromophenol (982 µL, 6.29 mmol, 1.00 eq) was added dropwise. The reaction was stirred for 30 min. at 0° C. at which point 5-bromopyrimidine (1.0 g, 6.3 mmol, 1.0 eq) was added and the reaction microwaved at 200° C. for 60 minutes. The reaction was diluted with ethyl acetate (50 mL) and was with water (3×). The organic layer was dried ($MgSO_4$), filtered and concentrated in vacuo. Purification by flash chromatography on silica gel afforded 750 mg (52%) of the title compound as an orange oil: $^1$H NMR (400 MHz, $CDCl_3$) δ 9.03 (s, 1H), 8.67 (s, 2H), 7.43-7.36 (m, 3H), 7.16 (dt, J=7.7, 1.9 Hz, 1H); ES-MS [M+1]$^+$: 251.0.

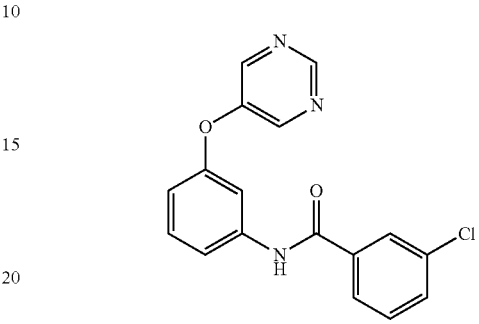

b. 3-Chloro-N-(3-(pyrimidin-5-yloxy)phenyl)benzamide (14)

Compound 13 (580 mg, 2.31 mmol, 1.00 eq), 3-chlorobenzamide (539 mg, 3.46 mmol, 1.50 eq), NaOt-Bu (311 mg, 3.24 mmol, 1.40 eq), $Pd(OAc)_2$ (26 mg, 0.12 mmol, 0.050 eq) and Xantphos (134 mg, 0.232 mmol, 0.100 eq) were dissolved in toluene (6 mL) in a flame-dried sealed tube and heated at 110° C. for 18 h. The reaction was cooled to rt, diluted with $CH_2Cl_2$ and filtered through a plug of celite. Purification by flash chromatography on silica gel afforded 68 mg (9%) of the title compound as an off white semi-solid: $^1$H NMR (400 MHz, DMSO-$d_6$) δ 10.44 (s, 1H), 9.03 (s, 1H), 8.68 (s, 2H), 7.97 (t, J=1.6 Hz, 1H), 7.88 (d, J=7.8 Hz, 1H), 7.65 (t, J=9.8 Hz, 2H), 7.59 (t, J=2.0 Hz, 1H), 7.56 (t, J=7.8 Hz, 1H), 7.42 (t, J=8.2 Hz, 1H), 6.91 (dd, J=8.1, 1.9 Hz, 1H); ES-MS [M+1]$^+$: 326.1.

6. Route 6

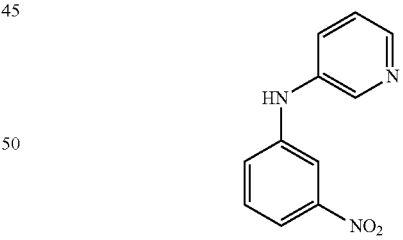

a. N-(3-Nitrophenyl)pyridin-3-amine (15)

3-nitroaniline (1.82 g, 13.2 mmol, 1.5 eq), 3-chloropyridine (1 g, 8.8 mmol, 1 eq), $Cs_2CO_3$ (4.02 g, 12.3 mmol, 1.4 eq), $Pd_2(dba)_3$ (403 mg, 0.44 mmol, 0.05 eq) and Xantphos (511 mg, 0.88 mmol, 0.1 eq) were dissolved in toluene (10 mL) in a flame-dried sealed tube and heated at 110° C. for 18 h. The reaction was cooled to rt, diluted with $CH_2Cl_2$ and filtered through a plug of celite. Purification by flash chromatography on silica gel afforded 1.55 g (82%) of the title compound as an orange solid: $^1$H NMR (400 MHz, DMSO-d$_6$) δ 8.89 (s, 1H), 8.42 (d, J=2.7 Hz, 1H), 8.17 (d, J=4.5, 1H), 7.79 (t, J=2.1 Hz, 1H), 7.64 (d, J=7.7 Hz, 1H), 7.59 (d, J=8.4 Hz, 1H), 7.52-7.45 (m, 2H), 7.33 (dd, J=8.2, 4.6 Hz, 1H); ES-MS [M+1]$^+$: 216.1.

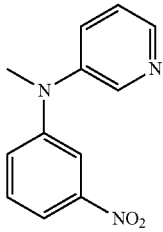

b. N-methyl-N-(3-nitrophenyl)pyridin-3-amine (16)

NaH (61 mg, 2.5 mmol, 1.1 eq) was added to a flame-dried round-bottom flask and anhydrous THF (6 mL) was added. The slurry was cooled to 0° C. and compound 15 (500 mg, 2.33 mmol, 1.00 eq) was added as a solution in THF (6 mL). After stirring at 0° C. for 30 minutes methyl iodide (159 μL, 2.54 mmol, 1.10 eq) was added and the reaction was allowed to warm to room temperature while stirring overnight. The reaction was diluted with EtOAc and washed with water (1×). The aqueous layer was back extracted (1×) with EtOAc and the combined organics were washed with brine, dried (MgSO$_4$), filtered and concentrated in vacuo. Purification by flash chromatography on silica gel afforded 340 mg (64%) of the title compound as a yellow solid: $^1$H NMR (400 MHz, DMSO-d$_6$) δ 8.48 (d, J=2.7 Hz, 1H), 8.35 (dd, J=4.7, 1.4 Hz, 1H), 7.70-7.66 (m, 1H), 7.66-7.64 (ddd, J=8.3, 2.7, 1.4 Hz, 1H), 7.60 (t, J=2.3 Hz, 1H), 7.50 (t, J=8.2 Hz, 1H), 7.42 (dd, J=8.3, 4.7 Hz, 1H), 7.32 (dd, J=8.3, 2.5 Hz, 1H), 3.37 (s, 3H); ES-MS [M+1]$^+$: 230.2.

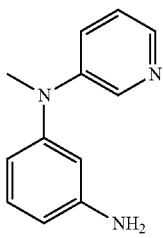

c. N$^1$-methyl-N$^1$-(pyridin-3-yl)benzene-1,3-diamine (17)

Compound 16 (330 mg, 1.44 mmol, 1.00 eq) was dissolved in dioxane (7 mL) and SnCl$_2$ (1.37 g, 7.22 mmol, 5.00 eq) dissolved in conc HCl (3 mL) was added dropwise over 15 min. After determination of completion by LCMS, the reaction was neutralized with 1N NaOH, filtered, diluted with water and extracted with CH$_2$Cl$_2$ (2×). The combined organics were dried (MgSO$_4$), filtered and concentrated in vacuo to give 284 mg (99%) of a brown oil that was used subsequently without purification. $^1$H NMR (400 MHz, CDCl$_3$) δ 8.16 (d, J=2.3 Hz, 1H), 7.99 (dd, J=4.2, 1.6 Hz, 1H), 7.24-7.17 (m, 2H), 7.01-6.95 (m, 1H), 6.32-6.28 (m, 2H), 6.27-6.23 (m, 1H), 5.08 (s, 2H), 3.19 (s, 3H); ES-MS [M+1]$^+$: 200.2.

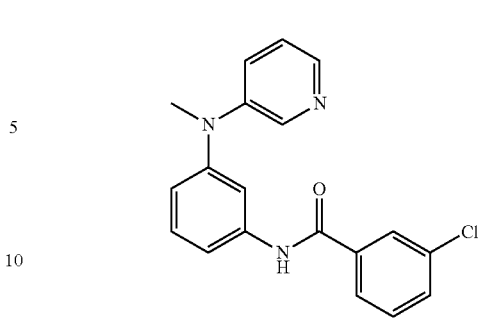

d. 3-chloro-N-(3-(methyl(pyridin-3-yl)amino)phenyl)benzamide (18)

Compound 17 (25 mg, 0.13 mmol, 1.0 eq) was dissolved in CH$_2$Cl$_2$ (1 mL) and DIEA (24 μL, 0.14 mmol, 1.1 eq) was added and the reaction stirred for 5 min. 3-Chlorobenzoyl chloride (16.1 μL, 0.125 mmol, 1.00 eq) was added and the reaction was stirred until determination of completion by LCMS. The reaction was diluted with CH$_2$Cl$_2$, washed with water (1×), dried (MgSO$_4$), filtered and concentrated in vacuo. Purification by flash chromatography on silica gel afforded 30 mg (71%) of the title compound as a light-yellow solid: $^1$H NMR (400 MHz, CDCl$_3$) δ 10.44 (s, 1H), 8.36-8.15 (m, 2H), 7.98 (s, 1H), 7.89 (d, J=7.8 Hz, 1H), 7.76-7.72 (m, 1H), 7.71-7.60 (m, 4H), 7.56 (t, J=7.9 Hz, 1H), 7.44 (t, J=8.1 Hz, 1H), 7.02 (d, J=8.0 Hz, 1H), 3.36 (s, 3H); ES-MS [M+1]$^+$: 338.2.

7. Route 7

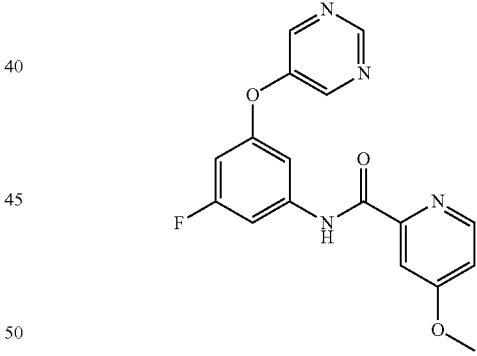

a. N-(3-Fluoro-5-(pyrimidin-5-yloxy)phenyl)-4-methoxypicolinamide (19)

4-Fluoro-N-(3-fluoro-5-(pyrimidin-5-yloxy)phenyl)picolinamide (508 mg, 1.8 mmol, 1 eq) was dissolved in 3N HCl in MeOH (9 mL) and stirred for 3 h. The solvent was removed in vacuo to afford 635 mg (99%) of the bis-HCl salt of the title compound as a white solid: $^1$H NMR (400 MHz, DMSO-d$_6$) δ 10.96 (s, 1H), 9.08 (s, 1H), 8.75 (s, 2H), 8.52 (d, J=5.6 Hz, 1H), 7.76 (dt, J=11.3. 2.0 Hz, 1H), 7.63 (d, J=2.6 Hz, 1H), 7.56 (bs, 1H), 7.23 (dd, J=5.7, 2.6 Hz, 1H), 6.85 (dt, J=9.8, 2.3 Hz, 1H), 3.92 (s, 3H); ES-MS [M+1]$^+$: 341.1.

8. Route 8

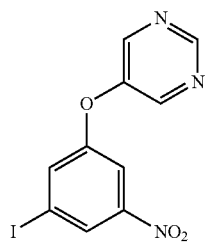 [SMILES: O=[N+]([O-])c1cc(I)cc(Oc2cncnc2)c1]

a. 5-(3-iodo-5-Nitrophenoxy)pyrimidine (20)

Two vials were each charged with 1-fluoro-3-iodo-5-nitrobenzene (1.0 g, 3.8 mmol, 1.0 eq), 5-hydroxypyrimidine (430 mg, 4.47 mmol, 1.20 eq), potassium carbonate (780 mg, 5.64 mmol, 1.50 eq), and DMF (12 mL) and stirred overnight at 100° C. The reaction mixtures were combined, diluted with 0.5N HCl, and extracted (3×) with $CH_2Cl_2$. The combined organics were dried ($MgSO_4$), filtered, and concentrated in vacuo. Purification by flash chromatography on silica gel afforded 2.2 g (87%) of the title compound as a yellow solid: $^1H$ NMR (400 MHz, $CDCl_3$) δ 9.13 (s, 1H), 8.58 (s, 2H), 8.38 (t, J=1.8 Hz, 1H), 7.82 (t, J=2.2 Hz, 1H), 7.70 (dd, J=2.3, 1.4 Hz, 1H); ES-MS [M+1]$^+$: 344.0.

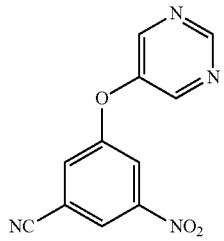

b. 3-nitro-5-(pyrimidin-5-yloxy)benzonitrile (21)

A mixture of polymer-bound triphenylphosphine (170 mg, 0.437 mmol, 0.150 eq) and palladium(II) acetate (46 mg, 0.20 mmol, 0.070 eq) in DMF (8.7 mL) stirred under argon for 2 h at rt. The supernatant DMF was removed, and fresh DMF (8.7 mL) was added. Compound 20 (1.0 g, 2.9 mmol, 1.0 eq) and zinc cyanide (340 mg, 2.90 mmol, 1.00 eq) were added, and the vial was subjected to microwave irradiation at 150° C. for 25 minutes. The resin was washed with ether, and the collected filtrate was washed (3×) with water and (1×) with brine. The organic layer was dried ($MgSO_4$), filtered, and concentrated in vacuo. Purification by flash chromatography on silica gel afforded 330 mg (47%) of the title compound as a yellow solid: $^1H$ NMR (400 MHz, $CDCl_3$) δ 9.20 (s, 1H), 8.63 (s, 2H), 8.32 (t, J=1.4 Hz, 1H), 8.07 (t, J=2.2 Hz, 1H), 7.62 (dd, J=2.3, 1.3 Hz, 1H); ES-MS [M+1]$^+$:243.0.

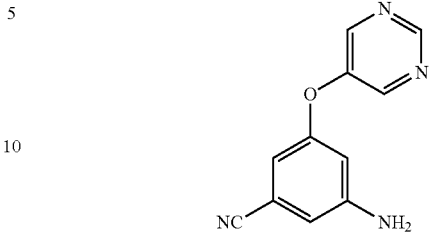

c. 3-amino-5-(pyrimidin-5-yloxy)benzonitrile (22)

Compound 21 (100 mg, 0.413 mmol, 1.00 eq) was dissolved in Dioxane (2.0 mL) and added to argon purged vial. Tin(II) chloride (390 mg, 2.06 mmol, 5.00 eq) was dissolved in concentrated HCl (0.66 mL) and added to the reaction vial dropwise. The solution stirred at rt for 1 h. The reaction was neutralized with 6N NaOH (2.0 mL) and extracted (3×) with $CH_2Cl_2$. The combined organics were dried ($MgSO_4$), filtered, and concentrated in vacuo. Purification by flash chromatography on silica gel afforded 58 mg (67%) of the title compound as a yellow solid: $^1H$ NMR (400 MHz, DMSO-$d_6$) δ 9.04 (s, 1H), 8.68 (s, 2H), 6.71 (t, J=1.5 Hz, 1H), 6.68 (t, J=2.2 Hz, 1H), 6.51 (t, J=2.2 Hz, 1H), 5.86 (s, 2H); ES-MS [M+1]$^+$: 213.1.

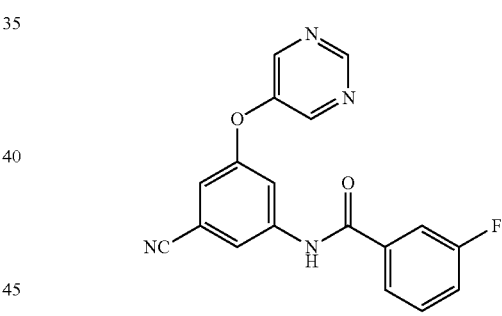

d. N-(3-cyano-5-(pyrimidin-5-yloxy)phenyl)-3-Fluorobenzamide (23)

Compound 22 (10 mg, 0.047 mmol, 1.2 eq), 3-fluorobenzoic acid (5.5 mg, 0.039 mmol, 1.0 eq), O-(7-Azabenzotriazol-1-yl)-N,N,N',N'-tetramethyluronium hexafluorophosphate (31 mg, 0.082 mmol, 2.1 eq), and N,N-Diisopropylethylamine (11 mg, 0.085 mmol, 2.1 eq) were dissolved in $CH_2Cl_2$ (0.43 mL) and DMF (0.09 mL) and stirred at rt overnight. The reaction was quenched with water, and the layers were separated via phase separation. The organic layer was dried on air concentrator and purified by flash chromatography on silica gel to give 5.5 mg (42%) of the title compound as a white solid: $^1H$ NMR (400 MHz, $CDCl_3$) δ 9.08 (s, 1H), 8.57 (s, 2H), 8.13 (s, 1H), 7.80 (s, 1H), 7.74 (s, 1H), 7.59 (dd, J=18.9, 8.4 Hz, 2H), 7.51-7.46 (m, 1H), 7.31-7.26 (m, 1H), 7.08 (s, 1H); ES-MS [M+1]$^+$: 335.1.

9. Route 9

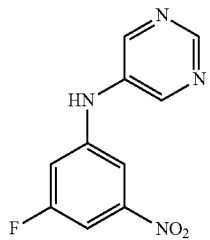 [SMILES: O=[N+]([O-])c1cc(F)cc(Nc2cncnc2)c1]

a. N-(3-fluoro-5-nitrophenyl)pyrimidin-5-amine (30)

1-fluoro-3-iodo-5-nitrobenzene (100 mg, 0.375 mmol, 1.00 eq), 5-aminopyrimidine (43 mg, 0.45 mmol, 1.2 eq, $Cs_2CO_3$ (171 mg, 0.525 mmol, 1.40 eq), $Pd_2(dba)_3$ (17 mg, 0.030 mmol, 0.080 eq), 4,5-bis(diphenylphosphino)-9,9-dimethylxanthene (26 mg, 0.045 mmol, 0.12 eq) and dioxane (0.8 mL) were added to a microwave vial. The vial was purged with argon, capped and heated at 100° C. for 18 h. After cooling the reaction was filtered over a plug of celite and the plug was washed with 5% $MeOH/CH_2Cl_2$. The solvents were removed in vacuo and the crude mixture was purified by flash chromatography on silica gel afforded 81 mg (93%) of the title compound as an orange solid: $^1$H NMR (400 MHz, DMSO-$d_6$) δ 9.23 (s, 1H), 8.84 (s, 1H), 8.72 (s, 2H), 7.68 (s, 1H), 7.53 (d, J=8.6 Hz, 1H), 7.36 (d, J=10.7 Hz, 1H); ES-MS [M+1]$^+$: 235.1.

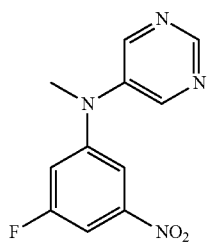 [SMILES: CN(c1cncnc1)c1cc(F)cc([N+](=O)[O-])c1]

b. N-(3-fluoro-5-nitrophenyl)-N-methylpyrimidin-5-amine (31)

NaH (4.5 mg, 0.18 mmol, 1.1 eq) was added to a flame-dried round-bottom flask and anhydrous THF (0.4 mL) was added. The slurry was cooled to 0° C. and compound 30 (40 mg, 0.17 mmol, 1.0 eq) was added as a solution in THF (0.4 mL). After stirring at 0° C. for 30 minutes methyl iodide (12 μL, 0.18 mmol, 1.1 eq) was added and the reaction was allowed to warm to room temperature while stirring overnight. The reaction was diluted with EtOAc and washed with water (1×). The aqueous layer was back extracted (1×) with EtOAc and the combined organics were washed with brine, dried ($MgSO_4$), filtered and concentrated in vacuo. Purification by flash chromatography on silica gel afforded 13 mg (31%) of the title compound as a yellow solid: $^1$H NMR (400 MHz, DMSO-$d_6$) δ 8.99 (s, 1H), 8.79 (s, 2H), 7.58 (dt, J=2.1, 8.5 Hz, 1H), 7.52 (t, J=1.8 Hz, 1H), 7.33 (dt, J=2.3, 11.2 Hz, 1H), 3.42 (s, 3H); ES-MS [M+1]$^+$: 249.1.

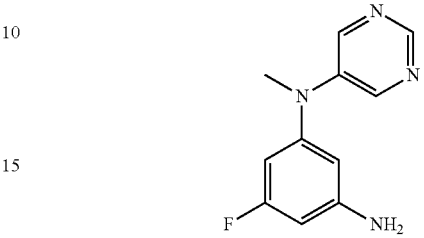

c. 5-Fluoro-$N^1$-methyl-$N^1$-(pyrimidin-5-yl)benzene-1,3-diamine (32)

Compound 31 (224 mg, 0.902 mmol, 1.00 eq) was dissolved in dioxane (4.5 mL) and $SnCl_2$ (856 mg, 4.51 mmol, 5.00 eq) dissolved in conc HCl (1.5 mL) was added dropwise over 15 min. After determination of completion by LCMS, the reaction was neutralized with 1N NaOH, filtered, diluted with water and extracted with $CH_2Cl_2$ (2×). The combined organics were dried ($MgSO_4$), filtered and concentrated in vacuo to give 224 mg (63%) of a tan solid that was used subsequently without purification. $^1$H NMR (400 MHz, $CDCl_3$) δ 8.67 (s, 1H), 8.44 (s, 2H), 6.11-6.10 (m, 1H), 6.09-6.07 (m, 1H), 6.07-6.04 (m, 1H), 5.46 (s, 2H), 3.23 (s, 3H); ES-MS [M+1]$^+$: 219.2.

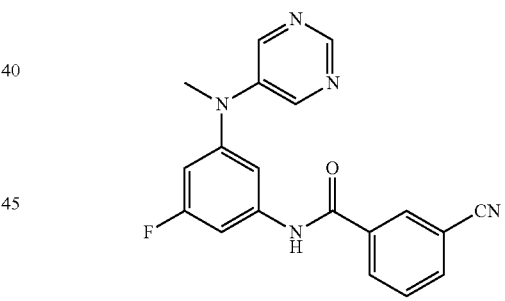

d. 3-Cyano-N-(3-fluoro-5-(methyl(pyrimidin-5-yl)amino)phenyl)-benzamide (33)

Compound 32 (15 mg, 0.069 mmol, 1.0 eq) was dissolved in $CH_2Cl_2$ (0.5 mL) and DMAP (9.2 mg, 0.075 mmol, 1.1 eq) was added and the reaction stirred for 5 min. 3-Cyanobenzoyl chloride (11 mg, 0.066 mmol, 1.0 eq) was added and the reaction was stirred until determination of completion by LCMS. The reaction was diluted with $CH_2Cl_2$, washed with water (1×), dried ($MgSO_4$), filtered and concentrated in vacuo. Purification by flash chromatography on silica gel afforded 6 mg (47%) of the title compound as a white solid: $^1$H NMR (400 MHz, $CDCl_3$) δ 10.48 (s, 1H), 8.82 (s, 1H), 8.63 (s, 2H), 8.34 (s, 1H), (8.19 (d, J=8.0 Hz, 1H), 8.06 (d, J=7.8 Hz, 1H), 7.74 (t, J=7.8 Hz, 1H), 7.44 (d, J=11.0 Hz, 1H), 7.22 (s, 1H), 6.79-6.73 (m, 1H), 3.34 (s, 3H); ES-MS [M+1]$^+$: 348.2.

10. Route 10

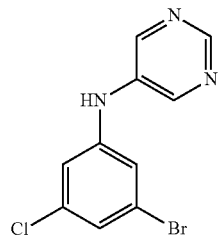 [SMILES: Clc1cc(Br)cc(Nc2cncnc2)c1]

a. N-(3-Bromo-5-chlorophenyl)pyrimidin-5-amine (34)

1-chloro-3,5-dibromobenzene (0.30 g, 1.1 mmol, 1.0 eq), 5-aminopyrimidine (106 mg, 1.11 mmol, 1.00 eq), $Cs_2CO_3$ (506 mg, 1.55 mmol, 1.40 eq), $Pd_2(dba)_3$ (51 mg, 0.089 mmol, 0.080 eq), 4,5-bis(diphenylphosphino)-9,9-dimethylxanthene (77 mg, 0.13 mmol, 0.12 eq) and toluene (3.7 mL) were added to a microwave vial. The vial was purged with argon, capped and heated at 100° C. for 18 h. After cooling the reaction was filtered over a plug of celite and the plug was washed with 5% $MeOH/CH_2Cl_2$. The solvents were removed in vacuo and the crude mixture was purified by flash chromatography on silica gel afforded 173 mg (55%) of the title compound as a light-orange solid: $^1H$ NMR (400 MHz, $CDCl_3$) δ 8.87 (s, 1H), 8.77 (s, 1H), 8.62 (s, 2H), 7.18 (t, J=1.8 Hz, 1H), 7.15 (t, J=1.7 Hz, 1H), 7.09 (t, J=1.9 Hz, 1H); ES-MS $[M+1]^+$: 284.0.

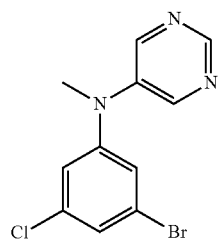 [SMILES: CN(c1cncnc1)c1cc(Cl)cc(Br)c1]

b. N-(3-Bromo-5-chlorophenyl)-N-methylpyrimidin-5-amine (35)

NaH (24 mg, 1.0 mmol, 1.1 eq) was added to a flame-dried round-bottom flask and anhydrous THF (2.2 mL) was added. The slurry was cooled to 0° C. and compound 34 (255 mg, 0.896 mmol, 1.00 eq) was added as a solution in THF (2.2 mL). After stirring at 0° C. for 30 minutes methyl iodide (61.5 µL, 1.00 mmol, 1.10 eq) was added and the reaction was allowed to warm to room temperature while stirring overnight. The reaction was diluted with EtOAc and washed with water (1×). The aqueous layer was back extracted (1×) with EtOAc and the combined organics were washed with brine, dried ($MgSO_4$), filtered and concentrated in vacuo. Purification by flash chromatography on silica gel afforded 248 mg (93%) of the title compound as an off-white solid: $^1H$ NMR (400 MHz, $CDCl_3$) δ 8.87 (s, 1H), 8.64 (s, 1H), 7.25 (t, J=1.7 Hz, 1H), 7.16 (t, J=1.9 Hz, 1H), 7.07 (t, J=1.9 Hz, 1H), 3.32 (s, 3H); ES-MS $[M+1]^+$: 298.1.

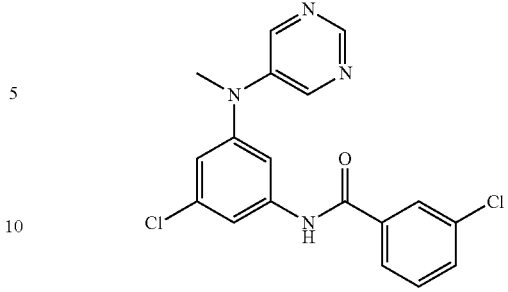

c. 3-Chloro-N-(3-chloro-5-(methyl(pyrimidin-5-yl)amino)phenyl)-benzamide (36)

Compound 35 (59 mg, 0.20 mmol, 1.0 eq), 3-chlorobenzamide (46 mg, 0.30 mmol, 1.5 eq), NaOt-Bu (27 mg, 0.28 mmol, 1.4 eq), $Pd(OAc)_2$ (2.2 mg, 0.0098 mmol, 0.050 eq) and Xantphos (11.4 mg, 0.0197 mmol, 0.100 eq) were dissolved in toluene (1 mL) in a microwave vial. The vial was purged with argon, capped, and heated at 110° C. for 18 h. After cooling the reaction was filtered over a plug of celite and the plug was washed with 5% $MeOH/CH_2Cl_2$. The solvents were removed in vacuo and the crude mixture was purified by flash chromatography on silica gel afforded 42 mg (57%) of the title compound as a white solid: $^1H$ NMR (400 MHz, $CDCl_3$) δ 10.4 (s, 1H), 8.8 (s, 1H), 8.6 (s, 2H), 7.96 (t, J=1.8 Hz, 1H), 7.97-7.85 (m, 1H), 7.67-7.65 (m, 2H), 7.55 (t, J=7.8 Hz, 1H), 7.41 (t, J=1.9 Hz, 1H), 6.95 (t, J=2.0 Hz, 1H), 3.34 (s, 3H); $[M+1]^+$: 373.1.

11. Metabotropic Glutamate Receptor Activity Assay

The utility of the compounds in accordance with the present invention as negative allosteric modulators of metabotropic glutamate receptor activity, in particular mGluR5 activity, can be demonstrated by methodology known in the art. Human embryonic kidney (HEK) cells transfected with rat or human mGluR5 were plated in clear bottom assay plates for assay in a Functional Drug Screening System (FDSS). The cells were loaded with a Ca2+-sensitive fluorescent dye (e.g., Fluo-4), and the plates were washed and placed in the FDSS instrument. Test compound was applied to cells 3 seconds after baseline readings were taken. Cells were incubated with the test compounds for 140 seconds and then stimulated with an $EC_{20}$ concentration of an mGluR5 agonist (e.g., glutamate, 3,5-dihydroxyphenylglycine, or quisqualate); 60-80 seconds later an $EC_{80}$ concentration of agonist was added and readings taken for an additional 40 seconds. Data were collected at 1 Hz. Negative allosteric modulation of the agonist response of mGluR5 by the compounds in the present invention was observed as a decrease in response to non-maximal concentrations of agonist (here, glutamate) in the presence of compound compared to the response to agonist in the absence of compound. Concentration response curves were generated using a four parameter logistical equation.

The above described assay was operated in two modes. In the first mode (utilizing a triple add protocol), a range of concentrations of the present compounds were added to cells, followed by two single fixed concentrations of agonist ($EC_{20}$ followed by $EC_{80}$). If a compound acted as a potentiator, an $EC_{50}$ value for potentiation of the $EC_{20}$ response and a maximum extent of potentiation by the compound at this concentration of agonist was determined by non-linear curve fitting. If a compound acted as an antagonist, an $IC_{50}$ value for antagonism of the $EC_{80}$ response and a maximum extent of antagonism by the compound at this concentration of agonist was determined by non-linear curve fitting. In the second mode (utilizing a double add protocol), several fixed concentrations of the present compounds were added to various wells on a plate, followed by a range of concentrations of agonist for each concentration of present compound; the $EC_{50}$ values for the agonist at each concentration of compound were determined by nonlinear curve fitting. A decrease in the $EC_{50}$ value of the agonist with increasing concentrations of the present compounds (a leftward shift of the agonist concentration-response curve) is an indication of the degree of mGluR5 positive allosteric modulation at a given concentration of the present compound. An increase in the $EC_{50}$ value of the agonist with increasing concentrations of the present compounds (a rightward shift of the agonist concentration response curve) is an indication of the degree of mGluR5 antagonism at a given concentration of the present compound. The second mode also indicates whether the present compounds also affect the maximum response to mGluR5 to agonists. Exemplary data are provided in Tables 1 and 2 above.

12. Inhibition of Marble Burying 1N Mice Assay

It is well known that mice will bury foreign objects such as glass marbles in deep bedding (Deacon, R. M. J. *Nature Protocols* 2006, 1, 122-124). Low doses of anxiolytic benzodiazepines have been demonstrated to inhibit this behavior (Njung'e, K.; Handley, S. L. *Brit. J. Pharmacol.* 1991, 104, 105-112; Broekkamp, C. L.; Rijk, H. W.; Joly-Gelouin, D.; Lloyd, K. L. *Eur. J. Pharmacol.* 1986, 126, 223-229). Moreover, the known mGlu$_5$ NAMs MPEP (3-((2-methyl-4-thiazolyl)ethynyl)-pyridine) and fenobam (1-(3-chlorophenyl)-3-(1-methyl-4-oxo-4,5-dihydro-1H-imidazol-2-yl)urea) are effective in this model (Spooren W. P. J. M.; Vassout A.; Neijt H. C.; Kuhn R.; Gasparini F.; Roux S.; Porsolt R. D.; Gentsch C. J. *Pharmacol. Exp. Ther.* 2000, 295, 1267-1275; Nicolas, L. B.; Kolb, Y.; Prinssen, E. P. M. *Eur. J. Pharmacol.* 2006, 547, 106-115). These facts along with the relative convenience of this assay make it a useful in vivo screening tool.

Doses of compound were suspended in vehicle (10% Tween 80 for intraperitoneal dosing and 0.5% methylcellulose for oral dosing), vortexed vigorously, heated gently with a Master Heat Gun (Master Appliance Corp., Racine, Wis.), and sonicated at 37° C. for 30 minutes. The pH was checked using 0-14 EMD strips and adjusted to approximately 7. All doses were administered at approximately 10 mL/kg.

Studies were conducted using male Harlan CD-1 mice (Harlan Sprague Dawley, Indianapolis, Ind.), weighing 30 to 35 grams. Subjects were housed in a large colony room under a 12 hour light/dark cycle (lights on at 6:00 a.m.) with food and water provided ad libitum. Test sessions were performed between 10:00 a.m. and 4:00 p.m. All dose groups consisted of ≧7 mice. All experiments were conducted in accordance with the National Institute of Health regulations of animal care covered in Principles of Laboratory Animal Care (National Institutes of Health publication 85-23, revised 1985) and were approved by the Institutional Animal Care and Use Committee.

Plexiglass cages (32×17×14 cm) were arranged on top of a large, round table. Mice were transported from the colony room to the testing room and allowed to habituate for 30 minutes. Mice were pretreated with a dose of a standard compound (either MTEP or fenobam) or novel compound for 15 or 30 minutes and individually placed in the cages in which 12 black glass marbles (14 mm diameter) had been evenly distributed (spaced 6.4 cm vertically and 4.25 cm horizontally from each other and the walls of the cage) on top of 2.5 cm Diamond Soft Bedding (Harlan Teklad, Madison, Wis.). The novel compound and comparator were evaluated in a counterbalanced design, in which all doses of compounds were tested in each session. Mice receiving the same dose were placed in cages on opposite sides of the table to control for effects of lighting and context. Clear, perforated plastic lids were set on top of each cage and the amount of marble burying was recorded over a 30 minute interval. The mice were then removed from the cages and the number of buried marbles was counted using the criteria of greater than ⅔ covered by bedding. Each session was videotaped with a Sony MiniDV camcorder equipped with a Sony wide-angle lens mounted on a 1.5 m tripod.

The data for the dose-response studies were analyzed by a between-group analysis of variance. If there was a main effect of dose, then each dose group was compared with the vehicle control group using a Dunnett's comparison. The calculations were performed using JMP IN 8 (SAS Institute, Cary, N.C.) statistical software and graphed using SigmaPlot9 (Sasgua, Mass.).

Figure 3:
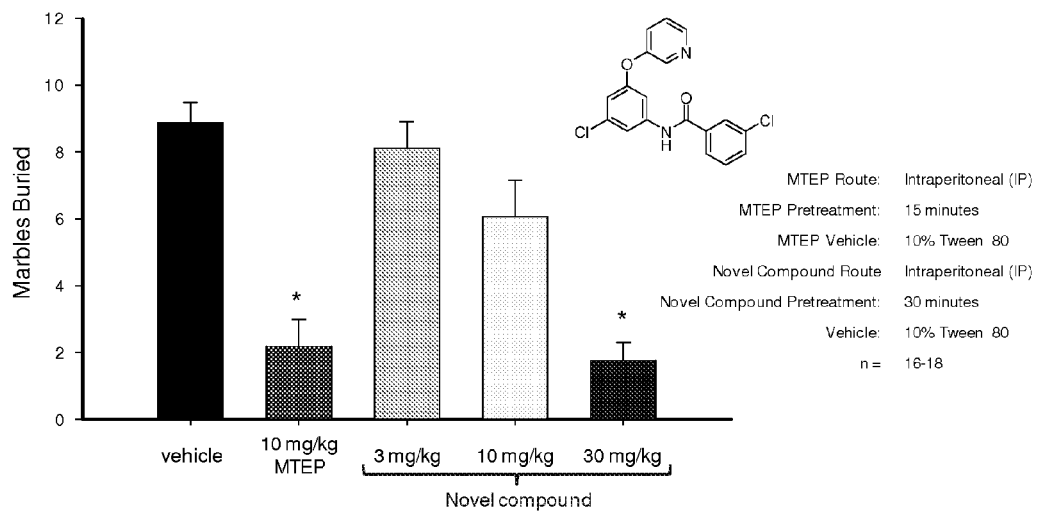
FIG. 3 shows representative data of the effect of an exemplary compound in a mouse model of anxiolytic behavior.

13. Inhibition of Marble Burying 1N Mice Assay by 3-chloro-N-(3-chloro-5-(pyridin-3-yloxy)phenyl)benzamide Inhibition of Marble Burying in Mice Dose response activity of 3-chloro-N-(3-chloro-5-(pyridin-3-yloxy)phenyl)benzamide in the marble burying assay (mouse model of anxiolytic behavior) is shown in FIG. 3, and was carried out as described above. The doses used (mg/kg) are as indicated and the activity of the compound is compared to a positive control compound, MTEP, at the dose indicated. Statistically significant results (p<0.05) are indicated by an asterick above the bar.

Figure 4:
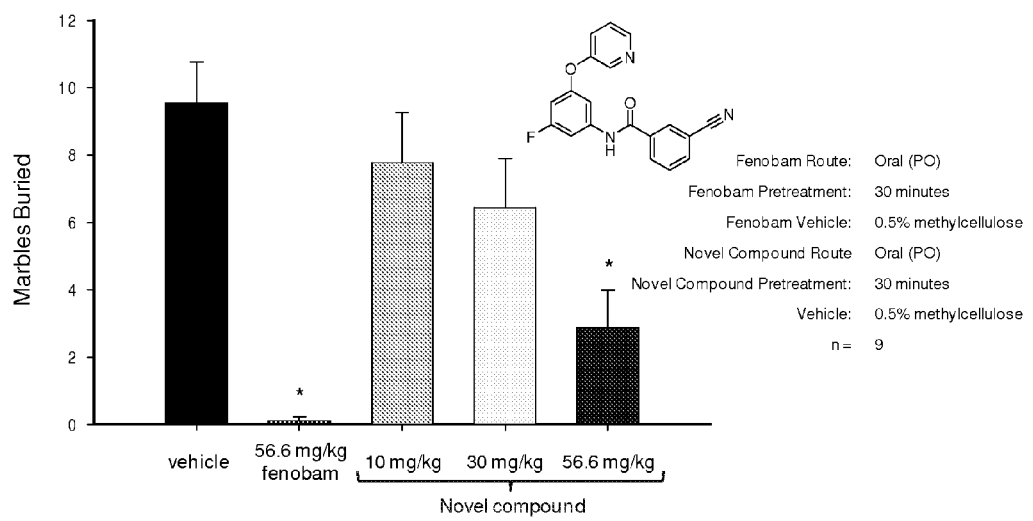
FIG. 4 shows representative data of the effect of an exemplary compound in a mouse model of anxiolytic behavior.

14. Inhibition of Marble Burying in Mice Assay by 3-cyano-N-(3-fluoro-5-(pyridin-3-yloxy)phenyl)benzamide Inhibition of Marble Burying in Mice Dose response activity of 3-cyano-N-(3-fluoro-5-(pyridin-3-yloxy)phenyl)benzamide in the marble burying assay (mouse model of anxiolytic behavior) is shown in FIG. 4, and was carried out as described above. The doses used (mg/kg) are as indicated and the activity of the compound is compared to a positive control compound, fenobam, at the dose indicated. Both 3-cyano-N-(3-fluoro-5-(pyridin-3-yloxy)phenyl) benzamide and MTEP were dosed intraperitoneal injection. Statistically significant results (p<0.05) are indicated by an asterick above the bar.

Figure 5:
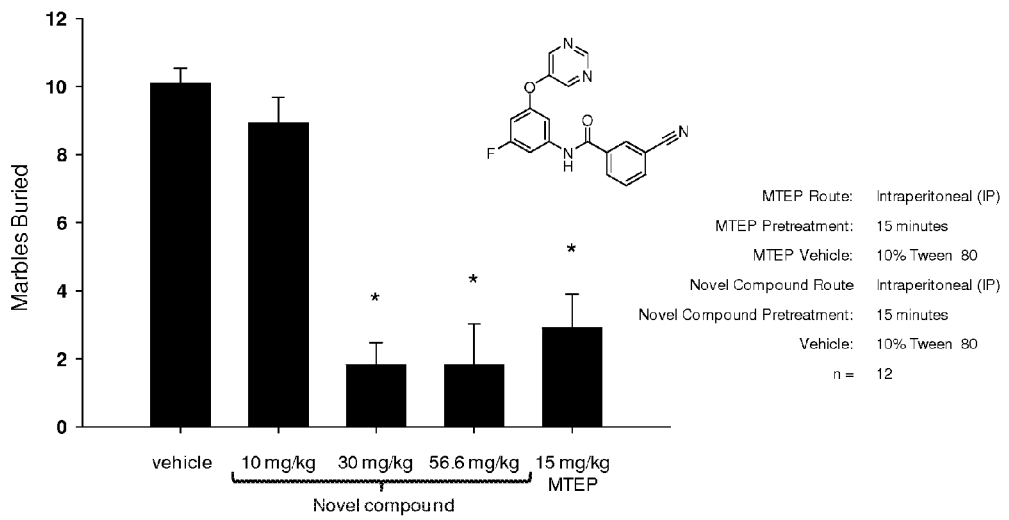
FIG. 5 shows representative data of the effect of an exemplary compound in a mouse model of anxiolytic behavior.

15. Inhibition of Marble Burying in Mice Assay by 3-cyano-N-(3-fluoro-5-(pyrimidin-5-yloxy)phenyl)benzamide Inhibition of Marble Burying in Mice Dose response activity of 3-cyano-N-(3-fluoro-5-(pyrimidin-5-yloxy)phenyl)benzamide in the marble burying assay (mouse model of anxiolytic behavior) is shown in FIG. 5, and was carried out as described above. The doses used (mg/kg) are as indicated and the activity of the compound is compared to a positive control compound, MTEP, at the dose indicated. Both 3-cyano-N-(3-fluoro-5-(pyrimidin-5-yloxy)phenyl) benzamide and MTEP were dosed intraperitoneal injection. Statistically significant results (p<0.05) are indicated by an asterick above the bar.

Figure 6:
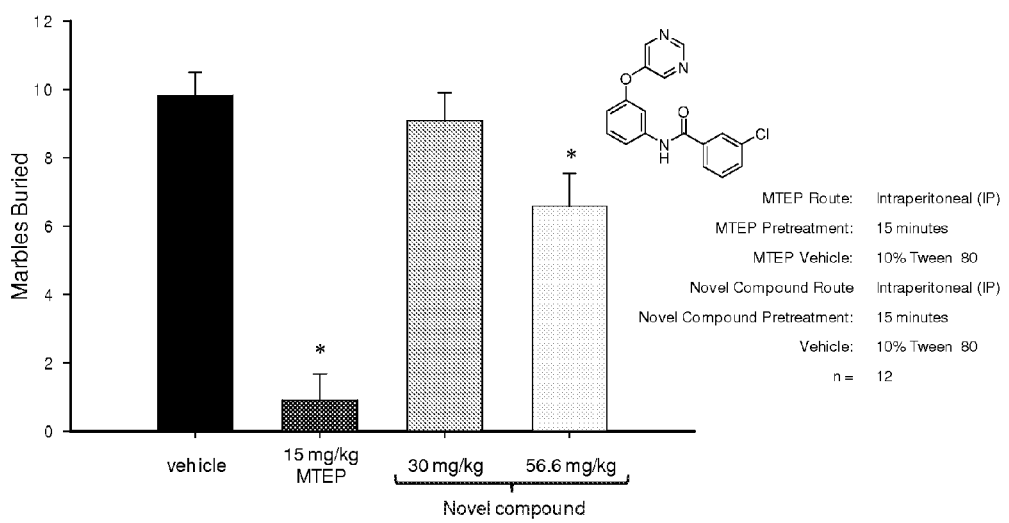
FIG. 6 shows representative data of the effect of in an exemplary compound a mouse model of anxiolytic behavior.

16. Inhibition of Marble Burying in Mice Assay by 3-chloro-N-(3-(pyrimidin-5-yloxy)phenyl)benzamide Inhibition of Marble Burying in Mice Dose response activity of 3-chloro-N-(3-(pyrimidin-5-yloxy)phenyl)benzamide in the marble burying assay (mouse model of anxiolytic behavior) is shown in FIG. 6, and was carried out as described above. The doses used (mg/kg) are as indicated and the activity of the compound is compared to a positive control compound, MTEP, at the dose indicated. Both 3-chloro-N-(3-(pyrimidin-5-yloxy)phenyl)benzamide and MTEP were dosed intraperitoneal injection. Statistically significant results (p<0.05) are indicated by an asterick above the bar.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound, or a pharmaceutically acceptable salt thereof, having a structure represented by a formula:

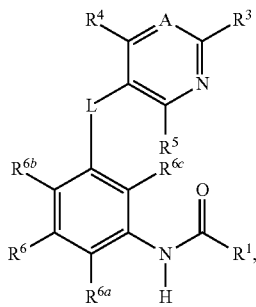

wherein A is $CR^2$ or N;
wherein L is O or $NR^7$,
wherein $R^1$ has from 1 to 10 carbons and is selected from phenyl substituted with 1-3 of $R^9$, wherein at least one $R^9$ is meta substituted; 2-pyridinyl substituted with 0-3 of $R^9$; and thiazole substituted with 0-2 of $R^9$;
wherein $R^2$ is hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$;
wherein $R^3$ is selected from hydrogen, halogen, C1-C6 alkyl, C1-C6 haloalkyl, C1-C6 alkoxy, hydroxyl, CN, $SO_2R^8$, and $COR^8$;
wherein $R^4$ and $R^5$ are independently hydrogen, halogen, C1-C6 alkyl, C1-C6 haloalkyl, C1-C6 alkoxy, C1-C6 haloalkoxy, amino, hydroxyl, alkylamino, dialkylamino, $NO_2$, CN, $SO_2R^8$, or $COR^8$;
wherein $R^6$ is selected from hydrogen, halogen, CN, C1-C4 alkyl, C1-C4 haloalkyl, C3-C4 cycloalkyl, and C3-C4 halocycloalkyl;
wherein each of $R^{6a}$, $R^{6b}$, and $R^{6c}$ is independently selected from hydrogen, halogen, C1-C6 alkyl, C1-C6 haloalkyl, C1-C6 alkoxy, amino, hydroxyl, alkylamino, dialkylamino, CN, $SO_2R^8$, and $COR^8$;
wherein $R^7$ is hydrogen, C1-C6 alkyl, or C1-C6 haloalkyl;
wherein $R^8$ is alkyl, cycloalkyl, amino, alkylamino, or dialkylamino; and
wherein each $R^9$, when present, is independently halogen, C1-C6 alkyl, C1-C6 haloalkyl, C3-C4 cycloalkyl, C3-C4 halocycloalkyl, C1-C6 alkoxy, C1-C6 haloalkoxy, hydroxyl, amino, alkylamino, dialkylamino, $NO_2$, CN, $SO_2R^8$, and $COR^8$;
wherein the compound exhibits partial or total inhibition of mGluR5 response to glutamate as a decrease in response to non-maximal concentrations of glutamate in human embryonic kidney cells transfected with rat mGluR5 in the presence of the compound, compared to the response to glutamate in the absence of the compound.

2. The compound of claim 1, wherein L is O.
3. The compound of claim 1, wherein L is $NR^7$, wherein $R^7$ is alkyl or haloalkyl.
4. The compound of claim 1, wherein $R^1$ is phenyl substituted with 1-3 of $R^9$ selected from halogen, CN, and alkyl.
5. The compound of claim 1, wherein $R^2$ is hydrogen, halogen, alkyl, haloalkyl, or alkoxy.
6. The compound of claim 1, wherein $R^3$ is halogen, alkyl, haloalkyl, alkoxy, hydroxyl, CN, $SO_2R^8$, or $COR^8$.
7. The compound of claim 1, wherein $R^4$ is halogen, alkyl, haloalkyl, alkoxy, amino, hydroxyl, alkylamino, dialkylamino, $NO_2$, CN, $SO_2R^8$, or $COR^8$.
8. The compound of claim 1, wherein $R^5$ is halogen, alkyl, haloalkyl, alkoxy, amino, hydroxyl, alkylamino, dialkylamino, $NO_2$, CN, $SO_2R^8$, or $COR^8$.
9. The compound of claim 1, wherein $R^6$ is selected from halogen, CN, C1-C4 alkyl, and C1-C4 haloalkyl.
10. The compound of claim 1, wherein $R^7$ is alkyl or haloalkyl.
11. The compound of claim 1, wherein $R^8$ is selected from alkyl and cycloalkyl.

* * * * *